(12) United States Patent
Datta et al.

(10) Patent No.: US 12,252,531 B2
(45) Date of Patent: Mar. 18, 2025

(54) METHODS OF SCREENING FOR HIGH-AFFINITY, ISOFORM-SELECTIVE TGFβ1 INHIBITORS

(71) Applicant: Scholar Rock, Inc., Cambridge, MA (US)

(72) Inventors: Abhishek Datta, Boston, MA (US); Allan Capili, Somerville, MA (US); Thomas Schurpf, Cambridge, MA (US); Constance Martin, Arlington, MA (US); Kevin B. Dagbay, Brighton, MA (US); Christopher Chapron, Watertown, MA (US); Stefan Wawersik, Westborough, MA (US); Christopher Littlefield, Marblehead, MA (US); Gregory J. Carven, Maynard, MA (US); Alan Buckler, Arlington, MA (US); Susan Lin, Boston, MA (US); Justin W. Jackson, Cambridge, MA (US); Caitlin Stein, Lebanon, NH (US); Andrew Avery, Lebanon, NH (US); Anthony Cooper, White River Junction, VT (US); Matthew Salotto, Hanover, NH (US)

(73) Assignee: Scholar Rock, Inc., Cambridge, MA (US)

( * ) Notice: Subject to any disclaimer, the term of this patent is extended or adjusted under 35 U.S.C. 154(b) by 624 days.

(21) Appl. No.: 17/258,771

(22) PCT Filed: Jul. 11, 2019

(86) PCT No.: PCT/US2019/041373
§ 371 (c)(1),
(2) Date: Jan. 8, 2021

(87) PCT Pub. No.: WO2020/014460
PCT Pub. Date: Jan. 16, 2020

(65) Prior Publication Data
US 2021/0122814 A1    Apr. 29, 2021

Related U.S. Application Data

(60) Provisional application No. 62/827,552, filed on Apr. 1, 2019, provisional application No. 62/810,263, filed on Feb. 25, 2019, provisional application No. 62/758,180, filed on Nov. 9, 2018, provisional application No. 62/737,534, filed on Sep. 27, 2018, provisional application No. 62/718,196, filed on Aug. 13, 2018, provisional application No. 62/696,752, filed on Jul. 11, 2018.

(51) Int. Cl.
G01N 33/74    (2006.01)
A61K 45/06    (2006.01)
A61P 35/00    (2006.01)
C07K 16/22    (2006.01)

(52) U.S. Cl.
CPC .............. C07K 16/22 (2013.01); A61K 45/06 (2013.01); A61P 35/00 (2018.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 6,248,723 B1 | 6/2001 | Irvin | |
| 6,492,497 B1 | 12/2002 | Thompson et al. | |
| 7,057,013 B1 | 6/2006 | Ezquerro Saenz et al. | |
| 9,399,676 B2 | 7/2016 | Schurpf et al. | |
| 9,573,995 B2 | 2/2017 | Schurpf et al. | |
| 9,580,500 B2 | 2/2017 | Schurpf et al. | |
| 9,758,576 B2 | 9/2017 | Schurpf et al. | |
| 9,758,577 B2 | 9/2017 | Schurpf et al. | |
| 10,597,443 B2 | 3/2020 | Schurpf et al. | |
| 2013/0225655 A1 | 8/2013 | Lu et al. | |
| 2015/0284455 A1 | 10/2015 | Springer et al. | |
| 2017/0073406 A1 | 3/2017 | Schurpf et al. | |
| 2017/0210798 A1 | 7/2017 | Schurpf et al. | |
| 2018/0016332 A1 | 1/2018 | Schurpf et al. | |
| 2018/0022798 A1 | 1/2018 | Schurpf et al. | |
| 2018/0207267 A1 | 7/2018 | Schurpf et al. | |
| 2019/0071493 A1 | 3/2019 | Schurpf et al. | |
| 2019/0085067 A1 | 3/2019 | Schurpf et al. | |
| 2019/0209682 A1 | 7/2019 | Schurpf et al. | |
| 2020/0024339 A1 | 1/2020 | Springer et al. | |
| 2020/0079840 A1 | 3/2020 | Datta et al. | |
| 2020/0131259 A1 | 4/2020 | Schurpf et al. | |
| 2021/0340238 A1 | 11/2021 | Datta et al. | |
| 2022/0064275 A1 | 3/2022 | Datta et al. | |

FOREIGN PATENT DOCUMENTS

| | | | |
|---|---|---|---|
| CN | 105229160 A | 1/2016 | |
| WO | 1990/02809 A1 | 3/1990 | |
| WO | 1991/017271 A1 | 11/1991 | |
| WO | 1992/001047 A1 | 1/1992 | |
| WO | 1992/009690 A2 | 6/1992 | |
| WO | 1992/015679 A1 | 9/1992 | |
| WO | 1992/018619 A1 | 10/1992 | |
| WO | 1992/020791 A1 | 11/1992 | |
| WO | 1993/001288 A1 | 1/1993 | |

(Continued)

OTHER PUBLICATIONS

Parasuraman, S. Toxicological screening. J. Pharmacol. Pharmacotherap. 2(2): 74-79, 2011.*

(Continued)

*Primary Examiner* — Christine J Saoud
(74) *Attorney, Agent, or Firm* — McCarter & English, LLP; Marcie B. Clarke; Nandini Mani

(57) ABSTRACT

Disclosed herein are monoclonal antibodies and antigen-binding fragments thereof capable of selectively inhibiting TGFβ1 with high potency. Related compositions, methods and therapeutic use are also disclosed.

5 Claims, 78 Drawing Sheets
Specification includes a Sequence Listing.

(56) References Cited

FOREIGN PATENT DOCUMENTS

| WO | 2014/074532 A2 | 5/2014 |
| WO | 2014/182676 A2 | 11/2014 |
| WO | 2015/171691 A2 | 11/2015 |
| WO | 2016/140884 A1 | 9/2016 |
| WO | 2016/141245 A1 | 9/2016 |
| WO | 2017/141208 A1 | 8/2017 |
| WO | 2017/156500 A8 | 9/2017 |
| WO | 2017/211873 A1 | 12/2017 |
| WO | 2018/013939 A1 | 1/2018 |
| WO | 2018/129329 A1 | 7/2018 |
| WO | 2018/134681 A1 | 7/2018 |
| WO | 2019/023661 A1 | 1/2019 |
| WO | 2020/014460 A1 | 1/2020 |
| WO | 2020/014473 A1 | 1/2020 |
| WO | 2021/142448 A2 | 7/2021 |

OTHER PUBLICATIONS

Hughes et al. Principles of early drug discovery. Brit. J. Pharmacol. 162: 1239-1249, 2011.*
Clackson et al., Making antibody fragments using phage display libraries. Nature. Aug. 15, 1991;352(6336):624-8.
Kohler et al., Continuous cultures of fused cells secreting antibody of predefined specificity. Nature. Aug. 7, 1975;256(5517):495-7.
Marks et al., By-passing immunization. Human antibodies from V-gene libraries displayed on phage. J Mol Biol. Dec. 5, 1991;222(3):581-97.
Smith, Filamentous fusion phage: novel expression vectors that display cloned antigens on the virion surface. Science. Jun. 14, 1985;228(4705):1315-7.
Wang et al., Modulation of TGF-beta activity by latent TGF-β-binding protein 1 in human osteoarthritis fibroblast-like synoviocytes. Mol Med Rep. Jan. 2018;17(1):1893-1900.

* cited by examiner

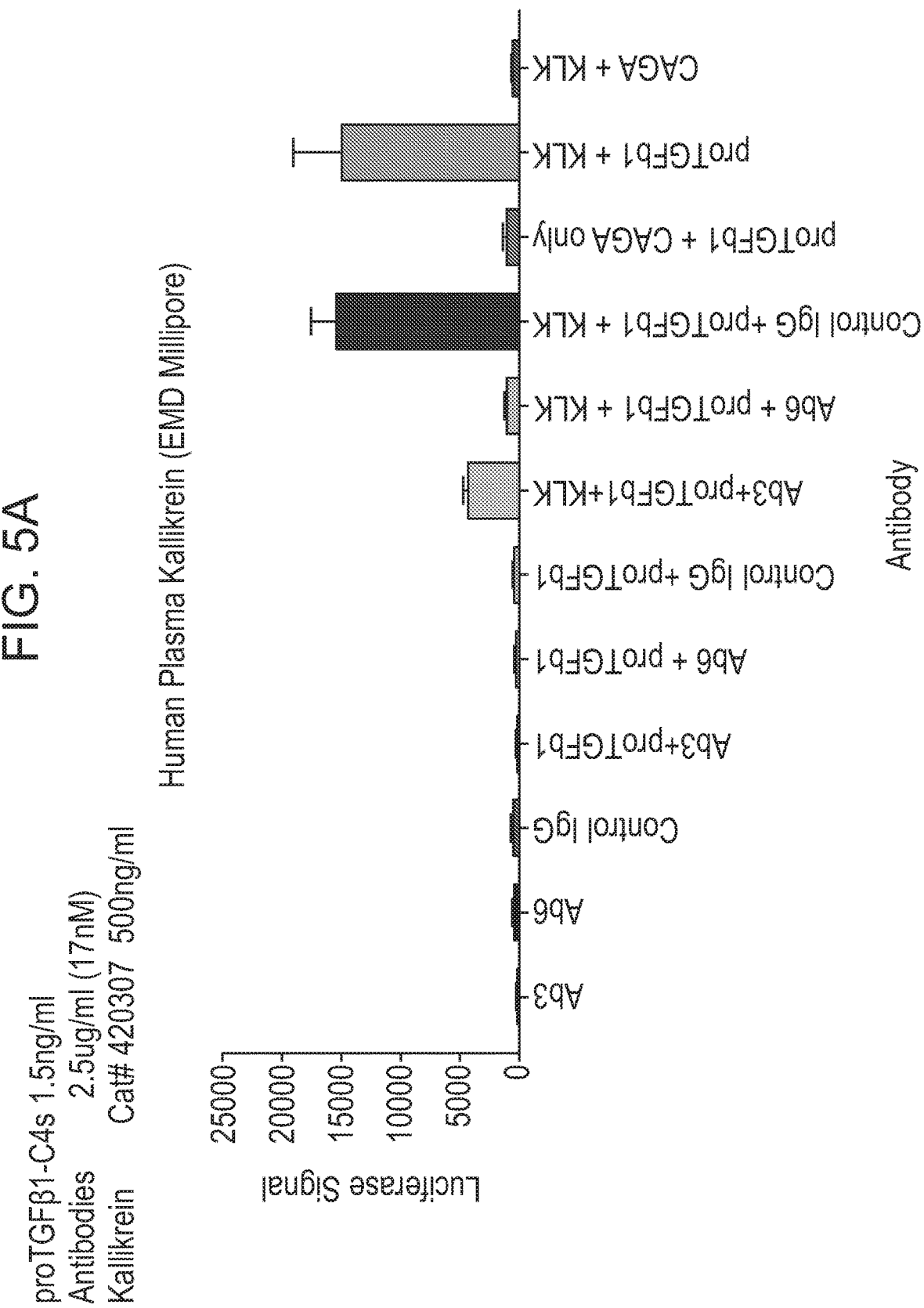

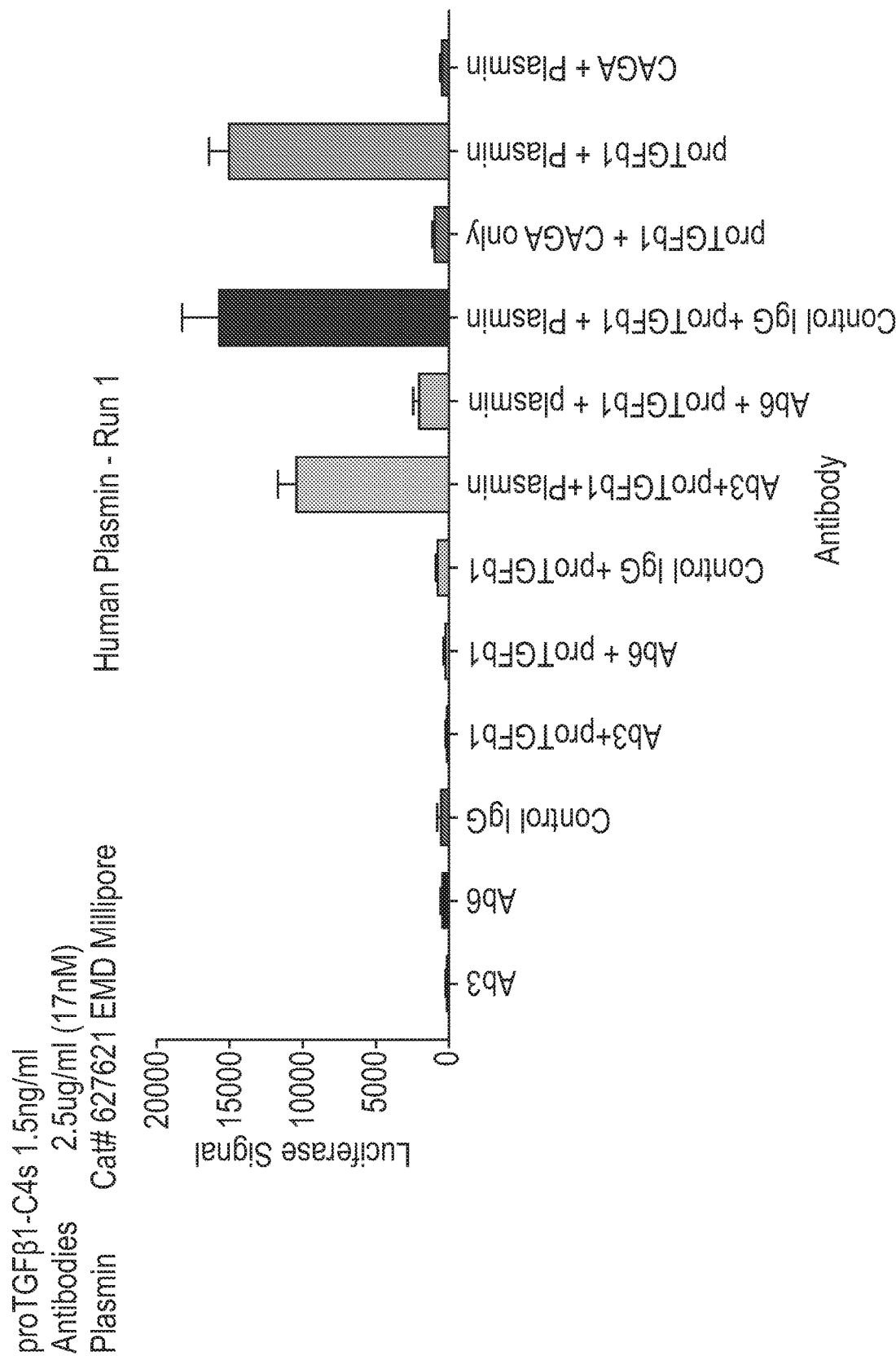

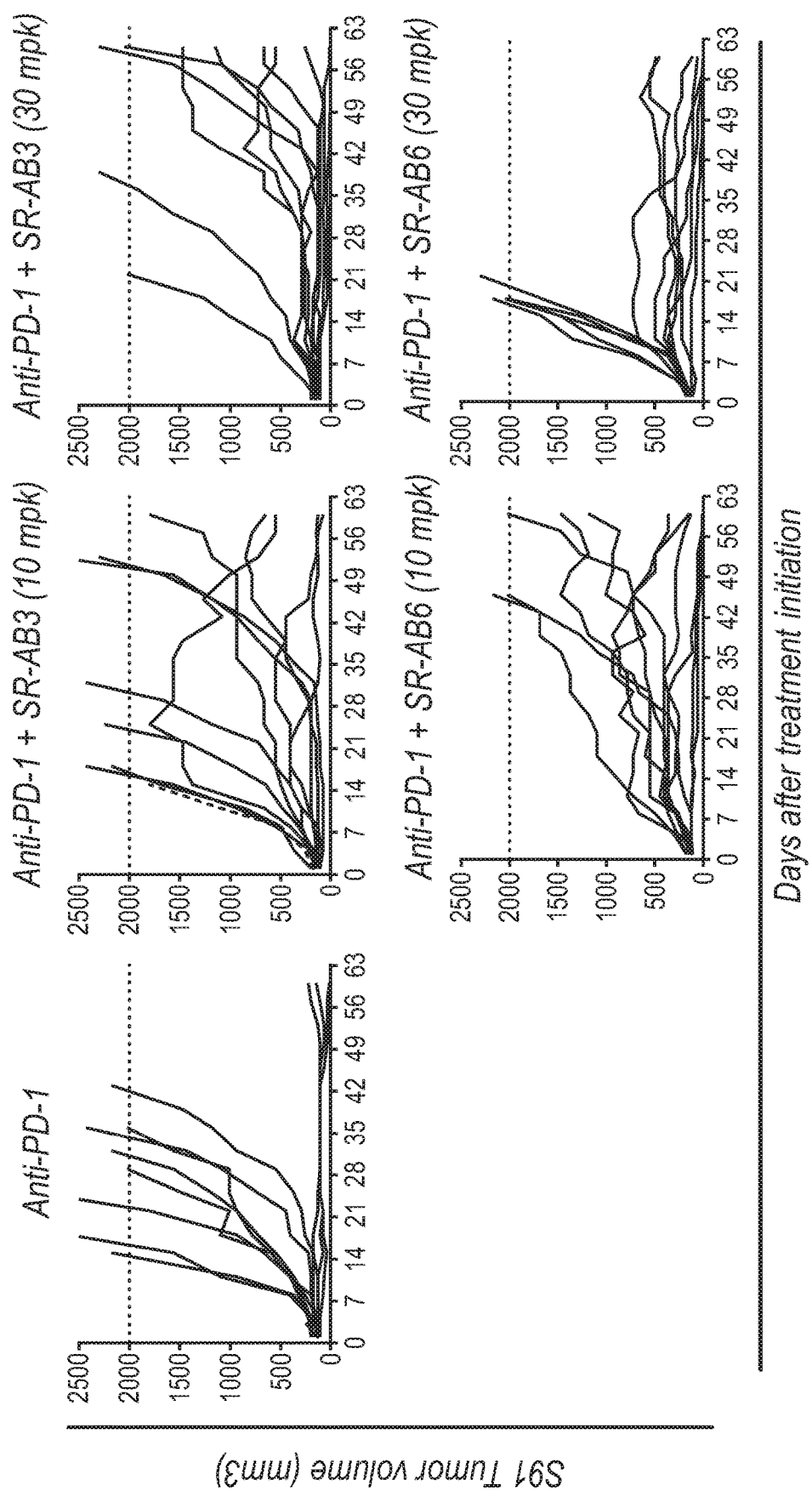

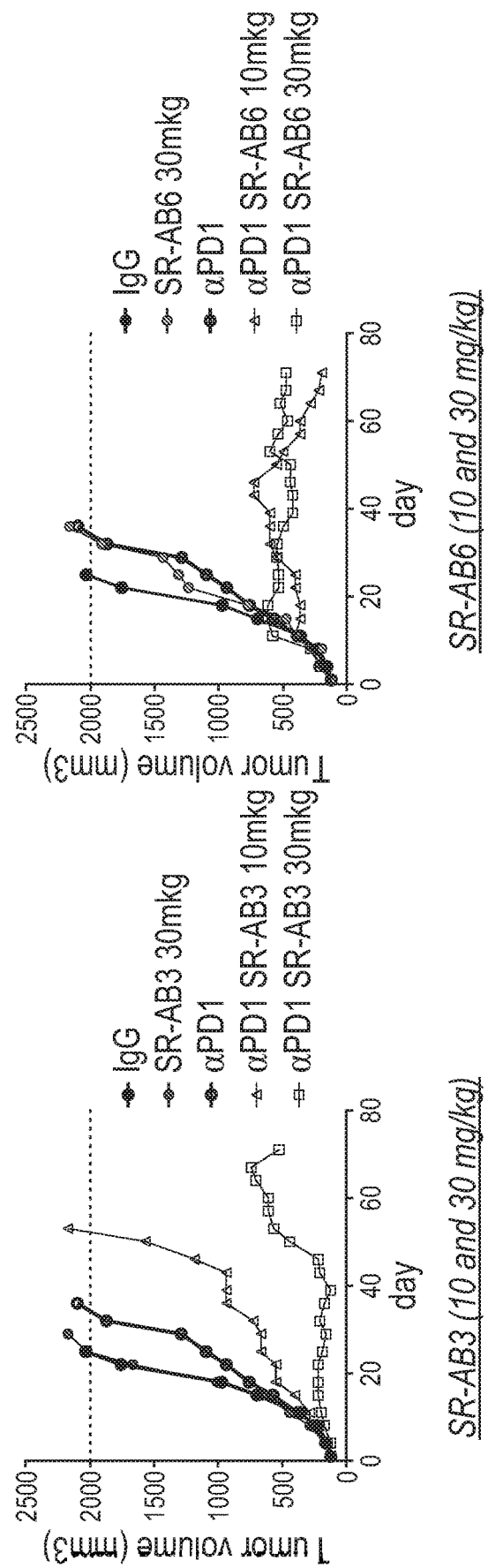

Durable anti-tumor effects of Ab6 and anti-PD-1 in S91 tumors

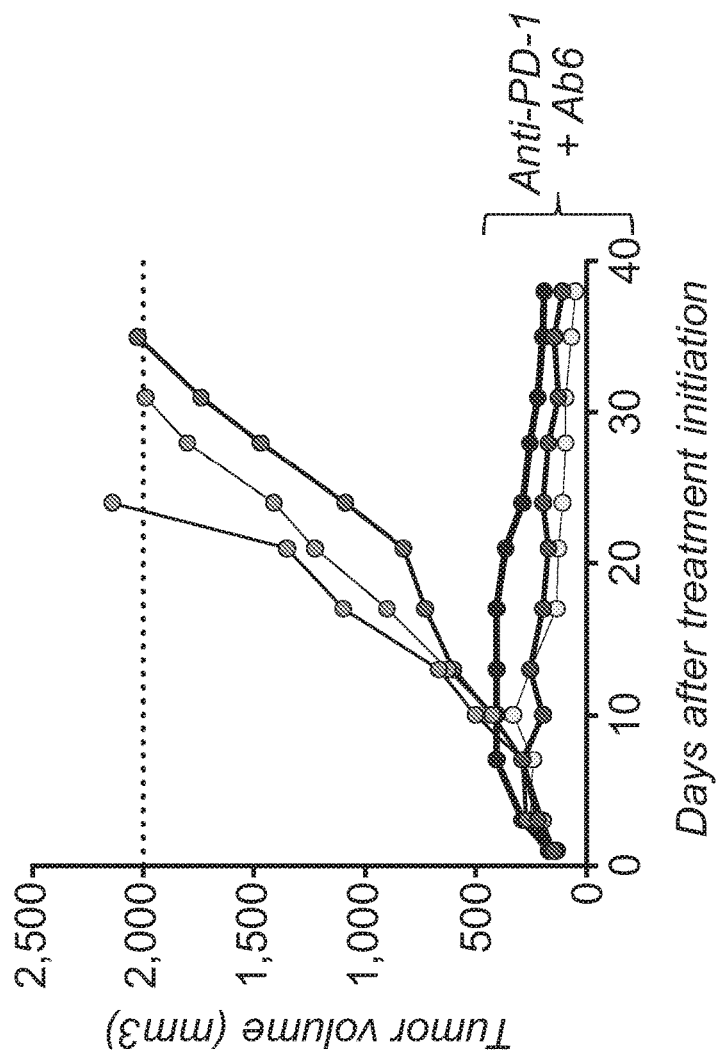

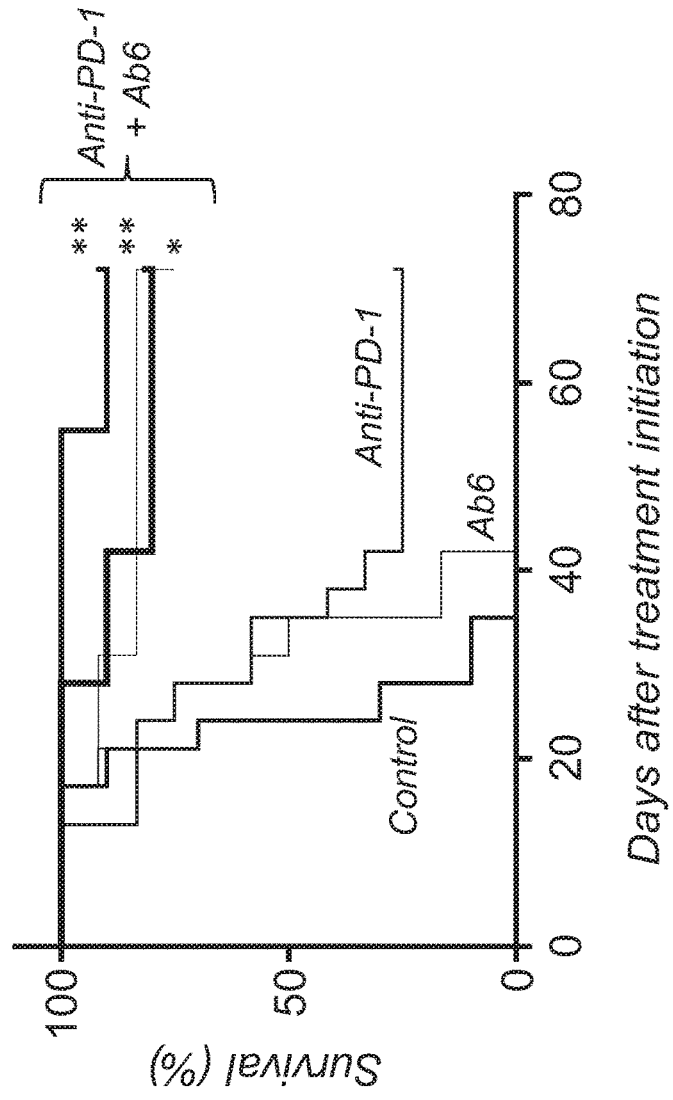

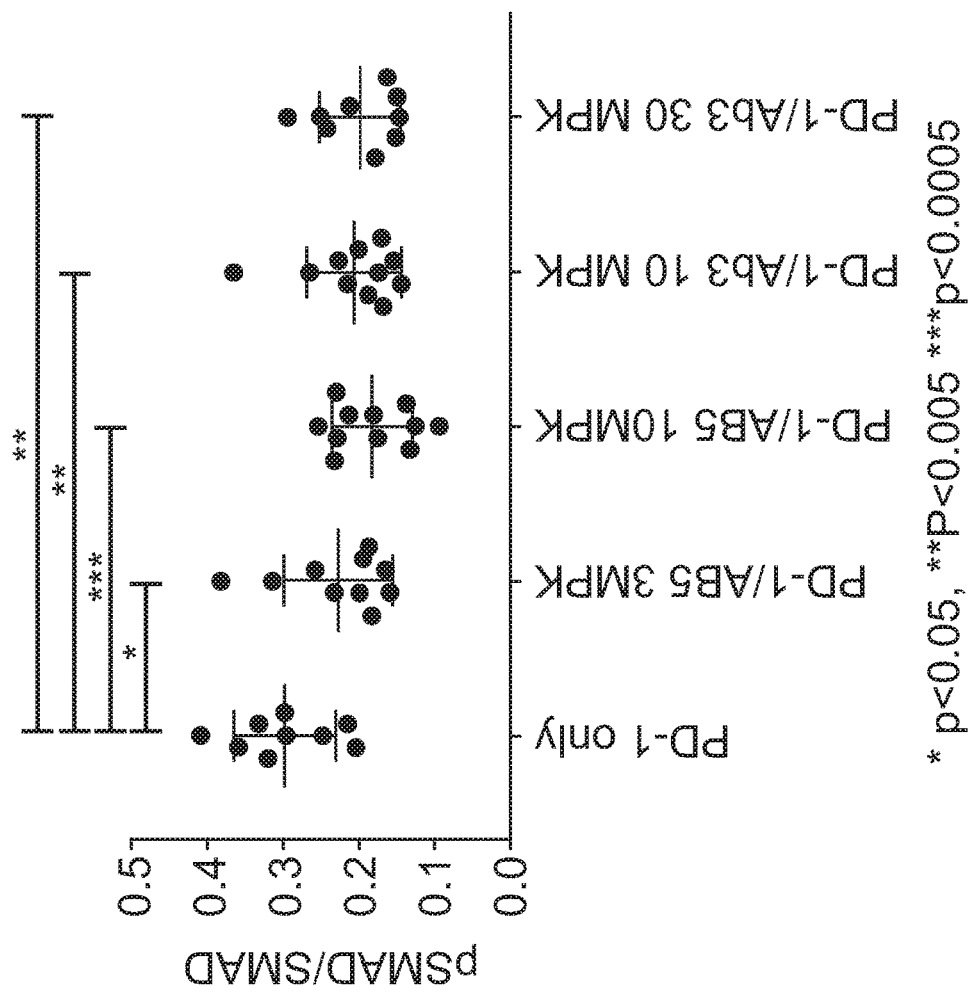

Effects of Ab3 and Ab6 in combination with anti-PD-1 antibody on tumor progression in the MBT2 syngeneic bladder cancer model (log scale)

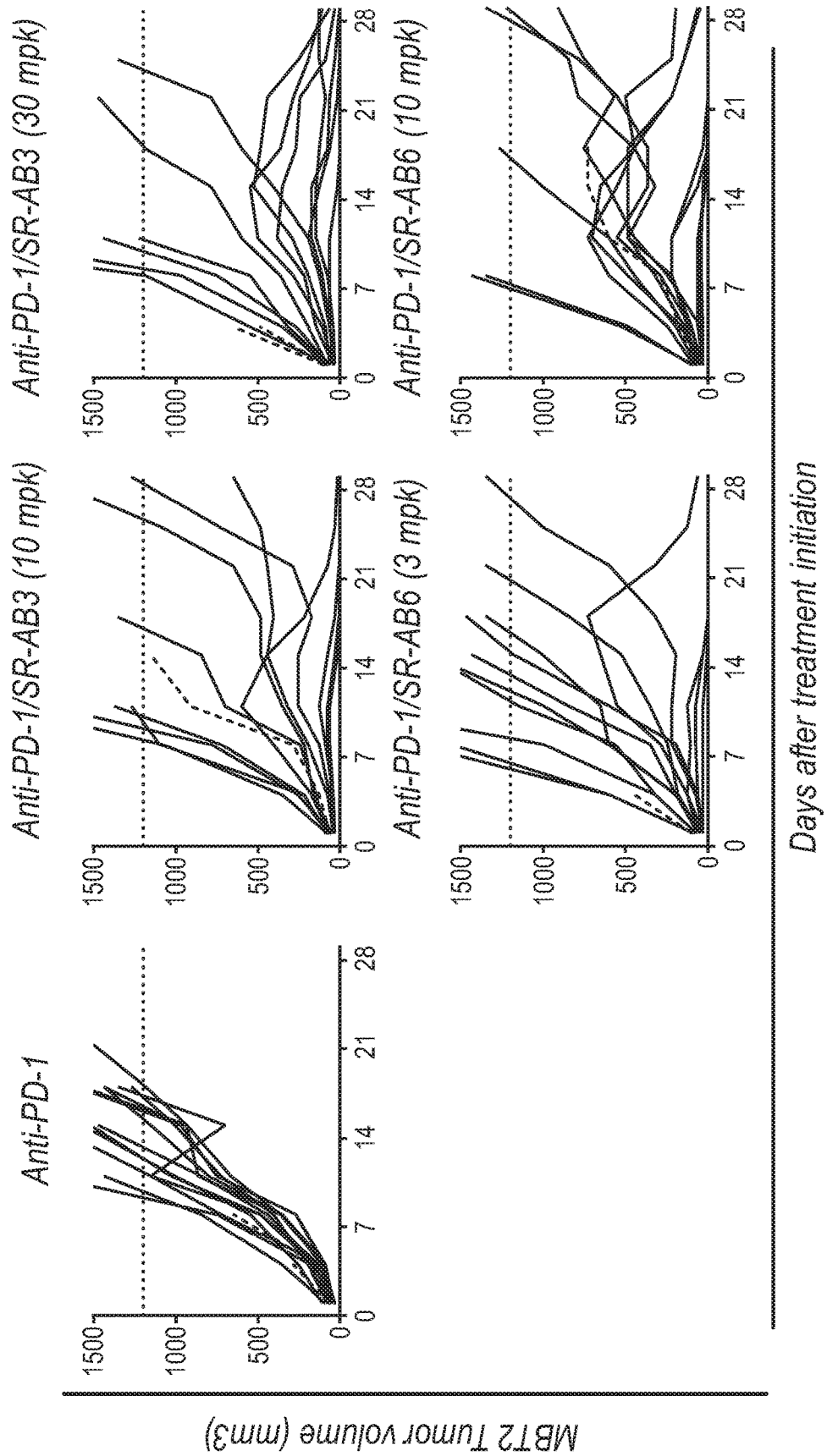

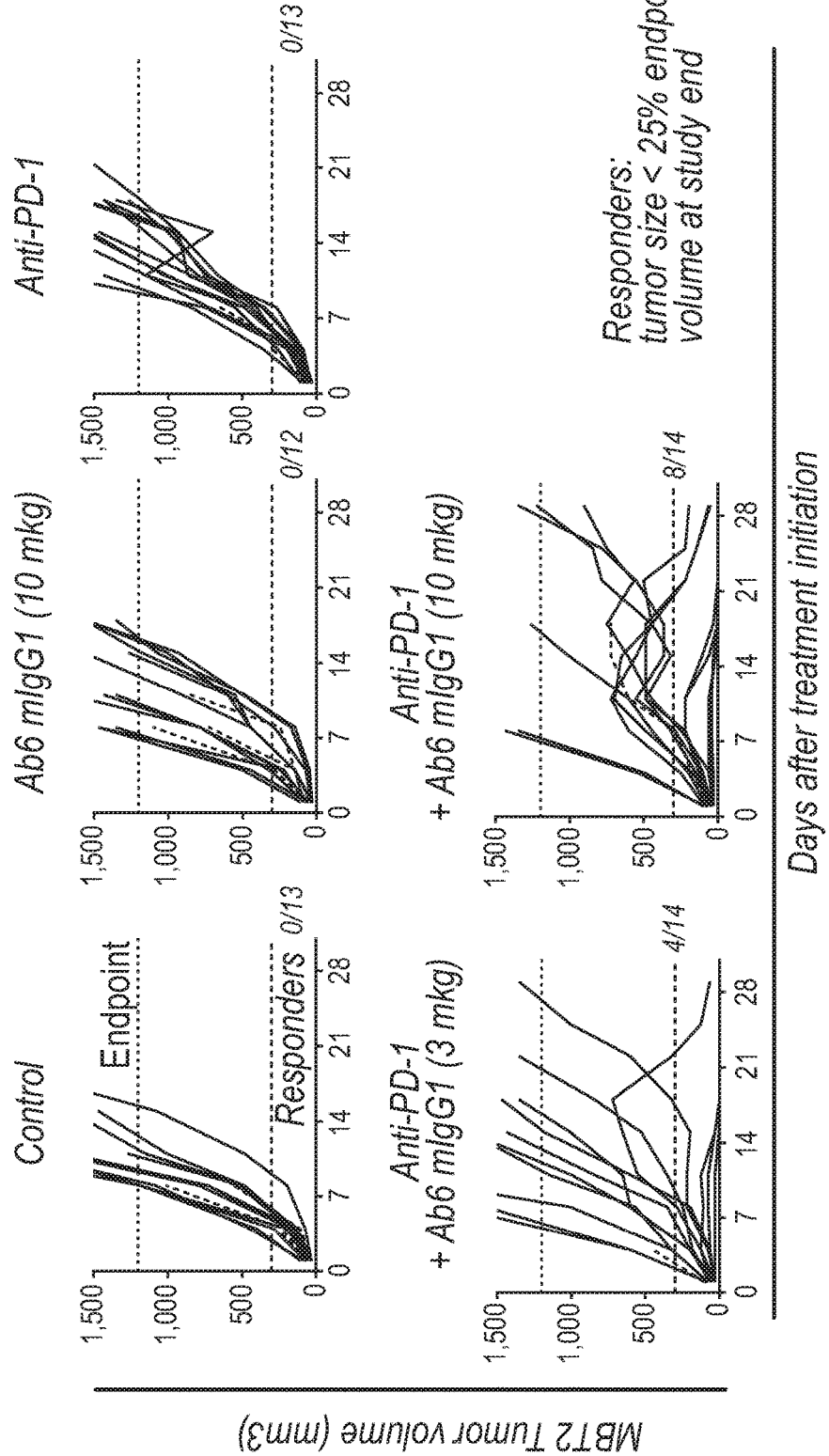

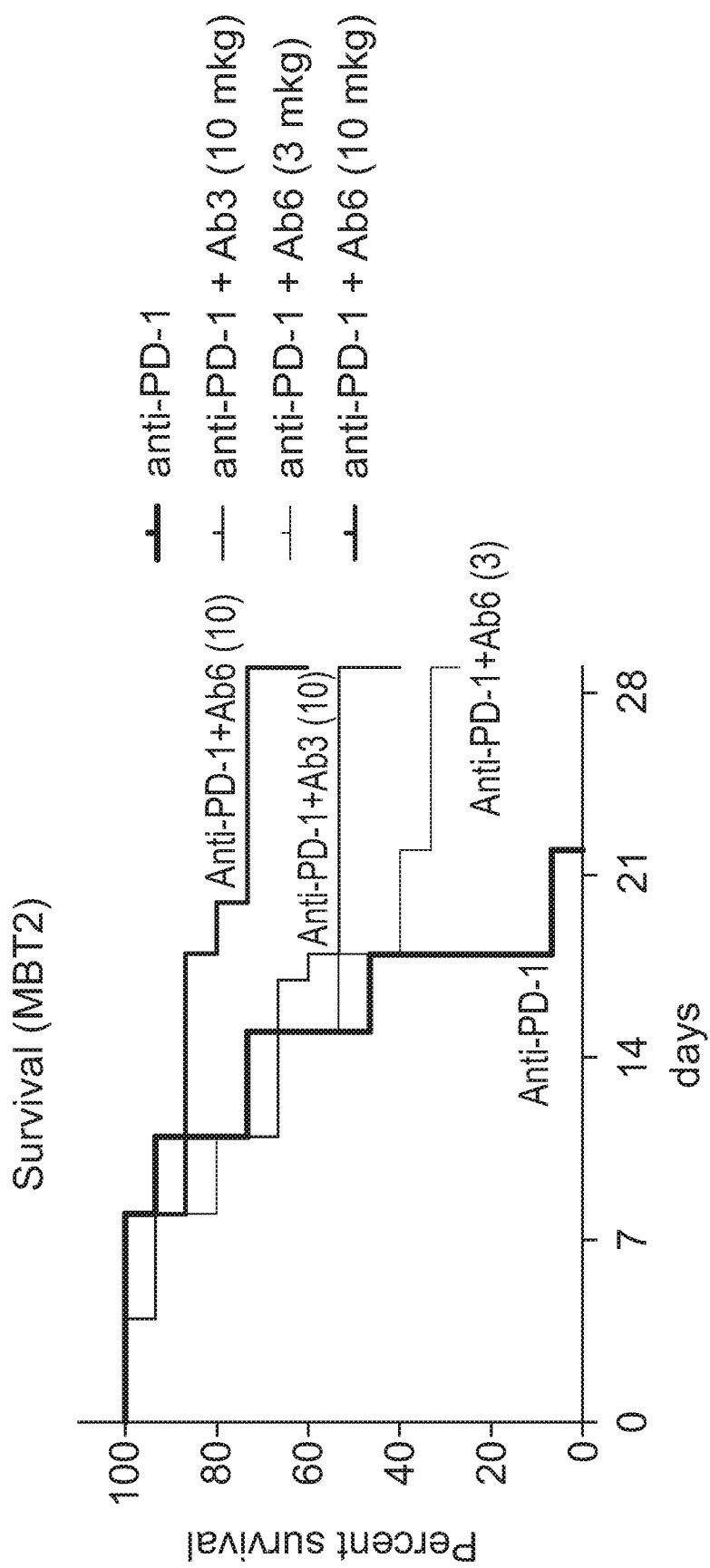

Durable Immune Memory in MBT2 Complete Responders

*Same protected region found in Ab5 (Region 1)
**Subset of protected region found Ab5 (Region 2)

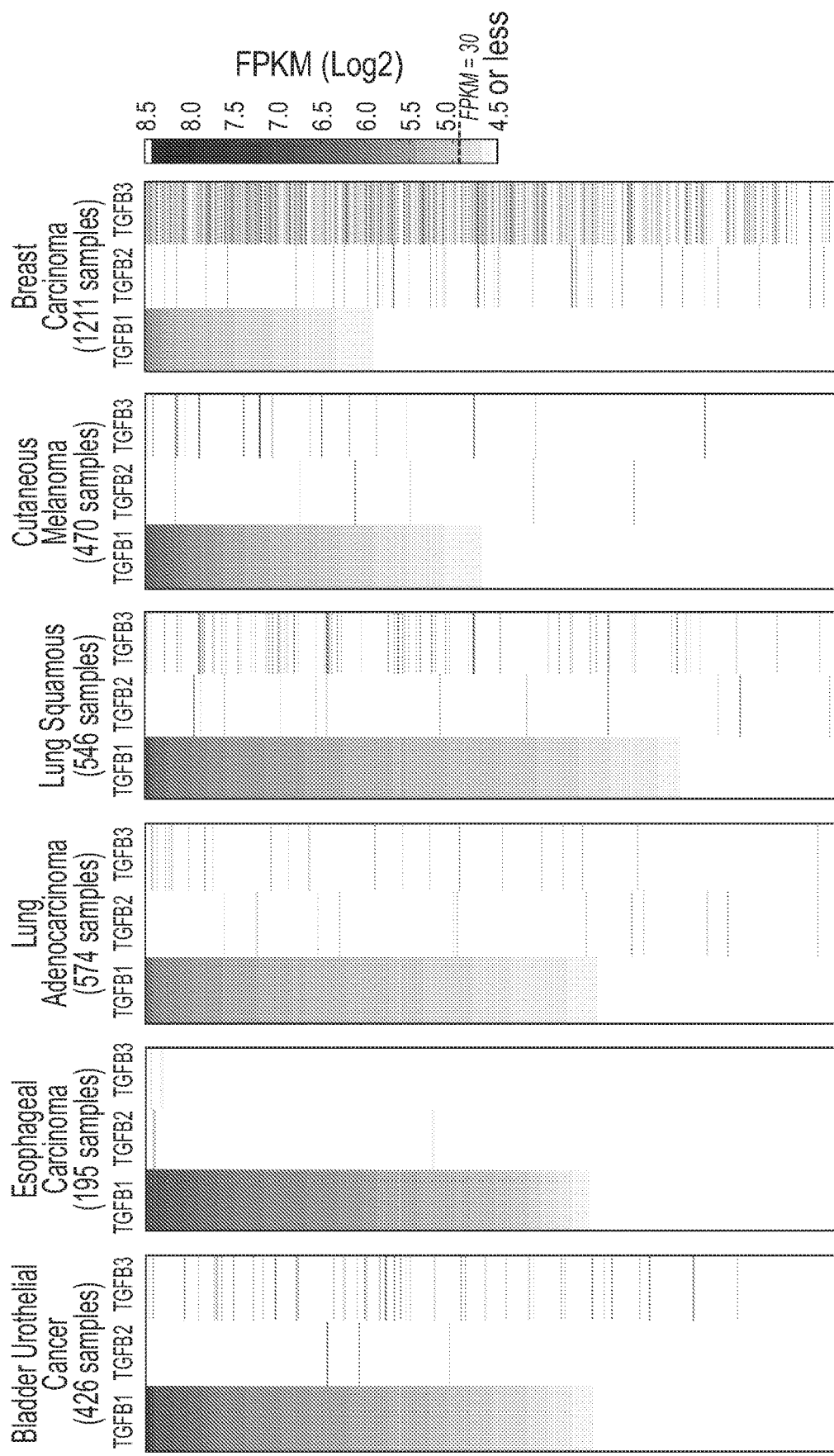

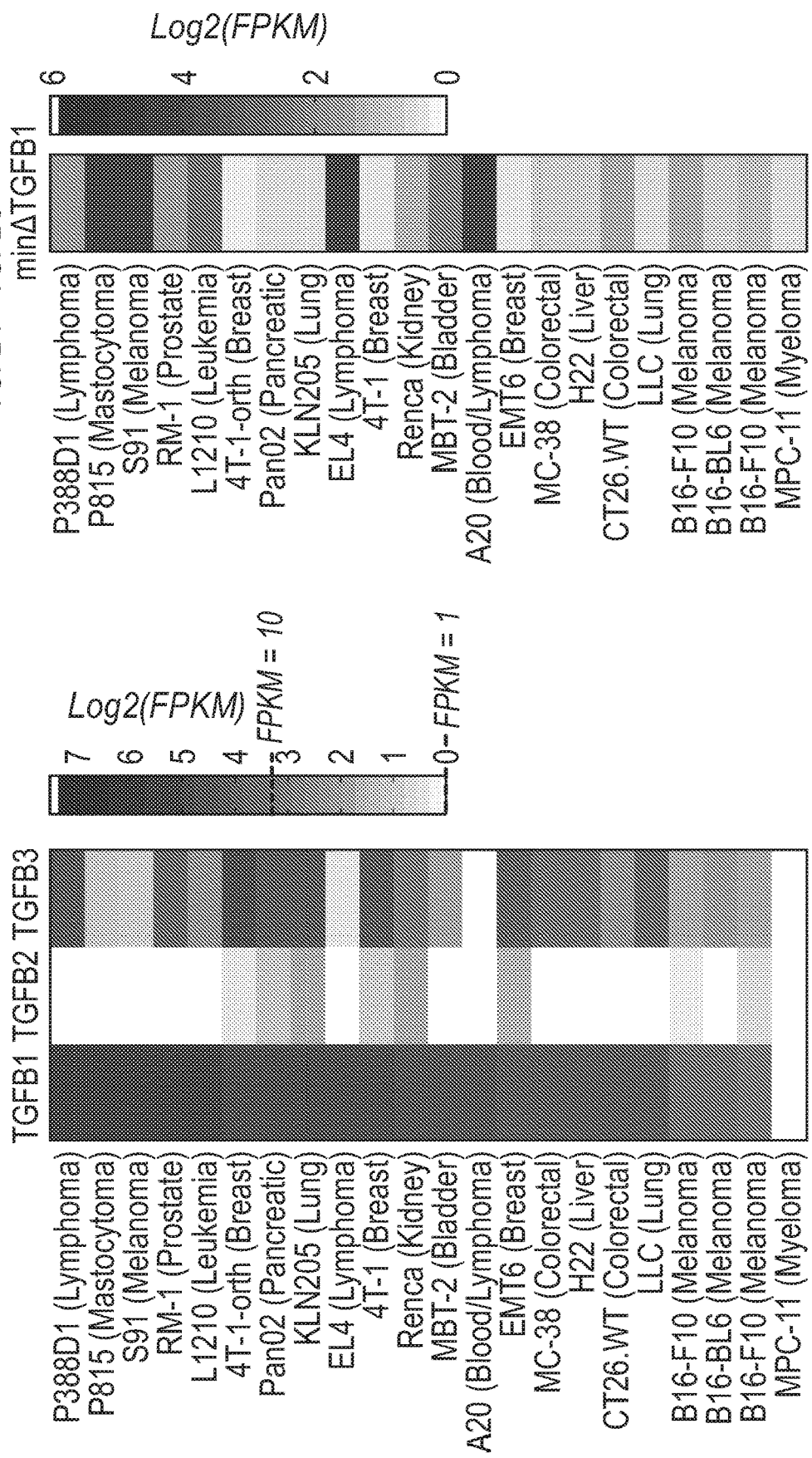
FIG. 20D TGFβ isoform expression in mouse syngeneic cancer cell model lines

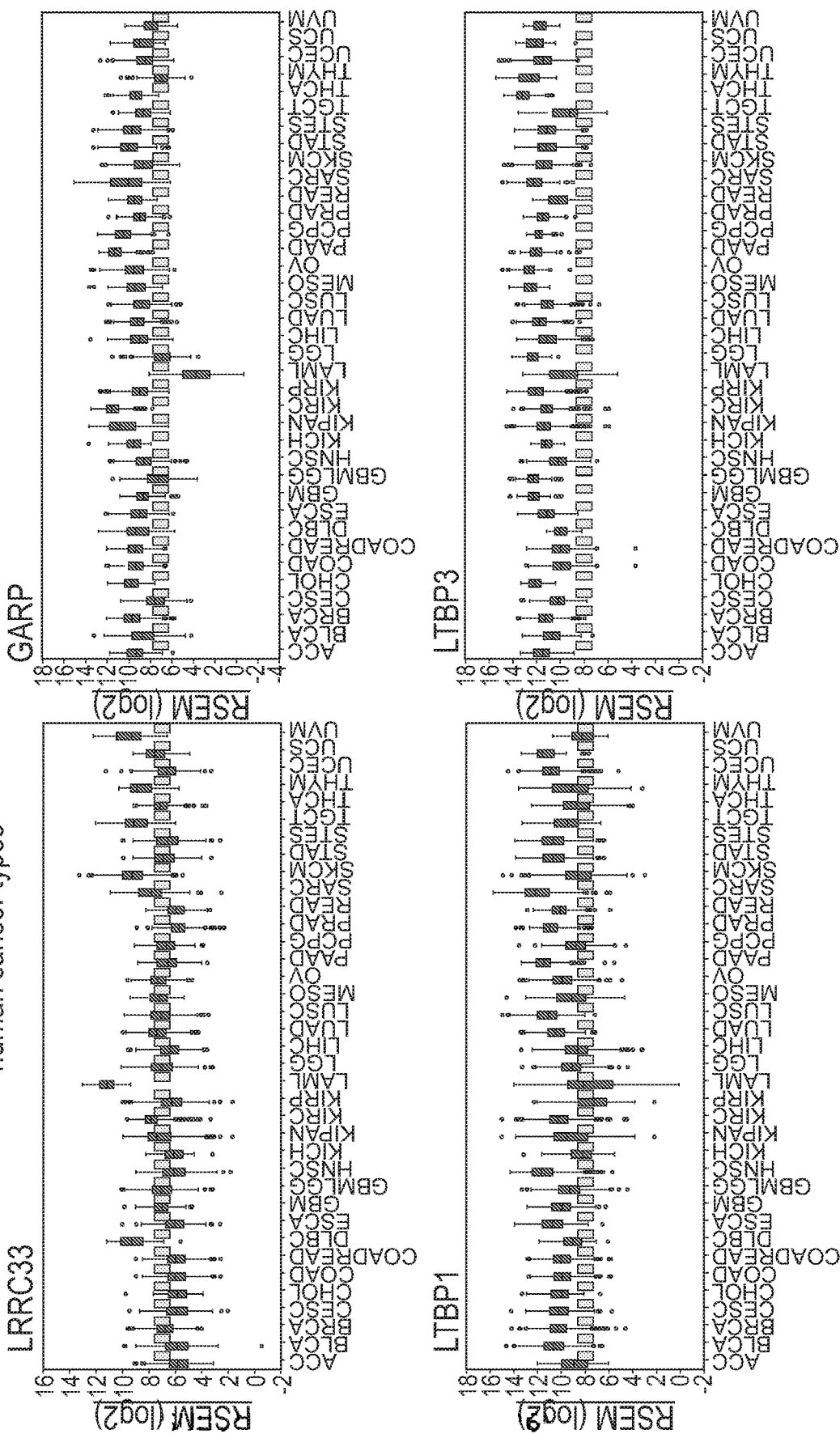
FIG. 20E All presentation molecules are highly expressed in most human cancer types

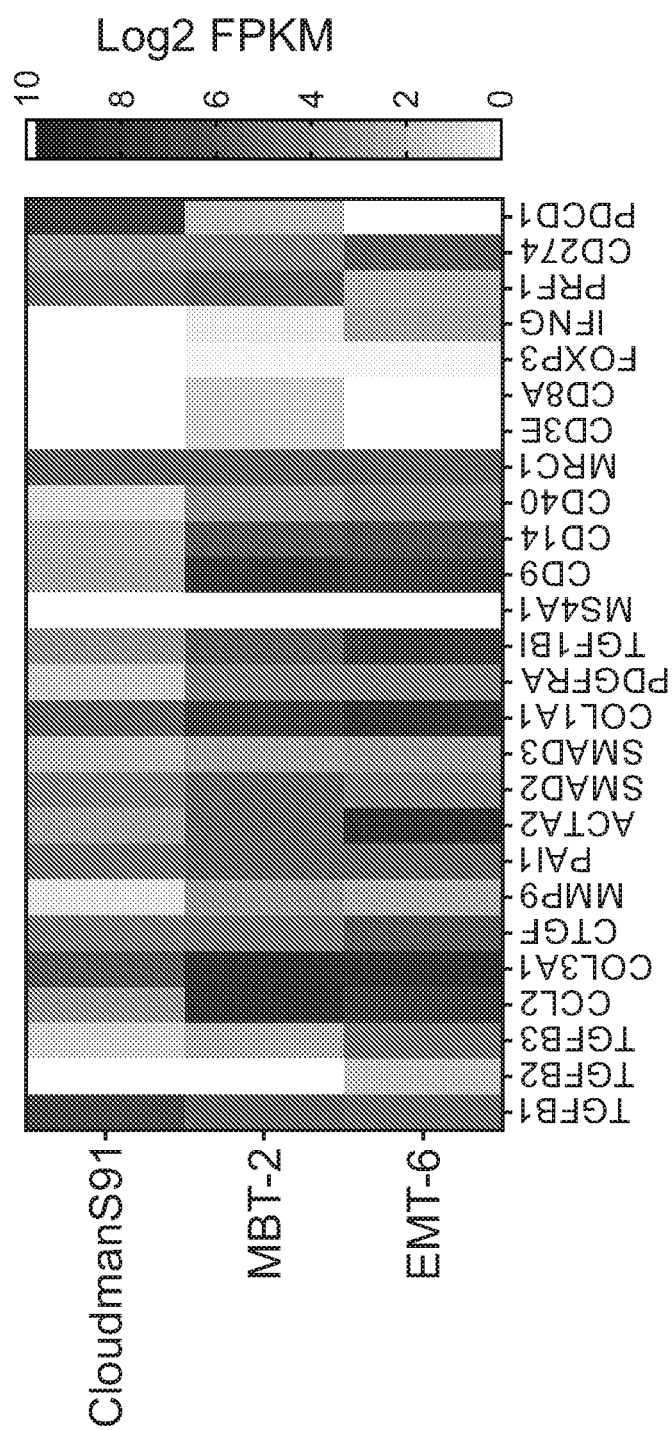

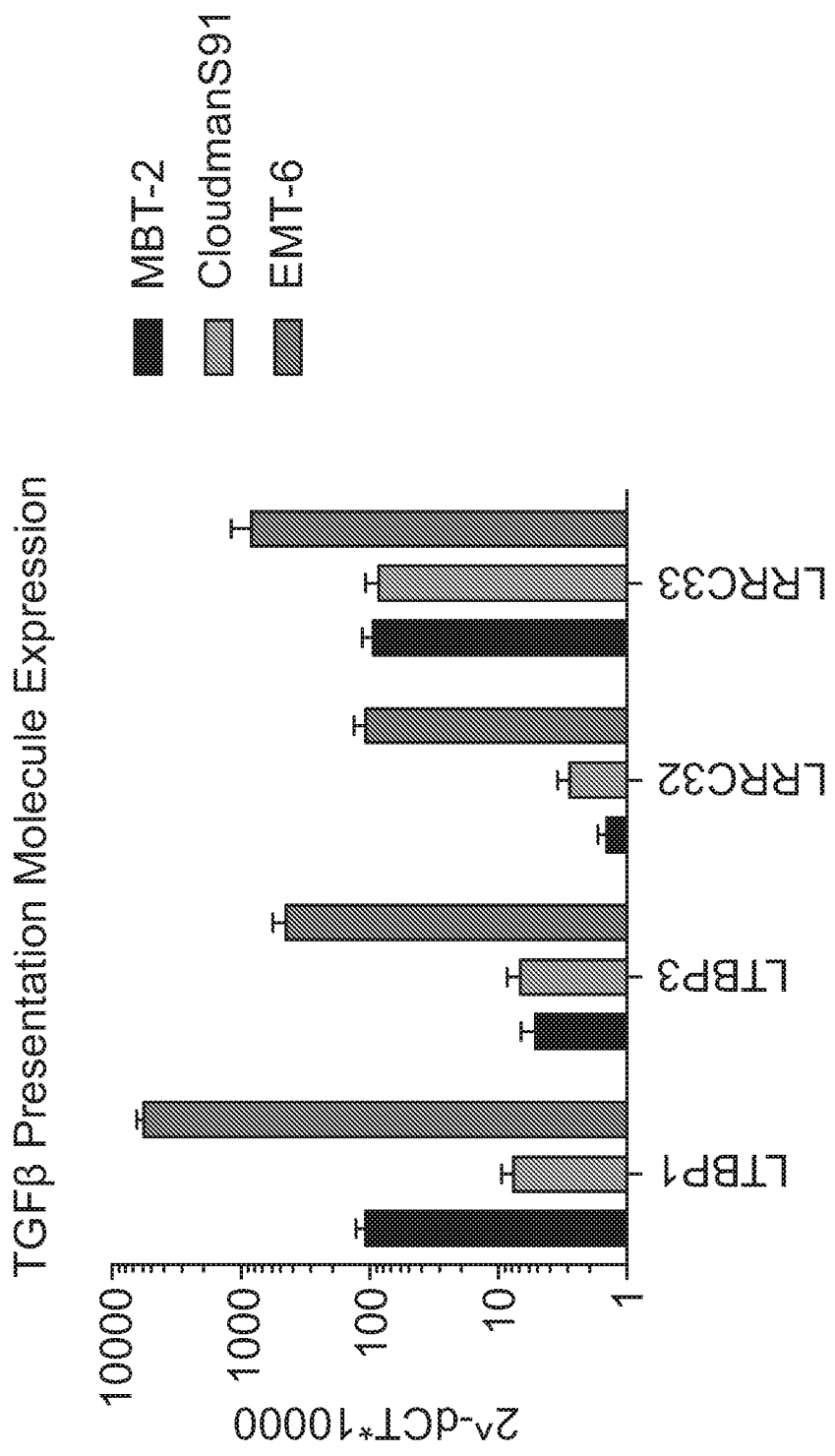

FIG. 21A

Pan-TGFβ Antibody Data from 1-Week Toxicology Safety Study

Heart Example, microscopic findings

*Pan-TGFβ Ab dosed weekly for 1 week*

Legend:
- Unremarkable: (white)
- Minimal: (light gray)
- Slight: (hatched)
- Moderate: (dark)
- Mortality: X

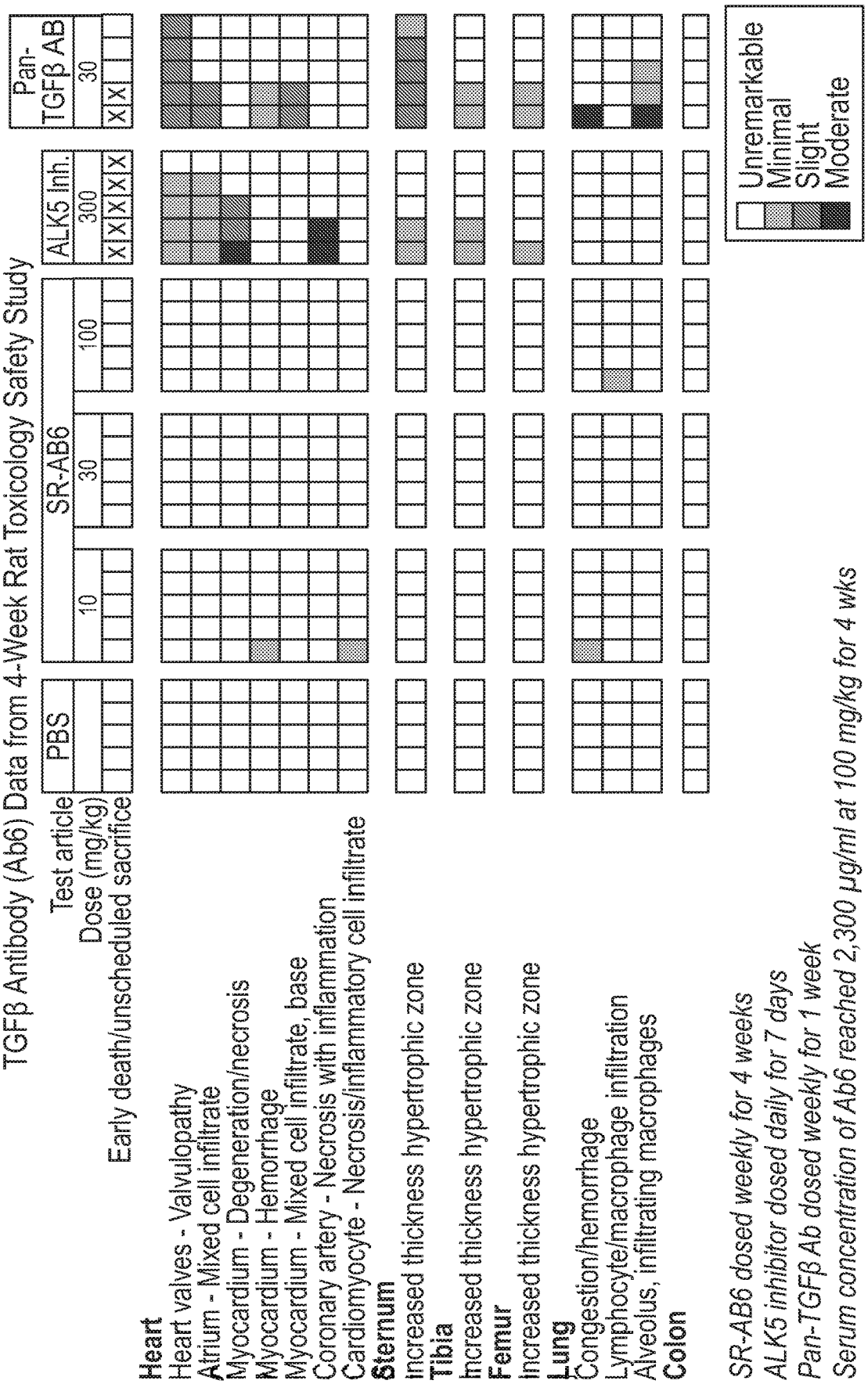

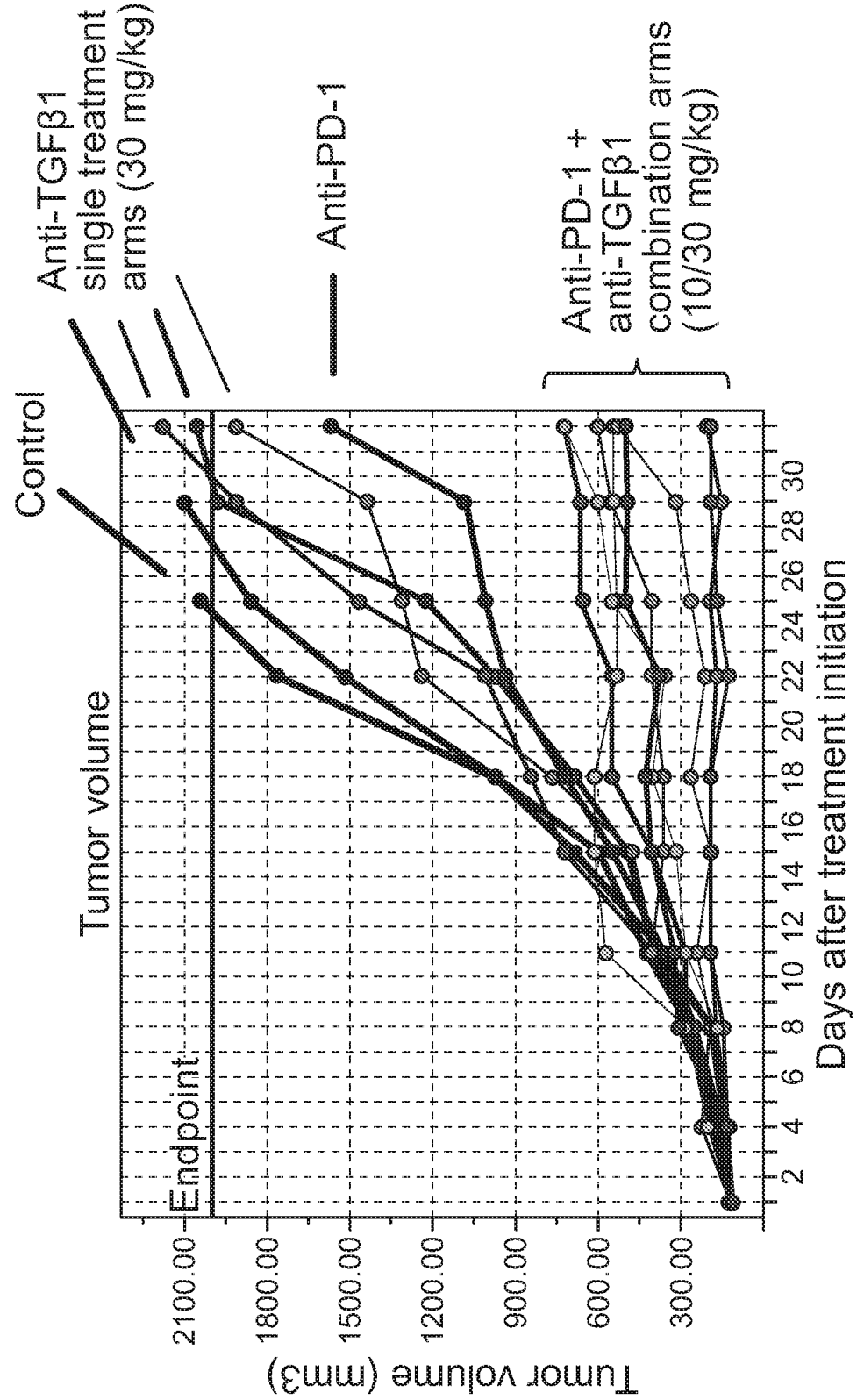
FIG. 22 Combination effect on S91 tumor growth observed with multiple context-independent TGFβ1 inhibitors Inhibition of TGFβ1 and PD-1 leads to increased CD8 T cells in S91 tumors Treated with anti-PD-1;
Stained with a CD8+ marker (CD8a)

Treated with anti-PD-1 + context-indep TGFβ1 inhibitor;
Stained with a CD8+ marker (CD8a)

Infiltration of macrophages into S91 tumors observed after combination treatment Treated with anti-PD-1 + context-indep TGFβ1 inhibitor;
Stained with a macrophage marker (F4/80)

Treated with anti-PD-1;
Stained with a macrophage marker (F4/80)

F4/80  CD163

Anti-PD1 plus context-indep TGFβ1 inhibitor 30 mg/kg

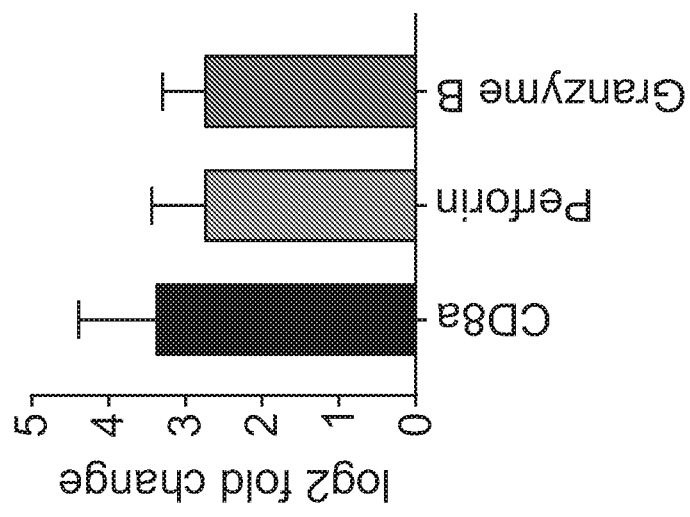

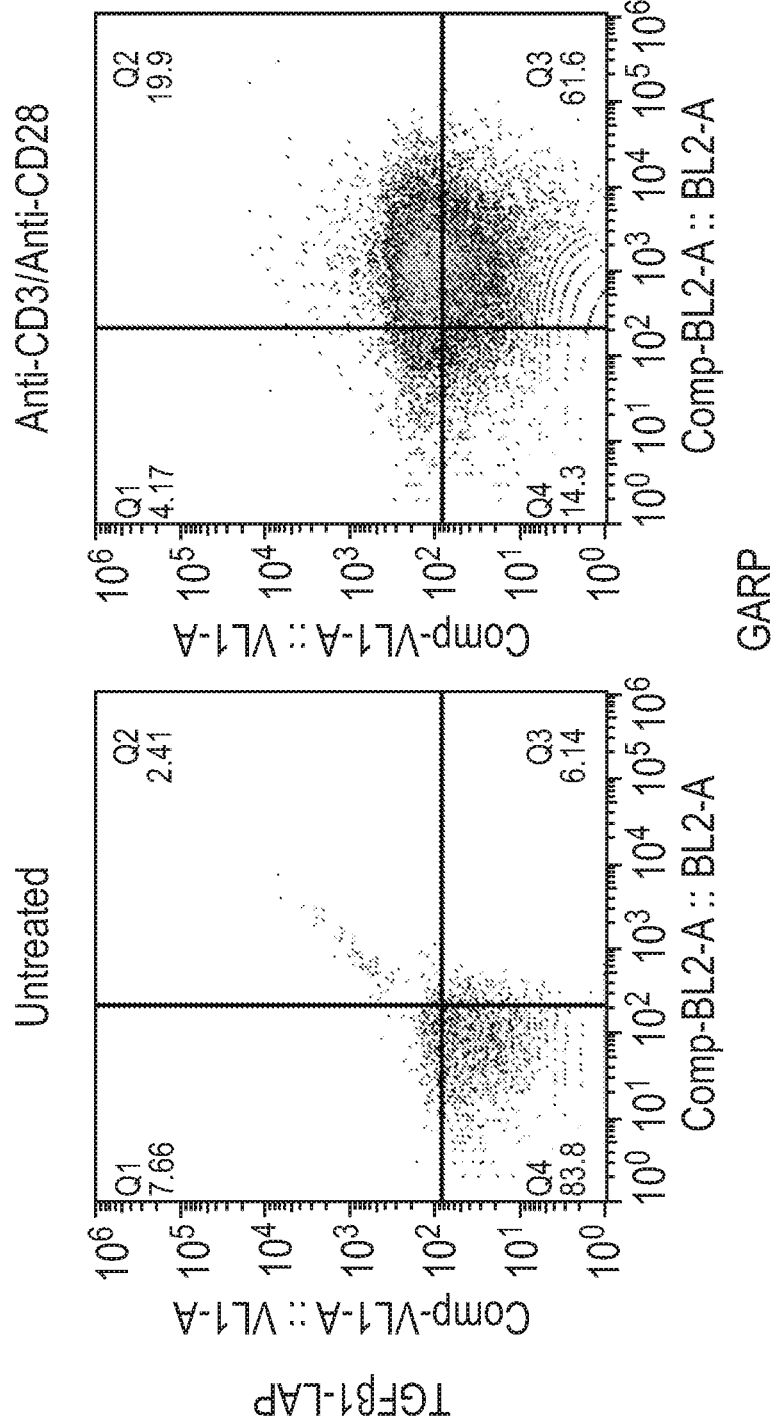

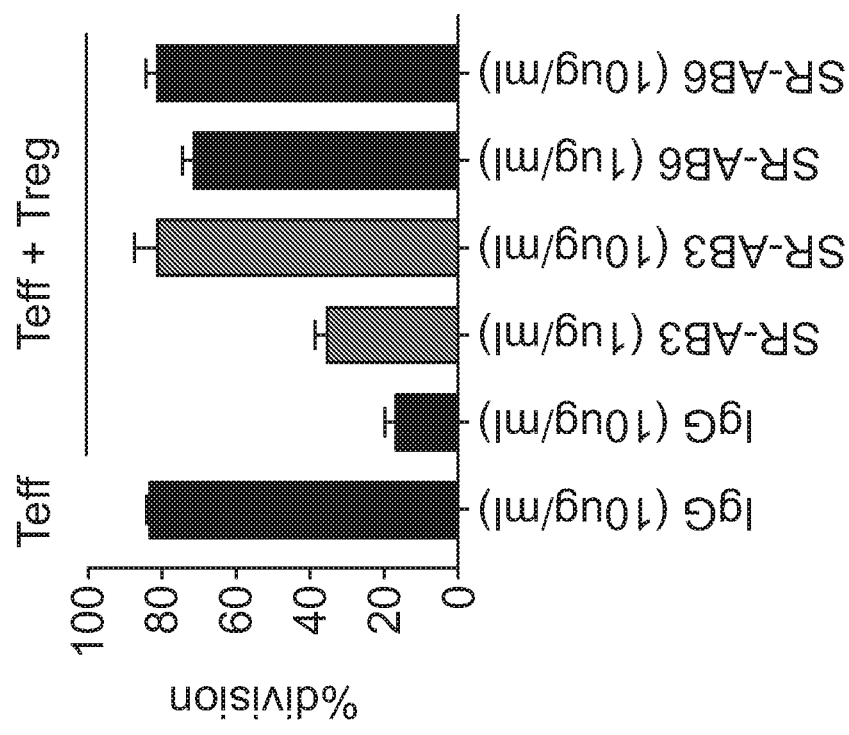

Gating Strategy to Elucidate T Cell Subsets in MBT-2 Tumors

T Cell Subsets in MBT-2 Tumors

Gating Strategy to Elucidate Myeloid Subsets in MBT-2 Tumors

MBT-2 infiltrating M2 TAMs express surface LRRC33

MBT-2 infiltrating MDSCs express surface LRRC33

Effect of Ab6 and anti-PD1 on T cell and M2 cell frequencies relative to total live cells in MBT2 tumors

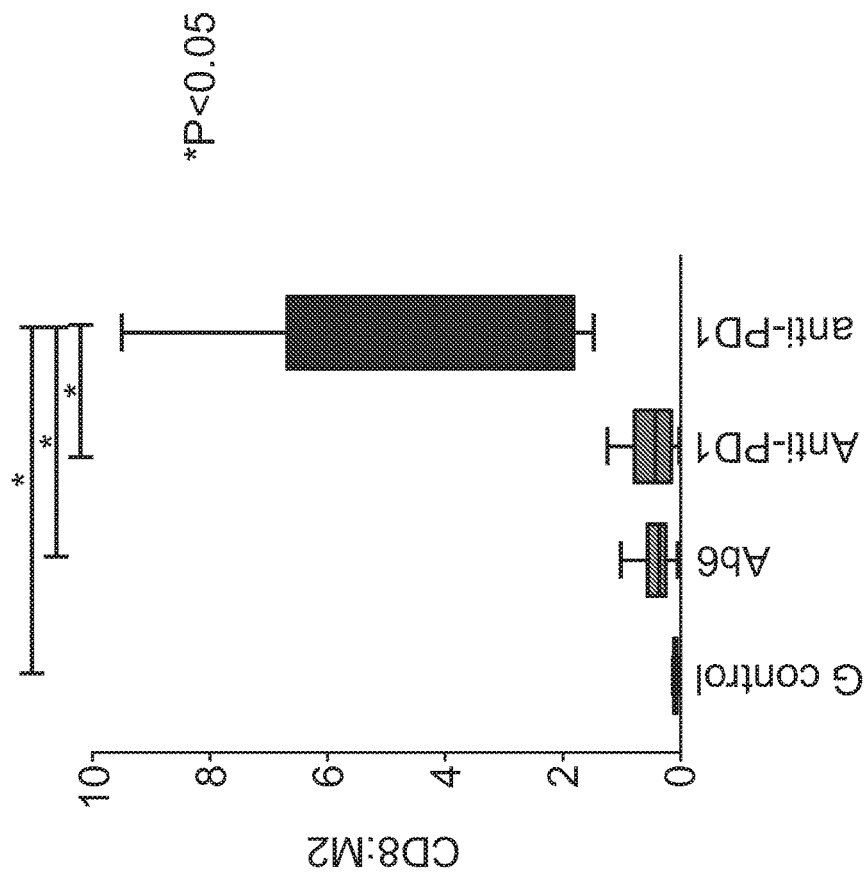

Effects of Ab6 and anti-PD1 on CD8+ T cells in MBT2 tumors

Effects of Ab6 and anti-PD1 on CD8+ T cells in MBT2 tumors

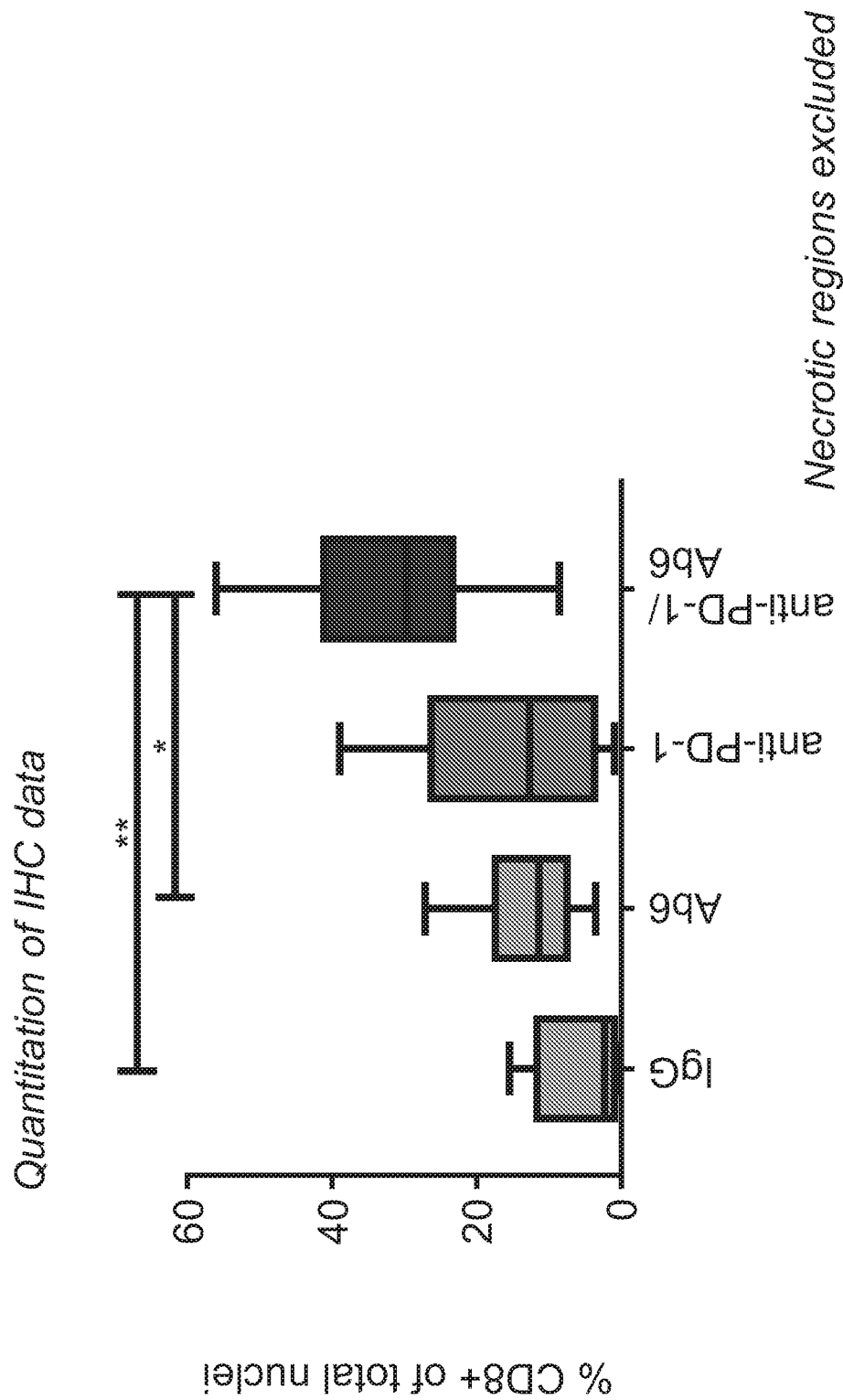

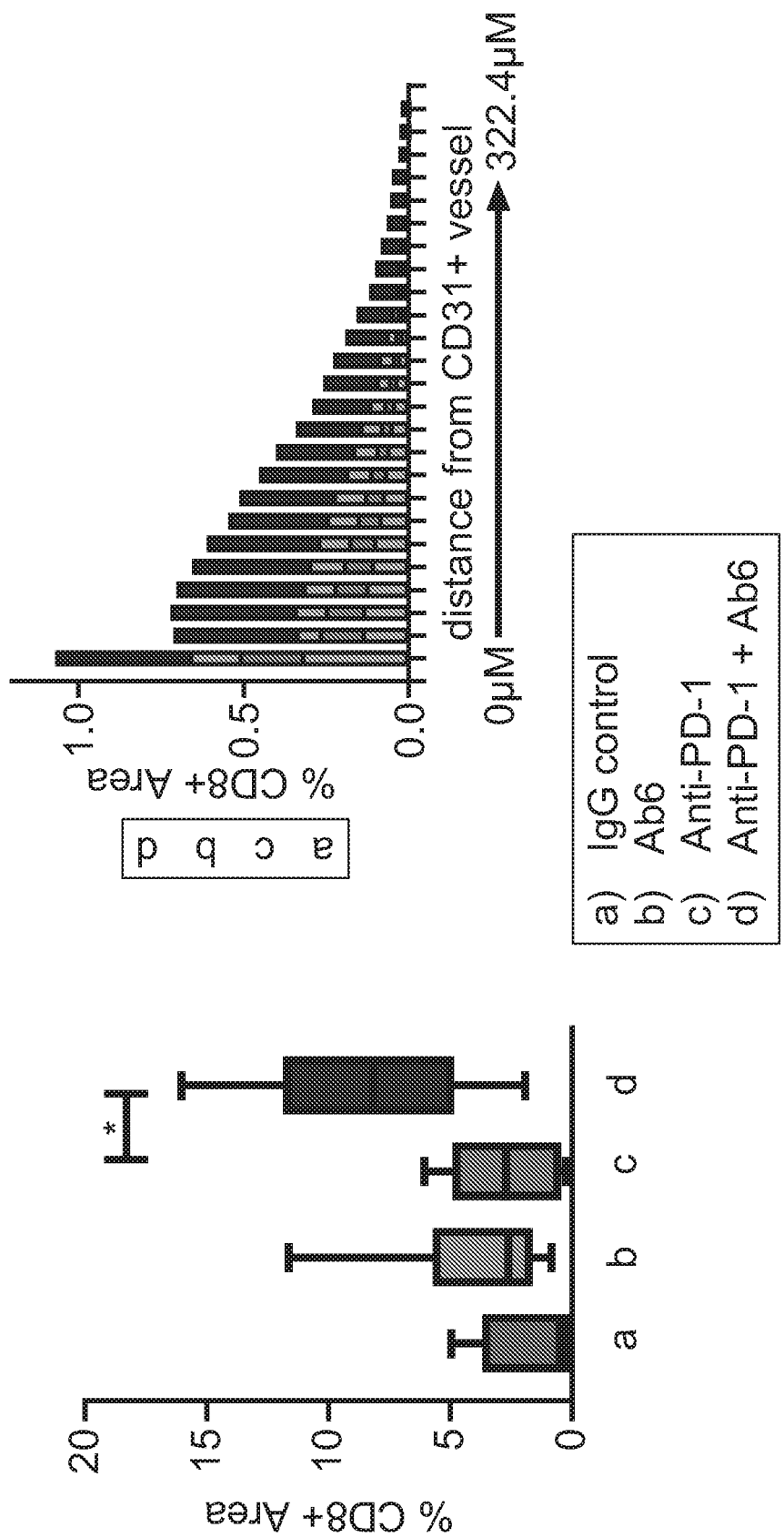
FIG. 30G Effects of Ab6 and anti-PD-1 on intratumoral distribution of CD8+ cells in MBT2 tumors Immune Response Gene Expression Markers in MBT2 Tumors

*$p<0.05$, $p<0.001$ *$p<0.0001$

Immune Response Gene Expression Markers in MBT2 Tumors qPCR Analyses of Marker Genes in MBT2 Tumors at Day 10

- Left bars (red) of each panel: anti-PD-1 alone
- Center bars (orange) of each panel: Ab6 mIgG1 alone
- Right bars (blue) of each panel: anti-PD-1 + Ab6 mIgG1

Study design: MBT-2 cells implanted subcutaneously. Treatment began when tumors averaged 40-80mm3. Anti-PD-1 (RMP1-14) administered 10 mg/kg 2x per week; Ab6 administered 1x per week at 10 mg/kg Ab6 binds large latent TGFβ1 complexes with picomolar affinities as measured by MSD-SET

FIG. 33B
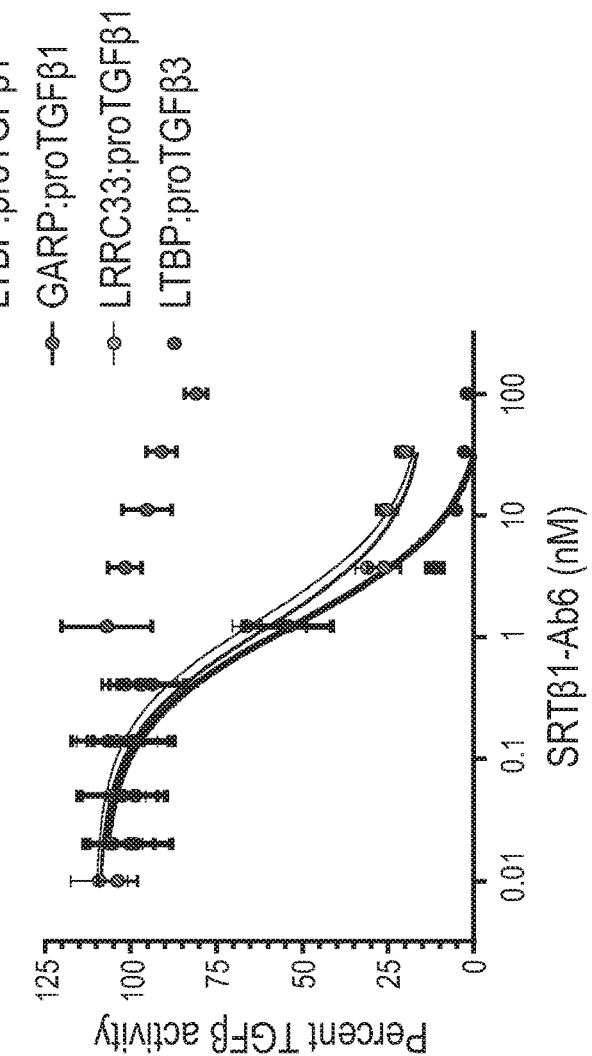
Inhibitory potency of Ab6 in LN229 assay
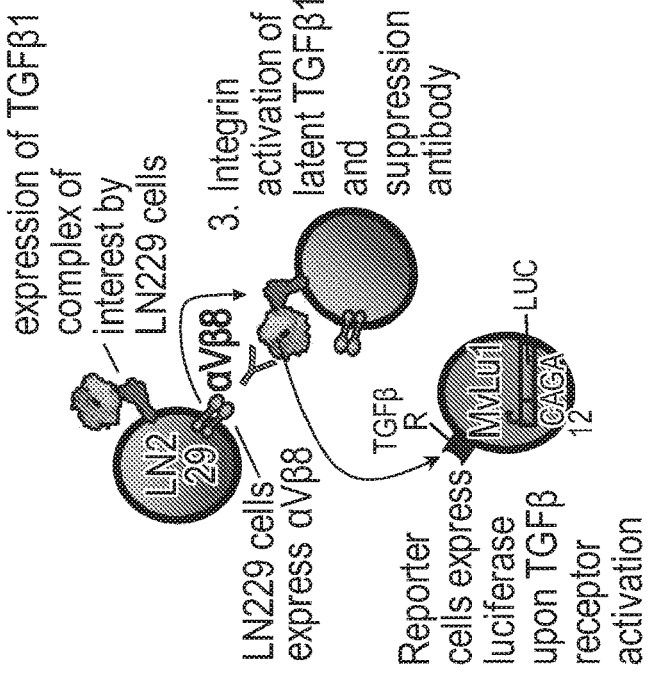
Ab6 inhibits activation of all large latent TGFβ1 complexes but not latent TGFβ3

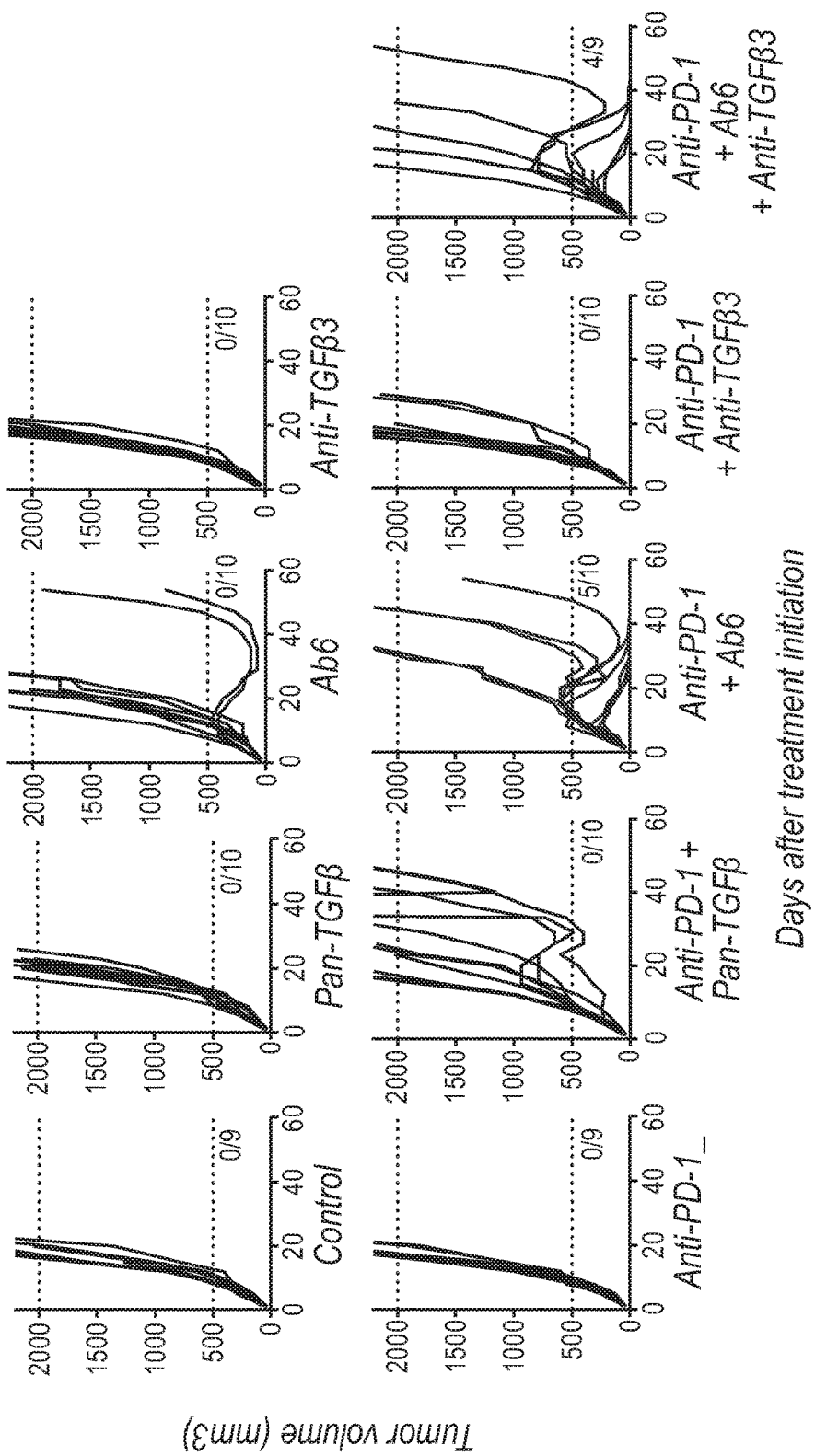

Effects of anti-PD-1/Ab6 in the EMT6 breast cancer model (Study 1)

*** Significant survival benefit compared to anti-PD-1 alone (P<0.0001; Log-rank Mantel-Cox test)

Study design: EMT6 cells implanted subcutaneously. Treatment began when tumors averaged 30-60mm3. Anti-PD-1 administered 10 mg/kg 1x per week. Ab6 administered 10 mg/kg 2x per week; Ab6 (mIgG1)

Anti-PD-1/Ab6 combination in the EMT6 breast cancer model induces lasting tumor control (Study 2)

Study design: EMT6 cells implanted subcutaneously. Treatment began when tumors averaged 30-60mm3. Anti-PD-1 administered 10 mg/kg 2x per week; Ab6 (mIgG1) administered 10 mg/kg 1x per week.

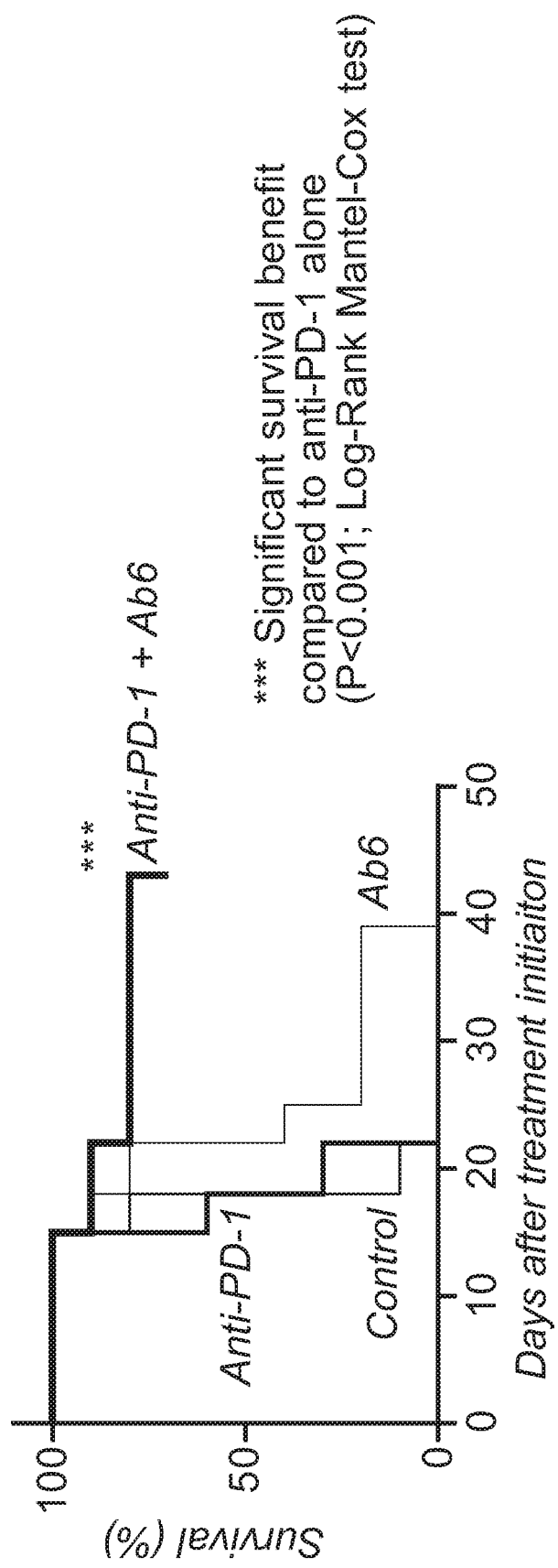

Anti-fibrotic effect of Ab6 in the MPL$^{W515L}$ model of myelofibrosis by bone marrow histopathology scoring

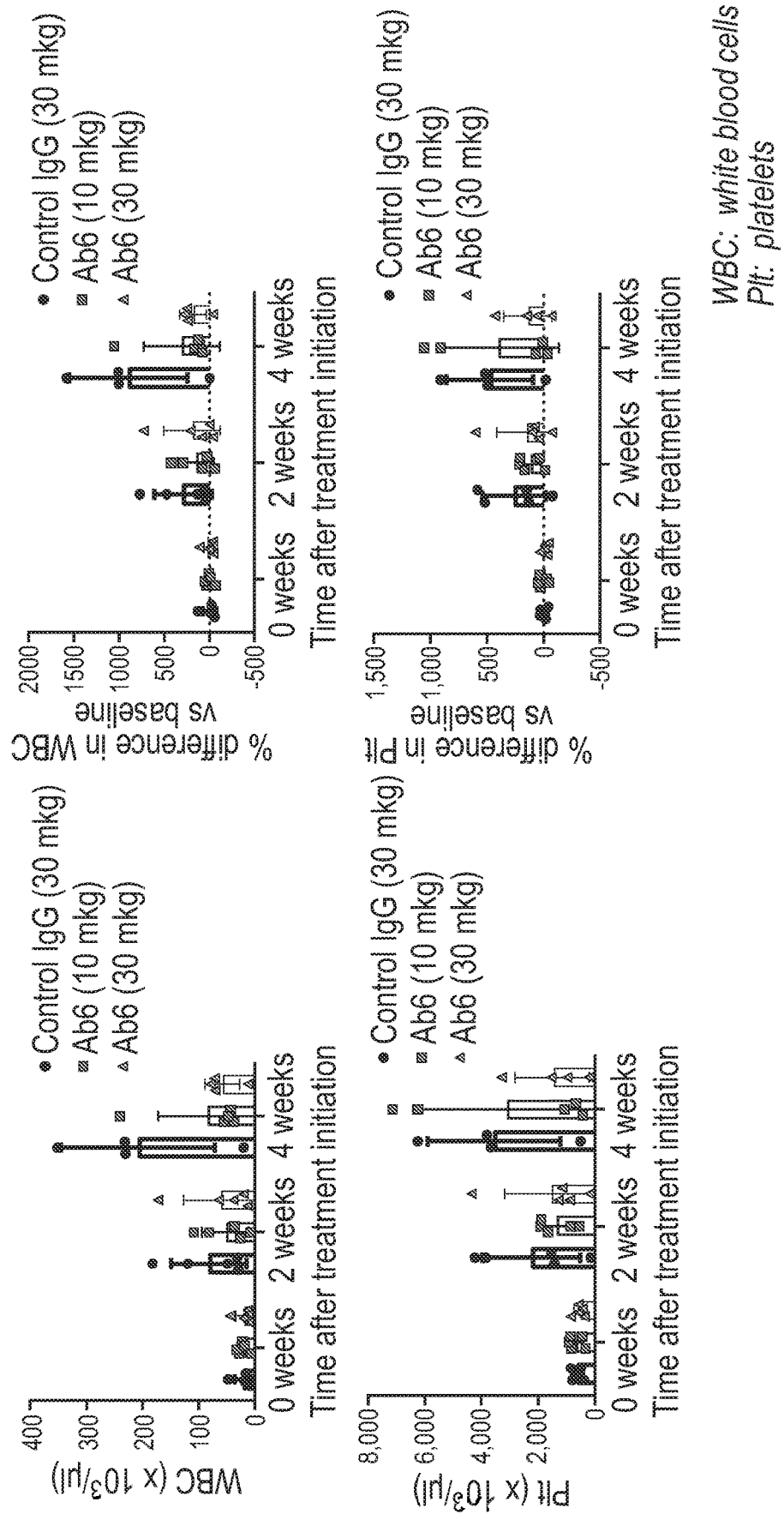
FIG. 36C Effects of Ab6 on hematological parameters in the MPL^W515L model of myelofibrosis

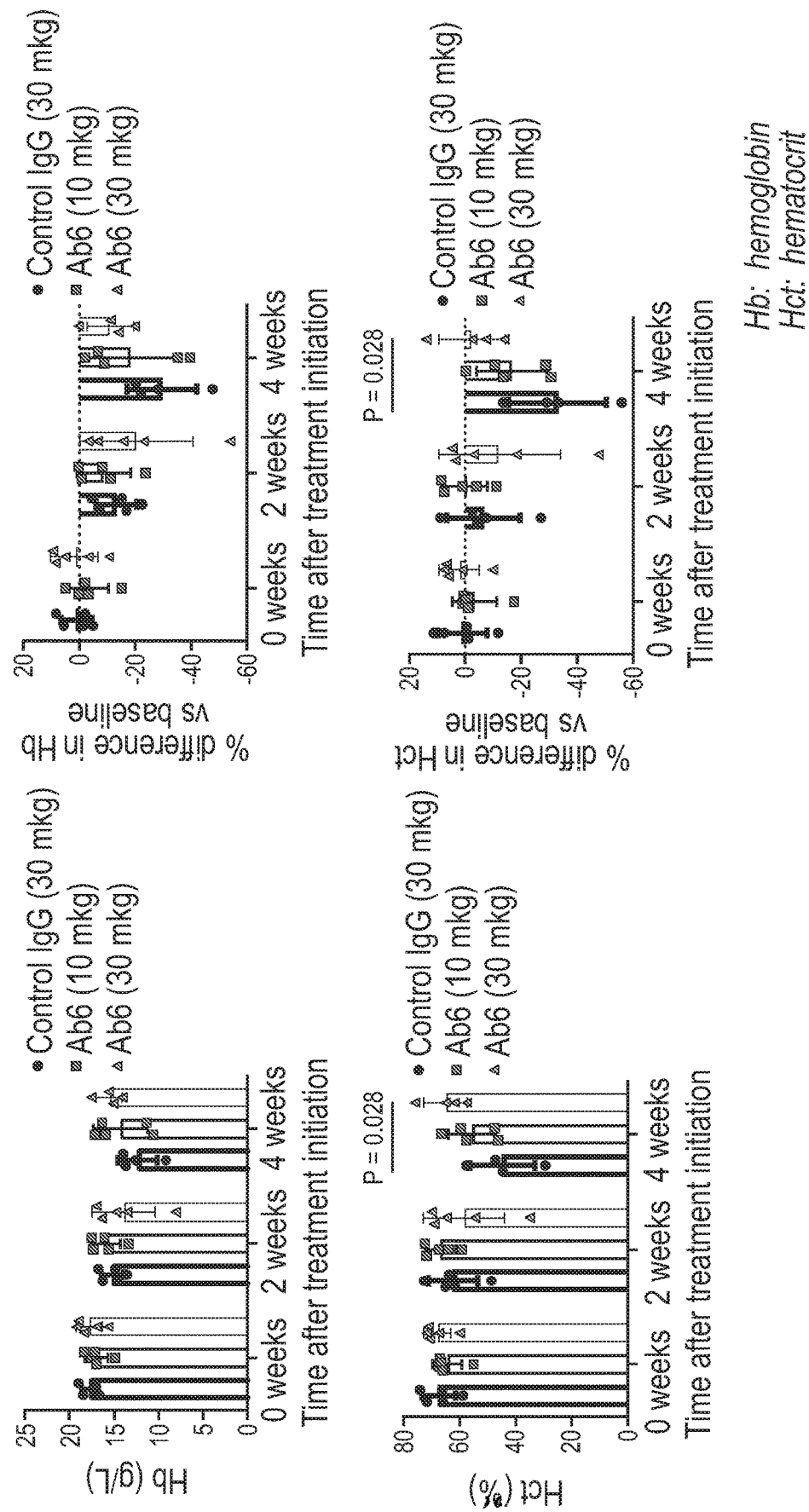
FIG. 36D Effects of Ab6 on hematological parameters in the MPL^{W515L} model of myelofibrosis
Hb: hemoglobin
Hct: hematocrit

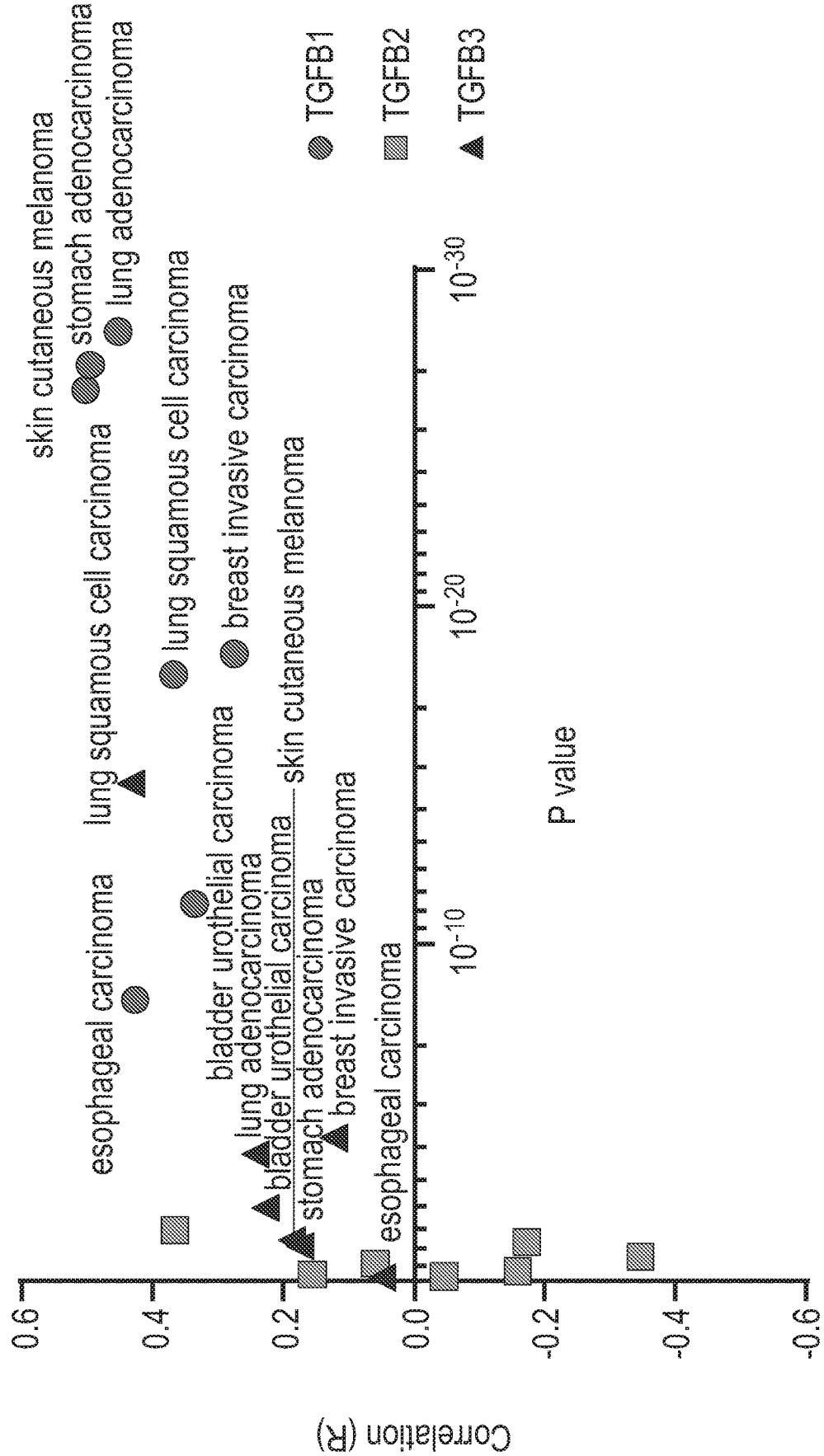

METHODS OF SCREENING FOR HIGH-AFFINITY, ISOFORM-SELECTIVE TGFβ1 INHIBITORS

This Application is a 35 U.S.C. § 371 national stage filing of International Application No. PCT/US2019/041373, filed on Jul. 11, 2019, which claims the benefit of and priority to U.S. Provisional Application Nos. 62/696,752 filed Jul. 11, 2018; 62/718,196 filed Aug. 13, 2018; 62/737,534 filed Sep. 27, 2018; 62/758,180 filed Nov. 9, 2018; 62/810,263 filed Feb. 25, 2019, and 62/827,552 filed Apr. 1, 2019, the contents of each of which are expressly incorporated herein by reference in their entirety.

REFERENCE TO SEQUENCE LISTING

This application contains a Sequence Listing in computer readable form, which has been submitted electronically via EFS-web in ASCII format. Said ASCII copy, created on Apr. 30, 2021, is named 127036_03507_Seq_Listing.txt and is 248,919 bytes in size. The computer readable form of the sequence listing is part of the specification or is otherwise incorporated herein by reference.

SEQUENCE LISTING

The instant application contains a Sequence Listing which has been submitted electronically via EFS-web in ASCII format and is hereby incorporated by reference in its entirety. Said ASCII copy, created on Apr. 30, 2021, is named 127036_03507_Seq_Listing.txt and is 248,919 bytes in size.

BACKGROUND OF THE INVENTION

Transforming growth factor beta 1 (TGFβ1) is a member of the TGFβ superfamily of growth factors, along with two other structurally related isoforms, namely, TGFβ2 and TGFβ3, each of which is encoded by a separate gene. These TGFβ isoforms function as pleiotropic cytokines that regulate cell proliferation, differentiation, immunomodulation (e.g., adaptive immune response), and other diverse biological processes both in homeostasis and in disease contexts. The three TGFβ isoforms signal through the same cell-surface receptors and trigger similar canonical downstream signal transduction events that include the SMAD2/3 pathway. However, gene knockout studies in mice show diverse phenotypes, suggesting that each isoform plays a discrete role in vivo. This may be achieved in part by differential expression patterns of the three isoforms.

Within the immune system, T cells are recognized as a major direct target for TGFβ. TGFβ signaling is important in effector cell proliferation, as well as in the regulation of effector and regulatory T cell differentiation. For example, TGFβ is a potent suppressor of Th1 and Th2 effector T cells. The effector functions of cytotoxic T cells have also been shown to be suppressed by TGFβ through multiple mechanisms. Moreover, evidence show other cell types of the immune system, such as dendritic cells such as Langerhans cells, and natural killer (NK) cells, are also regulated by the TGFβ signaling pathway. TGFβ dysregulation has been associated with a number of disease conditions, such as cancer, fibrosis and immune disorders.

Many biological processes in which the extracellular matrix plays a role are associated with TGFβ signaling. To name a few, TGFβ has been implicated in wound healing, tumor invasion and metastasis, as well as fibrosis progression.

For these and other reasons, TGFβ has been an attractive therapeutic target for the treatment of immune disorders, various proliferative disorders and fibrotic conditions. However, observations from preclinical studies, including in rats and dogs, have revealed serious toxicities associated with systemic inhibition of TGFβs in vivo. Moreover, although several TGFβ inhibitors have been developed to date, most clinical programs targeting TGFβ have been discontinued due to risk of serious side effects (summarized, for example, in WO 2017/156500). Thus, despite lines of direct and indirect evidence pointing to the involvement of TGFβ signaling in the progression of diseases such as cancer and fibrosis, there is no TGFβ therapeutics available in the market to date which are deemed safe and efficacious.

Previously, Applicant described a class of monoclonal antibodies that functions with a novel mechanism of action to modulate growth factor signaling (see, for example, WO 2014/182676). These antibodies were designed to exploit the fact that TGFβ1 is expressed as latent pro-protein complex comprised of prodomain and growth factor, which requires an activation step that releases the growth factor from the latent complex. Rather than taking the traditional approach of directly targeting the mature growth factor itself post-activation (such as neutralizing antibodies), the novel class of inhibitory antibodies specifically targets the inactive pro-proprotein complex itself so as to preemptively block the activation step, upstream of ligand-receptor interaction. It was reasoned that this unique mechanism of action should provide advantages for achieving both spatial and temporal benefits in that they act at the source, that is, by targeting the latent proTGFβ1 complex within a disease microenvironment before activation takes place.

Using this approach, monoclonal antibodies that specifically bind and inhibit the activation step of TGFβ1 (that is, release of mature growth factor from the latent complex) in an isoform-selective manner were generated (see, WO 2017/156500). Data presented therein support the notion that isoform-specific inhibition (as opposed to pan-inhibition) of TGFβ may render improved safety profiles of antagonizing TGFβ in vivo. Taking this into consideration, Applicant then sought to develop TGFβ1 inhibitors that are both i) isoform-specific; and, ii) capable of broadly targeting multiple TGFβ1 signaling complexes that are associated with different presenting molecules, as therapeutic agents for conditions driven by multifaceted TGFβ1 effects and dysregulation thereof.

Such antibodies were subsequently described in PCT/US2018/012601 (filed 5 Jan. 2018). Indeed, isoform-specific inhibitory agents described therein were capable of targeting both ECM-associated TGFβ1 and immune cell-associated TGFβ1, thereby blocking multiple sources of TGFβ1 in multiple biological contexts while maintaining the isoform-specificity. Data from a number of in vivo models showing efficacy and safety of isoform-selective TGFβ1 activation inhibitors were disclosed, demonstrating that such inhibitors are useful for the treatment of diseases that involve dysregulation of both ECM-associated TGFβ1 and immune cell-associated TGFβ1 in vivo.

While the earlier work referenced above demonstrated utility of antibodies capable of targeting each of known proTGFβ1 complexes and inhibitory activities, improved isoform-selective TGFβ1 inhibitors with even higher in vivo potency are desirable.

SUMMARY OF THE INVENTION

The present disclosure provides a novel class of high-affinity, isoform-selective antibodies, capable of inhibiting TGFβ1 activation with high potency. These include antibodies (including immunoglobulins and antigen-binding fragments or portions thereof, and engineered molecules incorporating such fragments) that are capable of targeting multiple presenting molecule-proTGFβ1 complexes (referred to as "large latent complexes" or "LLCs") with high affinities. These antibodies retain exquisite selectivity and safety profiles, and are shown to achieve improved in vivo efficacy in multiple preclinical models with translatability to human conditions. These attributes of the TGFβ1 inhibitors open opportunities for developing safe and effective TGFβ1 therapeutics for the treatment of diseases involving TGFβ1 dysregulation.

The following selection criteria were taken into consideration in generating proTGFβ1 antibodies of the present disclosure: 1) isoform selectivity; 2) high affinities for human LLCs, e.g., LTBP1-proTGFβ1, LTBP3-proTGFβ1, GARP-proTGFβ1 and LRRC33-proTGFβ1; 3) robust inhibitory potency; 4) favorable in vivo safety/toxicology profiles; and, 5) in vivo efficacy in a preclinicnal model that recapitulates human disease. Additionally, in assessing the effectiveness of TGFβ1 inhibitors used as combination therapy (e.g., add-on therapy), the ability to achieve synergistic effects (as opposed to mere additive effects) should be weighed. Based on these criteria, the inventors of the present disclosure have identified a class of high-affinity monoclonal antibodies and fragments thereof, capable of specifically targeting proTGFβ1 complexes and potently blocking TGFβ1 activation. In some embodiments, the novel antibodies disclosed herein show high affinities across all target LLCs (e.g., KD of nanomolar to sub-nanomolar range). In preferred embodiments, such antibody is unbiased across different proTGFβ1 complexes such that the antibody has equivalent affinities for all target complexes. Related compositions, therapeutic use, preparations, formulations, processes, and methods are encompassed by the invention.

Accordingly, in some embodiments, the invention includes a monoclonal antibody or antigen-binding fragment thereof that is capable of binding to each of the following human LLC complexes with a KD of <10 nM, as measured by solution equilibrium titration: LTBP1-proTGFβ1, LTBP3-proTGFβ1, GARP-proTGFβ1 and LRRC33-proTGFβ1. In some embodiments, the antibody binds each of the human LTBP1-proTGFβ1 and LTBP3-proTGFβ1 complexes with a KD of ≤1 nM. Preferably, the antibody has a KD of ≤1 nM for each of the four human LLCs.

In some embodiments, the antibody or the fragment binds Latency Lasso, or a portion thereof, of proTGFβ1. In some embodiments, the antibody or the fragment further binds a portion(s) of the growth factor domain, such as Finger-1 and Finger-2. For example, the antibody or the fragment may bind an epitope comprising one or more amino acid residues of Latency Lasso. Optionally, the epitope may further comprise one or more amino acid residues of the growth factor domain. Such epitope therefore may be a combinatorial epitope. In preferred embodiments, the antibody does not bind free TGFβ1 growth factor which is not in association with a proTGFβ1 complex.

The TGFβ1 inhibitors of the invention are functional antibodies in that they have inhibitory activities towards TGFβ1. The potency of such antibodies is isoform-specific, as measured by suitable in vitro potency assays such as cell-based reporter assays described herein. Thus, the antibody does not bind or inhibit TGFβ2 or TGFβ3 counterparts.

The TGFβ1 inhibitors of the invention are capable of blocking the release of mature growth factor from latent LLC complexes. In some embodiments, the TGFβ1 inhibitors can inhibit integrin-dependent activation of TGFβ1 and/or protease-dependent activation of TGFβ1. In some embodiments, the protease is Kallikrein, Plasmin, or an MMP protease. In some embodiments, the TGFβ1 inhibitors block integring-dependent TGFβ1 activation without blocking integrin binding to the LLCs.

In some embodiments, the TGFβ1 inhibitors of the invention may function through dual inhibitory modes of action towards cell-associated LLCs (e.g., GARP-proTGFβ1 and LRRC33-proTGFβ1). In one mechanism, such inhibitors block the activation step of TGFβ1 associated with the membrane-anchored GARP and/or LRRC33. In a second mechanism, such inhibitors may, upon target engagement, induce antibody-dependent internalization (hence removal) of the LLCs from cell surface, thereby reducing TGFβ1 signaling at the niche. In some embodiments, the antibody is a pH-sensitive antibody characterized in that the antibody binds to a proTGFβ1 complex with higher affinity in a neutral pH than in an acidic pH.

In some embodiments, the TGFβ1 inhibitors of the invention are effective to reduce expression of disease-associated genes, such as TGFB1, Acta2, Col1a1, Col3a1, Fn1, Itga11, Lox, Lox12, CCL2 and Mmp2.

In some embodiments, the TGFβ1 inhibitors of the invention are effective to reduce phosphorylation of the downstream effector SMAD2/3 in vivo.

In some embodiments, the TGFβ1 inhibitors of the invention are effective to treat TGFβ1-related indications. Such indications include diseases involving abnormal gene expression, diseases involving ECM dysregulation, diseases characterized by increased immunosuppressive cells (e.g., Tregs, MDSCs and/or M2 macrophages), diseases involving mesenchymal transition, diseases involving proteases, diseases related to abnormal stem cell proliferation and/or differentiation, etc., whilst these categories of diseases are not intended to be mutually exclusive. In some embodiments, the TGFβ1-related indication is a proliferative disorder such as myeloproliferative disorder and cancer with a solid tumor. In some embodiments, the TGFβ1-related indication is a fibrotic disorder, such as organ fibrosis. The cancer may be an advanced cancer, which includes a locally advanced tumor/cancer and metastatic cancer.

In some embodiments, the TGFβ1 inhibitors of the invention can reduce the number of immunosuppressive cell populations at a disease site, such as tumor microenvironment and fibrotic microenvironment. In some embodiments, the immunosuppressive cell populations may include, M2-polarized macrophages and/or MDSCs.

In some embodiments, the TGFβ1 inhibitors of the invention are effective to achieve tumor control (e.g., Partial Response and Complete Response), wherein the tumor is optionally an immunosuppressive (e.g., immune-excluded) phenotype. In some embodiments, the TGFβ1 inhibitors may achieve synergistic anti-tumor effects when used in conjunction with a cancer therapy, such as checkpoint blockade therapy, chemotherapy and radiation therapy. The checkpoint blockade therapy may comprise, for example, anti-PD-(L)1 antibody(ies). In such combination therapies, the TGFβ1 inhibitors may overcome treatment resistance (e.g., primary resistance), thereby rendering the cancer more susceptible to the cancer therapy. Thus, the TGFβ1 inhibitors may be used for the treatment of cancer comprising an immunosuppressive tumor in a subject. The subject may be i) a primary non-responder to a cancer therapy such as a checkpoint inhibitor; or, ii) diagnosed with a cancer for which at least one checkpoint inhibitor is approved by a regulatory authority as therapy. Response rates (combined partial and complete responders among those who received a therapy) for the cancer for which at least one checkpoint inhibitor is approved are less than 100%. Typically, response rates are between about 10-60%. The TGFβ1 inhibitors may increase the response rates among a patient population. Further, within a partial response group among the primary responders, the TGFβ1 inhibitors may provide improved clinical benefits. In some embodiments, among a primary responder group, the TGFβ1 inhibitors may reduce the rate of acquired resistance to the cancer therapy. The immunosuppressive tumor may be a locally advanced cancer/tumor or a metastatic cancer. In some embodiments, the cancer therapy may include, for example, checkpoint inhibitor therapy, chemotherapy and/or radiation therapy.

In some embodiments, the TGFβ1 inhibitors of the invention are effective to achieve survival benefit in subjects with a solid tumor, wherein the solid tumor is optionally a locally advanced or metastatic cancer.

In some embodiments, the TGFβ1 inhibitors of the invention are effective to achieve durable anti-tumor effects by inducing T cell memory function. Thus, the TGFβ1 inhibitors may reduce or delay recurrence of the disease.

In some embodiments, the TGFβ1 inhibitors of the invention are effective to achieve anti-tumor effects in tumors that predominantly express TGFB1 and/or TGFb3. In some embodiments, the tumor that co-expresses TGFβ1 and TGFβ3 is a carcinoma.

In some embodiments, the TGFβ1 inhibitors of the invention are capable of overcoming tumor's primary resistance to a cancer therapy. In some embodiments, such tumor is infiltrated with immunosuppressive cell types, such as regulatory T cells, M2-type macrophages, and/or myeloid-derived suppressive cells (MDSCs). Upon treatment, there is a reduction in the number of tumor-associated immunosuppressive cells, and a corresponding increase in the number of anti-tumor effector T cells.

In some embodiments, the TGFβ1 inhibitors of the invention promotes effector cell infiltration into tumors. In some embodiments, effector cells may enter the tumor via the vasculature of the tumor. In some embodiments, the TGFβ1 inhibitors of the invention promotes effector cell expansion (e.g., proliferation). This may be at least in part mediated by inhibition of GARP-positive regulatory T cells.

In some embodiments, the TGFβ1 inhibitors of the invention are effective to treat myelofibrosis. In some embodiments, TGFβ1 inhibitors achieves anti-fibrotic effects of the bone marrow of subjects with myelofibrosis. In some embodiments, TGFβ1 inhibitors are effective to normalize certain hematological parameters.

In some embodiments, the TGFβ1 inhibitors of the invention are effective to achieve anti-fibrotic effects in vivo. The anti-fibrotic effects may include reversal of established fibrosis, which may be partial reversal or complete reversal.

In some embodiments, the TGFβ1 inhibitors of the invention are well tolerated in preclinical safety/toxicology studies in doses up to 100, 200, or 300 mg/kg when dosed weekly for at least 4 weeks. Such studies may be carried out in animal models that are known to be sensitive to TGFβ inhibition, such as rats and non-human primates. In some embodiments, the TGFβ1 inhibitors of the invention do not cause observable toxicities associated with pan-inhibition of TGFβ, such as cardiovascular toxicities (e.g., valvulopathy) and epithelial hyperplasia and other toxicities known in the art.

In some embodiments, the TGFβ1 inhibitors of the invention achieves sufficient therapeutic window in that effective amounts of the inhibitors shown by in vivo efficacy studies are well below (such as at least 3-fold, at least 6-fold, or at least 10-fold) the amounts or concentrations that cause observable toxicities. In some embodiments, the therapeutically effective amounts of the inhibitors are between about 1 mg/kg and about 30 mg/kg per week.

BRIEF DESCRIPTION OF THE FIGURES

FIG. 5A shows inhibitory effects of Ab3 and Ab6 on Kallikrein-induced activation of TGFβ1 in vitro.

FIG. 5B shows inhibitory effects of Ab3 and Ab6 on Plasmin-induced activation of TGFβ1 in vitro.

FIG. 11A provides five graphs showing the change in tumor growth (tumor volume mm$^3$) expressed as median tumor progression in Cloudman S91 melanoma model, measured over time (days) after administration of Ab3 or Ab6 at 30 mg/kg or 10 mg/kg, each in combination with anti-PD-1. Anti-PD-1 alone was used as a control. Dashed lines represent animals that had to be sacrificed prior to reaching the 2000 mm$^3$ endpoint criteria due to tumor ulceration.

FIG. 11B provides two graphs showing the Cloudman S91 median tumor volumes as a function of time after administration of Ab3 (left) or Ab6 (right) at 30 mg/kg or 10 mg/kg, in combination with anti-PD-1. Anti-PD-1 alone, Ab3 alone, Ab6 alone, and IgG alone were used as controls.

FIG. 11E provides a graph summarizing the data, expressed as median tumor volume, from FIG. 11C.

FIG. 11F provides a graph showing survival of animals in each treatment group over time from FIG. 11C.

FIG. 12 is a graph that shows phosphorylated-to-total SMAD2/3 ratios (pSMAD/SMAD) in MBT2 bladder cancer model. Animals were treated as follows: (1) anti-PD-1 antibody only; (2) Ab5 (3 mg/kg) in combination with anti-PD-1 antibody; (3) Ab5 (10 mg/kg) in combination with anti-PD-1 antibody; (4) Ab3 (10 mg/kg) in combination with anti-PD-1 antibody; (5) Ab3 (30 mg/kg) in combination with anti-PD-1 antibody.

FIGS. 13A and 13B provide two sets of five graphs that show the change in MBT2 tumor growth (tumor volume $mm^3$) measured over time (days) after administration of Ab3 at 30 mg/kg or 10 mg/kg, or Ab6 at 3 mg/kg or 10 mg/kg, in combination with anti-PD-1. Anti-PD-1 alone was used as a control. Changes in tumor volume as a function of time is represented on a log scale (FIG. 13A) and on a linear scale (FIG. 13B). Dashed lines represent animals that had to be sacrificed prior to reaching the 1200 $mm^3$ endpoint criteria due to tumor ulceration.

FIG. 13D provides five graphs showing effects of Ab6 in combination with anti-PD-1 in the MBT2 syngeneic bladder cancer model. Responders are defined as those that achieved tumor size of less than 25% of the endpoint volume at the end of study.

FIG. 14 is a graph that shows percent survival over time (days) after administration of Ab3 at 10 mg/kg or Ab6 at 3 mg/kg or 10 mg/kg, in combination with anti-PD-1, in a MBT2 syngeneic bladder cancer model. Anti-PD-1 alone was used as a control.

FIGS. 20A-20D show relative RNA expression of TGFβ isoforms in various tissues and cells. FIG. 20A shows TGFβ isoform expression in various human cancer tissues vs. normal comparator (by cancer type). FIG. 20B shows frequency of TGFβ isoform expression by human cancer type based on analyses from over 10,000 samples of 33 tumor types. FIG. 20C shows TGFβ isoform expression in individual tumor samples, by cancer type. FIG. 20D shows TGFβ isoform expression in mouse syngeneic cancer cell model lines.

FIG. 20E provides 4 gene expression panels showing that all presenting molecules (LTBP1, LTBP3, GARP and LRRC33) are highly expressed in most human cancer types.

FIG. 20F provides expression analyses of TGFβ and related signaling pathway genes from the syngeneic mouse tumor models, Cloudman S91, MBT-2 and EMT-6.

FIG. 20H provides a graph comparing RNA expression level by whole tumor lysate qPCR of presenting molecules in the Cloudman S91, MBT-2 and EMT-6 tumor models.

FIG. 21A depicts microscopic heart findings from a pan-TGFβ antibody from a 1-week toxicology study. FIG. 21C depicts microscopic findings from Ab6 as compared to an ALK5 inhibitor or pan-TGFβ antibody from a 4-week rat toxicology study.

FIG. 22 provides a graph showing the S91 median tumor volumes as a function of time. The combination arms represent four different isoform-selective, context independent TGFβ1 inhibitors at two dose levels, each in combination with anti-PD-1 treatment.

FIG. 23A is a tumor section from an animal treated with anti-PD-1 alone. FIG. 23B is a tumor section from an animal treated with both anti-PD-1 and a representative context-independent TGFβ1 inhibitor.

FIG. 24A is a tumor section from an animal treated with anti-PD-1 alone. FIG. 24B is a tumor section from an animal treated with both anti-PD-1 and a representative context-independent TGFβ1 inhibitor. FIG. 24C is a tumor section from an animal treated with anti-PD-1 and Ab3 (30 mg/kg), using anti-F4/80 as a macrophage marker. FIG. 24D is a section using anti-CD163 as an M2 macrophage marker, showing that most cells are CD163-negative.

FIG. 25 is a graph that shows log 2 fold change in CD8+ T lymphocyte genes (CD8α, Perforin and Granzyme B) after 1-week treatment with anti-PD-1/Ab3 in MBT2 tumors, as compared to anti-PD-1 treated animals alone.

FIG. 26A provides FACS data showing CD3/CD28-induced upregulation of GARP in peripheral human regulatory T cells.

FIG. 26B is a graph that shows the effects of Ab3 or Ab6 on Treg-mediated inhibition of Teff proliferation. IgG was used as a control.

FIGS. 29A-29C provide additional FACS data analyses, showing effects of Ab6 and anti-PD-1 treatment in MBT2 tumors.

FIG. 30E provides the quantitation of the IHC data from FIGS. 30A-30D, expressed as fraction of CD8-positive cells in each treated group. Necrotic regions of the sections were excluded from the analysis.

FIG. 30G provides data demonstrating that Ab6 and anti-PD-1 in combination appears to trigger CD8+ T cell mobilization and infiltration into MBT2 tumors from CD31+ vessel.

FIG. 33B illustrates LN229 cell-based potency assay and provides a graph showing concentration-dependent potency of Ab6 towards four large latent complexes as indicated. Also shows that Ab6 does not inhibit proTGFβ3.

FIG. 34A provides a set of nine graphs showing the effect of Ab6 in combination with or without anti-PD1 and/or anti-TGFβ3 on tumor growth/regression over time in EMT6 (Study 1). The upper dotted line within each graph represents the endpoint tumor volume of 2000 mm$^3$, while the lower dotted line in each graph represents 25% of the endpoint volume (i.e., 500 mm$^3$).

FIG. 34D provides effects of anti-PD-1 and Ab6 combination on survival in the EMT6 breast cancer model.

FIG. 36C provides a set of graphs showing hematological parameters in MPL$^{W515L}$ mice treated with Ab6 or control IgG.

FIG. 36D provides a set of graphs showing additional hematological parameters in MPL$^{W515L}$ mice treated with Ab6 or control IgG.

FIG. 37A provides a gene set variation analysis (GSVA) showing correlation between TGFβ isoform expression and IPRES geneset.

DETAILED DESCRIPTION OF CERTAIN EMBODIMENTS

Definitions

Figure 1:
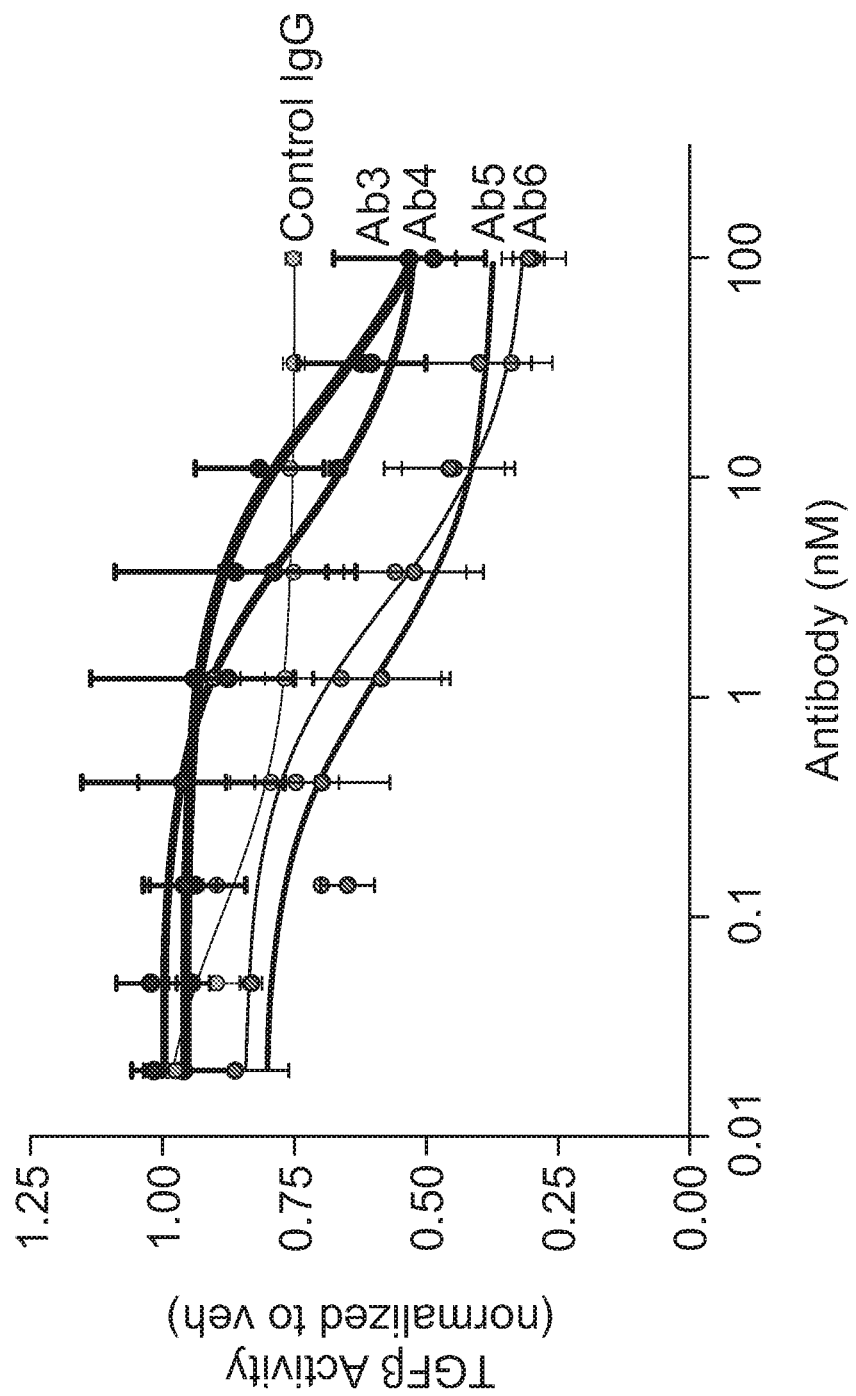
FIG. 1 is a graph that shows inhibition of LTBP1-proTGFβ activation in an LN229 assay.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Advanced cancer, advanced malignancy: The term "advanced cancer" or "advanced malignancy" as used herein has the meaning understood in the pertinent art, e.g., as understood by oncologists in the context of diagnosing or treating subjects/patients with cancer. Advanced malignancy with a solid tumor can be locally advanced or metastatic. The term "locally advanced cancer" is used to describe a cancer (e.g., tumor) that has grown outside the organ it started in but has not yet spread to distant parts of the body. Thus, the term includes cancer that has spread from where it started to nearby tissue or lymph nodes. By contrast, "metastatic cancer" is a cancer that has spread from the part of the body where it started (the primary site) to other parts (e.g., distant parts) of the body.

Affinity: Affinity is the strength of binding of a molecule (such as an antibody) to its ligand (such as an antigen). It is typically measured and reported by the equilibrium dissociation constant ($K_D$). In the context of antibody-antigen interactions, $K_D$ is the ratio of the antibody dissociation rate ("off rate" or $K_{off}$), how quickly it dissociates from its antigen, to the antibody association rate ("on rate" or $K_{on}$) of the antibody, how quickly it binds to its antigen. For example, an antibody with an affinity of <5 nM has a KD value that is 5 nM or lower (i.e., 5 nM or higher affinity) determined by a suitable in vitro binding assay. Suitable in vitro assays can be used to measure KD values of an antibody for its antigen, such as Biolayer Interferometry (BLI) and Solution Equilibrium Titration (e.g., MSD-SET).

Antibody: The term "antibody" encompasses any naturally-occurring, recombinant, modified or engineered immunoglobulin or immunoglobulin-like structure or antigen-binding fragment or portion thereof, or derivative thereof, as further described elsewhere herein. Thus, the term refers to an immunoglobulin molecule that specifically binds to a target antigen, and includes, for instance, chimeric, humanized, fully human, and bispecific antibodies. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen binding portions thereof, can be produced in hybridomas, by recombinant DNA techniques, or by enzymatic or chemical cleavage of intact antibodies. The term antibodies, as used herein, includes monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), respectively. In some embodiments, the term also encompasses peptibodies.

Antigen: The term "antigen" The term "antigen" broadly includes any molecules comprising an antigenic determinant within a binding region(s) to which an antibody or a fragment specifically binds. An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen binding proteins, e.g., antibodies. In the context of the present disclosure, a suitable antigen is a complex (e.g., multimeric complex comprised of multiple components in association) containing a proTGF dimer in association with a presenting molecule. Each monomer of the proTGF dimer comprises a prodomain and a growth factor domain, separated by a furin cleavage sequence. Two such monomers form the proTGF dimer complex (see FIG. 19). This in turn is covalently associated with a presenting molecule via disulfide bonds, which involve a cysteine residue present near the N-terminus of each of the proTGF monomer. This multi-complex formed by a proTGF dimer bound to a presenting molecule is generally referred to as a large latent complex. An antigen complex suitable for screening antibodies or antigen-binding fragments, for example, includes a presenting molecule component of a large latent complex. Such presenting molecule component may be a full-length presenting molecule or a fragment(s) thereof. Minimum required portions of the presenting molecule typically contain at least 50 amino acids, but more preferably at least 100 amino acids of the presenting molecule polypeptide, which comprises two cysteine residues capable of forming covalent bonds with the proTGFβ1 dimer.

Antigen-binding portion/fragment: The terms "antigen-binding portion" or "antigen-binding fragment" of an antibody, as used herein, refers to one or more fragments of an antibody that retain the ability to specifically bind to an antigen (e.g., TGFβ1). Antigen binding portions include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments, a monovalent fragment consisting of the VL, VH, CL and CH1 domains; (ii) F(ab')2 fragments, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules (see, e.g., Bird et al. (1988) SCIENCE 242:423-426; and Huston et al. (1988) PROC. NAT'L. ACAD. SCI. USA 85:5879-5883); (vi) dAb fragments (see, e.g., Ward et al. (1989) NATURE 341: 544-546); and (vii) minimal recognition units consisting of the amino acid residues that mimic the hypervariable region of an antibody (e.g., an isolated complementarity determining region (CDR)). Other forms of single chain antibodies, such as diabodies are also encompassed. The term antigen binding portion of an antibody includes a "single chain Fab fragment" otherwise known as an "scFab," comprising an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids.

Bias: In the context of the present disclosure, the term "bias" refers to skewed or uneven affinity towards or against a subset of antigens to which an antibody is capable of specifically binding. For example, an antibody is said to have bias when the affinity for one antigen complex and the affinity for another antigen complex are not equivalent. Context-independent antibodies according to the present disclosure have equivalent affinities towards such antigen complexes (i.e., unbiased).

Binding region: As used herein, a "binding region" is a portion of an antigen that, when bound to an antibody or a fragment thereof, can form an interface of the antibody-antigen interaction. Upon antibody binding, a binding region becomes protected from surface exposure, which can be detected by suitable techniques, such as HDX-MS. Antibody-antigen interaction may be mediated via multiple (e.g., two or more) binding regions. A binding region can comprise an antigenic determinant, or epitope.

Biolayer Interferometry (BLI):BLI is a label-free technology for optically measuring biomolecular interactions, e.g., between a ligand immobilized on the biosensor tip surface and an analyte in solution. BLI provides the ability to monitor binding specificity, rates of association and dissociation, or concentration, with precision and accuracy. BLI platform instruments are commercially available, for example, from ForteBio and are commonly referred to as the OCTET® System.

Cancer: The term "cancer" as used herein refers to the physiological condition in multicellular eukaryotes that is typically characterized by unregulated cell proliferation and malignancy. The term broadly encompasses, solid and liquid malignancies, including tumors, blood cancers (e.g., leukemias, lymphomas and myelomas), as well as myelofibrosis.

Cell-associatedproTGFβ1: The term refers to TGFβ1 or its signaling complex (e.g., pro/latent TGFβ1) that is membrane-bound (e.g., tethered to cell surface). Typically, such cell is an immune cell. TGFβ1 that is presented by GARP or LRRC33 is a cell-associated TGFβ1. GARP and LRRC33 are transmembrane presenting molecules that are expressed on cell surface of certain cells. GARP-proTGFβ1 and LRRC33- may be collectively referred to as "cell-associated" (or "cell-surface") proTGFβ1 complexes, that mediate cell proTGFβ1-associated (e.g., immune cell-associated) TGFβ1 activation/signaling. The term also includes recombinant, purified GARP-proTGFβ1 and LRRC33-proTGFβ1 complexes in solution (e.g., in vitro assays) which are not physically attached to cell membranes. Average KD values of an antibody (or its fragment) to a GARP-proTGFβ1 complex and an LRRC33-proTGFβ1 complex may be calculated to collectively represent affinities for cell-associated (e.g., immune cell-associated) proTGFβ1 complexes. See, for example, Table 8, column (G). Human counterpart of a presenting molecule or presenting molecule complex may be indicated by an "h" preceding the protein or protein complex, e.g., "hGARP," "hGARP-proTGFβ1," hLRRC33" and "hLRRC33-proTGFβ1." In addition to blocking release of active TGFβ1 growth factor from cell-tethered complexes, cell-associated proTGFβ1 may be a target for internalization (e.g., endocytosis) and/or cell killing such as ADCC, ADCP, or ADC-mediated depletion of the target cells expressing such cell surface complexes.

Checkpoint inhibitor: In the context of this disclosure, checkpoint inhibitors refer to immune checkpoint inhibitors and carries the meaning as understood in the art. Typically, target is a receptor molecule on T cells or NK cells, or corresponding cell surface ligand on antigen-presenting cells (APCs) or tumor cells. Immune checkpoints are activated in immune cells to prevent inflammatory immunity developing against the "self". Therefore, changing the balance of the immune system via checkpoint inhibition should allow it to be fully activated to detect and eliminate the cancer. The best known inhibitory receptors implicated in control of the immune response are cytotoxic T-lymphocyte antigen-4 (CTLA-4), programmed cell death protein 1 (PD-1), PD-L1, T-cell immunoglobulin domain and mucin domain-3 (TIM3), lymphocyte-activation gene 3 (LAG3), killer cell immunoglobulin-like receptor (KIR), glucocorticoid-induced tumor necrosis factor receptor (GITR) and V-domain immunoglobulin (Ig)-containing suppressor of T-cell activation (VISTA). Non-limiting examples of checkpoint inhibitors include: Nivolumab, Pembrolizumab, BMS-936559, Atezolizumab, Avelumab, Durvalumab, Ipilimumab, Tremelimumab, IMP-321, BMS-986016, and Lirilumab. KEYTRUDA® is one example of PD-1 inhibitors. Therapies that employ one or more of immune checkpoint inhibitors may be referred to as checkpoint blockade therapy (CBT).

Clinical benefit: As used herein, the term "clinical benefits" is intended to include both efficacy and safety of a therapy. Thus, therapeutic treatment that achieves a desirable clinical benefit is both efficacious (e.g., achieves therapeutically beneficial effects) and safe (e.g., with tolerable or acceptable levels of toxicities or adverse events).

Combination therapy: "Combination therapy" refers to treatment regimens for a clinical indication that comprise two or more therapeutic agents. Thus, the term refers to a therapeutic regimen in which a first therapy comprising a first composition (e.g., active ingredient) is administered in conjunction with a second therapy comprising a second composition (active ingredient) to a patient, intended to treat the same or overlapping disease or clinical condition. The first and second compositions may both act on the same cellular target, or discrete cellular targets. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies. When a subject who has been treated with a first therapy to treat a disease is administered with a second therapy to treat the same disease, the second therapy may be referred to as an add-on therapy or adjunct therapy.

Combinatory or combinatorial epitope: A combinatorial epitope is an epitope that is recognized and bound by a combinatorial antibody at a site (i.e., antigenic determinant) formed by non-contiguous portions of a component or components of an antigen, which, in a three-dimensional structure, come together in close proximity to form the epitope. Thus, antibodies of the invention may bind an epitope formed by two or more components (e.g., portions or segments) of a pro/latent TGFβ1 complex. A combinatory epitope may comprise amino acid residue(s) from a first component of the complex, and amino acid residue(s) from a second component of the complex, and so on. Each component may be of a single protein or of two or more proteins of an antigenic complex. A combinatory epitope is formed with structural contributions from two or more components (e.g., portions or segments, such as amino acid residues) of an antigen or antigen complex.

Compete or cross-compete; cross-block: The term "compete" when used in the context of antigen binding proteins (e.g., an antibody or antigen binding portion thereof) that compete for the same epitope means competition between antigen binding proteins as determined by an assay in which the antigen binding protein being tested prevents or inhibits (e.g., reduces) specific binding of a reference antigen binding protein to a common antigen (e.g., TGFβ1 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay; solid phase direct biotin-avidin EIA; solid phase direct labeled assay, and solid phase direct labeled sandwich assay. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

In some embodiments, a first antibody or antigen-binding portion thereof and a second antibody or antigen-binding portion thereof "cross-block" with each other with respect to the same antigen, for example, as assayed by Biacor or OCTET®, using standard test conditions, e.g., according to the manufacturer's instructions (e.g., binding assayed at room temperature, ~20-25° C.). In some embodiments, the first antibody or fragment thereof and the second antibody or fragment thereof may have the same epitope. In other embodiments, the first antibody or fragment thereof and the second antibody or fragment thereof may have non-identical but overlapping epitopes. In yet further embodiments, the first antibody or fragment thereof and the second antibody or fragment thereof may have separate (different) epitopes which are in close proximity in a three-dimensional space, such that antibody binding is cross-blocked via steric hindrance. "Cross-block" means that binding of the first antibody to an antigen prevents binding of the second antibody to the same antigen, and similarly, binding of the second antibody to an antigen prevents binding of the first antibody to the same antigen.

Antibody binning (sometimes referred to as epitope binning or epitope mapping) may be carried out to characterize and sort a set (e.g., "a library") of monoclonal antibodies made against a target protein or protein complex (i.e., antigen). Such antibodies against the same target are tested against all other antibodies in the library in a pairwise fashion to evaluate if antibodies block one another's binding to the antigen. Closely related binning profiles indicate that the antibodies have the same or closely related (e.g., overlapping) epitope and are "binned" together. Binning provides useful structure-function profiles of antibodies that share similar binding regions within the same antigen because biological activities (e.g., intervention; potency) effectuated by binding of an antibody to its target is likely to be carried over to another antibody in the same bin. Thus, among antibodies within the same epitope bin, those with higher affinities (lower KD) typically have greater potency.

Complementary determining region: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region that can bind the antigen. The exact boundaries of these CDRs have been defined differently according to different systems. The system described by Kabat (Kabat et al. (1987; 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk (1987) J. Mol. Biol. 196: 901-917; and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2 and L3 or H1, H2 and H3, or, L-CDR1, L-CDR2 and L-CDR3 or H-CDR1, H-CDR2 and H-CDR3, where the "L" and the "H" designate the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9: 133-139 and MacCallum (1996) J. Mol. Biol. 262(5): 732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding (see, for example: Lu X et al., MAbs. 2019 January; 11 (1):45-57). The methods used herein may utilize CDRs defined according to any of these systems, although certain embodiments use Kabat or Chothia defined CDRs.

Conformational epitope: A conformational epitope is an epitope that is recognized and bound by a conformational antibody in a three-dimensional conformation, but not in an unfolded peptide of the same amino acid sequence. A conformational epitope may be referred to as a conformation-specific epitope, conformation-dependent epitope, or conformation-sensitive epitope. A corresponding antibody or fragment thereof that specifically binds such an epitope may be referred to as conformation-specific antibody, conformation-selective antibody, or conformation-dependent antibody. Binding of an antigen to a conformational epitope depends on the three-dimensional structure (conformation) of the antigen or antigen complex.

Constant region: An immunoglobulin constant domain refers to a heavy or light chain constant domain. Human IgG heavy chain and light chain constant domain amino acid sequences are known in the art.

Context-biased: As used herein, "context-biased antibodies" refer to a type of conformational antibodies that binds an antigen with differential affinities when the antigen is associated with (i.e., bound to or attached to) an interacting protein or a fragment thereof. Thus, a context-biased antibody that specifically binds an epitope within proTGFβ1 may bind LTBP1-proTGFβ1, LTBP3-proTGFβ1, GARP-proTGFβ1 and LRRC33-proTGFβ1 with different affinities. For example, an antibody is said to be "matrix-biased" if it has higher affinities for matrix-associated proTGFβ1 complexes (e.g., LTBP1-proTGFβ1 and LTBP3-proTGFβ1) than for cell-associated proTGFβ1 complexes (e.g., GARP-proTGFβ1 and LRRC33-proTGFβ1). Relative affinities of [matrix-associated complexes]: [cell-associated complexes] may be obtained by taking average KD values of the former, taking average KD values of the latter, and calculating the ratio of the two, as exemplified herein.

Context-independent: According to the present disclosure, "a context-independent antibody" that binds proTGFβ1 has equivalent affinities across the four known presenting molecule-proTGFβ1 complexes, namely, LTBP1-proTGFβ1, LTBP3-proTGFβ1, GARP-proTGFβ1 and LRRC33-proTGFβ1. Context-independent antibodies disclosed in the present application may also be characterized as unbiased. Typically, context-independent antibodies show equivalent (i.e., no more than five-fold bias in) affinities, such that relative ratios of measured KD values between matrix-associated complexes and cell-associated complexes are no greater than 5 as measured by a suitable in vitro binding assay, such as surface plasmon resonance, Biolayer Interferometry (BLI), and/or solution equilibrium titration (e.g., MSD-SET).

ECM-associated TGFβ1/proTGFβ1: The term refers to TGFβ1 or its signaling complex (e.g., pro/latent TGFβ1) that is a component of (e.g., deposited into) the extracellular matrix. TGFβ1 that is presented by LTBP1 or LTBP3 is an ECM-associated TGFβ1, namely, LTBP1-proTGFβ1 and LTBP3-proTGFβ1, respectively. LTBPs are critical for correct deposition and subsequent bioavailability of TGFβ in the ECM, where fibrillin (Fbn) and fibronectin (FN) are believed to be the main matrix proteins responsible for the association of LTBPs with the ECM. Such matrix-associated latent complexes are enriched in connective tissues, as well as certain disease-associated tissues, such as tumor stroma and fibrotic tissues. Human counterpart of a presenting molecule or presenting molecule complex may be indicated by an "h" preceding the protein or protein complex, e.g., "hLTBP1," "hLTBP1-proTGFβ1," hLTBP3" and "hLTBP3-proTGFβ1."

Effective amount: An "effective amount" (or therapeutically effective amount, or therapeutic dose) is a dosage or dosing regimen that achieves statistically significant clinical benefits (e.g., efficacy) in a patient population. For example, Ab6 has been shown to be efficacious at doses as low as 3 mg/kg and as high as 30 mg/kg in preclinical models. Thus, it may be said that an effective amount for Ab6 is between about 3-30 mg/kg.

Effective tumor control: The term "effective tumor control" may be used to refer to a degree of tumor regression achieved in response to treatment, where, for example, the tumor is regressed by a defined fraction (such as <25%) of an endpoint tumor volume. For instance, in a particular model, if the endpoint tumor volume is set at 2,000 mm$^3$, effective tumor control is achieved if the tumor is reduced to less than 500 mm$^3$ assuming the threshold of <25%. Therefore, effective tumor control encompasses complete regression. Clinically, effective tumor control includes partial response (PR) and complete response (CR) based on art-recognized criteria, such as RECIST 1.1 and corresponding iRECIST. In some embodiments, effective tumor control in clinical settings also includes stable disease, where tumors that are typically expected to grow at certain rates are prevented from such growth by the treatment, even though shrinkage is not achieved.

Effector T cells: Effector T cells, as used herein, are T lymphocytes that actively respond immediately to a stimulus, such as co-stimulation and include, but are not limited to, CD4+ T cells (also referred to as T helper or Th cells) and CD8+ T cells (also referred to as cytotoxic T cells). Th cells assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including Th1, Th2, Th3, Th17, Th9, or TFh, which secrete different cytokines to facilitate different types of immune responses. Signaling from the APC directs T cells into particular subtypes. Cytotoxic (Killer). Cytotoxic T cells (TC cells, CTLs, T-killer cells, killer T cells), on the other hand, destroy virus-infected cells and cancer cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Cytotoxic effector cell (e.g., CD8+ cells) include, e.g., perforin and granzyme B.

Epitope: The term "epitope" may be also referred to as an antigenic determinant, is a molecular determinant (e.g., polypeptide determinant) that can be specifically bound by a binding agent, immunoglobulin or T-cell receptor. Epitope determinants include chemically active surface groupings of molecules, such as amino acids, sugar side chains, phosphoryl, or sulfonyl, and, in certain embodiments, may have specific three-dimensional structural characteristics, and/or specific charge characteristics. An epitope recognized by an antibody or an antigen-binding fragment of an antibody is a structural element of an antigen that interacts with CDRs (e.g., the complementary site) of the antibody or the fragment. An epitope may be formed by contributions from several amino acid residues, which interact with the CDRs of the antibody to produce specificity. An antigenic fragment can contain more than one epitope. In certain embodiments, an antibody specifically bind an antigen when it recognizes its target antigen in a complex mixture of proteins and/or macromolecules. For example, antibodies are said to "bind to the same epitope" if the antibodies cross-compete (one prevents the binding or modulating effect of the other).

Equivalent affinity: In the context of the present disclosure, the term "equivalent affinity/affinities" is intended to mean: i) the antibody binds matrix-associated proTGFb1 complexes and cell-associated proTGFb1 complexes with less than five-fold bias in affinity, as measured by suitable in vitro binding assays, such as solution equilibrium titration (such as MSD-SET), Biolayer Interferometry (such as OCTET®) or surface plasmon resonance (such as BIA-CORE® System; and/or, ii) relative affinities of the antibody for the four complexes are uniform in that: either, the lowest affinity (highest KD numerical value) that the antibody shows among the four antigen complexes is no more than five-fold less than the average value calculated from the remaining three affinities; or, the highest affinity (lowest KD numerical value) that the antibody shows among the four antigen complexes is no more than five-fold greater than the average calculated from the remaining three affinities. Antibodies with equivalent affinities may achieve more uniform inhibitory effects, irrespective of the particular presenting molecule associated with the proTGFβ1 complex (hence "context-independent"). In particularly preferred embodiments, bias observed in average affinities between matrix-associated complexes and cell-associated complexes is no more than three-fold.

Extended Latency Lasso: The term "Extended Latency Lasso" as used herein refers to a portion of the prodomain that comprises Latency Lasso and Alpha-2 Helix, e.g., LASPPSQGEVPPGPLPEAVLALYNSTR (SEQ ID NO: 154). In some embodiments, Extended Latency Lasso further comprises a portion of Alpha-1 Helix, e.g., LVKRKRIEA (SEQ ID NO: 159) or a portion thereof.

Fibrosis: The term "fibrosis" or "fibrotic condition/disorder" refers to the process or manifestation characterized by the pathological accumulation of extracellular matrix (ECM) components, such as collagens, within a tissue or organ.

Fibrotic microenvironment: The term "fibrotic microenvironment" refers to a local disease niche within a tissue, in which fibrosis occurs in vivo. The fibrotic microenvironment may comprise disease-associated molecular signature (a set of chemokines, cytokines, etc.), disease-associated cell populations (such as activated macrophages, MDSCs, etc.) as well as disease-associated ECM environments (alterations in ECM components and/or structure). Fibrotic microenvironment is thought to support the transition of fibroblast to α-smooth muscle actin-positive myofibroblast in a TGFβ3-dependent manner. Fibrotic microenvironment may be further characterized by the infiltration of certain immune cells (such as macrophages and MDSCs).

Finger-1 (of TGFβ1 Growth Factor): As used herein, "Finger-1" is a domain within the TGFβ1 growth factor domain. In its unmutated form, Finger-1 of human proTGFβ1 contains the following amino acid sequence: CVRQLYIDFRKDLGWKWIHEPKGYHANFC (SEQ ID NO: 151). In the 3D structure, the Finger-1 domain (a portion is shown as region "5a" in FIGS. 18 and 19) comes in close proximity to Latency Lasso.

Finger-2 (of TGFβ1 Growth Factor): As used herein, "Finger-2" is a domain within the TGFβ1 growth factor domain. In its unmutated form, Finger-2 of human proTGFβ1 contains the following amino acid sequence: CVPQALEPLPIVYYVGRKPKVEQLSNMIVRSCKCS (SEQ ID NO: 152). Finger-2 includes the "binding region 6" (i.e., "6a" and "6b") depicted in FIGS. 18 and 19, which spatially lies in close proximity to Latency Lasso.

GARP-proTGFβ1 complex: As used herein, the term "GARP-TGFβ1 complex" refers to a protein complex comprising a pro-protein form or latent form of a transforming growth factor-31 (TGFβ1) protein and a glycoprotein-A repetitions predominant protein (GARP) or fragment or variant thereof. In some embodiments, a pro-protein form or latent form of TGFβ1 protein may be referred to as "pro/latent TGFβ1 protein". In some embodiments, a GARP-TGFβ1 complex comprises GARP covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a GARP-TGFβ1 complex comprises GARP non-covalently linked with pro/latent TGFβ1. In some embodiments, a GARP-TGFβ1 complex is a naturally-occurring complex, for example a GARP-TGFβ1 complex in a cell. The term "hGARP" denotes human GARP.

High-affinity: As used herein, the term "high-affinity" as in "a high-affinity proTGFβ1 antibody" refers to in vitro binding activities having a KD value of <5 nM, more preferably <1 nM. Thus, a high-affinity, context-independent proTGFβ1 antibody encompassed by the invention herein has a KD value of <5 nM, more preferably <1 nM, towards each of the following antigen complexes: LTBP1-proTGFβ1, LTBP3-proTGFβ1, GARP-proTGFβ1 and LRRC33-proTGFβ1.

Human antibody: The term "human antibody," as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

Humanized antibody: The term "humanized antibody" refers to antibodies, which comprise heavy and light chain variable region sequences from a non-human species (e.g., a mouse) but in which at least a portion of the VH and/or VL sequence has been altered to be more "human-like," i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody, or a variant, derivative, analog or fragment thereof, which immunospecifically binds to an antigen of interest and which comprises an FR region having substantially the amino acid sequence of a human antibody and a CDR region having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the FR regions are those of a human immunoglobulin consensus sequence. In an embodiment a humanized antibody also comprises at least a portion of an immunoglobulin Fc region, typically that of a human immunoglobulin. In some embodiments a humanized antibody contains the light chain as well as at least the variable domain of a heavy chain. The antibody also may include the CH1, hinge, CH2, CH3, and CH4 regions of the heavy chain. In some embodiments a humanized antibody only contains a humanized light chain. In some embodiments a humanized antibody only contains a humanized heavy chain. In specific embodiments a humanized antibody only contains a humanized variable domain of a light chain and/or humanized heavy chain.

Hydrogen/deuterium exchange mass spectrometry (HDX-MS): HDX-MS is a well-known technique employed to interrogate protein confirmation and protein-protein interactions in solution by measuring the degree of solvent accessibility. See, for example, Wei et al., (2014) Drug Discov Today 19(1): 95-102. "Hydrogen/deuterium exchange mass spectrometry for probing higher order structure of protein therapeutics: methodology and applications." The HDX-MS technique may be employed to determine a region or regions of an antigen bound by an antibody (i.e., "binding region (s)"). Thus, such binding region(s) may contain or form an epitope.

Immune-excluded or immuno-excluded tumor: As used herein, tumors characterized as "immune excluded" are devoid of or substantially devoid of intratumoral anti-tumor lymphocytes. For example, tumors with poorly infiltrated T cells may have T cells that surround the tumor, e.g., the external perimeters of a tumor mass and/or near the vicinity of vasculatures ("perivascular") of a tumor, which nevertheless fail to effectively swarm into the tumor to exert cytotoxic function against cancer cells. In other situations, tumors fail to provoke a strong immune response (so-called "cold" or "immune desert" tumors) such that few T cells are present near and in the tumor environment. In contrast to immune-excluded tumors, tumors that are infiltrated with anti-tumor lymphocytes are sometimes characterized as "hot" or "inflamed" tumors; such tumors tend to be more responsive to and therefore are the target of immune checkpoint blockade therapies ("CBTs"). Typically, however, only a fraction of patients respond to a CBT due to immune exclusion that renders the tumor resistant to the CBT.

Immunosuppression, immunosuppressive: The terms refer to the ability to suppress immune cells, such as T cells, NK cells and B cells. The gold standard for evaluating immunosuppressive function is the inhibition of T cell activity, which may include antigen-specific suppression and non-specific suppression. Regulatory T cells (Tregs) and MDSCs may be considered immunosuppressive cells. M2-polarized macrophages (e.g., disease-localized macrophages such as TAMs and FAMs) may also be characterized as immunosuppressive.

Immunological memory: Immunological memory refers to the ability of the immune system to quickly and specifically recognize an antigen that the body has previously encountered and initiate a corresponding immune response. Generally, these are secondary, tertiary and other subsequent immune responses to the same antigen. Immunological memory is responsible for the adaptive component of the immune system, special T and B cells—the so-called memory T and B cells. Antigen-naïve T cells expand and differentiate into memory and effector T cells after they encounter their cognate antigen within the context of an MHC molecule on the surface of a professional antigen presenting cell (e.g. a dendritic cell). The single unifying theme for all memory T cell subtypes is that they are long-lived and can quickly expand to large numbers of effector T cells upon re-exposure to their cognate antigen. By this mechanism they provide the immune system with "memory" against previously encountered pathogens. Memory T cells may be either CD4+ or CD8+ and usually express CD45RO. In a preclinical setting, immunological memory may be tested in a tumor rechallenge paradigm.

Isoform-specific: The term "isoform specificity" refers to an agent's ability to discriminate one isoform over other structurally related isoforms (i.e., selectivity). An isoform-specific TGFβ inhibitor exerts its inhibitory activity towards one isoform of TGFβ but not the other isoforms of TGFβ at a given concentration. For example, an isoform-specific TGFβ1 antibody selectively binds TGFβ1. A TGFβ1-specific inhibitor (antibody) preferentially targets (binds thereby inhibits) the TGFβ1 isoform over TGFβ2 or TGFβ3 with substantially greater affinity. For example, the selectivity in this context may refer to at least a 500-1000-fold difference in respective affinities as measured by an in vitro binding assay such as OCTET® and Biacor. In some embodiments, the selectivity is such that the inhibitor when used at a dosage effective to inhibit TGFβ1 in vivo does not inhibit TGFβ2 and TGFβ3. For such an inhibitor to be useful as a therapeutic, dosage to achieve desirable effects (e.g., therapeutically effective amounts) must fall within the window within which the inhibitor can effectively inhibit the TGFβ1 isoform without inhibiting TGFβ2 or TGFβ3.

Isolated: An "isolated" antibody as used herein, refers to an antibody that is substantially free of other antibodies having different antigenic specificities. In some embodiments, an isolated antibody is substantially free of other unintended cellular material and/or chemicals.

Large Latent Complex: The term "large latent complex" ("LLC") in the context of the present disclosure refers to a complex comprised of a proTGFβ1 dimer bound to so-called a presenting molecule. Thus, a large latent complex is a presenting molecule-proTGFβ1 complex, such as LTBP1-proTGFβ1, LTBP3-proTGFβ1, GARP-proTGFβ1 and LRRC33-proTGFβ1. Such complexes may be formed in vitro using recombinant, purified components capable of forming the complex. For screening purposes, presenting molecules used for forming such LLCs need not be full length polypeptides; however, the portion of the protein capable of forming disulfide bonds with the proTGFβ1 dimer complex via the cysteine residues near its N-terminal regions is typically required.

Latency associated peptide (LAP): LAP is so-called the "prodomain" of proTGFβ1. As described in more detail herein, LAP is comprised of the "Straight Jacket" domain and the "Arm" domain. Straight Jacket itself is further divided into the Alpha-1 Helix and Latency Lasso domains.

Latency Lasso: As used herein, "Latency Lasso," sometimes also referred to as Latency Loop, is a domain flanked by Alpha-1 Helix and the Arm within the prodomain of proTGFb1. In its unmutated form, Latency Lasso of human proTGFβ1 comprises the amino acid sequence: LASPPSQGEVPPGPL (SEQ ID NO: 153) and substantially corresponds to regions "2a" and "2b" shown in FIG. 18A and is spanned by Region 1 identified in FIG. 19A. As used herein, the term Extended "Latency Lasso region" refers to the Latency Lasso together with its immediate C-terminal motif referred to as Alpha-2 Helix (a2-Helix) of the prodomain. The proline residue that is at the C-terminus of the Latency Lasso provides the perpendicular "turn" like an "elbow" that connects the lasso loop to the a2-Helix. Extended Latency Lasso comprises regions shown as "2a", "2b" and "2c" in FIGS. 18 and 19. Certain high affinity TGFβ1 activation inhibitors bind at least in part to Latency Lasso or a portion thereof to confer the inhibitory potency (e.g., the ability to block activation), wherein optionally the portion of the Latency Lasso is ASPPSQGEVPPGPL (SEQ ID NO: 266). In some embodiments, the antibodies of the present disclosure bind a proTGFβ1 complex at ASPPSQGEVPPGPL (SEQ ID NO: 266) or a portion thereof. Certain high affinity TGFβ1 activation inhibitors bind at least in part to Extended Latency Lasso or a portion thereof to confer the inhibitory potency (e.g., the ability to block activation), wherein optionally the portion of the Extended Latency Lasso is KLRLASPPSQGEVPPGPLPEAVL (SEQ ID NO: 169).

Localized: In the context of the present disclosure, the term "localized" (as in "localized tumor", "disease-localized" etc.) refers to anatomically isolated or isolatable abnormalities, such as solid malignancies, as opposed to systemic disease. Certain leukemia, for example, may have both a localized component (for instance the bone marrow) and a systemic component (for instance circulating blood cells) to the disease.

LRRC33-proTGFβ1 complex: As used herein, the term "LRRC33-TGFβ1 complex" refers to a complex between a pro-protein form or latent form of transforming growth factor-31 (TGFβ1) protein and a Leucine-Rich Repeat-Containing Protein 33 (LRRC33; also known as Negative Regulator Of Reactive Oxygen Species or NRROS) or fragment or variant thereof. In some embodiments, a LRRC33-TGFβ1 complex comprises LRRC33 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LRRC33-TGFβ1 complex comprises LRRC33 non-covalently linked with pro/latent TGFβ1. In some embodiments, a LRRC33-TGFβ1 complex is a naturally-occurring complex, for example a LRRC33-TGFβ1 complex in a cell. The term "hLRRC33" denotes human LRRC33. In vivo, LRRC33 and LRRC33-containing complexes on cell surface may be internalized. LRRC33 is expressed on a subset of myeloid cells, including M2-polarized macrophages (such as TAMs) and MDSCs.

LTBP1-proTGFβ1 complex: As used herein, the term "LTBP1-TGFβ1 complex" refers to a protein complex comprising a pro-protein form or latent form of transforming growth factor-β1 (TGFβ1) protein and a latent TGF-beta binding protein 1 (LTBP1) or fragment or variant thereof. In some embodiments, a LTBP1-TGFβ1 complex comprises LTBP1 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LTBP1-TGFβ1 complex comprises LTBP1 non-covalently linked with pro/latent TGFβ1. In some embodiments, a LTBP1-TGFβ1 complex is a naturally-occurring complex, for example a LTBP1-TGFβ1 complex in a cell. The term "hLTBP1" denotes human LTBP1.

LTBP3-proTGFβ1 complex: As used herein, the term "LTBP3-TGFβ1 complex" refers to a protein complex comprising a pro-protein form or latent form of transforming growth factor-β1 (TGFβ1) protein and a latent TGF-beta binding protein 3 (LTBP3) or fragment or variant thereof. In some embodiments, a LTBP3-TGFβ1 complex comprises LTBP3 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LTBP3-TGFβ1 complex comprises LTBP1 non-covalently linked with pro/latent TGFβ1. In some embodiments, a LTBP3-TGFβ1 complex is a naturally-occurring complex, for example a LTBP3-TGFβ1 complex in a cell. The term "hLTBP3" denotes human LTBP3.

M2 or M2-like macrophage: M2 macrophages represent a subset of activated or polarized macrophages and include disease-associated macrophages in both fibrotic and tumor microenvironments. Cell-surface markers for M2-polarized macrophages typically include CD206 and CD163 (i.e., CD206+/CD163+). M2-polarized macrophages may also express cell-surface LRRC33. Activation of M2 macrophages is promoted mainly by IL-4, IL-13, IL-10 and TGFβ; they secrete the same cytokines that activate them (IL-4, IL-13, IL-10 and TGFβ). These cells have high phagocytic capacity and produce ECM components, angiogenic and chemotactic factors. The release of TGFβ by macrophages may perpetuate the myofibroblast activation, EMT and EndMT induction in the disease tissues, such as fibrotic tissue and tumor stroma. For example, M2 macrophages are essential for TGFβ-driven lung fibrosis and are also enriched in a number of tumors.

Matrix-associatedproTGFβ1: LTBP1 and LTBP3 are presenting molecules that are components of the extracellular matrix (ECM). LTBP1-proTGFβ1 and LTBP3-proTGFβ1 may be collectively referred to as "ECM-associated" (or "matrix-associated") proTGFβ1 complexes, that mediate ECM-associated TGFβ1 activation/signaling. The term also includes recombinant, purified LTBP1-proTGFβ1 and LTBP3-proTGFβ1 complexes in solution (e.g., in vitro assays) which are not physically attached to a matrix or substrate.

Maximally tolerated dose (MTD): The term MTD generally refers to, in the context of safety/toxicology considerations, the highest amount of a test article (such as a TGFβ1 inhibitor) evaluated with no-observed-adverse-effect level (NOAEL). For example, the NOAEL for Ab6 in rats was the highest dose evaluated (100 mg/kg), suggesting that the MTD for Ab6 is >100 mg/kg, based on a four-week toxicology study. The NOAEL for Ab6 in non-human primates was the highest dose evaluated (300 mg/kg), suggesting that the MTD for Ab6 in the non-human primates is >300 mg/kg, based on a four-week toxicology study.

Meso-Scale Discovery: "Meso-Scale Discovery" or "MSD" is a type of immunoassays that employs electrochemiluminescence (ECL) as a detection technique. Typically, high binding carbon electrodes are used to capture proteins (e.g., antibodies). The antibodies can be incubated with particular antigens, which binding can be detected with secondary antibodies that are conjugated to electrochemiluminescent labels. Upon an electrical signal, light intensity can be measured to quantify analytes in the sample.

Myelofibrosis: "Myelofibrosis," also known as osteomyelofibrosis, is a relatively rare bone marrow proliferative disorder (e.g., cancer), which belongs to a group of diseases called myeloproliferative disorders. Myelofibrosis is classified into the Philadelphia chromosome-negative (−) branch of myeloproliferative neoplasms. Myelofibrosis is characterized by the proliferation of an abnormal clone of hematopoietic stem cells in the bone marrow and other sites results in fibrosis, or the replacement of the marrow with scar tissue. The term myelofibrosis encompasses primary myelofibrosis (PMF), also be referred to as chronic idiopathic myelofibrosis (cIMF) (the terms idiopathic and primary mean that in these cases the disease is of unknown or spontaneous origin), as well as secondary types of myelofibrosis, such as myelofibrosis that develops secondary to polycythemia vera (PV) or essential thrombocythaemia (ET). Myelofibrosis is a form of myeloid metaplasia, which refers to a change in cell type in the blood-forming tissue of the bone marrow, and often the two terms are used synonymously. The terms agnogenic myeloid metaplasia and myelofibrosis with myeloid metaplasia (MMM) are also used to refer to primary myelofibrosis. Myelofibrosis is characterized by mutations that cause upregulation or overactivation of the downstream JAK pathway.

Myeloid cells: In hematopoiesis, myeloid cells are blood cells that arise from a progenitor cell for granulocytes, monocytes, erythrocytes, or platelets (the common myeloid progenitor, that is, CMP or CFU-GEMM), or in a narrower sense also often used, specifically from the lineage of the myeloblast (the myelocytes, monocytes, and their daughter types), as distinguished from lymphoid cells, that is, lymphocytes, which come from common lymphoid progenitor cells that give rise to B cells and T cells. Certain myeloid cell types, their general morphology, typical cell surface markers, and their immune-suppressive ability in both mouse and human, are summarized below.

| Myeloid cells | Typical Morphology | Select surface phenotype | Immune suppression |
|---|---|---|---|
| Mouse | | | |
| Neutrophils | Round shape with a segmented nucleus | CD11b+ Ly6Ghi Ly6Clo | − |
| Monocytes | Round shape with an indented nucleus | CD11b+ Ly6G− Ly6Chi | − |

| Myeloid cells | Typical Morphology | Select surface phenotype | Immune suppression |
|---|---|---|---|
| Macrophages | Round shape with pseudopodia | CD11b+ F4/80hi Ly6G– Ly6Clo CD80+ (M1) | – |
| | | F4/80+ CD206+ CD163+ (M2) | – |
| Dendritic cells | Dendritic shape with polypodia | CD11b+ CD11c+ Ly6G– Ly6C–/lo (classical) | – |
| | | CD11b– CD11c+ Ly6G– Ly6C– (classical) | – |
| | | CD11b– CD11clo Ly6G– Ly6C+ PDCA-1+ (plasmacytoid) | – |
| Fibrocytes | Spindle shape | CD11b+ ColI+ Ly6G– Ly6C+ | |
| G-MDSCs (PMN-MDSCs) | Round shape with a banded nucleus | CD11b+ Ly6G+ Ly6Clo | + |
| M-MDSCs | Round shape with a indented nucleus | CD11b+ Ly6G– Ly6Chi | + |
| Human | | | |
| Neutrophils | Round shape with a segmented nucleus | CD11b+ CD14– CD15+ CD66b+ LOX-1– | – |
| Monocytes | Round shape with an indented nucleus | CD14+ CD15– CD16– HLA-DR+ (classical) | – |
| | | CD14+ CD15– CD16+ HLA-DR+ (intermediate) | – |
| | | CD14– CD15– CD16+ HLA-DR+ (non-classical) | – |
| Macrophages | Round shape with pseudopodia | CD15– CD16+ CD80+ HLA-DR+ CD33+ (M1) | – |
| | | CD11b+ CD15– CD206+ CD163+ HLA-DR+ (M2) | +/– |
| Dendritic cells | Dendritic shape with polypodia | CD14– CD16– CD1C+ CD83+ (classical) | – |
| | | CD14– CD16– CD141+ CD83+ (classical) | – |
| | | CD14– CD16– CD303+ CD83+ (plasmacytoid) | – |
| Fibrocytes | Spindle shape | CD11b+ ColI+ CD13+ CD34+ CD45RO+ HLA-DR+ | |
| G-MDSCs (PMN-MDSCs) | Round shape with an annular nucleus | CD11b+ CD33+ CD14– CD15+ CD66b+ LOX-1+ | + |
| M-MDSCs | Round shape with a indented nucleus | CD11b+ CD33+ CD14+ CD15– HLA-DR–/lo | + |

Myeloid-derived suppressor cell: Myeloid-derived suppressor cells (MDSCs) are a heterogeneous population of cells generated during various pathologic conditions and thought to represent a pathologic state of activation of monocytes and relatively immature neutrophils. MDSCs include at least two categories of cells termed i) "granulocytic" (G-MDSC) or polymorphonuclear (PMN-MDSC), which are phenotypically and morphologically similar to neutrophils; and ii) monocytic (M-MDSC) which are phenotypically and morphologically similar to monocytes. MDSCs are characterized by a distinct set of genomic and biochemical features, and can be distinguished by specific surface molecules. For example, human G-MDSCs/PMN-MDSCs typically express the cell-surface markers CD11b, CD33, CD15 and CD66. In addition, human G-MDSCs/PMN-MDSCs may also express HLA-DR and/or Arginase. By comparison, human M-MDSCs typically express the cell surface markers CD11b, CD33 and CD14. In addition, human M-MDSCs may also express HLA-DR. In addition to such cell-surface markers, MDSCs are characterized by the ability to suppress immune cells, such as T cells, NK cells and B cells. Immune suppressive functions of MDSCs may include inhibition of antigen-non-specific function and inhibition of antigen-specific function. MDSCs can express cell surface LRRC33 and/or LRRC33-proTGFβ1.

Myofibroblast: Myofibroblasts are cells with certain phenotypes of fibroblasts and smooth muscle cells and generally express vimentin, alpha-smooth muscle actin (α-SMA; human gene ACTA2) and paladin. In many disease conditions involving extracellular matrix dysregulations (such as increased matrix stiffness), normal fibroblast cells become de-differentiated into myofibroblasts in a TGFβ3-dependent manner. Aberrant overexpression of TGFβ is common among myofibroblast-driven pathologies. TGFβ is known to promote myofibroblast differentiation, cell proliferation, and matrix production. Myofibroblasts or myofibroblast-like cells within the fibrotic microenvironment may be referred to as fibrosis-associated fibroblasts (or "FAFs"), and myofibroblasts or myofibroblast-like cells within the tumor microenvironment may be referred to as cancer-associated fibroblasts (or "CAFs").

Pan-TGFβ inhibitor/pan-inhibition of TGFβ: The term "pan-TGFβ inhibitor" refers to any agent that is capable of inhibiting or antagonizing all three isoforms of TGFβ. Such an inhibitor may be a small molecule inhibitor of TGFβ isoforms, such as those known in the art. The term includes pan-TGFβ antibody which refers to any antibody capable of binding to each of TGFβ isoforms, i.e., TGFβ1, TGFβ2, and TGFβ3. In some embodiments, a pan-TGFβ antibody binds and neutralizes activities of all three isoforms, i.e., TGFβ1, TGFβ2, and TGFβ3. The antibody 1D11 (or the human analog Fresolimumab (GC1008)) is a well-known example of a pan-TGFβ antibody that neutralizes all three isoforms of TGFβ. Examples of small molecule pan-TGFβ inhibitors include galunisertib (LY2157299 monohydrate), which is an antagonist for the TGFβ receptor I kinase/ALK5 that mediates signaling of all three TGFβ isoforms.

Perivascular (infiltration): The prefix "peri-" means "around" "surrounding" or "near," hence "perivascular" literally translates to around the blood vessels. As used herein in the context of tumor cell infiltrates, the term "perivascular infiltration" refers to a mode of entry for tumor-infiltrating immune cells (e.g., lymphocytes) via the vasculature of a solid tumor.

Potency: The term "potency" as used herein refers to activity of a drug, such as an inhibitory antibody (or fragment) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured in cell-based assays, such as TGFβ activation/inhibition assays, whereby the degree of TGFβ activation, such as activation triggered by integrin binding, can be measured in the presence or absence of test article (e.g., inhibitory antibodies) in a cell-based system. Typically, among those capable of binding to the same or overlapping binding regions of an antigen (e.g., cross-blocking antibodies), antibodies with higher affinities (lower KD values) tend to show higher potency than antibodies with lower affinities (greater $K_D$ values).

Presenting molecule: Presenting molecules in the context of the present disclosure refer to proteins that form covalent bonds with latent pro-proteins (e.g., proTGFβ1) and tether ("present") the inactive complex to an extracellular niche (such as ECM or immune cell surface) thereby maintaining its latency until an activation event occurs. Known presenting molecules for proTGFβ1 include: LTBP1, LTBP3, GARP and LRRC33, each of which can form a presenting molecule-proTGFβ1 complex (i.e., LLC), namely, LTBP1-proTGFβ1, LTBP3-proTGFβ1, GARP-proTGFβ1 and LRRC33-proTGFβ1, respectively. In nature, LTBP1 and LTBP3 are components of the extracellular matrix (ECM); therefore, LTBP1-proTGFβ1 and LTBP3-proTGFβ1 may be collectively referred to as "ECM-associated" (or "matrix-associated") proTGFβ1 complexes, that mediate ECM-associated TGFβ1 signaling/activities. GARP and LRRC33, on the other hand, are transmembrane proteins expressed on cell surface of certain cells; therefore, GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 signaling/activities.

Protection (from solvent exposure): In the context of HDX-MS-based assessment of protein-protein interactions, such as antibody-antigen binding, the degree by which a protein (e.g., a region of a protein containing an epitope) is exposed to a solvent, thereby allowing proton exchange to occur, inversely correlates with the degree of binding/interaction. Therefore, when an antibody described herein binds to a region of an antigen, the binding region is "protected" from being exposed to the solvent because the protein-protein interaction precludes the binding region from being accessible by the surrounding solvent. Thus, the protected region is indicative of a site of interaction. Typically, suitable solvents are physiological buffers.

ProTGFβ1: The term "proTGFβ1" as used herein is intended to encompass precursor forms of inactive TGFβ1 complex that comprises a prodomain sequence of TGFβ1 within the complex. Thus, the term can include the pro-, as well as the latent-forms of TGFβ1. The expression "pro/latent TGFβ1" may be used interchangeably. The "pro" form of TGFβ1 exists prior to proteolytic cleavage at the furin site. Once cleaved, the resulting form is said to be the "latent" form of TGFβ1. The "latent" complex remains non-covalently associated until further activation trigger, such as integrin-driven activation event. The proTGFβ1 complex is comprised of dimeric TGFβ1 pro-protein polypeptides, linked with disulfide bonds. The latent dimer complex is covalently linked to a single presenting molecule via the cysteine residue at position 4 (Cys4) of each of the proTGFβ1 polypeptides. The adjective "latent" may be used generally/broadly to describe the "inactive" state of TGFβ1, prior to integrin-mediated or other activation events. The proTGFβ1 polypeptide contains a prodomain (LAP) and a growth factor domain (SEQ ID NO: 146).

Regression (tumor regression): Regression of tumor or tumor growth can be used as an in vivo efficacy measure. For example, in preclinical settings, median tumor volume (MTV) and Criteria for Regression Responses Treatment efficacy may be determined from the tumor volumes of animals remaining in the study on the last day. Treatment efficacy may also be determined from the incidence and magnitude of regression responses observed during the study. Treatment may cause partial regression (PR) or complete regression (CR) of the tumor in an animal. Complete regression achieved in response to therapy (e.g., administration of a drug) may be referred to as "complete response" and the subject that achieves complete response may be referred to as a "complete responder". Thus, complete response excludes spontaneous complete regression. In some embodiments of preclinical tumor models, a PR response is defined as the tumor volume that is 50% or less of its Day 1 volume for three consecutive measurements during the course of the study, and equal to or greater than 13.5 mm³ for one or more of these three measurements. In some embodiments, a CR response is defined as the tumor volume that is less than 13.5 mm³ for three consecutive measurements during the course of the study. In preclinical model, an animal with a CR response at the termination of a study may be additionally classified as a tumor-free survivor (TFS). The term "effective tumor control" may be used to refer to a degree of tumor regression achieved in response to treatment, where, for example, the tumor volume is reduced to <25% of the endpoint tumor volume in response to treatment. For instance, in a particular model, if the endpoint tumor volume is 2,000 mm³, effective tumor control is achieved if the tumor is reduced to less than 500 mm³. Therefore, effective tumor control encompasses complete regression, as well as partial regression that reaches the threshold reduction.

Regulatory T cells: "Regulatory T cells," or Tregs, are a type of immune cells characterized by the expression of the biomarkers CD4, FOXP3, and CD25. Tregs are sometimes referred to as suppressor T cells and represent a subpopulation of T cells that modulate the immune system, maintain tolerance to self-antigens, and prevent autoimmune disease. Tregs are immunosuppressive and generally suppress or downregulate induction and proliferation of effector T (Teff) cells. Tregs can develop in the thymus (so-called CD4+ Foxp3+"natural" Tregs) or differentiate from naïve CD4+ T cells in the periphery, for example, following exposure to TGFβ or retinoic acid. Tregs can express cell surface GARP-proTGFβ1.

Resistance (to therapy): Resistance to a particular therapy (such as CBT) may be due to the innate characteristics of the disease such as cancer ("primary resistance"), or due to acquired phenotypes that develop over time following the treatment ("acquired resistance"). Patients who do not show therapeutic response to a therapy (e.g., those who are non-responders or poorly responsive to the therapy) are said to have primary resistance to the therapy. Patients who initially show therapeutic response to a therapy but later lose effects (e.g., progression or recurrence despite continued therapy) are said to have acquired resistance to the therapy.

Response Evaluation Criteria in Solid Tumors (RECIST) and iRECIST: RECIST is a set of published rules that define when tumors in cancer patients improve ("respond"), stay the same ("stabilize"), or worsen ("progress") during treatment. The criteria were published in February 2000 by an international collaboration including the European Organisation for Research and Treatment of Cancer (EORTC), National Cancer Institute of the United States, and the National Cancer Institute of Canada Clinical Trials Group. Subsequently, a revised version of the RECIST guideline (RECIST v 1.1) has been widely adapted (see: Eisenhauera et al. (2009), "New response evaluation criteria in solid tumours: Revised RECIST guideline (version 1.1)" Eur J Cancer 45: 228-247, incorporated herein).

Response criteria are as follows: Complete response (CR): Disappearance of all target lesions; Partial response (PR): At least a 30% decrease in the sum of the LD of target lesions, taking as reference the baseline sum LD; Stable disease (SD): Neither sufficient shrinkage to qualify for PR nor sufficient increase to qualify for PD, taking as reference the smallest sum LD since the treatment started; Progressive disease (PD): At least a 20% increase in the sum of the LD of target lesions, taking as reference the smallest sum LD recorded since the treatment started or the appearance of one or more new lesions.

On the other hand, iRECIST provides a modified set of criteria that takes into account immune-related response (see: ncbi.nlm.nih.gov/pmc/articles/PMC5648544/contents of which are incorporated herein by reference). The RECIST and iRECIST criteria are standardized, may be revised from time to time as more data become available, and are well understood in the art.

Solid tumor: The term "solid tumor" refers to proliferative disorders resulting in an abnormal growth or mass of tissue that usually does not contain cysts or liquid areas. Solid tumors may be benign (non-cancerous), or malignant (cancerous). Solid tumors include tumors of advanced malignancies, such as locally advanced solid tumors and metastatic cancer. Solid tumors are typically comprised of multiple cell types, including, without limitation, cancerous (malignant) cells, stromal cells such as CAFs, and infiltrating leukocytes, such as macrophages, MDSCs and lymphocytes. Solid tumors to be treated with an isoform-selective inhibitor of TGFβ1, such as those described herein, are typically TGFβ1-positive (TGFβ1+) tumors, which may include multiple cell types that produce TGFβ1. In certain embodiments, the TGFβ1+ tumor may also co-express TGFβ3 (i.e., TGFβ3-positive). For example, certain tumors are TGFβ1/3-co-dominant. In some embodiments, such tumors are caused by cancer of epithelial cells, e.g., carcinoma.

Solution Equilibrium Titration (SET): The SET is an assay whereby binding between two molecules (such as an antigen and an antibody that binds the antigen) can be measured at equilibrium in a solution. For example, Meso-Scale Discovery ("MSD")-based SET, or MSD-SET, is a useful mode of determining dissociation constants for particularly high-affinity protein-protein interactions at equilibrium, such as picomolar-affinity antibodies binding to their antigens (see, for example: Ducata et al. (2015) J Biomolecular Screening 20(10): 1256-1267). The SET-based assays are particularly useful for determining $K_D$ values of antibodies with sub-nanomolar (e.g., picomolar) affinities.

Specific binding: As used herein, the term "specific binding" or "specifically binds" means that the interaction of the antibody, or antigen binding portion thereof, with an antigen is dependent upon the presence of a particular structure (e.g., an antigenic determinant or epitope). For example, the antibody, or antigen binding portion thereof, binds to a specific protein rather than to proteins generally. In some embodiments, an antibody, or antigen binding portion thereof, specifically binds to a target, e.g., TGFβ1, if the antibody has a $K_D$ for the target of at least about $10^{-8}$ M, $10^{-9}$ M, $10^{-10}$ M, $10^{-11}$ M, $10^{-12}$ M, or less. In some embodiments, the term "specific binding to an epitope of proTGFβ1", "specifically binds to an epitope of proTGFβ1", "specific binding to proTGFβ1", or "specifically binds to proTGFβ1" as used herein, refers to an antibody, or antigen binding portion thereof, that binds to proTGFβ1 and has a dissociation constant (KD) of $1.0 \times 10^{-8}$ M or less, as determined by suitable in vitro binding assays, such as surface plasmon resonance and Biolayer Interferometry (BLI). In one embodiment, an antibody, or antigen binding portion thereof, can specifically bind to both human and a non-human (e.g., mouse) orthologues of proTGFβ1.

Subject: The term "subject" in the context of therapeutic applications refers to an individual who receives clinical care or intervention, such as treatment, diagnosis, etc. Suitable subjects include vertebrates, including but not limited to mammals (e.g., human and non-human mammals). Where the subject is a human subject, the term "patient" may be used interchangeably. In a clinical context, the term "a patient population" or "patient subpopulation" is used to refer to a group of individuals that falls within a set of criteria, such as clinical criteria (e.g., disease presentations, disease stages, susceptibility to certain conditions, responsiveness to therapy, etc.), medical history, health status, gender, age group, genetic criteria (e.g., carrier of certain mutation, polymorphism, gene duplications, DNA sequence repeats, etc.) and lifestyle factors (e.g., smoking, alcohol consumption, exercise, etc.).

Surface plasmon resonance (SPR): Surface plasmon resonance is an optical phenomenon that enables detection of unlabeled interactants in real time. The SPR-based biosensors, such as those commercially available from BIA-CORE®, can be employed to measure biomolecular interactions, including protein-protein interactions, such as antigen-antibody binding. The technology is widely known in the art and is useful for the determination of parameters such as binding affinities, kinetic rate constants and thermodynamics.

TGFβ1-related indication: A "TGFβ1-related indication" is a TGFβ1-associated disorder and means any disease or disorder, and/or condition, in which at least part of the pathogenesis and/or progression is attributable to TGFβ1 signaling or dysregulation thereof. Certain TGFβ1-associated disorders are driven predominantly by the TGFβ1 isoform. Subjects having a TGFβ1-related indication may benefit from inhibition of the activity and/or levels TGFβ1. Certain TGFβ1-related indications are driven predominantly by the TGFβ1 isoform. TGFβ1-related indications include, but are not limited to: fibrotic conditions (such as organ fibrosis, and fibrosis of tissues involving chronic inflammation), proliferative disorders (such as cancer, e.g., solid tumors and myelofibrosis), disease associated with ECM dysregulation (such as conditions involving matrix stiffening and remodeling), disease involving mesenchymal transition (e.g., EndMT and/or EMT), disease involving proteases, disease with aberrant gene expression of certain markers described herein. These disease categories are not intended to be mutually exclusive.

TGFβ inhibitor: The term "TGFβ inhibitor" refers to any agent capable of antagonizing biological activities, signaling or function of TGFβ growth factor (e.g., TGFβ1, TGFβ2 and/or TGFβ3). The term is not intended to limit its mechanism of action and includes, for example, neutralizing inhibitors, receptor antagonists, soluble ligand traps, and activation inhibitors of TGFβ. TGFβ inhibitors also include antibodies that are capable of reducing the availability of latent proTGFβ which can be activated in the niche, for example, by inducing antibody-dependent cell mediated cytotoxicity (ADCC), and/or antibody-dependent cellular phagocytosis (ADPC), as well as antibodies that result in internalization of cell-surface complex comprising latent proTGFβ, thereby removing the precursor from the plasma membrane without depleting the cells themselves. Internalization may be a suitable mechanism of action for LRRC33-containing protein complexes (such as human LRRC33-proTGFβ1) which results in reduced levels of cells expressing LRRC33-containing protein complexes on cell surface.

The "TGFβ family" is a class within the TGFβ superfamily and in human contains three members: TGFβ1, TGFβ2, and TGFβ3, which are structurally similar. The three growth factors are known to signal via the same receptors.

TGFβ1-positive cancer/tumor: The term, as used herein, refers to a cancer/tumor with aberrant TGFβ1 expression (overexpression). Many human cancer/tumor types show predominant expression of the TGFβ1 (note that "TGFB" is sometimes used to refer to the gene as opposed to protein) isoform. In some cases, such cancer/tumor may show co-dominant expression of another isoform, such as TGFβ3. A number of epithelial cancers (e.g., carcinoma) may co-express TGFβ1 and TGFβ3. Within the tumor environment of TGFβ1-positive tumors, TGFβ1 may arise from multiple sources, including, for example, cancer cells, tumor-associated macrophages (TAMs), cancer-associated fibroblasts (CAFs), regulatory T cells (Tregs), myeloid-derived suppressor cells (MDSCs), and the surrounding extracellular matrix (ECM). In the context of the present disclosure, preclinical cancer/tumor models that recapitulate human conditions are TGFβ1-positive cancer/tumor.

Therapeutic window: The term "therapeutic window" refers to a dosage range that produces therapeutic response without causing significant/observable/unacceptable adverse effect (e.g., within adverse effects that are acceptable or tolerable) in subjects. Therapeutic window may be calculated as a ratio between minimum effective concentrations (MEC) to the minimum toxic concentrations (MTC). To illustrate, a TGFβ1 inhibitor that achieves in vivo efficacy at 10 mg/kg dosage and shows tolerability or acceptable toxicities at 100 mg/kg provides at least a 10-fold (e.g., 10×) therapeutic window. By contrast, a pan-inhibitor of TGFβ that is efficacious at 10 mg/kg but causes adverse effects at less than the effective dose is said to have "dose-limiting toxicities." Generally, the maximally tolerated dose (MTD) may set the upper limit of the therapeutic window.

For example, Ab6 was shown to be efficacious at dosage ranging between about 3-30 mg/kg/week and was also shown to be free of observable toxicities associated with pan-inhibition of TGFβ at dosage of at least 100 or 300 mg/kg/week for 4 weeks in rats or non-human primates. Based on this, Ab6 shows at minimum a 3.3-fold and up to 100-fold therapeutic window.

Toxicity: As used herein, the term "toxicity" or "toxicities" refers to unwanted in vivo effects in subjects (e.g., patients) associated with a therapy administered to the subjects (e.g., patients), such as undesirable side effects and adverse events. "Tolerability" refers to a level of toxicities associated with a therapy or therapeutic regimen, which can be reasonably tolerated by patients, without discontinuing the therapy due to the toxicities. Typically, toxicity/toxicology studies are carried out in one or more preclinical models prior to clinical development to assess safety profiles of a drug candidate (e.g., monoclonal antibody therapy). Toxicity/toxicology studies may help determine the "no-observed-adverse-effect level (NOAEL)" and the "maximally tolerated dose (MTD)" of a test article, based on which a therapeutic window may be deduced. Preferably, a species that is shown to be sensitive to the particular intervention should be chosen as a preclinical animal model in which safety/toxicity study is to be carried out. In case of TGFβ inhibition, suitable species include rats, dogs, and cynos. Mice are reported to be less sensitive to pharmacological inhibition of TGFβ and may not reveal toxicities that are potentially dangerous in other species, including human, although certain studies report toxicities observed with pan-inhibition of TGFβ in mice. To illustrate in the context of the present disclosure, the NOAEL for Ab6 in rats was the highest dose evaluated (100 mg/kg), suggesting that the MTD is >100 mg/kg, based on a four-week toxicology study. The MTD of Ab6 in non-human primates is >300 mg/kg based on a four-week toxicology study.

For determining NOAELs and MTDs, preferably, a species that is shown to be sensitive to the particular intervention should be chosen as a preclinical animal model in which safety/toxicology study is to be carried out. In case of TGFβ inhibition, suitable species include, but are not limited to, rats, dogs, and cynos. Mice are reported to be less sensitive to pharmacological inhibition of TGFβ and may not reveal toxicities that are potentially serious or dangerous in other species, including human.

Translatability: In the context of drug discovery and clinical development, the term "translatability" or "translatable" refers to certain quality or property of preclinical models or data that recapitulate human conditions. As used herein, a preclinical model that recapitulates a TGFβ1 indication typically shows predominant expression of TGFB1 (or TGFβ1), relative to TGFB2 (or TGFβ2) and TGFB3 (or TGFβ3). In combination therapy paradigms, for example, translatability may require the same underlining mechanisms of action that the combination of actives is aimed to effectuate in the model. As an example, many human tumors are immune excluded, TGFβ1-positive tumors that show primary resistance to a checkpoint blockade therapy (CBT). A second therapy (such as TGFβ1 inhibitors) may be used in combination to overcome the resistance to CBT. In this scenario, suitable translatable preclinical models include TGFβ1-positive tumors that show primary resistance to a checkpoint blockade therapy (CBT).

Treat/treatment: The term "treat" or "treatment" includes therapeutic treatments, prophylactic treatments, and applications in which one reduces the risk that a subject will develop a disorder or other risk factor. Thus the term is intended to broadly mean: causing therapeutic benefits in a patient by, for example, enhancing or boosting the body's immunity; reducing or reversing immune suppression; reducing, removing or eradicating harmful cells or substances from the body; reducing disease burden (e.g., tumor burden); preventing recurrence or relapse; prolonging a refractory period, and/or otherwise improving survival. The term includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In the context of combination therapy, the term may also refer to: i) the ability of a second therapeutic to reduce the effective dosage of a first therapeutic so as to reduce side effects and increase tolerability; ii) the ability of a second therapy to render the patient more responsive to a first therapy; and/or iii) the ability to effectuate additive or synergistic clinical benefits.

Tumor-associated macrophage (TAM): TAMs are polarized/activated macrophages with pro-tumor phenotypes (M2-like macrophages). TAMs can be either marrow-originated monocytes/macrophages recruited to the tumor site or tissue-resident macrophages which are derived from erythro-myeloid progenitors. Differentiation of monocytes/macrophages into TAMs is influenced by a number of factors, including local chemical signals such as cytokines, chemokines, growth factors and other molecules that act as ligands, as well as cell-cell interactions between the monocytes/macrophages that are present in the niche (tumor microenvironment). Generally, monocytes/macrophages can be polarized into so-called "M1" or "M2" subtypes, the latter being associated with more pro-tumor phenotype. In a solid tumor, up to 50% of the tumor mass may correspond to macrophages, which are preferentially M2-polarized. Among tumor-associated monocytes and myeloid cell populations, M1 macrophages typically express cell surface HLA-DR, CD68 and CD86, while M2 macrophages typically express cell surface HLA-DR, CD68, CD163 and CD206. Tumor-associated, M2-like macrophages (such as M2c and M2d subtypes) can express cell surface LRRC33 and/or LRRC33-proTGFβ1.

Tumor microenvironment: The term "tumor microenvironment (TME)" refers to a local disease niche, in which a tumor (e.g., solid tumor) resides in vivo. The TME may comprise disease-associated molecular signature (a set of chemokines, cytokines, etc.), disease-associated cell populations (such as TAMs, CAFs, MDSCs, etc.) as well as disease-associated ECM environments (alterations in ECM components and/or structure).

Variable region: The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

Other than in the operating examples, or where otherwise indicated, all numbers expressing quantities of ingredients or reaction conditions used herein should be understood as modified in all instances by the term "about." The term "about" when used in connection with percentages can mean±1%.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, e.g., 10-20, 1-10, 30-40, etc.

Transforming Growth Factor-Beta (TGFβ)

The Transforming Growth Factor-beta (TGFβ) activities and subsequent partial purification of the soluble growth factors were first described in the late 1970's to early 1980's, with which the TGFβ field began some 40 years ago. To date, 33 gene products have been identified that make up the large TGFβ superfamily. The TGFβ superfamily can be categorized into at least three subclasses by structural similarities: TGFβs, Growth-Differentiation Factors (GDFs) and Bone-Morphogenetic Proteins (BMPs). The TGFβ subclass is comprised of three highly conserved isoforms, namely, TGFβ1, TGFβ2 and TGFβ3, which are encoded by three separate genes in human.

The TGFβs are thought to play key roles in diverse processes, such as inhibition of cell proliferation, extracellular matrix (ECM) remodeling, and immune homeostasis.

The importance of TGFβ1 for T cell homeostasis is demonstrated by the observation that TGFβ1−/− mice survive only 3-4 weeks, succumbing to multi-organ failure due to massive immune activation (Kulkarni, A. B., et al., Proc Natl Acad Sci USA, 1993. 90(2): p. 770-4; Shull, M. M., et al., Nature, 1992. 359(6397): p. 693-9). The roles of TGFβ2 and TGFβ3 are less clear. Whilst the three TGFβ isoforms have distinct temporal and spatial expression patterns, they signal through the same receptors, TGFβRI and TGFβRII, although in some cases, for example for TGFβ2 signaling, type III receptors such as betaglycan are also required (Feng, X. H. and R. Derynck, Annu Rev Cell Dev Biol, 2005. 21: p. 659-93; Massague, J., Annu Rev Biochem, 1998. 67: p. 753-91). Ligand-induced oligomerization of TGFβRI/II triggers the phosphorylation of SMAD transcription factors, resulting in the transcription of target genes, such as Col1a1, Col3a1, ACTA2, and SERPINE1 (Massague, J., J. Seoane, and D. Wotton, Genes Dev, 2005. 19(23): p. 2783-810). SMAD-independent TGFβ signaling pathways have also been described, for example in cancer or in the aortic lesions of Marfan mice (Derynck, R. and Y. E. Zhang, Nature, 2003. 425(6958): p. 577-84; Holm, T. M., et al., Science, 2011. 332(6027): p. 358-61).

The biological importance of the TGFβ pathway in humans has been validated by genetic diseases. Camurati-Engelman disease results in bone dysplasia due to an autosomal dominant mutation in the TGFB1 gene, leading to constitutive activation of TGFβ1 signaling (Janssens, K., et al., J Med Genet, 2006. 43(1): p. 1-11). Patients with Loeys/Dietz syndrome carry autosomal dominant mutations in components of the TGFβ signaling pathway, which cause aortic aneurism, hypertelorism, and bifid uvula (Van Laer, L., H. Dietz, and B. Loeys, Adv Exp Med Biol, 2014. 802: p. 95-105). As TGFβ pathway dysregulation has been implicated in multiple diseases, several drugs that target the TGFβ pathway have been developed and tested in patients, but with limited success.

Dysregulation of the TGFβ signaling has been associated with a wide range of human diseases. Indeed, in a number of disease conditions, such dysregulation may involve multiple facets of TGFβ function. Diseased tissue, such as fibrotic and/or inflamed tissues and tumors, may create a local environment in which TGFβ activation can cause exacerbation or progression of the disease, which may be at least in part mediated by interactions between multiple TGFβ-responsive cells, which are activated in an autocrine and/or paracrine fashion, together with a number of other cytokines, chemokines and growth factors that play a role in a particular disease setting.

For example, a tumor microenvironment (TME) contains multiple cell types expressing TGFβ1, such as activated myofibroblast-like fibroblasts, stromal cells, infiltrating macrophages, MDSCs and other immune cells, in addition to cancer (i.e., malignant) cells. Thus, the TME represents a heterogeneous population of cells expressing and/or responsive to TGFβ1 but in association with more than one types of presenting molecules, e.g., LTBP1, LTBP3, LRRC33 and GARP, within the niche.

Advances in immunotherapy have transformed the effective treatment landscape for a growing number of cancer patients. Most prominent are the checkpoint blockade therapies (CBT), which have now become part of standard of care regimens for an increasing number of cancers. While profound and durable responses to CBT have been observed across a growing number of cancer types, it is now clear that a significant fraction of tumors appear to be refractory to CBT even at the outset of treatment, hence pointing to primary resistance as a major challenge to enabling many patients' immune systems to target and eliminate tumor cells. Efforts to understand and address the underlying mechanisms conferring primary resistance to CBT have been undertaken in order to broaden treatment efficacy for a greater number of patients. However, this enthusiasm has been curbed by lackluster clinical trial results and failures when combining CBTs with agents known to affect the same tumor type or to modulate seemingly relevant components of the immune system. A likely reason is that a clear mechanistic rationale for the given combination is often not rooted in clinically-derived data, and has thus led to uncertain and confounding outcomes in trials intended to enhance approved single-agent therapies. It has become clear that the design of combination immunotherapy should be rooted in scientific evidence of relevance to underlying tumor and immune system biology.

Recently, a phenomenon referred to as "immune exclusion" was coined to describe a tumor environment from which anti-tumor effector T cells (e.g., CD8+ T cells) are kept away (hence "excluded") by immunosuppressive local cues. More recently, a number of retrospective analyses of clinically-derived tumors have implicated TGFβ pathway activation in mediating primary resistance to CBT. For example, transcriptional profiling and analysis of pretreatment melanoma biopsies revealed an enrichment of TGFβ3-associated pathways and biological processes in tumors that are non-responsive to anti-PD-1 CBT. In an immune-excluded tumor, effector cells, which would otherwise be capable of attacking cancer cells by recognizing cell-surface tumor antigens, are prevented from gaining access to the site of cancer cells. In this way, cancer cells evade host immunity and immuno-oncologic therapeutics, such as checkpoint inhibitors, that exploit and rely on such immunity. Indeed, such tumors show resistance to checkpoint inhibition, such as anti-PD-1 and anti-PD-L1 antibodies, presumably because target T cells are blocked from entering the tumor hence failing to exert anti-cancer effects.

A number of retrospective analyses of clinically-derived tumors points to TGFβ pathway activation in mediating primary resistance to CBT. For example, transcriptional profiling and analysis of pretreatment melanoma biopsies revealed an enrichment of TGFβ3-associated pathways and biological processes in tumors that are non-responsive to anti-PD-1 CBT. More recently, similar analyses of tumors from metastatic urothelial cancer patients revealed that lack of response to PD-L1 blockade with atezolizumab was associated with transcriptional signatures of TGFβ signaling, particularly in tumors wherein CD8+ T cells appear to be excluded from entry into the tumor. The critical role of TGFβ signaling in mediating immune exclusion resulting in anti-PD-(L)1 resistance has been verified in the EMT-6 syngeneic mouse model of breast cancer. While the EMT-6 tumors are weakly responsive to treatment with an anti-PD-L1 antibody, combining this checkpoint inhibitor with 1 D11, an antibody that blocks the activity of all TGFβ isoforms, resulted in a profound increase in the frequency of complete responses when compared to treatment with individual inhibitors. The synergistic antitumor activity is proposed to be due to a change in cancer-associated fibroblast (CAF) phenotype and a breakdown of the immune excluded phenotype, resulting in infiltration of activated CD8+ T cells into the tumors. Similar results were found in a murine model of colorectal cancer and metastasis using a combination of an anti-PD-L1 antibody with galunisertib, a small molecule inhibitor of the type I TGFβ receptor ALK5 kinase. Collectively, these findings suggest that inhibiting the TGFβ pathway in CBT-resistant tumors could be a promising approach to improve or increase the number of clinical responses to CBT. While recent work has implicated a relationship between TGFβ pathway activation and primary CBT resistance, TGFβ signaling has long been linked to features of cancer pathogenesis. As a potent immunosuppressive factor, TGFβ prevents antitumor T cell activity and promotes immunosuppressive macrophages. Malignant cells often become resistant to TGFβ signaling as a mechanism to evade its growth and tumor-suppressive effects. TGFβ activates CAFs, inducing extracellular matrix production and promotion of tumor progression. Finally, TGFβ induces EMT, thus supporting tissue invasion and tumor metastases.

Mammals have distinct genes that encode and express the three TGFβ growth factors, TGFβ1, TGFβ2, and TGFβ3, all of which signal through the same heteromeric TGFβ receptor complex. Despite the common signaling pathway, each TGFβ isoform appears to have distinct biological functions, as evidenced by the non-overlapping TGFβ knockout mouse phenotypes. All three TGFβ isoforms are expressed as inactive prodomain-growth factor complexes, in which the TGFβ prodomain, also called latency-associated peptide (LAP), wraps around its growth factor and holds it in a latent, non-signaling state. Furthermore, latent TGFβ is co-expressed with latent TGFβ-binding proteins and forms large latent complexes (LLCs) through disulfide linkage. Association of latent TGFβ with Latent TGFβ Binding Protein-1 (LTBP1) or LTBP3 enables tethering to extracellular matrix, whereas association to the transmembrane proteins GARP or LRRC33 enables elaboration on the surface of Tregs or macrophages, respectively. In vivo, latent TGFβ1 and latent TGFβ3 are activated by a subset of αV integrins, which bind a consensus RGD sequence on LAP, triggering a conformational change to release the growth factor. The mechanism by which latent TGFβ2 is activated is less clear as it lacks a consensus RGD motif. TGFβ1 release by proteolytic cleavage of LAP has also been implicated as an activation mechanism, but its biological relevance is less clear.

Although the pathogenic role of TGFβ activation is clear in several disease states, it is equally clear that therapeutic targeting of the TGFβ pathway has been challenging due to the pleiotropic effects that result from broad and sustained pathway inhibition. For example, a number of studies have shown that small molecule-mediated inhibition of the TGFβ type I receptor kinase ALK5 (TGFBR1) or blockade of all three highly related TGFβ growth factors with a high-affinity antibody resulted in severe cardiac valvulopathies in mice, rats and dogs. These "pan"-TGFβ approaches that block all TGFβ signaling therefore have a very narrow therapeutic window, which has proven to be an impediment to the treatment of a number of disease-relevant processes with very high unmet medical need. No TGFβ-targeting therapy has been approved to date and clinical trial results with such modalities have largely been disappointing, likely due to the use of what proved to be inefficacious dosing regimens that were required in order to accommodate safety concerns.

The safety concerns that come with broad TGFβ inhibition, together with the compelling evidence for a critical role for this pathway in multiple disease processes, suggests that a better understanding of the specific roles played by of one or more TGFβ family members in disease pathology may lead to a viable avenue for therapeutic intervention. With respect to TGFβ and responses to CBT, herein we observe the prevalent expression of TGFβ1 in many human tumors, suggesting that this family member may be the key driver of this pathway's contribution to primary resistance.

As mentioned above, increasing evidence suggests that TGFβ may be a primary player in creating and/or maintaining immunosuppression in disease tissues, including the immune-excluded tumor environment. Therefore, TGFβ inhibition may unblock the immunosuppression and enable effector T cells (particularly cytotoxic CD8+ T cells) to access and kill target cancer cells. In addition to tumor infiltration, TGFβ inhibition may also promote CD8+ T cell expansion. Such expansion may occur in the lymph nodes and/or in the tumor (intratumorally). While the exact mechanism underlining this process has yet to be elucidated, it is contemplated that immunosuppression is at least in part mediated by immune cell-associated TGFβ1 activation involving regulatory T cells and activated macrophages.

It has been reported that TGFβ directly promotes Foxp3 expression in CD4+ T cells, thereby converting them into a regulatory (immunosuppressive) phenotype (i.e., Treg). Moreover, Tregs suppress effector T cell proliferation (see, for example, FIG. 26B), thereby reducing immune responses. This process is shown to be TGFβ1-dependent and likely involves GARP-associated TGFβ1 signaling. Observations in both humans and animal models have indicated that an increase in Tregs in TME is associated with poor prognosis in multiple types of cancer. In addition, Applicant has previously shown that M2-polarized macrophages exposed to tumor-derived factors such as M-CSF dramatically upregulate cell-surface expression of LRRC33, which is a presenting molecule for TGFβ1 (see, for example: PCT/US2018/031759). These so-called tumor-associated macrophages (or TAMs) are thought to contribute to the observed TGFβ1-dependent immunosuppression in TMEs and promote tumor growth.

A number of solid tumors are characterized by having tumor stroma enriched with myofibroblasts or myofibroblast-like cells. These cells produce collagenous matrix that surrounds or encases the tumor (such as desmoplasia), which at least in part may be caused by overactive TGFβ1 signaling. It is contemplated that the TGFβ1 activation is mediated via ECM-associated presenting molecules, e.g., LTBP1 and LTBP3 in the tumor stroma.

Applicant previously disclosed antibodies capable of inhibiting TGFβ1 activation in many of these biological contexts which showed promising effects both in vitro and in vivo (see, for example, PCT/US2018/012601). Challenge remained, however, i) to develop an improved antibody that shows less bias in affinities towards various antigen complexes in order to ensure uniformly inhibitory effects across different biological contexts or niches in which disease-associated TGFβ1 resides, and/or, ii) to develop such an antibody that provides even greater potency than previously described counterpart.

For the work presented herein, it was envisaged that improved antibodies should embody all or most of the following features: 1) selectivity towards TGFβ1 should be maintained to minimize unwanted toxicities associated with pan-inhibition ("isoform-selectivity") (see, for example, PCT/US2017/021972); 2) should exhibit broad binding activities across various biological contexts, or, both matrix-associated and cell-associated categories ("context-independent"); 3) should achieve more even or unbiased affinities across multiple antigen complexes ("uniformity"); 4) should show strong binding activities for each of the antigen complexes, ("high-affinity"); and, 5) should have robust inhibitory activities for each context ("potency"). Furthermore, the preferred mechanism of action is to inhibit the activation step so the inhibitor can target a tissue-tethered, latent TGFβ1 complex, so as to preemptively prevent downstream activation events to achieve durable effects, rather than to directly target soluble/free growth factors ("durability"). As disclosed in further detail herein, the novel, improved TGFβ1 inhibitors of the present disclosure are highly potent and highly selective inhibitor of latent TGFβ1 activation. Data presented herein demonstrate, inter alia, that this mechanism of isoform-specific inhibition is sufficient to overcome primary resistance to anti-PD-1 in syngeneic mouse models that closely recapitulate some of the features of primary resistance to CBT found in human cancers. Together with the improved preclinical safety profile of such antibodies compared to "pan"-TGFβ inhibitors, these efficacy data provide a rationale for exploring the therapeutic use of selective TGFβ1 inhibition to broaden and enhance clinical responses to checkpoint blockade in cancer immunotherapy, as well as to treat a number of additional TGFβ1-related indications.

Novel, High-Affinity, Isoform-Selective Antibodies of proTGFβ1

General Features

Disclosed herein are high-affinity, improved inhibitors of TGFβ1, characterized in that, as compared to TGFβ1-selective inhibitors of earlier disclosures, these antibodies have enhanced biding properties, increased inhibitory potency, and maintain the desirable safety profiles and isoform selectivity. These TGFβ1-selective inhibitors of the present disclosure are monoclonal antibodies (e.g., immunoglobulins, engineered immunoglobulin-like molecules, antigen-binding fragments or portions thereof) that specifically bind at least a portion of the prodomain (sometimes referred to as "LAP") of a latent proTGFβ1 complex and have isoform-selective inhibitory activity towards TGFβ1 (see "Core Properties" of Table 1).

Enhanced binding properties of the antibodies according to the present disclosure include increased affinities, as measured at equilibrium. In some embodiments, the antibody has a KD of ≤1 nM for at least one of the human LLC complexes (hLTBP1-proTGFβ1, hLTBP3-proTGFβ1, hGARP-proTGFβ1 and/or hLRRC33-proTGFβ1) as measured by MSD-SET. In some embodiments, such antibody has a KD of ≤1 nM for two of the human LLC complexes selected from: hLTBP1-proTGFβ1, hLTBP3-proTGFβ1, hGARP-proTGFβ1 and hLRRC33-proTGFβ1, as measured by MSD-SET. In some embodiments, such antibody has a KD of ≤1 nM for three of the human LLC complexes selected from: hLTBP1-proTGFβ1, hLTBP3-proTGFβ1, hGARP-proTGFβ1 and hLRRC33-proTGFβ1, as measured by MSD-SET. In preferred embodiments, such antibody has a KD of ≤1 nM for each of the human LLC complexes: hLTBP1-proTGFβ1, hLTBP3-proTGFβ1, hGARP-proTGFβ1 and hLRRC33-proTGFβ1, as measured by MSD-SET. According to the present disclosure, high-affinity antibodies may have a KD value for a particular antigen (e.g., antigen complex) that is 1 nM or less, e.g., ≤1 nM, ≤0.5 nM, ≤400 μM, ≤300 μM, ≤200 μM, and ≤100 μM, at equilibrium.

The present invention also includes antibodies or antigen-binding fragments thereof that are capable of specifically binding each of the human LLC complexes (hLTBP1-proTGFβ1, hLTBP3-proTGFβ1, hGARP-proTGFβ1, and hLRRC33-proTGFβ1) with a KD of ≤10 nM (e.g., ≤10 nM, ≤9 nM, ≤8 nM, ≤7 nM, ≤6 nM, ≤5 nM, ≤4 nM, ≤3 nM, ≤2 nM, ≤1 nM, ≤0.5 nM and ≤0.1 nM) as measured at equilibrium, such as MSD-SET. In some embodiments, the antibody binds each of the aforementioned LLC complexes with a KD of ≤5 nM, as measured by a solution equilibrium titration-based method. In some embodiments, the antibody binds each of the aforementioned LLC complexes with a KD of ≤1 nM, as measured by a solution equilibrium titration-based method.

For therapeutic use to treat a TGFβ1-related indication involving both the dysregulation of the extracellular matrix and an immune component, it is advantageous to select an antibody that has a high affinity (e.g., KD of ≤1 nM) for at least one of the ECM-associated proTGFβ1 complexes (hLTBP1-proTGFβ1 and/or hLTBP3-proTGFβ1) and additionally at least one of the cell-associated proTGFβ1 complexes (hGARP-proTGFβ1 and/or hLRRC33-proTGFβ1), so as to exert inhibitory effects on both contexts (e.g., at the ECM and drawn to immune cells). In some embodiments, the antibody has a high affinity (e.g., KD of ≤1 nM) for both hLTBP1-proTGFβ1 and hLTBP3-proTGFβ1 and additionally at least one of the cell-associated proTGFβ1 complexes (hGARP-proTGFβ1 or hLRRC33-proTGFβ1). Yet in other embodiments, the antibody has a high affinity (e.g., KD of ≤1 nM) for each of the aforementioned complexes (hLTBP1-proTGFβ1, hLTBP3-proTGFβ1, hGARP-proTGFβ1 and hLRRC33-proTGFβ1).

In preferred embodiments, such antibody has a KD of ≤200 μM for each of the human complexes, e.g., ≤100 μM, as measured by a solution equilibrium titration-based method, such as MSD-SET.

Embodiments of the present disclosure include high-affinity context-independent antibodies. Such antibodies are capable of binding with equivalent affinities to the four known presenting molecule-proTGFβ1 complexes, namely, LTBP1-proTGFβ1, LTBP3-proTGFβ1, GARP-proTGFβ1, and LRRC33-proTGFβ1. Equivalent affinities may mean, either, the lowest affinity (highest KD numerical value) that the antibody shows among the four antigen complexes is no more than five-fold less than the average value calculated from the remaining three affinities; or, the highest affinity (lowest KD numerical value) that the antibody shows among the four antigen complexes is no more than five-fold greater than the average calculated from the remaining three affinities. In some embodiments, when the ratio of average KD values of the two ECM-associated complexes and average KD values of the two cell-associated complexes is no more than three-fold, such antibodies may be said to have equivalent affinities.

Antibodies with equivalent affinities may achieve more uniform (e.g., unbiased) inhibitory effects, irrespective of the particular presenting molecule associated with the proTGFβ1 complex (hence "context-independent"). In particularly preferred embodiments, the antibody is a high-affinity, context-independent antibody in that the affinity for each of the four human LLCs is 1 nM or less (e.g., 200 μM or less) as measured by a solution equilibrium titration-based method, and, the antibody has equivalent affinities for all four human LLCs discussed above. For example, bias observed in average affinities between matrix-associated complexes and cell-associated complexes is no more than three-fold.

In some embodiments, such antibody specifically binds each of the aforementioned complexes (hLTBP1-proTGFβ1, hLTBP3-proTGFβ1, hGARP-proTGFβ1, and hLRRC33-proTGFβ1) with a KD of ≤10 nM (e.g., ≤10 nM, ≤9 nM, ≤8,nM, ≤7,nM, ≤6,nM, ≤5 nM, ≤4 nM, ≤3 nM, ≤2 nM, ≤1 nM, ≤0.5 nM and ≤0.1 nM) as measured by a solution equilibrium titration-based method, such as MSD-SET.

Any one of the inhibitory antibodies encompassed herein may bind each of the aforementioned large latent complexes (hLTBP1-proTGFβ1, hLTBP3-proTGFβ1, hGARP-proTGFβ1, and hLRRC33-proTGFβ1) at binding region(s)

that include at least a portion of Latency Lasso within the prodomain of the proTGFβ1 complex. Such binding regions may further include at least a portion of the growth factor domain. In particularly preferred embodiments, such antibodies bind to each of the LTBP1-proTGFβ1, LTBP3-proTGFβ1, GARP-proTGFβ1, and LRRC33-proTGFβ1 complexes with a $K_D$ value of ≤200 μM (such as ≤150 μM and ≤100 μM) at binding regions within the LLC complex including at least a portion of Latency Lasso and at least a portion of the growth factor domain.

In some embodiments, the high-affinity, context-independent antibody capable of selectively inhibiting TGFβ1 can inhibit TGFβ1 activated regardless of the mode of activation. For example, certain integrins are known to directly bind the RGD motifs within the prodomain of LLCs and mechanically "pull open" the cage-like prodomain structure, thereby causing the TGFβ1 growth factor to be unleashed from the latent complex. Separately, certain proteases present in the extracellular environment have been shown to activate TGFβ1 in an integrin-independent manner. An antibody that directly targets the RGD motif thereby interfering with the integrin binding may not inhibit protease-dependent activation of TGFβ1. Conversely, an antibody that directly targets one or more of the protease recognition or cleavage sites may not inhibit integrin-dependent activation of TGFβ1. By contrast, in preferred embodiments of the present invention, the high-affinity, context-independent antibody is capable of inhibiting integrin-dependent activation of TGFβ1 and protease-dependent activation of TGFβ1.

While high-affinity binding to target human proteins is an essential feature for an antibody therapeutic, ability to also cross-react with additional species counters is advantageous. In particular, given that most preclinical pharmacology models are in rodents, species cross-reactivity to murine/rat proteins provides convenient tools as surrogate antibodies for preclinical research. Accordingly, in some embodiments, the high-affinity antibodies of the present disclosure advantageously cross-react with other mammalian counterparts, such as mouse, rat, and/or non-human primates.

Among the novel antibodies encompassed by the present disclosure, particularly preferred classes of antibodies and their features are categorized and discussed below.

Preferred Features

In some embodiments, in addition to the Core Property features, preferred antibodies disclosed herein further meet the Antibody Criteria of one or more of Categories 1-5 as set forth in Table 1 herein.

In some embodiments, additional required criteria of the antibodies of the present invention are defined by their binding properties, e.g., affinity of the antibody towards antigen. The "antigen" in this context include at least four protein complexes, namely, human large latent complexes (LLCs) of TGFβ1, referred to as hLTBP1-proTGFβ1, hLTBP3-proTGFβ1, hGARP-proTGFβ1 and hLRRC33-proTGFβ1 complexes. According to the invention of the present disclosure, the antibodies are capable of binding to each of these complexes at certain affinities, typically measured as $K_D$ values. The Category 1 and Category 2 antibodies fall within these embodiments. For purposes of defining the criteria based on binding properties (e.g., Categories 1 and 2), affinity of the antibodies is determined at equilibrium, rather than by a kinetic assay (such as BLI).

Additionally or alternatively, additional required criteria of the antibodies of the present invention are defined by their amino acid sequences. The Category 3 and Category 4 antibodies are defined by the CDR sequences of the antibodies, whilst the Category 5 antibodies are defined by their heavy chain and light chain variable domain sequences.

TABLE 1

Preferred features of the novel, high-affinity, TGFβ1-selective inhibitors of the invention

| Category | Antibody Criteria | Exemplary Antibodies |
|---|---|---|
| (All) | Core Properties:<br>Selectively inhibits TGFβ1 signaling, over TGFβ2 and TGFβ3 signaling<br>Secifically binds each of: LTBP1-proTGFβ1, LTBP3-proTGFβ1, GARP-proTGFβ1 and LRRC33-proTGFβ1 complexes (human and/or murine)<br>Binding involves at least a portion of the prodomain of proTGFβ1<br>Improved safety/toxicology profiles, as compared to pan-TGFβ inhibitors | Present disclosure<br>WO 2018/129329 (Ab3)<br>WO 2017/156500 |
| | Additional required criteria defined by binding profiles (as determined by solution equilibrium titration) | |
| 1 | The antibody meets the Core Properties; and,<br>binds each of the following human complexes with a KD of ≤200 pM:<br>hLTBP1-proTGFβ1;<br>hLTBP3-proTGFβ1;<br>hGARP-proTGFβ1; and,<br>hLRRC33-proTGFβ1 | Ab6<br>Ab22<br>Ab24<br>Ab26<br>Ab29<br>Ab30<br>Ab31<br>Ab32<br>Ab33 |
| 2 | The antibody meets the Core Properties; and,<br>binds each of the following human complexes with a KD of ≤1 nM:<br>hLTBP1-proTGFβ1;<br>hLTBP3-proTGFβ1;<br>hGARP-proTGFβ1; and,<br>hLRRC33-proTGFβ1; and,<br>the binding region comprises at least a portion of Latency Lasso as determined by HD-X or crystallography | At least Ab5 and Ab6 |

TABLE 1-continued

Preferred features of the novel, high-affinity,
TGFβ1-selective inhibitors of the invention

| Category | Antibody Criteria | Exemplary Antibodies |
|---|---|---|
| | Additional required criteria defined by antibody sequences | |
| 3 | The antibody meets the Core Properties; and, H-CDR1 has an amino acid sequence represented by FTF(X₁)(X₂)(X₃)(X₄)M(X₅), wherein optionally: X₁ = S, G or A; X₂ = S or F; X₃ = F or Y; X₄ = S or A; and/or, X₅ = D, N or Y (SEQ ID NO: 143); H-CDR2 has an amino acid sequence represented by YI(X₁)(X₂)(X₃)A(X₄)TIYYA(X₅)SVKG, wherein optionally: X₁ = S or H; X₂ = P or S; X₃ = S or D; X₄ = D or S; and/or, X₅ = D or G (SEQ ID NO: 144); H-CDR3 has an amino acid sequence represented by (X₁)R(X₂)(X₃)(X₄)D(X₅)GDML(X₆)P, wherein optionally: X₁ = A or V; X₂ = G or A; X₃ = V or T; X₄ = L or W; X₅ = Y or M; and/or, X₆ = M or D (SEQ ID NO: 145); L-CDR1 has an amino acid sequence QASQDITNYLN, with optionally 1 or 2 amino acid changes (SEQ ID NO: 105); L-CDR2 has an amino acid sequence DASNLET, with optionally 1 or 2 amino acid changes (SEQ ID NO: 106); and, L-CDR3 has an amino acid sequence QQADNHPPWT, with optionally 1 or 2 amino acid changes (SEQ ID NO: 12). | Ab5 Ab6 Ab21 Ab22 Ab23 Ab24 Ab25 Ab26 Ab27 Ab28 Ab29 Ab30 Ab31 Ab32 Ab34 |
| 4 | The antibody meets the Core Properties; and, H-CDR1 has an amino acid sequence FTFSSFSMD, with optionally up to 4 amino acid changes, or, up to 2 amino acid changes (SEQ ID NO: 107); or, FTFSSFSMN, with optionally up to 4 amino acid changes, or, up to 2 amino acid changes (SEQ ID NO: 114); H-CDR2 has an amino acid sequence YISPDASTIYYADSVKG, with optionally up to 4 amino acid changes (SEQ ID NO: 111); H-CDR3 has an amino acid sequence ARGVLDYGDMLDP, with optionally up to 3 amino acid changes (SEQ ID NO: 110); L-CDR1 has an amino acid sequence QASQDITNYLN, with optionally 1 or 2 amino acid changes (SEQ ID NO: 105); L-CDR2 has an amino acid sequence DASNLET, with optionally 1 or 2 amino acid changes (SEQ ID NO: 106); and, L-CDR3 has an amino acid sequence QQADNHPPWT, with optionally 1 or 2 amino acid changes (SEQ ID NO: 12). | Ab4 Ab5 Ab6 Ab21 Ab22 Ab23 Ab24 Ab25 Ab26 Ab27 Ab28 Ab29 Ab30 Ab31 Ab32 Ab33 Ab34 |
| 5 | The antibody meets the Core Properties; and, comprises: a heavy chain variable domain (V$_H$) having at least 90% sequence identity to: EVQLVESGGGLVQPGGSLRLSCTASGFTFSS FSMDWVRQAPGKGLEWVSYISPSADTIYYAD SVKGRFTISRDNAKNTLYLQMNSLRAEDTAVY YCARGVLDYGDMLMPWGQGTLVTVSS (SEQ ID NO: 13) a light chain variable domain (V$_L$) having at least 90% sequence identity to: DIQMTQSPSSLSASVGDRVTITCQASQDITNYLN WYQQKPGKAPKLLIYDASNLETGVPSRFSGSGS GTDFTFTISSLQPEDIATYYCQQADNHPPWTFGG GTKVEIK (SEQ ID NO: 15) | Ab4 Ab5 Ab6 Ab21 Ab22 Ab23 Ab24 Ab25 Ab26 Ab27 Ab28 Ab29 Ab30 Ab31 Ab32 Ab33 Ab34 |

Non-limiting embodiments of each of the categories are provided below.

Category 1 Antibodies

Antibodies disclosed herein are high-affinity, isoform-selective antibodies capable of specifically targeting human latent large complexes of TGFβ1.

In one aspect, the invention provides an antibody or antigen-binding fragment thereof that specifically binds each of the following human LLCs with a K$_D$ of ≤200 μM: hLTBP1-proTGFβ1, hLTBP3-proTGFβ1, hGARP-proTGFβ1 and hLRRC33-proTGFβ1 complexes, where the affinity is measured at equilibrium using suitable assays such as solution equilibrium titration-based assays.

Such antibody or the fragment may bind each of the hLTBP1-proTGFβ1, hLTBP3-proTGFβ1, hGARP-proTGFβ1 and hLRRC33-proTGFβ1 complexes with a K$_D$ of ≤150 μM as measured by solution equilibrium titration. More preferably, such antibody or the fragment may bind each of the hLTBP1-proTGFβ1, hLTBP3-proTGFβ1, hGARP-proTGFβ1 and hLRRC33-proTGFβ1 complexes with a K$_D$ of ≤100 μM as measured by solution equilibrium titration. Any suitable in vitro affinity assays that are capable of determining K$_D$ values of the antibody at equilibrium may be employed, including for example, MSD-SET, which is described in more detail elsewhere herein. Non-limiting examples of antibodies disclosed herein which meet the Antibody Criteria of preferred antibodies of Category 1 include: Ab6, Ab22, Ab24, Ab26, Ab29, Ab30, Ab31, Ab32 and Ab33.

The antibody may also bind with high specificity and high affinities to corresponding LLCs of additional species. In preferred embodiments, the antibody shows species cross-reactivity to murine counterparts.

Category 2 Antibodies

Antibodies disclosed herein are high-affinity, isoform-selective antibodies capable of specifically targeting human latent large complexes of TGFβ1.

In another aspect, the invention provides an antibody or antigen-binding fragment thereof that specifically binds each of the following human LLCs with a $K_D$ of ≤1 nM: hLTBP1-proTGFβ1, hLTBP3-proTGFβ1, hGARP-proTGFβ1 and hLRRC33-proTGFβ1 complexes, where the affinity is measured at equilibrium using suitable assays such as solution equilibrium titration-based assays, and, wherein the antibody or the fragment binds the human LLCs at a binding region that comprises at least a portion of Latency Lasso. Latency Lasso is a protein domain that forms a part of so-called "Straight Jacket" of the prodomain. In its native form, Latency Lasso of the human proTGFβ1 polypeptide has the amino acid sequence LASPPSQGEVPPGPL (SEQ ID NO: 153). Any suitable techniques may be employed to determine whether an antibody binds a human TGFβ1 LLC at a region that includes at least portion of Latency Lasso. For example, competition assays that utilize corresponding polypeptides may be carried out. In some embodiments, binding regions may be determined by HD-X or X-ray crystallography.

In some embodiments, such antibody or the fragment may bind each of the hLTBP1-proTGFβ1, hLTBP3-proTGFβ1, hGARP-proTGFβ1 and hLRRC33-proTGFβ1 complexes with a $K_D$ of ≤500 μM (optionally ≤400 μM, ≤300 μM, <200 μM or <100 μM) as measured by solution equilibrium titration, wherein the antibody or the fragment binds the human LLCs at a binding region that comprises at least a portion of Latency Lasso. Non-limiting examples of antibodies disclosed herein which meet the Antibody Criteria of preferred antibodies of Category 2 include: Ab5 and Ab6.

In some embodiments, such antibody may further bind the human LLCs at additional binding region(s) that comprise at least a portion of the growth factor domain within the proTGFβ1 complex. In some embodiments, the additional binding occurs only in the context of the latency complex, such that the antibody does not specifically bind to free growth factor that is not in association with the prodomain complex. The additional binding region(s) within the growth factor domain of the LLC may include at least part of protein domains referred to as "Finger-1" and/or "Finger-2." Therefore, such antibody may bind a combinatorial epitope which comprises at least one amino acid residue of Latency Lasso and at least one amino acid residue of the growth factor domain.

The antibody may also bind with high specificity and high affinities to corresponding LLCs of additional species. In preferred embodiments, the antibody shows species cross-reactivity to murine counterparts.

Category 3 Antibodies

Antibodies disclosed herein are high-affinity, isoform-selective antibodies capable of specifically targeting human latent large complexes of TGFβ1.

In a further aspect, the invention provides an antibody or antigen-binding fragment thereof comprising an H-CDR1, an H-CDR2, an H-CDR3, an L-CDR1, an L-CDR2 and an L-CDR3, wherein the CDR-H1 has an amino acid sequence represented by FTF($X_1$)($X_2$)($X_3$)($X_4$)M($X_5$) (SEQ ID NO: 143). In some embodiments, $X_1$ may be S, G or A; $X_2$ may be S or F; $X_3$ may be F or Y; $X_4$ may be S or A; and/or, $X_5$ may be D, N or Y, in any combination. In some embodiments where the H-CDR1 contains at least one amino acid substitution, position X1 may be replaced with an S; position X2 may be replaced with an S; position X3 may be replaced with an F; position X4 may be replaced with an S; and/or, position X5 may be replaced with a D.

The CDR-H2 of the antibody has an amino acid sequence represented by YI($X_1$)($X_2$)($X_3$)A($X_4$)TIYYA($X_5$)SVKG (SEQ ID NO: 144). In some embodiments, $X_1$ may be S or H; $X_2$ may be P or S; $X_3$ may be S or D; $X_4$ may be D or S; and/or, $X_5$ may be D or G, in any combination. In some embodiments where the H-CDR2 contains at least one amino acid substitution, position X1 may be replaced with an S; position X2 may be replaced with a P; position X3 may be replaced with a D; position X4 may be replaced with an S; and/or, position X5 may be replaced with a D.

The CDR-H3 of the antibody has an amino acid sequence represented by ($X_1$)R($X_2$)($X_3$)($X_4$)D($X_5$)GDML($X_6$)P (SEQ ID NO: 145). In some embodiments, $X_1$ may be A or V; $X_2$ may be G or A; $X_3$ may be V or T; $X_4$ may be L or W; $X_5$ may be Y or M; and/or, $X_6$ may be M or D, in any combination. In some embodiments where the H-CDR3 contains at least one amino acid substitution, position X1 may be replaced with an A; position X2 may be replaced with a G; position X3 may be replaced with a V; position X4 may be replaced with an L; position X5 may be replaced with a Y; and/or, position X6 may be replaced with a D.

The CDR-L1 has an amino acid sequence QASQDIT-NYLN (SEQ ID NO: 105), with optionally 1 or 2 amino acid changes.

The CDR-L2 has an amino acid sequence DASNLET (SEQ ID NO: 106), with optionally 1 or 2 amino acid changes.

The CDR-L3 has an amino acid sequence QQADNHPPWT (SEQ ID NO: 12), with optionally 1 or 2 amino acid changes.

Non-limiting examples of antibodies disclosed herein which meet the Antibody Criteria of preferred antibodies of Category 3 include: Ab5, Ab6, Ab21, Ab22, Ab23, Ab24, Ab25, Ab26, Ab27, Ab28, Ab29, Ab30, Ab31, Ab32 and Ab34.

Table 2 below summarizes the CDR consensus sequences of the Category 3 antibodies. In some embodiments, each of the CDR sequences may optionally contain one or more of the amino acid substitutions set forth below.

TABLE 2

Heavy chain and light chain consensus CDR sequences and preferred amino acid substitutions CDR Consensus Sequences CDRH1 FTF($X_1$) ($X_2$) ($X_3$) ($X_4$)M($X_5$), wherein
optionally: $X_1$ = S, G or A; $X_2$ = S or F;
$X_3$ = F or Y; $X_4$ = S or A; and/or,
$X_5$ = D, N or Y (SEQ ID NO: 143)

CDRH2 YI($X_1$) ($X_2$) ($X_3$) A($X_4$)TIYYA($X_5$)SVKG,
wherein optionally: $X_1$ = S or H; $X_2$ = P
or S; $X_3$ = S or D; $X_4$ = D or S; and/or,
$X_5$ = D or G (SEQ ID NO: 144)

TABLE 2-continued

Heavy chain and light chain consensus CDR sequences
and preferred amino acid substitutions CDR Consensus Sequences CDRH3 ($X_1$)R($X_2$)($X_3$)($X_4$)D($X_5$)GDML($X_6$)P,
wherein optionally: $X_1$ = A or V; $X_2$ = G
or A; $X_3$ = V or T; $X_4$ = L or W; $X_5$ = Y or M;
and/or, $X_6$ = M or D (SEQ ID NO: 145)

CDRL1 QASQDITNYLN, with optionally
1 or 2 amino acid changes
(SEQ ID NO: 105)

CDRL2 DASNLET, with optionally 1 or
2 amino acid changes
(SEQ ID NO: 106)

CDRL3 QQADNHPPWT, with optionally
1 or 2 amino acid changes
(SEQ ID NO: 12)

In some embodiments, the Category 3 antibody or antigen-binding fragment thereof specifically binds each of the following human LLCs with a $K_D$ of ≤1 nM: hLTBP1-proTGFβ1, hLTBP3-proTGFβ1, hGARP-proTGFβ1 and hLRRC33-proTGFβ1 complexes, where the affinity is measured at equilibrium using suitable assays such as solution equilibrium titration-based assays.

In some embodiments, the antibody or the fragment binds the human LLCs at a binding region that comprises at least a portion of Latency Lasso. Latency Lasso is a protein domain that forms a part of so-called "Straight Jacket" of the prodomain. In its native form, Latency Lasso of the human proTGFβ1 polypeptide has the amino acid sequence LASPPSQGEVPPGPL (SEQ ID NO: 153). Any suitable techniques may be employed to determine whether an antibody binds a human TGFβ1 LLC at a region that includes at least portion of Latency Lasso. For example, competition assays that utilize corresponding polypeptides may be carried out. In some embodiments, binding regions may be determined by HD-X or X-ray crystallography.

In some embodiments, such antibody or the fragment may bind each of the hLTBP1-proTGFβ1, hLTBP3-proTGFβ1, hGARP-proTGFβ1 and hLRRC33-proTGFβ1 complexes with a $K_D$ of ≤500 μM (optionally ≤400 μM, ≤300 μM, ≤200 μM or ≤100 μM) as measured by solution equilibrium titration, wherein the antibody or the fragment binds the human LLCs at a binding region that comprises at least a portion of Latency Lasso.

In some embodiments, such antibody may further bind the human LLCs at additional binding region(s) that comprise at least a portion of the growth factor domain within the proTGFβ1 complex. In some embodiments, the additional binding occurs only in the context of the latency complex, such that the antibody does not specifically bind to free growth factor that is not in association with the prodomain complex. The additional binding region(s) within the growth factor domain of the LLC may include at least part of protein domains referred to as "Finger-1" and/or "Finger-2." Therefore, such antibody may bind a combinatorial epitope which comprises at least one amino acid residue of Latency Lasso and at least one amino acid residue of the growth factor domain.

The antibody may also bind with high specificity and high affinities to corresponding LLCs of additional species. In preferred embodiments, the antibody shows species cross-reactivity to murine counterparts.

Included herein are cross-blocking antibodies or antigen-binding fragments thereof. In some embodiments, the antibody or the fragment thereof cross-blocks or cross-competes with one of the Category 3 antibodies, wherein the antibody has a $K_D$ of ≤1 nM for at least one of the human LLC complexes (hLTBP1-proTGFβ1, hLTBP3-proTGFβ1, hGARP-proTGFβ1 and/or hLRRC33-proTGFβ1) as measured by MSD-SET. In some embodiments, such antibody has a $K_D$ of ≤1 nM for two of the human LLC complexes selected from: hLTBP1-proTGFβ1, hLTBP3-proTGFβ1, hGARP-proTGFβ1 and hLRRC33-proTGFβ1, as measured by MSD-SET. In some embodiments, such antibody has a $K_D$ of ≤1 nM for three of the human LLC complexes selected from: hLTBP1-proTGFβ1, hLTBP3-proTGFβ1, hGARP-proTGFβ1 and hLRRC33-proTGFβ1, as measured by MSD-SET. In preferred embodiments, such antibody has a $K_D$ of ≤1 nM for each of the human LLC complexes: hLTBP1-proTGFβ1, hLTBP3-proTGFβ1, hGARP-proTGFβ1 and hLRRC33-proTGFβ1, as measured by MSD-SET. According to the present disclosure, high-affinity antibodies may have a $K_D$ value for a particular antigen (e.g., antigen complex) that is 1 nM or less, e.g., ≤1 nM, ≤0.5 nM, ≤400 μM, ≤300 μM, ≤200 μM, and ≤100 μM, at equilibrium.

Category 4 Antibodies

Antibodies disclosed herein are high-affinity, isoform-selective antibodies capable of specifically targeting human latent large complexes of TGFβ1.

In a further aspect, the invention provides an antibody or antigen-binding fragment thereof comprising an H-CDR1, an H-CDR2, an H-CDR3, an L-CDR1, an L-CDR2 and an L-CDR3, wherein: the H-CDR1 comprises FTFSSFSMD (SEQ ID NO: 107) or FTFSSFSMN (SEQ ID NO: 114), wherein optionally each may contain up to 4 amino acid changes (optionally up to 4, up to 3, up to 2 or 1 amino acid changes); the H-CDR2 comprises YISPDASTIYY-ADSVKG (SEQ ID NO: 111), wherein optionally the H-CDR2 may contain up to 4 amino acid changes (optionally up to 4, up to 3, up to 2 or 1 amino acid changes), the H-CDR3 comprises ARGVLDYGDMLDP (SEQ ID NO: 110), wherein optionally the H-CDR3 may contain up to 3 amino acid changes (optionally up to 3, up to 2 or 1 amino acid changes); the L-CDR1 QASQDITNYLN (SEQ ID NO: 105), with optionally 1 or 2 amino acid changes; the L-CDR2 comprises DASNLET (SEQ ID NO: 106), with optionally 1 or 2 amino acid changes; and the L-CDR3 comprises QQADNHPPWT (SEQ ID NO: 12), with optionally 1 or 2 amino acid changes.

Non-limiting examples of antibodies disclosed herein which meet the Antibody Criteria of preferred antibodies of Category 4 include: Ab4, Ab5, Ab6, Ab21, Ab22, Ab23, Ab24, Ab25, Ab26, Ab27, Ab28, Ab29, Ab30, Ab31, Ab32, Ab33 and Ab34.

Table 3 below summarizes the CDR sequences of the Category 4 antibodies. In some embodiments, each of the CDR sequences may optionally contain one or more of the amino acid substitutions set forth below.

TABLE 3

CDR sequences and variants

CDRs and Variants

CDRH1 i) FTFSSFSMD, with optionally up to
4 amino acid changes or up to 2
amino acid changes (SEQ ID NO: 107; or,
ii) FTFSSFSMN, with optionally up to
4 amino acid changes, or, up to 2
amino acid changes (SEQ ID NO: 114)

TABLE 3-continued

CDR sequences and variants

| | CDRs and Variants |
|---|---|
| CDRH2 | YISPDASTIYYADSVKG, with optionally up to 4 amino acid changes (SEQ ID NO: 111) |
| CDRH3 | ARGVLDYGDMLDP, with optionally up to 3 amino acid changes (SEQ ID NO: 110) |
| CDRL1 | QASQDITNYLN, with optionally 1 or 2 amino acid changes (SEQ ID NO: 105) |
| CDRL2 | DASNLET, with optionally 1 or 2 amino acid changes (SEQ ID NO: 106) |
| CDRL3 | QQADNHPPWT, with optionally 1 or 2 amino acid changes (SEQ ID NO: 12) |

In some embodiments, the Category 4 antibody or antigen-binding fragment thereof specifically binds each of the following human LLCs with a $K_D$ of ≤1 nM: hLTBP1-proTGFβ1, hLTBP3-proTGFβ1, hGARP-proTGFβ1 and hLRRC33-proTGFβ1 complexes, where the affinity is measured at equilibrium using suitable assays such as solution equilibrium titration-based assays.

In some embodiments, the antibody or the fragment binds the human LLCs at a binding region that comprises at least a portion of Latency Lasso. Latency Lasso is a protein domain that forms a part of so-called "Straight Jacket" of the prodomain. In its native form, Latency Lasso of the human proTGFβ1 polypeptide has the amino acid sequence LASPPSQGEVPPGPL (SEQ ID NO: 153). Any suitable techniques may be employed to determine whether an antibody binds a human TGFβ1 LLC at a region that includes at least portion of Latency Lasso. For example, competition assays that utilize corresponding polypeptides may be carried out. In some embodiments, binding regions may be determined by HD-X or X-ray crystallography.

In some embodiments, such antibody or the fragment may bind each of the hLTBP1-proTGFβ1, hLTBP3-proTGFβ1, hGARP-proTGFβ1 and hLRRC33-proTGFβ1 complexes with a $K_D$ of ≤500 μM (optionally ≤400 μM, ≤300 μM, ≤200 μM or ≤100 μM) as measured by solution equilibrium titration, wherein the antibody or the fragment binds the human LLCs at a binding region that comprises at least a portion of Latency Lasso.

In some embodiments, such antibody may further bind the human LLCs at additional binding region(s) that comprise at least a portion of the growth factor domain within the proTGFβ1 complex. In some embodiments, the additional binding occurs only in the context of the latency complex, such that the antibody does not specifically bind to free growth factor that is not in association with the prodomain complex. The additional binding region(s) within the growth factor domain of the LLC may include at least part of protein domains referred to as "Finger-1" and/or "Finger-2." Therefore, such antibody may bind a combinatorial epitope which comprises at least one amino acid residue of Latency Lasso and at least one amino acid residue of the growth factor domain.

The antibody may also bind with high specificity and high affinities to corresponding LLCs of additional species. In preferred embodiments, the antibody shows species cross-reactivity to murine counterparts.

Included herein are cross-blocking antibodies or antigen-binding fragments thereof. In some embodiments, the antibody or the fragment thereof cross-blocks or cross-competes with one of the Category 4 antibodies, wherein the antibody has a $K_D$ of ≤1 nM for at least one of the human LLC complexes (hLTBP1-proTGFβ1, hLTBP3-proTGFβ1, hGARP-proTGFβ1 and/or hLRRC33-proTGFβ1) as measured by MSD-SET. In some embodiments, such antibody has a $K_D$ of ≤1 nM for two of the human LLC complexes selected from: hLTBP1-proTGFβ1, hLTBP3-proTGFβ1, hGARP-proTGFβ1 and hLRRC33-proTGFβ1, as measured by MSD-SET. In some embodiments, such antibody has a $K_D$ of ≤1 nM for three of the human LLC complexes selected from: hLTBP1-proTGFβ1, hLTBP3-proTGFβ1, hGARP-proTGFβ1 and hLRRC33-proTGFβ1, as measured by MSD-SET. In preferred embodiments, such antibody has a $K_D$ of ≤1 nM for each of the human LLC complexes: hLTBP1-proTGFβ1, hLTBP3-proTGFβ1, hGARP-proTGFβ1 and hLRRC33-proTGFβ1, as measured by MSD-SET. According to the present disclosure, high-affinity antibodies may have a $K_D$ value for a particular antigen (e.g., antigen complex) that is 1 nM or less, e.g., ≤1 nM, ≤0.5 nM, ≤400 μM, ≤300 μM, ≤200 μM, and ≤100 μM, at equilibrium.

Category 5 Antibodies

Antibodies disclosed herein are high-affinity, isoform-selective antibodies capable of specifically targeting human latent large complexes of TGFβ1.

In a further aspect, the invention provides an antibody or antigen-binding fragment thereof that comprises a heavy chain variable domain ($V_H$) having at least 90% sequence identity to: EVQLVESGGGLVQPGGSLRLSCTASGFTFS-SFSMDWVRQAPGKGLEWVSYISPSADTIYYADSVK-GRFTISRDNAKN TLYLQMNSLRAEDTAVYYCARG-VLDYGDMLMPWGQGTLVTVSS (SEQ ID NO: 13); and, a light chain variable domain ($V_L$) having at least 90% sequence identity to:

(SEQ ID NO: 15)
DIQMTQSPSSLSASVGDRVTITCQASQDITNYLNWYQQKPGKAPKLLI

YDASNLETGVPSRFSGSGSGTDFTFTISSLQPEDIATYYCQQADNHPP

WTFGGGTKVEIK.

In some embodiments, the heavy chain variable domain of the antibody is at least 90%, 91%, 92%, 93%, 94%, 95%, 96%, 97%, 98%, or 99% identical to the VH sequence set forth in SEQ ID NO: 13.

In some embodiments, the heavy chain variable domain of the antibody is at least 95% identical to the above VH sequence.

In some embodiments, the heavy chain variable domain of the antibody is at least 90%, 91%, 92%, 93%, 94%, 95%, 96%, 97%, 98%, or 99% identical to the VL sequence set forth in SEQ ID NO: 15.

In some embodiments, the light chain variable domain of the antibody is at least 95% identical to the above VL sequence.

Non-limiting examples of antibodies disclosed herein which meet the Antibody Criteria of preferred antibodies of Category 5 include: Ab4, Ab5, Ab6, Ab21, Ab22, Ab23, Ab24, Ab25, Ab26, Ab27, Ab28, Ab29, Ab30, Ab31, Ab32, Ab33 and Ab34.

In some embodiments, the Category 5 antibody or antigen-binding fragment thereof specifically binds each of the following human LLCs with a $K_D$ of ≤1 nM: hLTBP1-proTGFβ1, hLTBP3-proTGFβ1, hGARP-proTGFβ1 and hLRRC33-proTGFβ1 complexes, where the affinity is measured at equilibrium using suitable assays such as solution equilibrium titration-based assays.

In some embodiments, the antibody or the fragment binds the human LLCs at a binding region that comprises at least a portion of Latency Lasso. Latency Lasso is a protein domain that forms a part of so-called "Straight Jacket" of the prodomain. In its native form, Latency Lasso of the human proTGFβ1 polypeptide has the amino acid sequence LASPPSQGEVPPGPL (SEQ ID NO: 153). Any suitable techniques may be employed to determine whether an antibody binds a human TGFβ1 LLC at a region that includes at least portion of Latency Lasso. For example, competition assays that utilize corresponding polypeptides may be carried out. In some embodiments, binding regions may be determined by HD-X or X-ray crystallography.

In some embodiments, such antibody or the fragment may bind each of the hLTBP1-proTGFβ1, hLTBP3-proTGFβ1, hGARP-proTGFβ1 and hLRRC33-proTGFβ1 complexes with a $K_D$ of ≤500 μM (optionally ≤400 μM, ≤300 μM, ≤200 μM or ≤100 μM) as measured by solution equilibrium titration, wherein the antibody or the fragment binds the human LLCs at a binding region that comprises at least a portion of Latency Lasso.

In some embodiments, such antibody may further bind the human LLCs at additional binding region(s) that comprise at least a portion of the growth factor domain within the proTGFβ1 complex. In some embodiments, the additional binding occurs only in the context of the latency complex, such that the antibody does not specifically bind to free growth factor that is not in association with the prodomain complex. The additional binding region(s) within the growth factor domain of the LLC may include at least part of protein domains referred to as "Finger-1" and/or "Finger-2." Therefore, such antibody may bind a combinatorial epitope which comprises at least one amino acid residue of Latency Lasso and at least one amino acid residue of the growth factor domain.

The antibody may also bind with high specificity and high affinities to corresponding LLCs of additional species. In preferred embodiments, the antibody shows species cross-reactivity to murine counterparts.

Included herein are cross-blocking antibodies or antigen-binding fragments thereof. In some embodiments, the antibody or the fragment thereof cross-blocks or cross-competes with one of the Category 5 antibodies, wherein the antibody has a $K_D$ of ≤1 nM for at least one of the human LLC complexes (hLTBP1-proTGFβ1, hLTBP3-proTGFβ1, hGARP-proTGFβ1 and/or hLRRC33-proTGFβ1) as measured by MSD-SET. In some embodiments, such antibody has a $K_D$ of ≤1 nM for two of the human LLC complexes selected from: hLTBP1-proTGFβ1, hLTBP3-proTGFβ1, hGARP-proTGFβ1 and hLRRC33-proTGFβ1, as measured by MSD-SET. In some embodiments, such antibody has a $K_D$ of ≤1 nM for three of the human LLC complexes selected from: hLTBP1-proTGFβ1, hLTBP3-proTGFβ1, hGARP-proTGFβ1 and hLRRC33-proTGFβ1, as measured by MSD-SET. In preferred embodiments, such antibody has a $K_D$ of ≤1 nM for each of the human LLC complexes: hLTBP1-proTGFβ1, hLTBP3-proTGFβ1, hGARP-proTGFβ1 and hLRRC33-proTGFβ1, as measured by MSD-SET. According to the present disclosure, high-affinity antibodies may have a $K_D$ value for a particular antigen (e.g., antigen complex) that is 1 nM or less, e.g., ≤1 nM, ≤0.5 nM, ≤400 μM, ≤300 μM, ≤200 μM, and ≤100 μM, at equilibrium.

Exemplary Antibodies of the Invention

Exemplary antibodies and corresponding nucleic acid sequences that encode such antibodies useful for carrying out the present invention include one or more of the CDR amino acid sequences shown in Tables 4 and 5. Each set of the H-CDRs (H-CDR1, H-CDR2 and H-CDR3) listed in Table 5 can be combined with the L-CDRs (L-CDR1, L-CDR2 and L-CDR3) provided in Table 5.

Thus, the invention provides an isolated antibody or antigen-binding fragment thereof comprising six CDRs (e.g., an H-CDR1, an H-CDR2, an H-CDR3, an L-CDR1, an L-CDR2 and an L-CDR3), wherein the H-CDR1, H-CDR2 and H-CDR3 are selected from the sets of H-CDRs of the antibodies listed in Table 4, and wherein the L-CDR1 comprises QASQDITNYLN (SEQ ID NO: 105), the L-CDR2 comprises DASNLET (SEQ ID NO: 106), and the L-CDR3 comprises QQADNHPPWT (SEQ ID NO: 12), wherein optionally, the H-CDR1 may comprise FTFSSFSMD (SEQ ID NO: 107); the H-CDR-2 may comprise YISPSADTIYYADSVKG (SEQ ID NO: 103); and/or, the H-CDR3 may comprise ARGVLDYGDMLMP (SEQ ID NO: 6). In some embodiments, the antibody or the fragment comprises H-CDR1 having the amino acid sequence FTFSSFSMD (SEQ ID NO: 107), H-CDR2 having the amino acid sequence YISPSADTIYYADSVKG (SEQ ID NO: 103), and H-CDR-3 having the amino acid sequence ARGVLDYGDMLMP (SEQ ID NO: 6); L-CDR1 having the amino acid sequence QASQDITNYLN (SEQ ID NO: 105), L-CDR2 having the amino acid sequence DASNLET (SEQ ID NO: 106), and L-CDR3 having the amino acid sequence QQADNHPPWT (SEQ ID NO: 12).

TABLE 4

Complementary determining regions of the heavy chain of exemplary antibodies, as determined using the numbering scheme described in Lu et al.

| Ab | H-CDR1 | H-CDR2 | H-CDR3 |
|---|---|---|---|
| Ab4 | FTFSSYSMN (SEQ ID NO: 108) | YISSSSSTIYYADSVKG (SEQ ID NO: 109) | ARGVLDYGDMLDP (SEQ ID NO: 110) |
| Ab5 | FTFSSFSMD (SEQ ID NO: 107) | YISPDASTIYYADSVKG (SEQ ID NO: 111) | ARGVLDYGDMLDP (SEQ ID NO: 110) |
| Ab6 | FTFSSFSMD (SEQ ID NO: 107) | YISPSADTIYYADSVKG (SEQ ID NO: 103) | ARGVLDYGDMLMP (SEQ ID NO: 6) |
| Ab21 | FTFSSFSMD (SEQ ID NO: 107) | YISPDASTIYYADSVKG (SEQ ID NO: 111) | ARGVLDYGDMLDP (SEQ ID NO: 110) |

TABLE 4-continued

Complementary determining regions of the heavy chain of exemplary antibodies, as determined using the numbering scheme described in Lu et al.

| Ab | H-CDR1 | H-CDR2 | H-CDR3 |
|---|---|---|---|
| Ab22 | FTFGSFSMN (SEQ ID NO: 112) | YIHSDASTIYYADSVKG (SEQ ID NO: 113) | ARGVLDYGDMLDP (SEQ ID NO: 110) |
| Ab23 | FTFSSFSMN (SEQ ID NO: 114) | YISPSADTIYYADSVKG (SEQ ID NO: 103) | ARGVLDYGDMLDP (SEQ ID NO: 110) |
| Ab24 | FTFSSFAMY (SEQ ID NO: 115) | YISPDASTIYYADSVKG (SEQ ID NO: 111) | ARGVLDYGDMLDP (SEQ ID NO: 110) |
| Ab25 | FTFGSFSMD (SEQ ID NO: 116) | YISPDASTIYYADSVKG (SEQ ID NO: 111) | ARGVLDYGDMLDP (SEQ ID NO: 110) |
| Ab26 | FTFSSFSMD (SEQ ID NO: 107) | YISPDASTIYYADSVKG (SEQ ID NO: 111) | ARGVLDYGDMLDP (SEQ ID NO: 110) |
| Ab27 | FTFSFYAMN (SEQ ID NO: 117) | YISPDASTIYYADSVKG (SEQ ID NO: 111) | ARGVLDYGDMLDP (SEQ ID NO: 110) |
| Ab28 | FTFSSFSMD (SEQ ID NO: 107) | YISPDASTIYYADSVKG (SEQ ID NO: 111) | VRGVLDYGDMLDP (SEQ ID NO: 118) |
| Ab29 | FTFSSFAMN (SEQ ID NO: 119) | YISPDASTIYYAGSVKG (SEQ ID NO: 120) | VRAVLDYGDMLDP (SEQ ID NO: 121) |
| Ab30 | FTFSSFSMD (SEQ ID NO: 107) | YISPDASTIYYADSVKG (SEQ ID NO: 111) | ARGTLDYGDMLDP (SEQ ID NO: 122) |
| Ab31 | FTFSSFSMD (SEQ ID NO: 107) | YISPDASTIYYADSVKG (SEQ ID NO: 111) | ARAVLDYGDMLDP (SEQ ID NO: 123) |
| Ab32 | FTFSSFSMN (SEQ ID NO: 114) | YISPSADTIYYADSVKG (SEQ ID NO: 103) | ARGVWDMGDMLDP (SEQ ID NO: 124) |
| Ab33 | FTFSSFSMN (SEQ ID NO: 114) | YISPSADTIYYADSVKG (SEQ ID NO: 103) | AHGVLDYGDMLDP (SEQ ID NO: 125) |
| Ab34 | FTFAFYSMN (SEQ ID NO: 126) | YISPDASTIYYADSVKG (SEQ ID NO: 111) | ARGVLDYGDMLDP (SEQ ID NO: 110) |

TABLE 5

Complementary determining regions of the light chain of exemplary antibodies, as determined using the Kabat numbering scheme or the numbering system of Lu et al.

| L-CDR1 | L-CDR2 | L-CDR3 |
|---|---|---|
| QASQDITNYLN (SEQ ID NO: 105) | DASNLET (SEQ ID NO: 106) | QQADNHPPWT (SEQ ID NO: 12) |

Determination of CDR sequences within an antibody depends on the particular numbering scheme being employed. Commonly used systems include but are not limited to: Kabat numbering system, IMTG numbering system, Chothia numbering system, and others such as the numbering scheme described by Lu et al. (Lu X et al., MAbs. 2019 January; 11(1):45-57). To illustrate, 6 CDR sequences of Ab6 as defined by four different numbering systems are exemplified below. Any art-recognized CDR numbering systems may be used to define CDR sequences of the antibodies of the present disclosure.

TABLE 6

Six CDRs of an exemplary antibody (Ab6) based on four numbering schemes

| | IMTG numbering | Kabat numbering | Chothia numbering | System of Lu et al. |
|---|---|---|---|---|
| H-CDR1 | GFTFSSFS (SEQ ID NO: 2) | SFSMD (SEQ ID NO: 102) | GFTFSSF (SEQ ID NO: 233) | FTFSSFSMD (SEQ ID NO: 107) |
| H-CDR2 | ISPSADTI (SEQ ID NO: 4) | YISPSADTIYYADSVKG (SEQ ID NO: 103) | SPSADT (SEQ ID NO: 234) | YISPSADTIYYADSVKG (SEQ ID NO: 103) |
| H-CDR3 | ARGVLDYGDMLMP (SEQ ID NO: 6) | GVLDYGDMLMP (SEQ ID NO: 104) | GVLDYGDMLMP (SEQ ID NO: 104) | ARGVLDYGDMLMP (SEQ ID NO: 6) |
| L-CDR1 | QDITNY (SEQ ID NO: 8) | QASQDITNYLN (SEQ ID NO: 105) | QASQDITNYLN (SEQ ID NO: 105) | QASQDITNYLN (SEQ ID NO: 105) |

TABLE 6-continued

Six CDRs of an exemplary antibody (Ab6) based on four numbering schemes

|  | IMTG numbering | Kabat numbering | Chothia numbering | System of Lu et al. |
|---|---|---|---|---|
| L-CDR2 | DAS<br>(SEQ ID NO: 10) | DASNLET<br>(SEQ ID NO: 106) | DASNLET<br>(SEQ ID NO: 106) | DASNLET<br>(SEQ ID NO: 106) |
| L-CDR3 | QQADNHPPWT<br>(SEQ ID NO: 12) | QQADNHPPWT<br>(SEQ ID NO: 12) | QQADNHPPWT<br>(SEQ ID NO: 12) | QQADNHPPWT<br>(SEQ ID NO: 12) |

Amino acid sequences of the heavy chain variable domain and the light chain variable domain of exemplary antibodies of the present disclosure are provided in Table 7. Thus, in some embodiments, the high-affinity, isoform-selective TGFβ1 inhibitor of the present disclosure may be an antibody or an antigen-binding fragment thereof comprising a heavy chain variable domain ($V_H$) and a light chain variable domain ($V_L$), wherein the $V_H$ and the $V_L$ sequences are selected from any one of the sets of $V_H$ and $V_L$ sequences listed in Table 7 below.

TABLE 7

Heavy chain variable domains and light chain variable domains of exemplary antibodies

| | Heavy Chain Variable Domain (VH) | Light Chain Variable Domain (VL) |
|---|---|---|
| Ab4 | EVQLVESGGGLVQPGGSLRLSCAASGFTFSS<br>YSMNWVRQAPGKGLEWVSYISSSSSTIYYAD<br>SVKGRFTISRDNAKNSLYLQMNSLRAEDTAV<br>YYCARGVLDYGDMLDPWGQGTLVTVSS<br>(SEQ ID NO: 127) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab5 | EVQLVESGGGLVQPGGSLRLSCAASGFTFSS<br>FSMDWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 128) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab6 | EVQLVESGGGLVQPGGSLRLSCTASGFTFSS<br>FSMDWVRQAPGKGLEWVSYISPSADTIYYAD<br>SVKGRFTISRDNAKNTLYLQMNSLRAEDTAV<br>YYCARGVLDYGDMLMPWGQGTLVTVSS<br>(SEQ ID NO: 13) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab21 | EVQLVESGGGLVQPGGSLRLSCAASGFTFSS<br>FSMDWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 129) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab22 | EVQLVESGGGLVQPGGSLRLSCAASGFTFGS<br>FSMNWVRQAPGKGLEWVSYIHSDASTIYYAD<br>SVKGRFTISRDNAKNSLYLQMNSLRAEDTAV<br>YYCARGVLDYGDMLDPWGQGTLVTVSS<br>(SEQ ID NO: 130) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab23 | EVQLVESGGGLVQPGGSLRLSCAASGFTFSS<br>FSMNWVRQAPGKGLEWVSYISPSADTIYYAD<br>SVKGRFTISRDNAKNTLYLQMNSLRAEDTAV<br>YYCARGVLDYGDMLDPWGQGTLVTVSS<br>(SEQ ID NO: 131) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |
| Ab24 | EVQLVESGGGLVQPGRSLRLSCAASGFTFSS<br>FAMYWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 132) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab25 | EVQLVESGGGLVQPGGSLRLSCAASGFTFGS<br>FSMDWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 133) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab26 | EVQLVESGGGLVQPGGSLRLSCAASGFTFSS<br>FSMDWVRQAPGKGLEWVSYISPDASTIYYAD<br>SVKGRFTISRDNAKNTLYLQMNSLRAEDTAV<br>YYCARGVLDYGDMLDPWGQGTLVTVSS<br>(SEQ ID NO: 134) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |

TABLE 7-continued

Heavy chain variable domains and light chain variable domains of exemplary antibodies

| | Heavy Chain Variable Domain (VH) | Light Chain Variable Domain (VL) |
|---|---|---|
| Ab27 | EVQLVESGGGLVQPGGSLRLSCAASGFTFSF<br>YAMNWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 135) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab28 | EVQLVESGGGLVQPGGSLRLSCAASGFTFSS<br>FSMDWVRQAPGKGLEWVSYISPDASTIYYAD<br>SVKGRFTISRDNAKNSLYLQMNSLRAEDTAV<br>YYCVRGVLDYGDMLDPWGQGTLVTVSS<br>(SEQ ID NO: 136) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab29 | EVQLVESGGGLVQPGRSLRLSCAASGFTFSS<br>FAMNWVRQAPGKGLEWVSYISPDASTIYYAG<br>SVKGRFTISRDNAKNSLYLQMNSLRAEDTAV<br>YYCVRAVLDYGDMLDPWGQGTLVTVSS<br>(SEQ ID NO: 137) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab30 | EVQLVESGGGLVQPGGSLRLSCAASGFTFSS<br>FSMDWVRQAPGKGLEWVSYISPDASTIYYAD<br>SVKGRFTISRDNAKNSLYLQMNSLRAEDTAV<br>YYCARGTLDYGDMLDPWGQGTLVTVSS<br>(SEQ ID NO: 138) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab31 | EVQLVESGGGLVQPGGSLRLSCAASGFTFSS<br>FSMDWVRQAPGKGLEWVSYISPDASTIYYAD<br>SVKGRFTISRDNAKNTLYLQMNSLRAEDTAV<br>YYCARAVLDYGDMLDPWGQGTLVTVSS<br>(SEQ ID NO: 139) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab32 | EVQLVESGGGLVQPGGSLRLSCAASGFTFSS<br>FSMNWVRQAPGKGLEWVSYISPSADTIYYAD<br>SVKGRFTISRDNAKNTLYLQMNSLRAEDTAV<br>YYCARGVWDMGDMLDPWGQGTLVTVSS<br>(SEQ ID NO: 140) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab33 | EVQLVESGGGLVQPGGSLRLSCAASGFTFSS<br>FSMNWVRQAPGKGLEWVSYISPSADTIYYAD<br>SVKGRFTISRDNAKNTLYLQMNSLRAEDTAV<br>YYCAHGVLDYGDMLDPWGQGTLVTVSS<br>(SEQ ID NO: 141) | DIQMTQSPSSLSASVGDRVTITCQASQDITNYLN<br>WYQQKPGKAPKLLIYDASNLETGVPSRFSGSGSG<br>GTDFTFTISSLQPEDIATYYCQQADNHPPWTFGG<br>TKVEIK<br>(SEQ ID NO: 15) |
| Ab34 | EVQLVESGGGLVQPGGSLRLSCAASGFTFAF<br>YSMNWVRQAPGKGLEWVSYISPDASTIYYAD<br>SVKGRFTISRDNAKNSLYLQMNSLRAEDTAV<br>YYCARGVLDYGDMLDPWGQGTLVTVSS<br>(SEQ ID NO: 142) | DIQMTQSPSSLSASVGDRVTITCQASQDITNYLN<br>WYQQKPGKAPKLLIYDASNLETGVPSRFSGSGSG<br>TDFTFTISSLQPEDIATYYCQQADNHPPWTFGGG<br>TKVEIK<br>(SEQ ID NO: 15) |

Thus, the invention provides an antibody or an antigen-binding fragment thereof that comprises a heavy chain variable domain and a light chain variable domain, wherein, the heavy chain variable domain has at least 90% (e.g., at least 90%, 91%, 92%, 93%, 94%, 95%, 96%, 97%, 98% 99% and 100%) sequence identity with any one of the sequences selected from the group consisting of: Ab4, Ab5, Ab6, Ab21, Ab22, Ab23, Ab24, Ab25, Ab26, Ab27, Ab28, Ab29, Ab30, Ab31, Ab32, Ab33, and Ab34; and, wherein the light chain variable domain has at least 90% identity with any one of the sequences selected from Ab4, Ab5, Ab6, Ab21, Ab22, Ab23, Ab24, Ab25, Ab26, Ab27, Ab28, Ab29, Ab30, Ab31, Ab32, Ab33, and Ab34, wherein, optionally, the heavy chain variable domain may optionally have at least 95% sequence identity, and/or, the light chain variable domain may have at least 95% (e.g., at least 95%, 96%, 97%, 98% 99% and 100%) sequence identity. In some embodiments, the heavy chain variable domain of the antibody or the fragment has at least 90% sequence identity with SEQ ID NO: 13, and wherein optionally, the light chain variable domain of the antibody or the fragment has at least 90% sequence identity with SEQ ID NO: 15. In some embodiments, the heavy chain variable domain of the antibody or the fragment has at least 95% sequence identity with SEQ ID NO: 13, and wherein optionally, the light chain variable domain of the antibody or the fragment has at least 95% sequence identity with SEQ ID NO: 15. In some embodiments, the heavy chain variable domain of the antibody or the fragment has at least 98% sequence identity with SEQ ID NO: 13, and wherein optionally, the light chain variable domain of the antibody or the fragment has at least 98% sequence identity with SEQ ID NO: 15. In some embodiments, the heavy chain variable domain of the antibody or the fragment has 100% sequence identity with SEQ ID NO: 13, and wherein optionally, the light chain variable domain of the antibody or the fragment has 100% sequence identity with SEQ ID NO: 15.

In some embodiments, the antibody or antigen binding portion thereof, that specifically binds to a GARP-TGFβ1 complex, a LTBP1-TGFβ1 complex, a LTBP3-TGFβ1 complex, and/or a LRRC33-TGFβ1 complex comprises a heavy chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 14, and a light chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 16. In some embodiments, the antibody or antigen binding portion thereof, comprises a heavy chain variable domain amino acid sequence encoded by the nucleic acid sequence set forth in SEQ ID NO: 14, and a light chain variable domain amino acid sequence encoded by the nucleic acid sequence set forth in SEQ ID NO: 16.

In some examples, any of the antibodies of the disclosure that specifically bind to a GARP-TGFβ1 complex, a LTBP1-TGFβ1 complex, a LTBP3-TGFβ1 complex, and/or a LRRC33-TGFβ1 complex include any antibody (including antigen binding portions thereof) having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Table 4 containing up to 5, 4, 3, 2, or 1 amino acid residue variations as compared to the corresponding CDR region in any one of SEQ ID NOs: 6, 12, 103, 105, 106, 107, 108, 109, 110 111, 112, 113, 114, 115, 116, 117, 118, 119, 120, 121, 122, 123, 124, 125, and 126. In some embodiments, one or more of the six CDR sequences contain up to three (3) amino acid changes as compared to the sequences provided in Table 4. Such antibody variants comprising up to 3 amino acid changes per CDR are encompassed by the present invention. In some embodiments, such variant antibodies are generated by the process of optimization, such as affinity maturation. The complete amino acid sequences for the heavy chain variable region and light chain variable region of the antibodies listed in Table 7 (e.g., Ab6), as well as nucleic acid sequences encoding the heavy chain variable region and light chain variable region of certain antibodies are provided below:

```
Ab3-Heavy chain variable region amino acid
sequence
                                    (SEQ ID NO: 95)
EVQLLESGGGLVQPGGSLRLSCAASGFTFRNYAMSWVRQAPGKGLEWVSS

ISGSGGATYYADSVKGRFTISRDNSKNTLYLQMNSLRAEDTAVYYCARVS

SGHWDFDYVVGQGTLVTVSS

Ab6-Heavy chain variable region amino acid
sequence
                                    (SEQ ID NO: 13)
EVQLVESGGGLVQPGGSLRLSCTASGFTFSSFSMDWVRQAPGKGLEWVSY

ISPSADTIYYADSVKGRFTISRDNAKNTLYLQMNSLRAEDTAVYYCARGV

LDYGDMLMPWGQGTLVTVSS

Ab6-Light chain variable region amino acid
sequence
                                    (SEQ ID NO: 15)
DIQMTQSPSSLSASVGDRVTITCQASQDITNYLNWYQQKPGKAPKLLIYD

ASNLETGVPSRFSGSGSGTDFTFTISSLQPEDIATYYCQQADNHPPWTFG

GGTKVEIK

Ab6-Heavy chain amino acid sequence
                                    (SEQ ID NO: 17)
EVQLVESGGGLVQPGGSLRLSCTASGFTFSSFSMDWVRQAPGKGLEWVSY

ISPSADTIYYADSVKGRFTISRDNAKNTLYLQMNSLRAEDTAVYYCARGV

LDYGDMLMPWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG

Ab6-Heavy chain nucleic acid sequence
                                    (SEQ ID NO: 18)
GAGGTGCAGCTGGTGGAGTCTGGGGGAGGCTTGGTACAGCCTGGGGGGTC

CCTGAGACTCTCCTGTACAGCCTCTGGATTCACCTTCAGTAGCTTCAGCA

TGGACTGGGTCCGCCAGGCTCCAGGGAAGGGGCTGGAGTGGGTTTCATAC

ATTAGTCCCAGTGCAGACACCATATACTACGCAGACTCTGTGAAGGGCCG

ATTCACCATCTCCAGAGACAATGCCAAGAACACGCTGTATCTGCAAATGA

ACAGCCTGAGAGCCGAGGACACGGCGGTGTACTACTGCGCCAGAGGGGTG

CTCGACTACGGAGACATGTTAATGCCATGGGGCCAGGGAACCCTGGTCAC

CGTCTCCTCAGCGTCGACCAAGGGCCCTTCCGTGTTCCCTCTGGCCCCTT

GCTCCCGGTCCACCTCCGAGTCCACCGCCGCTCTGGGCTGTCTGGTGAAG

GACTACTTCCCTGAGCCTGTGACCGTGAGCTGGAACTCTGGCGCCCTGAC

CTCCGGCGTGCACACCTTCCCTGCCGTGCTGCAGTCCTCCGGCCTGTACT

CCCTGTCCTCCGTGGTGACCGTGCCTTCCTCCTCCCTGGGCACCAAGACC

TACACCTGCAACGTGGACCACAAGCCTTCCAACACCAAGGTGGACAAGCG

GGTGGAGTCCAAGTACGGCCCTCCTTGCCCTCCCTGCCCTGCCCCTGAGT

TCCTGGGCGGACCCTCCGTGTTCCTGTTCCCTCCTAAGCCTAAGGACACC

CTGATGATCTCCCGGACCCCTGAGGTGACCTGCGTGGTGGTGGACGTGTC

CCAGGAAGATCCTGAGGTCCAGTTCAATTGGTACGTGGATGGCGTGGAGG

TGCACAACGCCAAGACCAAGCCTCGGGAGGAACAGTTCAACTCCACCTAC

CGGGTGGTGTCTGTGCTGACCGTGCTGCACCAGGACTGGCTGAACGGCAA

GGAATACAAGTGCAAGGTCAGCAACAAGGGCCTGCCCTCCTCCATCGAGA

AAACCATCTCCAAGGCCAAGGGCCAGCCTCGCGAGCCTCAGGTGTACACC

CTGCCTCCTAGCCAGGAAGAGATGACCAAGAATCAGGTGTCCCTGACATG

CCTGGTGAAGGGCTTCTACCCTTCCGATATCGCCGTGGAGTGGGAGAGCA

ACGGCCAGCCAGAGAACAACTACAAGACCACCCCTCCTGTGCTGGACTCC

GACGGCTCCTTCTTCCTGTACTCCAGGCTGACCGTGGACAAGTCCCGGTG

GCAGGAAGGCAACGTCTTTTCCTGCTCCGTGATGCACGAGGCCCTGCACA

ACCACTACACCCAGAAGTCCCTGTCCCTGTCTCTGGGC

Ab6-Light chain amino acid sequence
                                    (SEQ ID NO: 19)
DIQMTQSPSSLSASVGDRVTITCQASQDITNYLNWYQQKPGKAPKLLIYD

ASNLETGVPSRFSGSGSGTDFTFTISSLQPEDIATYYCQQADNHPPWTFG

GGTKVEIKRTVAAPSVFIFPPSDEQLKSGTASVVCLLNNFYPREAKVQWK
```

-continued

VDNALQSGNSQESVTEQDSKDSTYSLSSTLTLSKADYEKHKVYACEVTHQ

GLSSPVTKSFNRGEC

Ab6-Light chain nucleic acid sequence
(human kappa)
(SEQ ID NO: 20)
GACATCCAGATGACCCAGTCTCCATCCTCCCTGTCTGCATCTGTAGGAGA

CAGAGTCACCATCACTTGCCAGGCGAGTCAGGACATTACCAACTATTTAA

ATTGGTATCAGCAGAAACCAGGGAAAGCCCCTAAGCTCCTGATCTACGAT

GCATCCAATTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGGCCGACAATCACCCTCCTTGGACTTTTGGC

GGAGGGACCAAGGTTGAGATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGT

In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a GARP-TGFβ1 complex, a LTBP1-TGFβ1 complex, a LTBP3-TGFβ1 complex, and a LRRC33-TGFβ1 complex as determined based on the crystal structure. In some embodiments, likely interface (e.g., residues involved in an antigen-antibody interaction) may be deduced from known structural information on another antigen sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 54)) hinge sequence. Accordingly, any of the antibodies may include a stabilizing 'Adair' mutation or the amino acid sequence CPPCP (SEQ ID NO: 54).

Isoform-specific, context-independent inhibitors of TGFβ1 of the present disclosure may optionally comprise antibody constant regions or parts thereof. For example, a VL domain may be attached at its C-terminal end to a light chain constant domain like CK or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

Additionally or alternatively, such antibodies may or may not include the framework region of the antibodies of SEQ ID NOs: 127, 128, 129, 130, 131, 132, 133, 134, 135, 136, 137, 138, 139, 140, 141, 142, and 15. In some embodiments, antibodies that specifically bind to a GARP-TGFβ1 complex, a LTBP1-TGFβ1 complex, a LTBP3-TGFβ1 complex, and a LRRC33-TGFβ1 complex are murine antibodies and include murine framework region sequences.

In some embodiments, such antibodies bind to a GARP-TGFβ1 complex, a LTBP1-TGFβ1 complex, a LTBP3-TGFβ1 complex, and a LRRC33-TGFβ1 complex with relatively high affinity, e.g., with a $K_D$ less than $10^{-9}$ M, $10^{-10}$ M, $10^{11}$ M or lower. For example, such antibodies may bind a GARP-TGFβ1 complex, a LTBP1-TGFβ1 complex, a LTBP3-TGFβ1 complex, and/or a LRRC33-TGFβ1 complex with an affinity between 5 μM and 1 nM, e.g., between 10 μM and 1 nM, e.g., between 10 μM and 100 μM. The disclosure also includes antibodies or antigen binding fragments that compete with any of the antibodies described herein for binding to a GARP-TGFβ1 complex, a LTBP1-TGFβ1 complex, a LTBP3-TGFβ1 complex, and/or a LRRC33-TGFβ1 complex and that have a $K_D$ value of 1 nM or lower (e.g., 1 nM or lower, 500 μM or lower, 100 μM or lower). The affinity and binding kinetics of the antibodies that specifically bind to a GARP-TGFβ1 complex, a LTBP1-TGFβ1 complex, a LTBP3-TGFβ1 complex, and/or a LRRC33-TGFβ1 complex can be tested using any suitable method including but not limited to biosensor-based technology (e.g., OCTET® or BIACORE®) and solution equilibrium titration-based technology (e.g., MSD-SET).

In some embodiments, inhibitors of cell-associated TGFβ1 (e.g., GARP-presented TGFβ1 and LRRC33-presented TGFβ1) according to the invention include antibodies or fragments thereof that specifically bind such complex (e.g., GARP-pro/latent TGFβ1 and LRRC33-pro/latent TGFβ1) and trigger internalization of the complex. This mode of action causes removal or depletion of the inactive TGFβ1 complexes (e.g., GARP-proTGFβ1 and LRRC33-proTGFβ1) from the cell surface (e.g., Treg, macrophages, etc.), hence reducing TGFβ1 available for activation. In some embodiments, such antibodies or fragments thereof bind the target complex in a pH-dependent manner such that binding occurs at a neutral or physiological pH, but the antibody dissociates from its antigen at an acidic pH; or, dissociation rates are higher at acidic pH than at neutral pH. Such antibodies or fragments thereof may function as recycling antibodies.

Antibodies Competing with High-Affinity, Isoform-Specific Inhibitory Antibodies of TGFβ1

Aspects of the disclosure relate to antibodies that compete or cross-compete with any of the antibodies provided herein. The term "compete", as used herein with regard to an antibody, means that a first antibody binds to an epitope (e.g., an epitope of a GARP-proTGFβ1 complex, a LTBP1-proTGFβ1 complex, a LTBP3-proTGFβ1 complex, and a LRRC33-proTGFβ1 complex) in a manner sufficiently similar to or overlapping with the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein. The term "cross-blocking" may be used interchangeably.

Two different monoclonal antibodies (or antigen-binding fragments) that bind the same antigen may be able to simultaneously bind to the antigen if the binding sites are sufficiently further apart in the three-dimensional space such that each binding does not interfere with the other binding. By contrast, two different monoclonal antibodies may have binding regions of an antigen that are the same or overlapping, in which case, binding of the first antibody may prevent the second antibody from being able to bind the antigen, or vice versa. In the latter case, the two antibodies are said to "cross-block" with each other with respect to the same antigen.

Antibody "binning" experiments are useful for classifying multiple antibodies that are made against the same antigen into various "bins" based on the relative cross-blocking activities. Each "bin" therefore represents a discrete binding region(s) of the antigen. Antibodies in the same bin by definition cross-block each other. Binning can be examined by standard in vitro binding assays, such as Biacor or OCTET®, using standard test conditions, e.g., according to the manufacturer's instructions (e.g., binding assayed at room temperature, ~20-25° C.).

Aspects of the disclosure relate to antibodies that compete or cross-compete with any of the specific antibodies, or antigen binding portions thereof, as provided herein. In some embodiments, an antibody, or antigen binding portion thereof, binds at or near the same epitope as any of the antibodies provided herein. In some embodiments, an antibody, or antigen binding portion thereof, binds near an epitope if it binds within 15 or fewer amino acid residues of the epitope. In some embodiments, any of the antibody, or antigen binding portion thereof, as provided herein, binds within 1, 2, 3, 4, 5, 6, 7, 8, 9, 10, 11, 12, 13, 14 or 15 amino acid residues of an epitope that is bound by any of the antibodies provided herein.

In another embodiment, provided herein is an antibody, or antigen binding portion thereof, competes or cross-competes for binding to any of the antigens provided herein (e.g., a GARP-TGFβ1 complex, a LTBP1-TGFβ1 complex, a LTBP3-TGFβ1 complex, and/or a LRRC33-TGFβ1 complex) with an equilibrium dissociation constant, $K_D$, between the antibody and the protein of less than $10^{-8}$ M. In other embodiments, an antibody competes or cross-competes for binding to any of the antigens provided herein with a $K_D$ in a range from $10^{12}$ M to $10^{-9}$ M. In some embodiments, provided herein is an anti-TGFβ1 antibody, or antigen binding portion thereof that competes for binding with an antibody, or antigen binding portion thereof, described herein. In some embodiments, provided herein is an anti-TGFβ1 antibody, or antigen binding portion thereof, that binds to the same epitope as an antibody, or antigen binding portion thereof, described herein.

Any of the antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). In some embodiments, the epitope is a TGFβ1 epitope that is only available for binding by the antibody, or antigen binding portion thereof, described herein, when the TGFβ1 is in a GARP-proTGFβ1 complex, a LTBP1-proTGFβ1 complex, a LTBP3-proTGFβ1 complex, or a LRRC33-proTGFβ1 complex. Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the GARP-proTGFβ1 complex, a LTBP1-proTGFβ1 complex, a LTBP3-proTGFβ1 complex, and/or a proLRRC33-TGFβ1 complex have been replaced (swapped) with sequences from a closely related, but antigenically distinct protein, such as another member of the TGFβ protein family (e.g., GDF11).

Alternatively, competition assays can be performed using other antibodies known to bind to the same antigen to determine whether an antibody binds to the same epitope as the other antibodies. Competition assays are well known to those of skill in the art.

In some embodiments, the invention includes antibodies (e.g., immunoglobulins, antigen-binding fragments, etc.) that cross-block (cross-compete) with any one of the antibodies of Category 1, Category 2, Category 3, Category 4 and/or Category 5. Thus, in some embodiments, a pharmaceutical composition may be made by the process comprising a step of: selecting an antibody or antigen-binding fragment thereof, which cross-competes with a Category 1 antibody; and, formulating the antibody into a pharmaceutical composition.

In some embodiments, a pharmaceutical composition may be made by the process comprising a step of: selecting an antibody or antigen-binding fragment thereof, which cross-competes with a Category 2 antibody; and, formulating the antibody into a pharmaceutical composition.

In some embodiments, a pharmaceutical composition may be made by the process comprising a step of: selecting an antibody or antigen-binding fragment thereof, which cross-competes with a Category 3 antibody; and, formulating the antibody into a pharmaceutical composition.

In some embodiments, a pharmaceutical composition may be made by the process comprising a step of: selecting an antibody or antigen-binding fragment thereof, which cross-competes with a Category 4 antibody; and, formulating the antibody into a pharmaceutical composition.

In some embodiments, a pharmaceutical composition may be made by the process comprising a step of: selecting an antibody or antigen-binding fragment thereof, which cross-competes with a Category 5 antibody; and, formulating the antibody into a pharmaceutical composition.

In some embodiments, a pharmaceutical composition may be made by the process comprising a step of: selecting an antibody or antigen-binding fragment thereof, which cross-competes with the antibody selected from the group consisting of Ab4, Ab5, Ab6, Ab21, Ab22, Ab23, Ab24, Ab25, Ab26, Ab27, Ab28, Ab29, Ab30, Ab31, Ab32, Ab33 and Ab34; and, formulating into a pharmaceutical composition.

Preferably, the antibody selected by the process is a high-affinity binder characterized in that the antibody or the antigen-binding fragment is capable of binding to each of human LLCs (e.g., hLTBP1-proTGFβ1, hLTBP3-proTGFβ1, hGARP-proTGFβ1 and hLRRC33-proTGFβ1) with a $K_D$ of ≤5 nM, as measured by solution equilibrium titration. In some embodiments, the antibody meets the criteria of one or more of Category 1, Category 2, Category 3, Category 4 and Category 5. Such cross-competing antibodies may be used in the treatment of TGFβ1-related indications a subject in accordance with the present disclosure.

Various Modifications and Variations of Antibodies

Non-limiting variations, modifications, and features of any of the antibodies or antigen-binding fragments thereof encompassed by the present disclosure are briefly discussed below. Embodiments of related analytical methods are also provided.

Naturally-occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human antibody light chains are typically classified as kappa and lambda light chains. Heavy chains are typically classified as mu, delta, gamma, alpha, or epsilon, and define the isotype of the antibody. An antibody can be of any type (e.g., IgM, IgD, IgG, IgA, IgY, and IgE) and class (e.g., $IgG_1$, $IgG_2$, $IgG_3$, $IgG_4$, $IgM_1$, $IgM_2$, $IgA_1$, and $IgA_2$). Within full-length light and heavy chains, typically, the variable and constant regions are joined by a "J" region of about 12 or more amino acids, with the heavy chain also including a "D" region of about 10 more amino acids (see, e.g., Fundamental Immunology, Ch. 7 (Paul, W., ed., 2nd ed. Raven Press, N.Y. (1989)) (incorporated by reference in its entirety)). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342: 878-883. The CDRs of a light chain can also be referred to as CDR-L1, CDR-L2, and CDR-L3, and the CDRs of a heavy chain can also be referred to as CDR-H1, CDR-H2, and CDR-H3. In some embodiments, an antibody can comprise a small number of amino acid deletions from the carboxy end of the heavy chain(s). In some embodiments, an antibody comprises a heavy chain having 1-5 amino acid deletions in the carboxy end of the heavy chain. In certain embodiments, definitive delineation of a CDR and identification of residues comprising the binding site of an antibody is accomplished by solving the structure of the antibody and/or solving the structure of the antibody-ligand complex.

In certain embodiments, that can be accomplished by any of a variety of techniques known to those skilled in the art, such as X-ray crystallography. In some embodiments, various methods of analysis can be employed to identify or approximate the CDR regions. Examples of such methods include, but are not limited to, the Kabat definition, the Chothia definition, the AbM definition, the definition described by Lu et al (see above), and the contact definition.

An "affinity matured" antibody is an antibody with one or more alterations in one or more CDRs thereof, which result in an improvement in the affinity of the antibody for antigen compared to a parent antibody, which does not possess those alteration(s). Exemplary affinity matured antibodies will have nanomolar or even picomolar affinities (e.g., $K_D$ of ~$10^{-9}$ M-$10^{-12}$ M range) for the target antigen. Affinity matured antibodies are produced by procedures known in the art. Marks et al. (1992) Bio/Technology 10: 779-783 describes affinity maturation by VH and VL domain shuffling. Random mutagenesis of CDR and/or framework residues is described by Barbas, et al. (1994) Proc Nat. Acad. Sci. USA 91: 3809-3813; Schier et al. (1995) Gene 169: 147-155; Yelton et al., (1995) J. Immunol. 155: 1994-2004; Jackson et al. (1995) J. Immunol. 154(7): 3310-9; and Hawkins et al. (1992) J. Mol. Biol. 226: 889-896; and selective mutation at selective mutagenesis positions, contact or hypermutation positions with an activity enhancing amino acid residue is described in U.S. Pat. No. 6,914,128. Typically, a parent antibody and its affinity-matured progeny (e.g., derivatives) retain the same binding region within an antigen, although certain interactions at the molecular level may be altered due to amino acid residue alternation(s) introduced by affinity maturation.

The term "CDR-grafted antibody" refers to antibodies, which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "chimeric antibody" refers to antibodies, which comprise heavy and light chain variable region sequences from one species and constant region sequences from another species, such as antibodies having murine heavy and light chain variable regions linked to human constant regions.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

In some embodiments, the antibody or antigen-binding fragment thereof comprises a heavy chain framework region 1 (H-FR1) having the following amino acid sequence with optionally 1, 2 or 3 amino acid changes: EVQLVESGG-GLVQPGGSLRLSCAASG (SEQ ID NO: 174). For example, the Gly residue at position 16 may be replaced with an Arg (R); and/or, the Ala residue at position 23 may be replaced with a Thr (T).

In some embodiments, the antibody or antigen-binding fragment thereof comprises a heavy chain framework region 2 (H-FR2) having the following amino acid sequence with optionally 1, 2 or 3 amino acid changes:

(SEQ ID NO: 175)
WVRQAPGKGLEWVS.

In some embodiments, the antibody or antigen-binding fragment thereof comprises a heavy chain framework region 3 (H-FR3) having the following amino acid sequence with optionally 1, 2 or 3 amino acid changes: RFTISRDNAKNS-LYLQMNSLRAEDTAVYYC (SEQ ID NO: 176). For example, the Ser residue at position 12 may be replaced with a Thr (T).

In some embodiments, the antibody or antigen-binding fragment thereof comprises a heavy chain framework region 4 (H-FR4) having the following amino acid sequence with optionally 1, 2 or 3 amino acid changes:

(SEQ ID NO: 177)
WGQGTLVTVSS.

In some embodiments, the antibody or antigen-binding fragment thereof comprises a light chain framework region 1 (L-FR1) having the following amino acid sequence with optionally 1, 2 or 3 amino acid changes:

(SEQ ID NO: 178)
DIQMTQSPSSLSASVGDRVTITC.

In some embodiments, the antibody or antigen-binding fragment thereof comprises a light chain framework region 2 (L-FR2) having the following amino acid sequence with optionally 1, 2 or 3 amino acid changes:

(SEQ ID NO: 179)
WYQQKPGKAPKLLIY.

In some embodiments, the antibody or antigen-binding fragment thereof comprises a light chain framework region 3 (L-FR3) having the following amino acid sequence with optionally 1, 2 or 3 amino acid changes:

(SEQ ID NO: 180)
GVPSRFSGSGSGTDFTFTISSLQPEDIATYYC.

In some embodiments, the antibody or antigen-binding fragment thereof comprises a light chain framework region 4 (L-FR4) having the following amino acid sequence with optionally 1, 2 or 3 amino acid changes: FGGGTKVEIK (SEQ ID NO: 181).

In some embodiments, the antibody, or antigen binding portion thereof, comprises a heavy chain immunoglobulin constant domain of a human IgM constant domain, a human IgG constant domain, a human IgG1 constant domain, a human IgG2 constant domain, a human IgG2A constant domain, a human IgG2B constant domain, a human IgG2 constant domain, a human IgG3 constant domain, a human IgG3 constant domain, a human IgG4 constant domain, a human IgA constant domain, a human $IgA_1$ constant domain, a human IgA₂ constant domain, a human IgD constant domain, or a human IgE constant domain. In some embodiments, the antibody, or antigen binding portion thereof, comprises a heavy chain immunoglobulin constant domain of a human IgG1 constant domain or a human IgG4 constant domain. In some embodiments, the antibody, or antigen binding portion thereof, comprises a heavy chain immunoglobulin constant domain of a human IgG4 constant domain. In some embodiments, the antibody, or antigen binding portion thereof, comprises a heavy chain immunoglobulin constant domain of a human IgG4 constant domain having a backbone substitution of Ser to Pro that produces an IgG1-like hinge and permits formation of inter-chain disulfide bonds.

In some embodiments, the antibody or antigen binding portion thereof, further comprises a light chain immunoglobulin constant domain comprising a human Ig lambda constant domain or a human Ig kappa constant domain.

In some embodiments, the antibody is an IgG having four polypeptide chains which are two heavy chains and two light chains.

In some embodiments, wherein the antibody is a humanized antibody, a diabody, or a chimeric antibody. In some embodiments, the antibody is a humanized antibody. In some embodiments, the antibody is a human antibody. In some embodiments, the antibody comprises a framework having a human germline amino acid sequence.

In some embodiments, the antigen binding portion is a Fab fragment, a F(ab')2 fragment, a scFab fragment, or an scFv fragment.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin (see, e.g., Shapiro et al. (2002) Crit. Rev. Immunol. 22(3): 183-200; Marchalonis et al. (2001) Adv. Exp. Med. Biol. 484: 13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "neutralizing" refers to counteracting the biological activity of an antigen (e.g., target protein) when a binding protein specifically binds to the antigen. In an embodiment, the neutralizing binding protein binds to the antigen/target, e.g., cytokine, kinase, growth factor, cell surface protein, soluble protein, phosphatase, or receptor ligand, and reduces its biologically activity by at least about 20%, 40%, 60%, 80%, 85%, 90%, 95%, 96%, 97%, 98%, 99% or more. In some embodiments, a neutralizing antibody to a growth factor specifically binds a mature, soluble growth factor that has been released from a latent complex, thereby preventing its ability to bind its receptor to elicit downstream signaling. In some embodiments, the mature growth factor is TGFβ1 or TGFβ3.

The term "binding protein" as used herein includes any polypeptide that specifically binds to an antigen (e.g., TGFβ1), including, but not limited to, an antibody, or antigen binding portions thereof, a DVD-Ig™, a TVD-Ig, a RAb-Ig, a bispecific antibody and a dual specific antibody.

The term "monoclonal antibody" or "mAb" when used in a context of a composition comprising the same may refer to an antibody preparation obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "recombinant human antibody," as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom, H. R. (1997) TIB Tech. 15: 62-70; Azzazy, H. and Highsmith, W. E. (2002) Clin. Biochem. 35: 425-445; Gavilondo, J. V. and Larrick, J. W. (2002) BioTechniques 29: 128-145; Hoogenboom, H. and Chames, P. (2000) Immunol. Today 21: 371-378, incorporated herein by reference), antibodies isolated from an animal (e.g., a mouse) that is transgenic for human immunoglobulin genes (see, Taylor, L. D. et al. (1992) Nucl. Acids Res. 20: 6287-6295; Kellermann, S-A. and Green, L. L. (2002) Cur. Opin. in Biotechnol. 13: 593-597; Little, M. et al. (2000) Immunol. Today 21: 364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "Dual Variable Domain Immunoglobulin" or "DVD-Ig™" and the like include binding proteins comprising a paired heavy chain DVD polypeptide and a light chain DVD polypeptide with each paired heavy and light chain providing two antigen binding sites. Each binding site includes a total of 6 CDRs involved in antigen binding per antigen binding site. A DVD-Ig™ is typically has two arms bound to each other at least in part by dimerization of the CH3 domains, with each arm of the DVD being bispecific, providing an immunoglobulin with four binding sites. DVD-Ig™ are provided in US Patent Publication Nos. 2010/0260668 and 2009/0304693, each of which are incorporated herein by reference including sequence listings.

As used herein, "Triple Variable Domain Immunoglobulin" or "TVD-Ig" and the like are binding proteins comprising a paired heavy chain TVD binding protein polypeptide and a light chain TVD binding protein polypeptide with each paired heavy and light chain providing three antigen binding sites. Each binding site includes a total of 6 CDRs involved in antigen binding per antigen binding site. A TVD binding protein may have two arms bound to each other at least in part by dimerization of the CH3 domains, with each arm of the TVD binding protein being trispecific, providing a binding protein with six binding sites.

As used herein, "Receptor-Antibody Immunoglobulin" or "RAb-Ig" and the like are binding proteins comprising a heavy chain RAb polypeptide, and a light chain RAb polypeptide, which together form three antigen binding sites in total. One antigen binding site is formed by the pairing of the heavy and light antibody variable domains present in each of the heavy chain RAb polypeptide and the light chain RAb polypeptide to form a single binding site with a total of 6 CDRs providing a first antigen binding site. Each the heavy chain RAb polypeptide and the light chain RAb polypeptide include a receptor sequence that independently binds a ligand providing the second and third "antigen" binding sites. A RAb-Ig is typically has two arms bound to each other at least in part by dimerization of the CH3 domains, with each arm of the RAb-Ig being trispecific, providing an immunoglobulin with six binding sites. RAb-Igs are described in US Patent Application Publication No. 2002/0127231, the entire contents of which including sequence listings are incorporated herein by reference).

The term "bispecific antibody," as used herein, and as differentiated from a "bispecific half-Ig binding protein" or "bispecific (half-Ig) binding protein", refers to full-length antibodies that are generated by quadroma technology (see Milstein, C. and Cuello, A. C. (1983) Nature 305(5934): p. 537-540), by chemical conjugation of two different monoclonal antibodies (see Staerz, U. D. et al. (1985) Nature 314(6012): 628-631), or by knob-into-hole or similar approaches, which introduce mutations in the Fc region that do not inhibit CH3-CH3 dimerization (see Holliger, P. et al. (1993) Proc. Natl. Acad. Sci USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds to.

The term "dual-specific antibody," as used herein, and as differentiated from a bispecific half-Ig binding protein or bispecific binding protein, refers to full-length antibodies that can bind two different antigens (or epitopes) in each of its two binding arms (a pair of HC/LC) (see PCT Publication No. WO 02/02773). Accordingly, a dual-specific binding protein has two identical antigen binding arms, with identical specificity and identical CDR sequences, and is bivalent for each antigen to which it binds.

The term "Kon," as used herein, is intended to refer to the on rate constant for association of a binding protein (e.g., an antibody) to the antigen to form the, e.g., antibody/antigen complex as is known in the art. The "Kon" also is known by the terms "association rate constant," or "ka," as used interchangeably herein. This value indicating the binding rate of an antibody to its target antigen or the rate of complex formation between an antibody and antigen also is shown by the equation: Antibody ("Ab")+Antigen ("Ag")→RAb-Ag.

The term "Koff," as used herein, is intended to refer to the off rate constant for dissociation of a binding protein (e.g., an antibody) from the, e.g., antibody/antigen complex as is known in the art. The "Koff" also is known by the terms "dissociation rate constant" or "kd" as used interchangeably herein. This value indicates the dissociation rate of an antibody from its target antigen or separation of Ab–Ag complex over time into free antibody and antigen as shown by the equation: Ab+Ag←Ab–Ag.

The terms "equilibrium dissociation constant" or "$K_D$," as used interchangeably herein, refer to the value obtained in a titration measurement at equilibrium, or by dividing the dissociation rate constant (koff) by the association rate constant (kon). The association rate constant, the dissociation rate constant, and the equilibrium dissociation constant are used to represent the binding affinity of a binding protein, e.g., antibody, to an antigen. Methods for determining association and dissociation rate constants are well known in the art. Using fluorescence-based techniques offers high sensitivity and the ability to examine samples in physiological buffers at equilibrium. Other experimental approaches and instruments, such as a BIACORE® (biomolecular interaction analysis) assay, can be used (e.g., instrument available from BIACORE® International AB, a GE HEALTHCARE® company, Uppsala, Sweden). Additionally, a KINEXA® (Kinetic Exclusion Assay) assay, available from Sapidyne Instruments (Boise, Idaho), can also be used.

The terms "crystal" and "crystallized" as used herein, refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 201-16, Oxford University Press, New York, New York, (1999). The term "linker" is used to denote polypeptides comprising two or more amino acid residues joined by peptide bonds and are used to link one or more antigen binding portions. Such linker polypeptides are well known in the art (see, e.g., Holliger, P. et al. (1993) Proc. Natl. Acad. Sci. USA 90: 6444-6448; Poljak, R. J. et al. (1994) Structure 2:1121-1123). Exemplary linkers include, but are not limited to, ASTKGPSVFPLAP (SEQ ID NO: 55), ASTKGP (SEQ ID NO: 56); TVAAPSVFIFPP (SEQ ID NO: 57); TVAAP (SEQ ID NO: 58); AKTTPKLEEGEFSEAR (SEQ ID NO: 59); AKTTPKLEEGEFSEARV (SEQ ID NO: 60); AKTTPKLGG (SEQ ID NO: 61); SAKTTPKLGG (SEQ ID NO: 62); SAKTTP (SEQ ID NO: 63); RADAAP (SEQ ID NO: 64); RADAAPTVS (SEQ ID NO: 65); RADAAAAGGPGS (SEQ ID NO: 66); RADAAAA(G4S)4 (SEQ ID NO: 67); SAKTTPKLEEGEFSEARV (SEQ ID NO: 68); ADAAP (SEQ ID NO: 69); ADAAPTVSIFPP (SEQ ID NO: 70); QPKAAP (SEQ ID NO: 71); QPKAAPSVTLFPP (SEQ ID NO: 72); AKTTPP (SEQ ID NO: 73); AKTTPPSVTPLAP (SEQ ID NO: 74); AKTTAP (SEQ ID NO: 75); AKTTAPSVYPLAP (SEQ ID NO: 76); GGGGSGGGGSGGGGS (SEQ ID NO: 77); GENKVEYAPALMALS (SEQ ID NO: 78); GPAKELTPLKEAKVS (SEQ ID NO: 79); GHEAAAVMQVQYPAS (SEQ ID NO: 80); TVAAPSVFIFPPTVAAPSVFIFPP (SEQ ID NO: 81); and ASTKGPSVFPLAPASTKGPSVFPLAP (SEQ ID NO: 82).

"Label" and "detectable label" or "detectable moiety" mean a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{18}$F, $^{11}$C, $^{13}$N, $^{15}$O, $^{68}$Ga, $^{18}$F, $^{89}$Zr, $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm); chromogens; fluorescent labels (e.g., FITC, rhodamine, and lanthanide phosphors); enzymatic labels (e.g., horseradish peroxidase, luciferase, and alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

In some embodiments, the binding affinity of an antibody, or antigen binding portion thereof, to an antigen (e.g., protein complex), such as presenting molecule-proTGFβ1 complexes, is determined using an OCTET® assay. In some embodiments, an OCTET® assay is an assay that determines one or more a kinetic parameters indicative of binding between an antibody and antigen. In some embodiments, an OCTET® system (ForteBio, Menlo Park, CA) is used to determine the binding affinity of an antibody, or antigen binding portion thereof, to presenting molecule-proTGFβ1 complexes. For example, binding affinities of antibodies may be determined using the fortéBio OCTET® QKe dip and read label free assay system utilizing bio-layer interferometry. In some embodiments, antigens are immobilized to biosensors (e.g., streptavidin-coated biosensors) and the antibodies and complexes (e.g., biotinylated presenting molecule-proTGFβ1 complexes) are presented in solution at high concentration (50 µg/mL) to measure binding interactions. In some embodiments, the binding affinity of an antibody, or antigen binding portion thereof, to a presenting molecule-proTGFβ1 complex is determined using the protocol outlined herein.

Characterization of the Novel, High-Affinity, Context-Independent Antibodies of proTGFβ1

Binding Profiles

Antibodies disclosed herein have enhanced binding activities. Included are a class of high-affinity, context-independent antibodies capable of selectively inhibiting TGFβ1 activation. Note that the term "context independent" is used herein with a greater degree of stringency as compared to previous more general usage. According to the present disclosure, the term confers a level of uniformity in relative affinities (i.e., unbias) that the antibody can exert towards different antigen complexes. Thus, the context-independent antibody of the present invention is capable of targeting multiple types of TGFβ1 precursor complexes (e.g., presenting molecule-proTGFβ1 complexes) and of binding to each such complex with equivalent affinities (i.e., no greater than three-fold differences in relative affinities across the complexes) with $K_D$ values lower than 10 nM, preferably lower than 5 nM, more preferably lower than 1 nM, even more preferably lower than 100 µM, as measured by, for example, MSD-SET. As presented below, many antibodies encompassed by the invention have $K_D$ values in a sub-nanomolar range.

Thus, the antibodies are capable of specifically binding to each of the human presenting molecule-proTGFβ1 complexes (sometimes referred to as "Large Latency Complex" which is a ternary complex comprised of a proTGFβ1 dimer coupled to a single presenting molecule), namely, LTBP1-proTGFβ1, LTBP3-proTGFβ1, GARP-proTGFβ1 and LRRC33-proTGFβ1. Typically, recombinantly produced, purified protein complexes are used as antigens (e.g., antigen complexes) to evaluate or confirm the ability of an antibody to bind the antigen complexes in suitable in vitro binding assays. Such assays are well known in the art and include, but are not limited to Bio-Layer Interferometry (BLI)-based assays (such as OCTET®) and solution equilibrium titration-based assays (such as MSD-SET).

BLI-based binding assays are widely used in the art for measuring affinities and kinetics of antibodies to antigens. It is a label-free technology in which biomolecular interactions are analyzed on the basis of optical interference. One of the proteins, for example, an antibody being tested, can be immobilized on the biosensor tip. When the other protein in solution, for example, an antigen, becomes bound to the immobilized antibody, it causes a shift in the interference pattern, which can be measured in real-time. This allows the monitoring of binding specificity, rates of association and dissociation, as well as concentration dependency. Thus, BLI is a kinetic measure that reveals the dynamics of the system. Due to its ease of use and fast results, BLI-based assays such as the OCTET® system (available from ForteBio/Molecular Devices, Fremont California), are particularly convenient when used as an initial screening method to identify and separate a pool of "binders" from a pool of "non-binders" or "weak binders" in the screening process.

BLI-based binding assays revealed that the novel antibodies are characterized as "context-balanced/context-independent" antibodies when binding affinity is measured by OCTET®. As can be seen in Table 8 summarizing BLI-based binding profiles of non-limiting examples of antibodies, these antibodies show relatively uniform $K_D$ values in a sub-nanomolar range across the four target complexes, with relatively low matrix-to-cell differentials (no greater than five-fold bias) (see column (H)). This can be contrasted against the previously identified antibody Ab3, provided as a reference antibody, which shows significantly higher relative affinities towards matrix-associated complexes (27+ fold bias) over cell-associated complexes.

Table 8 below provides non-limiting examples of high-affinity, context-independent proTGFβ1 antibodies encompassed by the present invention. The table provides representative results from in vitro binding assays, as measured by OCTET®. Similar results are also obtained by an SPR-based technique (BIACORE® System).

Column (A) of the table lists monoclonal antibodies with discrete amino acid sequences. Ab3 (shown in bold) is a reference antibody identified previously, which was shown to be potent in cell-based assays; efficacious in various animal models; and, with a clean toxicology profile (disclosed in: PCT/US2018/012601). Columns (B), (D), (E) and (F) provide affinities of each of the listed antibodies, measured in $K_D$. Column (B) shows the affinity to a recombinant human LTBP1-proTGFβ1 complex; column (C) shows the affinity to a recombinant human LTBP3-proTGFβ1 complex; (E) shows the affinity to a recombinant human GARP-proTGFβ1 complex; and (F) shows the affinity to a recombinant human LRRC33-proTGFβ1 complex, of each of the antibodies. Average $K_D$ values of (B) and (C) are shown in the corresponding column (D), which collectively represents affinities of the antibodies to ECM- or matrix-associated proTGFβ1 complexes. Similarly, Average $K_D$ values of (E) and (F) are shown in the corresponding column (G), which collectively represents affinities of the antibodies to cell-surface or cell-associated proTGFβ1 complexes. Finally, relative ratios between the average $K_D$ values from columns (D) and (G) are expressed as "fold bias" in column (H). Thus, the greater the number of column (H) is, the greater bias exists for the particular antibody, when comparing binding preferences of the antibody for matrix-associated complexes and cell-surface complexes. This is one way of quantitatively representing and comparing inherent bias of antibodies to their target complexes. Such analyses may be useful in guiding the selection process for a candidate antibody for particular therapeutic use.

affinity of <5 nM, ≤4 nM, ≤3 nM, ≤2 nM, ≤1 nM, ≤5 nM or ≤0.5 nM. In some embodiments, the antibody or the fragment binds a human GARP-proTGFβ1 complex with an affinity of <5 nM, ≤4 nM, ≤3 nM, ≤2 nM, ≤1 nM, ≤5 nM or ≤0.5 nM. In some embodiments, the antibody or the fragment binds a human LRRC33-proTGFβ1 complex with an affinity of <5 nM, ≤4 nM, ≤3 nM, ≤2 nM, ≤1 nM or ≤0.5 nM.

In preferred embodiments, such antibody is human- and murine-cross-reactive. Thus, in some embodiments, the antibody or the fragment binds a murine LTBP1-proTGFβ1 complex with an affinity of <5 nM, ≤4 nM, ≤3 nM, ≤2 nM, ≤1 nM, 5 nM or ≤0.5 nM. In some embodiments, the antibody or the fragment binds a murine LTBP3-proTGFβ1 complex with an affinity of <5 nM, ≤4 nM, ≤3 nM, ≤2 nM, ≤1 nM or ≤0.5 nM. In some embodiments, the antibody or the fragment binds a murine GARP-proTGFβ1 complex with an affinity of <5 nM, ≤4 nM, ≤3 nM, ≤2 nM, ≤1 nM or ≤0.5 nM. In some embodiments, the antibody or the fragment binds a murine LRRC33-proTGFβ1 complex with an affinity of <5 nM, ≤4 nM, ≤3 nM, ≤2 nM, ≤1 nM or ≤0.5 nM.

As shown, the proTGFβ1 antibodies of the present disclosure have particularly high affinities for matrix-associated proTGFβ1 complexes. In some embodiments, the aver-

TABLE 8

Non-limiting examples of context-independent TGFβ1 antibodies and $K_D$ values measured by BLI

| (A) | Matrix-associated proTGFb1 | | (D) | Cell-associated proTGFb1 | | | (H) |
|---|---|---|---|---|---|---|---|
| Ab Ref | (B) hLTBP1 | (C) hLTBP3 | ECM AVRG (nM) | (E) hGARP | (F) hLRRC33 | (G) Cell AVRG (nM) | G/D (fold bias) |
| Ab3 | 4.70E−10 | 4.59E−10 | 0.4645 | 1.73E−08 | 8.52E−09 | 12.91 | 27.79 |
| Ab21 | 2.25E−10 | 2.68E−10 | 0.2465 | 8.33E−10 | 4.55E−10 | 0.644 | 2.613 |
| Ab22 | 3.18E−10 | 3.29E−10 | 0.3235 | 9.74E−10 | 4.15E−10 | 0.6945 | 2.147 |
| Ab23 | 4.17E−10 | 4.68E−10 | 0.4425 | 1.34E−09 | 4.55E−10 | 0.8975 | 2.028 |
| Ab24 | 2.46E−10 | 1.98E−10 | 0.222 | 6.65E−10 | 4.10E−10 | 0.5375 | 2.421 |
| Ab25 | 2.17E−10 | 1.52E−10 | 0.1845 | 4.88E−10 | 4.09E−10 | 0.4485 | 2.431 |
| Ab26 | 2.21E−10 | 1.73E−10 | 0.197 | 6.25E−10 | 3.60E−10 | 0.4925 | 2.500 |
| Ab27 | 1.78E−10 | 2.38E−10 | 0.208 | 4.24E−10 | 2.99E−10 | 0.3615 | 1.738 |
| Ab28 | 3.40E−10 | 3.16E−10 | 0.328 | 7.97E−10 | 4.09E−10 | 0.603 | 1.838 |
| Ab29 | 1.89E−10 | 1.21E−10 | 0.155 | 3.07E−10 | 3.02E−10 | 0.3045 | 1.965 |
| AB30 | 3.32E−10 | 2.61E−10 | 0.2965 | 8.33E−10 | 5.35E−10 | 0.684 | 2.307 |
| Ab31 | 2.36E−10 | 1.81E−10 | 0.2085 | 5.81E−10 | 4.10E−10 | 0.4955 | 2.376 |
| Ab6 | 2.07E−10 | 1.23E−10 | 0.165 | 4.04E−10 | 3.36E−10 | 0.37 | 2.242 |
| Ab32 | 2.69E−10 | 2.15E−10 | 0.242 | 4.96E−10 | 6.98E−10 | 0.597 | 2.467 |
| Ab33 | 1.79E−10 | 1.11E−10 | 0.145 | 2.65E−10 | 3.39E−10 | 0.302 | 2.083 |

The invention provides a class of high-affinity, context-independent antibodies, each of which is capable of binding with equivalent affinities to each of the four known presenting molecule-proTGFβ1 complexes, namely, LTBP1-proTGFβ1, LTBP3-proTGFβ1, GARP-proTGFβ1, and LRRC33-proTGFβ1. In some embodiments, the antibody binds each of the presenting molecule-proTGFβ1 complexes with equivalent or higher affinities, as compared to the previously described reference antibody, Ab3. According to the invention, such antibody specifically binds each of the aforementioned complexes with an affinity (determined by $K_D$) of <5 nM as measured by a suitable in vitro binding assay, such as Biolayer Interferometry and surface plasmon resonance. In some embodiments, the antibody or the fragment binds a human LTBP1-proTGFβ1 complex with an affinity of <5 nM, ≤4 nM, ≤3 nM, ≤2 nM, ≤1 nM, 5 nM or ≤0.5 nM. In some embodiments, the antibody or the fragment binds a human LTBP3-proTGFβ1 complex with an age $K_D$ value of the matrix-associated complexes (i.e., LTBP1-proTGFβ1 and LTBP3-proTGFβ1) is <1 nM or ≤0.5 nM.

As shown, the proTGFβ1 antibodies of the present disclosure have high affinities for cell-associated proTGFβ1 complexes. In some embodiments, the average $K_D$ value of the cell-associated complexes (i.e., GARP-proTGFβ1 and LRRC33-proTGFβ1) is <2 nM or ≤1 nM.

The high-affinity proTGFβ1 antibodies of the present disclosure are characterized by their uniform (unbiased) affinities towards the all four antigen complexes (compare, for example, to Ab3). No single antigen complex among the four known presenting molecule-proTGFβ1 complexes described herein deviates significantly in $K_D$. In other words, more uniform binding activities have been achieved by the present disclosure relative to previously described proTGFβ1 antibodies (including Ab3) in that each such antibody shows equivalent affinities across the four antigen complexes. In some embodiments, the antibody or the fragment shows unbiased or uniform binding profiles, characterized in that the difference (or range) of affinities of the antibody or the fragments across the four proTGFβ1 antigen complexes is no more than five-fold between the lowest and the highest $K_D$ values. In some embodiments, the relative difference (or range) of affinities is no more than three-fold.

The concept of "uniformity" or lack of bias is further illustrated in Table 8. Average $K_D$ values between the two matrix-associated and cell-associated complexes are calculated, respectively (see columns (D) and (G)). These average $K_D$ values can then be used to ask whether bias in binding activities exists between complexes associated with matrix vs. complexes associated with cell surface (e.g., immune cells). Bias may be expressed as "fold-difference" in the average $K_D$ values, as illustrated in Table 8. As compared to the previously described antibody, Ab3, the high-affinity, context-independent proTGFβ1 antibodies encompassed by the present disclosure are remarkably unbiased in that many show no more than three-fold difference in average $K_D$ values between matrix- and cell-associated complexes (compare this to 25+ fold bias in Ab3).

Accordingly, a class of context-independent monoclonal antibodies or fragments is provided, each of which is capable of binding with equivalent affinities to each of the following presenting molecule-proTGFβ1 complexes with an affinity of ≤1 nM as measured by Biolayer Interferometry or surface plasmon resonance: LTBP1-proTGFβ1, LTBP3-proTGFβ1, GARP-proTGFβ1, and LRRC33-proTGFβ1. Such antibody specifically binds each of the aforementioned complexes with an affinity of ≤5 nM as measured by Biolayer Interferometry or surface plasmon resonance, wherein the monoclonal antibody or the fragment shows no more than a three-fold bias in affinity towards any one of the above complexes relative to the other complexes, and wherein the monoclonal antibody or the fragment inhibits release of mature TGFβ1 growth factor from each of the proTGFβ1 complexes but not from proTGFβ2 or proTGFβ3 complexes.

Whilst the kinetics of binding profiles (e.g., "on" and "off" rates) obtainable from BLI-based assays provide useful information, Applicant of the present disclosure contemplated that, based on the mechanism of action of the activation inhibitors disclosed herein, that is, antibodies that work by binding to a tethered (e.g., tissue-localized) inactive (e.g., latent) target thereby preventing it from getting activated, binding properties measured at equilibrium might more accurately reflect their in vivo behavior and potency. To put this in perspective, as an example, antibodies with fast "on" rate ("$K_{on}$") which would be reflected in binding measurements obtained by BLI, may provide relevant parameters for evaluating neutralizing antibodies (e.g., antibodies that directly target and must rapidly sequester the active, soluble growth factor itself for them to function as effective inhibitors). However, the same may not necessarily apply for antibodies that function as activation inhibitors, such as those disclosed herein. As described, the mechanism of action of the novel TGFβ1 inhibitors of the present invention is via the inhibition of the activation step, which is achieved by targeting the tissue/cell-tethered latent complex, as opposed to sequestration of soluble, post-activation growth factor. This is because an activation inhibitor of TGFβ1 targets the inactive precursor localized to respective tissues (e.g., within the ECM, immune cell surface, etc.) thereby preemptively prevent the mature growth factor from being released from the complex. This mechanism of action is thought to allow the inhibitor to achieve target saturation (e.g., equilibrium) in vivo, without the need for rapidly competing for transient growth factor molecules against endogenous receptors as required by conventional neutralizing inhibitors.

Taking this difference in the mechanism of action into consideration, further evaluation of binding properties was carried out by the use of another mode of in vitro binding assays that allows the determination of affinity at equilibrium.

In view of this, it is contemplated that assays that measure binding affinities of such antibodies at equilibrium may more accurately represent the mode of target engagement in vivo. Thus, MSD-SET-based binding assays (or other suitable assays) may be performed, as exemplified in Table 9 below.

Solution equilibrium titration ("SET") is an assay whereby binding between two molecules (such as an antigen and an antibody that binds the antigen) can be measured at equilibrium in a solution. For example, Meso-Scale Discovery ("MSD")-based SET, or MSD-SET, is a useful mode of determining dissociation constants for particularly high-affinity protein-protein interactions at equilibrium (see, for example: Ducata et al. (2015) J Biomolecular Screening 20(10): 1256-1267). The SET-based assays are particularly useful for determining KD values of antibodies with sub-nanomolar (e.g., picomolar) affinities.

TABLE 9

Non-limiting examples of high-affinity context-independent TGFβ1 antibodies (hIgG4) and $K_D$ values measured by MSD-SET

| | Matrix-associated proTGFβ1 | | | Cell-associated proTGFβ1 | | | |
|---|---|---|---|---|---|---|---|
| (A) Ab Ref | (B) hLTBP1 | (C) hLTBP3 | (D) ECM AVRG (nM) | (E) hGARP | (F) hLRRC33 | (G) Cell AVRG (nM) | (H) G/D (fold bias) |
| C1 | 3.30E−08 | 1.40E−08 | 23.2 | 5.10E−09 | 2.20E−09 | 3.65 | 0.16 |
| C2 | 2.10E−08 | 1.20E−08 | 16.5 | 8.80E−09 | 6.10E−09 | 7.45 | 0.48 |
| Ab3 | 1.30E−08 | 1.62E−08 | 14.6 | 2.80E−08 | 3.50E−08 | 31.5 | 2.16 |
| Ab6 | 1.8E−11 | 2.9E−11 | 0.024 | 2.7E−11 | 6.3E−11 | 0.045 | 1.88 |
| Ab22 | 5.00E−11 | 3.30E−11 | 0.042 | 2.70E−11 | 2.00E−10 | 0.114 | 2.71 |
| Ab24 | 2.40E−11 | 2.10E−11 | 0.023 | 1.90E−11 | 1.80E−10 | 0.100 | 4.35 |
| AB26 | 2.80E−11 | 2.30E−11 | 0.026 | 1.40E−11 | 1.30E−10 | 0.072 | 2.77 |
| Ab29 | 1.20E−11 | 1.10E−11 | 0.012 | 5.50E−12 | 4.30E−11 | 0.024 | 2.00 |
| Ab30 | 3.10E−11 | 2.60E−11 | 0.029 | 2.20E−11 | 1.40E−10 | 0.081 | 2.80 |
| Ab31 | 1.90E−11 | 1.40E−11 | 0.017 | 1.90E−11 | 9.60E−11 | 0.058 | 3.41 |
| Ab32 | 3.70E−11 | 2.60E−11 | 0.032 | 1.50E−11 | 8.70E−11 | 0.051 | 1.60 |

TABLE 9-continued

Non-limiting examples of high-affinity context-independent
TGFβ1 antibodies (hIgG4) and $K_D$ values measured by MSD-SET

| | | | Matrix-associated proTGFβ1 | | Cell-associated proTGFβ1 | | |
| --- | --- | --- | --- | --- | --- | --- | --- |
| (A)<br>Ab Ref | (B)<br>hLTBP1 | (C)<br>hLTBP3 | (D)<br>ECM AVRG<br>(nM) | (E)<br>hGARP | (F)<br>hLRRC33 | (G)<br>Cell AVRG<br>(nM) | (H)<br>G/D (fold<br>bias) |
| Ab33 | 1.10E−11 | 7.00E−12 | 0.009 | 7.80E−12 | 4.60E−11 | 0.027 | 3.00 |
| Ab4 | 4.6E−9 | 5.5E−9 | 5.05 | 2.5E−9 | 2.1E−9 | 2.3 | 0.42 |

("h" denotes human complex)

Table 9 also includes three previously described TGFβ1-selective antibodies (C1, C2 and Ab3) as reference antibodies. C1 and C2 were first disclosed in PCT/US2017/021972 published as WO 2017/156500, and Ab3 was described in PCT/US2018/012601 published as WO 2018/129329.

As can be seen from the affinity data provide in Table 9, binding activities of the novel antibodies according to the present disclosure are significantly higher than the previously identified reference antibodies. Moreover, the novel TGFβ1 antibodies are "context-independent" in that they bind to each of the human LLC complexes with equivalent affinities (e.g., ~sub-nanomolar range, e.g., with KD of <1 nM). The high-affinity, context-independent binding profiles suggest that these antibodies may be advantageous for use in the treatment of TGFβ1-related indications that involve dysregulation of both the ECM-related and immune components, such as cancer.

For solution equilibrium titration-based binding assays, protein complexes that comprise one of the presenting molecules such as those shown above may be employed as antigen (presenting molecule-TGFβ1 complex, or an LLC). Test antibodies are allowed to form antigen-antibody complex in solution. Antigen-antibody reaction mixtures are incubated to allow an equilibrium to be reached; the amount of the antigen-antibody complex present in the assay reactions can be measured by suitable means well known in the art. As compared to BLI-based assays, SET-based assays are less affected by on/off rates of the antigen-antibody complex, allowing sensitive detection of very high affinity interactions. As shown in Table 9, in the present disclosure, preferred high-affinity inhibitors of TGFβ1 show a sub-nanomolar (e.g., picomolar) range of affinities across all large latent complexes tested, as determined by SET-based assays.

Accordingly, a class of context-independent monoclonal antibodies or fragments is provided, each of which is capable of binding with equivalent affinities to each of the following human presenting molecule-proTGFβ1 complexes with a $K_D$ of ≤1 nM as measured by a solution equilibrium titration assay, such as MSD-SET: hLTBP1-proTGFβ1, hLTBP3-proTGFβ1, hGARP-proTGFβ1, and hLRRC33-proTGFβ1. Such antibody specifically binds each of the aforementioned complexes with a $K_D$ of ≤1 nM as measured by MSD-SET, and wherein the monoclonal antibody or the fragment inhibits release of mature TGFβ1 growth factor from each of the proTGFβ1 complexes but not from proTGFβ2 or proTGFβ3 complexes. In preferred embodiments, such antibody or the fragment binds each of the aforementioned complexes with a $K_D$ of 500 μM or less (i.e., ≤500 μM), 250 μM or less (i.e., ≤250 μM), or 200 μM or less (i.e., ≤200 μM). Even more preferably, such antibody or the fragment binds each of the aforementioned complexes with a $K_D$ of 100 μM or less (i.e., ≤100 μM). In some embodiments, the antibody or the fragment does not bind to free TGFβ1 growth factor which is not associated with the prodomain complex. This can be tested or confirmed by suitable in vitro binding assays known in the art, such as biolayer interferometry.

In further preferred embodiments, such antibodies or the fragments are also cross-reactive with murine (e.g., rat and/or mouse) and/or non-human primate (e.g., cyno) counterparts. To give but one example, Ab6 is capable of binding with high affinity to each of the large latent complexes of multiple species, including: human, murine, rat, and cynomolgus monkey, as exemplified in Table 10 and Example 9 below.

TABLE 10

Non-limiting example of high-affinity context-independent TGFβ1
antibody with cross-species reactivities as measured by MSD-SET

| Ag<br>complex | hLTBP1-<br>proTGFβ1 | hLTBP3-<br>proTGFβ1 | hGARP-<br>proTGFβ1 | hLRRC33-<br>proTGFβ1 | mLTBP1-<br>proTGFβ1 | mLTBP3-<br>proTGFβ1 | mGARP-<br>proTGFβ1 | mLRRC33-<br>proTGFβ1 |
| --- | --- | --- | --- | --- | --- | --- | --- | --- |
| Ab6 | 1.80E−11 | 2.90E−11 | 2.70E−11 | 6.30E−11 | 2.40E−11 | 2.80E−11 | 2.10E−11 | 4.80E−11 |

("h" denotes human; "m" denotes murine)

Potency

Antibodies disclosed herein may be broadly characterized as "functional antibodies" for their ability to inhibit TGFβ1 signaling. As used herein, "a functional antibody" confers one or more biological activities by virtue of its ability to bind a target protein (e.g., antigen), in such a way as to modulate its function. Functional antibodies therefore broadly include those capable of modulating the activity/function of target molecules (i.e., antigen). Such modulating antibodies include inhibiting antibodies (or inhibitory antibodies) and activating antibodies. The present disclosure is drawn to antibodies which can inhibit a biological process mediated by TGFβ1 signaling associated with multiple contexts of TGFβ1. Inhibitory agents used to carry out the present invention, such as the antibodies described herein, are intended to be TGFβ1-selective and not to target or interfere with TGFβ2 and TGFβ3 when administered at a therapeutically effective dose (dose at which sufficient efficacy is achieved within acceptable toxicity levels). The novel antibodies of the present disclosure have enhanced inhibitory activities (potency) as compared to previously identified activation inhibitors of TGFβ1.

In some embodiments, potency of an inhibitory antibody may be measured in suitable cell-based assays, such as CAGA reporter cell assays described herein. Generally, cultured cells, such as heterologous cells and primary cells, may be used for carrying out cell-based potency assays. Cells that express endogenous TGFβ1 and/or a presenting molecule of interest, such as LTBP1, LTBP3, GARP and LRRC33, may be used. Alternatively, exogenous nucleic acids encoding protein(s) of interest, such as TGFβ1 and/or a presenting molecule of interest, such as LTBP1, LTBP3, GARP and LRRC33, may be introduced into such cells for expression, for example by transfection (e.g., stable transfection or transient transfection) or by viral vector-based infection. In some embodiments, LN229 cells are employed for such assays. The cells expressing TGFβ1 and a presenting molecule of interest (e.g., LTBP1, LTBP3, GARP or LRRC33) are grown in culture, which "present" the large latent complex either on cell surface (when associated with GARP or LRRC33) or deposit into the ECM (when associated with an LTBP). Activation of TGFβ1 may be triggered by integrin, expressed on another cell surface. The integrin-expressing cells may be the same cells co-expressing the large latent complex or a separate cell type. Reporter cells are added to the assay system, which incorporates a TGFβ3-responsive element. In this way, the degree of TGFβ activation may be measured by detecting the signal from the reporter cells (e.g., TGFβ-responsive reporter genes, such as luciferase coupled to a TGFβ3-responsive promoter element) upon TGFβ activation. Using such cell-based assay systems, inhibitory activities of the antibodies can be determined by measuring the change (reduction) or difference in the reporter signal (e.g., luciferase activities as measured by fluorescence readouts) either in the presence or absence of test antibodies. Such assays are exemplified in Example 2 herein.

Thus, in some embodiments, the inhibitory potency ($IC_{50}$) of the novel antibodies of the present disclosure calculated based on cell-based reporter assays for measuring TGFβ1 activation (such as LN229 cell assays described elsewhere herein) may be 5 nM or less, measured against each of the hLTBP1-proTGFβ1, hLTBP3-proTGFβ1, hGARP-proTGFβ1 and hLRRC33-proTGFβ1 complexes. In some embodiments, the antibodies have an $IC_{50}$ of 2 nM or less (i.e., ≤2 nM) measured against each of the LLCs. In preferred embodiments, the $IC_{50}$ of the antibody measured against each of the LLC complexes is 1 nM or less. In some embodiments, the antibody has an $IC_{50}$ of less than 1 nM against each of the hLTBP1-proTGFβ1, hLTBP3-proTGFβ1, hGARP-proTGFβ1 and hLRRC33-proTGFβ1 complexes.

TABLE 11

Inhibitory potencies (in $IC_{50}$) of select antibodies as measured by reporter cell assays

| | $IC_{50}$ (nM) | | | |
|---|---|---|---|---|
| Ab Ref. | hLTBP1-proTGFβ1 | hLTBP3-proTGFβ1 | hGARP-proTGFβ1 | hLRRC33-proTGFβ1 |
| Ab3 | 24.29 | 10.42 | 0.981 | 0.8578 |
| Ab4 | 5.222 | 5.647 | 0.8221 | 3.499 |
| Ab5 | 1.288 | 1.004 | 0.14 | 0.6158 |
| Ab6 | 2.741 | 0.8214 | 0.324 | 0.4953 |
| Ab21 | 1.607 | 0.7647 | 0.4005 | 0.5958 |
| Ab23 | 0.8353 | 0.8788 | 0.2639 | 0.5793 |
| Ab25 | 6.081 | 0.538 | 0.4418 | 0.6529 |
| Ab26 | 0.7131 | 0.7164 | 0.2619 | 0.3406 |
| Ab29 | 0.4711 | 0.803 | 0.2637 | 0.458 |
| Ab33 | 1.56 | 1.112 | 0.1981 | 0.7383 |

Activation of TGFβ1 may be triggered by an integrin-dependent mechanism or protease-dependent mechanism. The inhibitory activities (e.g., potency) of the antibodies according to the present disclosure may be evaluated for the ability to block TGFβ1 activation induced by one or both of the modes of activation. The reporter cell assays described above are designed to measure the ability of the antibodies to block or inhibit integrin-dependent activation of TGFβ1 activation. Inhibitory potency may also be assessed by measuring the ability of the antibodies to block protease-induced activation of TGFβ1. Example 3 of the present disclosure provides non-limiting embodiments of such assays. Results are summarized in FIGS. 5A and 5B. Accordingly, in some embodiments of the invention, the isoform-selective inhibitor according to the present disclosure is capable of inhibiting integrin-dependent activation of TGFβ1 and protease-dependent activation of TGFβ1. Such inhibitor may be used to treat a TGFβ1-related indication characterized by EDM dysregulation involving protease activities. For example, such TGFβ1-related indication may be associated with elevated myofibroblasts, increased stiffness of the ECM, excess or abnormal collagen deposition, or any combination thereof. Such conditions include, for example, fibrotic disorders and cancer comprising a solid tumor (such as metastatic carcinoma) or myelofibrosis.

In some embodiments, potency may be evaluated in suitable in vivo models as a measure of efficacy and/or pharmacodynamics effects. For example, if the first antibody is efficacious in an in vivo model at a certain concentration, and the second antibody is equally efficacious at a lower concentration than the first in the same in vivo model, then, the second antibody can be said to me more potent than the first antibody. Any suitable disease models known in the art may be used to assess relative potencies of TGFβ1 inhibitors, depending on the particular indication of interest, e.g., cancer models and fibrosis models. Preferably, multiple doses or concentrations of each test antibody are included in such studies.

Similarly, pharmacodynamics (PD) effects may be measured to determine relative potencies of inhibitory antibodies. Commonly used PD measures for the TGFβ signaling pathway include, without limitation, phosphorylation of SMAD2/3 and expression of downstream effector genes, the transcription of which is sensitive to TGFβ activation, such as those with a TGFβ3-responsive promoter element (e.g., Smad-binding elements). In some embodiments, the antibodies of the present disclosure are capable of completely blocking disease-induced SMAD2/3 phosphorylation in preclinical fibrosis models when the animals are administered at a dose of 3 mg/kg or less. In some embodiments, the antibodies of the present disclosure are capable of significantly suppressing fibrosis-induced expression of a panel of marker genes including Acta2, Col1a1, Col3a1, Fn1, Itga11, Lox, Lox12, when the animals are administered at a dose of 10 mg/kg or less in the UUO model of kidney fibrosis.

In some embodiments, the selection process of an antibody or antigen-binding fragment thereof for therapeutic use may therefore include identifying an antibody or fragment that shows sufficient inhibitory potency. For example, the selection process may include a step of carrying out a cell-based TGFβ1 activation assay to measure potency (e.g., $IC_{50}$) of one or more test antibodies or fragments thereof, and, selecting a candidate antibody or fragment thereof that shows desirable potency. In some embodiments, $IC_{50}$ for each of the human LLCs 5 nM or less. The selected antibody or the fragment may then be used in the treatment of a TGFβ1-related indication described herein.

Binding Regions

In the context of the present disclosure, "binding region(s)" of an antigen provides a structural basis for the antibody-antigen interaction. As used herein, a "binding region" refers to the areas of interface between the antibody and the antigen, such that, when bound to the proTGFβ1 complex ("antigen") in a physiological solution, the antibody or the fragment protects the binding region from solvent exposure, as determined by suitable techniques, such as hydrogen-deuterium exchange mass spectrometry (HDX-MS). Identification of binding regions is useful in gaining insight into the antigen-antibody interaction and the mechanism of action for the particular antibody. Identification of additional antibodies with similar or overlapping binding regions may be facilitated by cross-blocking experiments that enable epitope binning. Optionally, X-ray crystallography may be employed to identify the exact amino acid residues of the epitope that mediate antigen-antibody interactions.

The art is familiar with HDX-MS, which is a widely used technique for exploring protein conformation or protein-protein interactions in solution. This method relies on the exchange of hydrogens in the protein backbone amide with deuterium present in the solution. By measuring hydrogen-deuterium exchange rates, one can obtain information on protein dynamics and conformation (reviewed in: Wei et al. (2014) "Hydrogen/deuterium exchange mass spectrometry for probing higher order structure of protein therapeutics: methodology and applications." Drug Disco Today. 19(1): 95-102; incorporated by reference). The application of this technique is based on the premise that when an antibody-antigen complex forms, the interface between the binding partners may occlude solvent, thereby reducing or preventing the exchange rate due to steric exclusion of solvent.

The present disclosure includes antibodies or antigen-binding fragments thereof that bind a human LLC at a region ("binding region") comprising Latency Lasso or a portion thereof. Latency Lasso is a protein module within the prodomain. It is contemplated that many potent activation inhibitors may bind this region of a proTGFβ1 complex in such a way that the antibody binding would "lock in" the growth factor thereby preventing its release. Interestingly, this is the section of the complex where the butterfly-like elongated regions of the growth factor (e.g., corresponding to, for example, Finger-1 and Finger-2) closely interact with the cage-like structure of the prodomain.

Figure 18A:
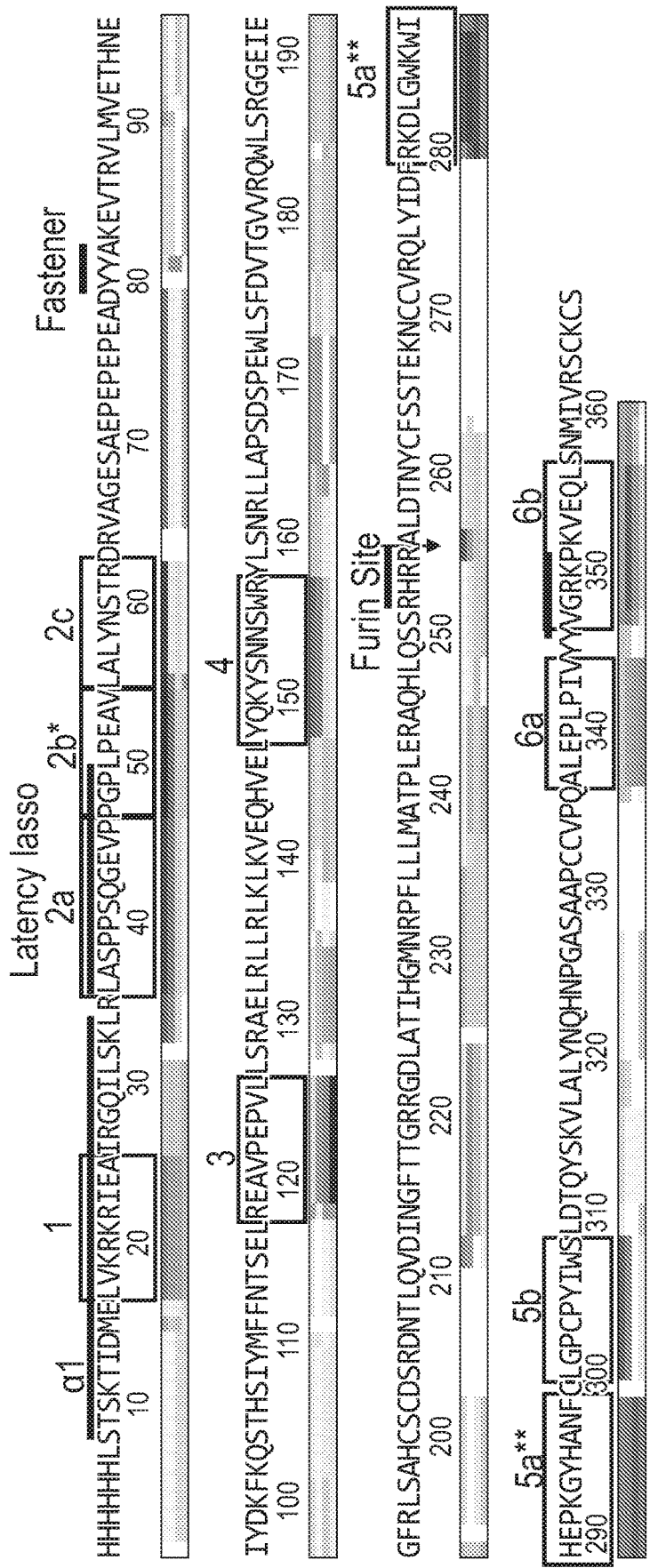
FIG. 18A is a heat map that shows protection effects of Ab6 Fab binding to proTGFβ1 (C4S) (SEQ ID NO: 183). Regions affected by the antibody-antigen interaction are indicated by red boxes (1, 2a, 2b, 2c, 3, 4, 5a, 5b, 6a and 6b).
Figure 18B:
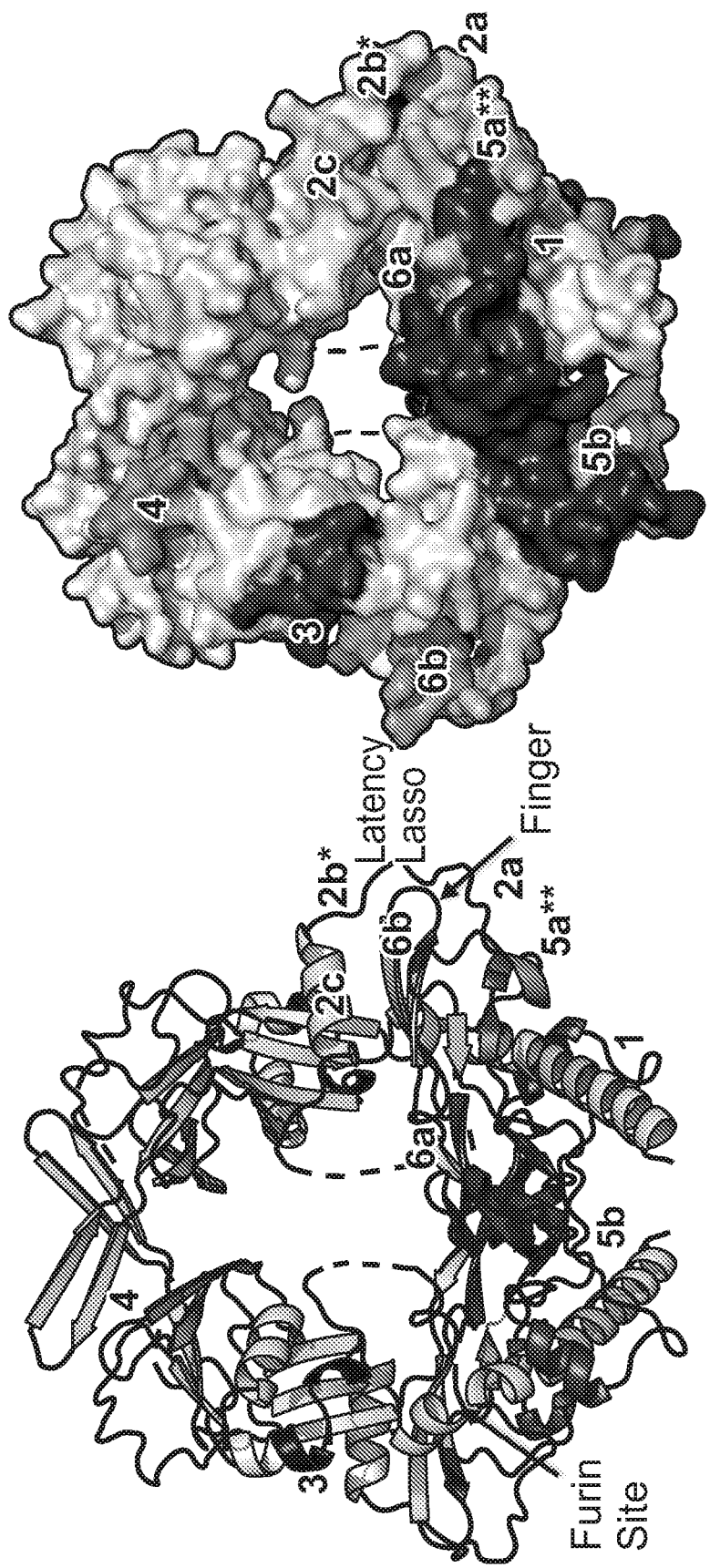
FIG. 18B provides HDX data overlaid to the crystal structure of TGFβ1. The regions identified in FIG. 18A are shown.

As depicted in FIG. 18B, Latency Lasso includes the regions labeled as 2a and a part of 2b, which are part of the prodomain. Note that immediately adjacent to Latency Lasso, the region labeled as 5a corresponds to so-called Finger-1 within the growth factor domain, and the region labeled as 6b around the opposite side, is part of Finger-2 within the growth factor domain. Based on this, it is not difficult to envisage that an antibody that tightly wraps around these regions could effectively prevent the proTGFβ1 complex from disengaging, thereby blocking activation.

Using the HDX-MS technique, binding regions of proTGFβ1 can be determined. In some embodiments, a portion on proTGFβ1 identified to be important in binding an antibody or fragment includes at least a portion of the prodomain and at least a portion of the growth factor domain. Antibodies or fragments that bind a first binding region ("Region 1" in FIG. 19A) comprising at least a portion of Latency Lasso are preferable. More preferably, such antibodies or fragments further bind a second binding region ("Region 2" in FIG. 19A) comprising at least a portion of the growth factor domain at Finger-1 of the growth factor domain. Such antibodies or fragments may further bind a third binding region ("Region 3" in FIG. 19A) comprising at least a portion of Finger-2 of the growth factor domain.

Additional regions within the proTGFβ1 may also contribute, directly or indirectly, to the high-affinity interaction of these antibodies disclosed herein. Regions that are considered important for mediating the high-affinity binding of the antibody to the proTGFβ1 complex (see FIG. 18A) may include, but are not limited to: LVKRKRIEA (SEQ ID NO: 159); LASPPSQGEVP (SEQ ID NO: 160); PGPLPEAV (SEQ ID NO: 161); LALYNSTR (SEQ ID NO: 162); REAVPEPVL (SEQ ID NO: 163); YQKYSNNSWR (SEQ ID NO: 164); RKDLGWKWIHEPKGYHANF (SEQ ID NO: 165); LGPCPYIWS (SEQ ID NO: 166); ALEPLPIV (SEQ ID NO: 167); and, VGRKPKVEQL (SEQ ID NO: 168) (based on the native sequence of human proTGFβ1).

Among regions that may contribute to the antibody-antigen interaction, in some embodiments, the high-affinity antibody of the present disclosure may bind an epitope that comprises at least one residue of the amino acid sequence KLRLASPPSQGEVPPGPLPEAVL ("Region 1") (SEQ ID NO: 169).

In some embodiments, the high-affinity antibody of the present disclosure may bind an epitope that comprises at least one residue of the amino acid sequence RKDLGWKWIHEPKGYHANF ("Region 2") (SEQ ID NO: 165).

In some embodiments, the high-affinity antibody of the present disclosure may bind an epitope that comprises at least one residue of the amino acid sequence VGRKPKVEQL ("Region 3") (SEQ ID NO: 168).

In some embodiments, the high-affinity antibody of the present disclosure may bind an epitope that comprises at least one residue of the amino acid sequence KLRLASPP-SQGEVPPGPLPEAVL ("Region 1") (SEQ ID NO: 169) and at least one residue of the amino acid sequence RKDLGWKWIHEPKGYHANF ("Region 2") (SEQ ID NO: 165).

In some embodiments, the high-affinity antibody of the present disclosure may bind an epitope that comprises at least one residue of the amino acid sequence KLRLASPP-SQGEVPPGPLPEAVL ("Region 1") (SEQ ID NO: 169) and at least one residue of the amino acid sequence VGRKPKVEQL ("Region 3") (SEQ ID NO: 168).

In some embodiments, the high-affinity antibody of the present disclosure may bind an epitope that comprises at least one residue of the amino acid sequence KLRLASPP-SQGEVPPGPLPEAVL ("Region 1") (SEQ ID NO: 169), at least one residue of the amino acid sequence RKDLGWKWIHEPKGYHANF ("Region 2") (SEQ ID NO: 165), and, at least one residue of the amino acid sequence VGRKPKVEQL ("Region 3") (SEQ ID NO: 168).

In addition to contributions from Regions 1, 2 and/or 3, such epitope may further include at least one amino acid residues from a sequence selected from the group consisting of: LVKRKRIEA (SEQ ID NO: 159); LASPPSQGEVP (SEQ ID NO: 160); PGPLPEAV (SEQ ID NO: 161); LALYNSTR (SEQ ID NO: 162); REAVPEPVL (SEQ ID NO: 163); YQKYSNNSWR (SEQ ID NO: 164); RKDLGWKWIHEPKGYHANF (SEQ ID NO: 165); LGPCPYIWS (SEQ ID NO: 166); ALEPLPIV (SEQ ID NO: 167); and, VGRKPKVEQL (SEQ ID NO: 168).

Notably, many of the binding regions identified in structural studies using four representative isoform-selective TGFβ1 antibodies are found to be overlapping, pointing to certain regions within the proTGFβ1 complex that may be particularly important in maintaining latency of the proTGFβ1 complex. Thus, advantageously, antibodies or fragments thereof may be selected at least in part on the basis of their binding region(s) that include the overlapping portions identified across multiple inhibitors described herein. These overlapping portions of binding regions include, for example, SPPSQGEVPPGPLPEAVL (SEQ ID NO: 201), WKWIHEPKGYHANF (SEQ ID NO: 202), and PGPLPEAVL (SEQ ID NO: 203). Thus, the high-affinity, isoform-selective TGFβ1 inhibitor according to the present disclosure may bind a proTGFβ1 complex (e.g., human LLCs) at an epitope that comprises one or more amino acid residues of SPPSQGEVPPGPLPEAVL (SEQ ID NO: 201), WKWIHEPKGYHANF (SEQ ID NO: 202), and/or PGPLPEAVL (SEQ ID NO: 203).

Thus, any of the antibody or antigen-binding fragment encompassed by the present disclosure, such as antibodies or fragments of Categories 1 through 5 disclosed herein, may bind one or more of the binding regions identified herein. Such antibodies may be used in the treatment of a TGFβ1 indication in a subject as described herein. Accordingly, selection of an antibody or antigen-binding fragment thereof suitable for therapeutic use in accordance with the present disclosure may include identifying or selecting an antibody or a fragment thereof that binds SPPSQGEVPPGPLPEAVL (SEQ ID NO: 201), WKWIHEPKGYHANF (SEQ ID NO: 202), PGPLPEAVL (SEQ ID NO: 203), or any portion(s) thereof.

Non-limiting examples of protein domains or motifs of human proTGFβ1 as previously described (WO 2014/182676) are provided in Table 12.

TABLE 12

Select protein domains/motifs of human TGFβ1-related polypeptides

| Human TGFβ1 domain/module | Amino Acid Sequence | SEQ ID NO |
|---|---|---|
| Latency Associated Peptide (LAP) (prodomain) | LSTCKTIDMELVKRKRIEAIRGQILSKLRLASPPSQGEVPPGPLPEAVLALYNSTRD RVAGESAEPEPEPEADYYAKEVTRVLMVETHNEIYDKFKQSTHSIYMFFNTSELREA VPEPVLLSRAELRLLRLKLKVEQHVELYQKYSNNSWRYLSNRLLAPSDSPEWLSFDV TGVVRQWLSRGGEIEGFRLSAHCSCDSRDNTLQVDINGFTTGRRGDLATIHGMNRPF LLLMATPLERAQHLQSSRHRR ("First binding region" is underlined) | 146 |
| Straight Jacket | LSTCKTIDMELVKRKRIEAIRGQILSKLRLASPPSQGEVPPGPLP ("Latency Lasso" is underlined) | 147 |
| Growth Factor Domain | ALDTNYCFSSTEKNCCVRQLYIDFRKDLGWKWIHEPKGYHANFCLGPCPYIWSLDTQ YSKVLALYNQHNPGASAAPCCVPQALEPLPIVYYVGRKPKVEQLSNMIVRSCKCS ("Finger-1" and "Finger-2" are underlined, respectively) | 148 |
| Fastener | residues 74-76, YYA | n/a |
| Furin cleavage site | RHRR | 149 |
| Arm | EAVLALYNSTRDRVAGESAEPEPEPEADYYAKEVTRVLMVETHNEIYDKFKQSTHSI YMFFNTSELREAVPEPVLLSRAELRLLRLKLKVEQHVELYQKYSNNSWRYLSNRLLA PSDSPEWLSFDVTGVVRQWLSRGGEIEGFRLSAHCSCDSRDNTLQVDINGFTTGRRG DLATIHGMNRPFLLLMATPLERAQHLQSSRHRR | 150 |
| Finger-1 | CVRQLYIDFRKDLGWKWIHEPKGYHANFC ("Second binding region" is underlined) | 151 |
| Finger-2 | CVPQALEPLPIVYYVGRKPKVEQLSNMIVRSCKCS ("Third binding region" is underlined) | 152 |
| Residue for presenting molecule association | Cys 4 | n/a |
| Latency Lasso | LASPPSQGEVPPGPL (Portion of the binding regions shared across 4 different isoform-selective proTGFβ1 antibodies is underlined) | 153 |

TABLE 12-continued

| Select protein domains/motifs of human TGFβ1-related polypeptides | | |
|---|---|---|
| Human TGFβ1 domain/module | Amino Acid Sequence | SEQ ID NO |
| Extended Latency Lasso | LASPPSQGEVPPGPLPEAVLALYNSTR (Portion of the binding regions shared across 4 different isoform-selective proTGFβ1 antibodies is underlined) | 154 |
| Alpha-1 Helix | LSTCKTIDMELVKRKRIEAIRGQILSKLR | 155 |
| Alpha-2 Helix | AVLALYNSTR | 156 |
| Trigger Loop | NGFTTGRRGDLATIHGMNRP | 157 |
| lntegrin binding | residue 215-217, RGD | n/a |
| Bowtie | CSCDSRDNTLQVD | 158 |

Safety/Toxicology

Conventional pan-inhibitors of TGFβ capable of antagonizing multiple isoforms have been known to cause a number of toxicities, including, for example, cardiovascular toxicities (cardiac lesions, most notably valvulopathy) reported across multiple species including dogs and rats. These include, hyperplasia in aortic valve, right AV valve, and left AV valve; inflammation in aortic valve, left AV valve, and ascending aorta; hemorrhage in ascending aorta, aortic valve and left AV valve; connective tissue degeneration in ascending aorta (see for example, Strauber et al. (2014) "Nonclinical safety evaluation of a Transforming Growth Factor β receptor I kinase inhibitor in Fischer 344 rats and beagle dogs" J. Clin. Pract 4(3): 1000196). See also FIG. 21A.

In addition, neutralizing antibodies that bind all three TGFβ isoforms have been associated with certain epithelial toxicities observed across multiple species, some of which are summarized below.

TABLE 13

| Epithelial toxicities associated with pan-inhibitors of TGFβ | | | |
|---|---|---|---|
| | Mice | Cyno | Human |
| Toxicities | Hyperplasia and inflammation of tongue, gingiva, and esophagus. Findings not reversible (12 wk recovery) | Hyperplasia of gingiva, nasal epithelium, and bladder Anemia lead to cessation of treatment Changes were reversible (except bladder) | Gigival bleeding Epistaxis Headache Fatigue Various skin disorders, including keratoacanthomas (KA), hyperkeratosis, cutaneous SCC, and basal cell carcinoma |
| Drug/Dose/ Duration | 1D11 Dosing: 50 mg/kg (3×/week) Duration: 9-12 weeks | GC1008 Dosing: 10 and 50 mg/kg Duration: 6 months | GC1008 Dose: 0.1, 0.3, 1,3, 10, 15 mg/kg Duration: 4 monthly doses |
| Exposure | Serum conc. = 1-2 mg/mL (over 4-12 weeks) | Not disclosed | Half life: 21.7 d DN Cmax~(350 ng/mL)mg |

*Vitsky et. Al. Am. J Pathology vol. 174, 2009; and Lonning et. al. Current Pharmaceutical Biotech, 2011

Building upon the earlier recognition by the applicant of the present disclosure (see PCT/US2017/021972) that lack of isoform-specificity of conventional TGFβ antagonists may underlie the source of toxicities associated with TGFβ inhibition, the present inventors sought to further achieve broad-spectrum TGFβ1 inhibition for treating various diseases that manifest multifaceted TGFβ1 dysregulation, while maintaining the safety/tolerability aspect of isoform-selective inhibitors.

In clinical setting, therapeutic benefit is achieved only when the minimum effective concentrations (MEC) of a drug (e.g., monoclonal antibody) are below the minimum toxic concentrations (MTC) of the drug. This was not achieved with most, if not all, conventional pan-inhibitors of TGFβ, which in fact appeared to cause dose-limiting toxicities. Applicant's previous work described isoform-selective inhibitors of TGFβ1 that showed markedly improved safety profile, as compared to conventional pan-inhibitors, such as small molecule receptor antagonists and neutralizing antibodies. WO 2017/156500 disclosed an isoform-selective inhibitor of TGFβ1 activation, which, when administered at a dose of up to 100 mg/kg per week for 4 weeks in rats, no test article-related toxicities was observed, establishing the NOAEL for the antibody as the highest dose tested, i.e., 100 mg/kg. Applicant's subsequent work also showed that an antibody with enhanced function also showed the equivalent safety profiles. Here, one of the objectives was to identify antibodies with even higher affinities and potencies, but with at least the same or equivalent levels of safety.

Results from four-week rat toxicology studies are provided in FIGS. 21B and 21C. Two isoform-selective TGFβ1 inhibitors (Ab3 and Ab6) were tested in separate studies, together with a small molecule ALK5 inhibitor and a monoclonal neutralizing antibody as control. No test article-related toxicities were noted with either of the isoform-selective antibodies, while the non-selective inhibitors as expected caused a variety of adverse events consistent with published studies. Moreover, Ab6 was shown to be safe (e.g., no observed adverse events) at a dose level as high as 300 mg/kg in cynomolgus monkeys when dosed weekly for 4 weeks. Since Ab6 has been shown to be efficacious in a number of in vivo models at a dose as low as 3 mg/kg, this offers an up to 100-fold of a therapeutic window. Importantly, this demonstrates that high potency does not have to mean greater risk of toxicity. Without wishing to be bound by a particular theory, it is contemplated that the highly selective nature of the antibodies disclosed herein likely account for the lack of observed toxicities.

Thus, in some embodiments, the novel antibody according to the present disclosure has the maximally tolerated dose (MTD) of >100 mg/kg when dosed weekly for at least 4 weeks. In some embodiments, the novel antibody according to the present disclosure has the no-observed-adverse-effect level (NOAEL) of up to 100 mg/kg when dosed weekly for at least 4 weeks. Suitable animal models to be used for conducting safety/toxicology studies for TGFβ inhibitors and TGFβ1 inhibitors include, but are not limited to: rats, dogs, cynos, and mice. In preferred embodiments, the minimum effective amount of the antibody based on a suitable preclinical efficacy study is below the NOAEL. More preferably, the minimum effective amount of the antibody is about one-third or less of the NOAEL. In particularly preferred embodiments, the minimum effective amount of the antibody is about one-sixth or less of the NOAEL. In some embodiments, the minimum effective amount of the antibody is about one-tenth or less of the NOAEL.

In some embodiments, the invention encompasses an isoform-selective antibody capable of inhibiting TGFβ1 signaling, which, when administered to a subject, does not cause cardiovascular or known epithelial toxicities at a dose effective to treat a TGFβ1-related indication. In some embodiments, the antibody has a minimum effective amount of about 3-10 mg/kg administered weekly, biweekly or monthly. Preferably, the antibody causes no to minimum toxicities at a dose that is at least six-times the minimum effective amount (e.g., a six-fold therapeutic window). More preferably, the antibody causes no to minimum toxicities at a dose that is at least ten-times the minimum effective amount (e.g., a ten-fold therapeutic window). Even more preferably, the antibody causes no to minimum toxicities at a dose that is at least fifteen-times the minimum effective amount (e.g., a fifteen-fold therapeutic window).

Thus, selection of an antibody or an antigen-binding fragment thereof for therapeutic use may include: selecting an antibody or antigen-binding fragment that meets the criteria of one or more of Categories 1-5 described herein; carrying out an in vivo efficacy study in a suitable preclinical model to determine an effective amount of the antibody or the fragment; carrying out an in vivo safety/toxicology study in a suitable model to determine an amount of the antibody that is safe or toxic (e.g., MTD, NOAEL, or any art-recognized parameters for evaluating safety/toxicity); and, selecting the antibody or the fragment that provides at least a three-fold therapeutic window (preferably 6-fold, more preferably a 10-fold therapeutic window, even more preferably a 15-fold therapeutic window). In preferred embodiments, the in vivo efficacy study is carried out in two or more suitable preclinical models that recapitulate human conditions. In some embodiments, such preclinical models comprise TGFβ1-positive cancer, which may optionally comprise an immunosuppressive tumor. The immunosuppressive tumor may be resistant to a cancer therapy such as CBT, chemotherapy and radiation therapy. In some embodiments, the preclinical models are selected from MBT-2, Cloudman S91 and EMT6 tumor models.

The selected antibody or the fragment may be used in the manufacture of a pharmaceutical composition comprising the antibody or the fragment. Such pharmaceutical composition may be used in the treatment of a TGFβ1 indication in a subject as described herein. For example, the TGFβ1 indication may be a proliferative disorder and/or a fibrotic disorder.

Mechanism of Action

Antibodies of the present invention that are useful as therapeutics are inhibitory antibodies of TGFβ1. Further, the antibodies are activation inhibitors, that is, the antibodies block the activation step of TGFβ1, rather than directly chasing after already activated growth factor.

In a broad sense, the term "inhibiting antibody" refers to an antibody that antagonizes or neutralizes the target function, e.g., growth factor activity. Advantageously, preferred inhibitory antibodies of the present disclosure are capable of inhibiting mature growth factor release from a latent complex, thereby reducing growth factor signaling. Inhibiting antibodies include antibodies targeting any epitope that reduces growth factor release or activity when associated with such antibodies. Such epitopes may lie on the prodomains of TGFβ proteins (e.g. TGFβ1), growth factors or other epitopes that lead to reduced growth factor activity when bound by antibody. Inhibiting antibodies of the present invention include, but are not limited to, TGFβ1-inhibiting antibodies. In some embodiments, inhibitory antibodies of the present disclosure specifically bind a combinatory epitope, i.e., an epitope formed by two or more components/portions of an antigen or antigen complex. For example, a combinatorial epitope may be formed by contributions from multiple portions of a single protein, i.e., amino acid residues from more than one non-contiguous segments of the same protein. Alternatively, a combinatorial epitope may be formed by contributions from multiple protein components of an antigen complex. In some embodiments, inhibitory antibodies of the present disclosure specifically bind a conformational epitope (or conformation-specific epitope), e.g., an epitope that is sensitive to the three-dimensional structure (i.e., conformation) of an antigen or antigen complex.

Traditional approaches to antagonizing TGFβ signaling have been to i) directly neutralize the mature growth factor after it has already become active so as to deplete free ligands (e.g., released from its latent precursor complex) that are available for receptor binding; ii) employ soluble receptor fragments capable of sequestering free ligands (e.g., so-called ligand traps); or, iii) target its cell-surface receptor(s) to block ligand-receptor interactions. Each of these conventional approaches requires the antagonist to compete against endogenous counterparts. Moreover, the first two approaches (i and ii) above target the active ligand, which is a transient species. Therefore, such antagonist must be capable of kinetically outcompeting the endogenous receptor during the brief temporal window. The third approach may provide a more durable effect in comparison but inadvertently results in unwanted inhibitory effects (hence possible toxicities) because many growth factors (e.g., up to ~20) signal via the same receptor(s).

To provide solutions to these drawbacks, and to further enable greater selectivity and localized action, the preferred mechanism of action underlining the inhibitory antibodies such as those described herein acts upstream of TGFβ1 activation and ligand-receptor interaction. Thus, it is contemplated that high-affinity, isoform-specific, context-independent inhibitors of TGFβ1 suitable for carrying out the present invention should preferably target the inactive (e.g., latent) precursor TGFβ1 complex (e.g., a complex comprising pro/latent TGFβ1) prior to its activation, in order to block the activation step at its source (such as in a disease microenvironment, e.g., TME). According to preferred embodiments of the invention, such inhibitors target with equivalent affinities both ECM-associated and cell surface-tethered pro/latent TGFβ1 complexes, rather than free ligands that are transiently available for receptor binding.

Advantages of locally targeting tissue/cell-tethered complex at the source, as opposed to soluble active species (i.e., mature growth factors after being released from the source), are further supported by a recent study. Ishihara et al. (Sci. Transl. Med. 11, eaau3259 (2019) "Targeted antibody and cytokine cancer immunotherapies through collagen affinity") reported that when systemically administered drugs are targeted to the tumor sites by conjugating with a collagen-binding moiety, they were able to enhance anti-tumor immunity and reduce treatment-related toxicities, as compared to non-targeted counterparts.

The mechanism of action achieved by the antibodies of the present disclosure may further contribute to enhanced durability of effect, as well as overall greater potency and safety.

Figure 6:
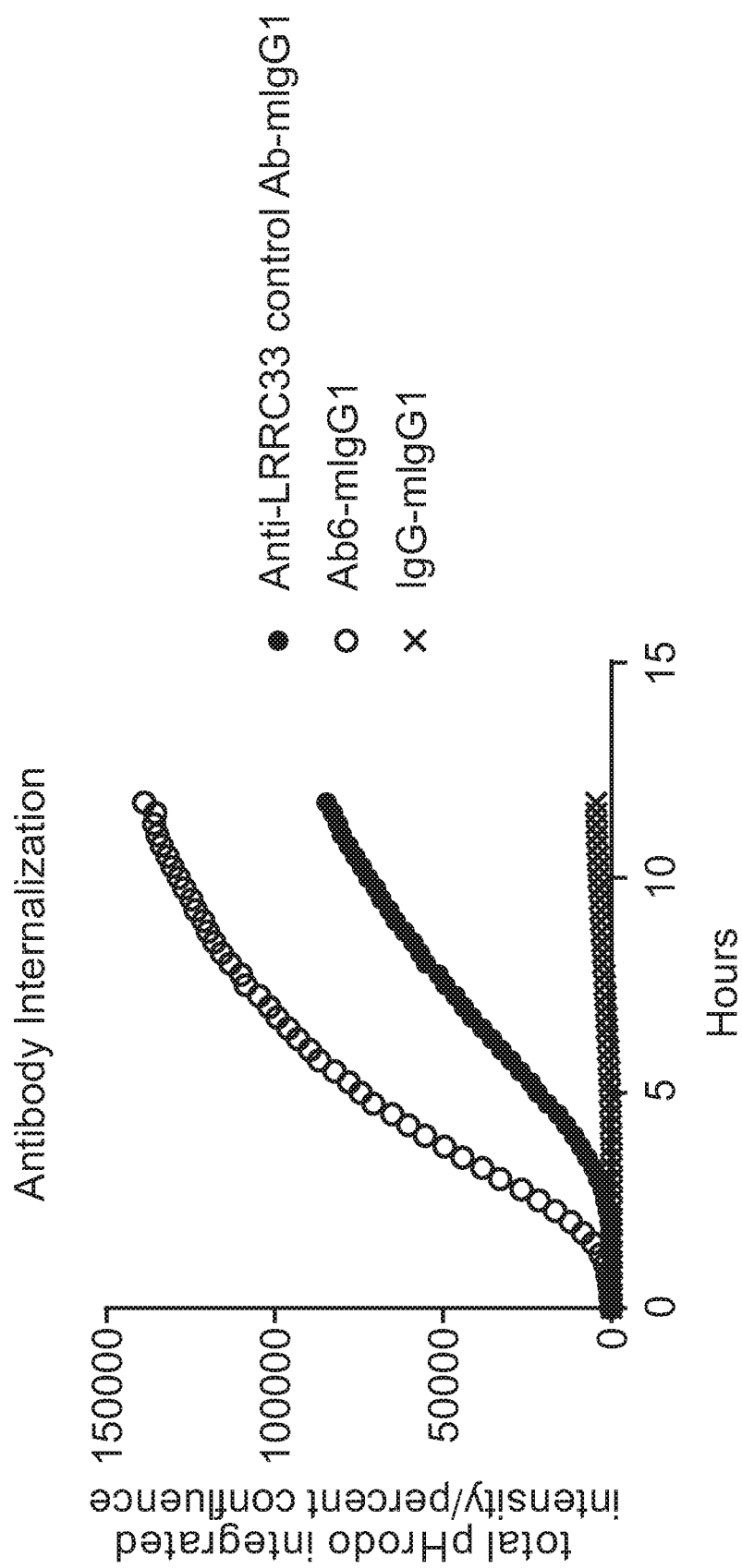
FIG. 6 provides a graph showing rapid internalization of LRRC33-proTGFb1 upon Ab6 binding in heterologous cells transfected with LRRC33 and proTGFβ1.

Interestingly, these antibodies may exert additional inhibitory activities toward cell-associated TGFβ1 (LRRC33-proTGFβ1 and GARP-proTGFβ1). Applicant has found that LRRC33-binding antibodies tend to become internalized upon binding to cell-surface LRRC33. Whether the internalization is actively induced by antibody binding, or alternatively, whether this phenomenon results from natural (e.g., passive) endocytic activities of macrophages is unclear. However, the high-affinity, isoform-selective TGFβ1 inhibitor, Ab6, is capable of becoming rapidly internalized in cells transfected with LRRC33 and proTGFβ1, and the rate of internalization achieved with Ab6 is significantly higher than that with a reference antibody that recognizes cell-surface LRRC33 (FIG. 6). Similar results are obtained from primary human macrophages. These observations raise the possibility that Ab6 can induce internalization upon binding to its target, LRRC33-proTGFβ1, thereby removing the LRRC33-containing complexes from the cell surface. At the disease loci, this may reduce the availability of activatable latent LRRC33-proTGFβ1 levels. Therefore, the isoform-selective TGFβ1 inhibitors may inhibit the LRRC33 arm of TGFβ1 via two parallel mechanisms of action: i) blocking the release of mature growth factor from the latent complex; and, ii) removing LRRC33-proTGFβ1 complexes from cell-surface via internalization. It is possible that similar inhibitory mechanisms of action may apply to GARP-proTGFβ1.

In some embodiments, the antibody is a pH-sensitive antibody that binds its antigen with higher affinity at a neutral pH (such as pH of around 7) than at an acidic pH (such as pH of around 5). Such antibodies may have higher dissociation rates at acidic conditions than neutral or physiological conditions. For example, the ratio between dissociation rates measured at an acidic pH and dissociation rates measured at neutral pH (e.g., $K_{off}$ at pH5 over $K_{off}$ at pH 7) may be at least 1.2. Optionally, the ratio is at least 1.5. In some embodiments, the ratio is at least 2. Such pH-sensitive antibodies may be useful as recycling antibodies. Upon target engagement on cell surface, the antibody may trigger antibody-dependent internalization of (hence removal of) membrane-bound proTGFβ1 complexes (associated with LRRC33 or GARP). Subsequently, in an acidic intracellular compartment such as lysosome, the antibody-antigen complex dissociates, and the free antibody may be transported back to the extracellular domain.

Thus, in some embodiments, selection of an antibody or an antigen-binding fragment for therapeutic use may be in part based on the ability to induce antibody-dependent internalization and/or pH-dependency of the antibody.

Antigen Complexes and Components Thereof

The novel antibodies of the present disclosure specifically binds each of the four known human large latency complexes (e.g., hLTBP1-proTGFβ1, hLTBP3-proTGFβ1, hGARP-proTGFβ1 and hLRRC33-proTGFβ1), selectively inhibits TGFβ1 activation. Preferred antibodies further satisfy the criteria of one or more of Categories 1-5 set forth in Table 1.

Screening (e.g., identification and selection) of such antibodies involves the use of suitable antigen complexes, which are typically recombinantly produced. Useful protein components that may comprise such antigen complexes are provided, including TGFβ isoforms and related polypeptides, fragments and variants, presenting molecules (e.g., LTBPs, GARP, LRRC33) and related polypeptides, fragments and variants. These components may be expressed, purified, and allowed to form a protein complex (such as large latent complexes), which can be used in the process of antibody screening. The screening may include positive selection, in which desirable binders are selected from a pool or library of binders and non-binders, and negative selection, in which undesirable binders are removed from the pool. Typically, at least one matrix-associated complex (e.g., LTBP1-proTGFβ1 and/or LTBP1-proTGFβ1) and at least one cell-associated complex (e.g., GARP-proTGFβ1 and/or LRRC33-proTGFβ1) are included for positive screening to ensure that binders being selected have affinities for both such biological contexts.

In some embodiments, the TGFβ1 comprises a naturally occurring mammalian amino acid sequence. In some embodiment, the TGFβ1 comprises a naturally occurring human amino acid sequence. In some embodiments, the TGFβ1 comprises a human, a monkey, a rat or a mouse amino acid sequence. In some embodiments, an antibody, or antigen binding portion thereof, described herein does not specifically bind to TGFβ2. In some embodiments, an antibody, or antigen binding portion thereof, described herein does not specifically bind to TGFβ3. In some embodiments, an antibody, or antigen binding portion thereof, described herein does not specifically bind to TGFβ2 or TGFβ3. In some embodiments, an antibody, or antigen binding portion thereof, described herein specifically binds to a TGFβ1 comprising the amino acid sequence set forth in SEQ ID NO: 34. The amino acid sequences of TGFβ2, and TGFβ3 amino acid sequence are set forth in SEQ ID NOs: 38 and 32, respectively. In some embodiments, an antibody, or antigen binding portion thereof, described herein specifically binds to a TGFβ1 comprising a non-naturally-occurring amino acid sequence (otherwise referred to herein as a non-naturally-occurring TGFβ1). For example, a non-naturally-occurring TGFβ1 may comprise one or more recombinantly generated mutations relative to a naturally-occurring TGFβ1 amino acid sequence. In some embodiments, a TGFβ1, TGFβ2, or TGFβ3 amino acid sequence comprises the amino acid sequence as set forth in SEQ ID NOs: 24-35, as shown in Table 14. In some embodiments, a TGFβ1, TGFβ2, or TGFβ3 amino acid sequence comprises the amino acid sequence as set forth in SEQ ID NOs: 36-43, as shown in Table 15.

TGFβ1 (prodomain + growth factor domain)
(SEQ ID NO: 24)
LSTCKTIDMELVKRKRIEAIRGQILSKLRLASPPSQGEVPPGPLPEAVLA

LYNSTRDRVAGESAEPEPEPEADYYAKEVTRVLMVETHNEIYDKFKQSTH

SIYMFFNTSELREAVPEPVLLSRAELRLLRLKLKVEQHVELYQKYSNNSW

RYLSNRLLAPSDSPEWLSFDVTGVVRQWLSRGGEIEGFRLSAHCSCDSRD

NTLQVDINGFTTGRRGDLATIHGMNRPFLLLMATPLERAQHLQSSRHRRA

LDTNYCFSSTEKNCCVRQLYIDFRKDLGWKWIHEPKGYHANFCLGPCPYI

WSLDTQYSKVLALYNQHNPGASAAPCCVPQALEPLPIVYYVGRKPKVEQL

SNMIVRSCKCS

TGFβ2 (prodomain + growth factor domain)
(SEQ ID NO: 28)
SLSTCSTLDMDQFMRKRIEAIRGQILSKLKLTSPPEDYPEPEEVPPEVIS

IYNSTRDLLQEKASRRAAACERERSDEEYYAKEVYKIDMPPFFPSENAIP

PTFYRPYFRIVRFDVSAMEKNASNLVKAEFRVFRLQNPKARVPEQRIELY

QILKSKDLTSPTQRYIDSKVVKTRAEGEWLSFDVTDAVHEWLHHKDRNLG

FKISLHCPCCTFVPSNNYIIPNKSEELEARFAGIDGTSTYTSGDQKTIKS

TRKKNSGKTPHLLLMLLPSYRLESQQTNRRKKRALDAAYCFRNVQDNCCL

RPLYIDFKRDLGWKWIHEPKGYNANFCAGACPYLWSSDTQHSRVLSLYNT

INPEASASPCCVSQDLEPLTILYYIGKTPKIEQLSNMIVKSCKCS

TGFβ3 (prodomain + growth factor domain)
(SEQ ID NO: 32)
SLSLSTCTTLDFGHIKKKRVEAIRGQILSKLRLTSPPEPTVMTHVPYQVL

ALYNSTRELLEEMHGEREEGCTQENTESEYYAKEIHKFDMIQGLAEHNEL

AVCPKGITSKVFRFNVSSVEKNRTNLFRAEFRVLRVPNPSSKRNEQRIEL

FQILRPDEHIAKQRYIGGKNLPTRGTAEWLSFDVTDTVREWLLRRESNLG

LEISIHCPCHTFQPNGDILENIHEVMEIKFKGVDNEDDHGRGDLGRLKKQ

KDHHNPHLILMMIPPHRLDNPGQGGQRKKRALDTNYCFRNLEENCCVRPL

YIDFRQDLGWKWVHEPKGYYANFCSGPCPYLRSADTTHSTVLGLYNTLNP

EASASPCCVPQDLEPLTILYYVGRTPKVEQLSNMVVKSCKCS

TABLE 14

Exemplary TGFβ1, TGFβ2, and TGFβ3 amino acid sequences

| Protein | Sequence | SEQ ID NO |
|---|---|---|
| proTGFβ1 | LSTCKTIDMELVKRKRIEAIRGQILSKLRLASPPSQGEVPPGPLPEAVLAL YNSTRDRVAGESAEPEPEPEADYYAKEVTRVLMVETHNEIYDKFKQSTHSI YMFFNTSELREAVPEPVLLSRAELRLLRLKLKVEQHVELYQKYSNNSWRYL SNRLLAPSDSPEWLSFDVTGVVRQWLSRGGEIEGFRLSAHCSCDSRDNTLQ VDINGFTTGRRGDLATIHGMNRPFLLLMATPLERAQHLQSSRHRRALDTNY CFSSTEKNCCVRQLYIDFRKDLGWKWIHEPKGYHANFCLGPCPYIWSLDTQ YSKVLALYNQHNPGASAAPCCVPQALEPLPIVYYVGRKPKVEQLSNMIVRS CKCS | 24 |
| proTGFβ1 C4S | LSTSKTIDMELVKRKRIEAIRGQILSKLRLASPPSQGEVPPGPLPEAVLAL YNSTRDRVAGESAEPEPEPEADYYAKEVTRVLMVETHNEIYDKFKQSTHSI YMFFNTSELREAVPEPVLLSRAELRLLRLKLKVEQHVELYQKYSNNSWRYL SNRLLAPSDSPEWLSFDVTGVVRQWLSRGGEIEGFRLSAHCSCDSRDNTLQ VDINGFTTGRRGDLATIHGMNRPFLLLMATPLERAQHLQSSRHRRALDTNY CFSSTEKNCCVRQLYIDFRKDLGWKWIHEPKGYHANFCLGPCPYIWSLDTQ YSKVLALYNQHNPGASAAPCCVPQALEPLPIVYYVGRKPKVEQLSNMIVRS CKCS | 25 |
| proTGFβ1 D2G | LSTCKTIDMELVKRKRIEAIRGQILSKLRLASPPSQGEVPPGPLPEAVLAL YNSTRDRVAGESAEPEPEPEADYYAKEVTRVLMVETHNEIYDKFKQSTHSI YMFFNTSELREAVPEPVLLSRAELRLLRLKLKVEQHVELYQKYSNNSWRYL SNRLLAPSDSPEWLSFDVTGVVRQWLSRGGEIEGFRLSAHCSCDSRDNTLQ VDINGFTTGRRGDLATIHGMNRPFLLLMATPLERAQHLQSSRHGALDTNYC FSSTEKNCCVRQLYIDFRKDLGWKWIHEPKGYHANFCLGPCPYIWSLDTQY SKVLALYNQHNPGASAAPCCVPQALEPLPIVYYVGRKPKVEQLSNMIVRSC KCS | 26 |
| proTGFβ1 C4S D2G | LSTSKTIDMELVKRKRIEAIRGQILSKLRLASPPSQGEVPPGPLPEAVLAL YNSTRDRVAGESAEPEPEPEADYYAKEVTRVLMVETHNEIYDKFKQSTHSI YMFFNTSELREAVPEPVLLSRAELRLLRLKLKVEQHVELYQKYSNNSWRYL SNRLLAPSDSPEWLSFDVTGVVRQWLSRGGEIEGFRLSAHCSCDSRDNTLQ VDINGFTTGRRGDLATIHGMNRPFLLLMATPLERAQHLQSSRHGALDTNYC FSSTEKNCCVRQLYIDFRKDLGWKWIHEPKGYHANFCLGPCPYIWSLDTQY SKVLALYNQHNPGASAAPCCVPQALEPLPIVYYVGRKPKVEQLSNMIVRSC KCS | 27 |
| proTGFβ2 | SLSTCSTLDMDQFMRKRIEAIRGQILSKLKLTSPPEDYPEPEEVPPEVISI YNSTRDLLQEKASRRAAACERERSDEEYYAKEVYKIDMPPFFPSENAIPPT FYRPYFRIVRFDVSAMEKNASNLVKAEFRVFRLQNPKARVPEQRIELYQIL KSKDLTSPTQRYIDSKVVKTRAEGEWLSFDVTDAVHEWLHHKDRNLGFKIS LHCPCCTFVPSNNYIIPNKSEELEARFAGIDGTSTYTSGDQKTIKSTRKKN SGKTPHLLLMLLPSYRLESQQTNRRKKRALDAAYCFRNVQDNCCLRPLYID FKRDLGWKWIHEPKGYNANFCAGACPYLWSSDTQHSRVL SLYNTINPEASASPCCVSQDLEPLTILYYIGKTPKIEQLSNMIVKSCKCS | 28 |

TABLE 14-continued

Exemplary TGFβ1, TGFβ2, and TGFβ3 amino acid sequences

| Protein | Sequence | SEQ ID NO |
|---|---|---|
| proTGFβ2 C5S | SLSTSSTLDMDQFMRKRIEAIRGQILSKLKLTSPPEDYPEPEEVPPEVISI<br>YNSTRDLLQEKASRRAAACERERSDEEYYAKEVYKIDMPPFFPSENAIPPT<br>FYRPYFRIVRFDVSAMEKNASNLVKAEFRVFRLQNPKARVPEQRIELYQIL<br>KSKDLTSPTQRYIDSKVVKTRAEGEWLSFDVTDAVHEWLHHKDRNLGFKIS<br>LHCPCCTFVPSNNYIIPNKSEELEARFAGIDGTSTYTSGDQKTIKSTRKKN<br>SGKTPHLLLMLLPSYRLESQQTNRRKKRALDAAYCFRNVQDNCCLRPLYID<br>FKRDLGWKWIHEPKGYNANFCAGACPYLWSSDTQHSRVL<br>SLYNTINPEASASPCCVSQDLEPLTILYYIGKTPKIEQLSNMIVKSCKCS | 29 |
| proTGFβ2 C5S D2G | SLSTSSTLDMDQFMRKRIEAIRGQILSKLKLTSPPEDYPEPEEVPPEVISI<br>YNSTRDLLQEKASRRAAACERERSDEEYYAKEVYKIDMPPFFPSENAIPPT<br>FYRPYFRIVRFDVSAMEKNASNLVKAEFRVFRLQNPKARVPEQRIELYQIL<br>KSKDLTSPTQRYIDSKVVKTRAEGEWLSFDVTDAVHEWLHHKDRNLGFKIS<br>LHCPCCTFVPSNNYIIPNKSEELEARFAGIDGTSTYTSGDQKTIKSTRKKN<br>SGKTPHLLLMLLPSYRLESQQTNRRKGALDAAYCFRNVQDNCCLRPLYIDF<br>KRDLGWKWIHEPKGYNANFCAGACPYLWSSDTQHSRVLSLYNTINPEASAS<br>PCCVSQDLEPLTILYYIGKTPKIEQLSNMIVKSCKCS | 30 |
| proTGFβ2 D2G | SLSTCSTLDMDQFMRKRIEAIRGQILSKLKLTSPPEDYPEPEEVPPEVISI<br>YNSTRDLLQEKASRRAAACERERSDEEYYAKEVYKIDMPPFFPSENAIPPT<br>FYRPYFRIVRFDVSAMEKNASNLVKAEFRVFRLQNPKARVPEQRIELYQIL<br>KSKDLTSPTQRYIDSKVVKTRAEGEWLSFDVTDAVHEWLHHKDRNLGFKIS<br>LHCPCCTFVPSNNYIIPNKSEELEARFAGIDGTSTYTSGDQKTIKSTRKKN<br>SGKTPHLLLMLLPSYRLESQQTNRRKGALDAAYCFRNVQDNCCLRPLYIDF<br>KRDLGWKWIHEPKGYNANFCAGACPYLWSSDTQHSRVLSLYNTINPEASAS<br>PCCVSQDLEPLTILYYIGKTPKIEQLSNMIVKSCKCS | 31 |
| proTGFβ3 | SLSLSTCTTLDFGHIKKKRVEAIRGQILSKLRLTSPPEPTVMTHVPYQVLA<br>LYNSTRELLEEMHGEREEGCTQENTESEYYAKEIHKFDMIQGLAEHNELAV<br>CPKGITSKVFRFNVSSVEKNRTNLFRAEFRVLRVPNPSSKRNEQRIELFQI<br>LRPDEHIAKQRYIGGKNLPTRGTAEWLSFDVTDTVREWLLRRESNLGLEIS<br>IHCPCHTFQPNGDILENIHEVMEIKFKGVDNEDDHGRGDLGRLKKQKDHHN<br>PHLILMMIPPHRLDNPGQGGQRKKRALDTNYCFRNLEENCCVRPLYIDFRQ<br>DLGWKWVHEPKGYYANFCSGPCPYLRSADTTHSTVLGLYNTLNPEASASPC<br>CVPQDLEPLTILYYVGRTPKVEQLSNMVVKSCKCS | 32 |
| proTGFβ3 C7S | SLSLSTSTTLDFGHIKKKRVEAIRGQILSKLRLTSPPEPTVMTHVPYQVLA<br>LYNSTRELLEEMHGEREEGCTQENTESEYYAKEIHKFDMIQGLAEHNELAV<br>CPKGITSKVFRFNVSSVEKNRTNLFRAEFRVLRVPNPSSKRNEQRIELFQI<br>LRPDEHIAKQRYIGGKNLPTRGTAEWLSFDVTDTVREWLLRRESNLGLEIS<br>IHCPCHTFQPNGDILENIHEVMEIKFKGVDNEDDHGRGDLGRLKKQKDHHN<br>PHLILMMIPPHRLDNPGQGGQRKKRALDTNYCFRNLEENCCVRPLYIDFRQ<br>DLGWKWVHEPKGYYANFCSGPCPYLRSADTTHSTVLGLYNTLNPEASASPC<br>CVPQDLEPLTILYYVGRTPKVEQLSNMVVKSCKCS | 33 |
| proTGFβ3 C7S D2G | SLSLSTSTTLDFGHIKKKRVEAIRGQILSKLRLTSPPEPTVMTHVPYQVLA<br>LYNSTRELLEEMHGEREEGCTQENTESEYYAKEIHKFDMIQGLAEHNELAV<br>CPKGITSKVFRFNVSSVEKNRTNLFRAEFRVLRVPNPSSKRNEQRIELFQI<br>LRPDEHIAKQRYIGGKNLPTRGTAEWLSFDVTDTVREWLLRRESNLGLEIS<br>IHCPCHTFQPNGDILENIHEVMEIKFKGVDNEDDHGRGDLGRLKKQKDHHN<br>PHLILMMIPPHRLDNPGQGGQRKGALDTNYCFRNLEENCCVRPLYIDFRQD<br>LGWKWVHEPKGYYANFCSGPCPYLRSADTTHSTVLGLYNTLNPEASASPCC<br>VPQDLEPLTILYYVGRTPKVEQLSNMVVKSCKCS | 34 |
| proTGFβ3 D2G | SLSLSTCTTLDFGHIKKKRVEAIRGQILSKLRLTSPPEPTVMTHVPYQVLA<br>LYNSTRELLEEMHGEREEGCTQENTESEYYAKEIHKFDMIQGLAEHNELAV<br>CPKGITSKVFRFNVSSVEKNRTNLFRAEFRVLRVPNPSSKRNEQRIELFQI<br>LRPDEHIAKQRYIGGKNLPTRGTAEWLSFDVTDTVREWLLRRESNLGLEIS<br>IHCPCHTFQPNGDILENIHEVMEIKFKGVDNEDDHGRGDLGRLKKQKDHHN<br>PHLILMMIPPHRLDNPGQGGQRKGALDTNYCFRNLEENCCVRPLYIDFRQD<br>LGWKWVHEPKGYYANFCSGPCPYLRSADTTHSTVLGLYNTLNPEASASPCC<br>VPQDLEPLTILYYVGRTPKVEQLSNMVVKSCKCS | 35 |

TABLE 15

Exemplary non-human amino acid sequences

| Protein | Species | Sequence | SEQ ID NO |
|---|---|---|---|
| proTGFβ1 | Mouse | LSTCKTIDMELVKRKRIEAIRGQILSKLRLASPPSQGEVPPGPLPEAVL<br>ALYNSTRDRVAGESADPEPEPEADYYAKEVTRVLMVDRNNAIYEKTKDI<br>SHSIYMFFNTSDIREAVPEPPLLSRAELRLQRLKSSVEQHVELYQKYSN | 36 |

TABLE 15-continued

Exemplary non-human amino acid sequences

| Protein | Species | Sequence | SEQ ID NO |
|---|---|---|---|
| | | NSWRYLGNRLLTPTDTPEWLSFDVTGVVRQWLNQGDGIQGFRFSAHCSC<br>DSKDNKLHVEINGISPKRRGDLGTIHDMNRPFLLLMATPLERAQHLHSS<br>RHRRALDTNYCFSSTEKNCCVRQLYIDFRKDLGWKWIHEPKGYHANFCL<br>GPCPYIWSLDTQYSKVLALYNQHNPGASASPCCVPQALEPLPIVYYVGR<br>KPKVEQLSNMIVRSCKCS | |
| proTGFβ1 | Cyno | LSTCKTIDMELVKRKRIEAIRGQILSKLRLASPPSQGEVPPGPLPEAVL<br>ALYNSTRDRVAGESAEPEPEPEADYYAKEVTRVLMVETHNEIYDKFKQS<br>THSIYMFFNTSELREAVPEPVLLSRAELRLLRLKLKVEQHVELYQKYSN<br>NSWRYLSNRLLAPSDSPEWLSFDVTGVVRQWLSRGGEIEGFRLSAHCSC<br>DSKDNTLQVDINGFTTGRRGDLATIHGMNRPFLLLMATPLERAQHLQSS<br>RHRRALDTNYCFSSTEKNCCVRQLYIDFRKDLGWKWIHEPKGYHANFCL<br>GPCPYIWSLDTQYSKVLALYNQHNPGASAAPCCVPQALEPLPIVYYVGR<br>KPKVEQLSNMIVRSCKCS | 37 |
| TGFβ1 LAP C4S | Mouse | LSTSKTIDMELVKRKRIEAIRGQILSKLRLASPPSQGEVPPGPLPEAVL<br>ALYNSTRDRVAGESADPEPEPEADYYAKEVTRVLMVDRNNAIYEKTKDI<br>SHSIYMFFNTSDIREAVPEPPLLSRAELRLQRLKSSVEQHVELYQKYSN<br>NSWRYLGNRLLTPTDTPEWLSFDVTGVVRQWLNQGDGIQGFRFSAHCSC<br>DSKDNKLHVEINGISPKRRGDLGTIHDMNRPFLLLMATPLERAQHLHSS<br>RHRR | 38 |
| TGFβ1 LAP C4S | Cyno | LSTSKTIDMELVKRKRIEAIRGQILSKLRLASPPSQGEVPPGPLPEAVL<br>ALYNSTRDRVAGESAEPEPEPEADYYAKEVTRVLMVETHNEIYDKFKQS<br>THSIYMFFNTSELREAVPEPVLLSRAELRLLRLKLKVEQHVELYQKYSN<br>NSWRYLSNRLLAPSDSPEWLSFDVTGVVRQWLSRGGEIEGFRLSAHCSC<br>DSKDNTLQVDINGFTTGRRGDLATIHGMNRPFLLLMATPLERAQHLQSS<br>RHRR | 39 |
| proTGFβ1 C4S D2G | Mouse | LSTSKTIDMELVKRKRIEAIRGQILSKLRLASPPSQGEVPPGPLPEAVL<br>ALYNSTRDRVAGESADPEPEPEADYYAKEVTRVLMVDRNNAIYEKTKDI<br>SHSIYMFFNTSDIREAVPEPPLLSRAELRLQRLKSSVEQHVELYQKYSN<br>NSWRYLGNRLLTPTDTPEWLSFDVTGVVRQWLNQGDGIQGFRFSAHCSC<br>DSKDNKLHVEINGISPKRRGDLGTIHDMNRPFLLLMATPLERAQHLHSS<br>RHGALDTNYCFSSTEKNCCVRQLYIDFRKDLGWKWIHEPKGYHANFCLG<br>PCPYIWSLDTQYSKVLALYNQHNPGASASPCCVPQALEPLPIVYYVGRK<br>PKVEQLSNMIVRSCKCS | 40 |
| proTGFβ1 C4S | Mouse | LSTSKTIDMELVKRKRIEAIRGQILSKLRLASPPSQGEVPPGPLPEAVL<br>ALYNSTRDRVAGESADPEPEPEADYYAKEVTRVLMVDRNNAIYEKTKDI<br>SHSIYMFFNTSDIREAVPEPPLLSRAELRLQRLKSSVEQHVELYQKYSN<br>NSWRYLGNRLLTPTDTPEWLSFDVTGVVRQWLNQGDGIQGFRFSAHCSC<br>DSKDNKLHVEINGISPKRRGDLGTIHDMNRPFLLLMATPLERAQHLHSS<br>RHRRALDTNYCFSSTEKNCCVRQLYIDFRKDLGWKWIHEPKGYHANFCL<br>GPCPYIWSLDTQYSKVLALYNQHNPGASASPCCVPQALEPLPIVYYVGR<br>KPKVEQLSNMIVRSCKCS | 41 |
| proTGFβ1 C4S | Cyno | LSTSKTIDMELVKRKRIEAIRGQILSKLRLASPPSQGEVPPGPLPEAVL<br>ALYNSTRDRVAGESAEPEPEPEADYYAKEVTRVLMVETHNEIYDKFKQS<br>THSIYMFFNTSELREAVPEPVLLSRAELRLLRLKLKVEQHVELYQKYSN<br>NSWRYLSNRLLAPSDSPEWLSFDVTGVVRQWLSRGGEIEGFRLSAHCSC<br>DSKDNTLQVDINGFTTGRRGDLATIHGMNRPFLLLMATPLERAQHLQSS<br>RHRRALDTNYCFSSTEKNCCVRQLYIDFRKDLGWKWIHEPKGYHANFCL<br>GPCPYIWSLDTQYSKVLALYNQHNPGASAAPCCVPQALEPLPIVYYVGR<br>KPKVEQLSNMIVRSCKCS | 42 |
| proTGFβ1 C4S D2G | Cyno | LSTSKTIDMELVKRKRIEAIRGQILSKLRLASPPSQGEVPPGPLPEAVL<br>ALYNSTRDRVAGESAEPEPEPEADYYAKEVTRVLMVETHNEIYDKFKQS<br>THSIYMFFNTSELREAVPEPVLLSRAELRLLRLKLKVEQHVELYQKYSN<br>NSWRYLSNRLLAPSDSPEWLSFDVTGVVRQWLSRGGEIEGFRLSAHCSC<br>DSKDNTLQVDINGFTTGRRGDLATIHGMNRPFLLLMATPLERAQHLQSS<br>RHGALDTNYCFSSTEKNCCVRQLYIDFRKDLGWKWIHEPKGYHANFCLG<br>PCPYIWSLDTQYSKVLALYNQHNPGASAAPCCVPQALEPLPIVYYVGRK<br>PKVEQLSNMIVRSCKCS | 43 |
| LTBP3 | CYNO | GPAGERGAGGGGALARERFKVVFAPVICKRTCLKGQCRDSCQQGSNMTL<br>IGENGHSTDTLTGSGFRVVVCPLPCMNGGQCSSRNQCLCPPDFTGRFCQ<br>VPAGGAGGGTGGSGPGLSRAGALSTGALPPLAPEGDSVASKHAIYAVQV<br>IADPPGPGEGPPAQHAAFLVPLGPGQISAEVQAPPPVVNRVHHPPEAS<br>VQVHRIESSNAEGAAPSQHLLPHPKPSHPRPPTQKPLGRCFQDTLPKQP<br>CGSNPLPGLTKQEDCCGSIGTAWGQSKCHKCPQLQYTGVQKPGPVRGEV<br>GADCPQGYKRLNSTHCQDINECAMPGVCRHGDCLNNPGSYRCVCPPGHS<br>LGPSRTQCIADKPEEKSLCFRLVSPEHQCQHPLTTRLTRQLCCCSVGKA<br>WGARCQRCPADGTAAFKEICPAGKGYHILTSHQTLTIQGESDFSLFLHP<br>DGPPKPQQLPESPSQAPPPEDTEEERGVTTDSPVSEERSVQQSHPTATT<br>SPARPYPELISRPSPPTMRWFLPDLPPSRSAVEIAPTQVTETDECRLNQ | 44 |

TABLE 15-continued

Exemplary non-human amino acid sequences

| Protein | Species | Sequence | SEQ ID NO |
|---|---|---|---|
| | | NICGHGECVPGPPDYSCHCNPGYRSHPQHRYCVDVNECEAEPCGPRGI<br>CMNTGGSYNCHCNRGYRLHVGAGGRSCVDLNECAKPHLCGDGGFCINFP<br>GHYKCNCYPGYRLKASRPPVCEDIDECRDPSSCPDGKCENKPGSFKCIA<br>CQPGYRSQGGGACRDVNECAEGSPCSPGWCENLPGSFRCTCAQGYAPAP<br>DGRSCVDVDECEAGDVCDNGICTNTPGSFQCQCLSGYHLSRDRSHCEDI<br>DECDFPAACIGGDCINTNGSYRCLCPQGHRLVGGRKCQDIDECTQDPGL<br>CLPHGACKNLQGSYVCVCDEGFTPTQDQHGCEEVEQPHHKKECYLNFDD<br>TVFCDSVLATNVTQQECCCSLGAGWGDHCEIYPCPVYSSAEFHSLCPDG<br>KGYTQDNNIVNYGIPAHRDIDECMLFGAEICKEGKCVNTQPGYECYCKQ<br>GFYYDGNLLECVDVDECLDESNCRNGVCENTRGGYRCACTPPAEYSPAQ<br>RQCLSPEEMDVDECQDPAACRPGRCVNLPGSYRCECRPPWVPGPSGRDC<br>QLPESPAERAPERRDVCWSQRGEDGMCAGPQAGPALTFDDCCCRQGRGW<br>GAQCRPCPPRGAGSQCPTSQSESNSFWDTSPLLLGKPRRDEDSSEEDSD<br>ECRCVSGRCVPRPGGAVCECPGGFQLDASRARCVDIDECRELNQRGLLC<br>KSERCVNTSGSFRCVCKAGFARSRPHGACVPQRRR | |
| LTBP3 | Mouse | GPAGERGTGGGGALARERFKVVFAPVICKRTCLKGQCRDSCQQGSNMTL<br>IGENGHSTDTLTGSAFRVVVCPLPCMNGGQCSSRNQCLCPPDFTGRFCQ<br>VPAAGTGAGTGSSGPGLARTGAMSTGPLPPLAPEGESVASKHAIYAVQV<br>IADPPGPGEGPPAQHAAFLVPLGPGQISAEVQAPPPVVNVRVHHPPEAS<br>VQVHRIEGPNAEGPASSQHLLPHPKPPHPRPPTQKPLGRCFQDTLPKQP<br>CGSNPLPGLTKQEDCCGSIGTAWGQSKCHKCPQLQYTGVQKPVPVRGEV<br>GADCPQGYKRLNSTHCQDINECAMPGNVCHGDCLNNPGSYRCVCPPGHS<br>LGPLAAQCIADKPEEKSLCFRLVSTEHQCQHPLTTRLTRQLCCCSVGKA<br>WGARCQRCPADGTAAFKEICPGKGYHILTSHQTLTIQGESDFSLFLHPD<br>GPPKPQQLPESPSRAPPLEDTEEERGVTMDPPVSEERSVQQSHPTTTTS<br>PPRPYPELISRPSPPTFHRFLPDLPPSRSAVEIAPTQVTETDECRLNQN<br>ICGHGQCVPGPSDYSCHCNAGYRSHPQHRYCVDVNECEAEPCGPGKGIC<br>MNTGGSYNCHCNRGYRLHVGAGGRSCVDLNECAKPHLCGDGGFCINFPG<br>HYKCNCYPGYRLKASRPPICEDIDECRDPSTCPDGKCENKPGSFKCIAC<br>QPGYRSQGGGACRDVNECSEGTPCSPGWCENLPGSYRCTCAQYEPAQDG<br>LSCIDVDECEAGKVCQDGICTNTPGSFQCQCLSGYHLSRDRSRCEDIDE<br>CDFPAACIGGDCINTNGSYRCLCPLGHRLVGGRKCKKDIDECSQDPGLC<br>LPHACENLQGSYVCVCDEGFTLTQDQHGCEEVEQPHHKKECYLNFDDTV<br>FCDSVLATNVTQQECCCSLGAGWGDHCEIYPCPVYSSAEFHSLVPDGKR<br>LHSGQQHCELCIPAHRDIDECILFGAEICKEGKCVNTQPGYECYCKQGF<br>YYDGNLLECVDVDECLDESNCRNGVCENTRGGYRCACTPPAEYSPAQAQ<br>CLIPERWSTPQRDVKCAGASEERTACVWGPWAGPALTFDDCCCRQPRLG<br>TQCRPCPPRGTGSQCPTSQSESNSFWDTSPLLLGKSPRDEDSSEEDSDE<br>CRCVSGRCVPRPGGAVCECPGGFQLDASRARCVDIDECRELNQRGLLCK<br>SERCVNTSGSFRCVCKAGFTRSRPHGPACLSAAADDAAIAHTSVIDHRG<br>YFH | 45 |
| LTBP1S | Cyno | NHTGRIKVVFTPSICKVTCTKGSCQNSCEKGNTTTLISENGHAADTLTA<br>TNFRVVLCHLPCMNGGQCSSRDKCQCPPNFTGKLCQIPVHGASVPKLYQ<br>HSQQPGKALGTHVIHSTHTLPLTVTSQQGVKVKFPPNIVNIHVKHPPEA<br>SVQIHQVSRIDGPTGQKTKEAQPGQSQVSYQGLPVQKTQTIHSTYSHQQ<br>VIPHVYPVAAKTQLGRCFQETIGSQCGKALPGLSKQEDCCGTVGTSWGF<br>NKCQKCPKKPSYHGYNQMMECLPGYKRVNNTFCQDINECQLQGVCPNGE<br>CLNTMGSYRCTCKIGFGPDDPTFSSCVPDDPPVISEEKGPCYRLVSSGRQC<br>MHPLSVHLTKQLCCCSVGKAWGPHCEKCPLPGTAAFKEICPGGMGYTVS<br>GVHRRRPIHHHVGKGPVFVKPKNTQPVAKSTHPPPLPAKEEPVEALTFS<br>REHGPGVAEPEVATAPPEKEIPSLDQEKTKLEPGQPQLSPGISTIHLHP<br>QFPVVIEKTSPPVPVEVAPEASTSSASQVIAPTQVTEINECTVNPDICG<br>AGHCINLPVRYTCICYEGYKFSEQQRKCVDIDECTQVQHLCSQGRCENT<br>EGSFLCICPAGFMASEEGTNCIDVDECLRPDVCGEGHCVNTVGAFRCEY<br>CDSGYRMTQRGRCEDIDECLNPSTCPDEQCVNSPGSYQCVPCTEGFRGW<br>NGGQCLDVDECLEPNVCTNGDCSNLEGSYMCSCHKGYTRTPDHKHCKDID<br>ECQQGNLCVNGQCKNTEGSFRCTCGQGYQLSAAKDQCEDIDECQHHHLC<br>AHGQCRNTEGSFQCVCDQGYRASGLGDHCEDINECLEDKSVCQRGDCIN<br>TAGSYDCTCPDGFQLDDNKTCQDINECEHPGLCGPQGECLNTEGSFHCV<br>CQQGFSISADGRTCEDIDECVNNTVCDSHGFCDNTAGSFRCLCYQGFQA<br>PQDGQGCVDVNECELLSGVCGEAFCENVEGSFLCVCADENQEYSPMTGQ<br>CRSRTSTDLDVEQPKEEKKECYYNLNDASLCDNVLAPNVTKQECCCTSG<br>AGWGDNCEIFPCPVLGTAEFTEMCPKGKGFVPAGESSSEAGGENYKDAD<br>ECLLFGQEICKNGFCLNTRPGYECYCKQGTYYDPVKLQCFDMDECQDPS<br>SCIDGQCVNTEGSYNCFCTHPMVLDASEKRCIRPAESNEQIEETDVYQD<br>LCWEHLSDEYVCSRPLVGKQTTYTECCCLYGEAWGMQCALCPMKDSDDY<br>AQLCNIPVTGRRQPYGRDALVDFSEQYAPEADPYFIQDRFLNSFEELQA<br>EECGILNGCENGRCVRVQEGYTCDCFDGYHLDTAKMTCVDVNECDELNN<br>RMSLCKNAKCINTEGSYKCLCLPGYVPSDKPNYCTPLNTALNLEKDSDL<br>E | 46 |
| LTBP1S | mouse | NHTGRIKVVFTPSICKVTCTKGNCQNSCQKGNTTTLISENGHAADTLTA<br>TNFRVVICHLPCMNGGQCSSRDKCQCPPNFTGKLCQIPVLGASMPKLYQ<br>HAQQQGKALGSHVIHSTHTLPLTMTSQQGVKVKFPPNIVNIHVKHPPEA | 47 |

TABLE 15-continued

Exemplary non-human amino acid sequences

| Protein | Species | Sequence | SEQ ID NO |
|---|---|---|---|
| | | SVQIHQVSRIDSPGGQKVKEAQPGQSQVSYQGLPVQKTQTVHSTYSHQQ<br>LIPHVYPVAAKTQLGRCFQETIGSQCGKALPGLSKQEDCCGTVGTSWGF<br>NKCQKCPKKQSYHGYTQMMECLQGYKRVNNTFCQDINECQLQGVCPNGE<br>CLNTMGSYRCSCKMGFGPDPTFSSCVPDPPVISEEKGPCYRLVSPGRHC<br>MHPLSVHLTKQICCCSVGKAWGPHCEKCPLPGTAAFKEICPGGMGYTVS<br>GVHRRRPIHQHIGKEAVYVKPKNTQPVAKSTHPPPLPAKEEPVEALTSS<br>WEHGPRGAEPEVVTAPPEKEIPSLDQEKTRLEPGQPQLSPGVSTIHLHP<br>QFPVVVEKTSPPVPVEVAPEASTSSASQVIAPTQVTEINECTVNPDICG<br>AGHCINLPVRYTCICYEGYKFSEQLRKCVDIDECAQVRHLCSQGRCENT<br>EGSFLCVCPAGFMASEEGTNCIDVDECLRPDMCRDGRCINTAGAFRCEY<br>CDSGYRMSRRGYCEDIDECLKPSTCPEEQCVNTPGSYQCVPCTEGFRGW<br>NGQCLDVDECLQPKVCTNGSCTNLEGSYMCSCHRGYSPTPDHRHCQDID<br>ECQQGNLCMNGQCRNTDGSFRCTCGQGYQLSAAKDQCEDIDECEHHHLC<br>SHGQCRNTEGSFQCVCNQGYRASVLGDHCEDINECLEDSSVCQGGDCIN<br>TAGSYDCTCPDGFQLNDNKGCQDINECAQPGLCGSHGECLNTQGSFHCV<br>CEQGFSISADGRTCEDIDECVNNTVCDSHGFCDNTAGSFRCLCYQGFQA<br>PQDGQGCVDVNECELLSGVCGEAFCENVEGSFLCVCADENQEYSPMTGQ<br>CRSRVTEDSGVDRQPREEKKECYYNLNDASLCDNVLAPNVTKQECCCTS<br>GAGWGDNCEIFPCPVQGTAEFTEMCPRGKGLVPAGESSYDTGGENYKDA<br>DECLLFGEEICKNGYCLNTQPGYECYCKQGTYYDPVKLQCFDMDECQDP<br>NSCIDGQCVNTEGSYNCFCTHPMVLDASEKRCVQPTESNEQIEETDVYQ<br>DLCWEHLSEEYVCSRPLVGKQTTYTECCCLYGEAWGMQCALCPMKDSDD<br>YAQLCNIPVTGRRRPYGRDALVDFSEQYGPETDPYFIQDRFLNSFEELQ<br>AEECGILNGCENGRCVRVQEGYTCDCFDGYHLDMAKMTCVDVNECSELN<br>NRMSLCKNAKCINTEGSYKCLCLPGYIPSDKPNYCTPLNSALNLDKESD<br>LE | |
| GARP | mouse | ISQRREQVPCRTVNKEALCHGLGLLQVPSVLSLDIQALYLSGNQLQSIL<br>VSPLGFYTALRHLDLSDNQISFLQAGVFQALPYLEHLNLAHNRLATGMA<br>LNSGGLGRLPLLVSLDLSGNSLHGNLVERLLGETPRLRTLSLAENSLTR<br>LARHTFWGMPAVEQLDLHSNVLMDIEDGAFEALPHLTHLNLSRNSLTCI<br>SDFSLQQLQVLDLSCNSIEAFQTAPEPQAQFQLAWLDLRENKLLHFPDL<br>AVFPRLIYLNVSNNLIQLPAGLPRGSEDLHAPSEGWSASPLSNPSRNAS<br>THPLSQLLNLDLSYNEIELVPASFLEHLTSLRFLNLSRNCLRSFEARQV<br>DSLPCLVLLDLSHNVLEALELGTKVLGSLQTLLLQDNALQELPPYTFAS<br>LASLQRLNLQGNQVSPCGGPAEPGPPGCVDFSGIPTLHVLNMAGNSMGM<br>LRAGSFLHTPLTELDLSTNPGLDVATGALVGLEASLEVLELQGNGLTVL<br>RVDLPCFLRLKRLNLAENQLSHLPAWTRAVSLEVLDLRNNSFSLLPGNA<br>MGGLETSLRRLYLQGNPLSCCGNGWLAAQLHQGRVDVDATQDLICRFGS<br>QEELSLSLVRPEDCEKGGLKNVNLILLLSFTLVSAIVLTTLATICFLRR<br>QKLSQQYKA | 48 |
| sGARP | mouse | ISQRREQVPCRTVNKEALCHGLGLLQVPSVLSLDIQALYLSGNQLQSIL<br>VSPLGFYTALRHLDLSDNQISFLQAGVFQALPYLEHLNLAHNRLATGMA<br>LNSGGLGRLPLLVSLDLSGNSLHGNLVERLLGETPRLRTLSLAENSLTR<br>LARHTFWGMPAVEQLDLHSNVLMDIEDGAFEALPHLTHLNLSRNSLTCI<br>SDFSLQQLQVLDLSCNSIEAFQTAPEPQAQFQLAWLDLRENKLLHFPDL<br>AVFPRLIYLNVSNNLIQLPAGLPRGSEDLHAPSEGWSASPLSNPSRNAS<br>THPLSQLLNLDLSYNEIELVPASFLEHLTSLRFLNLSRNCLRSFEARQV<br>DSLPCLVLLDLSHNVLEALELGTKVLGSLQTLLLQDNALQELPPYTFAS<br>LASLQRLNLQGNQVSPCGGPAEPGPPGCVDFSGIPTLHVLNMAGNSMGM<br>LRAGSFLHTPLTELDLSTNPGLDVATGALVGLEASLEVLELQGNGLTVL<br>RVDLPCFLRLKRLNLAENQLSHLPAWTRAVSLEVLDLRNNSFSLLPGNA<br>MGGLETSLRRLYLQGNPLSCCGNGWLAAQLHQGRVDVDATQDLICRFGS<br>QEELSLSLVRPEDCEKGGLKNVN | 49 |

In some embodiments, antigenic protein complexes (e.g., a LTBP-TGFβ1 complex) may comprise one or more presenting molecules, such as LTBP proteins (e.g., LTBP1, LTBP2, LTBP3, and LTBP4), GARP proteins, LRRC33 proteins, or fragment(s) thereof. Typically, a minimum required fragment suitable for carrying out the embodiments disclosed herein includes at least 50 amino acids, preferably at least 100 amino acids, of a presenting molecule protein, comprising at least two cysteine residues capable of forming disulfide bonds with a proTGFβ1 complex. Specifically, these Cys residues form covalent bonds with Cysteine resides present near the N-terminus of each monomer of the proTGFβ1 complex. In the three-dimensional structure of a proTGFβ1 dimer complex, the N-terminal so-called "Alpha-1 Helix" of each monomer comes in close proximity to each other (see, for example, FIG. 18B, the two helices near the bottom of the structure in gray), setting the distance between the two cysteine residues (one from each helix) required to form productive covalent bonds with a corresponding pair of cysteines present in a presenting molecule (see, for example, Cuende et al. (2015) Sci. Trans. Med. 7: 284ra56). Therefore, when a fragment of a presenting molecule is used to form an LLC in the screening process (e.g., immunization, library screening, identification and selection), such fragment should include the cysteine residues separated by the right distance, which will allow proper disulfide bond formation with a proTGFβ1 complex in order to preserve correct conformation of the resulting LLC. LTBPs (e.g., LTBP1, LTBP3 and LTBP4), for example, may contain "cysteine-rich domains" to mediate covalent interactions with proTGFβ1.

An antibody, or antigen binding portion thereof, as described herein, is capable of binding to a LTBP1-TGFβ1 complex. In some embodiments, the LTBP1 protein is a naturally-occurring protein or fragment thereof. In some embodiments, the LTBP1 protein is a non-naturally occurring protein or fragment thereof. In some embodiments, the LTBP1 protein is a recombinant protein. Such recombinant LTBP1 protein may comprise LTBP1, alternatively spliced variants thereof and/or fragments thereof. Recombinant LTBP1 proteins may also be modified to comprise one or more detectable labels. In some embodiments, the LTBP1 protein comprises a leader sequence (e.g., a native or non-native leader sequence). In some embodiments, the LTBP1 protein does not comprise a leader sequence (i.e., the leader sequence has been processed or cleaved). Such detectable labels may include, but are not limited to biotin labels, polyhistidine tags, myc tags, HA tags and/or fluorescent tags. In some embodiments, the LTBP1 protein is a mammalian LTBP1 protein. In some embodiments, the LTBP1 protein is a human, a monkey, a mouse, or a rat LTBP1 protein. In some embodiments, the LTBP1 protein comprises an amino acid sequence as set forth in SEQ ID NOs: 46 and 47 in Table 15. In some embodiments, the LTBP1 protein comprises an amino acid sequence as set forth in SEQ ID NO: 50 in Table 17.

An antibody, or antigen binding portion thereof, as described herein, is capable of binding to a LTBP3-TGFβ1 complex. In some embodiments, the LTBP3 protein is a naturally-occurring protein or fragment thereof. In some embodiments, the LTBP3 protein is a non-naturally occurring protein or fragment thereof. In some embodiments, the LTBP3 protein is a recombinant protein. Such recombinant LTBP3 protein may comprise LTBP3, alternatively spliced variants thereof and/or fragments thereof. In some embodiments, the LTBP3 protein comprises a leader sequence (e.g., a native or non-native leader sequence). In some embodiments, the LTBP3 protein does not comprise a leader sequence (i.e., the leader sequence has been processed or cleaved). Recombinant LTBP3 proteins may also be modified to comprise one or more detectable labels. Such detectable labels may include, but are not limited to biotin labels, polyhistidine tags, myc tags, HA tags and/or fluorescent tags. In some embodiments, the LTBP3 protein is a mammalian LTBP3 protein. In some embodiments, the LTBP3 protein is a human, a monkey, a mouse, or a rat LTBP3 protein. In some embodiments, the LTBP3 protein comprises an amino acid sequence as set forth in SEQ ID NOs: 44 and 45 in Table 15. In some embodiments, the LTBP1 protein comprises an amino acid sequence as set forth in SEQ ID NO: 51 in Table 17.

An antibody, or antigen binding portion thereof, as described herein, is capable of binding to a GARP-TGFβ1 complex. In some embodiments, the GARP protein is a naturally-occurring protein or fragment thereof. In some embodiments, the GARP protein is a non-naturally occurring protein or fragment thereof. In some embodiments, the GARP protein is a recombinant protein. Such a GARP may be recombinant, referred to herein as recombinant GARP. Some recombinant GARPs may comprise one or more modifications, truncations and/or mutations as compared to wild type GARP. Recombinant GARPs may be modified to be soluble. In some embodiments, the GARP protein comprises a leader sequence (e.g., a native or non-native leader sequence). In some embodiments, the GARP protein does not comprise a leader sequence (i.e., the leader sequence has been processed or cleaved). In other embodiments, recombinant GARPs are modified to comprise one or more detectable labels. In further embodiments, such detectable labels may include, but are not limited to biotin labels, polyhistidine tags, flag tags, myc tags, HA tags and/or fluorescent tags. In some embodiments, the GARP protein is a mammalian GARP protein. In some embodiments, the GARP protein is a human, a monkey, a mouse, or a rat GARP protein. In some embodiments, the GARP protein comprises an amino acid sequence as set forth in SEQ ID NOs: 48-49 in Table 15. In some embodiments, the GARP protein comprises an amino acid sequence as set forth in SEQ ID NOs: 52 and 53 in Table 18. In some embodiments, the antibodies, or antigen binding portions thereof, described herein do not bind to TGFβ1 in a context-dependent manner, for example binding to TGFβ1 would only occur when the TGFβ1 molecule was complexed with a specific presenting molecule, such as GARP. Instead, the antibodies, and antigen-binding portions thereof, bind to TGFβ1 in a context-independent manner. In other words, the antibodies, or antigen-binding portions thereof, bind to TGFβ1 when bound to any presenting molecule: GARP, LTBP1, LTBP3, and/or LRCC33.

An antibody, or antigen binding portion thereof, as described herein, is capable of binding to a LRRC33-TGFβ1 complex. In some embodiments, the LRRC33 protein is a naturally-occurring protein or fragment thereof. In some embodiments, the LRRC33 protein is a non-naturally occurring protein or fragment thereof. In some embodiments, the LRRC33 protein is a recombinant protein. Such a LRRC33 may be recombinant, referred to herein as recombinant LRRC33. Some recombinant LRRC33 proteins may comprise one or more modifications, truncations and/or mutations as compared to wild type LRRC33. Recombinant LRRC33 proteins may be modified to be soluble. For example, in some embodiments, the ectodomain of LRRC33 may be expressed with a C-terminal His-tag in order to express soluble LRRC33 protein (sLRRC33; see, e.g., SEQ ID NO: 84). In some embodiments, the LRRC33 protein comprises a leader sequence (e.g., a native or non-native leader sequence). In some embodiments, the LRRC33 protein does not comprise a leader sequence (i.e., the leader sequence has been processed or cleaved). In other embodiments, recombinant LRRC33 proteins are modified to comprise one or more detectable labels. In further embodiments, such detectable labels may include, but are not limited to biotin labels, polyhistidine tags, flag tags, myc tags, HA tags and/or fluorescent tags. In some embodiments, the LRRC33 protein is a mammalian LRRC33 protein. In some embodiments, the LRRC33 protein is a human, a monkey, a mouse, or a rat LRRC33 protein. In some embodiments, the LRRC33 protein comprises an amino acid sequence as set forth in SEQ ID NOs: 83, 84, and 101 in Table 18.

TABLE 17

Exemplary LTBP amino acid sequences

| Protein | Sequence | SEQ ID NO |
|---|---|---|
| LTBP1S | NHTGRIKVVFTPSICKVTCTKGSCQNSCEKGNTTTLISENGHAADTLT ATNFRVVICHLPCMNGGQCSSRDKCQCPPNFTGKLCQIPVHGASVPKL YQHSQQPGKALGTHVIHSTHTLPLTVTSQQGVKVKFPPNIVNIHVKHP PEASVQIHQVSRIDGPTGQKTKEAQPGQSQVSYQGLPVQKTQTIHSTY SHQQVIPHVYPVAAKTQLGRCFQETIGSQCGKALPGLSKQEDCCGTVG | 50 |

TABLE 17-continued

Exemplary LTBP amino acid sequences

| Protein | Sequence | SEQ ID NO |
|---|---|---|
| | TSWGFNKCQKCPKKPSYHGYNQMMECLPGYKRVNNTFCQDINECQLQG<br>VCPNGECLNTMGSYRCTCKIGFGPDPTFSSCVPDPPVISEEKGPCYRL<br>VSSGRQCMHPLSVHLTKQLCCCSVGKAWGPHCEKCPLPGTAAFKEICP<br>GGMGYTVSGVHRRRPIHHHVGKGPVFVKPKNTQPVAKSTHPPPLPAKE<br>EPVEALTFSREHGPGVAEPEVATAPPEKEIPSLDQEKTKLEPGQPQLS<br>PGISTIHLHPQFPVVIEKTSPPVPVEVAPEASTSSASQVIAPTQVTEI<br>NECTVNPDICGAGHCINLPVRYTCICYEGYRFSEQQRKCVDIDECTQV<br>QHLCSQGRCENTEGSFLCICPAGFMASEEGTNCIDVDECLRPDVCGEG<br>HCVNTVGAFRCEYCDSGYRMTQRGRCEDIDECLNPSTCPDEQCVNSPG<br>SYQCVPCTEGFRGWNGQCLDVDECLEPNVCANGDCSNLEGSYMCSCHK<br>GYTRTPDHKHCRDIDECQQGNLCVNGQCKNTEGSFRCTCGQGYQLSAA<br>KDQCEDIDECQHRHLCAHGQCRNTEGSFQCVCDQGYRASGLGDHCEDI<br>NECLEDKSVCQRGDCINTAGSYDCTCPDGFQLDDNKTCQDINECEHPG<br>LCGPQGECLNTEGSFHCVCQQGFSISADGRTCEDIDECVNNTVCDSHG<br>FCDNTAGSFRCLCYQGFQAPQDGQGCVDVNECELLSGVCGEAFCENVE<br>GSFLCVCADENQEYSPMTGQCRSRTSTDLDVDVDQPKEEKKECYYNLN<br>DASLCDNVLAPNVTKQECCCTSGVGWGDNCEIFPCPVLGTAEFTEMCP<br>KGKGFVPAGESSSEAGGENYKDADECLLFGQEICKNGFCLNTRPGYEC<br>YCKQGTYYDPVKLQCFDMDECQDPSSCIDGQCVNTEGSYNCFCTHPMV<br>LDASEKRCIRPAESNEQIEETDVYQDLCWEHLSDEYVCSRPLVGKQTT<br>YTECCCLYGEAWGMQCALCPLKDSDDYAQLCNIPVTGRRQPYGRDALV<br>DFSEQYTPEADPYFIQDRFLNSFEELQAEECGILNGCENGRCVRVQEG<br>YTCDCFDGYHLDTAKMTCVDVNECDELNNRMSLCKNAKCINTDGSYKC<br>LCLPGYVPSDKPNYCTPLNTALNLEKDSDLE | |
| LTBP3 | GPAGERGAGGGGALARERFKVVFAPVICKRTCLKGQCRDSCQQGSNMT<br>LIGENGHSTDTLTGSGFRVVVCPLPCMNGGQCSSRNQCLCPPDFTGRF<br>CQVPAGGAGGGTGGSGPGLSRTGALSTGALPPLAPEGDSVASKHAIYA<br>VQVIADPPGPGEGPPAQHAAFLVPLGPGQISAEVQAPPPVVNVRVHHP<br>PEASVQVHRIESSNAESAAPSQHLLPHPKPSHPRPPTQKPLGRCFQDT<br>LPKQPCGSNPLPGLTKQEDCCGSIGTAWGQSKCHKCPQLQYTGVQKPG<br>PVRGEVGADCPQGYKRLNSTHCQDINECAMPGVCRHGDCLNNPGSYRC<br>VCPPGHSLGPSRTQCIADKPEEKSLCFRLVSPEHQCQHPLTTRLTRQL<br>CCCSVGKAWGARCQRCPTDGTAAFKEICPAGKGYHILTSHQTLTIQGE<br>SDFSLFLHPDGPPKPQQLPESPSQAPPPEDTEEERGVTTDSPVSEERS<br>VQQSHPTATTTPARPYPELISRPSPPTMRWFLPDLPPSRSAVEIAPTQ<br>VTETDECRLNQNICGHGECVPGPPDYSCHCNPGYRSHPQHRYCVDVNE<br>CEAEPCGPGRGICMNTGGSYNCHCNRGYRLHVGAGGRSCVDLNECAKP<br>HLCGDGGFCINFPGHYKCNCYPGYRLKASRPPVCEDIDECRDPSSCPD<br>GKCENKPGSFKCIACQPGYRSQGGGACRDVNECAEGSPCSPGWCENLP<br>GSFRCTCAQGYAPAPDGRSCLDVDECEAGDVCDNGICSNTPGSFQCQC<br>LSGYHLSRDRSHCEDIDECDFPAACIGGDCINTNGSYRCLCPQGHRLV<br>GGRKCQDIDECSQDPSLCLPHGACKNLQGSYVCVCDEGFTPTQDQHGC<br>EEVEQPHHKKECYLNFDDTVFCDSVLATNVTQQECCCSLGAGWGDHCE<br>IYPCPVYSSAEFHSLCPDGKGYTQDNNIVNYGIPAHRDIDECMLFGSE<br>ICKEGKCVNTQPGYECYCKQGFYYDGNLLECVDVDECLDESNCRNGVC<br>ENTRGGYRCACTPPAEYSPAQRQCLSPEEMDVDECQDPAACRPGRCVN<br>LPGSYRCECRPPWVPGPSGRDCQLPESPAERAPERRDVCWSQRGEDGM<br>CAGPLAGPALTFDDCCCRQGRGWGAQCRPCPPRGAGSHCPTSQSESNS<br>FWDTSPLLLGKPPRDEDSSEEDSDECRCVSGRCVPRPGGAVCECPGGF<br>QLDASRARCVDIDECRELNQRGLLCKSERCVNTSGSFRCVCKAGFARS<br>RPHGACVPQRRR | 51 |

TABLE 18

Exemplary GARP and LRRC33 amino acid sequences

| Protein | Sequence | SEQ ID NO |
|---|---|---|
| GARP | AQHQDKVPCKMVDKKVSCQVLGLLQVPSVLPPDTETLDLSGNQLRSILASP<br>LGFYTALRHLDLSTNEISFLQPGAFQALTHLEHLSLAHNRLAMATALSAGG<br>LGPLPRVTSLDLSGNSLYSGLLERLLGEAPSLHTLSLAENSLTRLTRHTFR<br>DMPALEQLDLHSNVLMDIEDGAFEGLPRLTHLNLSRNSLTCISDFSLQQLR<br>VLDLSCNSIEAFQTASQPQAEFQLTWLDLRENKLLHFPDLAALPRLIYLNL<br>SNNLIRLPTGPPQDSKGIHAPSEGWSALPLSAPSGNASGRPLSQLLNLDLS<br>YNEIELIPDSFLEHLTSLCFLNLSRNCLRTFEARRLGSLPCLMLLDLSHNA<br>LETLELGARALGSLRTLLLQGNALRDLPPYTFANLASLQRLNLQGNRVSPC<br>GGPDEPGPSGCVAFSGITSLRSLSLVDNEIELLRAGAFLHTPLTELDLSSN<br>PGLEVATGALGGLEASLEVLALQGNGLMVLQVDLPCFICLKRLNLAENRLS<br>HLPAWTQAVSLEVLDLRNNSFSLLPGSAMGGLETSLRRLYLQGNPLSCCGN<br>GWLAAQLHQGRVDVDATQDLICRFSSQEEVSLSHVRPEDCEKGGLKNINLI<br>IILTFILVSAILLTTLAACCCVRRQKFNQQYKA | 52 |

TABLE 18-continued

Exemplary GARP and LRRC33 amino acid sequences

| Protein | Sequence | SEQ ID NO |
|---|---|---|
| sGARP | AQHQDKVPCKMVDKKVSCQVLGLLQVPSVLPPDTETLDLSGNQLRSILASP LGFYTALRHLDLSTNEISFLQPGAFQALTHLEHLSLAHNRLAMATALSAGG LGPLPRVTSLDLSGNSLYSGLLERLLGEAPSLHTLSLAENSLTRLTRHTFR DMPALEQLDLHSNVLMDIEDGAFEGLPRLTHLNLSRNSLTCISDFSLQQLR VLDLSCNSIEAFQTASQPQAEFQLTWLDLRENKLLHFPDLAALPRLIYLNL SNNLIRLPTGPPQDSKGIHAPSEGWSALPLSAPSGNASGRPLSQLLNLDLS YNEIELIPDSFLEHLTSLCFLNLSRNCLRTFEARRLGSLPCLMLLDLSHNA LETLELGARALGSLRTLLLQGNALRDLPPYTFANLASLQRLNLQGNRVSPC GGPDEPGPSGCVAFSGITSLRSLSLVDNEIELLRAGAFLHTPLTELDLSSN PGLEVATGALGGLEASLEVLALQGNGLMVLQVDLPCFICLKRLNLAENRLS HLPAWTQAVSLEVLDLRNNSFSLLPGSAMGGLETSLRRLYLQGNPLSCCGN GWLAAQLHQGRVDVDATQDLICRFSSQEEVSLSHVRPEDCEKGGLKNIN | 53 |
| LRRC33 (also known as NRROS; Uniprot Accession No. Q86YC3) | MELLPLWLCLGFHFLTVGWRNRSGTATAASQGVCKLVGGAADCRGQSLASV PSSLPPHARMLTLDANPLKTLWNHSLQPYPLLESLSLHSCHLERISRGAFQ EQGHLRSLVLGDNCLSENYEETAAALHALPGLRRLDLSGNALTEDMAALML QNLSSLRSVSLAGNTIMRLDDSVFEGLERLRELDLQRNYIFEIEGGAFDGL AELRHLNLAFNNLPCIVDFGLTRLRVLNVSYNVLEWFLATGGEAAFELETL DLSHNQLLFFPLLPQYSKLRTLLLRDNNMGFYRDLYNTSSPREMVAQFLLV DGNVTNITTVSLWEEFSSSDLADLRFLDMSQNQFQYLPDGFLRKMPSLSHL NLHQNCLMTLHIREHEPPGALTELDLSHNQLSELHLAPGLASCLGSLRLFN LSSNQLLGVPPGLFANARNITTLDMSHNQISLCPLPAASDRVGPPSCVDFR NMASLRSLSLEGCGLGALPDCPFQGTSLTYLDLSSNWGVLNGSLAPLQDVA PMLQVLSLRNMGLHSSFMALDFSGFGNLRDLDLSGNCLTTFPRFGGSLALE TLDLRRNSLTALPQKAVSEQLSRGLRTIYLSQNPYDCCGVDGWGALQHGQT VADWAMVTCNLSSKIIRVTELPGGVPRDCKWERLDLGLLYLVLILPSCLTL LVACTVIVLTFKKPLLQVIKSRCHWSSVY<br>*Native signal peptide is depicted in bold font. | 83 |
| soluble LRRC33 (sLRRC33) | MDMRVPAQLLGLLLLWFSGVLGWRNRSGTATAASQGVCKLVGGAADCRGQS LASVPSSLPPHARMLTLDANPLKTLWNHSLQPYPLLESLSLHSCHLERISR GAFQEQGHLRSLVLGDNCLSENYEETAAALHALPGLRRLDLSGNALTEDMA ALMLQNLSSLRSVSLAGNTIMRLDDSVFEGLERLRELDLQRNYIFEIEGGA FDGLAELRHLNLAFNNLPCIVDFGLTRLRVLNVSYNVLEWFLATGGEAAFE LETLDLSHNQLLFFPLLPQYSKLRTLLLRDNNMGFYRDLYNTSSPREMVAQ FLLVDGNVTNITTVSLWEEFSSSDLADLRFLDMSQNQFQYLPDGFLRKMPS LSHLNLHQNCLMTLHIREHEPPGALTELDLSHNQLSELHLAPGLASCLGSL RLFNLSSNQLLGVPPGLFANARNITTLDMSHNQISLCPLPAASDRVGPPSC VDFRNMASLRSLSLEGCGLGALPDCPFQGTSLTYLDLSSNWGVLNGSLAPL QDVAPMLQVLSLRNMGLHSSFMALDFSGFGNLRDLDLSGNCLTTFPRFGGS LALETLDLRRNSLTALPQKAVSEQLSRGLRTIYLSQNPYDCCGVDGWGALQ HGQTVADWAMVTCNLSSKIIRVTELPGGVPRDCKWERLDLGLHHHHHH<br>*Modified human kappa light chain signal peptide is depicted in bold font.<br>**Histidine tag is underlined. | 84 |
| Human LRRC33-GARP chimera | MDMRVPAQLLGLLLLWFSGVLG<u>WRNRSGTATAASQGVCKLVGGAADCRGQS LASVPSSLPPHARMLTLDANPLKTLWNHSLQPYPLLESLSLHSCHLERISR GAFQEQGHLRSLVLGDNCLSENYEETAAALHALPGLRRLDLSGNALTEDMA ALMLQNLSSLRSVSLAGNTIMRLDDSVFEGLERLRELDLQRNYIFEIEGGA FDGLAELRHLNLAFNNLPCIVDFGLTRLRVLNVSYNVLEWFLATGGEAAFE LETLDLSHNQLLFFPLLPQYSKLRTLLLRDNNMGFYRDLYNTSSPREMVAQ FLLVDGNVTNITTVSLWEEFSSSDLADLRFLDMSQNQFQYLPDGFLRKMPS LSHLNLHQNCLMTLHIREHEPPGALTELDLSHNQLSELHLAPGLASCLGSL RLFNLSSNQLLGVPPGLFANARNITTLDMSHNQISLCPLPAASDRVGPPSC VDFRNMASLRSLSLEGCGLGALPDCPFQGTSLTYLDLSSNWGVLNGSLAPL QDVAPMLQVLSLRNMGLHSSFMALDFSGFGNLRDLDLSGNCLTTFPRFGGS LALETLDLRRNSLTALPQKAVSEQLSRGLRTIYLSQNPYDCCGVDGWGALQ HGQTVADWAMVTCNLSSKIIRVTELPGGVPRDCKWERLDLGL</u>*LIIILTFIL VSAILLTTLAACCC*<u>VRRQKFNQQYKA</u><br>*Modified human kappa light chain signal pepide is depicted in bold font.<br>**LRRC33 ectodomain is underlined.<br># GARP transmembrane domain is italicized.<br>## GARP intracellular tail is double underlined. | 101 |

Pharmaceutical Compositions and Formulations

The invention further provides pharmaceutical compositions used as a medicament suitable for administration in human and non-human subjects. One or more high-affinity, context-independent antibodies encompassed by the invention can be formulated or admixed with a pharmaceutically acceptable carrier (excipient), including, for example, a buffer, to form a pharmaceutical composition. Such formulations may be used for the treatment of a disease or disorder that involves TGFβ signaling. In particularly preferred embodiments, such formulations may be used for immuno-oncology applications.

The pharmaceutical compositions of the invention may be administered to patients for alleviating a TGFβ-related indication (e.g., fibrosis, immune disorders, and/or cancer). "Acceptable" means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one antibody that specifically binds a GARP-proTGFβ1 complex, a LTBP1-proTGFβ1 complex, a LTBP3-proTGFβ1 complex, and a LRRC33-proTGFβ1 complex where the antibodies recognize different epitopes/residues of the complex.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The invention also includes pharmaceutical compositions that comprise an antibody or fragment thereof according to the present invention, and a pharmaceutically acceptable excipient.

Thus, the antibody or a molecule comprising an antigen-binding fragment of such antibody can be formulated into a pharmaceutical composition suitable for human administration.

The pharmaceutical formulation may include one or more excipients. In some embodiments, excipient(s) may be selected from the list provided in the following: accessdata.fda.gov/scripts/cder/iig/index.Cfm?event=browseBy Letter.page&Letter=A The pharmaceutical composition is typically formulated to a final concentration of the active biologic (e.g., monoclonal antibody, engineered binding molecule comprising an antigen-binding fragment, etc.) to be between about 2 mg/mL and about 200 mg/mL. For example, the final concentration (wt/vol) of the formulations may range between about 2-200, 2-180, 2-160, 2-150, 2-120, 2-100, 2-80, 2-70, 2-60, 2-50, 2-40, 5-200, 5-180, 5-160, 5-150, 5-120, 5-100, 5-80, 5-70, 5-60, 5-50, 5-40, 10-200, 10-180, 10-160, 10-150, 10-120, 10-100, 10-80, 10-70, 10-60, 10-50, 10-40, 20-200, 20-180, 20-160, 20-150, 20-120, 20-100, 20-80, 20-70, 20-60, 20-50, 20-40, 30-200, 30-180, 30-160, 30-150, 30-120, 30-100, 30-80, 30-70, 30-60, 30-50, 30-40, 40-200, 40-180, 40-160, 40-150, 40-120, 40-100, 40-80, 40-70, 40-60, 40-50, 50-200, 50-180, 50-160, 50-150, 50-120, 50-100, 50-80, 50-70, 50-60, 60-200, 60-180, 60-160, 60-150, 60-120, 60-100, 60-80, 60-70, 70-200, 70-180, 70-160, 70-150, 70-120, 70-100, 70-80 mg/mL. In some embodiments, the final concentration of the biologic in the formulation is about 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg/mL.

The pharmaceutical compositions of the present invention are preferably formulated with suitable buffers. Suitable buffers include but are not limited to: phosphate buffer, citric buffer, and histidine buffer.

The final pH of the formulation is typically between pH 5.0 and 8.0. For example, the pH of the pharmaceutical composition may be about 5.0, 5.2, 5.5, 6.0, 6.2, 6.5, 6.8, 7.0, 7.2, 7.4, 7.5, 7.6, or 7.8.

The pharmaceutical composition of the present disclosure may comprise a surfactant, such as nonionic detergent, approved for the use in pharmaceutical formulations. Such surfactants include, for example, polysorbates, such as Polysorbate 20 (Tween-20), Polysorbate 80 (Tween-80) and NP-40.

The pharmaceutical composition of the present disclosure may comprise a stabilizer. For liquid-protein preparations, stability can be enhanced by selection of pH-buffering salts, and often amino acids can also be used. It is often interactions at the liquid/air interface or liquid/solid interface (with the packaging) that lead to aggregation following adsorption and unfolding of the protein. Suitable stabilizers include but are not limited to: sucrose, maltose, sorbitol, as well as certain amino acids such as histidine, glycine, methionine and arginine.

The pharmaceutical composition of the present disclosure may contain one or any combinations of the following excipients: Sodium Phosphate, Arginine, Sucrose, Sodium Chloride, Tromethamine, Mannitol, Benzyl Alcohol, Histidine, Sucrose, Polysorbate 80, Sodium Citrate, Glycine, Polysorbate 20, Trehalose, Poloxamer 188, Methionine, Trehalose, rhHyaluronidase, Sodium Succinate, Potassium Phosphate, Disodium Edetate, Sodium Chloride, Potassium Chloride, Maltose, Histidine Acetate, Sorbitol, Pentetic Acid, Human Serum Albumin, Pentetic Acid.

In some embodiments, the pharmaceutical composition of the present disclosure may contain a preservative.

The pharmaceutical composition of the present disclosure is typically presented as a liquid or a lyophilized form. Typically, the products can be presented in vial (e.g., glass vial). Products available in syringes, pens, or autoinjectors may be presented as pre-filled liquids in these container/closure systems.

In some examples, the pharmaceutical composition described herein comprises liposomes containing an antibody that specifically binds a GARP-proTGFβ1 complex, a LTBP1-proTGFβ1 complex, a LTBP3-proTGFβ1 complex, and a LRRC33-proTGFβ1 complex, which can be prepared by any suitable method, such as described in Epstein et al., Proc. Natl. Acad. Sci. USA 82:3688 (1985); Hwang et al. Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In some embodiments, liposomes with targeting properties are selected to preferentially deliver or localize the pharmaceutical composition to certain tissues or cell types. For example, certain nanoparticle-based carriers with bone marrow-targeting properties may be employed, e.g., lipid-based nanoparticles or liposomes. See, for example, Sou (2012) "Advanced drug carriers targeting bone marrow", ResearchGate publication 232725109.

In some embodiments, pharmaceutical compositions of the invention may comprise or may be used in conjunction with an adjuvant. It is contemplated that certain adjuvant can boost the subject's immune responses to, for example, tumor antigens, and facilitate Teffector function, DC differentiation from monocytes, enhanced antigen uptake and presentation by APCs, etc. Suitable adjuvants include but are not limited to retinoic acid-based adjuvants and derivatives thereof, oil-in-water emulsion-based adjuvants, such as MF59 and other squalene-containing adjuvants, Toll-like receptor (TRL) ligands (e.g., CpGs), α-tocopherol (vitamin E) and derivatives thereof.

The antibodies described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%.

It will be appreciated that other ingredients may be added, for example mannitol or other pharmaceutically acceptable vehicles, if necessary.

Suitable emulsions may be prepared using commercially available fat emulsions, such as Intralipid™ Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody of the invention with Intralipid™ or the components thereof (soybean oil, egg phospholipids, glycerol and water).

Kits for Use in Detecting, Monitoring or Alleviating a TGFβ-Related Indication

The present disclosure also provides kits for use in alleviating diseases/disorders associated with a TGFβ-related indication. Such kits can include one or more containers comprising an antibody, or antigen binding portion thereof, that specifically binds to a GARP-TGFβ1 complex, a LTBP1-TGFβ1 complex, a LTBP3-TGFβ1 complex, and/or a LRRC33-TGFβ1 complex, e.g., any of those described herein.

In some embodiments, the kit can comprise instructions for use in accordance with any of the methods described herein. The included instructions can comprise a description of administration of the antibody, or antigen binding portion thereof, that specifically binds a GARP-TGFβ1 complex, a LTBP1-TGFβ1 complex, a LTBP3-TGFβ1 complex, and/or a LRRC33-TGFβ1 complex to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen binding portion thereof, to an individual at risk of the target disease.

The instructions relating to the use of antibodies, or antigen binding portions thereof, that specifically binds a GARP-TGFβ1 complex, a LTBP1-TGFβ1 complex, a LTBP3-TGFβ1 complex, and/or a LRRC33-TGFβ1 complex generally include information as to dosage, dosing schedule, and route of administration for the intended treatment.

The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with a TGFβ-related indication. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody, or antigen binding portion thereof, that specifically binds a GARP-TGFβ1 complex, a LTBP1-TGFβ1 complex, a LTBP3-TGFβ1 complex, and/or a LRRC33-TGFβ1 complex as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Process of Screening, Identification and Manufacture of High-Affinity, Isoform-Specific Inhibitors of TGFβ1

The invention encompasses screening/selection methods, production methods and manufacture processes of antibodies or fragments thereof capable of binding each of: a GARP-proTGFβ1 complex, a LTBP1-proTGFβ1 complex, a LTBP3-proTGFβ1 complex, and a LRRC33-proTGFβ1 complex with equivalent affinities, and pharmaceutical compositions and related kits comprising the same. For screening purposes, I tis preferable that at least one of the LTBP1-proTGFβ1 and LTBP3-proTGFβ1 complexes and at least one of the GARP-proTGFβ1 and LRRC33-proTGFβ1 complexes are included to maximize the chance of identifying desirable antibodies with broad binding specificities toward both ECM-associated complexes and cell-associated complexes. Antibodies or fragments thereof identified in the screening process are preferably further tested to confirm its ability to bind each of the LLCs of interest with high affinity.

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET® or BIACORE®) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597; WO 92/18619; WO 91/17271; WO 92/20791; WO 92/15679; WO 93/01288; WO 92/01047; WO 92/09690; and WO 90/02809.

In addition to the use of display libraries, the specified antigen (e.g., presenting molecule-TGFβ1 complexes) can be used to immunize a non-human host, e.g., rabbit, guinea pig, rat, mouse, hamster, sheep, goat, chicken, camelid, as well as non-mammalian hosts such as shark. In one embodiment, the non-human animal is a mouse.

Immunization of a non-human host may be carried out with the use of a purified recombinant protein complex as an immunogen, such as proTGFβ1 with or without a presenting molecule (or fragment thereof) associated thereto. These include, but are not limited to: LTBP1-proTGFβ1, LTBP3-proTGFβ1, GARP-proTGFβ1 and LRRC33-proTGFβ1. The associated presenting molecule need not be full length counterpart but preferably includes the two cysteine residues that form covalent bonds with the proTGFβ1 dimer complex.

Alternatively, immunization of a non-human host may be carried out with the use of a cell-based antigen. The term cell-based antigen refers to cells (e.g., heterologous cells) expressing the proTGFβ1 protein complex. This may be achieved by overexpression of proTGFβ1, optionally with co-expression of a preferred presenting molecule. In some embodiments, endogenous counterpart(s) may be utilized as cell-based antigen. Cell-surface expression of the proteins that form the proTGFβ1-containing protein complex may be confirmed by well-known methods such as FACS. Upon immunization of the host with such cells (a cell-based antigen), immune responses to the antigen are elicited in the host, allowing antibody production and subsequent screening. In some embodiments, suitable knockout animals are used to facilitate stronger immune responses to the antigen. Alternatively, structural differences among different species may be sufficient to trigger antibody production in the host.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the $V_H$ and/or $V_L$ of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain (s) of the immunoglobulin chains encoding sequences and expression control sequences) can be transferred into the host cell by suitable methods, which vary depending on the type of cellular host.

The screening methods may include a step of evaluating or confirming desired activities of the antibody or fragment thereof. In some embodiments, the step comprises selecting for the ability to inhibit target function, e.g., inhibition of release of mature/soluble growth factor (e.g., TGFβ1) from a latent complex. In preferred embodiments, such step comprises a cell-based potency assay, in which inhibitory activities of test antibody or antibodies are assayed by measuring the level of growth factor released in the medium (e.g., assay solution) upon activation, when proTGFβ complex is expressed on cell surface. The level of growth factor released into the medium/solution can be assayed by, for example, measuring TGFβ activities. Non-limiting examples of useful cell-based potency assays are described in Example 2 herein.

In some embodiments, the step of screening desirable antibodies or fragments comprises selecting for antibodies or fragments thereof that promote internalization and subsequent removal of antibody-antigen complexes from the cell surface. In some embodiments, the step comprises selecting for antibodies or fragments thereof that induce ADCC. In some embodiments, the step comprises selecting for antibodies or fragments thereof that accumulate to a desired site(s) in vivo (e.g., cell type, tissue or organ). In some embodiments, the step comprises selecting for antibodies or fragments thereof with the ability to cross the blood brain barrier. The methods may optionally include a step of optimizing one or more antibodies or fragments thereof to provide variant counterparts that possess desirable profiles, as determined by criteria such as stability, binding affinity, functionality (e.g., inhibitory activities, Fc function, etc.), immunogenicity, pH sensitivity and developability (e.g., high solubility, low self-association, etc.).

The process for making a composition comprising an antibody or a fragment according to the invention may include optimization of an antibody or antibodies that are identified to possess desirable binding and functional (e.g., inhibitory) properties. Optimization may comprise affinity maturation of an antibody or fragment thereof. Further optimization steps may be carried out to provide physicochemical properties that are advantageous for therapeutic compositions. Such steps may include, but are not limited to, mutagenesis or engineering to provide improved solubility, lack of self-aggregation, stability, pH sensitivity, Fc function, and so on. The resulting optimized antibody is preferably a fully human antibody or humanized antibody suitable for human administration.

Manufacture process for a pharmaceutical composition comprising such an antibody or fragment thereof may comprise the steps of purification, formulation, sterile filtration, packaging, etc. Certain steps such as sterile filtration, for example, are performed in accordance with the guidelines set forth by relevant regulatory agencies, such as the FDA. Such compositions may be made available in a form of single-use containers, such as pre-filled syringes, or multi-dosage containers, such as vials.

Modifications

Antibodies, or antigen binding portions thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and isolation of a GARP-proTGFβ1 complex, a LTBP1-proTGFβ1 complex, a LTBP3-proTGFβ1 complex, and/or a LRRC33-proTGFβ1 complex. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, Lu (177Lu), 159Gd, 149Pm, 140La, 175Yb, 166Ho, 90Y, 47Sc, 86R, 188Re, 142Pr, 105Rh, 97Ru, 68Ge, 57Co, 65Zn, 85Sr, 32P, 153Gd, 169Yb, 51Cr, 54Mn, 75Se, Zirconium ($^{89}$Zr) and tin (113Sn, 117Sn). In some embodiments, the radio label may be selected from the group consisting of: $^{11}$C, $^{13}$N, $^{15}$O, $^{68}$Ga, $^{177}$Lu, $^{18}$F and $^{89}$Zr. In some embodiments, useful labels are positron-emitting isotopes, which may be detected by positron-emission tomography. The detectable substance may be coupled or conjugated either directly to the antibodies of the disclosure that bind specifically to a GARP-proTGFβ1 complex, a LTBP1-proTGFβ1 complex, a LTBP3-proTGFβ1 complex, and/or a LRRC33-proTGFβ1 complex, or indirectly, through an intermediate (such as, for example, a linker) using suitable techniques. Any of the antibodies provided herein that are conjugated to a detectable substance may be used for any suitable diagnostic assays, such as those described herein.

In addition, antibodies, or antigen binding portions thereof, of the disclosure may also be modified with a drug. The drug may be coupled or conjugated either directly to the polypeptides of the disclosure, or indirectly, through an intermediate (such as, for example, a linker (e.g., a cleavable linker)) using suitable techniques.

Targeting Agents

In some embodiments methods of the present disclosure comprise the use of one or more targeting agents to target an antibody, or antigen binding portion thereof, as disclosed herein, to a particular site in a subject for purposes of modulating mature TGFβ release from a GARP-proTGFβ1 complex, a LTBP1-proTGFβ1 complex, a LTBP3-proTGFβ1 complex, and/or a LRRC33-proTGFβ1 complex. For example, LTBP1-proTGFβ1 and LTBP3-proTGFβ1 complexes are typically localized to extracellular matrix. Thus, in some embodiments, antibodies disclosed herein can be conjugated to extracellular matrix targeting agents for purposes of localizing the antibodies to sites where LTBP-associated TGFβ1 complexes reside. In such embodiments, selective targeting of antibodies leads to selective modulation of LTBP1-proTGFβ1 and LTBP3-proTGFβ1 complexes. In some embodiments, extracellular matrix targeting agents include heparin binding agents, matrix metalloproteinase binding agents, lysyl oxidase binding domains, fibrillin-binding agents, hyaluronic acid binding agents, and others.

Similarly, GARP-proTGFβ1 and LRRC33-proTGFβ1 complexes are typically localized and anchored to the surface of cells. The former is expressed on activated FOXP3+ regulatory T cells (Tregs), while the latter is expressed on certain myeloid cells and some cancer cells such as AML. Thus, in some embodiments, antibodies disclosed herein can be conjugated to immune cell (e.g., Treg cell, activated macrophages, etc.) binding agents for purposes of localizing antibodies to sites where these cell-associated proTGFβ1 complexes reside. In such embodiments, selective targeting of antibodies leads to selective inhibition of cell associated-proTGFβ1 complexes (e.g., selective inhibition of the release of mature TGFβ1 for purposes of immune modulation, e.g., in the treatment of cancer). In such embodiments, immune cell targeting agents may include, for example, CCL22 and CXCL12 proteins or fragments thereof.

In some embodiments, bispecific antibodies may be used having a first portion that selectively binds a proTGFβ1 complex and a second portion that selectively binds a component of a target site, e.g., a component of the ECM (e.g., fibrillin) or a component of a Treg cell (e.g., CTLA-4).

As further detailed herein, the present invention contemplates that isoform-selective TGFβ1 inhibitors, such as those described herein, may be used for promoting or restoring hematopoiesis in the bone marrow. Accordingly, in some embodiments, a composition comprising such an inhibitor (e.g., high-affinity, isoform-selective inhibitor of TGFβ1) may be targeted to the bone marrow. One mode of achieving bone marrow targeting is the use of certain carriers that preferentially target the bone marrow localization or accumulation. For example, certain nanoparticle-based carriers with bone marrow-targeting properties may be employed, e.g., lipid-based nanoparticles or liposomes. See, for example, Sou (2012) "Advanced drug carriers targeting bone marrow", ResearchGate publication 232725109.

In some embodiments, targeting agents include immune-potentiators, such as adjuvants comprising squalene and/or α-tocopherol and adjuvants comprising a TLR ligand/agonist (such as TLR3 ligands/agonists). For example, squalene-containing adjuvant may preferentially target certain immune cells such as monocytes, macrophages and antigen-presenting cells to potentiate priming, antigen processing and/or immune cell differentiation to boost host immunity. In some embodiments, such adjuvant may stimulate host immune responses to neo-epitopes for T cell activation.

Therapeutic Targets and In Vivo Mechanisms of Action

Accordingly, the high-affinity, isoform-selective TGFβ1 inhibitors disclosed herein may be used to inhibit TGFβ1 in any suitable biological systems, such as in vitro, ex vivo and/or in vivo systems. Related methods may comprise contacting a biological system with the TGFβ1 inhibitor. The biological system may be an assay system, a biological sample, a cell culture, and so on. In some cases, these methods include modifying the level of free growth factor in the biological system.

Accordingly, such pharmaceutical compositions and formulations may be used to target TGFβ-containing latent complexes accessible by the inhibitors in vivo. Thus, the antibody of the invention is aimed to target the following complexes in a disease site (e.g., TME) where it preemptively binds the latent complex thereby preventing the growth factor from being released: i) proTGFβ1 presented by GARP; ii) proTGFβ1 presented by LRRC33; iii) proTGFβ1 presented by LTBP1; and iv) proTGFβ1 presented by LTBP3. Typically, complexes (i) and (ii) above are present on cell surface because both GARP and LRRC33 are transmembrane proteins capable of anchoring or tethering latent proTGFβ1 on the extracellular face of the cell expressing LRRC33, whilst complexes (iii) and (iv) are components of the extracellular matrix. In this way, the inhibitors embodied herein do away with having to complete binding with endogenous high affinity receptors for exerting inhibitory effects. Moreover, targeting upstream of the ligand/receptor interaction may enable more durable effects since the window of target accessibility is longer and more localized to relevant tissues than conventional inhibitors that target transient, soluble growth factors only after it has been released from the latent complex. Thus, targeting the latent complex tethered to certain niches may facilitate improved target engagement in vivo, as compared to conventional neutralizing antibodies that must compete binding with endogenous receptors during its short half-life as a soluble (free) growth factor, e.g., ~two minutes, once it is released from the latent complex.

A number of studies have shed light on the mechanisms of TGFβ1 activation. Three integrins, αVβ6, αVβ8, and αVβ1 have been demonstrated to be key activators of latent TGFβ1 (Reed, N. I., et al., Sci Transl Med, 2015. 7(288): p. 288ra79; Travis, M. A. and D. Sheppard, Annu Rev Immunol, 2014. 32: p. 51-82; Munger, J. S., et al., Cell, 1999. 96(3): p. 319-28). αV integrins bind the RGD sequence present in TGFβ1 and TGFβ1 LAPs with high affinity (Dong, X., et al., Nat Struct Mol Biol, 2014. 21(12): p. 1091-6). Transgenic mice with a mutation in the TGFβ1 RGD site that prevents integrin binding, but not secretion, phenocopy the TGFβ1−/− mouse (Yang, Z., et al., J Cell Biol, 2007. 176(6): p. 787-93). Mice that lack both (36 and (38 integrins recapitulate all essential phenotypes of TGFβ1 and TGFβ3 knockout mice, including multiorgan inflammation and cleft palate, confirming the essential role of these two integrins for TGFβ1 activation in development and homeostasis (Aluwihare, P., et al., J Cell Sci, 2009. 122(Pt 2): p. 227-32). Key for integrin-dependent activation of latent TGFβ1 is the covalent tether to presenting molecules; disruption of the disulfide bonds between GARP and TGFβ1 LAP by mutagenesis does not impair complex formation, but completely abolishes TGFβ1 activation by αVβ6 (Wang, R., et al., Mol Biol Cell, 2012. 23(6): p. 1129-39). The recent structure study of latent TGFβ1 illuminates how integrins enable release of active TGFβ1 from the latent complex: the covalent link of latent TGFβ1 to its presenting molecule anchors latent TGFβ1, either to the ECM through LTBPs, or to the cytoskeleton through GARP or LRRC33. Integrin binding to the RGD sequence results in a force-dependent change in the structure of LAP, allowing active TGFβ1 to be released and bind nearby receptors (Shi, M., et al., Nature, 2011. 474(7351): p. 343-9). The importance of integrin-dependent TGFβ1 activation in disease has also been well validated. A small molecule inhibitor of αVβ1 protects against bleomycin-induced lung fibrosis and carbon tetrachloride-induced liver fibrosis (Reed, N. I., et al., Sci Transl Med, 2015. 7(288): p. 288ra79), and αVβ6 blockade with an antibody or loss of integrin β6 expression suppresses bleomycin-induced lung fibrosis and radiation-induced fibrosis (Munger, J. S., et al., Cell, 1999. 96(3): p. 319-28); Horan, G. S., et al., Am J Respir Crit Care Med, 2008. 177(1): p. 56-65).

In addition to integrins, other mechanisms of TGFβ1 activation have been implicated, including thrombospondin-1 and activation by proteases such as Plasmin, matrix metalloproteinases (MMPs, e.g., MMP2, MMP9 and MMP12), cathepsin D, kallikrein, and the ADAMs family of zinc proteases (e.g., ADAM10, ADAM12 and ADAM17). Knockout of thrombospondin-1 recapitulates some aspects of the TGFβ1-/- phenotype in some tissues, but is not protective in bleomycin-induced lung fibrosis, known to be TGFβ3-dependent (Ezzie, M. E., et al., Am J Respir Cell Mol Biol, 2011. 44(4): p. 556-61). Additionally, knockout of candidate proteases did not result in a TGFβ1 phenotype (Worthington, J. J., J. E. Klementowicz, and M. A. Travis, Trends Biochem Sci, 2011. 36(1): p. 47-54). This could be explained by redundancies or by these mechanisms being critical in specific diseases rather than development and homeostasis.

Thus, the high-affinity, isoform-specific inhibitors of TGFβ1 described herein include inhibitors that work by preventing the step of TGFβ1 activation. In some embodiments, such inhibitors can inhibit integrin-dependent (e.g., mechanical or force-driven) activation of TGFβ1. In some embodiments, such inhibitors can inhibit protease-dependent or protease-induced activation of TGFβ1. The latter includes inhibitors that inhibit the TGFβ1 activation step in an integrin-independent manner. In some embodiments, such inhibitors can inhibit TGFβ1 activation irrespective of the mode of activation, e.g., inhibit both integrin-dependent activation and protease-dependent activation of TGFβ1. Non-limiting examples of proteases which may activate TGFβ1 include serine proteases, such as Kallikreins, Chemotrypsin, Trypsin, Elastases, Plasmin, as well as zinc metalloproteases (MMP family) such as MMP-2, MMP-9 and MMP-13. Kallikreins include plasma-Kallikreins and tissue Kallikreins, such as KLK1, KLK2, KLK3, KLK4, KLK5, KLK6, KLK7, KLK8, KLK9, KLK10, KLK11, KLK12, KLK13, KLK14 and KLK15. Data presented herein demonstrate examples of an isoform-specific TGFβ1 inhibitors, capable of inhibiting Kallikrein-dependent activation of TGFβ1 in vitro. In some embodiments, inhibitors of the present invention prevent release or dissociation of active (mature) TGFβ1 growth factor from the latent complex. In some embodiment, such inhibitors may work by stabilizing the inactive (e.g., latent) conformation of the complex. Data further demonstrate that a high-affinity, context-independent TGFβ1 inhibitor (Ab6) can also inhibit Plasmin-dependent TGFβ1 activation. Surprisingly, however, a context-biased TGFβ1 inhibitor (Ab3) failed to inhibit this process. Both Ab3 and Ab6 have similar affinities for matrix-associated proTGFβ1 complexes. However, Ab3 has a significantly weaker binding affinity for cell-associated proTGFβ1 complexes. The relative difference between the two categories is more than 20 fold ("bias"). By comparison, Ab6 shows equivalent high affinities towards both categories of the antigen complexes. One possible explanation is that the observed functional difference may stem from the bias feature of Ab3. Another possible explanation is that it is mediated by differences in epitopes or binding regions.

The invention is particularly useful for therapeutic use for certain diseases that are associated with multiple biological roles of TGFβ1 signaling that are not limited to a single context of TGFβ1 function. In such situations, it may be beneficial to inhibit TGFβ1 effects across multiple contexts. Thus, the present disclosure provides methods for targeting and inhibiting TGFβ1 in an isoform-specific manner, rather than in a context-specific manner. Such agents may be referred to as "isoform-specific, context-independent" TGFβ1 modulators.

A body of evidence supports the notion that many diseases manifest complex perturbations of TGFβ signaling, which likely involve participation of heterogeneous cell types that confer different effects of TGFβ function, which are mediated by its interactions with so-called presenting molecules. At least four such presenting molecules have been identified, which can "present" TGFβ in various extracellular niches to enable its activation in response to local stimuli. In one category, TGFβ is deposited into the ECM in association with ECM-associated presenting molecules, such as LTBP1 and LTBP3, which mediate ECM-associated TGFβ activities. In another category, TGFβ is tethered onto the surface of immune cells, via presenting molecules such as GARP and LRRC33, which mediate certain immune function. These presenting molecules show differential expression, localization and/or function in different tissues and cell types, indicating that triggering events and outcome of TGFβ activation will vary, depending on the microenvironment. Based on the notion that many TGFβ effects may interact and contribute to disease progression, therapeutic agents that can antagonize multiple facets of TGFβ function may provide greater efficacy.

The rationale for the advantageous use of context-independent inhibitors of TGFβ1 over context-biased inhibitors of TGFβ1 as a therapeutic to treat certain diseases (as described in further detail herein) includes the following:

Work disclosed herein confirms the involvement of heterogeneous TGFβ1 complexes in a disease environment and extends the understanding of the underlining mechanisms, providing insights into an improved therapeutic approach for a number of diseases.

It has been recognized that various diseases involve heterogeneous populations of cells as sources of TGFβ1 that collectively contribute to the pathogenesis and/or progression of the disease. More than one types of TGFβ1-containing complexes ("contexts") likely coexist within the same disease microenvironment. In particular, such diseases may involve both an ECM (or "matrix") component of TGFβ1 signaling and an immune component of TGFβ1 signaling. In such situations, selectively targeting only a single TGFβ1 context (e.g., TGFβ1 associated with one particular type of presenting molecule) may provide limited relief. Thus, broadly inhibitory TGFβ1 antagonists are desirable for therapeutic use. Previously described inhibitory antibodies that broadly targeted multiple latent complexes of TGFβ1 exhibited skewed binding profiles among the target complexes. The inventors therefore set out to identify more uniformly inhibitory antibodies that selectively inhibit TGFβ1 activation, irrespective of particular presenting molecule linked thereto. It was reasoned that particularly for immune-oncology applications, it is advantageous to potently inhibit both matrix-associated TGFβ1 and immune cell-associated TGFβ1.

Second, remarkable similarities in tissue/cellular characteristics are observed between the tumor stroma and fibrotic tissues, highlighting common mechanisms underlining various indications. Indicating crosstalk between and among: i) TGFβ1-dependent pro-fibrotic phenotypes; ii) TGFβ1-dependent pro-tumor phenotypes; and, iii) TGFβ-dependent immunosuppressive phenotypes, observed in a number of pathological conditions. Thus, the use of context-independent inhibitors that broadly act upon many of these constituents with equivalent potency may provide optimal therapeutic effects across a diverse types of disease conditions. For example, clinical manifestations of primary myelofibrosis include abnormal proliferation of certain cell populations and fibrosis in the bone marrow.

Third, lines of evidence have raised the possibility that TGFβ 1 may be at least in part responsible for drug resistance to anti-cancer therapies (such as immune checkpoint inhibitors, cancer vaccines, engineered immune cell therapy, chemotherapy, radiation therapy, etc.) observed in many types of cancer (cancer patients). In some cases, such resistance appears intrinsic to the particular cancer/tumor-type against the patient's background (typically referred to as innate resistance, primary resistance, intrinsic resistance, or inherent resistance; these terms are used interchangeably herein). Such resistance may be represented in a subset of patients poorly responsive to cancer therapies such as immune checkpoint inhibitors and possibly reflect immune-excluded environment. This is likely mediated at least in part by a TGFβ1-dependent pathway. Thus, isoform-selective inhibitor described herein may render the resistant cancers more responsive to such therapies. In particular, in situations where resistance to therapy is associated with immune exclusion at a disease site (such as tumor), TGFβ1 inhibition may unblock immunosuppression and allow effector cells to access their target (e.g., cancer cells). The same mechanism of action is applicable in a number of therapeutic paradigms where effects of a therapy must come in contact with the disease or insured tissue to be treated. High-affinity, context-independent TGFβ1 inhibitors of the present invention are thought to facilitate this process by working through the multiple arms of TGFβ1 function, e.g., inhibition of Tregs, modulating of macrophages, and regulation of ECM, thereby overcoming the drug resistance.

Alternatively, resistance may develop over time such that patients who show material clinical responsiveness to a treatment become poorly responsive over time (i.e., adaptive or acquired resistance). For example, it has been reported that PD-1 therapy can lead to adaptive resistance which is correlated with upregulation of other T cell antigens (e.g., TCR components) suggesting that cancer cells evolve to evade the PD-1 blockade via another mechanism. Subsequently, a second checkpoint inhibitor that targets a different T cell receptor component such as TIM3 can restore responsiveness to the immunotherapy. These observations suggest that blocking multiple pathways to counter adaptive responses of cancer cells may reduce the likelihood of cancer cells' ability to evade host immunity. The inhibitors of TGFβ1 which are capable of targeting multiple TGFβ1 contexts may advantageously circumvent acquired drug resistance by providing blockade at multiple points of the TGFβ1 function.

And finally, based on the notion that expression of various presenting molecules may vary over time, for example, in response to local cues (e.g., cytokines, chemokines, ECM environment, etc.) and/or with changes in a disease microenvironment, it is reasoned that isoform-selective inhibitors of TGFβ1 such as those described herein may be used to withstand such plasticity and provide broad, durable inhibitory effects even when abnormal changes in expression of the presenting molecules occur.

In any of these scenarios, the context-independent inhibitors of TGFβ1 are advantageously aimed to target the pro/latent forms of TGFβ1 in association with various presenting molecules, all of which or different combinations of which are present in a disease microenvironment(s). More specifically, in one modality, the inhibitor targets ECM-associated TGFβ1 (LTBP1/3-TGFβ1 complexes). In another modality, the inhibitor targets immune cell-associated TGFβ1. This includes GARP-presented TGFβ1, such as GARP-TGFβ1 complexes expressed on Treg cells and LRRC33-TGFβ1 complexes expressed on macrophages and other myeloid/lymphoid cells, as well as certain cancer cells.

Such antibodies include isoform-specific inhibitors of TGFβ1 that bind and prevent activation (or release) of mature TGFβ1 growth factor from a pro/latent TGFβ1 complex in a context-independent manner, such that the antibodies can inhibit activation (or release) of TGFβ1 associated with multiple types of presenting molecules. In particular, the present invention provides antibodies capable of blocking ECM-associated TGFβ1 (LTBP-presented and LTBP3-presented complexes) and cell-associated TGFβ1 (GARP-presented and LRRC33-presented complexes).

Various disease conditions have been suggested to involve dysregulation of TGFβ signaling as a contributing factor. Indeed, the pathogenesis and/or progression of certain human conditions appear to be predominantly driven by or dependent on TGFβ1 activities. In particular, many such diseases and disorders involve both an ECM component and an immune component of TGFβ1 function, suggesting that TGFβ1 activation in multiple contexts (e.g., mediated by more than one type of presenting molecules) is involved. Moreover, it is contemplated that there is crosstalk among TGFβ1-responsive cells. In some cases, interplays between multifaceted activities of the TGFβ1 axis may trigger a cascade of events that lead to disease progression, aggravation, and/or suppression of the host's ability to combat disease. For example, certain disease microenvironments, such as tumor microenvironment (TME) and fibrotic microenvironment (FME), may be associated with TGFβ1 presented by multiple different presenting molecules, e.g., LTBP1-proTGFβ1, LTBP3-proTGFβ1, GARP-proTGFβ1, LRRC33-proTGFβ1, and any combinations thereof. TGFβ1 activities of one context may in turn regulate or influence TGFβ1 activities of another context, raising the possibility that when dysregulated, this may result in exacerbation of disease conditions. Therefore, it is desirable to broadly inhibit across multiple modes of TGFβ1 function (i.e., multiple contexts) while selectively limiting such inhibitory effects to the TGFβ1 isoform. The aim is not to perturb homeostatic TGFβ signaling mediated by the other isoforms, including TGFβ3, which plays an important role in would healing.

Immune components of TGFβ1 activities are largely mediated by cell-associated TGFβ1 (e.g., GARP-proTGFβ1 and LRRC33-proTGFβ1). Both the GARP- and LRRC33-arms of TGFβ1 function are associated with immunosuppressive features that contribute to the progression of many diseases. Thus, the high-affinity, isoform-selective TGFβ1 inhibitor may be used to inhibit TGFβ1 associated with immunosuppressive cells. The immunosuppressive cells include regulatory T-cells (Tregs), M2 macrophages, and MDSCs. Thus, the TGFβ1 inhibitor may inhibit or reverse immunosuppressive phenotype at a disease site, e.g., TME and FME in vivo.

In some embodiments, the TGFβ1 inhibitor inhibits TGFβ1 associated with a cell expressing the GARP-TGFβ1 complex or the LRRC33-TGFβ1 complex, wherein optionally the cell may be a T-cell, a fibroblast, a myofibroblast, a macrophage, a monocyte, a dendritic cell, an antigen presenting cell, a neutrophil, a myeloid-derived suppressor cell (MDSC), a lymphocyte, a mast cell, or a microglia. The T-cell may be a regulatory T cell (e.g., immunosuppressive T cell). The neutrophil may be an activated neutrophil. The macrophage may be an activated (e.g., polarized) macrophage, including profibrotic and/or tumor-associated macrophages (TAM), e.g., M2c subtype and M2d subtype macrophages. In some embodiments, macrophages are exposed to tumor-derived factors (e.g., cytokines, growth factors, etc.) which may further induce pro-cancer phenotypes in macrophages. In some embodiments, such tumor-derived factor is CSF-1/M-CSF.

In some embodiments, the cell expressing the GARP-TGFβ1 complex or the LRRC33-TGFβ1 complex is a cancer cell, e.g., circulating cancer cells and tumor cells.

GARP-proTGFβ1 as Target

Regulatory T cells (Tregs) represent a small subset of CD4-positive T lymphocytes and play an important role of acting as a "break" in dampening immune responses to maintain homeostasis. In disease conditions (such as cancer), elevated levels of Tregs are reported, and this is associated with poorer prognosis. Human Tregs isolated from peripheral blood cells of donors can be activated by CD3/CD28 stimulation. Treg activation is shown to induce a marked increase in GARP-proTGFβ1 cell surface expression (FIG. 26A). As reported previously, Tregs exert immune suppressive activities, which include powerful suppression of effector T cell (Teff) proliferation. As shown herein (FIG. 26B), under the standard experimental conditions where most Teffs undergo cell division, co-cultured Tregs reduce this to a mere fraction. And this Treg inhibition of Teff proliferation can be effectively overcome (i.e., dis-inhibition) by treating the co-culture of Teffs and Tregs with isoform-selective inhibitors of TGFβ1, demonstrating that isoform-selective TGFβ1 disclosed herein are effective in inhibiting the GARP-arm of TGFβ1 function. In disease environments (such as tumor microenvironment and fibrotic environment), this would translate to the ability of these inhibitors to block Treg-mediated immunosuppression. This should in turn lead to enhanced proliferation of effector T cells to boost immunity. The GARP-arm of the isoform-selective inhibitors of TGFβ1 may target this facet of TGFβ1 function. In some embodiments, the antibodies, or the antigen binding portions thereof, as described herein, may reduce the suppressive activity of regulatory T cells (Tregs).

LRRC33-proTGFβ1 as Target

LRRC33 is expressed in selective cell types, in particular those of myeloid lineage, including monocytes and macrophages. Monocytes originated from progenitors in the bone marrow and circulate in the bloodstream and reach peripheral tissues. Circulating monocytes can then migrate into tissues where they become exposed to the local environment (e.g., tissue-specific, disease-associated, etc.) that includes a panel of various factors, such as cytokines and chemokines, triggering differentiation of monocytes into macrophages, dendritic cells, etc. These include, for example, alveolar macrophages in the lung, osteoclasts in bone marrow, microglia in the CNS, histiocytes in connective tissues, Kupffer cells in the liver, and brown adipose tissue macrophages in brown adipose tissues. In a solid tumor, infiltrated macrophages may be tumor-associated macrophages (TAMs), tumor-associated neutrophils (TANs), and myeloid-derived suppressor cells (MDSCs), etc. Such macrophages may activate and/or be associated with activated fibroblasts, such as carcinoma-associated (or cancer-associated) fibroblasts (CAFs) and/or the stroma. Thus, inhibitors of TGFβ1 activation described herein which inhibits release of mature TGFβ1 from LRRC33-containing complexes can target any of these cells expressing LRRC33-proTGFβ1 on cell surface. At a fibrotic microenvironment, LRRC33-expressing cells may include M2 macrophages, tissue resident macrophages, and/or MDSCs.

In some embodiments, the LRRC33-TGFβ1 complex is present at the outer surface of profibrotic (M2-like) macrophages. In some embodiments, the profibrotic (M2-like) macrophages are present in the fibrotic microenvironment. In some embodiments, targeting of the LRRC33-TGFβ1 complex at the outer surface of profibrotic (M2-like) macrophages provides a superior effect as compared to solely targeting LTBP1-TGFβ1 and/or LTBP1-TGFβ1 complexes. In some embodiments, M2-like macrophages, are further polarized into multiple subtypes with differential phenotypes, such as M2c and M2d TAM-like macrophages. In some embodiments, macrophages may become activated by various factors (e.g., growth factors, chemokines, cytokines and ECM-remodeling molecules) present in the tumor microenvironment, including but are not limited to TGFβ1, CCL2 (MCP-1), CCL22, SDF-1/CXCL12, M-CSF (CSF-1), IL-6, IL-8, IL-10, IL-11, CXCR4, VEGF, PDGF, prostaglandin-regulating agents such as arachidonic acid and cyclooxygenase-2 (COX-2), parathyroid hormone-related protein (PTHrP), RUNX2, HIF1α, and metalloproteinases. Exposures to one or more of such factors may further drive monocytes/macrophages into pro-tumor phenotypes. To give but one example, CCL2 and VEGF co-expression in tumors has been shown to be correlated with increased TAM and poor diagnosis. In turn, activated tumor-associated cells may also facilitate recruitment and/or differentiation of other cells into pro-tumor cells, e.g., CAFs, TANs, MDSCs, and the like. Stromal cells may also respond to macrophage activation and affect ECM remodeling, and ultimately vascularization, invasion, and metastasis. For example, CCL2 not only functions as a monocyte attractant but also promotes cell adhesion by upregulating MAC-1, which is a receptor for ICAM-1, expressed in activated endothelium. This may lead to CCL2-dependent arteriogenesis and cancer progression. Thus, TGFβ1 inhibitors described herein may be used in a method for inhibiting arteriogenesis by interfering with the CCL2 signaling axis.

A subset of myeloid cells express cell surface LRRC33, including M2-polarized macrophages and myeloid-derived suppressor cells (MDSCs), both of which have immunosuppressive phenotypes and are enriched at disease environments (e.g., TME and FME). Bone marrow-derived circulating monocytes do not appear to express cell surface LRRC33. The restrictive expression of LRRC33 makes this a particularly appealing therapeutic target. While a majority of studies available in the literature have focused on effector T cell biology (e.g., CD8+ cytotoxic cells) in cancer, increasing evidence (such as data presented herein) points to important roles of suppressive myeloid cell populations in diseases. Importantly, the highly selective TGFβ1 inhibitory antibodies disclosed herein, are capable of targeting this arm of TGFβ1 function in vivo. More specifically, data presented herein show that tumor-associated M2 macrophages and MDSCs express cell-surface LRRC33, with a strong correlation to disease progression. The high-affinity, TGFβ1-selective antibodies disclosed herein are capable of overcoming primary resistance to checkpoint blockade therapy (CBT) of tumors in multiple pharmacological models. Indeed, anti-tumor efficacy coincides with a significant decrease in tumor-associated macrophages and MDSC levels, suggesting that targeting this facet of TGFβ1 function may contribute to therapeutically beneficial effects. This is likely applicable to other disease where these immunosuppressive cells are enriched. A number of fibrotic conditions are also associated with elevated local frequencies of these cell populations. Thus, the high-affinity, TGFβ1-selective antibodies are expected to exert similar in vivo effects in such indications.

LTBP1/3-proTGFβ1 as Target

The extracellular matrix is the site at which complex signaling events at the cellular, tissue, organ, and systemic levels are orchestrated. Dysregulation of the ECM is observed in a number of pathologies. A reservoir of TGFβ1 growth factor is present in the ECM in the form of latent proTGFβ1 complex. Latent proTGFβ1 complexes are anchored to the matrix via covalent interactions with the ECM components, LTBP1 and/or LTBP3. Other ECM proteins such as fibronectin and fibrillins (e.g., fibrillin-1) are believed to be important in mediating ECM deposition and localization of LTBPs. Targeting of LLCs to the ECM is an essential step in the TGFβ1 activation process. Because most, if not all, TGFβ1-related indications likely involve some aspects of ECM function that are TGFβ1-dependent, it is imperative that TGFβ inhibitors considered for therapeutics should be capable of targeting this pool of TGFβ1 signaling. Indeed, the high-affinity, isoform-selective inhibitors of TGFβ1 according to the present disclosure show remarkably high affinities and potency for human LTBP1/3-proTGFβ1 complexes. Because these antibodies directly target the ECM-localized complexes in their pre-activation state, this mechanism of action would do away with having to compete with endogenous high-affinity receptors for ligand binding. Further, because the inhibitory activities of these antibodies are localized at the site of disease associated with increased TGFβ1 activation (e.g., dysregulated niche within the ECM), it is envisaged that these antibodies should achieve enhanced efficacy while limiting side effects.

In some embodiments, the LTBP1-TGFβ1 complex or the LTBP3-TGFβ1 complex is a component of the extracellular matrix. The N-terminus of LTBPs may be covalently bound to the ECM via an isopeptide bond, the formation of which may be catalyzed by transglutaminases. The structural integrity of the ECM is believed to be important in mediating LTBP-associated TGFβ1 activity. For example, stiffness of the matrix can significantly affect TGFβ1 activation. In addition, incorporating fibronectin and/or fibrillin in the scaffold may significantly increase the LTBP-mediated TGFβ1 activation. Similarly, presence of fibronectin and/or fibrillin in LTBP assays (e.g., cell-based potency assays) may increase an assay window. In some embodiments, the extracellular matrix comprises fibrillin and/or fibronectin. In some embodiments, the extracellular matrix comprises a protein comprising an RGD motif.

Thus, the high-affinity, isoform-selective inhibitors of TGFβ1 provided herein enable potent inhibition of each of the biological contexts of TGFβ1 function, namely, the GARP-arm, the LRRC33-arm, and the LTBP1/3-arm.

Selection of Therapeutic Indications and/or Subjects Likely to Respond to a Therapy Comprising a TGFβ1-Selective, High Affinity, Broadly-Inhibiting Agent Three inquiries may be made as to the identification/screening/selection of suitable indications and/or patient populations for which high-affinity, isoform-specific inhibitors of TGFβ1, such as those described herein, are likely to have advantageous therapeutic benefits: i) whether the disease is driven by or dependent predominantly on the TGFβ1 isoform over the other isoforms in human (or at least co-dominant); ii) whether the condition (or affected tissue) is associated with an immunosuppressive phenotype; and, iii) whether the disease involves both matrix-associated and cell-associated TGFβ1 function.

Differential expression of the three known TGFβ isoforms, namely, TGFβ1, TGFβ2, and TGFβ3, has been observed under normal (healthy; homeostatic) as well as disease conditions in various tissues. Nevertheless, the concept of isoform selectivity has neither been fully exploited nor robustly achieved with conventional approaches that favor pan-inhibition of TGFβ across multiple isoforms. Moreover, expression patterns of the isoforms may be differentially regulated, not only in normal (homeostatic) vs, abnormal (pathologic) conditions, but also in different sub-populations of patients. Because most preclinical studies are conducted in a limited number of animal models, which may or may not recapitulate human conditions, data obtained with the use of such models may be biased, resulting in misinterpretations of data or misleading conclusions as to the translatability for purposes of developing therapeutics.

Accordingly, the present invention includes the recognition that differential expression of TGFβ isoforms in preclinical animal models should be taken into account in predicting effectiveness of particular drug candidates (e.g., TGFβ1 inhibitors), as well as in interpreting preclinical data as to the translatability into human conditions.

Previous analyses of human tumor samples implicated TGFβ signaling as an important contributor to primary resistance to disease progression and treatment response, including checkpoint blockade therapy ("CBT") for various types of malignancies. Studies reported in literature reveal that the TGFB gene expression may be particularly relevant to treatment resistance, suggesting that activity of this isoform may be driving TGFβ signaling in these diseases. As detailed in example 11, across the majority of human tumor types profiled at The Cancer Genome Atlas (TCGA), TGFB1 expression appears to be the most prevalent, suggesting that selection of preclinical models that more closely recapitulate human disease expression patterns of TGFβ isoforms may be beneficial.

As exemplified herein, TGFβ1 and TGFβ3 are co-dominant (co-expressed at similar levels) in certain murine syngeneic cancer models (e.g., EMT-6 and 4T1) that are widely used in preclinical studies (see FIG. 20D). By contrast, numerous other cancer models (e.g., S91, B16 and MBT-2) express almost exclusively TGFβ1, similar to that observed in many human tumors, in which TGFβ1 appears to be more frequently the dominant isoform over TGFβ2/3 (see FIGS. 20B and 20C). Furthermore, the TGFβ isoform(s) predominantly expressed under homeostatic conditions may not be the disease-associated isoform(s). For example, in normal lung tissues in healthy rats, tonic TGFβ signaling appears to be mediated mainly by TGFβ3. However, TGFβ1 appears to become markedly upregulated in disease conditions, such as lung fibrosis. Taken together, while not prerequisite, it may be beneficial to test or confirm relative expression of TGFβ isoforms in clinical samples so as to select suitable therapeutics to which the patient is likely to respond. In some embodiments, determination of relative isoform expression may be made post-treatment. In such circumstances, patients' responsiveness (e.g., clinical response/benefit) in response to TGFβ1 inhibition therapy may be correlated with relative expression levels of TGFβ isoforms. In some embodiments, overexpression of the TGFβ1 isoform shown ex post facto correlates with greater responsiveness to the treatment.

As described herein, the isoform-selective TGFβ1 inhibitors are particularly advantageous for the treatment of diseases in which the TGFβ1 isoform is predominantly expressed relative to the other isoforms (e.g., referred to as TGFβ1-dominant). As an example, a non-limiting list of human cancer clinical samples with relative expression levels of TGFB1 (left), TGFB2 (center) and TGFB3 (right) is provided in FIGS. 20B and 20C. Each horizontal lime across the three isoforms represents a single patient. As can be seen, overall TGFβ1 expression (TGFB1) is significantly higher in most of these human tumors/cancers than the other two isoforms across many tumor/cancer types, suggesting that TGFβ1-selective inhibition may be beneficial in these disease types. Taken together, these lines of evidence support the notion that selective inhibition of TGFβ1 activity may overcome primary resistance to CBT. Generation of highly selective TGFβ1 inhibitors will also enable evaluation of whether such an approach will address key safety issues observed with pan-TGFβ inhibition, which will be important for assessment of their therapeutic utility.

Certain exceptions should be noted, however. First, such trend is not always applicable in certain individual patients within the disease type. That is, even in a type of cancer that shows almost uniformly TGFβ1-dominance over TGFβ2/3 overall, there are a few individuals that do not follow this general rule, as represented in FIG. 20C. Patients that fall within the minority subpopulation therefore may not respond to a TGFβ1 isoform-specific inhibitor therapy in the way that works for a majority of patients. Second, there are a few cancer types in which TGFβ1 is co-dominant with another isoform or in which TGFβ2 and/or TGFβ3 expression is significantly greater than TGFβ1. In these situations, TGFβ1-selective inhibitors such as those described herein are not likely to be efficacious used alone. Rather, suitable additional inhibitor(s) that target other isoform(s) may be employed in conjunction (see, for example, WO 2016/201282). To manage potentially serious toxicities, however, pan-TGFβ inhibitors, as well as inhibitors that antagonize both TGFβ2 and TGFβ3, should be avoided.

For example, in diseases (such as certain types of carcinoma and sarcoma) or individual patients where TGFβ1 is co-dominant (e.g., co-expressed at similar levels) with TGFβ3 (for example as shown by biopsy analysis), suitable therapeutic regimen may include both a TGFβ1 inhibitor and a TGFβ3 inhibitor. Preferably, each of the inhibitors is an isoform-selective inhibitor, so as to avoid unwanted side effects or toxicities associated with pan-inhibition of all TGFβ isoforms. In some embodiments, one or both of the isoform-selective inhibitors inhibit(s) the activation step of the TGFβ isoform (e.g., TGFβ1 and/or TGFβ3). In preferred embodiments, the isoform-selective TGFβ1 inhibitor is a high-affinity, context-independent activation inhibitor such as those described herein. In some embodiments, the isoform-selective TGFβ3 inhibitor is a context-independent activation inhibitor of TGFβ3, made by the process comprising the step of selecting an antibody or antigen-binding fragment that specifically binds a proTGFβ3 complex. Typically, such process further includes selection or confirmation of antibody or fragment for the ability to bind multiple antigen complexes, e.g., LTBP1-proTGFβ3, LTBP3-proTGFβ3, GARP-proTGFβ3, and/or LRRC33-proTGFβ3. Preferably, such process further includes selection or confirmation of antibody or fragment for the ability to inhibit the release of the growth factor (TGFβ3) from the latent complex (i.e., activation inhibition).

When suitable therapeutic regimens include two isoform-selective TGFβ inhibitors, such as TGFβ1 and TGFβ3 (as in the example above), such therapy may comprise a single formulation that includes both TGFβ1 and TGFβ3 inhibitors. Such formulation may contain, for example, 10-50 mg/mL of each inhibitor and one or more pharmaceutically acceptable excipients.

Alternatively, such therapy may comprise the use of two separate formulations each comprising a single inhibitor for administration to a patient or patient population. This offers added flexibility in adjusting the ratios of the two inhibitor dosages to be administered to the patient or patient population, depending on (and tailored to) relative expression levels (above healthy levels) of the two TGFβ isoforms shown to be present in one or more biological samples collected from the patient or patient population. For example, for use in the treatment of TGFβ1-positive, TGFβ3-positive cancer/tumors (such as breast cancer), where the former is the dominant disease-associated isoform relative to the latter, TGFβ1 inhibitor may be used at higher dose and/or longer duration as part of the therapeutic regimens.

Therefore, it is beneficial to test or confirm relative expression levels of the three TGFβ isoforms (i.e., TGFβ1, TGFβ2 and TGFβ3) in clinical samples collected from individual patients. Such information may provide better prediction as to the effectiveness of a particular therapy in individual patients or patient populations, which can help ensure selection of appropriate treatment regimen (e.g., individualized/personalized treatment) in order to increase the likelihood of a clinical response.

Figure 35:
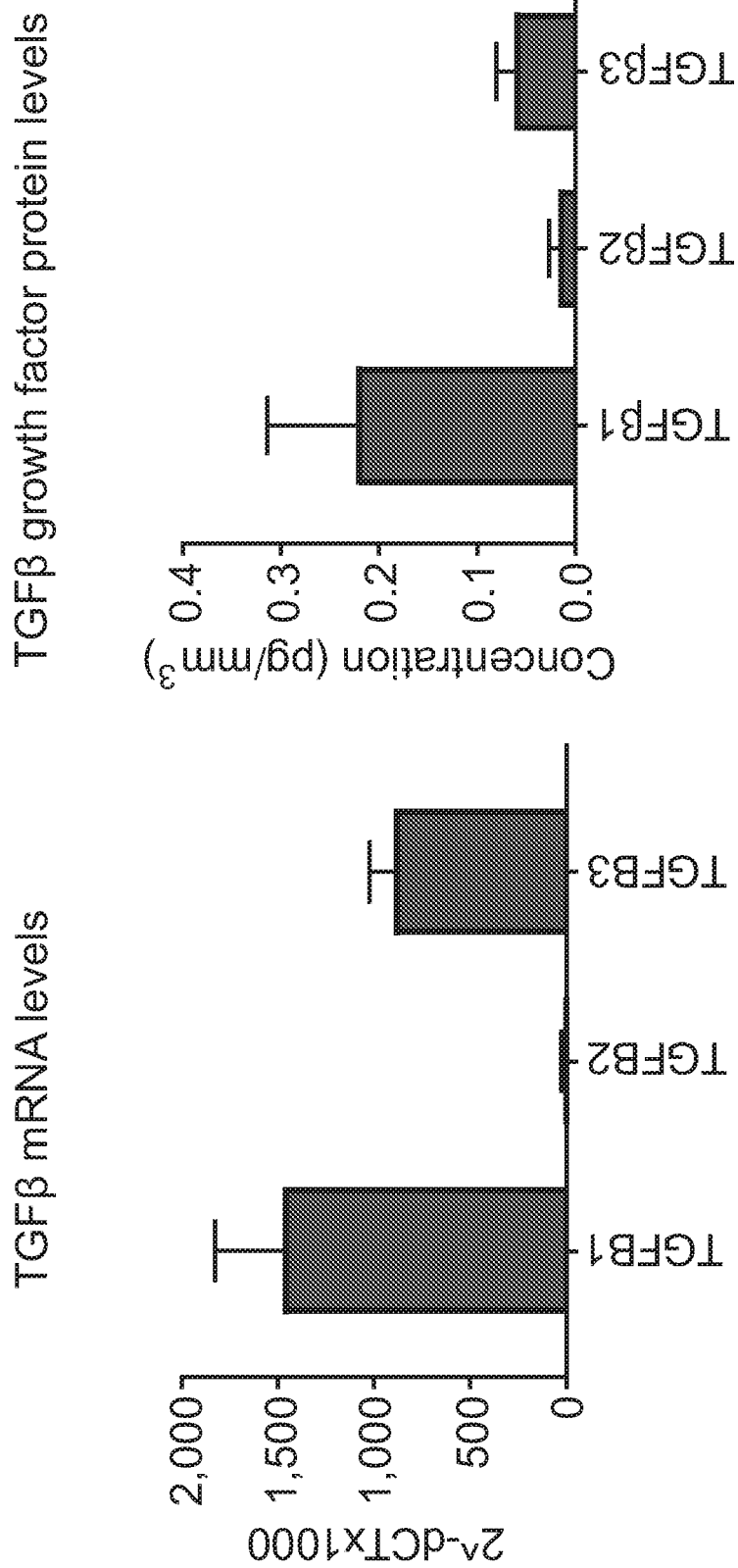
FIG. 35 provides two graphs showing relative expression of the three TGFβ isoforms in EMT6 tumors as measured in mRNA levels (left) and protein levels (right).

More recently, the inventors of the present application have made an unexpected finding that a high-affinity, TGFβ1-selective inhibitor (e.g., Ab6), used in conjunction with a checkpoint inhibitor (e.g., anti-PD-1 antibody), is capable of causing significant tumor regression in the EMT-6 model, which is known to express both TGFβ1 and TGFβ3 at similar levels. The co-dominance has been confirmed by both RNA measurements and ELISA assays (see FIG. 35). This observation is surprising because it had been previously hypothesized that in order to achieve material efficacy in TGFβ1-positive, TGFβ3-positive tumors in a checkpoint blockade context, both of the co-dominant isoforms would have to be specifically inhibited. Unexpectedly, however, a TGFβ1-selective inhibitor alone (in conjunction with anti-PD-1), without a TGFβ3-selective inhibitor, is sufficient to overcome primary resistance to CBT and achieve in vivo efficacy in reducing tumor volume and enhancing survival benefit (See Example 18). Without being bound by a particular theory, this may be due to TGFβ1 being the truly disease-driving isoform even though TGFβ is co-expressed in the tumor. Another possibility is that inhibition of TGFβ1 causes downregulation of TGFβ3 downstream. It is also possible that the two isoforms are subject to differential temporal and/or spatial regulation. For example, the two isoforms may be localized to discrete cellular or tissue compartments. Additionally or alternatively, it remains possible that a potent inhibitor of the TGFβ1, used in conjunction with a checkpoint inhibitor, may be sufficient to overcome the immunosuppressive threshold. Accordingly, the invention includes the use of TGFβ1 inhibitor for promoting tumor regression, where the tumor is TGFβ1+/TGFβ3+. Such tumor may include, for example, cancers of epithelial origin, i.e., carcinoma (e.g., basal cell carcinoma, squamous cell carcinoma, renal cell carcinoma, ductal carcinoma in situ (DCIS), invasive ductal carcinoma, and adenocarcinoma). In some embodiments, TGFβ1 is predominantly the disease-associated isoform, whilst TGFβ3 supports homeostatic function in the tissue, such as epithelia.

Certain tumors, such as various carcinomas, may be characterized as low mutational burden tumors (MBTs). Such tumors are often poorly immunogenic and fail to elicit sufficient T cell response. Cancer therapies that include chemotherapy, radiation therapy, cancer vaccines and/or oncolytic virus, may be helpful to elicit T cell immunity in such tumors. Therefore, TGFβ1 inhibition therapy detailed herein can be used in conjunction with one or more of these cancer therapies to increase anti-tumor effects. Essentially, such combination therapy is aimed at converting "cold" tumors (e.g., poorly immunogenic tumors) into "hot" tumors by promoting neo-antigens and facilitating effector cells to attack the tumor. Examples of such tumors include breast cancer, ovarian cancer and pancreatic cancer, e.g., pancreatic ductal adenocarcinoma (PDAC). Accordingly, any one or more of the antibodies or fragments thereof described herein may be used to treat poorly immunogenic tumor ("cold tumor") sensitized with a cancer therapy aimed to promote T cell immunity.

In immune-excluded tumors where effector T cells are kept away from the site of tumor (hence "excluded"), the immunosuppressive tumor environment may be mediated in a TGFβ1-dependent fashion. These are tumors that are typically immunogenic; however, T cells cannot sufficiently infiltrate, proliferate and elicit their cytotoxic effects due to the immune-suppressed environment. Typically, such tumors are poorly responsive to cancer therapies such as CBTs. As data provided herein suggest, adjunct therapy comprising a TGFβ1 inhibitor may overcome the immunosuppressive phenotype, allowing T cell infiltration, proliferation and anti-tumor function, thereby rendering such tumor more responsive to cancer therapy such as CBT.

Thus, the second inquiry is drawn to identification or selection of patients who have immunosuppressive tumor(s), who are likely to benefit from a TGFβ1 inhibitor therapy. The presence or the degree of frequencies of effector T cells in a tumor is indicative of anti-tumor immunity. Therefore, detecting anti-tumor cells such as CD8+ cells in a tumor provides useful information for assessing whether the patient may benefit from a CBT and/or TGFβ1 inhibitor therapy.

Detection may be carried out by known methods such as immunohistochemical analysis of tumor biopsy samples. More recently, non-invasive imaging methods are being developed which will allow the detection of cells of interest (e.g., cytotoxic T cells) in vivo. See for example, imaginab.com/technology/; Tavare et al. (2014) PNAS, 111(3): 1108-1113; Tavare et al. (2015) J Nucl Med 56(8): 1258-1264; Rashidian et al. (2017) J Exp Med 214(8): 2243-2255; Beckford Vera et al. (2018) PLoS ONE 13(3): e0193832; and Tavare et al. (2015) Cancer Res 76(1): 73-82, each of which is incorporated herein by reference. Typically, antibodies or antibody-like molecules engineered with a detection moiety (e.g., radiolabel) can be infused into a patient, which then will distribute and localize to sites of the particular marker (for instance CD8+). In this way, it is possible to determine whether the tumor has an immune-excluded phenotype. If the tumor is determined to have an immune-excluded phenotype, cancer therapy (such as CBT) alone may not be efficacious because the tumor lacks sufficient cytotoxic cells within the tumor environment. Add-on therapy with a TGFβ1 inhibitor such as those described herein may reduce immuno-suppression thereby rendering the cancer therapy-resistant tumor more responsive to a cancer therapy.

Non-invasive in vivo imaging techniques may be applied in a variety of suitable methods for purposes of diagnosing patients; selecting or identifying patients who are likely to benefit from TGFβ1 inhibitor therapy; and/or, monitoring patients for therapeutic response upon treatment. Any cells with a known cell-surface marker may be detected/localized by virtue of employing an antibody or similar molecules that specifically bind to the cell marker. Typically, cells to be detected by the use of such techniques are immune cells, such as cytotoxic T lymphocytes, regulatory T cells, MDSCs, tumor-associated macrophages, NK cells, dendritic cells, and neutrophils. Antibodies or engineered antibody-like molecules that recognize such markers can be coupled to a detection moiety.

Non-limiting examples of suitable immune cell markers include monocyte markers, macrophage markers (e.g., M1 and/or M2 macrophage markers), CTL markers, suppressive immune cell markers, MDSC markers (e.g., markers for G- and/or M-MDSCs), including but are not limited to: CD8, CD3, CD4, CD11b, CD163, CD206, CD68, CD14, CD15, CD66, CD34, CD25, and CD47.

In some embodiments, the in vivo imaging comprises T cell tracking, such as cytotoxic CD8-positive T cells. Accordingly, any one of the high-affinity, isoform-selective inhibitor of TGFβ1 of the present disclosure may be used in the treatment of cancer in a subject with a solid tumor, wherein the treatment comprises: i) carrying out an in vivo imaging analysis to detect T cells in the subject, wherein optionally the T cells are CD8+ T cells, and if the solid tumor is determined to be an immune-excluded solid tumor based on the in vivo imaging analysis of step (i), then, administering to the subject a therapeutically effective amount of the high-affinity, isoform-selective inhibitor of TGFβ1. In some embodiments, the subject has received a CBT, wherein optionally the solid tumor is resistant to the CBT. In some embodiments, the subject is administered with a CBT in conjunction with the TGFβ1 inhibitor, as a combination therapy. The combination may comprise administration of a single formulation that comprises both a checkpoint inhibitor and a TGFβ1 inhibitor. Alternatively, the combination therapy may comprise administration of a first formulation comprising a checkpoint inhibitor and a second formulation comprising a TGFβ1 inhibitor.

In some embodiments, the in vivo imaging comprises MDSC tracking, such as G-MDSCs (also known as PMN-MDSCs) and M-MDSCs. For example, MDSCs may be enriched at a disease site (such as fibrotic tissues and solid tumors) at the baseline. Upon therapy (e.g., TGFβ1 inhibitor therapy), fewer MDSCs may be observed, as measured by reduced intensity of the label (such as radioisotope and fluorescence), indicative of therapeutic effects.

In some embodiments, the in vivo imaging comprises tracking or localization of LRRC33-positive cells. LRRC33-positive cells include, for example, MDSCs and activated M2-like macrophages (e.g., TAMs and activated macrophages associated with fibrotic tissues). For example, LRRC33-positive cells may be enriched at a disease site (such as fibrotic tissues and solid tumors) at the baseline. Upon therapy (e.g., TGFβ1 inhibitor therapy), fewer cells expressing cell surface LRRC33 may be observed, as measured by reduced intensity of the label (such as radioisotope and fluorescence), indicative of therapeutic effects.

In some embodiments, the in vivo imaging comprises the use of PET-SPECT, MRI and/or optical fluorescence/bioluminescence in order to detect target of interest (e.g., molecules or entities which can be bound by the labeled reagent, such as cells and tissues expressing appropriate marker(s)).

In some embodiments, labeling of antibodies or antibody-like molecules with a detection moiety may comprise direct labeling or indirect labeling.

In some embodiments, the detection moiety may be a tracer. In some embodiments, the tracer may be a radioisotope, wherein optionally the radioisotope may be a positron-emitting isotope. In some embodiments, the radioisotope is selected from the group consisting of: $^{18}$F, $^{11}$C, $^{13}$N, $^{15}$O, $^{68}$Ga, $^{177}$Lu, $^{18}$F and $^{89}$Zr.

Thus, such methods may be employed to carry out in vivo imaging with the use of labeled antibodies in immune-PET.

In some embodiments, such in vivo imaging is performed for monitoring a therapeutic response to the TGFβ1 inhibition therapy in the subject. For example, the therapeutic response may comprise conversion of an immune excluded tumor into an inflamed tumor, which correlates with increased immune cell infiltration into a tumor. This may be visualized by increased intratumoral immune cell frequency or degree of detection signals, such as radiolabeling and fluorescence.

Accordingly, the invention includes a method for treating cancer which may comprise the following steps: i) selecting a patient diagnosed with cancer comprising a solid tumor, wherein the solid tumor is or is suspected to be an immune excluded tumor; and, ii) administering to the patient an antibody or the fragment encompassed herein in an amount effective to treat the cancer. In some embodiments, the patient has received, or is a candidate for receiving a cancer therapy such as immune checkpoint inhibition therapies (e.g., PD-(L)1 antibodies), chemotherapies, radiation therapies, engineered immune cell therapies, and cancer vaccine therapies. In some embodiments, the selection step (i) comprises detection of immune cells or one or more markers thereof, wherein optionally the detection comprises a tumor biopsy analysis, serum marker analysis, and/or in vivo imaging.

In some embodiments, the patient is diagnosed with cancer for which a CBT has been approved, wherein optionally, statistically a similar patient population with the particular cancer shows relatively low response rates to the approved CBT, e.g., under 25%. For example, the response rates for the CBT may be between about 10-25%, for example about 10-15%. Such cancer may include, for example, ovarian cancer, gastric cancer, and triple-negative breast cancer. The high-affinity, isoform-selective TGFβ1 inhibitors of the present disclosure may be used in the treatment of such cancer, where the subject has not yet received a CBT. The TGFβ1 inhibitor may be administered to the subject in combination with a CBT. In some embodiments, the subject may receive or may have received additional cancer therapy, such as chemotherapy and radiation therapy.

In vivo imaging techniques described above may be employed to detect, localize and/or track certain MDSCs in a patient diagnosed with a TGFβ1-associated disease, such as cancer and fibrosis. Healthy individuals have no or low frequency of MDSCs in circulation. With the onset of or progression of such a disease, elevated levels of circulating and/or disease-localized MDSCs may be detected. For example, CCR2-positive M-MDSCs have been reported to accumulate to tissues with inflammation and may cause progression of fibrosis in the tissue (such as pulmonary fibrosis), and this is shown to correlate with TGFβ1 expression. Similarly, MDSCs are enriched in a number of solid tumors (including triple-negative breast cancer) and in part contribute to the immunosuppressive phenotype of the TME. Therefore, treatment response to TGFβ1 inhibition therapy according to the present disclosure may be monitored by localizing or tracking MDSCs. Reduction of or low frequency of detectable MDSCs is typically indicative of therapeutic benefits or better prognosis.

Thus, the high affinity, context-independent inhibitor of TGFβ1 activation may be used in the treatment of cancer in a subject, wherein the cancer is characterized by immune suppression, wherein the cancer optionally comprises a solid tumor that is TGFβ1-positive and TGFβ3-positive. Such subject may be diagnosed with carcinoma. In some embodiments, the carcinoma is breast carcinoma, wherein optionally the breast carcinoma is triple-negative breast cancer (TNBC). Such treatment can further comprise a cancer therapy, including, without limitation, chemotherapies, radiation therapies, cancer vaccines, engineered immune cell therapies (such as CAR-T), and immune checkpoint blockade therapies, such as anti-PD(L)-1 antibodies.

In some embodiments, a cold tumor is identified, in which few effector cells are present or is known to be a type of cancer characterized as poorly immunogenic. A subject/patient with such a tumor is treated with an immune-sensitizing cancer therapy, such as chemotherapy, radiation therapy, oncolytic viral therapy, and cancer vaccine, in order to elicit stronger T cell response to tumor antigens (e.g., neo-antigens). This step may convert the cold tumor into an "immune excluded" tumor. The subject optionally further receives a CBT, such as anti-PD-(L)1. The subject is further treated with a TGFβ1 inhibitor, such as the antibodies disclosed herein. This may convert the cold or immune excluded tumor into an "inflamed" or "hot" tumor, which confers responsiveness to immunotherapy. Non-limiting examples of poorly immunogenic cancers include breast cancer (such as TNBC), prostate cancer (such as Castration resistant prostate cancer (CRPC)) and pancreatic cancer (such as pancreatic adenocarcinoma (PDAC)).

As shown in FIG. 5B, high affinity, isoform-selective inhibitors of TGFβ1 of the present invention, such as Ab6, can inhibit Plasmin-induced activation of TGFβ1. The plasmin-plasminogen axis has been implicated in certain tumorigenesis, invasion and/or metastasis, of various cancer types, carcinoma in particular, such as breast cancer. Therefore, it is possible that the high affinity, isoform-selective inhibitors of TGFβ1, such as those described herein, may exert the inhibitory effects via this mechanism in tumors or tumor models, such as EMT6, involving the epithelia. Indeed, Plasmin-dependent destruction or remodeling of epithelia may contribute to the pathogenesis of conditions involving epithelial injuries and invasion/dissemination of carcinoma. The latter may be triggered by epithelial to mesenchymal transition ("EMT"). It has been reported that Plasminogen activation and plasminogen-dependent invasion were more prominent in epithelial-like cells and were partly dictated by the expression of S100A10 and PAI-1 (Bydoun et al. (2018) Scientific Reports, 8:14091).

The invention includes a method for selecting a patient population or a subject who is likely to respond to a therapy comprising an isoform-specific, context-independent TGFβ1 inhibitor. Such method may comprise the steps of: providing a biological sample (e.g., clinical sample) collected from a subject, determining (e.g., measuring or assaying) relative levels of TGFβ1, TGFβ2 and TGFβ3 in the sample, and, administering to the subject a composition comprising an isoform-specific, context-independent TGFβ1 inhibitor, if TGFβ1 is the dominant isoform over TGFβ2 and TGFβ3; and/or, if TGFβ1 is significantly overexpressed or upregulated as compared to control. In some embodiments, such method comprises the steps of: obtaining information on the relative expression levels of TGFβ1, TGFβ2 and TGFβ3 which was previously determined; identifying a subject to have TGFβ1-positive, preferably TGFβ1-dominant, disease; and, administering to the subject a composition comprising an isoform-specific, context-independent TGFβ1 inhibitor. In some embodiments, such subject has a disease (such as cancer) that is resistant to a therapy (such as cancer therapy). In some embodiments, such subject shows intolerance to the therapy and therefore has or is likely to discontinue the therapy. Addition of the TGFβ1 inhibitor to the therapeutic regimen may enable reducing the dosage of the first therapy and still achieve clinical benefits in combination. In some embodiments, the TGFβ1 inhibitor may delay or reduce the need for surgeries.

Relative levels of the isoforms may be determined by RNA-based assays and/or protein-based assays, which are well-known in the art. In some embodiments, the step of administration may also include another therapy, such as immune checkpoint inhibitors, or other agents provided elsewhere herein. Such methods may optionally include a step of evaluating a therapeutic response by monitoring changes in relative levels of TGFβ1, TGFβ2 and TGFβ3 at two or more time points. In some embodiments, clinical samples (such as biopsies) are collected both prior to and following administration. In some embodiments, clinical samples (such as biopsies) are collected multiple times following treatment to assess in vivo effects over time.

In addition to the above inquiries, the third inquiry interrogates the breadth of TGFβ1 function involved in a particular disease. This may be represented by the number of TGFβ1 contexts, namely, which presenting molecule(s) mediate disease-associated TGFβ1 function. TGFβ1-specific, broad-context inhibitors, such as context-independent inhibitors, are advantageous for the treatment of diseases that involve both an ECM component and an immune component of TGFβ1 function. Such disease may be associated with dysregulation in the ECM as well as perturbation in immune cell function or immune response. Thus, the TGFβ1 inhibitors described herein are capable of targeting ECM-associated TGFβ1 (e.g., presented by LTBP1 or LTBP3) as well as immune cell-associated TGFβ1 (e.g., presented by GARP or LRRC33). Such inhibitors inhibit all four of the therapeutic targets (e.g., "context-independent" inhibitors): GARP-associated pro/latent TGFβ1; LRRC33-associated pro/latent TGFβ1; LTBP1-associated pro/latent TGFβ1; and, LTBP3-associated pro/latent TGFβ1, so as to broadly inhibit TGFβ1 function in these contexts.

Whether or not a particular condition of a patient involves or is driven by multiple aspects of TGFβ1 function may be assessed by evaluating expression profiles of the presenting molecules, in a clinical sample collected from the patient. Various assays are known in the art, including RNA-based assays and protein-based assays, which may be performed to obtain expression profiles. Relative expression levels (and/or changes/alterations thereof) of LTBP1, LTBP3, GARP, and LRRC33 in the sample(s) may indicate the source and/or context of TGFβ1 activities associated with the condition. For instance, a biopsy sample taken from a solid tumor may exhibit high expression of all four presenting molecules. For example, LTBP1 and LTBP3 may be highly expressed in CAFs within the tumor stroma, while GARP and LRRC33 may be highly expressed by tumor-associated immune cells, such as Tregs and leukocyte infiltrate, respectively.

Accordingly, the invention includes a method for determining (e.g., testing or confirming) the involvement of TGFβ1 in the disease, relative to TGFβ2 and TGFβ3. In some embodiments, the method further comprises a step of: identifying a source (or context) of disease-associated TGFβ1. In some embodiments, the source/context is assessed by determining the expression of TGFβ presenting molecules, e.g., LTBP1, LTBP3, GARP and LRRC33 in a clinical sample taken from patients. In some embodiments, such methods are performed expost facto.

With respect to LRRC33-positive cells, Applicant of the present disclosure has recognized that there can be a significant discrepancy between RNA expression and protein expression of LRRC33. In particular, whilst a select cell types appear to express LRRC33 at the RNA level, only a subset of such cells express the LRRC33 protein on the cell-surface. It is contemplated that LRRC33 expression may be highly regulated via protein trafficking/localization, for example, in terms of plasma membrane insertion and rapid internalization. Therefore, in preferred embodiments, LRRC33 protein expression may be used as a marker associated with a diseased tissue (such as tumor and fibrotic tissues) enriched with, for example, activated/M2-like macrophages and MDSCs.

TGFβ1-Related Indications
General Features of TGFβ1-Related Indications

Isoform-selective TGFβ1 inhibitors, such as those described herein, may be used to treat a wide variety of diseases, disorders and/or conditions that are associated with TGFβ1 dysregulation (i.e., "TGFβ1-related indications") in human subjects, As used herein, "disease (disorder or condition) associated with TGFβ1 dysregulation" or "TGFβ1-related indication" means any disease, disorder and/or condition related to expression, activity and/or metabolism of a TGFβ1 or any disease, disorder and/or condition that may benefit from inhibition of the activity and/or levels TGFβ1.

Accordingly, the present invention includes the use of an isoform-specific, context-independent TGFβ1 inhibitor in a method for treating a TGFβ1-related indication in a human subject. Such inhibitor is typically formulated into a pharmaceutical composition that further comprises a pharmaceutically acceptable excipient. Advantageously, the inhibitor targets both ECM-associated TGFβ1 and immune cell-associated TGFβ1 but does not target TGFβ2 or TGFβ3 in vivo. In some embodiments, the inhibitor inhibits the activation step of TGFβ1. The disease may be characterized by dysregulation or impairment in at least two of the following attributes: a) regulatory T cells (Treg); b) effector T cell (Teff) proliferation or function; c) myeloid cell proliferation or differentiation; d) monocyte recruitment or differentiation; e) macrophage function; f) epithelial-to-mesenchymal transition (EMT) and/or endothelial-to-mesenchymal transition (EndMT); g) gene expression in one or more of marker genes selected from the group consisting of: PAI-1, ACTA2, CCL2, Col1a1, Col3a1, FN-1, CTGF, and TGFB1; h) ECM components or function; i) fibroblast differentiation. A therapeutically effective amount of such inhibitor is administered to the subject suffering from or diagnosed with the disease.

In some embodiments, the disease involves dysregulation or impairment of ECM components or function comprises that show increased collagen I deposition. In some embodiments, the dysregulation of the ECM includes increased stiffness of the matrix. In some embodiments, the dysregulation of the ECM involves fibronectin and/or fibrillin.

In some embodiments, the dysregulation or impairment of fibroblast differentiation comprises increased myofibroblasts or myofibroblast-like cells. In some embodiments, the myofibroblasts or myofibroblast-like cells are cancer-associated fibroblasts (CAFs). In some embodiments, the CAFs are associated with a tumor stroma and may produce CCL2/MCP-1 and/or CXCL12/SDF-1. In some embodiments, the myofibroblasts or myofibroblast-like cells are localized to a fibrotic tissue.

In some embodiments, the dysregulation or impairment of regulatory T cells comprises increased Treg activity.

In some embodiments, the dysregulation or impairment of effector T cell (Teff) proliferation or function comprises suppressed CD4+/CD8+ cell proliferation.

In some embodiments, the dysregulation or impairment of myeloid cell proliferation or differentiation comprises increased proliferation of myeloid progenitor cells. The increased proliferation of myeloid cells may occur in a bone marrow, In some embodiments, the dysregulation or impairment of monocyte differentiation comprises increased differentiation of bone marrow-derived and/or tissue resident monocytes into macrophages at a disease site, such as a fibrotic tissue and/or a solid tumor.

In some embodiments, the dysregulation or impairment of monocyte recruitment comprises increased bone marrow-derived monocyte recruitment into a disease site such as TME, leading to increased macrophage differentiation and M2 polarization, followed by increased TAMs.

In some embodiments, the dysregulation or impairment of macrophage function comprises increased polarization of the macrophages into M2 phenotypes.

In some embodiments, the dysregulation or impairment of myeloid cell proliferation or differentiation comprises an increased number of Tregs, MDSCs and/or TANs.

TGFβ-related indications may include conditions comprising an immune-excluded disease microenvironment, such as tumor or cancerous tissue that suppresses the body's normal defense mechanism/immunity in part by excluding effector immune cells (e.g., CD4+ and/or CD8+ T cells). In some embodiments, such immune-excluding conditions are associated with poor responsiveness to treatment (e.g., cancer therapy). Non-limiting examples of the cancer therapies, to which patients are poorly responsive, include but are not limited to: checkpoint inhibitor therapy, cancer vaccines, chemotherapy, and radiation therapy. Without intending to be bound by particular theory, it is contemplated that TGFβ inhibitors, such as those described herein, may help counter the tumor's ability to evade or exclude anti-cancer immunity by restoring immune cell access, e.g., T cell (e.g., CD8+ cells) and macrophage (e.g., F4/80+ cells, M1-polarized macrophages) access by promoting T cell expansion and/or infiltration into tumor.

Thus, TGFβ inhibition may overcome treatment resistance (e.g., immune checkpoint resistance, cancer vaccine resistance, CAR-T resistance, chemotherapy resistance, radiation therapy resistance, etc.) in immune-excluded disease environment (such as TME) by unblocking and restoring effector T cell access and cytotoxic effector functions. Such effects of TGFβ inhibition may further provide long-lasting immunological memory mediated, for example, by CD8+ T cells.

In some embodiments, tumor is poorly immunogenic (e.g., "desert" or "cold" tumors). Patients may benefit from cancer therapy that triggers neo-antigens or promote immune responses. Such therapies include, but are not limited to, chemotherapy, radiation therapy, oncolytic viral therapy, oncolytic peptides, tyrosine kinase inhibitors, neo-epitope vaccines, anti-CTLA4, instability inducers, DDR agents, NK cell activators, and various adjuvants such as TLR ligands/agonists. TGFβ1 inhibitors, such as those described herein, can be used in conjunction to boost the effects of cancer therapies. One mode of action for TGFβ1 inhibitors may be to normalize or restore MHC expression, thereby promoting T cell immunity.

Non-limiting examples of TGFβ-related indications include: fibrosis, including organ fibrosis (e.g., kidney fibrosis, liver fibrosis, cardiac/cardiovascular fibrosis, muscle fibrosis, skin fibrosis, uterine fibrosis/endometriosis and lung fibrosis), scleroderma, Alport syndrome, cancer (including, but not limited to: blood cancers such as leukemia, myelofibrosis, multiple myeloma, colon cancer, renal cancer, breast cancer, malignant melanoma, glioblastoma), fibrosis associated with solid tumors (e.g., cancer desmoplasia, such as desmoplastic melanoma, pancreatic cancer-associated desmoplasia and breast carcinoma desmoplasia), stromal fibrosis (e.g., stromal fibrosis of the breast), radiation-induced fibrosis (e.g., radiation fibrosis syndrome), facilitation of rapid hematopoiesis following chemotherapy, bone healing, wound healing, dementia, myelofibrosis, myelodysplasia (e.g., myelodysplasic syndrome or MDS), a renal disease (e.g., end-stage renal disease or ESRD), unilateral ureteral obstruction (UUO), tooth loss and/or degeneration, endothelial proliferation syndromes, asthma and allergy, gastrointestinal disorders, anemia of the aging, aortic aneurysm, orphan indications (such as Marfan's syndrome and Camurati-Engelmann disease), obesity, diabetes, arthritis, multiple sclerosis, muscular dystrophy, bone disorders, amyotrophic lateral sclerosis (ALS), Parkinson's disease, osteoporosis, osteoarthritis, osteopenia, metabolic syndromes, nutritional disorders, organ atrophy, chronic obstructive pulmonary disease (COPD), and anorexia.

Evidence suggests that the ectonucleotidases CD39 and CD73 may at least in part contribute to elevated levels of adenosine in disease conditions. Notably, the CD39/CD73-TGFβ axis may play a role in modulating immune cells implicated in the TGFβ signaling, including Tregs and MDSCs. Both regulatory T cells (Tregs) and myeloid-derived suppressive cells (MDSCs) generally exhibit immunosuppressive phenotypes. In many pathologic conditions (e.g., cancer, fibrosis), these cells are enriched at disease sites and may contribute to creating and/or maintaining an immunosuppressive environment. This may be at least in part mediated by the ectonucleotidases CD39 and CD73 which together participates in the breakdown of ATP into nucleoside adenosine, leading to elevated local concentrations of adenosine in the disease environment, such as tumor microenvironment and fibrotic environment. Adenosine can bind to its receptors expressed on target cells such as T cells and NK cell, which in turn suppress anti-tumor function of these target cells.

Diseases with Aberrant Gene Expression; Biomarkers

It has been observed that abnormal activation of the TGFβ1 signal transduction pathway in various disease conditions is associated with altered gene expression of a number of markers. These gene expression markers (e.g., as measured by mRNA) include, but are not limited to: Serpine 1 (encoding PAI-1), MCP-1 (also known as CCL2), Col1a1, Col3a1, FN1, TGFB1, CTGF, ACTA2 (encoding α-SMA), SNAI1 (drives EMT in fibrosis and metastasis by down-regulating E-cadherin (Cdh1), MMP2 (matrix metalloprotease associated with EMT), MMP9 (matrix metalloprotease associated with EMT), TIMP1 (matrix metalloprotease associated with EMT), FOXP3 (marker of Treg induction), CDH1 (E cadherin (marker of epithelial cells) which is downregulated by TGFβ), and, CDH2 (N cadherin (marker of mesenchymal cells) which is upregulated by TGFβ). Interestingly, many of these genes are implicated to play a role in a diverse set of disease conditions, including various types of organ fibrosis, as well as in many cancers, which include myelofibrosis. Indeed, pathophysiological link between fibrotic conditions and abnormal cell proliferation, tumorigenesis and metastasis has been suggested. See for example, Cox and Erler (2014) Clinical Cancer Research 20(14): 3637-43 "Molecular pathways: connecting fibrosis and solid tumor metastasis"; Shiga et al. (2015) Cancers 7:2443-2458 "Cancer-associated fibroblasts: their characteristics and their roles in tumor growth"; Wynn and Barron (2010) Semin. Liver Dis. 30(3): 245-257 "Macrophages: master regulators of inflammation and fibrosis", contents of which are incorporated herein by reference. Without wishing to be bound by a particular theory, the inventors of the present disclosure contemplate that the TGFβ1 signaling pathway may in fact be a key link between these broad pathologies.

The ability of chemotactic cytokines (or chemokines) to mediate leukocyte recruitment (e.g., monocytes/macrophages) to injured or disease tissues has crucial consequences in disease progression. Members of the C-C chemokine family, such as monocyte chemoattractant protein 1 (MCP-1), also known as CCL2, macrophage inflammatory protein 1-alpha (MIP-1α), also known as CCL3, and MIP-1β, also known as CCL4, and MIP-2α, also known as CXCL2, have been implicated in this process.

For example, MCP-1/CCL2 is thought to play a role in both fibrosis and cancer. MCP-1/CCL2 is characterized as a profibrotic chemokine and is a monocyte chemoattractant, and evidence suggests that it may be involved in both initiation and progression of cancer. In fibrosis, MCP-1/CCL2 has been shown to play an important role in the inflammatory phase of fibrosis. For example, neutralization of MCP-1 resulted in a dramatic decrease in glomerular crescent formation and deposition of type I collagen. Similarly, passive immunotherapy with either anti-MCP-1 or anti-MIP-1 alpha antibodies is shown to significantly reduce mononuclear phagocyte accumulation in bleomycin-challenged mice, suggesting that MIP-1 alpha and MCP-1 contribute to the recruitment of leukocytes during the pulmonary inflammatory response (Smith, Biol Signals. 1996 July-August; 5(4):223-31, "Chemotactic cytokines mediate leukocyte recruitment in fibrotic lung disease"). Elevated levels of MIP-1alpha in patients with cystic fibrosis and multiple myeloma have been reported (see, for example: Mrugacz et al., J Interferon Cytokine Res. 2007 June; 27(6):491-5), supporting the notion that MIP-1a is associated with localized or systemic inflammatory responses.

Lines of evidence point to the involvement of C-C chemokines in tumor progression/metastasis. For example, tumor-derived MCP-1/CCL2 can promote "pro-cancer" phenotypes in macrophages. For example, in lung cancer, MCP-1/CCL2 has been shown to be produced by stromal cells and promote metastasis. In human pancreatic cancer, tumors secrete CCL2, and immunosuppressive CCR2-positive macrophages infiltrate these tumors. Patients with tumors that exhibit high CCL2 expression/low CD8 T-cell infiltrate have significantly decreased survival. Without wishing to be bound by particular theory, it is contemplated that monocytes that are recruited to an injured or diseased tissue environment may subsequently become polarized in response to local cues (such as in response to tumor-derived cytokines), thereby further contributing to disease progression. These M2-like macrophages are likely to contribute to immune evasion by suppressing effector cells, such as CD4+ and CD8+ T cells. In some embodiments, this process is in part mediated by LRRC33-TGFβ1 expressed by activated macrophages. In some embodiments, the process is in part mediated by GARP-TGFβ1 expressed by Tregs.

Similarly, in certain carcinomas, such as breast cancer (e.g., triple negative breast cancer), CXCL2/CCL22-mediated recruitment of MDSCs has been shown to promote angiogenesis and metastasis (see, for example, Kumar et al. (2018) J Clin Invest 128(11): 5095-5109). It is therefore contemplated that this process is at least in part mediated by TGFβ1, such as LRRC33-TGFβ1. Moreover, because proteases such as MMP9 are implicated in the process of matrix remodeling that contributes to tumor invasion and metastasis, the same or overlapping signaling pathways may also play a role in fibrosis.

Involvement of PAI-1/Serpine1 has been implicated in a variety of fibrotic conditions, cancers, angiogenesis, inflammation, as well as neurodegenerative diseases (e.g., Alzheimer's Disease). Elevated expression of PAI-1 in tumor and/or serum is correlated with poor prognosis (e.g., shorter survival, increased metastasis) in various cancers, such as breast cancer and bladder cancer (e.g., transitional cell carcinoma) as well as myelofibrosis. In the context of fibrotic conditions, PAI-1 has been recognized as an important downstream effector of TGFβ1-induced fibrosis, and increased PAI-1 expression has been observed in various forms of tissue fibrosis, including lung fibrosis (such as IPF), kidney fibrosis, liver fibrosis and scleroderma. In some embodiments, the process is in part mediated by ECM-associated TGFβ1, e.g., via LTBP1-proTGFβ1 and/or LTBP3-proTGFβ1.

In some embodiments, in vivo effects of the TGFβ1 inhibitor therapy may be assessed by measuring changes in expression levels of suitable gene markers. Suitable markers include TGFβ (e.g., TGFB1, TGFB2, and TGFB3). Suitable markers may also include one or more presenting molecules for TGFβ (e.g., TGFβ1, TGFβ2, and TGFβ3), such as LTBP1, LTBP3, GARP (or LRRC32) and LRRC33. In some embodiments, suitable markers include mesenchymal transition genes (e.g., AXL, ROR2, WNT5A, LOXL2, TWIST2, TAGLN, and/or FAP), immunosuppressive genes (e.g., IL10, VEGFA, VEGFC), monocyte and macrophage chemotactic genes (e.g., CCL2, CCL3, CCL4, CCL7, CCL8, CCL13 and CCL22), and/or various fibrotic markers discussed herein. Preferred markers are plasma/serum markers.

As shown in the Example herein, isoform-specific, context-independent inhibitors of TGFβ1 described herein can be used to reduce expression levels of many of these markers in suitable preclinical models, including mechanistic animal models, such as UUO, which has been shown to be TGFβ1-dependent. Therefore, such inhibitors may be used to treat a disease or disorder characterized by abnormal expression (e.g., overexpression/upregulation or underexpression/downregulation) of one or more of the gene expression markers of the disease.

Thus, in some embodiments, an isoform-specific, context-independent inhibitor of TGFβ1 is used in the treatment of a disease associated with overexpression of one or more of the following: PAI-1 (encoded by Serpine1), MCP-1 (also known as CCL2), Col1a1, Col3a1, FN1, TGFB1, CTGF, α-SMA, ITGA11, and ACTA2, wherein the treatment comprises administration of the inhibitor to a subject suffering from the disease in an amount effective to treat the disease. In some embodiments, the inhibitor is used to treat a disease associated with overexpression of PAI-1, MCP-1/CCL2, CTGF, and/or α-SMA. In some embodiments, the disease is myelofibrosis. In some embodiments, the disease is cancer, for example, cancer comprising a solid tumor. In some embodiments, the disease is organ fibrosis, e.g., fibrosis of the liver (e.g., associated with NASH), the kidney, the lung, the muscle, the skin and/or the cardiac or cardiovascular tissue.

Involvement of the TGFβ1 pathway in controlling key facets of both the ECM and immune components may explain the observations that a remarkable number of dysregulated genes are shared across a wide range of pathologies such as proliferative disorders and fibrotic disorders. This supports the notion that the aberrant pattern of expression in the genes involving TGFβ1 signaling is likely a generalizable phenomenon. These marker genes may be classified into several categories such as: genes involved in mesenchymal transition (e.g., EndMT and EMT); genes involved in angiogenesis; genes involved in hypoxia; genes involved in wound healing; and genes involved in tissue injury-triggered inflammatory response.

A comprehensive study carried out by Hugo et al. (Cell, 165(1): 35-44) elegantly demonstrated the correlation between differential gene expression patterns of these classes of markers and the responsiveness to checkpoint blockade therapy (CBT) in metastatic melanoma. The authors found co-enrichment of the set of genes coined "IPRES signatures" defined a transcriptomic subset within not only melanoma, but also all major common human malignancies analyzed. Indeed, the work links tumor cell phenotypic plasticity (i.e., mesenchymal transition) and the resultant impacts on the microenvironment (e.g., ECM remodeling, cell adhesion, and angiogenesis features of immune suppressive wound healing) to CBT resistance.

Recognizing that each of these IPRES gene categories has been implicated in disease involving TGFβ dysregulation, Applicant previously contemplated that the TGFβ1 isoform in particular may mediate these processes in disease conditions (see, for example, WO 2017/156500). Work disclosed herein further supports this notion (e.g., Example 11; FIG. 37A), further confirming that therapies that selectively target TGFβ1 (as opposed to non-selective alternatives) may offer an advantage both with respect to efficacy and safety.

Accordingly, the present disclosure includes a method/process of selecting or identifying a candidate patient or patient population likely to respond to a TGFβ1 inhibition therapy, and administering to the patient(s) an effective amount of a high-affinity isoform-selective inhibitor of TGFβ1. Observation of a patient's lack of responsiveness to a CBT (e.g., resistance) may indicate that the patient is a candidate for the TGFβ1 inhibition therapy described herein. Thus, a high-affinity, isoform-selective inhibitor of TGFβ1 such as those disclosed herein may be used in the treatment of cancer in a subject, wherein the subject is poorly responsive to a CBT. The subject may have advanced cancer, such as a locally advanced solid tumor or metastatic cancer. A patient is said to be "poorly responsive" when there is no or little meaningful therapeutic effects achieved (e.g., do not meet the criteria of partial response or compete response based on standard guidelines, such as RECIST and iRECIST) following a duration of time which is expected to be sufficient to show meaningful therapeutic effects of the particular therapy. Typically, such duration of time for CBTs is at least about 3 months of treatment, either with or without additional therapies such as chemotherapy. Such patients may be referred to as "non-responders." Where such patients are poorly responsive to the initial CBT, the patients may be referred to as "primary non-responders." Cancer (or patients with such cancer) in this category may be characterized as having "primary resistance" to the CBT. In some embodiments, the subject is a primary non-responder after receiving at least about 3 months of the CBT treatment, wherein optionally, after at least about 4 months of the CBT treatment. In some embodiments, the subject also received additional therapy in combination with the CBT, such as chemotherapy.

Upon identification of the subject as a non-responder of a CBT, the high-affinity, isoform-selective inhibitor of TGFβ1 may be administered to the subject in conjunction with a CBT, which may or may not comprise the same checkpoint inhibitor as the first CBT to which the subject failed to respond. Any suitable immune checkpoint inhibitors may be used, e.g., approved checkpoint inhibitors. In some embodiments, the high-affinity, isoform-selective inhibitor of TGFβ1 is administered to the subject in conjunction with a CBT comprising an anti-PD-1 antibody or anti-PD-L1 antibody. The high-affinity, isoform-selective inhibitor of TGFβ1 is aimed to overcome the resistance by rendering the cancer more susceptible to the CBT.

The process of selecting or identifying a candidate patient or patient population likely to respond to a TGFβ1 inhibition therapy may comprise a step of testing a biological sample collected from the patient (or patient population), such as biopsy samples, for the expression of one or more of the markers discussed herein. Similarly, such genetic marker(s) may be used for purposes of monitoring the patient's responsiveness to a therapy. Monitoring may include testing two or more biological samples collected from the patient, for example, before and after administration of a therapy, and during the course of a therapeutic regimen over time, to evaluate changes in gene expression levels of one or more of the markers, indicative of therapeutic response or effectiveness. In some embodiments, a liquid biopsy may be used.

In some embodiments, a method of selecting a candidate patient or patient population likely to respond to a TGFβ1 inhibition therapy may comprise a step of identifying a patient or patient population previously tested for the genetic marker(s), such as those described herein, which showed aberrant expression thereof. These same methods are also applicable to later confirming or correlating with the patients' response to the therapy.

In some embodiments, the aberrant marker expression includes elevated levels of at least one of the following: TGFβ1, LRRC33, GARP, LTBP1, LTBP3, CCL2, CCL3, PAI-1/Serpine1. In some embodiments, the patient or patient population (e.g., biological samples collected therefrom) shows elevated TGFβ1 activation, phospho-Smad2/3, or combination thereof. In some embodiments, the patient or patient population (e.g., biological samples collected therefrom) shows elevated MDSCs. In some embodiments, such patient or patient population has cancer, which may comprise a solid tumor that is TGFβ1-positive. The solid tumor may be a TGFβ1-dominant tumor, in which TGFβ1 is the predominant isoform expressed in the tumor, relative to the other isoforms. In some embodiments, the solid tumor may be a TGFβ1-co-dominant tumor, in which TGFβ1 is the co-dominant isoform expressed in the tumor, e.g., TGFβ1+/TGFβ3+. In some embodiments, such patient or patient population exhibits resistance to a cancer therapy, such as chemotherapy, radiation therapy and/or immune checkpoint therapy, e.g., anti-PD-1 (e.g., Pembrolizumab and Nivolumab), anti-PD-L1 (e.g., Atezolizumab), anti-CTLA4 (e.g., Ipilimumab), engineered immune cell therapy (e.g., CAR-T), and cancer vaccines, etc. According to the invention, the high-affinity, context-independent TGFβ1 inhibitor, such as those disclosed herein, overcomes the resistance by unblocking immunosuppression so as to allow effector cells to gain access to cancer cells thereby achieving anti-tumor effects. TGFβ1 inhibitor therapy may therefore promote effector cell infiltration and/or expansion in the tumor. Additionally, TGFβ1 inhibitor therapy may reduce the frequency of immunosuppressive immune cells, such as Tregs and MDSCs, in the tumor.

In some embodiments, the aberrant marker expression includes one or more panels of genes: mesenchymal transition markers (e.g., AXL, ROR2, WNT5A, LOXL2, TWIST2, TAGLN, FAP); immunosuppressive genes (e.g., IL10, VEGFA, VEGFC); monocyte and macrophage chemotactic genes (e.g., CCL2, CCL7, CCL8, CCL13); genes involved in angiogenesis and wound healing (e.g., T cell suppressive); cell adhesion markers; ECM remodeling; skeletal system and bone development markers; and genes involved in tissue injury-triggered inflammatory response.

In some embodiments, lack or downregulation of MHC expression (such as MHC class 1) may serve as a biomarker for TGFβ1-associated conditions for which the antibodies or antigen-binding fragments encompassed by the present disclosure may be used as therapy. Reduced MHC levels may signal immune escape, which may correlate with poor responsiveness of the patients to immune-therapies, such as CBT. Selective inhibition of TGFβ1 therefore may at least in part restore effector cell function.

Diseases Involving Mesenchymal Transition

Mesenchymal transition is a process of phenotypic shift of cells, such as epithelial cells and endothelial cells, towards a mesenchymal phenotype (such as myofibroblasts). Examples of genetic markers indicative of mesenchymal transition include AXL, ROR2, WNT5, LOXL2, TWIST2, TAGLN and FAP. In cancer, for example, mesenchymal transition (e.g., increased EndMT and EMT signatures) indicates tumor cell phenotypic plasticity. Thus, high-affinity, isoform-specific, inhibitors of TGFβ1, such as those described herein, may be used to treat a disease that is initiated or driven by mesenchymal transition, such as EMT and EndMT.

EMT (epithelial-to-mesenchymal transition) is the process by which epithelial cells with tight junctions switch to mesenchymal properties (phenotypes) such as loose cell-cell contacts. The process is observed in a number of normal biological processes as well as pathological situations, including embryogenesis, wound healing, cancer metastasis and fibrosis (reviewed in, for example, Shiga et al. (2015) "Cancer-Associated Fibroblasts: Their Characteristics and Their Roles in Tumor Growth." Cancers, 7: 2443-2458). Generally, it is believed that EMT signals are induced mainly by TGFβ. Many types of cancer, for example, appear to involve transdifferentiation of cells towards mesenchymal phenotype (such as myofibroblasts and CAFs) which correlate with poorer prognosis. Thus, isoform-specific, context-independent inhibitors of TGFβ1, such as those described herein, may be used to treat a disease that is initiated or driven by EMT. Indeed, data exemplified herein (e.g., FIGS. 7-9) show that such inhibitors have the ability to suppress expression of myofibroblast/CAF markers in vivo, such as α-SMA, LOXL2, Col1 (Type I collagen), and FN (fibronectin). Thus, high-affinity, isoform-specific, inhibitors of TGFβ1, such as those described herein, may be used for the treatment of a disease characterized by EMT. A therapeutically effective amount of the inhibitor may be an amount sufficient to reduce expression of markers such as α-SMA/ACTA2, LOXL2Col1 (Type I collagen), and FN (fibronectin). In some embodiments, the disease is a fibrotic disorder. In some embodiments, the disease is a proliferative disorder, such as cancer.

Similarly, TGFβ is also a key regulator of the endothelial-to-mesenchymal transition (EndMT) observed in normal development, such as heart formation. However, the same or similar phenomenon is also seen in many disease-associated tissues, such as cancer stroma and fibrotic sites. In some disease processes, endothelial markers such as CD31 become downregulated upon TGFβ1 exposure and instead the expression of mesenchymal markers such as FSP-1, α-SMA/ACTA2 and fibronectin becomes induced. Indeed, stromal CAFs may be derived from vascular endothelial cells. Thus, high-affinity, isoform-specific, inhibitors of TGFβ1, such as those described herein, may be used for the treatment of a disease characterized by EndMT. A therapeutically effective amount of the inhibitor may be an amount sufficient to reduce expression of markers such as FSP-1, α-SMA/ACTA2 and fibronectin. In some embodiments, the disease is a fibrotic disorder. In some embodiments, the disease is a proliferative disorder, such as cancer.

Diseases Involving Matrix Stiffening and Remodeling

Progression of various TGFβ1-related indications, such as fibrotic conditions and cancer, involves increased levels of matrix components deposited into the ECM and/or maintenance/remodeling of the ECM. It has been reported that increased deposition of ECM components such as collagens can alter the mechanophysical properties of the ECM (e.g., the stiffness of the matrix/substrate) and this phenomenon is associated with TGFβ1 signaling. Applicant previously demonstrated the role of matrix stiffness on integrin-dependent activation of TGFβ, using primary fibroblasts transfected with proTGFβ1 and LTBP1 and grown on silicon-based substrates with defined stiffness (e.g., 5 kPa, 15 kPa or 100 kPa). As disclosed in WO 2018/129329, matrices with greater stiffness enhance TGFβ1 activation, and this can be suppressed by isoform-specific inhibitors of TGFβ1. These observations suggest that TGFβ1 influences ECM properties (such as stiffness), which in turn can further induce TGFβ1 activation, reflective of disease progression.

Thus, high-affinity, isoform-specific inhibitors of TGFβ1, such as those described herein, may be used to block this process to counter disease progression involving ECM alterations, such as fibrosis, tumor growth, invasion, metastasis and desmoplasia. The LTBP-arm of such inhibitors can directly block ECM-associated pro/latent TGFβ1 complexes which are presented by LTBP1 and/or LTBP3, thereby preventing activation/release of the growth factor from the complex in the disease niche. In some embodiments, the high-affinity, isoform-specific TGFβ1 inhibitors may normalize ECM stiffness to treat a disease that involves integrin-dependent signaling. In some embodiments, the integrin comprises an all chain, 31 chain, or both. The architecture of the ECM, e.g., ECM components and organization, can also be altered by matrix-associated proteases.

As reviewed in Lampi and Reinhart-King (Science Translational Medicine, 10(422): eaao0475, "Targeting extracellular matrix stiffness to attenuate disease: From molecular mechanisms to clinical trials"), increased stiffness of tissue ECMs occurs during pathological progression of cancer, fibrosis and cardiovascular disease. The mechanical properties associated with the process involve phenotypically converted myofibroblasts, TGFβ and matrix cross-linking. A major cause of increased ECM stiffness during cancer and fibrotic diseases is dysregulated matrix synthesis and remodeling by activated fibroblasts that have de-differentiated into myofibroblasts (e.g., CAFs and FAFs). Remodeling of the tumor stroma and organ fibrosis exhibit striking similarities to the wound healing response, except that in the pathological state the response is sustained. Myofibroblass are a heterogeneous cell population with pathology-specific precursor cells originating from multiple cell sources, such as bone marrow-derived and tissue resident cells. Commonly used myofibroblast markers include alpha-smooth muscle actin (α-SMA). As shown herein, high-affinity, isoform-specific TGFβ1 inhibitors are able to reduce ACTA2 expression (which encodes α-SMA), collagens, as well as FN (fibronectin) in in vivo studies. Fibronectin is important in the anchoring of LTBP-associated proTGFβ1 complexes onto the matrix structure.

The importance of the TGFβ pathway in ECM regulation is well-established. Because TGFβ1 (and TGFβ3) can be mechanically activated by certain integrins (e.g., αv integrins), the integrin-TGFβ1 interaction has become a therapeutic target. For example, a monoclonal antibody to αvβ6 is being investigated for idiopathic lung fibrosis. However, such approach may also interfere with TGFβ3 signaling which shares the same integrin-binding motif, RGD, and furthermore, such antibody will not be effective in blocking TGFβ1 activated via other modes, such as protease-induced activation. In comparison, high-affinity, isoform-specific TGFβ1 inhibitors can block protease-dependent activation of TGFβ1 (FIGS. 5A & 5B), as well as integrin-dependent activation of TGFβ1 (FIGS. 1-4 and 33B). Therefore, the high-affinity isoform-selective inhibitors of TGFβ1 may provide superior attributes. Data presented herein, together with Applicant's previous work, support that high-affinity isoform-selective inhibitors of TGFβ1 may be effective in treating disease associated with ECM stiffening.

Thus, the invention includes therapeutic use of the high-affinity isoform-selective inhibitors of TGFβ1 in the treatment of a disease associated with matrix stiffening, or in a method for reducing matrix stiffness, in a subject. Such use comprises administration of a therapeutically effective amount of the high-affinity isoform-selective inhibitor of TGFβ1.

Diseases Involving Proteases

Activation of TGFβ from its latent complex may be triggered by integrin in a force-dependent manner, and/or by proteases. Evidence suggests that certain classes of proteases may be involved in the process, including but are not limited to Ser/Thr proteases such as Kallikreins, chemotrypsin, elastases, plasmin, as well as zinc metalloproteases of MMP family, such as MMP-2, MMP-9 and MMP-13, and the Adam family of proteases, such as Adam10 and Adam17. MMP-2 degrades the most abundant component of the basement membrane, Collagen IV, raising the possibility that it may play a role in ECM-associated TGFβ1 regulation. MMP-9 has been implicated to play a central role in tumor progression, angiogenesis, stromal remodeling and metastasis, including in carcinoma, such as breast cancer. Thus, protease-dependent activation of TGFβ1 in the ECM may be important for treating cancer.

Kallikreins (KLKs) are trypsin- or chymotrypsin-like serine proteases that include plasma Kallikreins and tissue Kallikreins. The ECM plays a role in tissue homeostasis acting as a structural and signaling scaffold and barrier to suppress malignant outgrowth. KLKs may play a role in degrading ECM proteins and other components which may facilitate tumor expansion and invasion. For example, KLK1 is highly upregulated in certain breast cancers and can activate pro-MMP-2 and pro-MMP-9. KLK2 activates latent TGFβ1, rendering prostate cancer adjacent to fibroblasts permissive to cancer growth. KLK3 has been widely studied as a diagnostic marker for prostate cancer (PSA). KLK3 may directly activate TGFβ1 by processing plasminogen into plasmin, which proteolytically cleaves LAP, thereby causing the TGFβ1 growth factor to be released from the latent complex. KLK6 may be a potential marker for Alzheimer's disease.

Moreover, data provided in Example 8 indicate that such proteases may be a Kallikrein. Thus, the invention encompasses the use of an isoform-specific, context-independent inhibitor of TGFβ1 in a method for treating a disease associated with Kallikrein or a Kallikrein-like protease. In some embodiments, the TGFβ1 inhibitor is Ab3, Ab6, or derivatives thereof.

Known activators of TGFβ1, such as plasmin, TSP-1 and αVβ6 integrin, all interact directly with LAP. It is postulated that proteolytic cleavage of LAP may destabilize the LAP-TGFβ interaction, thereby releasing active TGFβ1. It has been suggested that the region containing 54-LSKLRL-59 is important for maintaining TGFβ1 latency. Thus, agents (e.g., antibodies) that stabilize the interaction, or block the proteolytic cleavage of LAP may prevent TGFβ1 activation.

Many of these proteases associated with pathological conditions (e.g., cancer) function through distinct mechanisms of action. Thus, targeted inhibition of particular proteases, or combinations of proteases, may provide therapeutic benefits for the treatment of conditions involving the protease-TGFβ axis. Accordingly, it is contemplated that inhibitors (e.g., TGFβ1 antibodies) that selectively inhibit protease-induced activation of TGFβ1 may be advantageous in the treatment of such diseases (e.g., cancer). Similarly, selective inhibition of TGFβ1 activation by one protease over another protease may also be preferred, depending on the condition being treated.

Plasmin is a serine protease produced as a precursor form called Plasminogen. Upon release, Plasmin enters circulation and therefore is detected in serum. Elevated levels of serum Plasmin appear to correlate with cancer progression, possibly through mechanisms involving disruption of the extracellular matrix (e.g., basement membrane and stromal barriers) which facilitates tumor cell motility, invasion, and metastasis. Plasmin may also affect adhesion, proliferation, apoptosis, cancer nutrition, oxygen supply, formation of blood vessels, and activation of VEGF (Didiasova et al., *Int. J. Mol. Sci*, 2014, 15, 21229-21252). In addition, Plasmin may promote the migration of macrophages into the tumor microenvironment (Philips et al., *Cancer Res.* 2011 Nov. 1; 71(21):6676-83 and Choong et al., *Clin. Orthop. Relat. Res.* 2003, 415S, S46-S58). Indeed, tumor-associated macrophages (TAMs) are well characterized drivers of tumorigenesis through their ability to promote tumor growth, invasion, metastasis, and angiogenesis.

Plasmin activities have been primarily tied to the disruption of the ECM. However, there is mounting evidence that Plasmin also regulates downstream MMP and TGFβ activation. Specifically, Plasmin has been suggested to cause activation of TGFβ through proteolytic cleavage of the Latency Associated Peptide (LAP), which is derived from the N-terminal region of the TGFβ gene product (Horiguchi et al., *J Biochem.* 2012 October; 152(4):321-9), resulting in the release of active growth factor. Since TGFβ1 may promote cancer progression, this raises the possibility that plasmin-induced activation of TGFβ may at least in part mediate this process.

TGFβ1 has also been shown to regulate expression of uPA, which is a critical player in the conversion of Plasminogen into Plasmin (Santibanez, Juan F., *ISRN Dermatology*, 2013: 597927). uPA has independently been shown to promote cancer progression (e.g., adhesion, proliferation, and migration) by binding to its cell surface receptor (uPAR) and promoting conversion of Plasminogen into Plasmin. Moreover, studies have shown that expression of uPA and/or plasminogen activator inhibitor-1 (PAI-1) are predictors of poor prognosis in colorectal cancer (D. Q. Seetoo, et al., *Journal of Surgical Oncology*, vol. 82, no. 3, pp. 184-193, 2003), breast cancer (N. Harbeck et al., *Clinical Breast Cancer*, vol. 5, no. 5, pp. 348-352, 2004), and skin cancer (Santibanez, Juan F., *ISRN Dermatology*, 2013: 597927). Thus, without wishing to be bound by a particular theory, the interplay between Plasmin, TGFβ1, and uPA may create a positive feedback loop towards promoting cancer progression. Accordingly, inhibitors that selectively inhibit Plasmin-dependent TGFβ1 activation may be particularly suitable for the treatment of cancers reliant on the Plasmin/TGFβ1 signaling axis.

In one aspect of the invention, the isoform-specific inhibitors of TGFβ1 described herein include inhibitors that can inhibit protease-dependent activation of TGFβ1. In some embodiments, the inhibitors can inhibit protease-dependent TGFβ1 activation in an integrin-independent manner. In some embodiments, such inhibitors can inhibit TGFβ1 activation irrespective of the mode of activation, e.g., inhibit both integrin-dependent activation and protease-dependent activation of TGFβ1. In some embodiments, the protease is selected from the group consisting of: serine proteases, such as Kallikreins, Chemotrypsin, Trypsin, Elastases, Plasmin, as well as zinc metalloproteases (MMP family) such as MMP-2, MMP-9 and MMP-13.

In some embodiments, the inhibitors can inhibit Plasmin-induced activation of TGFβ1. In some embodiments, the inhibitors can inhibit Plasmin- and integrin-induced TGFβ1 activation. In some embodiments, the antibody is a monoclonal antibody that specifically binds proTGFβ1. In some embodiments, the antibody binds latent proTGFβ1 thereby inhibiting release of mature growth factor from the latent complex. In some embodiments, the high-affinity, context-independent inhibitor of TGFβ1 activation suitable for use in the method of inhibiting Plasmin-dependent activation of TGFβ1 is Ab6 or a derivative or variant thereof.

In some embodiments, the inhibitor (e.g., TGFβ1 antibody) inhibits cancer cell migration. In some embodiments, the inhibitor inhibits macrophage migration. In some embodiments, the inhibitor inhibits accumulation of TAMs.

In another aspect, provided herein is a method for treating cancer in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby treating cancer in the subject.

In another aspect, provided herein is a method of reducing tumor growth in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby reducing tumor growth in the subject.

Cancer/Malignancies

Various cancers involve TGFβ1 activities and may be treated with antibodies and/or compositions of the present disclosure. As used herein, the term "cancer" refers to any of various malignant neoplasms, associated with TGFβ1-positive cells. Such malignant neoplasms are characterized by the proliferation of anaplastic cells that tend to invade surrounding tissue and metastasize to new body sites and also refers to the pathological condition characterized by such malignant neoplastic growths. The source of TGFβ1 may vary and may include the malignant (cancer) cells themselves, as well as their surrounding or support cells/tissues, including, for example, the extracellular matrix, various immune cells, and any combinations thereof.

Affirmative identification of cancer as "TGFβ1-positive" is not required for carrying out the therapeutic methods described herein. Typically, certain cancer types are known to be or suspected, based on credible evidence, to be associated with TGFβ1 signaling.

Cancers may be localized (e.g., solid tumors) or systemic. In the context of the present disclosure, the term "localized" (as in "localized tumor") refers to anatomically isolated or isolatable abnormalities/lesions, such as solid malignancies, as opposed to systemic disease (e.g., so-called liquid tumors or blood cancers). Certain cancers, such as certain types of leukemia (e.g., myelofibrosis) and multiple myeloma, for example, may have both a localized component (for instance the bone marrow) and a systemic component (for instance circulating blood cells) to the disease. In some embodiments, cancers may be systemic, such as hematological malignancies. Cancers that may be treated according to the present disclosure are TGFβ1-positive and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. In some embodiments, the cancer may be an advanced cancer, such as a locally advanced solid tumor and metastatic cancer.

Antibodies or antigen-binding fragments thereof encompassed by the present disclosure may be used in the treatment of cancer, including, without limitation: myelofibrosis, melanoma, adjuvant melanoma, renal cell carcinoma (RCC), bladder cancer, colorectal cancer (CRC), colon cancer, rectal cancer, anal cancer, breast cancer, triple-negative breast cancer (TNBC), HER2-negative breast cancer, BRCA-mutated breast cancer, hematologic malignancies, non-small cell carcinoma, non-small cell lung cancer (NSCLC), small cell lung cancer (SCLC), extensive-stage small cell lung cancer (ES-SCLC), lymphoma (classical Hodgkin's and non-Hodgkin's), primary mediastinal large B-cell lymphoma (PMBCL), T-cell lymphoma, diffuse large B-cell lymphoma, histiocytic sarcoma, follicular dendritic cell sarcoma, interdigitating dendritic cell sarcoma, myeloma, chronic lymphocytic leukemia (CLL), acute myeloid leukemia (AML), small lymphocytic lymphoma (SLL), head and neck cancer, urothelial cancer, merkel cell carcinoma, merkel cell skin cancer, cancer with high microsatellite instability (MSI-H), cancer with mismatch repair deficiency (dMMR), mesothelioma, gastric cancer, gastroesophageal junction cancer (GEJ), gastric adenocarcinoma, neuroendocrine tumors, gastrointestinal stromal tumors (GIST), gastric cardia adenocarcinoma, renal cancer, biliary cancer, cholangiocarcinoma, pancreatic cancer, prostate cancer, adenocarcinoma, squamous cell carcinoma, non-squamous cell carcinoma, cutaneous squamous cell carcinoma (CSCC), ovarian cancer, endometrial cancer, fallopian tube cancer, cervical cancer, peritoneal cancer, stomach cancer, brain cancers, malignant glioma, glioblastoma, gliosarcoma, neuroblastoma, thyroid cancer, adrenocortical carcinoma, oral intra-epithelial neoplasia, esophageal cancer, nasal cavity and paranasal sinus squamous cell carcinoma, nasopharynx carcinoma, salivary gland cancer, liver cancer, and hepatocellular cancer (HCC). However, any cancer (e.g., patients with such cancer) in which TGFβ1 is overexpressed or is at least a predominant isoform, as determined by, for example biopsy, may be treated with an isoform-selective inhibitor of TGFβ1 in accordance with the present disclosure.

In cancer, TGFβ (e.g., TGFβ1) may be either growth promoting or growth inhibitory. As an example, in pancreatic cancers, SMAD4 wild type tumors may experience inhibited growth in response to TGFβ, but as the disease progresses, constitutively activated type II receptor is typically present. Additionally, there are SMAD4-null pancreatic cancers. In some embodiments, antibodies, antigen binding portions thereof, and/or compositions of the present disclosure are designed to selectively target components of TGFβ signaling pathways that function uniquely in one or more forms of cancer. Leukemias, or cancers of the blood or bone marrow that are characterized by an abnormal proliferation of white blood cells, i.e., leukocytes, can be divided into four major classifications including acute lymphoblastic leukemia (ALL), chronic lymphocytic leukemia (CLL), acute myelogenous leukemia or acute myeloid leukemia (AML) (AML with translocations between chromosome 10 and 11 [t(10, 11)], chromosome 8 and 21 [t(8;21)], chromosome 15 and 17 [t(15;17)], and inversions in chromosome 16 [inv(16)]; AML with multilineage dysplasia, which includes patients who have had a prior myelodysplastic syndrome (MDS) or myeloproliferative disease that transforms into AML; AML and myelodysplastic syndrome (MDS), therapy-related, which category includes patients who have had prior chemotherapy and/or radiation and subsequently develop AML or MDS; d) AML not otherwise categorized, which includes subtypes of AML that do not fall into the above categories; and e) acute leukemias of ambiguous lineage, which occur when the leukemic cells cannot be classified as either myeloid or lymphoid cells, or where both types of cells are present); and chronic myelogenous leukemia (CML).

In some embodiments, any one of the above referenced TGFβ1-positive cancer may also be TGFβ3-positive. In some embodiments, tumors that are both TGFβ1-positive and TGFβ3-positive may be TGFβ1/TGFβ3 co-dominant. In some embodiments, such cancer is carcinoma comprising a solid tumor. In some embodiments, such tumors are breast carcinoma. In some embodiments, the breast carcinoma may be of triple-negative genotype (triple-negative breast cancer). In some embodiments, subjects with TGFβ1-positive cancer have elevated levels of MDSCs. For example, such tumors may comprise MDSCs recruited to the tumor site resulting in an increased number of MDSC infiltrates. In some embodiments, subjects with breast cancer show elevated levels of C-Reactive Protein (CRP), an inflammatory marker associated with recurrence and poor prognosis. In some embodiments, subjects with breast cancer show elevated levels of IL-6.

The isoform-selective TGFβ1 inhibitors of the invention may be used to treat patients suffering from chronic myeloid leukemia, which is a stem cell disease, in which the BCR/ABL oncoprotein is considered essential for abnormal growth and accumulation of neoplastic cells. Imatinib is an approved therapy to treat this condition; however, a significant fraction of myeloid leukemia patients show Imatinib-resistance. TGFβ1 inhibition achieved by the inhibitor such as those described herein may potentiate repopulation/expansion to counter BCR/ABL-driven abnormal growth and accumulation of neoplastic cells, thereby providing clinical benefit.

Isoform-specific inhibitors of TGFβ1, such as those described herein, may be used to treat multiple myeloma. Multiple myeloma is a cancer of B lymphocytes (e.g., plasma cells, plasmablasts, memory B cells) that develops and expands in the bone marrow, causing destructive bone lesions (i.e., osteolytic lesion). Typically, the disease manifests enhanced osteoclastic bone resorption, suppressed osteoblast differentiation (e.g., differentiation arrest) and impaired bone formation, characterized in part, by osteolytic lesions, osteopenia, osteoporosis, hypercalcemia, as well as plasmacytoma, thrombocytopenia, neutropenia and neuropathy. The TGFβ1-selective, context-independent inhibitor therapy described herein may be effective to ameliorate one or more such clinical manifestations or symptoms in patients. The TGFβ1 inhibitor may be administered to patients who receive additional therapy or therapies to treat multiple myeloma, including those listed elsewhere herein. In some embodiments, multiple myeloma may be treated with a TGFβ1 inhibitor (such as an isoform-specific context-independent inhibitor) in combination with a myostatin inhibitor or an IL-6 inhibitor. In some embodiments, the TGFβ1 inhibitor may be used in conjunction with traditional multiple myeloma therapies, such as bortezomib, lenalidomide, carfilzomib, pomalidomide, thalidomide, doxorubicin, corticosteroids (e.g., dexamethasone and prednisone), chemotherapy (e.g., melphalan), radiation therapy, stem cell transplantation, plitidepsin, Elotuzumab, Ixazomib, Masitinib, and/or Panobinostat.

The types of carcinomas which may be treated by the methods of the present invention include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

The types of sarcomas include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

Isoform-selective, context-independent inhibitors of TGFβ1 activation, such as those described herein, may be suited for treating malignancies involving cells of neural crest origin. Cancers of the neural crest lineage (i.e., neural crest-derived tumors) include, but are not limited to: melanoma (cancer of melanocytes), neuroblastoma (cancer of sympathoadrenal precursors), ganglioneuroma (cancer of peripheral nervous system ganglia), medullary thyroid carcinoma (cancer of thyroid C cells), pheochromocytoma (cancer of chromaffin cells of the adrenal medulla), and MPNST (cancer of Schwann cells). In some embodiments, antibodies and methods of the disclosure may be used to treat one or more types of cancer or cancer-related conditions that may include, but are not limited to colon cancer, renal cancer, breast cancer, malignant melanoma and glioblastomas (Schlingensiepen et al., 2008; Ouhtit et al., 2013).

Under normal conditions, regulatory T cells (Tregs) represent a small subset of the overall CD4-positive lymphocyte population and play key roles for maintaining immune system in homeostasis. In nearly all cancers, however, the number of Tregs is markedly increased. While Tregs play an important role in dampening immune responses in healthy individuals, an elevated number of Tregs in cancer has been associated with poor prognosis. Elevated Tregs in cancer may dampen the host's anti-cancer immunity and may contribute to tumor progression, metastasis, tumor recurrence and/or treatment resistance. For example, human ovarian cancer ascites are infiltrated with Foxp3+ GARP+ Tregs (Downs-Canner et al., Nat Commun. 2017, 8: 14649). Similarly, Tregs positively correlated with a more immunosuppressive and more aggressive phenotype in advanced hepatocellular carcinoma (Kalathil et al., Cancer Res. 2013, 73(8): 2435-44). Tregs can suppress the proliferation of effector T cells (FIG. 26B). In addition, Tregs exert contact-dependent inhibition of immune cells (e.g., naïve CD4+ T cells) through the production of TGFβ1 (see for example FIG. 26A). To combat a tumor, therefore, it is advantageous to inhibit Tregs so sufficient effector T cells can be available to exert anti-tumor effects.

Increasing lines of evidence suggest the role of macrophages in tumor/cancer progression. The present invention encompasses the notion that this is in part mediated by TGFβ1 activation in the disease environment, such as TME. Bone marrow-derived monocytes (e.g., CD11b+) are recruited to tumor sites in response to tumor-derived cytokines/chemokines (such as CCL2, CCL3 and CCL4), where monocytes undergo differentiation and polarization to acquire pro-cancer phenotype (e.g., M2-biased or M2-like macrophages, TAMs). As previously demonstrated (WO 2018/129329), monocytes isolated from human PBMCs can be induced to polarize into different subtypes of macrophages, e.g., M1 (pro-fibrotic, anti-cancer) and M2 (pro-cancer). A majority of TAMs in many tumors are M2-biased. Among the M2-like macrophages, M2c and M2d subtypes, but not M1, are found to express elevated LRRC33 on the cell surface. Moreover, macrophages can be further skewed or activated by certain cytokine exposure, such as M-CSF, resulting in a marked increase in LRRC33 expression, which coincides with TGFβ1 expression. Increased levels of circulating M-CSF (i.e., serum M-CSF concentrations) in patients with myeloproliferative disease (e.g., myelofibrosis) have also been observed. Generally, tumors with high macrophage (TAM) and/or MDSC infiltrate are associated with poor prognosis. Similarly, elevated levels of M-CSF are also indicative of poor prognosis. Thus, the high-affinity, isoform-selective TGFβ1 inhibitor such as those encompassed herein, can be used in the treatment of cancer that is characterized by elevated levels of pro-cancer macrophages and/or MDSCs. The LRRC33-arm of the inhibitor may at least in part mediate its inhibitory effects against disease-associated immunosuppressive myeloid cells, e.g., M2-macrophages and MDSCs.

High prevalence of tumor-associated M2-like macrophages is recapitulated in murine syngeneic tumor models described herein. In MBT-2 tumors, for example, nearly 40% of CD45-positive cells isolated from an established tumor are M2 macrophages (FIG. 28B). This is reduced by half in animals treated with a combination of a high-affinity, isoform-selective TGFβ1 and anti-PD-1. By comparison, no significant change in the number of tumor-associated M1 macrophages is observed in the same animals. Like M2 macrophages, tumor-associated MDSCs are also elevated in established tumors (about $10^{-12}$% of CD45+ cells), and are markedly reduced (to negligible levels) by inhibiting both PD-1 and TGFβ1 in the treated animals (FIG. 28B). As disclosed herein, a majority of tumor-infiltrating M2 macrophages and MDSCs express cell-surface LRRC33 and/or LRRC33-proTGFβ1 complex (FIGS. 28C & 28D). Interestingly, cell-surface expression of LRRC33 (or LRRC33-proTGFβ1 complex) appears to be highly regulated. The high-affinity, isoform-selective TGFβ1 inhibitor, Ab6, is capable of becoming rapidly internalized in cells expressing LRRC33 and proTGFβ1, and the rate of internalization achieved with Ab6 is significantly higher than that with a reference antibody that recognizes cell-surface LRRC33 (FIG. 6). Similar results are obtained from primary human macrophages. These observation show that Ab6 can promote internalization upon binding to its target, LRRC33-proTGFβ1, thereby removing the LRRC33-containing complexes from the cell surface. Thus, target engagement by a high-affinity, isoform-selective TGFβ1 inhibitor (such as Ab6) may induce antibody-dependent downregulation of the target protein (e.g., cell-associated proTGFβ1 complexes). At the disease loci, this may reduce the availability of activatable latent LRRC33-proTGFβ1 levels. Therefore, the isoform-selective TGFβ1 inhibitors may inhibit the LRRC33 arm of TGFβ1 via dual mechanisms of action: i) blocking the release of mature growth factor from the latent complex; and, ii) removing LRRC33-proTGFβ1 complexes from cell-surface via internalization. In the tumor microenvironment, the antibodies may target cell-associated latent proTGFβ1 complexes, augmenting the inhibitory effects on the target cells, such as M2 macrophages (e.g., TAMs), MDSCs, and Tregs. Phenotypically, these are immunosuppressive cells, contributing to the immunosuppressive tumor microenvironment, which is at least in part mediated by the TGFβ1 pathway. Given that many tumors are enriched with these cells, the antibodies that are capable of targeting multiple arms of TGFβ1 function should provide a functional advantage.

Many human cancers are known to cause elevated levels of MDSCs in patients, as compared to healthy control (reviewed, for example, in Elliott et al. (2017) "Human tumor-infiltrating myeloid cells: phenotypic and functional diversity" Frontiers in Immunology, Vol. 8, Article 86). These human cancers include but are not limited to: bladder cancer, colorectal cancer, prostate cancer, breast cancer, glioblastoma, hepatocellular carcinoma, head and neck squamous cell carcinoma, lung cancer, melanoma, NSCL, ovarian cancer, pancreatic cancer, and renal cell carcinoma. Elevated levels of MDSCs may be detected in biological samples such as peripheral blood mononuclear cell (PBMC) and tissue samples (e.g., tumor biopsy). For example, frequency of or changes in the number of MDSCs may be measured as: percent (%) of total PBMCs, percent (%) of CD14+ cells, percent (%) of CD45+ cells; percent (%) of mononuclear cells, percent (%) of total cells, percent (%) of CD 11 b+ cells, percent (%) of monocytes, percent (%) of non-lymphocytic MNCs, percent (%) of KLA-DR cells, using suitable cell surface markers (phenotype).

On the other hand, macrophage infiltration into a tumor may also signify effectiveness of a therapy. As exemplified in FIGS. 23, 24 and 27B, tumors that are effectively penetrated by effector T cells (e.g., CD8+ T cells) following the treatment with a combination of a checkpoint inhibitor and a context-independent TGFβ1 inhibitor. Intratumoral effector T cells may lead to recruitment of phagocytic monocytes/macrophages that clean up cell debris.

Figure 23A:
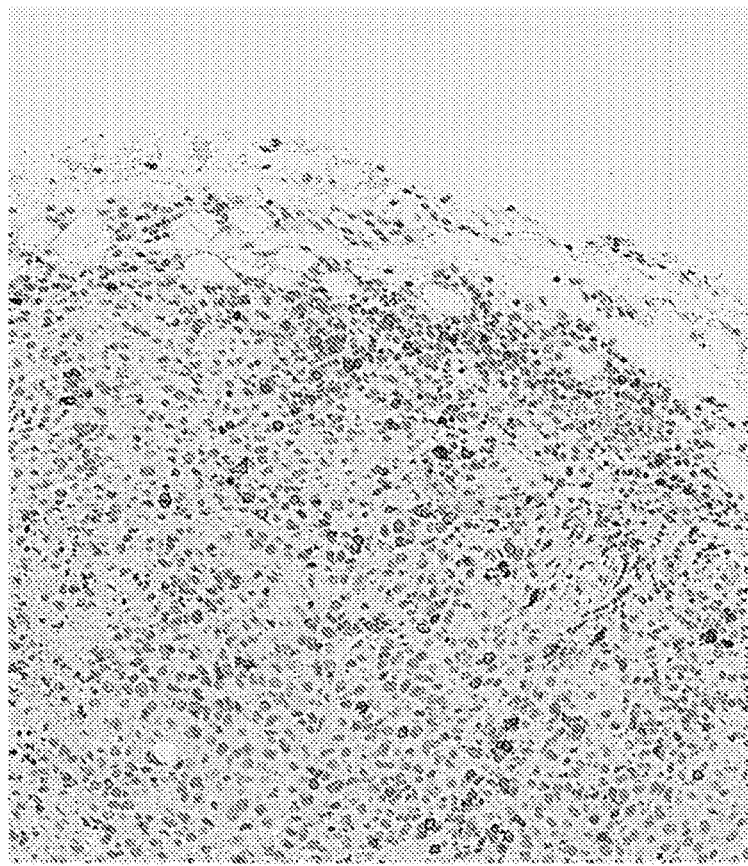
FIGS. 23A-23B provide representative immunohistochemistry sections of S91 tumors, stained with a CD8+ cell marker.
Figure 23B:
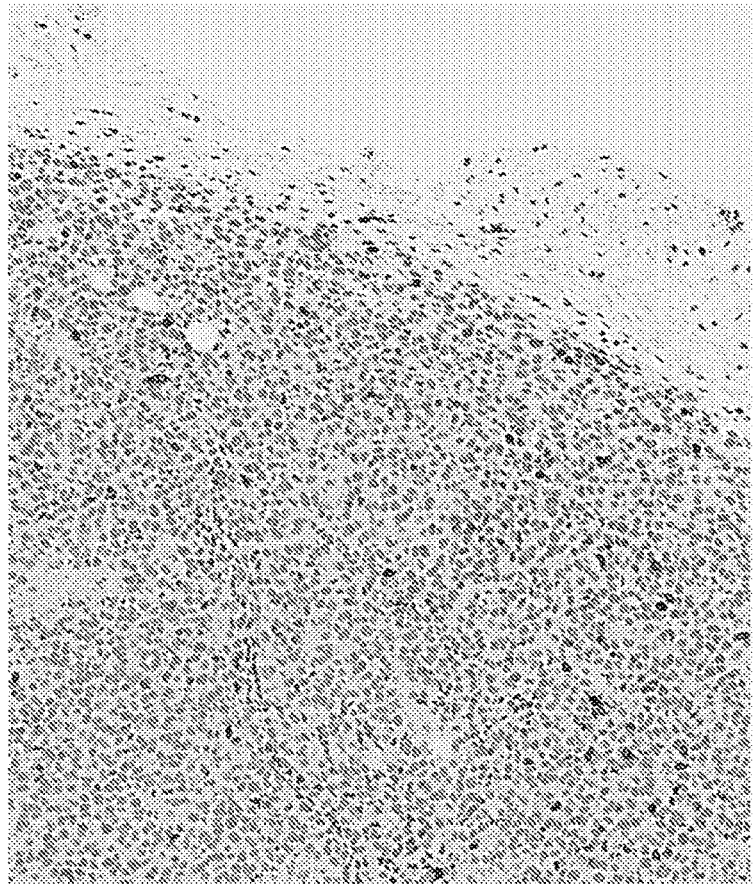

As clear from FIG. 23, the combination of anti-PD-1 and a TGFβ1 inhibitor resulted in robust CD8 T cell influx/expansion throughout the tumor, as compared to anti-PD-1 treatment alone. Correspondingly, robust increase in CD8 effector genes may be achieved by the combination treatment. Thus, the TGFβ1 inhibitors of the present invention may be used to promote effector T-cell infiltration into tumors.

In addition, extensive infiltration/expansion of the tumor by F4/80-positive macrophages is observed (see FIG. 24). This may be indicative of M1 (anti-tumor) macrophages clearing cancer cell debris generated by cytotoxic cells and is presumably a direct consequence of TGFβ1 inhibition. As described in further detail in the Examples herein, these tumor-infiltrating macrophages are identified predominantly as non-M2 macrophages for their lack of CD163 expression, indicating that circulating monocytes are recruited to the tumor site upon checkpoint inhibitor and TGFβ1 inhibitor treatment and differentiate into M1 macrophages, and this observation is accompanied by a marked influx of CD8+ T cells into the tumor site. Thus, the TGFβ1 inhibitors of the present invention may be used to increase non-M2 macrophages associated with tumor.

Figure 20A:
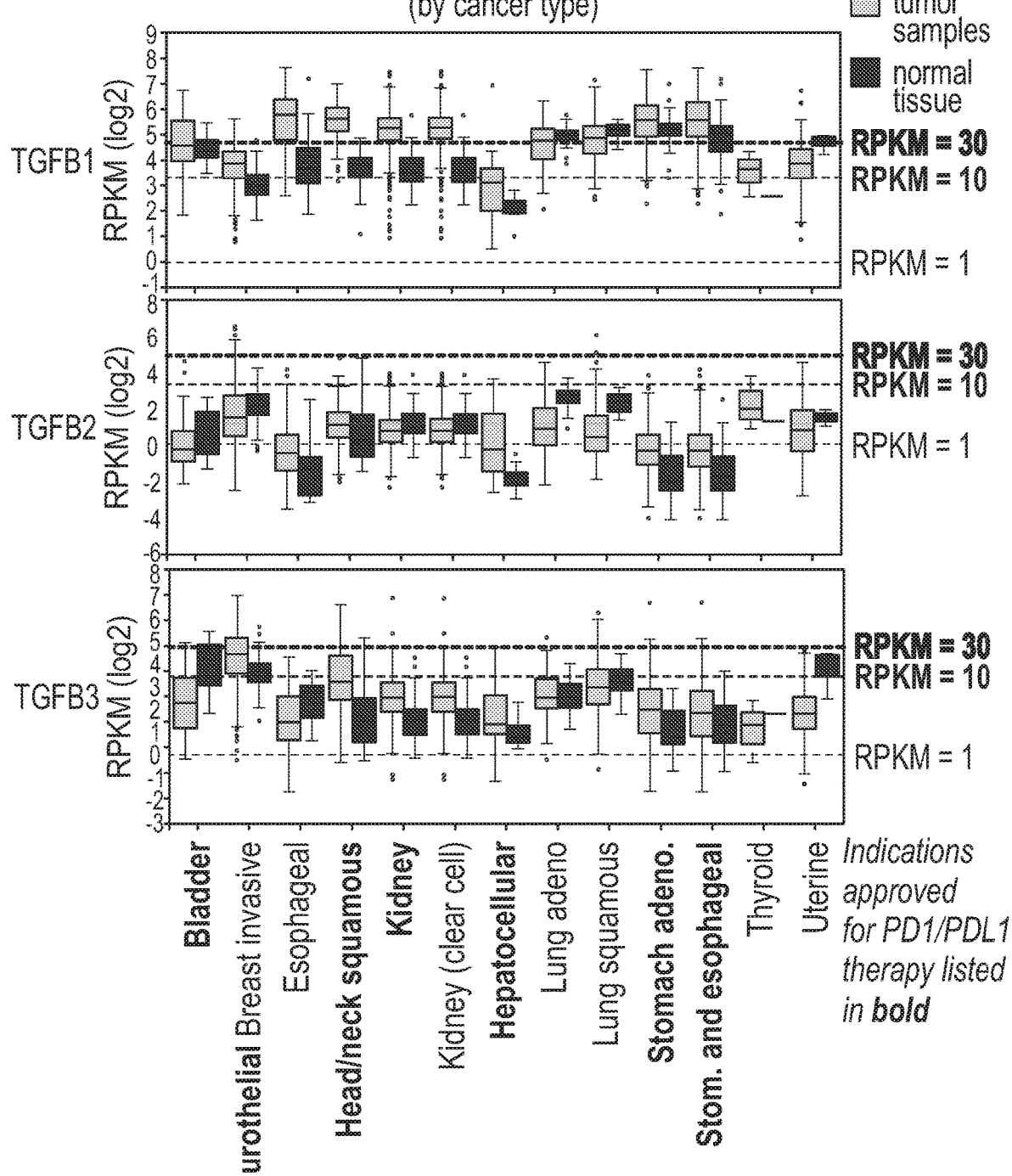
Figure 20B:
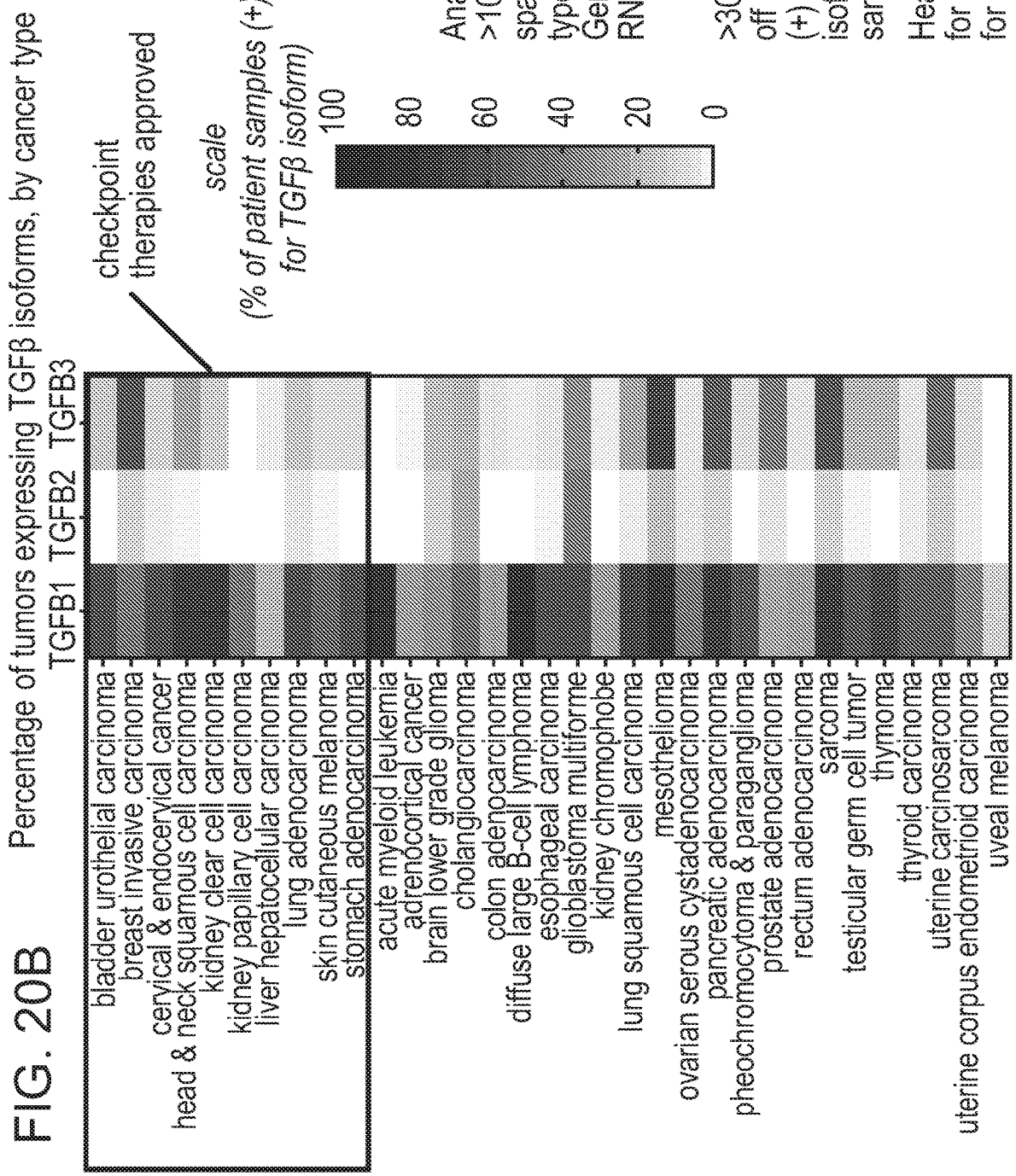

Recently, checkpoint blockade therapy (CBT) has become a standard of care for treating a number of cancer types (see, for example, FIG. 20B). Despite the profound advances in cancer immunotherapy, primary resistance to CBT remains a major unmet need for patients; a majority of patients' cancers still fail to respond to PD-(L)1 inhibition. Retrospective analysis of urothelial cancer and melanoma tumors has recently implicated TGFβ activation as a potential driver of primary resistance, very likely via multiple mechanisms including exclusion of cytotoxic T cells from the tumor as well as their expansion within the tumor microenvironment (immune exclusion). These observations and subsequent preclinical validation have pointed to TGFβ pathway inhibition as a promising avenue for overcoming primary resistance to CBT. However, therapeutic targeting of the TGFβ pathway has been hindered by dose-limiting preclinical cardiotoxicities, most likely due to inhibition of signaling from one or more TGFβ isoforms.

Many tumors lack of primary response to CBT. In this scenario, CD8+ T cells are commonly excluded from the tumor parenchyma, suggesting that tumors may co-opt the immunomodulatory functions of TGFβ signaling to generate an immunosuppressive microenvironment. These insights from retrospective clinical tumor sample analyses provided the rationale for investigating the role of TGFβ signaling in primary resistance to CBT.

Several key conclusions can be drawn based on the results from the present study. First, gene expression analysis of TCGA data indicates that TGFβ1 is the most prevalent isoform in most human tumor types and is therefore the most likely driver of TGFβ signaling, hence the immunosuppressive culprit driving primary resistance to CBT, in these tumors.

Second, selective inhibition of TGFβ1 activation appears sufficient to overcome primary resistance to CBT. By targeting the prodomain of latent TGFβ1, a high-affinity, isoform-selective inhibitor of TGFβ1 achieves exquisite isoform specificity and inhibits latent TGFβ1 activation in all known molecular contexts. Pharmacological evaluation of one such antibody in syngeneic tumor models demonstrated that treatment with this antibody is sufficient to render anti-PD-1-resistant tumors sensitive to checkpoint blockade therapy. Importantly, antitumor efficacy of the anti-PD-1/TGFβ1 inhibitor combination was shown in three different tumor types, including one model in which TGFβ1 was not the only TGFβ isoform present in the tumor. This suggests that, within the tumor microenvironment, TGFβ1 is likely positioned to play an immunomodulatory role whereas other isoforms may not be relevant to this biology. This observation opens up the possibility that selective TGFβ1 inhibition may have therapeutic potential in overcoming primary resistance to CBT across a broad spectrum of cancers irrespective of the expression of other TGFβ isoforms.

Third, selective inhibition of TGFβ1-driven pathway activity results in significantly improved preclinical safety versus broad inhibition of all isoform activity. Pleiotropic effects associated with broad TGFβ pathway inhibition have hindered therapeutic targeting of the TGFβ pathway. Most experimental therapeutics to date (e.g., galunisertib, LY3200882, fresolimumab) lack selectivity for a single TGFβ isoform, potentially contributing to the dose-limiting toxicities observed in nonclinical and clinical studies. Genetic data from knockout mice and human loss-of-function mutations in the TGFβ2 or TGFβ3 genes suggest that the cardiac toxicities observed with nonspecific TGFβ inhibitors may be due to inhibition of TGFβ2 or TGFβ3. The present disclosure teaches that selective inhibition of TGFβ1 activation with such an antibody has an improved safety profile and is sufficient to elicit robust antitumor responses when combined with PD-1 blockade, enabling the evaluation of the TGFβ1 inhibitor efficacy at clinically tractable dose levels.

To dissect the immunological processes associated with anti-tumor immunity during TGFβ1 inhibitor/anti-PD-1 combination treatment, a more detailed analysis of responses in the MBT-2 bladder cancer model was conducted. Simultaneous blockade of PD-1 and TGFβ1 activity induced a profound change in the intratumoral immune contexture, largely driven by a 10-fold increase in CD8+ T cells. These CD8+ T cells were likely engaged in tumor cell killing, as the key cytolytic genes, perforin and granzyme B, were also upregulated in tumors by the combination treatment. Notably, the significant enrichment of Treg cells by the combination treatment with anti-PD-1/TGFβ1 inhibitor was somewhat unexpected, given the importance of TGFβ signaling for peripheral Treg maintenance. However, as Treg cells are recruited to sites of inflammation, their numerical increase can be interpreted as a marker for a robust immune response. Nonetheless, CD8+ T cells were able to adopt an activated phenotype and elicit a strong anti-tumor response despite an increase in Treg cell numbers. A potential explanation could be that Treg cells do not significantly contribute to the immunosuppressive MBT-2 tumor microenvironment and that other suppressive immune cell populations, for example myeloid cells, play a more important role. Alternatively, and not mutually exclusive of this possibility, given that TGFβ1 is a key mediator of Treg-driven immunosuppression, the presence of the TGFβ1 inhibitor may also abrogate this activity in spite of the increase in Treg numbers.

A surprising finding provided herein includes the histological observation of a close association of CD8+ T cells with CD31+ tumor vasculature. This pattern of enrichment supports the hypothesis that a key route of T cell entry into the tumor is through the tumor vasculature, and that cells start to migrate outward radially into the tumor once they extravasate from tumor blood vessels. Mariathasan et al. found that CD8+ T cells appeared to build up along the collagenous matrix and fibroblast-rich layer at the tumor's leading edge in the EMT-6 breast cancer model, leading to speculation that this matrix contributed to T cell exclusion. In contrast to this observation, it was not possible to consistently detect a dense fibroblastic area near the leading edge of MBT-2 tumors. Applicant's observation of T cell enrichment in close proximity to vasculature (e.g., perivascular enrichment) suggests that, in addition to the cancer-associated fibroblast layer, immune exclusion might also be imposed by TGFβ1-responsive vascular endothelial cells or by other cells in close proximity to the endothelium. Consistent with the possibility that TGFβ1 signaling may be influencing endothelial function, Applicant's observation includes that phospho-SMAD3 staining in control tumors was strongest in nuclei within what appear to be tumor vascular endothelial cells. This staining was sensitive to selective TGFβ1 inhibition, suggesting that these cells are responding to TGFβ1 and may be key in enforcing immune exclusion, perhaps through influencing T cell extravasation via regulating performance of vascular barrier integrity. Furthermore, tumor-associated macrophages have also been described to be in close proximity to tumor vasculature and may be involved in generating an immune-excluded tumor microenvironment, either by activation of TGFβ1 or by releasing other immunosuppressive surface proteins or secreted factors at or near the vasculature. It is likely that multiple routes for T cells to enter into a tumor are at play, and a better understanding of these mechanisms will aid in identification of novel therapeutic targets or inform on possible tumor resistance mechanisms.

In addition to the expected and observed impact on the disposition of cytotoxic T cells within tumors, the TGFβ1 inhibitor/anti-PD-1 combination treatment also beneficially impacts the immunosuppressive myeloid compartment. CD11b+ myeloid cells comprised nearly 80% of the immune infiltrate in untreated MBT-2 tumors, but their representation was reduced to less than 40% upon combination treatment. This was entirely driven by a loss of M2-like immunosuppressive macrophages and an even more profound reduction in MDSCs, while the proinflammatory M1-like macrophage population remained unchanged in representation. The mechanism by which combination treatment drives the specific reduction of immunosuppressive myeloid cells is unclear, as is the role of TGFβ1 signaling in the recruitment, development, or maintenance of these cells in the tumor microenvironment. It is known that TGFβ signaling, amongst other factors, polarizes macrophages into an M2-like. Additionally, there is evidence to suggest that TGFβ is partially responsible for MDSC development and acquisition of suppressive functions. Further, it is likely that the influx of IFNγ-secreting T cells paired with the altered tumor microenvironment contributed to both re-polarization and reduction of trafficking of immunosuppressive myeloid cells. Regardless of the underlying mechanism, a reduction of intratumoral immunosuppressive myeloid cells would be highly desired as part of a tumor immunotherapy approach, as the presence of this cell population is correlated with poor patient prognosis and resistance to checkpoint blockade therapy. Therefore, a therapeutic strategy that includes targeting of these important immunosuppressive cell types may have a greater effect than targeting a single immunosuppressive cell type (i.e., only Treg cells) in the tumor microenvironment. Thus, the TGFβ1 inhibitors of the present invention may be used to reduce tumor-associated immunosuppressive cells, such as M2 macrophages and MDSCs.

As mentioned previously, it is important to note that TGFβ1 is likely expressed by multiple cell types in the tumor microenvironment, including Treg cells, suppressive myeloid cells, fibroblasts, as well as tumor cells. Each of these cellular sources produce TGFβ1 in different LLCs: Activated Treg cells express GARP LLCs on their surface; suppressive myeloid cells express LRRC33 LLCs on their surface, and fibroblasts likely express and deposit LTBP LLCs into surrounding extracellular matrix. It is likely that each of these sources of "activatable" TGFβ1 could play a role in promoting immune exclusion and immune suppression in the tumor, and that the relative contributions of each source could vary across different tumor types. Interestingly, mRNA profiling of the MBT-2 and EMT6 tumors used in these studies indicated that LRRC33 and LTBP1 are the most highly expressed LLC components, and the Cloudman S91 tumors appear to exclusively express LRRC33 (FIG. 20H). As such, the profound antitumor effects of TGFβ1-selective inhibitor/anti-PD-1 combination in these models, along with the demonstrated ability of the TGFβ1 inhibitor disclosed herein to potently block TGFβ1 activation in all the known LLC contexts, strongly suggest that selective inhibition of specific LLCs (e.g., GARP on Treg cells) may not be sufficient for creating a maximal anti-tumor response in some tumors.

Thus, the preclinical studies and results presented herein demonstrate that highly specific inhibition of TGFβ1 activation enables the host immune system to overcome a key mechanism of primary resistance to checkpoint blockade therapy, while avoiding the previously recognized toxicities of broader TGFβ inhibition that have been a key limitation for clinical application. Results disclosed herein suggest that treatment with a high-affinity TGFβ1 inhibitor may meaningfully expand the number of patients who could benefit from checkpoint blockade therapies.

Accordingly as demonstrated in the Examples herein, high-affinity, isoform-selective inhibitors of TGFβ1 can be used to counter primary resistance to CBT, thereby rendering the tumor/cancer more susceptible to the CBT. Such effects may be applicable to treating a wide spectrum of malignancy types, where the cancer/tumor is TGFβ1-positive. In some embodiments, such tumor/cancer may further express additional isoform, such as TGFβ3. Non-limiting examples of the latter may include certain types of carcinoma, such as breast cancer.

Accordingly, the invention provides preferred selection criteria for identifying or selecting a patient or patient populations/sub-populations for which the high-affinity, context-independent inhibitors of TGFβ1 are likely to achieve clinical benefit. In some embodiments, suitable phenotypes of human tumors include: i) a subset(s) are shown to be responsive to CBT (e.g., PD-(L)1 axis blockade); ii) evidence of immune exclusion; and/or, iii) evidence of TGFB1 expression and/or TGFβ signaling. Various cancer types fit the profile, including, for example, melanoma and bladder cancer.

As mentioned above, context-independent inhibitors of TGFβ1 activation may be used in the treatment of Melanoma. The types of melanoma that may be treated with such inhibitors include, but are not limited to: Lentigo maligna; Lentigo maligna melanoma; Superficial spreading melanoma; Acral lentiginous melanoma; Mucosal melanoma; Nodular melanoma; Polypoid melanoma and Desmoplastic melanoma. In some embodiments, the melanoma is a metastatic melanoma.

More recently, immune checkpoint inhibitors have been used to effectively treat advanced melanoma patients. In particular, anti-programmed death (PD)-1 antibodies (e.g., nivolumab and pembrolizumab) have now become the standard of care for certain types of cancer such as advanced melanoma, which have demonstrated significant activity and durable response with a manageable toxicity profile. However, effective clinical application of PD-1 antagonists is encumbered by a high rate of innate resistance (~60-70%) (see Hugo et al. (2016) Cell 165: 35-44), illustrating that ongoing challenges continue to include the questions of patient selection and predictors of response and resistance as well as optimizing combination strategies (Perrot et al. (2013) Ann Dermatol 25(2): 135-144). Moreover, studies have suggested that approximately 25% of melanoma patients who initially responded to an anti-PD-1 therapy eventually developed acquired resistance (Ribas et al. (2016) JAMA 315: 1600-9).

The number of tumor-infiltrating CD8+ T cells expressing PD-1 and/or CTLA-4 appears to be a key indicator of success with checkpoint inhibition, and both PD-1 and CTLA-4 blockade may increase the infiltrating T cells. In patients with higher presence of tumor-associated macrophages, however, anti-cancer effects of the CD8 cells may be suppressed.

It is contemplated that LRRC33-expressing cells, such as myeloid cells, including myeloid precursors, MDSCs and TAMs, may create or support an immunosuppressive environment (such as TME and myelofibrotic bone marrow) by inhibiting T cells (e.g., T cell depletion), such as CD4 and/or CD8 T cells, which may at least in part underline the observed anti-PD-1 resistance in certain patient populations. Indeed, evidence suggests that resistance to anti-PD-1 monotherapy was marked by failure to accumulate CD8+ cytotoxic T cells and reduced Teff/Treg ratio. Notably, the present inventors have recognized that there is a bifurcation among certain cancer patients, such as a melanoma patient population, with respect to LRRC33 expression levels: one group exhibits high LRRC33 expression (LRRC33$^{high}$), while the other group exhibits relatively low LRRC33 expression (LRRC33$^{low}$). Thus, the invention includes the notion that the LRRC33$^{high}$ patient population may represent those who are poorly responsive to or resistant to immuno checkpoint inhibitor therapy. Accordingly, agents that inhibit LRRC33, such as those described herein, may be particularly beneficial for the treatment of cancer, such as melanoma, lymphoma, and myeloproliferative disorders, that is resistant to checkpoint inhibitor therapy (e.g., anti-PD-1).

In some embodiments, cancer/tumor is intrinsically resistant to or unresponsive to an immune checkpoint inhibitor (e.g., primary resistance). To give but one example, certain lymphomas appear poorly responsive to immune checkpoint inhibition such as anti-PD-1 therapy. Similarly, a subset of melanoma patient population is known to show resistance to immune checkpoint inhibitors. Without intending to be bound by particular theory, the inventors of the present disclosure contemplate that this may be at least partly due to upregulation of TGFβ1 signaling pathways, which may create an immunosuppressive microenvironment where checkpoint inhibitors fail to exert their effects. TGFβ1 inhibition may render such cancer more responsive to checkpoint inhibitor therapy. Non-limiting examples of cancer types which may benefit from a combination of an immune checkpoint inhibitor and a TGFβ1 inhibitor include: myelofibrosis, melanoma, renal cell carcinoma, bladder cancer, colon cancer, hematologic malignancies, non-small cell carcinoma, non-small cell lung cancer (NSCLC), lymphoma (classical Hodgkin's and non-Hodgkin's), head and neck cancer, urothelial cancer, cancer with high microsatellite instability, cancer with mismatch repair deficiency, gastric cancer, renal cancer, and hepatocellular cancer. However, any cancer (e.g., patients with such cancer) in which TGFβ1 is overexpressed or is the dominant isoform over TGFβ2/3, as determined by, for example biopsy, may be treated with an isoform-selective inhibitor of TGFβ1 in accordance with the present disclosure.

In some embodiments, a cancer/tumor becomes resistant over time. This phenomenon is referred to as acquired resistance. Like primary resistance, in some embodiments, acquired resistance is at least in part mediated by TGFβ1-dependent pathways. Isoform-specific TGFβ1 inhibitors described herein may be effective in restoring anti-cancer immunity in these cases. The TGFβ1 inhibitors of the present invention may be used to reduce recurrence of tumor. The TGFβ1 inhibitors of the present invention may be used to enhance durability of cancer therapy such as CBT. The term "durability" used in the context of therapies refers to the time between clinical effects (e.g., tumor control) and tumor re-growth (e.g., recurrence). Presumably, durability and recurrence may correlate with secondary or acquired resistance, where the therapy to which the patient initially responded stops working. Thus, the TGFβ1 inhibitors of the present invention may be used to increase the duration of time the cancer therapy remains effective. The TGFβ1 inhibitors of the present invention may be used to reduce the probability of developing acquired resistance among the responders of the therapy. The TGFβ1 inhibitors of the present invention may be used to enhance progression-free survival in patients.

In some embodiments, the TGFβ1 inhibitors of the present invention may be used to improve rates or ratios of complete verses partial responses among the responders of a cancer therapy. Typically, even in cancer types where response rates to a cancer therapy (such as CBT) are relatively high (e.g., >35%), CR rates are quite low. The TGFβ1 inhibitors of the present invention are therefore used to increase the fraction of complete responders within the responder population.

In addition, the inhibitors may be also effective to enhance or augment the degree of partial responses among partial responders.

In some embodiments, combination therapy comprising an immuno checkpoint inhibitor and an LRRC33 inhibitor (such as those described herein) may be effective to treat such cancer. In addition, high LRRC33-positive cell infiltrate in tumors, or otherwise sites/tissues with abnormal cell proliferation, may serve as a biomarker for host immunosuppression and immuno checkpoint resistance. Similarly, effector T cells may be precluded from the immunosuppressive niche which limits the body's ability to combat cancer. Moreover, as demonstrated in the Example section below, Tregs that express GARP-presented TGFβ1 suppress effector T cell proliferation. Together, TGFβ1 is likely a key driver in the generation and maintenance of an immune inhibitory disease microenvironment (such as TME), and multiple TGFβ1 presentation contexts are relevant for tumors. In some embodiments, the combination therapy may achieve more favorable Teff/Treg ratios.

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for treating cancer in a subject in need thereof, said method comprising administering the antibody, or antigen binding portion thereof, to the subject such that the cancer is treated. In certain embodiments, the cancer is colon cancer. In certain embodiments, the cancer is melanoma. In certain embodiments, the cancer is bladder cancer. In certain embodiments, the cancer is head and neck cancer. In certain embodiments, the cancer is lung cancer.

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for treating solid tumors. In some embodiments, solid tumors may be desmoplastic tumors, which are typically dense and hard for therapeutic molecules to penetrate. By targeting the ECM component of such tumors, such antibodies may "loosen" the dense tumor tissue to disintegrate, facilitating therapeutic access to exert its anti-cancer effects. Thus, additional therapeutics, such as any known anti-tumor drugs, may be used in combination.

Additionally or alternatively, isoform-specific, context-independent antibodies for fragments thereof that are capable of inhibiting TGFβ1 activation, such as those disclosed herein, may be used in conjunction with the chimeric antigen receptor T-cell ("CAR-T") technology as cell-based immunotherapy, such as cancer immunotherapy for combatting cancer.

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for inhibiting or decreasing solid tumor growth in a subject having a solid tumor, said method comprising administering the antibody, or antigen binding portion thereof, to the subject such that the solid tumor growth is inhibited or decreased. In certain embodiments, the solid tumor is a colon carcinoma tumor. In some embodiments, the antibodies, or antigen binding portions thereof useful for treating a cancer is an isoform-specific, context-independent inhibitor of TGFβ1 activation. In some embodiments, such antibodies target a GARP-TGFβ1 complex, a LTBP1-TGFβ1 complex, a LTBP3-TGFβ1 complex, and a LRRC33-TGFβ1 complex. In some embodiments, such antibodies target a GARP-TGFβ1 complex, a LTBP1-TGFβ1 complex, and a LTBP3-TGFβ1 complex. In some embodiments, such antibodies target a LTBP1-TGFβ1 complex, a LTBP3-TGFβ1 complex, and a LRRC33-TGFβ1 complex. In some embodiments, such antibodies target a GARP-TGFβ1 complex and a LRRC33-TGFβ1 complex.

The invention includes the use of context-independent, isoform-specific inhibitors of TGFβ1 in the treatment of cancer comprising a solid tumor in a subject. In some embodiments, such context-independent, isoform-specific inhibitor may inhibit the activation of TGFβ1. In preferred embodiments, such activation inhibitor is an antibody or antigen-binding portion thereof that binds a proTGFβ1 complex. The binding can occur when the complex is associated with any one of the presenting molecules, e.g., LTBP1, LTBP3, GARP or LRRC33, thereby inhibiting release of mature TGFβ1 growth factor from the complex. In some embodiments, the solid tumor is characterized by having stroma enriched with CD8+ T cells making direct contact with CAFs and collagen fibers. Such a tumor may create an immuno-suppressive environment that prevents anti-tumor immune cells (e.g., effector T cells) from effectively infiltrating the tumor, limiting the body's ability to fight cancer. Instead, such cells may accumulate within or near the tumor stroma. These features may render such tumors poorly responsive to an immune checkpoint inhibitor therapy. As discussed in more detail below, TGFβ1 inhibitors disclosed herein may unblock the suppression so as to allow effector cells to reach and kill cancer cells, for example, used in conjunction with an immune checkpoint inhibitor.

TGFβ1 is contemplated to play multifaceted roles in a tumor microenvironment, including tumor growth, host immune suppression, malignant cell proliferation, vascularity, angiogenesis, migration, invasion, metastasis, and chemo-resistance. Each "context" of TGFβ1 presentation in the environment may therefore participate in the regulation (or dysregulation) of disease progression. For example, the GARP axis is particularly important in Treg response that regulates effector T cell response for mediating host immune response to combat cancer cells. The LTBP1/3 axis may regulate the ECM, including the stroma, where cancer-associated fibroblasts (CAFs) play a role in the pathogenesis and progression of cancer. The LRRC33 axis may play a crucial role in recruitment of circulating monocytes to the tumor microenvironment, subsequent differentiation into tumor-associated macrophages (TAMs), infiltration into the tumor tissue and exacerbation of the disease.

In some embodiments, TGFβ1-expressing cells infiltrate the tumor, creating or contributing to an immunosuppressive local environment. The degree by which such infiltration is observed may correlate with worse prognosis. In some embodiments, higher infiltration is indicative of poorer treatment response to another cancer therapy, such as immune checkpoint inhibitors. In some embodiments, TGFβ1-expressing cells in the tumor microenvironment comprise immunosuppressive immune cells such as Tregs and/or myeloid cells. In some embodiments, the myeloid cells include, but are not limited to: macrophages, monocytes (tissue resident or bone marrow-derived), and MDSCs.

In some embodiments, LRRC33-expressing cells in the TME are myeloid-derived suppressor cells (MDSCs). MDSC infiltration (e.g., solid tumor infiltrate) may underline at least one mechanism of immune escape, by creating an immunosuppressive niche from which host's anti-tumor immune cells become excluded. Evidence suggest that MDSCs are mobilized by inflammation-associated signals, such as tumor-associated inflammatory factors, Opon mobilization, MDSCs can influence immunosuppressive effects by impairing disease-combating cells, such as CD8+ T cells and NK cells. In addition, MDSCs may induce differentiation of Tregs by secreting TGFβ and IL-10, further adding to the immunosuppressive effects. Thus, an isoform-specific TGFβ1 inhibitor, such as those described herein, may be administered to patients with immune evasion (e.g., compromised immune surveillance) to restore or boost the body's ability to fight the disease (such as tumor). As described in more detail herein, this may further enhance (e.g., restore or potentiate) the body's responsiveness or sensitivity to another therapy, such as cancer therapy.

In some embodiments, elevated frequencies (e.g., number) of circulating MDSCs in patients are predictive of poor responsiveness to checkpoint blockade therapies, such as PD-1 antagonists and PD-L1 antagonists. For example, biomarker studies showed that circulating pre-treatment HLA-DR lo/CD14+/CD11b+ myeloid-derived suppressor cells (MDSC) were associated with progression and worse OS (p=0.0001 and 0.0009). In addition, resistance to PD-1 checkpoint blockade in inflamed head and neck carcinoma (HNC) associates with expression of GM-CSF and Myeloid Derived Suppressor Cell (MDSC) markers. This observation suggested that strategies to deplete MDSCs, such as chemotherapy, should be considered in combination or sequentially with anti-PD-1. LRRC33 or LRRC33-TGFβ complexes represent a novel target for cancer immunotherapy due to selective expression on immunosuppressive myeloid cells. Therefore, without intending to be bound by particular theory, targeting this complex may enhance the effectiveness of standard-of-care checkpoint inhibitor therapies in the patient population.

The invention therefore provides the use of a high-affinity isoform-specific TGFβ1 inhibitor described herein for the treatment of cancer that comprises a solid tumor. Such treatment comprises administration of the TGFβ1 inhibitor to a subject diagnosed with cancer that includes at least one localized tumor (solid tumor) in an amount effective to treat the cancer. Preferably, the subject is further treated with a cancer therapy, such as CBT, chemotherapy and/or radiation therapy. In some embodiments, the TGFβ1 inhibitor increases the rate/fraction of a primary responder patient population to the cancer therapy. In some embodiments, TGFβ1 inhibitor increases the degree of responsiveness of primary responders to the cancer therapy. In some embodiments, TGFβ1 inhibitor increases the ratio of complete responders to partial responders to the cancer therapy. In some embodiments, TGFβ1 inhibitor increases the durability of the cancer therapy such that the duration before recurrence and/or before the cancer therapy becomes ineffective is prolonged. In some embodiments, TGFβ1 inhibitor reduces occurrences or probability of acquired resistance to the cancer therapy among primary responders.

Evidence suggests that cancer progression (e.g., tumor proliferation/growth, invasion, angiogenesis and metastasis) may be at least in part driven by tumor-stroma interaction. In particular, CAFs may contribute to this process by secretion of various cytokines and growth factors and ECM remodeling. Factors involved in the process include but are not limited to stromal-cell-derived factor 1 (SCD-1), MMP2, MMP9, MMP3, MMP-13, TNF-α, TGFβ1, VEGF, IL-6, M-CSF. In addition, CAFs may recruit TAMs by secreting factors such as CCL2/MCP-1 and SDF-1/CXCL12 to a tumor site; subsequently, a pro-TAM niche (e.g., hyaluronan-enriched stromal areas) is created where TAMs preferentially attach. Since TGFβ1 has been suggested to promote activation of normal fibroblasts into myofibroblast-like CAFs, administration of an isoform-specific, context-independent TGFβ1 inhibitor such as those described herein may be effective to counter cancer-promoting activities of CAFs. Indeed, data presented herein suggest that an isoform-specific context-independent antibody that blocks activation of TGFβ1 can inhibit UUO-induced upregulation of maker genes such as CCL2/MCP-1, α-SMA. FN1 and Col1, which are also implicated in many cancers.

In certain embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, are administered to a subject having cancer or a tumor, either alone or in combination with an additional agent, e.g., an anti-PD-1 antibody (e.g., an anti-PD-1 antagonist). Other combination therapies which are included in the invention are the administration of an antibody, or antigen binding portion thereof, described herein, with radiation (radiation therapy), or a chemotherapeutic agent (chemotherapy). Exemplary additional agents include, but are not limited to, a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody (OX40 agonist), an anti-CD27 antibody, an anti-CD70 antibody, an anti-CD47 antibody, an anti-41 BB antibody, an anti-PD-1 antibody, an anti-CD20 antibody, a CDK inhibitor, an oncolytic virus, and a PARP inhibitor. Examples of useful oncolytic viruses include, adenovirus, reovirus, measles, herpes simplex, Newcastle disease virus, senecavirus, enterovirus and vaccinia. In preferred embodiments, the oncolytic virus is engineered for tumor selectivity.

In some embodiments, determination or selection of therapeutic approach for combination therapy that suits particular cancer types or patient population may involve the following: a) considerations regarding cancer types for which a standard-of-care therapy is available (e.g., immunotherapy-approved indications); b) considerations regarding treatment-resistant subpopulations (e.g., immune excluded/cold tumors); and c) considerations regarding cancers/tumors that are or generally suspected to be "TGFβ1 pathway-active" or otherwise at least in part TGFβ1-dependent (e.g., TGFβ1 inhibition-sensitive). For example, many cancer samples show that TGFβ1 is the predominant isoform by, for instance, TCGA RNAseq analysis. In some embodiments, over 50% (e.g., over 50%, 60%, 70%, 80% and 90%) of samples from each tumor type are positive for TGFβ1 isoform expression. In some embodiments, the cancers/tumors that are "TGFβ1 pathway-active" or otherwise at least in part TGFβ1-dependent (e.g., TGFβ1 inhibition-sensitive) contain at least one Ras mutation, such as mutations in K-ras, N-ras and/or H-ras. In some embodiments, the cancer/tumor comprises at least one K-ras mutation.

Confirmation of TGFβ1 expression in clinical samples collected from patients (such as biopsy samples) is not prerequisite to TGFβ1 inhibition therapy, where the particular condition has been generally known or suspected to involve the TGFβ pathway.

In some embodiments, the isoform-specific, context-independent TGFβ1 inhibitor is administered in conjunction with checkpoint inhibitory therapy to patients diagnosed with cancer for which one or more checkpoint inhibitor therapies are approved or shown effective. These include, but are not limited to: bladder urothelial carcinoma, squamous cell carcinoma (such as head & neck), kidney clear cell carcinoma, kidney papillary cell carcinoma, liver hepatocellular carcinoma, lung adenocarcinoma, skin cutaneous melanoma, and stomach adenocarcinoma. In preferred embodiments, such patients are poorly responsive or non-responsive to the checkpoint inhibitor therapy. In some embodiments, the poor responsiveness is due to primary resistance. In some embodiments, the cancer that is resistant to checkpoint blockade shows downregulation of TCF7 expression. In some embodiments, TCF7 downregulation in checkpoint inhibition-resistant tumor may be correlated with a low number of intratumoral CD8+ T cells.

The isoform-specific, context-independent TGFβ1 inhibitor may be used in the treatment of chemotherapy- or radiotherapy-resistant cancers. Thus, in some embodiments, the isoform-specific, context-independent TGFβ1 inhibitor is administered to patients diagnosed with cancer for which they receive or have received chemotherapy and/or radiation therapy. In particular, the use of the TGFβ1 inhibitor is advantageous where the cancer (patient) is resistant to such therapy. In some embodiments, such cancer comprises quiescent tumor propagating cancer cells (TPCs), in which TGFβ signaling controls their reversible entry into a growth arrested state, which protects TPCs from chemotherapy or radiation therapy. It is contemplated that upon pharmacological inhibition of TGFβ1, TPCs with compromised fail to enter quiescence and thus rendered susceptible to chemotherapy and/or radiation therapy. Such cancer includes various carcinomas, e.g., squamous cell carcinomas. See, for example, Brown et al. (2017) "TGF-3-Induced Quiescence Mediates Chemoresistance of Tumor-Propagating Cells in Squamous Cell Carcinoma." Cell Stem Cell. 21(5):650-664.

In some embodiments, TGFβ1-positive cancer to be treated with the TGFβ1 inhibitor is also TGFβ3-positive (i.e., TGFβ1+/TGFβ3+ cancer) characterized in that the disease tissue (e.g., tumor) co-expresses both the isoforms. In some embodiments, such tumors are co-dominant with both the TGFβ1 and TGFβ3 isoforms. Accordingly, the invention includes the use of isoform-selective TGFβ1 inhibitor in conjunction with an isoform-selective TGFβ3 inhibitor in the treatment of such conditions. Non-limiting examples of TGFβ1+/TGFβ3+ cancers include but are not limited to: breast carcinoma (e.g., breast invasive carcinoma), cholangiocarcinoma, glioblastoma multiforme, head & neck squamous cell carcinoma, kidney clear cell carcinoma, lung squamous cell carcinoma, mesothelioma, pancreatic adenocarcinoma, prostate adenocarcinoma, sarcoma, thymoma and uterine carcinosarcoma.

Myeloproliferative Disorders/Myelofibrosis

The present disclosure provides therapeutic use of high-affinity, isoform-selective inhibitors of TGFβ1 such as those disclosed herein in the treatment of myeloproliferative disorders. These include, for example, myelodysplastic syndrome (MDS) and myelofibrosis (e.g., primary myelofibrosis and secondary myelofibrosis).

Myelofibrosis, also known as osteomyelofibrosis, is a relatively rare bone marrow proliferative disorder (cancer), which belongs to a group of diseases called myeloproliferative disorders. Myelofibrosis is classified into the Philadelphia chromosome-negative (−) branch of myeloproliferative neoplasms. Myelofibrosis is characterized by clonal myeloproliferation, aberrant cytokine production, extramedullary hematopoiesis, and bone marrow fibrosis. The proliferation of an abnormal clone of hematopoietic stem cells in the bone marrow and other sites results in fibrosis, or the replacement of the marrow with scar tissue. The term myelofibrosis, unless otherwise specified, refers to primary myelofibrosis (PMF). This may also be referred to as chronic idiopathic myelofibrosis (cIMF) (the terms idiopathic and primary mean that in these cases the disease is of unknown or spontaneous origin). This is in contrast with myelofibrosis that develops secondary to polycythemia vera or essential thrombocythaemia. Myelofibrosis is a form of myeloid metaplasia, which refers to a change in cell type in the blood-forming tissue of the bone marrow, and often the two terms are used synonymously. The terms agnogenic myeloid metaplasia and myelofibrosis with myeloid metaplasia (MMM) are also used to refer to primary myelofibrosis. In some embodiments, the hematologic proliferative disorders which may be treated in accordance with the present invention include myeloproliferative disorders, such as myelofibrosis. So-called "classical" group of BCR-ABL (Ph) negative chronic myeloproliferative disorders includes essential thrombocythemia (ET), polycythemia vera (PV) and primary myelofibrosis (PMF).

Myelofibrosis disrupts the body's normal production of blood cells. The result is extensive scarring in the bone marrow, leading to severe anemia, weakness, fatigue and often an enlarged spleen. Production of cytokines such as fibroblast growth factor by the abnormal hematopoietic cell clone (particularly by megakaryocytes) leads to replacement of the hematopoietic tissue of the bone marrow by connective tissue via collagen fibrosis. The decrease in hematopoietic tissue impairs the patient's ability to generate new blood cells, resulting in progressive pancytopenia, a shortage of all blood cell types. However, the proliferation of fibroblasts and deposition of collagen is thought to be a secondary phenomenon, and the fibroblasts themselves may not be part of the abnormal cell clone.

Myelofibrosis may be caused by abnormal blood stem cells in the bone marrow. The abnormal stem cells produce mature and poorly differentiated cells that grow quickly and take over the bone marrow, causing both fibrosis (scar tissue formation) and chronic inflammation.

Primary myelofibrosis is associated with mutations in Janus kinase 2 (JAK2), thrombopoietin receptor (MPL) and calreticulin (CALR), which can lead to constitutive activation of the JAK-STAT pathway, progressive scarring, or fibrosis, of the bone marrow occurs. Patients may develop extramedullary hematopoiesis, i.e., blood cell formation occurring in sites other than the bone marrow, as the haemopoetic cells are forced to migrate to other areas, particularly the liver and spleen. This causes an enlargement of these organs. In the liver, the abnormal size is called hepatomegaly. Enlargement of the spleen is called splenomegaly, which also contributes to causing pancytopenia, particularly thrombocytopenia and anemia. Another complication of extramedullary hematopoiesis is poikilocytosis, or the presence of abnormally shaped red blood cells.

The principal site of extramedullary hematopoiesis in myelofibrosis is the spleen, which is usually markedly enlarged in patients suffering from myelofibrosis. As a result of massive enlargement of the spleen, multiple subcapsular infarcts often occur in the spleen, meaning that due to interrupted oxygen supply to the spleen partial or complete tissue death happens. On the cellular level, the spleen contains red blood cell precursors, granulocyte precursors and megakaryocytes, with the megakaryocytes prominent in their number and in their abnormal shapes. Megakaryocytes may be involved in causing the secondary fibrosis seen in this condition.

It has been suggested that TGFβ may be involved in the fibrotic aspect of the pathogenesis of myelofibrosis (see, for example, Agarwal et al., "Bone marrow fibrosis in primary myelofibrosis: pathogenic mechanisms and the role of TGFβ" (2016) Stem Cell Investig 3:5). Bone marrow pathology in primary myelofibrosis is characterized by fibrosis, neoangeogenesis and osteosclerosis, and the fibrosis is associated with an increase in production of collagens deposited in the ECM.

A number of biomarkers have been described, alternations of which are indicative of or correlate with the disease. In some embodiments, the biomarkers are cellular markers. Such disease-associated biomarkers are useful for the diagnosis and/or monitoring of the disease progression as well as effectiveness of therapy (e.g., patients' responsiveness to the therapy). These biomarkers include a number of fibrotic markers, as well as cellular markers. In lung cancer, for example, TGFβ1 concentrations in the bronchoalveolar lavages (BAL) fluid are reported to be significantly higher in patients with lung cancer compared with patients with benign diseases (~2+ fold increase), which may also serve as a biomarker for diagnosing and/or monitoring the progression or treatment effects of lung cancer.

Because myelofibrosis is associated with abnormal megakaryocyte development, certain cellular markers of megakaryocytes as well as their progenitors of the stem cell lineage may serve as markers to diagnose and/or monitor the disease progression as well as effectiveness of therapy. In some embodiments, useful markers include, but are not limited to: cellular markers of differentiated megakaryocytes (e.g., CD41, CD42 and Tpo R), cellular markers of megakaryocyte-erythroid progenitor cells (e.g., CD34, CD38, and CD45RA−), cellular markers of common myeloid progenitor cells (e.g., IL-3a/CD127, CD34, SCF R/c-kit and Flt-3/Flk-2), and cellular markers of hematopoietic stem cells (e.g., CD34, CD38−, Flt-3/Flk-2). In some embodiments, useful biomarkers include fibrotic markers. These include, without limitation: TGFβ1/TGFB1, PAI-1 (also known as Serpine1), MCP-1 (also known as CCL2), Col1a1, Col3a1, FN1, CTGF, α-SMA, ACTA2, Timp1, Mmp8, and Mmp9. In some embodiments, useful biomarkers are serum markers (e.g., proteins or fragments found and detected in serum samples).

Based on the finding that TGFβ is a component of the leukemic bone marrow niche, it is contemplated that targeting the bone marrow microenvironment with TGFβ inhibitors may be a promising approach to reduce leukemic cells expressing presenting molecules that regulate local TGFβ availability in the effected tissue.

Indeed, due to the multifaceted nature of the pathology which manifests TGFβ3-dependent dysregulation in both myelo-proliferative and fibrotic aspects (as the term "myelofibrosis" itself suggests), isoform-specific, context-independent inhibitors of TGFβ1, such as those described herein, may provide particularly advantageous therapeutic effects for patients suffering from myelofibrosis. It is contemplated that the LTBP-arm of such inhibitor can target ECM-associated TGFβ1 complex in the bone marrow, whilst the LRRC33-arm of the inhibitor can block myeloid cell-associated TGFβ1. In addition, abnormal megakaryocyte biology associated with myelofibrosis may involve both GARP- and LTBP-mediated TGFβ1 activities. The isoform-specific, context-independent inhibitor of TGFβ1 is capable of targeting such complexes thereby inhibiting release of active TGFβ1 in the niche.

Thus, such TGFβ1 inhibitors are useful for treatment of patients with primary and secondary myelofibrosis, who have had an inadequate response to or are intolerant of other (or standard-of-care) treatments, such as hydroxyurea and JAK inhibitors. Such inhibitors are also useful for treatment of patients with intermediate or high-risk myelofibrosis (MF), including primary MF, post-polycythemia vera MF and post-essential thrombocythemia MF.

Accordingly, one aspect of the invention relates to methods for treating primary myelofibrosis. The method comprises administering to a patient suffering from primary myelofibrosis a therapeutically effective amount of a composition comprising a TGFβ inhibitor that causes reduced TGFβ availability. In some embodiments, an isoform-specific, context-context-independent monoclonal antibody inhibitor of TGFβ1 activation is administered to patients with myelofibrosis. Such antibody may be administered at dosages ranging between 0.1 and 100 mg/kg, such as between 1 and 30 mg, e.g., 1 mg/kg, 3 mg/kg, 5 mg/kg, 10 mg/kg, 15 mg/kg, 20 mg/kg, 30 mg/kg, etc. For example, suitable dosing regimens include between 1-30 mg/kg administered weekly. In some embodiments, the TGFβ1 inhibitor is dosed at about 10 mg/kg per week. Optionally, the frequency of administration may be adjusted after the initial phase, for example, from about once a week (during an initial phase) to once a month (during a maintenance phase).

Preferred routes of administration of a pharmaceutical composition comprising the antibody is intravenous or subcutaneous administration. When the composition is administered intravenously, the patient may be given the therapeutic over a suitable duration of time, e.g., approximately 30-120 minutes (e.g., 30 min, 60 min, 75 min, 90 min, and 120 min), per treatment, and then repeated every several weeks, e.g., 3 weeks, 4 weeks, 6 weeks, etc., for a total of several cycles, e.g., 4 cycles, 6, cycles, 8 cycles, 10 cycles, 12 cycles, etc. In some embodiments, patients are treated with a composition comprising the inhibitory antibody at dose level of 1-10 mg/kg (e.g., 1, 2, 3, 4, 5, 6, 7, 8, 9, or 10 mg/kg per dosing) via intravenous administration every 28 days (4 weeks) for 6 cycles or 12 cycles. In some embodiments, such treatment is administered as a chronic (long-term) therapy (e.g., to be continued indefinitely, as long as deemed beneficial) in lieu of discontinuing following a set number of cycles of administration.

While myelofibrosis is considered a type of leukemia, it is also characterized by the manifestation of fibrosis. Because TGFβ is known to regulate aspects of ECM homeostasis, the dysregulation of which can lead to tissue fibrosis, it is desirable to inhibit TGFβ activities associated with the ECM. Accordingly, antibodies or fragments thereof that bind and inhibit proTGFβ presented by LTBPs (such as LTBP1 and LTBP3) are encompassed by this invention. In some embodiments, antibodies or fragments thereof suitable for treating myelofibrosis are "context-independent" in that they can bind multiple contexts of proTGFβ complex, such as those associated with LRRC33, GARP, LTBP1, LTBP3, or any combination thereof. In some embodiments, such antibody is a context-independent inhibitor of TGFβ activation, characterized in that the antibody can bind and inhibit any of the following latent complexes: LTBP1-proTGFβ, LTBP3-proTGFβ, GARP-proTGFβ and LRRC33-proTGFβ. In some embodiments, such an antibody is an isoform-specific antibody that binds and inhibits such latent complexes that comprise one but not the other isoforms of TGFβ. These include, for example, LTBP1-proTGFβ1, LTBP3-proTGFβ1, GARP-proTGFβ1 and LRRC33-proTGFβ1. In some embodiments, such antibody is an isoform-selective antibody that preferentially binds with high affinity and inhibits TGFβ1 signaling.

Early in vivo data indicate that an isoform-selective context-independent inhibitor of TGFβ1, such as those described herein, can be used to treat myelofibrosis in a translatable murine model of primary myelofibrosis. Unlike the current standard of care JAK2 inhibitor, which only provides symptomic relief but does not provide clinical or survival benefits, the isoform-selective context-independent inhibitor of TGFβ1 achieves significant anti-fibrotic effects in the bone marrow of the diseased mice and may also prolong survival, supporting the notion that the TGFβ1 inhibitor may be effective to treat myeloproliferative disorders in human patients.

Suitable patient populations of myeloproliferative neoplasms who may be treated with the compositions and methods described herein may include, but are not limited to: a) a patient population that is Philadelphia (+); b) a patient population that is Philadelphia (−); c) a patient population that is categorized "classical" (PV, ET and PMF); d) a patient population carrying the mutation JAK2V617F (+); e) a patient population carrying JAK2V617F(−); f) a patient population with JAK2 exon 12(+); g) a patient population with MPL(+); and h) a patient population with CALR(+).

In some embodiments, the patient population includes patients with intermediate-2 or high-risk myelofibrosis. In some embodiments, the patient population comprises subjects with myelofibrosis who are refractory to or not candidates for available therapy. In some embodiments, the subject has platelet counts between 100-200×10$^9$/L. In some embodiments, the subject has platelet counts $>200\times10^9$/L prior to receiving the treatment.

In some embodiments, a subject to receive (and who may benefit from receiving) an isoform-specific, context-independent TGFβ1 inhibitor therapy is diagnosed with intermediate-1 or higher primary myelofibrosis (PMF), or post-polycythemmia vera/essential thrombocythemia myelofibrosis (post-PV/ET MF). In some embodiments, the subject has documented bone marrow fibrosis prior to the treatment. In some embodiments, the subject has MF-2 or higher as assessed by the European consensus grading score and grade 3 or higher by modified Bauermeister scale prior to the treatment. In some embodiments, the subject has the ECOG performance status of 1 prior to the treatment. In some embodiments, the subject has white blood cell count ($10^9$/L) ranging between 5 and 120 prior to the treatment.

In some embodiments, the subject has the JAK2V617Fallele burden that ranges between 10-100%. In some embodiments, a subject to receive (and who may benefit from receiving) an isoform-specific, context-independent TGFβ1 inhibitor therapy is transfusion-dependent (prior to the treatment) characterized in that the subject has a history of at least two units of red blood cell transfusions in the last month for a hemoglobin level of less than 8.5 g/dL that is not associated with clinically overt bleeding.

In some embodiments, a subject to receive (and who may benefit from receiving) an isoform-specific, context-independent TGFβ1 inhibitor therapy previously received a therapy to treat myelofibrosis. In some embodiments, the subject has been treated with one or more of therapies, including but are not limited to: AZD1480, panobinostat, EPO, IFNα, hydroxyurea, pegylated interferon, thalidomide, prednisone, and JAK2 inhibitor (e.g., Lestaurtinib, CEP-701).

In some embodiments, the patient has extramedullary hematopoiesis. In some embodiments, the extramedullary hematopoiesis is in the liver, lung, spleen, and/or lymph nodes. In some embodiments, the pharmaceutical composition of the present invention is administered locally to one or more of the localized sites of disease manifestation.

The isoform-specific, context-independent TGFβ1 inhibitor is administered to patients in an amount effective to treat myelofibrosis. The therapeutically effective amount is an amount sufficient to relieve one or more symptoms and/or complications of myelofibrosis in patients, including but are not limited to: excessive deposition of ECM in bone marrow stroma (fibrosis of the bone marrow), neoangiogenesis, osteosclerosis, splenomegaly, hematomegaly, anemia, bleeding, bone pain and other bone-related morbidity, extramedullary hematopoiesis, thrombocytosis, leukopenia, cachexia, infections, thrombosis and death. Thus, TGFβ1 inhibition therapies comprising the antibodies or antigen-binding fragments of the disclosure may achieve clinical benefits, which include, inter alia, anti-fibrotic effects and/or normalization of blood cell counts. Such therapy may prolong survival and/or reduce the need for bone marrow transplantation.

In some embodiments, the amount is effective to reduce TGFβ1 expression and/or secretion (such as of megakaryocytic cells) in patients. Such inhibitor may therefore reduce TGFβ1 mRNA levels in treated patients. In some embodiments, such inhibitor reduces TGFβ1 mRNA levels in bone marrow, such as in mononuclear cells. PMF patients typically show elevated plasma TGFβ1 levels of above ~2,500 μg/mL, e.g., above 3,000, 3,500, 4,000, 4,500, 5,000, 6,000, 7,000, 8,000, 9,000, and 10,000 μg/mL (contrast to normal ranges of ~600-2,000 μg/mL as measured by ELISA) (see, for example, Mascaremhas et al. (Leukemia & Lymphoma, 2014, 55(2): 450-452)). Zingariello (Blood, 2013, 121(17): 3345-3363) quantified bioactive and total TGFβ1 contents in the plasma of PMF patients and control individuals. According to this reference, the median bioactive TGFβ1 in PMF patients was 43 ng/mL (ranging between 4-218 ng/mL) and total TGFβ1 was 153 ng/mL (32-1000 ng/mL), while in control counterparts, the values were 18 (0.05-144) and 52 (8-860), respectively. Thus, based on these reports, plasma TGFβ1 contents in PMF patients are elevated by several fold, e.g., 2-fold, 3-fold, 4-fold, 5-fold, etc., as compared to control or healthy plasma samples. Treatment with the inhibitor, e.g., following 4-12 cycles of administration (e.g., 2, 4, 6, 8, 10, 12 cycles) or chronic or long-term treatment, for example every 4 weeks, at dosage of 0.1-100 mg/kg, for example, 1-30 mg/kg monoclonal antibody) described herein may reduce the plasma TGFβ1 levels by at least 10% relative to the corresponding baseline (pre-treatment), e.g., at least 15%, 20%, 25%, 30%, 35%, 40%, 45%, and 50%.

Some of the therapeutic effects may be observed relatively rapidly following the commencement of the treatment, for example, after 1 week, 2 weeks, 3 weeks, 4 weeks, 5 weeks or 6 weeks. For example, the inhibitor may effectively increase the number of stem cells and/or precursor cells within the bone marrow of patients treated with the inhibitor within 1-8 weeks. These include hematopoietic stem cells and blood precursor cells. A bone marrow biopsy may be performed to assess changes in the frequencies/number of marrow cells. Correspondingly, the patient may show improved symptoms such as bone pain and fatigue.

Subjects suffering from a myeloproliferative disorder (e.g., myelofibrosis) may manifest an elevated level of white blood cell counts (e.g., leukemic). In some embodiments, the therapeutically effective amount of the TGFβ1 inhibitor is an amount that is effective to normalize blood cell counts. In some embodiments, the amount is effective to reduce total white cell counts in the subject, as compared to pre-treatment. In some embodiments, the amount is effective to reduce total platelet counts in the subject, as compared to pre-treatment. In some embodiments, the amount is effective to increase (e.g., normalize or restore) hemoglobin levels in the subject, as compared to pre-treatment. In some embodiments, the amount is effective to increase (e.g., normalize or restore) hematocrit levels in the subject, as compared to pre-treatment.

One of the morphological hallmarks of myelofibrosis is fibrosis in the bone marrow (e.g., marrow stroma), characterized in part by aberrant ECM. In some embodiments, the amount is effective to reduce fibrosis, characterized by excessive collagen deposition, e.g., by mesenchymal stromal cells. In some embodiments, the inhibitor is effective to reduce the number of CD41-positive cells, e.g., megakaryocytes, in treated subjects, as compared to control subjects that do not receive the treatment. In some embodiments, baseline frequencies of megakaryocytes in PMF bone marrow may range between 200-700 cells per square millimeters ($mm^2$), and between 40-300 megakaryocites per square-millimeters ($mm^2$) in PMF spleen, as determined with randomly chosen sections. In contrast, megakaryocyte frequencies in bone marrow and spleen of normal donors are fewer than 140 and fewer than 10, respectively. Treatment with the inhibitor may reduce the number (e.g., frequencies) of megakaryocytes in bone marrow and/or spleen. In some embodiments, treatments with the inhibitor can cause reduced levels of downstream effector signaling, such as phosphorylation of SMAD2/3. In some embodiments, the inhibitor is effective to reduce expression levels of fibrotic markers, such as those described herein.

Patients with myelofibrosis may suffer from enlarged spleen. Thus, clinical effects of a therapeutic may be evaluated by monitoring changes in spleen size. Spleen size may be examined by known techniques, such as assessment of the spleen length by palpation and/or assessment of the spleen volume by ultrasound. In some embodiments, the subject to be treated with an isoform-specific, context-independent inhibitor of TGFβ1 has a baseline spleen length (prior to the treatment) of 5 cm or greater, e.g., ranging between 5 and 30 cm as assessed by palpation. In some embodiments, the subject to be treated with an isoform-specific, context-independent inhibitor of TGFβ1 has a baseline spleen volume (prior to the treatment) of 300 mL or greater, e.g., ranging between 300-1500 mL, as assessed by ultrasound. Treatment with the inhibitor, e.g., following 4-12 cycles of administration (e.g., 2, 4, 6, 8, 10, 12 cycles), for example every 4 weeks, at dosage of 0.1-30 mg/kg monoclonal antibody) described herein may reduce spleen size in the subject. In some embodiments, the effective amount of the inhibitor is sufficient to reduce spleen size in a patient population that receives the inhibitor treatment by at least 10%, 20%, 30%, 35%, 40%, 50%, and 60%, relative to corresponding baseline values. For example, the treatment is effective to achieve a ≥35% reduction in spleen volume from baseline in 12-24 weeks as measured by MRI or CT scan, as compared to placebo control. In some embodiments, the treatment is effective to achieve a ≥35% reduction in spleen volume from baseline in 24-48 weeks as measured by MRI or CT scan, as compare to best available therapy control. Best available therapy may include hydroxyurea, glucocorticoids, as well as no medication, anagrelide, epoetin alfa, thalidomide, lenalidomide, mercaptopurine, thioguanine, danazol, peginterferon alfa-2a, interferon-α, melphalan, acetylsalicylic acid, cytarabine, and colchicine.

In some embodiments, a patient population treated with an isoform-specific, context-independent TGFβ1 inhibitor such as those described herein, shows a statistically improved treatment response as assessed by, for example, International Working Group for Myelofibrosis Research and Treatment (IWG-MRT) criteria, degree of change in bone marrow fibrosis grade measured by the modified Bauermeister scale and European consensus grading system after treatment (e.g., 4, 6, 8, or 12 cycles), symptom response using the Myeloproliferative Neoplasm Symptom Assessment Form (MPN-SAF).

In some embodiments, the treatment with an isoform-specific, context-independent TGFβ1 inhibitor such as those described herein, achieves a statistically improved treatment response as assessed by, for example, modified Myelofibrosis Symptom Assessment Form (MFSAF), in which symptoms are measured by the MFSAF tool (such as v2.0), a daukt diary capturing the debilitating symptoms of myelofibrosis (abdominal discomfort, early satiety, pain under left ribs, pruritus, night sweats, and bone/muscle pain) using a scale of 0 to 10, where 0 is absent and 10 is the worst imaginable. In some embodiments, the treatment is effective to achieve a 50%≥reduction in total MFSAF score from the baseline in, for example, 12-24 weeks. In some embodiments, a significant fraction of patients who receive the therapy achieves a ≥50% improvement in Total Symptom Score, as compared to patients taking placebo. For example, the fraction of the patient pool to achieve ≥50% improvement may be over 40%, 50%, 55%, 60%, 65%, 70%, 75% or 80%.

In some embodiments, the therapeutically effective amount of the inhibitor is an amount sufficient to attain clinical improvement as assessed by an anemia response. For example, an improved anemia response may include longer durations of transfusion-independence, e.g., 8 weeks or longer, following the treatment of 4-12 cycles, e.g., 6 cycles.

In some embodiments, the therapeutically effective amount of the inhibitor is an amount sufficient to maintain stable disease for a duration of time, e.g., 6 weeks, 8 weeks, 12 weeks, six months, etc. In some embodiments, progression of the disease may be evaluated by changes in overall bone marrow cellularity, the degree of reticulin or collagen fibrosis, and/or a change in JAK2V617Fallele burden.

In some embodiments, a patient population treated with an isoform-specific, context-independent TGFβ1 inhibitor such as those described herein, shows statistically improved (prolonged) survival, as compared to a control population that does not receive the treatment. For example, in control groups, median survival of PMF patients is approximately six years (approximately 16 months in high-risk patients), and fewer than 20% of the patients are expected to survive 10 years or longer post-diagnosis. Treatment with the isoform-specific, context-independent TGFβ1 inhibitor such as those described herein, may prolong the survival time by, at least 6 months, 12 months, 18 months, 24 months, 30 months, 36 months, or 48 months. In some embodiments, the treatment is effective to achieve improved overall survival at 26 weeks, 52 weeks, 78 weeks, 104 weeks, 130 weeks, 144 weeks, or 156 weeks, as compared to patients who receive placebo.

Clinical benefits of the therapy, such as those exemplified above, may be seen in patients with or without new onset anemia.

One of the advantageous features of the isoform-specific, context-independent TGFβ1 inhibitors is that they maintain improved safety profiles enabled by isoform selectivity, as compared to conventional TGFβ antagonists that lack the selectivity. Therefore, it is anticipated that treatment with an isoform-specific, context-independent inhibitor, such as those described herein, may reduce adverse events in a patient population, in comparison to equivalent patient populations treated with conventional TGFβ antagonists, with respect to the frequency and/or severity of such events. Thus, the isoform-specific, context-independent TGFβ1 inhibitors may provide a greater therapeutic window as to dosage and/or duration of treatment.

Adverse events may be graded by art-recognized suitable methods, such as Common Terminology Criteria for Adverse Events (CTCAE) version 4. Previously reported adverse events in human patients who received TGFβ antagonists, such as GC1008, include: leukocytosis (grade 3), fatigue (grade 3), hypoxia (grade 3), asystole (grade 5), leukopenia (grade 1), recurrent, transient, tender erythematous, nodular skin lesions, suppurative dermatitis, and herpes zoster.

The isoform-specific, context-independent TGFβ1 inhibitor therapy may cause less frequent and/or less severe adverse events (side effects) as compared to JAK inhibitor therapy in myelofibrosis patients, with respect to, for example, anemia, thrombocytopenia, neutropenia, hypercholesterolemia, elevated alanine transaminase (ALT), elevated aspartate transaminase (AST), bruising, dizziness, and headache, thus offering a safer treatment option.

It is contemplated that inhibitors of TGFβ1 signaling may be used in conjunction with one or more therapeutics for the treatment of myelofibrosis as a combination (e.g., "add-on")

therapy. In some embodiments, an inhibitor of TGFβ1 activation described herein is administered to patients suffering from myelofibrosis, who have received or are candidates for receiving a JAK1 inhibitor, JAK2 inhibitor or JAK1/JAK2 inhibitor. In some embodiments, such patients are responsive to the JAK1 inhibitor, JAK2 inhibitor or JAK1/JAK2 inhibitor therapy, while in other embodiments such patients are poorly responsive or not responsive to the JAK1 inhibitor, JAK2 inhibitor or JAK1/JAK2 inhibitor therapy. In some embodiments, use of an isoform-specific inhibitor of TGFβ1 described herein may render those who are poorly responsive or not responsive to the JAK1 inhibitor, JAK2 inhibitor or JAK1/JAK2 inhibitor therapy more responsive. In some embodiments, use of an isoform-specific inhibitor of TGFβ1 described herein may allow reduced dosage of the JAK1 inhibitor, JAK2 inhibitor or JAK1/JAK2 inhibitor which still produces equivalent or meaningful clinical efficacy or benefits in patients but with fewer or lesser degrees of drug-related toxicities or adverse events (such as those listed above). In some embodiments, treatment with the inhibitor of TGFβ1 activation described herein used in conjunction with JAK1 inhibitor, JAK2 inhibitor or JAK1/JAK2 inhibitor therapy may produce synergistic or additive therapeutic effects in patients. In some embodiments, treatment with the inhibitor of TGFβ1 activation described herein may boost the benefits of JAK1 inhibitor, JAK2 inhibitor or JAK1/JAK2 inhibitor or other therapy given to treat myelofibrosis. In some embodiments, patients may additionally receive a therapeutic to address anemia associated with myelofibrosis.

Fibrotic Conditions

In response to tissue injury due physical damage/trauma, toxic substances, and/or infection, a natural reparative process begins which involves several cell types including fibroblasts, several different types of immune cells, and resident epithelial and endothelial cells. However, if left unchecked, this process can lead to excessive accumulation of extracellular matrix (ECM) and fibrosis, which in turn can lead to progressive loss of tissue function and organ failure (Caja et al., *Int. J. Mol. Sci.* 2018, 19, 1294).

Fibrosis can occur in a number of organs, including lung, kidney, liver, heart, and skin. Independent of the organ, the fibrotic response is characterized by inflammation, altered epithelial-mesenchymal interactions, and proliferation of fibroblasts. One of the hallmarks of fibrosis is the differentiation of fibroblasts into myofibroblasts, which greatly contribute to the dysregulation of the ECM. However, myofibroblasts have also been proposed to come from other cellular sources (e.g., endothelial cells, epithelial cells, and mesenchymal stem cells (Kim, K. K. et al, Cold Spring Harb. Perspect. Biol., 2017; Okabe, H. *Histol. Histopathol.*, 2016, 31, 141-148; and Li, C et al, Nat Commun., 2016, 7, 11455 and). Moreover, immune cells play an important role in the process by secreting cytokines and chemokines which promote differentiation of myofibroblasts, stimulate ECM deposition, and recruit additional immune cells to the damaged tissue (Caja et al., Int. J. Mol. Sci. 2018, 19, 1294).

Similar to fibrotic tissue, activation of cancer-associate fibroblasts can occur in the tumor milieu, which produces excessive amounts of ECM. The ECM provides a scaffold for the infiltration of other cells (e.g., pro-tumorigenic immune cells) and a substrate for cell migration. In other cases, excessive ECM may act as a barrier against anti-tumorigenic immune cells.

TGFβ is recognized as the central orchestrator of the fibrotic response. TGFβ can promote myofibroblast differentiation, recruit immune cells, and affect epithelial and endothelial cell differentiation. Particularly, TGFβ upregulates the production of ECM and basement membrane proteins, such as fibronectin, collagen, laminin, osteopontin, tenascin, elastin, decorin. TGFβ3-induced myofibroblast differentiation can lead to additional deposition of ECM proteins, secretion of matric metalloproteinases (MMPs), and myofibroblast proliferation (Fabregat et al, *FEBS J.* 2016, 283, 2219-2232; Meng et al, *Nat. Rev. Nephrol.* 2016, 12, 325-338; and Kulkarni et al., *Am. J. Respir. Cell Mol. Biol.*, 2016, 54, 751-760). Additionally, TGFβ mediates phenotypic changes affecting contractile proteins and collagen I in vascular smooth muscle cells (VSCM), and can activate myofibroblasts and other stromal cells to enhance the synthesis of collagen cross-linking proteins, such as lysyl oxidase (LOX) family of matrix-remodeling enzymes (Busnadiego et al., *Mol. Cell. Biol.* 2013, 33, 2388-2401). Moreover, TGFβ has been shown to regulate both EMT and EndMT, which contributes to the differentiation of pro-fibrotic cell types, such as myofibroblasts and CAFs. Moreover, TGFβ has been shown to induce epithelial apoptosis, which can promote lung and liver fibrosis among other tissues (Barbas-Filho et al., *J. Clin. Pathol.* 2001, 54, 132-138; and Wang et al., *Dev. Dyn.* 2017, 247, 492-508).

Whether innate or recruited, macrophages play an important role in responding to tissue damage and repair. However, upon certain signals they can become pro-fibrotic. TGFβ, among other cytokines, has also been shown to activate M2 macrophages, which are pro-inflammatory. Upon activation, these macrophages secrete their own cytokines, including TGFβ, ECM components, angiogenic factors, and chemotactic factors. M2 macrophages have been shown to be essential for TGFβ-driven lung fibrosis (Murray et al., *Int. J. Biochem. Cell Biol.* 2011, 43, 154-162).

Thus, according to the invention, isoform-specific, inhibitors TGFβ1 such as those described herein are used in the treatment of fibrosis (e.g., fibrotic indications, fibrotic conditions) in a subject. Suitable inhibitors to carry out the present invention include antibodies and/or compositions according to the present disclosure which may be useful for altering or ameliorating fibrosis. More specifically, such antibodies and/or compositions are selective antagonists of TGFβ1 that are capable of targeting TGFβ1 presented by various types of presenting molecules.

Antibodies targeting TGFβ decrease fibrosis in numerous preclinical models. Such antibodies and/or antibody-based compounds include LY2382770 (Eli Lilly, Indianapolis, IN). Also included are those described in U.S. Pat. Nos. 6,492, 497, 7,151,169, 7,723,486 and U.S. Appl. Publ. No. 2011/0008364, the contents of each of which are herein incorporated by reference in their entirety. Prior art TGFβ antagonists include, for example, agents that target and block integrin-dependent activation of TGFβ.

However, evidence suggests that such prior art agents may not mediate isoform-specific inhibition and may cause unwanted effects by inadvertently blocking normal function of TGFβ2 and/or TGFβ3. Indeed, Applicant previously noted that normal (undiseased) lung tissues contain relatively low but measurable levels of TGFβ2 and TGFβ3, but notably less TGFβ1. In comparison, in certain disease conditions such as fibrosis, TGFβ1 becomes preferentially upregulated relative to the other isoforms (WO 2018/129329). Preferably, TGFβ antagonists for use in the treatment of such conditions exert their inhibitory activities only towards the disease-induced or disease-associated isoform, while preserving the function of the other isoforms that are normally expressed to mediate tonic signaling in the tissue.

Prior art inhibitors (LY2109761, a small molecule TGFβ receptor antagonist, and a monoclonal antibody that targets αVβ6 integrin) both are shown to inhibit TGFβ downstream tonic signaling in non-diseased rat BAL, raising the possibility that these inhibitors may cause unwanted side effects. Alternatively or additionally, agents that target and block integrin-dependent activation of TGFβ may be capable of blocking only a subset of integrins responsible for disease-associated TGFβ1 activation, among numerous integrin types that are expressed by various cell types and play a role in the pathogenesis. Furthermore, even where such antagonists may selectively block integrin-mediated activation of the TGFβ1 isoform, it may be ineffective in blocking TGFβ1 activation triggered by other modes, such as protease-dependent activation. By contrast, the isoform-specific, inhibitors of TGFβ1 such as those described herein are aimed to prevent the activation step of TGFβ1 regardless of the particular mode of activation, while maintaining isoform selectivity.

It is further contemplated that isoform-specific TGFβ3 inhibitors may offer a therapeutic benefit in particular disease states. For example, certain fibrotic diseases to be treated with a TGFβ1 inhibitor may also be TGFβ3-positive (i.e., TGFβ1+/TGFβ3+ fibrotic tissue) characterized in that the disease tissue (e.g., fibrotic tissue) expresses both the isoforms. Accordingly, the invention includes the use of isoform-selective TGFβ1 inhibitor in conjunction with an isoform-selective TGFβ3 inhibitor in the treatment of such conditions. Such TGFβ3 inhibitors may be context-independent or context-biased.

Fibrotic indications for which antibodies and/or compositions of the present disclosure may be used therapeutically include, but are not limited to lung indications (e.g. idiopathic pulmonary fibrosis (IPF), chronic obstructive pulmonary disorder (COPD), allergic asthma, acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease (CKD), fibrosis associated with kidney transplantation and chronic rejection, IgA nephropathy, and hemolytic uremic syndrome), liver fibrosis (e.g., associated with or caused by non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g. skin fibrosis in systemic sclerosis, diffuse cutaneous systemic sclerosis, scleroderma, pathological skin scarring, keloid, post-surgical scarring, scar revision surgery, radiation-induced scarring and chronic wounds), eye-related conditions such as subretinal fibrosis, uveitis syndrome, uveitis associated with idiopathic retroperitoneal fibrosis, extraocular muscle fibrosis, eye diseases associated with the major histocompatibility complex (MHC class I) or histocompatibility antigens, subretinal fibrosis in macular degeneration (e.g., age-related macular degeneration), and cancers or secondary fibrosis (e.g. myelofibrosis, head and neck cancer, M7 acute megakaryoblastic leukemia and mucositis). Other diseases, disorders or conditions related to fibrosis (including degenerative disorders) that may be treated using compounds and/or compositions of the present disclosure, include, but are not limited to adenomyosis, endometriosis, Marfan's syndrome, stiff skin syndrome, scleroderma, rheumatoid arthritis, bone marrow fibrosis, Crohn's disease, ulcerative colitis, systemic lupus erythematosus, muscular dystrophy (such as DMD), Parkinson's disease, ALS, Dupuytren's contracture, Camurati-Engelmann disease, neural scarring, dementia, proliferative vitreoretinopathy, corneal injury, complications after glaucoma drainage surgery, and multiple sclerosis (MS).

Many fibrotic indications are also associated with inflammation of the affected tissue(s), indicating involvement of an immune component. Such inflammation may be accompanied by aberrant immune cell populations, such as increased numbers of Th17 cells, reduced numbers of Treg cells, and/or both. In each case, the affected patient may exhibit increased Th17/Treg cell ratios. The GARP- and/or LRRC33-targeting activities of the isoform-selective antibodies may provide inhibitory effects on these contexts.

In some embodiments, fibrotic indications that may be treated with the compositions and/or methods described herein include organ fibrosis, such as fibrosis of the lung (e.g., IPF), fibrosis of the kidney (e.g., fibrosis associated with CKD), fibrosis of the liver (e.g., associated with or due to NASH), fibrosis of the heart or cardiac tissues, fibrosis of the skin (e.g., scleroderma), fibrosis of the uterus (e.g., endometrium, myometrium), fibrosis of muscle (e.g., skeletal muscle), and fibrosis of the bone marrow. In some embodiments, such therapy may reduce or delay the need for organ transplantation in patients. In some embodiments, such therapy may prolong the survival of the patients.

To treat IPF, patients who may benefit from the treatment include those with familial IPF and those with sporadic IPF. Administration of a therapeutically effective amount of an isoform-specific, inhibitor of TGFβ1 may reduce myofibroblast accumulation in the lung tissues, reduce collagen deposits, reduce IPF symptoms, improve or maintain lung function, and prolong survival. In some embodiments, the inhibitor blocks activation of ECM-associated TGFβ1 (e.g., pro/latent TGFβ1 presented by LTBP1/3) within the fibrotic environment of IPF. The inhibitor may optionally further block activation of macrophage-associated TGFβ1 (e.g., pro/latent TGFβ1 presented by LRRC33), for example, alveolar macrophages. As a result, the inhibitor may suppress fibronectin release and other fibrosis-associated factors. In some embodiments, the inhibitor blocks hepatic stellate cell activation.

It is well-established that the activation of hepatic stellate cells (HSCs) are the central drivers of fibrosis in liver injury. In this process, quiescent, vitamin-A-storing cells, transdifferentiated into proliferative, fibrogenic myofibroblasts (the principal source of extracellular matrix (ECM) protein accumulation). However, this process has been shown to be mediated by many different pathways, including autophagy, endoplasmic reticulum stress, oxidative stress, retinol and cholesterol metabolism, epigenetics, and receptor-mediated signals. Moreover, inflammatory cells including macrophages, hepatocytes, liver sinusoidal endothelial cells, natural killer cells, natural killer T cells, platelets and B cells have also been shown to modulate HSC activation (Tsuchida and Friedman, Nature Reviews Gastroenterology & Hepatology volume 14, pages 397-411 (2017)). In just one particular example, Seki et al demonstrated that TLR4 (which recognizes LPS presented by bacteria) activation leads to upregulation of chemokine secretion and induces chemotaxis of Kupffer cells, and also sensitizes HSCs to TGFβ-induced signals and allows for unrestricted activation of Kupffer cells (Seki et al. Nature Medicine volume 13, pages 1324-1332 (2007)).

It is well known that inflammation plays a key role in liver fibrosis development and progression. Specifically, liver injury leads to inflammation and the recruitment of monocytes/macrophages (as well as lymphocytes, eosinophils, and plasma cells) which produce pro-fibrotic factors, including TGFβ. Moreover, the research indicates that both hepatic tissue-resident macrophages (Kupffer cells) and bone marrow-derived recruited macrophages play important roles in the progression of liver fibrosis, and that the TGFβ pathway can promote the polarization and pro-fibrotic functions of macrophages during liver fibrosis. Indeed, it has been shown that both Kupffer cells and recruited macrophages can activate HSCs and induce their transdifferentiation into myofibroblasts by paracrine mechanisms, including TGFβ. The myofibroblasts in turn produce and deposit ECM components leading to fibrosis (Fabregat and Caballero-Diaz, Front Oncol. 2018; 8: 357).

However, myofibroblasts may originate from other sources as well, including portal and resident fibroblasts, bone marrow-derived fibrocytes, liver epithelial cells that undergo EMT, endothelial cells that undergo EndMT, and vascular smooth muscle cells and pericytes. Indeed, TGFβ has also been shown to regulate both EndMT and EMT resulting in increased myofibroblasts, which drive liver fibrosis. (Pardali et al., Int J Mol Sci. 2017 October; 18(10): 2157). Accordingly, targeting TGFβ has been an attractive therapeutic target for the treatment of fibrotic conditions.

TGFβ has been shown to play many roles in liver fibrosis and disease progression. For example, TGFβ has been shown to be responsible for the activation HSCs to myofibroblasts. TGFβ also has been shown to mediate epithelial-mesenchymal transition (EMT) in hepatocytes that may contribute to increase the myofibroblast population. Moreover, TGFβ has been shown to induce changes in tumor cell plasticity (Fabregat and Caballero-Diaz, Front Oncol. 2018; 8: 357).

Although TGFβ can be found on many different cellular sources in the fibrotic and/or tumor microenvironment, thus suggesting TGFb presentation by multiple different presenting molecules (e.g., LTBP1, LTBP3, GARP, and/or LRRC33), it may be beneficial in certain situations to target particular sources of TGFβ over others. For example, Henderson et al, showed that deleting αv integrin in HSCs, protected mice form $CCL_4$-induced liver fibrosis (Henderson et al, Nat. Med. 2013, 19, 1617-16-24). Because integrins are the main activators of LTBP-presented TGFβ, this result suggests that targeting LTBP-presented TGFβ may be sufficient to treat fibrosis in certain situations. However, because immune cells play an important role in the fibrotic response, TGFβ inhibitors that target TGFβ presented by most or all of the presenting-molecule TGFβ complexes may be beneficial.

In recent years, the treatment of liver fibrosis has become an area of increased interest due to its increasing prevalence around the world. For example, non-alcoholic fatty liver disease (NAFLD) is associated with metabolic abnormalities such as obesity, insulin resistance, fasting hyperglycemia, dyslipidaemia, and altered adipokine profiles. NAFLD is characterized by excessive lipid accumulation in hepatocytes and is a spectrum of diseases progressing from liver steatosis (lipid/fat droplet accumulation in hepatocytes) to non-alcoholic steatohepatitis (NASH), liver fibrosis, and eventually cirrhosis in the most severe cases. NASH with fibrosis or cirrhosis increases the risk of developing hepatocellular carcinoma (HCC) (Starley B Q, et al. Hepatology 2010; 51: 1820-1832). The progression from steatosis to NASH has been proposed to be regulated by a 'multiple-hit' model, wherein the first hit is insulin resistance and metabolic disturbance, which leads to liver steatosis, followed by oxidative stress, proinflammatory cytokine-mediated hepatocyte injury, altered lipid partitioning and hepatoxicity mediated by free fatty acids, abnormal intrahepatic cholesterol loading, hyperinsulinaemia, hyperleptinaemia, and hypoadiponectinaemia (Tilg H, Moschen A R, Hepatology 2010; 52: 1836-1846; and Yilmaz Y., Aliment Pharmacol Ther 2012; 36: 815-823).

While many animal models have been developed for studying liver fibrosis, any suitable preclinical models may be employed. For example, a high fat diet in mice has been shown to mimic both the histopathology and pathogenesis of human NAFLD. Moreover, some genetic models also display features of human metabolic syndrome and NAFLD, such as db/db and ob/ob mouse models. There are also animal models for the study of NASH, which mainly consist of various diet-induced models, including, but not limited to, methionine and choline-deficient diet (MCD), high-cholesterol diet (HCD), choline-deficient high fat diet (CDHFD), choline-deficient L-amino acid-deficient diet, choline-deficient L-amino acid-deficient diet+carbon tetrachloride, high-fat diet+streptozotocin, high fat+high cholesterol diet (HFHC), high-fructose diet (HFD), and high-fructose high fat diet (HFHF). Genetic mouse models for the study of NASH include, but are not limited to foz/foz mice, Hepatocyte-specific PTEN-deficient mice, Db/db mice+diethylnitrosamine (DEN), and db/db mice+MCD. The details of all of these models, including the pluses and minus of each, are outlined in Jennie Ka Ching Lau et al., J Pathol 2017; 241: 36-44; the contents of which are incorporated herein by reference.

Another model useful for testing the efficacy of isoform-specific TGFβ inhibitors in liver fibrosis include the carbon tetrachloride ($CCL_4$) model. Another model useful for testing the efficacy of isoform-specific TGFβ inhibitors in liver fibrosis include the bile duct ligation (BDL) model (see, e.g., Tag et al., J Vis Exp. 2015; (96): 52438).

The isoform-specific, TGFβ1 inhibitors such as those provided herein may be used to treat fibrotic conditions of the liver, such as fatty liver (, e.g., non-alcoholic fatty liver disease (NAFLD) and non-alcoholic steatohepatitis (NASH). The fatty liver may or may not be inflamed. Inflammation of the liver due to fatty liver (i.e., steatohepatitis) may develop into scarring (fibrosis), which then often progresses to cirrhosis (scarring that distorts the structure of the liver and impairs its function). The inhibitor may therefore be used to treat such conditions. In some embodiments, the inhibitor blocks activation of ECM-associated TGFβ1 (e.g., pro/latent TGFβ1 presented by LTBP1/3) within the fibrotic environment of the liver. The inhibitor may optionally further block activation of macrophage-associated TGFβ1 (e.g., pro/latent TGFβ1 presented by LRRC33), for example, Kupffer cells (also known as stellate macrophages) as well as infiltrating monocyte-derived macrophages and MDSCs. As a result, the inhibitor may suppress fibrosis-associated factors (e.g., fibrotic markers described herein). Administration of the inhibitor in a subject with such conditions may reduce one or more symptoms, prevent or retard progression of the disease, reduce or stabilize fat accumulations in the liver, reduce disease-associated biomarkers (such as serum collagen fragments), reduce liver scarring, reduce liver stiffness, and/or otherwise produce clinically meaningful outcome in a patient population treated with the inhibitor, as compared to a control population not treated with the inhibitor. In some embodiments, an effective amount of the inhibitor may achieve both reduced liver fat and reduced fibrosis (e.g., scarring) in NASH patients. In some embodiments, an effective amount of the inhibitor may achieve improvement in fibrosis by at least one stage with no worsening steatohepatitis in NASH patients. In some embodiments, an effective amount of the inhibitor may reduce the rate of occurrence of liver failure and/or liver cancer in NASH patients.

In some embodiments, an effective amount of the inhibitor may normalize, as compared to control, the levels of multiple inflammatory or fibrotic serum biomarkers as assessed following the start of the therapy, at, for example, 12-36 weeks. In some embodiments, inflammatory or fibrotic biomarkers may be used to assess severity of NAFLD (by measure levels of hepatic steatosis), select patients for treatment, and/or monitor disease progression or treatment response. For example, blood biomarkers and panels may include, but are not limited to:
  i) the Fatty liver index (BMI, waist circumference, serum triglycerides, and gamma-glutamyltransferase (GGT);
  ii) the Hepatic steatisis index (serum aspartate aminotransferase (AST):alanine aminotransferase (ALT) ratio, BMI, gender, and presence of diabetes mellitus);
  i) the NAFLD liver fat score (serum ALT, HDL cholesterol, triglycerides, haemoglobin $A_{1c}$ and leukocyte count);
  ii) the SteatoTest (BioPredictive) (serum levels of total bilirubin, GGT, α2-macroglobulin, haptoglobin, ALT, apolipoprotein AI, total cholesterol, triglycerides, glucose (adjusted for age and gender) and BMI); and
  iii) the NAFLD ridge score (serum levels of ALT, HDL cholesterol, triglycerides, haemoglobin $A_{1c}$, leukocyte count, and comorbidity data (and the presence of hypertension)).

In some embodiments, imaging biomarkers can be used to assess levels of hepatic steatosis. For example, imaging biomarkers may include but are not limited to: ultrasonography, controlled attenuation parameter (CAP), MRI-estimated proton density fat fraction (MRI-PDFF), and magnetic resonance spectroscopy (MRS).

Liver biopsies are the current standard for diagnosis NASH, however, variability among pathologists limits the effectiveness of such diagnostic method. Accordingly, use of the Fatty Liver Inhibition of Progression (FLIP) algorithm (comprising histological steatosis, activity and fibrosis scores) may be used to improve the consistency of NASH diagnosis by biopsy. Moreover, many noninvasive biomarkers may also be useful for diagnosing and monitoring disease. Accordingly, in some embodiments, inflammatory or fibrotic biomarkers may be used to assess severity of NASH, select patients for treatment, and/or monitor disease progression or treatment response. Blood biomarkers may include:
  i) apoptosis markers, such as CK18 fragments, total cytokeratin and sFAS;
  ii) inflammatory markers, such as CRP, TNF, IL-8, and CXCL10;
  iii) lipid oxidation products, such as 11-HETE, 9-HODE, 13-HODE, 12-oxo-ODE, LA-13-HODE (oxNASH-score), and 11,12-diHETrE;
  iv) lysosomal enzymes, such as cathepsin D; and
  v) combination panels, such as NASHTest (BioPredictive) and NASH Diagnostics Panel (comprising, presence of diabetes mellitus, sex, BMI, and serum levels of triglyceride, CK18 fragments, and total CK18).

In some embodiments, biomarkers and related panels may be useful in diagnosis levels of fibrosis and/or cirrhosis, select patients for treatment, and/or monitor disease progression or treatment response. For example, noninvasive tests of liver fibrosis and cirrhosis include, but are not limited to: AST:ALT ratio, AST:platelet ratio index, fibrosis-4 index (age, AST, ALT, and platelet count), NAFLD fibrosis score (age, BMI, impaired fasting glucose and/or diabetes, AST ALT, platelet count, and albumin), BARD score (AST, ALT, BMI, and diabetes).

Specific fibrosis markers and panels may also be useful, and include, but are not limited to: hyaluronic acid; PIIPNP; Pro-C3; TIMP1; Laminin; enhanced liver fibrosis (ELF) panel (PIINP, hyaluronic acid, TIMP1); FibroTest (GGT, total bilirubin, $α_2$m, apolipoprotein AI, and haptoglobin); and FibroMeter NAFLD (body weight, prothrombin index, ALT, AST, ferritin, and fasting glucose). Imaging biomarkers for liver fibrosis may include, but are not limited to: FibroScan (TE), point shear wave elastography (pSWE) (aka acoustic radiation force impulse (ARFI)), 2D-3D SWE, magnetic resonance elastography (MRE), and multiparameteric MRI.

In some embodiments, genetic and genomic biomarkers may be useful in assessing NAFLD risk and severity, which include the assessment of various SNPs, cell-free ncRNAs, and miRNAs. A comprehensive review of known genetic and genomic biomarkers, as well as the above-discussed blood biomarkers, panels, imaging biomarkers, and tests are summarized in VWS Wong et al., Nat Rev Gastroenterol Hepatol. 2018 August; 15(8):461-478; the contents of which are incorporated herein by reference.

In some embodiments in NASH patients, the isoform-specific, TGFβ1 inhibitors may be administered in patients who receive one or more additional therapies, including, but are not limited to myostatin inhibitors, which may generally enhance metabolic regulation in patients with clinical manifestation of metabolic syndrome, including NASH and NAFLD.

In some embodiments, the additional therapy may comprise a TGFβ3 inhibitor. In some embodiments, the TGFβ3 inhibitor is an isoform-specific TGFβ3 inhibitor. In some embodiments, the TGFβ3 inhibitor is a context-independent or context-bias TGFβ3 inhibitor. In some embodiments, the NASH patient has TGFβ1-positive and TGFβ3-positive fibrotic tissue. In some embodiments, the NASH patient is, or has been determined to be, partially responsive to the TGFβ1 inhibitor therapy.

In some embodiments, in NASH patients, the isoform-specific, TGFβ1 inhibitors may be administered in patients who receive an Acetyl CoA Carboxylase inhibitor (ACCi) (e.g., firsocostat (GS-0976) or PF-05221304). Other therapeutics which may be useful in combination with the improved isoform-specific TGFβ1 inhibitors described herein, include, but are not limited to: GLP-1 receptor agonists or analogues (e.g., semaglutide), farnesoid X receptor (FXR) agonists (e.g., GS-9674; aka Cilofexor), ASK1 inhibitors (e.g., selonsertib); obeticholic acid, PPAR agonists (e.g., GFT505; aka elafibranor); nitazoxanide, ketohexokinase (KHK) inhibitors (e.g., PF-06835919); and/or Diacylglycerol O-Acyltransferase 2 (DGAT2) inhibitors (e.g., PF-06865571). In some embodiments, any one or more of the above-mentioned therapeutics can be used in combination with an isoform specific TGFβ1 inhibitor of the present disclosure, for example, an isoform-specific TGFβ1 inhibitor in combination with a FXR agonist, an ACC inhibitor, and/or a GLP-1 analogue. In some embodiments, the isoform-selective TGFβ1 inhibitors may be used in combination with a myostatin inhibitor, such as myostatin activation inhibitors (e.g., SRK-015, e.g., WO 2016/073853 and WO 2017/049011). In some embodiments, the isoform-selective TGFβ1 inhibitors may be used in combination with a GDF11 inhibitor, such as GDF11 activation inhibitors (e.g., WO 2017/015622).

In some embodiments, treatment with the isoform specific TGFβ1 inhibitors alone or in combination with one or more additional therapeutics reduces hepatic fat as measured by MRI-PDFF. In some embodiments, the reduction of hepatic fat is at least 20%, e.g., ≥20%, ≥25%, ≥30%, ≥35%, ≥40%, ≥45%, or ≥50%. In some embodiments, treatment with the isoform specific TGFβ1 inhibitors alone or in combination with one or more additional therapeutics reduces serum ALT and/or GGT by at least 20%, e.g., ≥20%, ≥25%, ≥30%, ≥35%, ≥40%, ≥45%, or ≥50%. In some embodiments, treatment with the isoform specific TGFβ1 inhibitors alone or in combination with one or more additional therapeutics reduces bile acid synthesis.

In some embodiments, the NASH patients may have advanced liver fibrosis (stage F3/F4). In some embodiments, such patients have stage F3 advanced liver fibrosis. In some embodiments, such patients have stage F4 liver fibrosis characterized by cirrhosis. In some embodiments, the NASH patients develop or at risk of developing hepatocellular carcinoma and/or esophageal varices.

Fibrosis staging in non-alcoholic fatty liver disease according to the classification derived by the Nonalcoholic Steatohepatitis Clinical Research Network Pathology Committee is provided below:

| Fibrotic manifestation | Fibrosis Stage |
| --- | --- |
| Perisinusoidal or periportal fibrosis | 1 |
| Mild perisinusoidal fibrosis (zone 3) | 1A |
| Moderate perisinusoidal fibrosis (zone 3) | 1B |
| Portal/periportal fibrosis | 10 |
| Perisinusoidal and portal/periportal fibrosis | 2 |
| Bridging fibrosis | 3 |
| Cirrhosis | 4 |

To enable assessment of the various histologic features during therapy and encompass the whole spectrum of NAFLD, the NASH Clinical Research Network (CRN) Pathology Committee performed a thorough univariate and multivariate analysis on the associations between the different histologic features observed in NASH and the diagnosis of NASH according to the Pathology Committee. The result was a scoring system of both NASH activity (Grade), and collagen deposition plus architectural remodeling (Stage). The grading system, the NASH Activity Score (NAS), was the unweighted sum of three histological components: steatosis (0-3), lobular inflammation (0-3) and ballooning degeneration (0-2). It ranged from 0 to 8. NAS includes the features of active injury that are potentially reversible. Additionally, the fibrosis staging system of Brunt et al. was further developed. In the NASH CRN system, the fibrosis score for stage 1 was subdivided into delicate (1A) and dense (1B) peri-sinusoidal fibrosis, whereas stage 1C was defined as portal fibrosis without concomitant peri-sinusoidal fibrosis (reviewed by Stal, World J Gastroenterol. 2015 Oct. 21; 21(39): 11077-11087, incorporated by reference herein).

The isoform-specific, TGFβ1 inhibitors such as those provided herein may be used to treat fibrotic conditions of the kidney, e.g., diseases characterized by extracellular matrix accumulation (IgA nephropathy, focal and segmental glomerulosclerosis, crescentic glomerulonephritis, lupus nephritis and diabetic nephropathy) in which significantly increased expression of TGFβ in glomeruli and the tubulointerstitium has been observed. While glomerular and tubulointerstitial deposition of two matrix components induced by TGFβ, fibronectin EDA+ and PAI-1, was significantly elevated in all diseases with matrix accumulation, correlation analysis has revealed a close relationship primarily with the TGFβ1 isoform. Accordingly, the isoform-specific, TGFβ1 inhibitors are useful as therapeutic for a spectrum of human glomerular disorders, in which TGFβ is associated with pathological accumulation of extracellular matrix.

In some embodiments, the fibrotic condition of the kidney is associated with chronic kidney disease (CKD). CKD is caused primarily by high blood pressure or diabetes and claims more than one million lives each year. CKD patients require lifetime medical care that ranges from strict diets and medications to dialysis and transplants. In some embodiments, the TGFβ1 inhibitor therapy described herein may reduce or delay the need for dialysis and/or transplantation. In some embodiments, such therapy may reduce the need (e.g., dosage, frequency) for other treatments. In some embodiments, the isoform-specific, TGFβ1 inhibitors may be administered in patients who receive one or more additional therapies, including, but are not limited to myostatin inhibitors, which may generally enhance metabolic regulation in patients with CKD.

Fibrotic conditions that may be treated with the TGFβ1 inhibitor of the present disclosure include conditions involving fibrosis and/or chronic inflammation. Such conditions may be neuromuscular disorders, including but are not limited to Duchenne muscular dystrophy (DMD), and other genetic disorders such as multiple sclerosis (MS) and cystic fibrosis (CF). Through the inhibition of both the ECM- and immune cell-associated TGFβ1 arms, the TGFβ1 inhibitor such as those described herein is thought to suppress fibrotic progression and restore M1/M2 macrophage polarization.

Models useful for studying CKD and kidney fibrosis include but are not limited to, NZB/W, MRL/lpr and BXSB mouse strains, anti-GBM models, anti-Thy1 models, 5/6 nephrectomy, Radiation nephropathy, puromycin aminonucleoside nephrosis (PAN) and adriamycin nephropathy, Folic acid nephropathy, CyA nephropathy, DOCA-salt nephropathy, HIV-associated nephropathy (HIVAN) transgenic mouse model, Spontaneously hypertensive rats (SHR), Buffalo/mna rats, Munich Wistar Frömter (MWF) rat, unilateral ureteral obstruction (UUO), Col4A knock-out mice (Alport Syndrome) (see Yang et al. Drug Discov Today Dis Models. 2010; 7(1-2): 13-19; the contents of which are incorporated herein by reference).

The organ fibrosis which may be treated with the methods provided herein includes cardiac (e.g., cardiovascular) fibrosis. In some embodiments, the cardiac fibrosis is associated with heart failure, e.g., chronic heart failure (CHF). In some embodiments, the heart failure may be associated with myocardial diseases and/or metabolic diseases. In some embodiments, the isoform-specific, TGFβ1 inhibitors may be administered in patients who receive one or more additional therapies, including, but are not limited to myostatin inhibitors in patients with cardiac dysfunction that involves heart fibrosis and metabolic disorder.

Genetic models useful for studying cardiac fibrosis include but are not limited to, cardiac myocyte-specific FAK-KO mouse, genetically modified SR-BI/apoE double KO (dKO) mice, syndecan-1 null mice, EC-SOD-overexpressing mice, PKC-δ knockout mice. Surgical mouse models useful for studying cardiac fibrosis include but are not limited to, coronary artery ligation, ischemic-reperfusion model (open and closed chest), Chronic ischemia model, ischemia-reperfusion with ischemic preconditioning model, Langendorff model, traverse aortic constriction (TAC), ascending aortic constriction, abdominal aorta constriction, pulmonary artery banding, TAC with distal left anterior coronary ligation, aortocaval fistula (ACF) model, and aortic insufficiency model (see Rai et al., Mol Cell Biochem. 2017 January; 424(1-2): 123-145; the contents of which are incorporated herein by reference).

In some embodiments, fibrotic conditions that may be treated with the compositions and/or methods described herein include desmoplasia. Desmoplasia may occur around a neoplasm, causing dense fibrosis around the tumor (e.g., desmoplastic stroma), or scar tissue within the abdomen after abdominal surgery. In some embodiments, desmoplasia is associated with malignant tumor. Due to its dense formation surrounding the malignancy, conventional anti-cancer therapeutics (e.g., chemotherapy) may not effectively penetrate to reach cancerous cells for clinical effects. Isoform-specific, inhibitors of TGFβ1 such as those described herein may be used to disrupt the desmoplasia, such that the fibrotic formation can be loosened to aid effects of anti-cancer therapy. In some embodiments, the isoform-specific, inhibitors of TGFβ1 can be used as monotherapy (more below).

In some embodiments, a patient has a fibrotic solid tumor (e.g., desmoplasia) and is or has been excluded from a surgical candidate pool, such that the fibrotic solid tumor is considered to be non-resectable or non-operative. Such patient may be a candidate for receiving a TGFβ1 inhibition therapy of the present disclosure. The TGFβ1 inhibitor of the present invention may render the tumor become resectable or operable after administration so that the patient may become a candidate for surgical resection.

To treat patients with fibrotic conditions, TGFβ1 isoform-specific, inhibitors are administered to a subject in an amount effective to treat the fibrosis. The effective amount of such an antibody is an amount effective to achieve both therapeutic efficacy and clinical safety in the subject. In some embodiments, the inhibitor is an antibody that can block activation of an LTBP-mediated TGFβ1 localized (e.g., tethered) in the ECM and GARP-mediated TGFβ1 localized in (e.g., tethered on) immune cells. In some embodiments, antibody is an antibody that can block activation of an LTBP-mediated TGFβ1 localized in the ECM and LRRC33-mediated TGFβ1 localized in (e.g., tethered on) monocytes/macrophages. In some embodiments, the LTBP is LTBP1 and/or LTBP3. In some embodiments, targeting and inhibiting TGFβ1 presented by LRRC33 on profibrotic, M2-like macrophages in the fibrotic microenvironment may be beneficial.

Assays useful in determining the efficacy of the antibodies and/or compositions of the present disclosure for the alteration of fibrosis include, but are not limited to, histological assays for counting fibroblasts and basic immunohistochemical analyses known in the art.

In some embodiments, circulating LAP fragment(s) may be used as a serum marker of fibrogenesis. Antibodies that specifically recognize the cleaved ends of such fragments may be used to detect LAP fragments from serum samples. See for example, U.S. Pat. No. 8,198,412, the contents of which are incorporated herein by reference.

Role of TGFβ in Diabetes

Loss of insulin-secreting β-cells in the pancreas is a primary mechanism of type 2 diabetes. Recent studies suggest a role for TGFβ family ligands in regulating β-cell function and glucose homeostasis. These ligands might influence β-cell proliferation and/or incorporation of new β-cells from progenitors in adults. Genetic manipulation to cause transgenic overexpression of TGF-β through insulin promoter has been reported to cause Decreased development of exocrine pancreas and islets, maintenance of glucose control. Similarly, Transgenic overexpresssion of TGF-β through glucagon promoter has been reported to cause B-cell hypoplasia, decreased insulin secretion, impaired glucose tolerance (reviewed, for example, in Trends Endocrinol Metab. 2010 July; 21(7): 441-448). Expansion and renewal of pancreatic beta cells is crucial for both normal development of the pancreas and maintenance of function in the adult islet. Recently, several studies have identified some of the key roles for TGFβ signaling in the developing pancreas. Specifically, TGFβ signaling promotes the endocrine commitment of progenitor cells and their subsequent maturation. Mice overexpressing the dominant negative form of TGFβ type II receptor Tulachan et al. inhibited TGFβ signaling at the receptor level and found an increase in the number of endocrine precursors, as well as a proliferation of endocrine cells. In the adult islet, all three TGFβ isoforms are expressed in the endocrine cells in a diffuse pattern. However, the intensity was higher for TGFβ2 and TGFβ3 in insulin-positive cells. In the exocrine pancreas, most of the acinar cells were positive for TGFβ1, while all three ligands appeared to be equally expressed in the ductal cells. Adult beta cells have very low turnover and a low proliferation rate. The isoform-selective TGFβ1 inhibitor such as those encompassed herein may be used to promote pancreatic beta cell replication in the treatment or prevention of diabetes and/or glucose intolerance. Because replication of β-cells is the primary mechanism for maintenance and expansion of β-cell mass in response to changing insulin demands, and failure of such adaptive expansion can result in diabetes (see, for example, Dhawan et al., Diabetes. 2016 May; 65(5): 1208-1218), the isoform-selective TGFβ1 inhibitor may be advantageously used to ameliorate diabetes without causing unwanted side effects associated with pan-inhibition of TGFβ signaling. In some embodiments, the isoform-selective TGFβ1 inhibitor may be used in conjunction with a myostatin-selective inhibitor (e.g., antibodies that selectively bind pro/latent myostatin/GDH8 thereby inhibiting activation of myostatin), as described, for example, in PCT/US2015/059468 and PCT/US2016/052014, in the treatment or prevention of diabetes or glucose intolerance. In some embodiments, the diabetes is type 2 diabetes.

Conditions related to diabetes include diabetic nephropathy (DN), which is also referred to as diabetic kidney disease. Diabetic nephropathy is a serious kidney-related complication of type 1 diabetes and type 2 diabetes. Up to 40 percent of people with diabetes eventually develop kidney disease. Over time, DN may lead to pulmonary edema, cardiovascular disease and end-stage kidney stage, which eventually requires either dialysis or a kidney transplant for survival.

The major clinical features of human DN include albuminuria, progressive reduction of GFR and hypertension, and increased risk for cardiovascular diseases. The DN pathogenesis is associated with glomerular angiogenesis and hyperfiltration. In addition, thickening of the glomerular basement membrane, the expansion of mesangial cells, glomerulosclerosis and tubulointerstitial fibrosis are observed in patients with DN. TGFβ1 and its receptors are upregulated in both experimental and human diabetic nephropathy. Enhanced expression of TGFβ1 receptors, TGFβ1 bioactivity, and responsiveness to exogenous TGFβ1 have been reported to occur in response to high glucose in glomerular cells, and extracellular adenosine is implicated to play a role in this process (See, for example, Roa et al., (2009) "Adenosine mediates transforming growth factor-beta 1 release in kidney glomeruli of diabetic rats" FEBS Let 583(19): 3192-3198). In some embodiments, DN comprises dysregulation of the adenosine biosynthesis or signaling. In some embodiments, the dysregulation involves CD39 and/or CD73.

Role of TGFβ in Musculoskeletal Conditions

In musculoskeletal system, which is comprised of the bones of the skeleton, muscles, cartilage, tendons, ligaments, joints, and other connective tissue that supports and binds tissues and organs together, TGFβ plays a variety of roles including inhibition of proliferation and differentiation, induction of atrophy, and development of fibrosis. TGFβ reduces satellite cell proliferation and prevents differentiation (via inhibition of MyoD and myogenin) (Allen, R. E. and L. K. J Cell Physiol, 1987. 133(3): p. 567-72; Brennan, T. J., et al., Proc Natl Acad Sci USA, 1991. 88(9): p. 3822-6; Massague, J., et al., Proc Natl Acad Sci USA, 1986. 83(21): p. 8206-10; Olson, E. N., et al., J Cell Biol, 1986. 103(5): p. 1799-805). The isoform of TGFβ (i.e., TGFβ1, 2, or 3) is not specified in these early papers, but is presumed to be TGFβ1. TGFβ also contributes to muscle fibrosis; direct injection of recombinant TGFβ1 results in skeletal muscle fibrosis, and pan-TGFβ inhibition decreases fibrosis in acute and chronically injured muscle (Li, Y., et al., Am J Pathol, 2004. 164(3): p. 1007-19; Mendias, C. L., et al., Muscle Nerve, 2012. 45(1): p. 55-9; Nelson, C. A., et al., Am J Pathol, 2011. 178(6): p. 2611-21). TGFβ1 is expressed by myofibers, macrophages, regulatory T cells, fibroblasts, and fibrocytes within the skeletal muscle (Li, Y., et al., Am J Pathol, 2004. 164(3): p. 1007-19; Lemos, D. R., et al., Nat Med, 2015. 21(7): p. 786-94; Villalta, S. A., et al., Sci Transl Med, 2014. 6(258): p. 258ra142; Wang, X., et al., J Immunol, 2016. 197(12): p. 4750-4761); and expression is increased upon injury and in disease (Li, Y., et al., Am J Pathol, 2004. 164(3): p. 1007-19; Nelson, C. A., et al., Am J Pathol, 2011. 178(6): p. 2611-21; Bernasconi, P., et al., J Clin Invest, 1995. 96(2): p. 1137-44; Ishitobi, M., et al., Neuroreport, 2000. 11(18): p. 4033-5). TGFβ2 and TGFβ3 are also upregulated (at the mRNA level) in mdx muscle, although to a lesser extent than TGFβ1 (Nelson, C. A., et al., Am J Pathol, 2011. 178(6): p. 2611-21; Zhou, L., et al., Neuromuscul Disord, 2006. 16(1): p. 32-8). Pessina, et al., recently used lineage tracing experiments to show that cells of multiple origins within dystrophic muscle adopt a fibrogenic fate via a TGFβ3-dependent pathway (Pessina, P., et al., Stem Cell Reports, 2015. 4(6): p. 1046-60).

The bone is the largest storehouse of TGFβ in the body. Indeed, the TGFβ pathway is thought to play an important role in bone homeostasis and remodeling at least in part by regulating osteoblast differentiation and/or osteoclastic bone resorption. This process is involved in both normal and abnormal situations, which, when dysregulated, may cause or exacerbate disease, such as bone-related conditions and cancer. Thus, TGFβ1-selective inhibitors such as those described herein may be used to treat such conditions. In some embodiments, administration of such inhibitors is effective to restore or normalize bone formation-resorption balance. In some embodiments, the TGFβ1 inhibitor is administered to subjects in conjunction with another therapy, such as a myostatin inhibitor and/or bone-enhancing agents, as combination therapy.

Bone conditions (e.g., skeletal diseases) include osteoporosis, dysplasia, osteogenesis imperfecta and bone cancer. In addition to primary bone cancer that originates in the bone, many malignancies are known to metastasize to bone; these include, but are not limited to. breast cancer, lung cancer (e.g., squamous cell carcinoma), thyroid cancer, testicular cancer, renal cell carcinoma, prostate cancer, and multiple myeloma.

Among bone-related conditions, osteogenesis imperfecta is a genetic condition that is usually caused by mutations affecting collagen type I encoding genes and causes fragile bones to break extremely easily. Currently, there are few treatment options, where bisphosphonate drugs remain the standard of care. Antigens or antigen-binding fragments that selectively inhibit TGFβ1 activation may be used to treat osteogenesis imperfect either alone as monotherapy or in conjunction with another therapy aimed to treat the disease.

Therapeutic effects of TGFβ1 inhibitors such as those described herein may be monitored using suitable biomarkers, such as serum markers of bone formation (alkaline phosphatase activity) or resorption (tartrate-resistant acid phosphatase).

In some embodiments, such conditions are associated with muscle weakness.

In some embodiments, the musculoskeletal condition involves dysregulation of myogenic and non-myogenic stem/progenitor cells associated with the musculoskeletal system, such as satellite cells. The isoform-selective TGFβ1 inhibitor may be used to promote expansion/differentiation of myogenic and non-myogenic stem/progenitor cells.

TGFβ1 may play a role in fibrotic conditions that accompany chronic inflammation of the affected tissue, such as human muscular dystrophies. Duchenne muscular dystrophy (DMD) is a severe, progressive, and ultimately fatal disease caused by the absence of dystrophin (Bushby, K., et al., Lancet Neurol, 2010. 9(1): p. 77-93). Lack of dystrophin results in increased susceptibility to contraction-induced injury, leading to continual muscle degeneration (Petrof, B. J., et al., Proc Natl Acad Sci USA, 1993. 90(8): p. 3710-4; Dellorusso, C., et al., J Muscle Res Cell Motil, 2001. 22(5): p. 467-75; Pratt, S. J., et al., Cell Mol Life Sci, 2015. 72(1): p. 153-64). Repeated rounds of repair contribute to chronic inflammation, fibrosis, exhaustion of the satellite cell pool, eventual loss of mobility and death (Bushby, K., et al., Lancet Neurol, 2010. 9(1): p. 77-93; McDonald, C. M., et al., Muscle Nerve, 2013. 48(3): p. 343-56). Expression of TGFβ1 is significantly increased in patients with DMD and correlates with the extent of fibrosis observed in these patients (Bernasconi, P., et al., J Clin Invest, 1995. 96(2): p. 1137-44; Chen, Y. W., et al., Neurology, 2005. 65(6): p. 826-34). Excessive ECM deposition has detrimental effects on the contractile properties of the muscle and can limit access to nutrition as the myofibers are isolated from their blood supply (Klingler, W., et al., Acta Myol, 2012. 31(3): p. 184-95). Recently, additional data has further implicated TGFβ1 in muscular dystrophies. Variants in LTBP4 have been found to modify disease severity in mouse and human. In mouse, a variant of LTBP4 is protective in mice lacking dystrophin or γ-sarcoglycan (Coley, W. D., et al., Hum Mol Genet, 2016. 25(1): p. 130-45; Heydemann, A., et al., J Clin Invest, 2009. 119(12): p. 3703-12). In humans, two groups independently identified a variant of LTBP4 as protective in DMD, delaying loss of ambulation by several years (Flanigan, K. M., et al., Ann Neurol, 2013. 73(4): p. 481-8; van den Bergen, J. C., et al., J Neurol Neurosurg Psychiatry, 2015. 86(10): p. 1060-5). Although the nature of the genetic variants in mouse and human differs, in both species the protective variant results in decreased TGFβ signaling (Heydemann, A., et al., J Clin Invest, 2009. 119(12): p. 3703-12); Ceco, E., et al., Sci Transl Med, 2014. 6(259): p. 259ra144).

Many of the functions of TGFβ1 in skeletal muscle biology have been inferred from experiments in which purified active growth factor is injected into animals or added to cells in culture (Massague, J., et al., Proc Natl Acad Sci USA, 1986. 83(21): p. 8206-10; Li, Y., et al., Am J Pathol, 2004. 164(3): p. 1007-19; Mendias, C. L., et al., Muscle Nerve, 2012. 45(1): p. 55-9). Given the importance of cellular context for specific functions of TGFβ1 (see, for example, Hinck et al., Cold Spring Harb. Perspect. Biol, 2016. 8(12)) it is possible that some of the effects observed in these experiments do not reflect the endogenous role(s) of the cytokine in vivo. For example, treatment of human dermal fibroblasts with recombinant TGFβ1, myostatin, or GDF11 results in nearly identical changes in gene expression in these cells, although in vivo the roles of these proteins are quite different (Tanner, J. W., Khalil, A., Hill, J., Franti, M., MacDonnell, S. M., Growth Differentiation Factor 11 Potentiates Myofibroblast Activation, in Fibrosis: From Basic Mechanisms to Targeted therapies. 2016: Keystone, CO).

Multiple investigators have used inhibitors of TGFβ to clarify the role of the growth factor in vivo. Treatment of mdx mice with the pan-TGFβ neutralizing antibody 1 D11 clearly results in reduced fibrosis (by histology and hydroxyproline content), reduced muscle damage (reduced serum creatine kinase and greater myofiber density), and improved muscle function (by plethysmography, force generation of isolated EDL muscles, and increased forelimb grip strength) (Nelson, C. A., et al., Am J Pathol, 2011. 178(6): p. 2611-21; Andreetta, F., et al., J Neuroimmunol, 2006. 175(1-2): p. 77-86; Gumucio, J. P., et al., J Appl Physiol (1985), 2013. 115(4): p. 539-45). In addition, myofiber-specific expression of a dominant negative TGFβ type II receptor protects against muscle damage after cardiotoxin injury and in 5-sarcoglycan−/− mice (Accornero, F., et al., Hum Mol Genet, 2014. 23(25): p. 6903-15). The proteoglycan decorin, which is abundant in skeletal muscle and inhibits TGFβ activity, decreases muscle fibrosis in mdx mice and following laceration injury (Li, Y., et al., Mol Ther, 2007. 15(9): p. 1616-22; Gosselin, L. E., et al., Muscle Nerve, 2004. 30(5): p. 645-53). Other molecules with TGFβ inhibitory activity, such as suramin (an anti-neoplastic agent) and losartan (an angiotensin receptor blocker) have been effective in improving muscle pathology and reducing fibrosis in mouse models of injury, Marfan's syndrome, and muscular dystrophy (Spurney, C. F., et al., J Cardiovasc Pharmacol Ther, 2011. 16(1): p. 87-95; Taniguti, A. P., et al., Muscle Nerve, 2011. 43(1): p. 82-7; Bedair, H. S., et al., Am J Sports Med, 2008. 36(8): p. 1548-54; Cohn, R. D., et al., Nat Med, 2007. 13(2): p. 204-10). While all of the therapeutic agents described above do inhibit TGFβ1 or its signaling, none of them is specific for the TGFβ1 isoform. For example, 1 D11 binds to and inhibits the TGFβ1, 2, and 3 isoforms (Dasch, J. R., et al., J Immunol, 1989. 142(5): p. 1536-41). Suramin inhibits the ability of multiple growth factors to bind to their receptors, including PDGF, FGF, and EGF, in addition to TGFβ1 (Hosang, M., J Cell Biochem, 1985. 29(3): p. 265-73; Olivier, S., et al., Eur J Cancer, 1990. 26(8): p. 867-71; Scher, H. I. and W. D. Heston, Cancer Treat Res, 1992. 59: p. 131-51). Decorin also inhibits myostatin activity, both by direct binding and through upregulation of follistatin, a myostatin inhibitor (Miura, T., et al., Biochem Biophys Res Commun, 2006. 340(2): p. 675-80; Brandan, E., C. Cabello-Verrugio, and C. Vial, Matrix Biol, 2008. 27(8): p. 700-8; Zhu, J., et al., J Biol Chem, 2007. 282(35): p. 25852-63). Losartan affects additional signaling pathways through its effects on the renin-angiotensin-aldosterone system, including the IGF-1/AKT/mTOR pathway (Burks, T. N., et al., Sci Transl Med, 2011. 3(82): p. 82ra37; Sabharwal, R. and M. W. Chapleau, Exp Physiol, 2014. 99(4): p. 627-31; McIntyre, M., et al., Pharmacol Ther, 1997. 74(2): p. 181-94). Therefore, all of these therapies inhibit additional molecules which may contribute to their therapeutic effects, as well as toxicities.

Considering the postulated role of TGFβ in muscle homeostasis, repair, and regeneration, agents, such as monoclonal antibodies described herein, that selectively modulate TGFβ1 signaling may be effective for treating damaged muscle fibers, such as in chronic/genetic muscular dystrophies and acute muscle injuries, without the toxicities associated with more broadly-acting TGFβ inhibitors developed to date.

Accordingly, the present invention provides methods for treating damaged muscle fibers using an agent that preferentially modulates a subset, but not all, of TGFβ effects in vivo. Such agents can selectively modulate TGFβ1 signaling ("isoform-specific modulation").

Muscle Fiber Repair in Chronic Muscular Diseases

The invention encompasses methods to improve muscle quality and function in DMD patients, by limiting fibrosis and contributing to a normalization of muscle morphology and function. As TGFβ1 also inhibits myogenesis, TGFβ1 blockade may promote regeneration in dystrophic muscle, adding further therapeutic benefit. TGFβ1 inhibitors may be used in combination with dystrophin upregulating therapies, such as Exondys 51 (Eteplirsen). Given the potential therapeutic benefits of TGFβ1 inhibition in muscular dystrophy, it is critical to (1) differentiate the role(s) of TGFβ1 from those of TGFβ2 and TGFβ3, and (2) clarify in which molecular context(s) TGFβ1 inhibition would be most beneficial. As mentioned above, pan-TGFβ inhibitors have been associated with significant toxicities, limiting the clinical use of these compounds (Anderton, M. J., et al., Toxicol Pathol, 2011. 39(6): p. 916-24; Stauber, A., et al., Clinical Toxicology, 2014. 4(3): p. 1-10). It is unclear which of the TGFβ isoform(s) causes these toxicities. Some of the described toxicities may be due to TGFβ1 inhibition in the immune system. For example, while 1 D11 significantly reduced levels of fibrosis in the diaphragm, treatment also increased numbers of CD4+ and CD8+ T cells in the muscle, suggesting an increased inflammatory response upon pan-TGFβ inhibition which could be detrimental with long-term treatment (Andreetta, F., et al., J Neuroimmunol, 2006. 175(1-2): p. 77-86). Indeed, depletion of T cells from muscle improves the muscle pathology of mdx mice, suggesting T-cell mediated inflammatory responses are detrimental to dystrophic muscle (Spencer, M. J., et al., Clin Immunol, 2001. 98(2): p. 235-43). Increases in T cell numbers upon 1 D11 administration are likely due to the effects of TGFβ1 on regulatory T (Treg) cells. Tregs present TGFβ1 on their cell surface via GARP, and release of TGFβ1 from this complex enhances Treg suppressive activity, thus limiting T cell mediated inflammation (Wang, R., et al., Mol Biol Cell, 2012. 23(6): p. 1129-39; Edwards, J. P., A. M. Thornton, and E. M. Shevach, J Immunol, 2014. 193(6): p. 2843-9; Nakamura, K., et al., J Immunol, 2004. 172(2): p. 834-42; Nakamura, K., A. Kitani, and W. Strober, J Exp Med, 2001. 194(5): p. 629-44). Indeed, depletion of Tregs using the PC61 antibody resulted in increased inflammation and muscle damage in the diaphragm of mdx mice, while augmentation of Treg numbers and activity reduced muscle damage (Villalta, S. A., et al., Sci Transl Med, 2014. 6(258): p. 258ra142). Interestingly, an additional population of immunosuppressive T cells, Tr1 cells, has recently been identified. These cells produce large amounts of TGFβ3, which is required for their suppressive activity (Gagliani, N., et al., Nat Med, 2013. 19(6): p. 739-46; Okamura, T., et al., Proc Natl Acad Sci USA, 2009. 106(33): p. 13974-9; Okamura, T., et al., Nat Commun, 2015. 6: p. 6329). While the role of Tr1 cells in skeletal muscle is unknown, the possibility exists that inhibition of both TGFβ1 and TGFβ3 by 1 D11 could have additive pro-inflammatory effects by inhibiting both Tregs and Tr1 cells.

The structural insights described above regarding TGFβ1 latency and activation allow for novel approaches to drugs discovery that specifically target activation of TGFβ1 (Shi, M., et al., Nature, 2011. 474(7351): p. 343-9). The high degree of sequence identity shared between the three mature TGFβ growth factors is not shared by the latent complexes, allowing for the discovery of antibodies that are exquisitely specific to proTGFβ1. Using proprietary approaches to antibody discovery, the instant inventors have identified antibodies (Ab1, Ab2 and Ab3) which specifically bind to proTGFβ1. Using an in vitro co-culture system these antibodies were demonstrated to inhibit integrin-mediated release of TGFβ1. In this system, fibroblasts derived from human skin or mouse skeletal muscles are the source of latent TGFβ1, a cell line expressing αVβ6 allows for release of active TGFβ1, which is then measured using a third cell line expressing a SMAD2/3 responsive luciferase reporter (FIG. 12). One of these antibodies, Ab1, has been tested in vivo and shown efficacy in the UUO (unilateral ureteral obstruction) mouse model of kidney fibrosis. In this model, treatment of mice (n=10) with 9 mg/kg/week Ab1 prevented upregulation of TGFβ1-responsive genes and reduced the extent of fibrosis following injury (by picrosirius red staining). TGFβ1 specific therapies may have improved efficacy and safety profiles compared to pan-TGFβ inhibitors, a critical aspect for a therapeutic which would be used long term as in the DMD population. TGFβ1 inhibitory antibodies can be used to determine if specific TGFβ1 inhibition has potential as a therapeutic for DMD or other muscle diseases, and to clarify the role of TGFβ1 in skeletal muscle regeneration.

Chronic Vs. Acute Myofiber Injuries and Selection of Optimal Therapeutics

In normal, but regenerating muscle following an acute injury (such as traumatic injury to otherwise healthy muscles or motor neurons), it is believed that the initial infiltration of inflammatory macrophages is required to clear out the damaged tissue and to secrete factors (e.g., cytokines) necessary for satellite cell activation. Subsequently, these cells switch to the M2 phenotype to drive wound resolution.

By contrast, in chronic conditions, such as diseases including DMD, the pro-inflammatory macrophages predominated at all time, and that switch to M2 does not happen (or at least not efficiently enough), and the pro-inflammatory macrophages continue to drive inflammation and muscle damage. In DMD, the NFkB pathway is perpetually active, resulting in constitutive inflammation. In some embodiments, therefore, an NFkB inhibitor may be administered to DMD patients in order to reduce the chronic inflammation.

Thus, in chronic conditions such as DMD, therapeutic focus may be on muscle repair as opposed to muscle regeneration. This is because DMD muscle fibers are defective but not destroyed—they are damaged by tears in the membrane, dysregulation of calcium transients, and ROS damage from the macrophages. In comparison, in cases of injuries to healthy muscles, therapeutic focus may be on regeneration. For example, in cardiotoxin models, muscle fibers are killed and have to be regenerated. This simulates the process of recovery after a traumatic injury, such as crush injury.

Evidence suggests that LRRC33 is expressed in thioglycollate-induced peritoneal macrophages, which have an M2-like phenotype (characterized in that they express high levels of Arginase, no iNOS, and high levels of CD206).

In situations where LRRC33 is expressed primarily on the M2 cells and where its presentation of TGFβ1 ("context") is important for the pro-wound healing effects of these cells, it may be beneficial to activate LRRC33-mediated TGFβ1 to promote repair and/or myogenesis. On the other hand, in situations where LRRC33 is also expressed on the pro-inflammatory M1 cells, then it may be beneficial to inhibit LRRC33-mediated TGFβ1, given that inflammation drives the fibrosis, especially in the dystrophic setting, such as DMD. Thus, identifying the source/context of disease-associated TGFβ1 can be an important step in selecting the right modulator of the TGFβ signaling, which will inform what level of selectivity should be considered (e.g., isoform-specific, context-independent TGFβ1 modulators, or, context-specific TGFβ1 modulators; TGFβ1 inhibitors or activators, etc.).

Apart from chronic inflammation, the hallmark of DMD is excessive, and progressive, fibrosis. In advanced disease the fibrosis is so severe that it can actually isolate individual muscle fibers from their blood supply. It also alters the contractile properties of the muscle. In human patients, there is a strong correlation between the extent of TGFβ1 upregulation and fibrosis, and a strong link between the extent of fibrosis and negative mobility outcomes. Therefore, in some embodiments, LTBP-proTGFβ1 inhibitors may be administered to dystrophic patients for the prevention and/or reduction of fibrosis to selectively target the ECM-associated TGFβ1 effects in the disease. In some embodiments, various isoform- and/or context-selective agents described herein can be employed to achieve inhibition of TGFβ1 signaling to prevent fibrosis and promote myogenesis, but without having unwanted effects on the immune system (e.g., through GARP or LRRC33).

Conditions Involving MHC Downregulation or Mutation

TGFβ-related indications may also include conditions in which major histocompatibility complex (MHC) class I is deleted or deficient (e.g., downregulated). Such conditions include genetic disorders in which one or more components of the MHC-mediated signaling is impaired, as well as conditions in which MHC expression is altered by other factors, such as cancer, infections, fibrosis, and medications.

For example, MHC I downregulation in tumor is associated with tumor escape from immune surveillance. Indeed, immune escape strategies aimed to avoid T-cell recognition, including the loss of tumor MHC class I expression, are commonly found in malignant cells. Tumor immune escape has been observed to have a negative effect on the clinical outcome of cancer immunotherapy, including treatment with antibodies blocking immune checkpoint molecules (reviewed in, for example: Garrido et al. (2017) Curr Opin Immunol 39: 44-51. "The urgent need to recover MHC class I in cancers for effective immunotherapy", incorporated by reference herein). Thus, the isoform-selective, context-independent TGFβ1 inhibitors encompassed by the present disclosure may be administered either as a monotherapy or in conjunction with another therapy (such as checkpoint inhibitor, chemotherapy, radiation therapy, etc.) to unleash or boost anti-cancer immunity and/or enhance responsiveness to or effectiveness of another therapy.

In some embodiments, MHC downregulation is associated with acquired resistance to a cancer therapy, such as CBT. It is contemplated that the high-affinity, isoform-selective inhibitors of TGFβ1 may be used to treat patients who are primary responders of a cancer therapy such as CBT, to reduce the probability of developing acquired resistance. Thus, among those treated with the TGFβ1 inhibitor, who are primary responders of cancer therapy, occurrence of secondary or acquired resistance to the cancer therapy over time may be reduced.

Downregulation of MHC class I proteins are also associated with certain infectious diseases, including viral infections such as HIV. See for example, Cohen et al. (1999) Immunity 10(6): 661-671. "The selective downregulation of class I major histocompatibility complex proteins by HIV-1 protects HIV-infected cells from NK Cells", incorporated herein by reference. Thus, the isoform-selective, context-independent TGFβ1 inhibitors encompassed by the present disclosure may be administered either as a monotherapy or in conjunction with another therapy (such as anti-viral therapy, protease inhibitor therapy, etc.) to unleash or boost host immunity and/or enhance responsiveness to or effectiveness of another therapy.

Conditions Involving Stem Cell Self-Renewal, Tissue Regeneration and Stem Cell Repopulation Evidence suggests that TGFβ1 plays a role in regulating the homeostasis of various stem cell populations and their differentiation/repopulation within a tissue. During homeostasis, tissue-specific stem cells are held predominantly quiescent but are triggered to enter cell cycle upon certain stress. TGFβ1 is thought to function as a "break" during the process that tightly regulates stem cell differentiation and reconstitution, and the stress that triggers cell cycle entry coincides with TGFβ1 inhibition that removes the "break." Thus, it is contemplated that isoform-selective inhibitors of TGFβ1, such as those described herein, may be used to skew or correct cell cycle and GO entry decision of stem cells/progenitor cells within a particular tissue.

Accordingly, the inventors of the present disclosure contemplate the use of isoform-selective TGFβ1 inhibitors in conditions in which: i) stem cell/progenitor cell differentiation/reconstitution is halted or perturbed due to a disease or induced as a side effect of a therapy/mediation; ii) patients are on a therapy or mediation that causes healthy cells to be killed or depleted; iii) patients may benefit from increased stem cell/progenitor cell differentiation/reconstitution; iv) disease is associated with abnormal stem cell differentiation or reconstitution.

In self-renewing tissues, such as bone marrow (blood cell production) and the epidermis, the balance between proliferation and differentiation processes is tightly regulated to ensure the maintenance of the stem cell population during lifetime. Reviewed by D'Arcangel et al. (2017) Int. J Mol Sci. 18(7): 1591. TGFβ1 acts as a potent negative regulator of the cell cycle and tumor suppressor in part through induction of cyclin-dependent kinase inhibitors, p15/INK4b, p21 and p57. Evidence suggests that TGFβ1 contributes to the induction of p16/INK4a and p19/ARF to mediate growth arrest and senescence in certain cell types. Accordingly, in some embodiments, a high-affinity isoform-selective inhibitor of TGFβ1 activation, such as those described herein, is used to regulate p16/INK4a-dependent cellular senescence and stem cell dynamics in various stem cell populations.

For example, mesenchymal stromal/stem cells (MSCs) are a small population of stromal cells present in most adult connective tissues, such as bone marrow, fat tissue, and umbilical cord blood. MSCs are maintained in a relative state of quiescence in vivo but, in response to a variety of physiological and pathological stimuli, are capable of proliferating then differentiating into osteoblasts, chondrocytes, adipocytes, or other mesoderm-type lineages like smooth muscle cells (SMCs) and cardiomyocytes. Multiple signaling networks orchestrate MSCs differentiating into functional mesenchymal lineages, among which TGF-31 has emerged as a key player (reviewed for example by Zhao & Hantash (2011. Vitam Horm 87:127-41).

Similarly, hematopoietic stem cells are required for life-long blood cell production; to prevent exhaustion, the majority of hematopoietic stem cells remain quiescent during steady-state hematopoiesis. During hematologic stress, however, these cells are rapidly recruited into cell cycle and undergo extensive self-renewal and differentiation to meet increased hematopoietic demands. TGFβ1 may work as the "switch" to control the quiescence-repopulation transition/balance.

Thus, the isoform-selective inhibitors of TGFβ1 can be used in the treatment of conditions involving hematopoietic stem cell defects and bone marrow failure. In some embodiments, depletion or impairment of the hematopoietic stem cell reservoir leads to hematopoietic failure or hematologic malignancies. In some embodiments, such conditions are DNA repair disorder characterized by progressive bone marrow failure. In some embodiments, such condition is caused by stem and progenitor cell attrition. In some embodiments, such conditions are associated with anemia. In some embodiments, such condition is Fanconi Anemia (FA). In some embodiments, such conditions are characterized by hyperactive TGFβ pathway that suppresses the survival of certain cell types upon DNA damage. Thus, it is contemplated that the isoform-selective inhibitors of TGFβ1 can be used for rescuing proliferation defects of FA hematopoietic stem cells and/or bone marrow failure in subjects with FA. See, for example, zhang et al. (2016), Cell Stem Cell, 18: 668-681, "TGF-3 inhibition rescues hematopoietic stem cell defects and bone marrow failure in Fanconi Anemia."

Conditions Involving Treatment-Induced Hematopoietic Dysregulation

It is recognized that certain drugs which are designed to treat various disease conditions, often induce or exacerbate anemia in the patient being treated (e.g., treatment- or drug-induced anemia, such as chemotherapy-induced anemia and radiation therapy-induced anemia). In some embodiments, the patient is treated with a myelosuppressive drug that may cause side effects that include anemia. Such patient may benefit from pharmacological TGFβ1 inhibition in order to boost hematopoiesis. In some embodiments, the TGFβ1 inhibitor may promote hematopoiesis in patients by preventing entry into a quiescent state. In some embodiments, the patient may receive a G-CSF therapy (e.g., Filgrastim).

Accordingly, the invention includes the use of an isoform-selective inhibitor of TGFβ1, such as those disclosed herein, to be administered to patients who receive myelosuppressive therapy (e.g., therapy with side effects including myelosuppressive effects). Examples of myelosuppressive therapies include but are not limited to: peginterferon alfa-2a, interferon alfa-n3, peginterferon alfa-2b, aldesleukin, gemtuzumab ozogamicin, interferon alfacon-1, rituximab, ibritumomab tiuxetan, tositumomab, alemtuzumab, bevacizumab, L-Phenylalanine, bortezomib, cladribine, carmustine, amsacrine, chlorambucil, raltitrexed, mitomycin, bexarotene, vindesine, floxuridine, tioguanine, vinorelbine, dexrazoxane, sorafenib, streptozocin, gemcitabine, teniposide, epirubicin, chloramphenicol, lenalidomide, altretamine, zidovudine, cisplatin, oxaliplatin, cyclophosphamide, fluorouracil, propylthiouracil, pentostatin, methotrexate, carbamazepine, vinblastine, linezolid, imatinib, clofarabine, pemetrexed, daunorubicin, irinotecan, methimazole, etoposide, dacarbazine, temozolomide, tacrolimus, sirolimus, mechlorethamine, azacitidine, carboplatin, dactinomycin, cytarabine, doxorubicin, hydroxyurea, busulfan, topotecan, mercaptopurine, thalidomide, melphalan, fludarabine, flucytosine, capecitabine, procarbazine, arsenic trioxide, idarubicin, ifosfamide, mitoxantrone, lomustine, paclitaxel, docetaxel, dasatinib, decitabine, nelarabine, everolimus, vorinostat, thiotepa, ixabepilone, nilotinib, belinostat, trabectedin, trastuzumab emtansine, temsirolimus, bosutinib, bendamustine, cabazitaxel, eribulin, ruxolitinib, carfilzomib, tofacitinib, ponatinib, pomalidomide, obinutuzumab, tedizolid phosphate, blinatumomab, ibrutinib, palbociclib, olaparib, dinutuximab, and colchicine.

Additional TGFβ-related indications may include any of those disclosed in US Pub. No. 2013/0122007, U.S. Pat. No. 8,415,459 or International Pub. No. WO 2011/151432, the contents of each of which are herein incorporated by reference in their entirety.

In preferred embodiments, antibodies, antigen binding portions thereof, and compositions of the disclosure may be used to treat a wide variety of diseases, disorders and/or conditions associated with TGFβ1 signaling. In some embodiment, target tissues/cells preferentially express the TGFβ1 isoform over the other isoforms. Thus, the invention includes methods for treating such a condition associated with TGFβ1 expression (e.g., dysregulation of TGFβ1 signaling and/or upregulation of TGFβ1 expression) using a pharmaceutical composition that comprises an antibody or antigen-binding portion thereof described herein.

In some embodiments, the disease involves TGFβ1 associated with (e.g., presented on or deposited from) multiple cellular sources. In some embodiments, such disease involves both an immune component and an ECM component of TGFβ1 function. In some embodiments, such disease involves: i) dysregulation of the ECM (e.g., overproduction/deposition of ECM components such as collagens and proteases; altered stiffness of the ECM substrate; abnormal or pathological activation or differentiation of fibroblasts, such as myofibroblasts, fibrocytes and CAFs); ii) immune suppression due to increased Tregs and/or suppressed effector T cells (Teff), e.g., elevated ratios of Treg/Teff; increased leukocyte infiltrate (e.g., macrophage and MDSCs) that causes suppression of CD4 and/or CD8 T cells; and/or iii) abnormal or pathological activation, differentiation, and/or recruitment of myeloid cells, such as macrophages (e.g., bone marrow-derived monocytic/macrophages and tissue resident macrophages), monocytes, myeloid-derived suppresser cells (MDSCs), neutrophils, dendritic cells, and NK cells.

In some embodiments, the condition involves TGFβ1 presented by more than one types of presenting molecules (e.g., two or more of: GARP, LRRC33, LTBP1 and/or LTBP3). In some embodiments, an affected tissues/organs/cells that include TGFβ1 from multiple cellular sources. To give but one example, a solid tumor (which may also include a proliferative disease involving the bone marrow, e.g., myelofibrosis and multiple myeloma) may include TGFβ1 from multiple sources, such as the cancer cells, stromal cells, surrounding healthy cells, and/or infiltrating immune cells (e.g., CD45+ leukocytes), involving different types of presenting molecules. Relevant immune cells include but are not limited to myeloid cells and lymphoid cells, for example, neutrophils, eosinophils, basophils, lymphocytes (e.g., B cells, T cells, and NK cells), and monocytes. Context-independent inhibitors of TGFβ1 may be useful for treating such conditions.

Non-limiting examples of conditions or disorders that may be treated with isoform-specific context-independent inhibitors of TGFβ1, such as antibodies or fragments thereof described herein, are provided below.

Treatment Regimen, Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a TGFβ-related indication, such as those noted above. A subject having a TGFβ-related indication can be identified by routine medical examination, e.g., laboratory tests, organ functional tests, CT scans, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose (s), i.e., a desired biological or medicinal response in a tissue or subject at an acceptable benefit/risk ratio. For example, in certain embodiments of the present invention, the intended purpose may be to inhibit TGFβ-1 activation in vivo, to achieve clinically meaningful outcome associated with the TGFβ-1 inhibition. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a TGFβ-related indication. Alternatively, sustained continuous release formulations of an antibody that specifically binds a GARP-TGFβ1 complex, a LTBP1-TGFβ1 complex, a LTBP3-TGFβ1 complex, and/or a LRRC33-TGFβ1 complex may be appropriate. Various formulations and devices for achieving sustained release would be apparent to the skilled artisan and are within the scope of this disclosure.

In one example, dosages for an antibody as described herein may be determined empirically in individuals who have been given one or more administration(s) of the antibody. Individuals are given incremental dosages of the antagonist. To assess efficacy, an indicator of the TGFβ-related indication can be followed. For example, methods for measuring for myofiber damage, myofiber repair, inflammation levels in muscle, and/or fibrosis levels in muscle are well known to one of ordinary skill in the art.

The present invention encompasses the recognition that agents capable of modulating the activation step of TGFβs in an isoform-specific manner may provide improved safety profiles when used as a medicament. Accordingly, the invention includes antibodies and antigen-binding fragments thereof that specifically bind and inhibit activation of TGFβ1, but not TGFβ2 or TGFβ3, thereby conferring specific inhibition of the TGFβ1 signaling in vivo while minimizing unwanted side effects from affecting TGFβ2 and/or TGFβ3 signaling.

In some embodiments, the antibodies, or antigen binding portions thereof, as described herein, are not toxic when administered to a subject. In some embodiments, the antibodies, or antigen binding portions thereof, as described herein, exhibit reduced toxicity when administered to a subject as compared to an antibody that specifically binds to both TGFβ1 and TGFβ2. In some embodiments, the antibodies, or antigen binding portions thereof, as described herein, exhibit reduced toxicity when administered to a subject as compared to an antibody that specifically binds to both TGFβ1 and TGFβ3. In some embodiments, the antibodies, or antigen binding portions thereof, as described herein, exhibit reduced toxicity when administered to a subject as compared to an antibody that specifically binds to TGFβ1, TGFβ2 and TGFβ3.

Generally, for administration of any of the antibodies described herein, an initial candidate dosage can be about 1-20 mg/kg per administration, e.g., weekly, every 2 weeks, every 3 weeks, monthly, etc. For example, patients may receive an injection of about 1-10 mg/kg per 1 week, per 2 weeks, per 3 weeks, or per 4 weeks, etc., in an amount effective to treat a disease (e.g., cancer) wherein the amount is well-tolerated (within acceptable toxicities or adverse events).

For the purpose of the present disclosure, a typical dosage (per administration, such as an injection and infusion) might range from about 0.1 mg/kg to 30 mg/kg, depending on the factors mentioned above. For repeated administrations over several days or longer, depending on the condition, the treatment is sustained until a desired suppression of symptoms occurs or until sufficient therapeutic levels are achieved to alleviate a TGFβ-related indication, or a symptom thereof. For example, suitable effective dosage for Ab6 may be between 1 mg/kg and 30 mg/kg (e.g., 1-10 mg/kg, 1-15 mg/kg, 3-20 mg/kg, 5-30 mg/kg, etc.) dosed twice a week, once a week, every two weeks, every 4 weeks or once a month. Suitable effective dose for Ab6 includes, about 1 mg/kg, about 3 mg/kg, about 5 mg/kg, about 10 mg/kg, for example, dosed weekly.

An exemplary dosing regimen comprises administering an initial dose, followed by one or more of maintenance doses. For example, an initial dose may be between about 1 and 30 mg/kg, for instance, once a week or twice a week. Thereafter, maintenance dose(s) may follow, for example, between about 0.1 and 20 mg/kg, for instance, once a week, every other week, once a month, etc. However, other dosage regimens may be useful, depending on the pattern of pharmacokinetic decay that the practitioner wishes to achieve. Pharmacokinetics experiments have shown that the serum concentration of an antibody disclosed herein (e.g., Ab3) remains stable for at least 7 days after administration to a preclinical animal model (e.g., a mouse model). Without wishing to be bound by any particular theory, this stability post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

Serum concentrations of the high-affinity isoform-selective antibody that are therapeutically effective to treat a TGFβ1-related indication in accordance with the present disclosure may be at least about 10 μg/mL, e.g., between about 10 μg/mL and 1.0 mg/mL. In some embodiments, effective amounts of the antibody as measured by serum concentrations are about 20-400 μg/mL. In some embodiments, effective amounts of the antibody as measured by serum concentrations are about 100-800 μg/mL. In some embodiments, effective amounts of the antibody as measured by serum concentrations are at least about 20 μg/mL, e.g., at least about 50 μg/mL, 100 μg/mL, 150 μg/mL or 200 μg/mL. As detailed in Example 12 herein, in non-human primates, there were no observed toxicities (for example: no cardiotoxicities, hyperplasia and inflammation, dental and gingival findings) associated with Ab6 after maintaining serum concentration levels of about 2,000-3,000 μg/mL for at least 8 weeks. Therefore, about $10^{-100}$ fold therapeutic window may be achieved.

For the purpose of the present disclosure, the appropriate dosage of an antibody that specifically binds a GARP-TGFβ1 complex, a LTBP1-TGFβ1 complex, a LTBP3-TGFβ1 complex, and/or a LRRC33-TGFβ1 complex will depend on the specific antibody (or compositions thereof) employed, the type and severity of the indication, whether the antibody is administered for preventive or therapeutic purposes, previous therapy, the patient's clinical history and response to the antagonist, and the discretion of the attending physician. In some embodiments, a clinician will administer an antibody that specifically binds a GARP-TGFβ1 complex, a LTBP1-TGFβ1 complex, a LTBP3-TGFβ1 complex, and/or a LRRC33-TGFβ1 complex, until a dosage is reached that achieves the desired result. Administration of an antibody that specifically binds a GARP-TGFβ1 complex, a LTBP1-TGFβ1 complex, a LTBP3-TGFβ1 complex, and/or a LRRC33-TGFβ1 complex can be continuous or intermittent, depending, for example, upon the recipient's physiological condition, whether the purpose of the administration is therapeutic or prophylactic, and other factors known to skilled practitioners. The administration of antibody that specifically binds a GARP-TGFβ1 complex, a LTBP1-TGFβ1 complex, a LTBP3-TGFβ1 complex, and/or a LRRC33-TGFβ1 complex may be essentially continuous over a preselected period of time or may be in a series of spaced dose, e.g., either before, during, or after developing a TGFβ-related indication.

As used herein, the term "treating" refers to the application or administration of a composition including one or more active agents to a subject, who has a TGFβ-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a TGFβ-related indication with an antibody that specifically binds a GARP-TGFβ1 complex, a LTBP1-TGFβ1 complex, a LTBP3-TGFβ1 complex, and/or a LRRC33-TGFβ1 complex includes delaying the development or progression of the indication, or reducing indication's severity. Alleviating the indication does not necessarily require curative results. As used therein, "delaying" the development of an indication associated with a TGFβ-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

DBA2/J mice have a 40 bp deletion in the LTBP4 allele. Dysregulation of the ECM to which latent TGFb1 is associated may expose the epitope to which Ab1 binds. There may be diseases in which the epitope to which Ab1 binds gets exposed, and those diseases may be therapeutic opportunities for Ab1 if TGFb1 inhibition is indicated.

Combination Therapy

The disclosure further encompasses pharmaceutical compositions and related methods used as combination therapies for treating subjects who may benefit from TGFβ inhibition in vivo. In any of these embodiments, such subjects may receive combination therapies that include a first composition comprising at least one TGFβ inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition associated with TGFβ signaling, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the reduction of TGFβ1 protein activation and the treatment or prevention of diseases or conditions associated with TGFβ1 signaling, as described herein. Accordingly, the methods or the pharmaceutical compositions further comprise a second therapy. In some embodiments, the second therapy may be useful in treating or preventing diseases or conditions associated with TGFβ1 signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more anti-TGFβ antibodies, or antigen binding portions thereof, of the invention may be used in combination with one or more of additional therapeutic agents. Examples of the additional therapeutic agents which can be used with an anti-TGFβ antibody of the invention include, but are not limited to: cancer vaccines, engineered immune cell therapies, chemotherapies, radiation therapies, a modulator of a member of the TGFβ superfamily, such as a myostatin inhibitor and a GDF11 inhibitor; a VEGF agonist; an IGF1 agonist; an FXR agonist; a CCR2 inhibitor; a CCR5 inhibitor; a dual CCR2/CCR5 inhibitor; CCR4 inhibitor, a lysyl oxidase-like-2 inhibitor; an ASK1 inhibitor; an Acetyl-CoA Carboxylase (ACC) inhibitor; a p38 kinase inhibitor; Pirfenidone; Nintedanib; an M-CSF inhibitor (e.g., M-CSF receptor antagonist and M-CSF neutralizing agents); a MAPK inhibitor (e.g., Erk inhibitor), an immune checkpoint agonist or antagonist; an IL-11 antagonist; and IL-6 antagonist, and the like. Other examples of the additional therapeutic agents which can be used with the TGFβ inhibitors include, but are not limited to, an indoleamine 2,3-dioxygenase (IDO) inhibitor, an arginase inhibitor, a tyrosine kinase inhibitor, Ser/Thr kinase inhibitor, a dual-specific kinase inhibitor. In some embodiments, such an agent may be a PI3K inhibitor, a PKC inhibitor, or a JAK inhibitor.

In some embodiments, the additional agent is a checkpoint inhibitor. In some embodiments, the additional agent is selected from the group consisting of a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody (OX40 agonist), an anti-CD27 antibody, an anti-CD70 antibody, an anti-CD47 antibody, an anti-41 BB antibody, an anti-PD-1 antibody, an oncolytic virus, and a PARP inhibitor. In some embodiments, the high-affinity, context-independent inhibitor of TGFβ1 activation disclosed herein is used in the treatment of cancer in a subject who is a poor responder or non-responder of a checkpoint inhibition therapy, such as those listed herein.

In some embodiments, the additional agent binds a T-cell costimulation molecule, such as inhibitory costimulation molecules and activating costimulation molecules. In some embodiments, the additional agent is selected from the group consisting of an anti-CD40 antibody, an anti-CD38 antibody, an anti-KIR antibody, an anti-CD33 antibody, an anti-CD137 antibody, and an anti-CD74 antibody.

In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that specifically binds a pro/latent myostatin complex and blocks activation of myostatin. In some embodiments, the monoclonal antibody that specifically binds a pro/latent myostatin complex and blocks activation of myostatin does not bind free, mature myostatin.

In some embodiments, an additional therapy comprises cell therapy, such as CAR-T therapy.

In some embodiments, an additional therapy is a cancer vaccine. Numerous clinical trials that tested peptide-based cancer vaccines have targeted hematological malignancies (cancers of the blood), melanoma (skin cancer), breast cancer, head and neck cancer, gastroesophageal cancer, lung cancer, pancreatic cancer, prostate cancer, ovarian cancer, and colorectal cancers. The antigens included peptides from HER2, telomerase (TERT), survivin (BIRC5), and Wilms' tumor 1 (WT1). Several trials also used "personalized" mixtures of 12-15 distinct peptides. That is, they contain a mixture of peptides from the patient's tumor that the patient exhibits an immune response against. Some trials are targeting solid tumors, glioma, glioblastoma, melanoma, and breast, cervical, ovarian, colorectal, and non-small lung cell cancers and include antigens from MUC1, IDO1 (Indoleamine 2,3-dioxygenase), CTAG1B, and two VEGF receptors, FLT1 and KDR. Notably, the IDO1 vaccine is tested in patients with melanoma in combination with the immune checkpoint inhibitor ipilimumab and the BRAF (gene) inhibitor vemurafenib.

Non-limiting examples of tumor antigens useful as cancer vaccines include: NY-ESO-1, HER2, HPV16 E7 (Papillomaviridae #E7), CEA (Carcinoembryonic antigen), WT1, MART-1, gp100, tyrosinase, URLC10, VEGFR1, VEGFR2, surviving, MUC1 and MUC2.

Activated immune cells primed by such cancer vaccine may, however, be excluded from the TME in part through TGFβ1-dependent mechanisms. To overcome the immunosuppression, use of high-affinity, context-independent TGFβ1 inhibitors of the present disclosure may be considered so as to unleash the potential of the vaccine.

Combination therapies contemplated herein may advantageously utilize lower dosages of the administered therapeutic agents, thus avoiding possible toxicities or complications associated with the various monotherapies. In some embodiments, use of an isoform-specific inhibitor of TGFβ1 described herein may render those who are poorly responsive or not responsive to a therapy (e.g., standard of care) more responsive. In some embodiments, use of an isoform-specific inhibitor of TGFβ1 described herein may allow reduced dosage of the therapy (e.g., standard of care) which still produces equivalent clinical efficacy in patients but fewer or lesser degrees of drug-related toxicities or adverse events.

In some embodiments, the isoform-selective inhibitors of TGFβ1 contemplated herein may be used in conjunction with (e.g., combination therapy, add-on therapy, etc.) an isoform-selective inhibitor of TGFβ3. Such use may further comprise additional therapy, such as cancer therapy, e.g., immune checkpoint inhibitor, cancer vaccine, radiation therapy, and/or chemotherapy.

In some embodiments, the isoform-selective inhibitors of TGFβ1 contemplated herein may be used in conjunction with (e.g., combination therapy, add-on therapy, etc.) a selective inhibitor of myostatin (GDF8).

Diagnostics, Patient Selection, Monitoring

Therapeutic methods that include TGFβ1 inhibition therapy may comprise diagnosis of a TGFβ1 indication and/or selection of patients likely to respond to such therapy. Additionally, patients who receive the TGFβ1 inhibitor may be monitored for therapeutic effects of the treatment, which typically involves measuring one or more suitable parameters which are indicative of the condition and which can be measured (e.g., assayed) before and after the treatment and evaluating treatment-related changes in the parameters. For example, such parameters may include levels of biomarkers present in biological samples collected from the patients. Biomarkers may be RNA-based, protein-based, cell-based and/or tissue-based. For example, genes that are overexpressed in certain disease conditions may serve as the biomarkers to diagnose and/or monitor the disease or response to the therapy. Cell-surface proteins of disease-associated cell populations may serve as biomarkers. Such methods may include the direct measurements of disease parameters indicative of the extent of the particular disease, such as tumor size/volume. Any suitable sampling methods may be employed, such as serum/blood samples, biopsies, and imaging. The biopsy may include tissue biopsies (such as tumor) and liquid biopsies.

While biopsies have traditionally been the standard for diagnosing and monitoring various diseases, such as fibrosis (e.g., organ fibrosis) and proliferative disorders (e.g., cancer), less invasive alternatives may be preferred. For example, many non-invasive in vivo imaging techniques may be used to diagnose, monitor, and select patients for treatment. Thus, the invention includes the use of in vivo imaging techniques to diagnose and/or monitor disease in a patient or subject. In some embodiments, the patient or subject is receiving an isoform-specific TGFβ1 inhibitor as described herein. In other embodiments, an in vivo imaging technique may be used to select patients for treatment with an isoform-specific TGFβ1 inhibitor. In some embodiments, such techniques may be used to determine if or how patients respond to a therapy, e.g., TGFβ1 inhibition therapy.

Exemplary in vivo imaging techniques used for the methods include, but are not limited to X-ray radiography, magnetic resonance imaging (MRI), medical ultrasonography or ultrasound, endoscopy, elastography, tactile imaging, thermography, medical photography. Other imaging techniques include nuclear medicine functional imaging, e.g., positron emission tomography (PET) and Single-photon emission computed tomography (SPECT). Methods for conducting these techniques and analyzing the results are known in the art.

Non-invasive imaging techniques commonly used to diagnose and monitor cancer include, but are not limited to: magnetic resonance imaging (MRI), computed tomography (CT), ultrasound, positron emission tomography (PET), single-photon emission computed tomography (SPECT), fluorescence reflectance imaging (FRI), and fluorescence mediated tomography (FMT). Hybrid imaging platforms may also be used to diagnose and monitor cancer. For example, hybrid techniques include, but are not limited to: PET-CT, FMT-CT, FMT-MRI, and PET-MRI. Dynamic contrast enhanced MRI (DCE-MRI) is another imaging technique commonly used to detect breast cancers. Methods for conducting these techniques and analyzing the results are known in the art.

Non-invasive imaging techniques commonly used to diagnosis and monitor fibrosis include, but are not limited to: ultrasound (e.g., conventional or contrast-enhanced ultrasound), ultrasound elastography (e.g., transient elastography, point shear wave elastography and 2D-shear wave elastography), CT scan (e.g., conventional CT or CT perfusion imaging), magnetic resonance imaging (MRI) (e.g., conventional MRI, Magnetic resonance elastography, diffusion weighted magnetic resonance imaging, gadoxetic acid disodium, and magnetic resonance perfusion imaging).

In some embodiments, non-invasive imaging techniques are used to assess levels of liver fibrosis or hepatic steatosis. For example, imaging techniques particularly useful to assess liver fibrosis may include but are not limited to: FibroScan (transient elastography; TE), point shear wave elastography (pSWE; a.k.a. acoustic radiation force impulse (ARFI)), 2D-3D SWE, magnetic resonance elastography (MRE), and multiparameteric MRI. Imaging techniques particularly useful to assess hepatic steatosis may include but are not limited to: ultrasonography, controlled attenuation parameter (CAP) elastography, MRI-estimated proton density fat fraction (MRI-PDFF), and magnetic resonance spectroscopy (MRS). In some embodiments, the in vivo imaging technique is used to assess liver stiffness. In some embodiments, the in vivo imaging technique is used to detect and assess intrahepatic triglyceride levels. In some embodiments, in vivo imaging technique is used to assess liver surface nodularity (LSN; a.k.a. "liver score"), liver stiffness, and/or liver segmental volume ratio (LSVR), which are all beneficial in the staging of hepatic fibrosis and sub-staging cirrhosis. Methods for conducting these techniques and analyzing the results are known in the art.

More recently, non-invasive imaging methods are being developed which will allow the detection of cells of interest (e.g., cytotoxic T cells, macrophages, and cancer cells) in vivo. See for example, imaginab.com/technology/; Tavare et al. (2014) PNAS, 111(3): 1108-1113; Tavare et al. (2015) J Nucl Med 56(8): 1258-1264; Rashidian et al. (2017) J Exp Med 214(8): 2243-2255; Beckford Vera et al. (2018) PLoS ONE 13(3): e0193832; and Tavare et al. (2015) Cancer Res 76(1): 73-82, each of which is incorporated herein by reference. So-called "T-cell tracking" is aimed to detect and localize anti-tumor effector T-cells in vivo. This may provide useful insights into understanding the immunosuppressive phenotype of solid tumors. Tumors that are well-infiltrated with cytotoxic T cells ("inflamed" or "hot" tumors) are likely to respond to cancer therapies such as checkpoint blockade therapy (CBT). On the other hand, tumors with immunosuppressive phenotypes tend to have poor T-cell infiltration even when there is an anti-tumor immune response. These so-called "immune excluded" tumors likely fail to respond to cancer therapies such as CBT. T-cell tracking techniques may reveal these different phenotypes and provide information to guide in therapeutic approach that would likely benefit the patients. For example, patients with an "immune excluded" tumor are likely benefit from a TGFβ1 inhibitor therapy to help reverse the immunosuppressive phenotype. It is contemplate that similar techniques may be used to diagnose and monitor other diseases, for example, fibrosis. Typically, antibodies or antibody-like molecules engineered with a detection moiety (e.g., radiolabel, fluorescence, etc.) can be infused into a patient, which then will distribute and localize to sites of the particular marker (for instance CD8+ and M2 macrophages).

Non-invasive in vivo imaging techniques may be applied in a variety of suitable methods for purposes of diagnosing patients; selecting or identifying patients who are likely to benefit from TGFβ1 inhibitor therapy; and/or, monitoring patients for therapeutic response upon treatment. Any cells with a known cell-surface marker may be detected/localized by virtue of employing an antibody or similar molecules that specifically bind to the cell marker. Typically, cells to be detected by the use of such techniques are immune cells, such as cytotoxic T lymphocytes, regulatory T cells, MDSCs, disease-associated macrophages (M2 macropahges such as TAMs and FAMs), NK cells, dendritic cells, and neutrophils.

Non-limiting examples of suitable immune cell markers include monocyte markers, macrophage markers (e.g., M1 and/or M2 macrophage markers), CTL markers, suppressive immune cell markers, MDSC markers (e.g., markers for G- and/or M-MDSCs), including but are not limited to: CD8, CD3, CD4, CD11b, CD163, CD206, CD68, CD14, CD15, CD66, CD34, CD25, and CD47.

In vivo imaging techniques described above may be employed to detect, localize and/or track certain MDSCs in a patient diagnosed with a TGFβ1-associated disease, such as cancer and fibrosis. Healthy individuals have no or low frequency of MDSCs in circulation. With the onset of or progression of such a disease, elevated levels of circulating and/or disease-associated MDSCs may be detected. For example, CCR2-positive M-MDSCs have been reported to accumulate to tissues with inflammation and may cause progression of fibrosis in the tissue (such as pulmonary fibrosis), and this is shown to correlate with TGFβ1 expression. Similarly, MDSCs are enriched in a number of solid tumors (including triple-negative breast cancer) and in part contribute to the immunosuppressive phenotype of the TME. Therefore, treatment response to TGFβ1 inhibition therapy according to the present disclosure may be monitored by localizing or tracking MDSCs. Reduction of or low frequency of detectable MDSCs is typically indicative of therapeutic benefits or better prognosis.

Many human cancers are known to cause elevated levels of MDSCs in patients, as compared to healthy control (reviewed, for example, in Elliott et al. (2017) "Human tumor-infiltrating myeloid cells: phenotypic and functional diversity" Frontiers in Immunology, Vol. 8, Article 86). These human cancers include but are not limited to: bladder cancer, colorectal cancer, prostate cancer, breast cancer, glioblastoma, hepatocellular carcinoma, head and neck squamous cell carcinoma, lung cancer, melanoma, NSCL, ovarian cancer, pancreatic cancer, and renal cell carcinoma. Elevated levels of MDSCs may be detected in biological samples such as peripheral blood mononuclear cell (PBMC) and tissue samples (e.g., tumor biopsy). For example, frequency of or changes in the number of MDSCs may be measured as: percent (%) of total PBMCs, percent (%) of CD14+ cells, percent (%) of CD45+ cells; percent (%) of mononuclear cells, percent (%) of total cells, percent (%) of CD 11 b+ cells, percent (%) of monocytes, percent (%) of non-lymphocytic MNCs, percent (%) of KLA-DR cells, using suitable cell surface markers (phenotype).

Additionally, using immune cell markers, in the case of cancer, it is possible to determine whether the tumor has an immune-excluded phenotype. If the tumor is determined to have an immune-excluded phenotype, cancer therapy (such as CBT) alone may not be efficacious because the tumor lacks sufficient cytotoxic cells within the tumor environment. Thus, an add-on therapy with a TGFβ1 inhibitor such as those described herein may reduce immuno-suppression thereby rendering the cancer therapy-resistant tumor more responsive to a cancer therapy. It is contemplated, that immune markers could also be used to track immune cells in the fibrotic context, and/or determine the immune cell composition of fibrotic tissue (e.g., to track the presence of macrophages and/or myofibroblasts).

Accordingly, the invention also includes a method for treating a TGFβ1-related disease or condition which may comprise the following steps: i) selecting a patient diagnosed with a TGFβ1-related disease or condition; and, ii) administering to the patient an antibody or the fragment encompassed herein in an amount effective to treat the disease or condition. In some embodiments, the selection step (i) comprises detection of disease markers (e.g., fibrosis or cancer markers as described herein), wherein optionally the detection comprises a biopsy analysis, serum marker analysis, and/or in vivo imaging. In some embodiments, the selection step (i) comprises an in vivo imaging technique as described herein.

In some embodiments, the TGFβ1-related disease or condition is a fibrotic condition. In some embodiments, the selection step (i) comprises detection of myofibroblasts cells, or one or more markers thereof. In some embodiments, the selection step (i) comprises detection of hepatic steatosis, hepatic triglycerides, immune cells, and/or myofibroblasts. In some embodiments, the detection comprises a biopsy analysis, serum marker analysis, and/or in vivo imaging. In some embodiments, the in vivo imaging comprises ultrasound, ultrasound elastography, CT scan, MRI, PET-SPECT, optical fluorescence/bioluminescence Fibro-Scan (TE), pSWE, 2D-3D SWE, MRE, ultrasonography, CAP, MRI-PDFF, and/or MRS. In some embodiments, in vivo imaging comprises direct or indirect labeling of immune cells or antibody that binds a cell-surface marker of immune cells. In some embodiments, the in vivo imaging comprises the use of a tracer.

In some embodiments, the in vivo imaging technique measures hepatic steatosis, hepatic triglycerides, immune cells (e.g., as described below), and/or myofibroblasts. In some embodiments, the treatment reduces triglycerides, steatosis, liver surface nodules, inflammation, and/or macrophages, in the diseased tissue. In some embodiments, the treatment reduces intrahepatic triglyceride content to <5.5%. In some embodiments, the treatment reduces MDSCs in the diseased tissue. In some embodiments, the treatment reduces macrophages in the diseased tissue. In some embodiments, the effective amount is from 0.1 mg/kg to 30 mg/kg, optionally 3 mg/kg to 30 mg/kg. In some embodiments, the method further comprises monitoring the subject for a therapeutic response as described herein (e.g., reduced triglycerides, reduced steatosis, reduced liver surface nodules, reduced inflammation, reduced macrophages, and/or reduced liver score).

The invention also includes a method for treating cancer which may comprise the following steps: i) selecting a patient diagnosed with cancer comprising a solid tumor, wherein the solid tumor is or is suspected to be an immune excluded tumor; and, ii) administering to the patient an antibody or the fragment encompassed herein in an amount effective to treat the cancer. Preferably, the patient has received, or is a candidate for receiving a cancer therapy such as immune checkpoint inhibition therapies (e.g., PD-(L)1 antibodies), chemotherapies, radiation therapies, engineered immune cell therapies, and cancer vaccine therapies. In some embodiments, the selection step (i) comprises detection of immune cells or one or more markers thereof, wherein optionally the detection comprises a tumor biopsy analysis, serum marker analysis, and/or in vivo imaging. In some embodiments, the selection step (i) comprises an in vivo imaging technique as described here. In some embodiments, the method further comprises monitoring for a therapeutic response as described herein.

In some embodiments, in vivo imaging is performed for monitoring a therapeutic response to the TGFβ1 inhibition therapy in the subject. The in vivo imaging can comprises any one of the imaging techniques described herein and measure any one of the markers and/or parameters described herein. For example, in the case of liver fibrosis, the therapeutic response may comprise reduced liver steatosis, reduced triglyceride content, reduced ECM deposition/fibrosis, reduced cirrhosis, and/or reduced disease progression. In some embodiments, treatment with an isoform-specific TGFB1 inhibitor as described herein reduces intrahepatic triglyceride content to levels of ≤5.5% as measured by MRI. In the case of cancer, the therapeutic response may comprise conversion of an immune excluded tumor into an inflamed tumor (which correlates with increased immune cell infiltration into a tumor), reduced tumor size, and/or reduced disease progression. Increased immune cell infiltration may be visualized by increased intratumoral immune cell frequency or degree of detection signals, such as radiolabeling and fluorescence.

In some embodiments, the in vivo imaging used for diagnosing, selecting, treating, or monitoring patients, comprises MDSC tracking, such as G-MDSCs (also known as PMN-MDSCs) and M-MDSCs. For example, MDSCs may be enriched at a disease site (such as fibrotic tissues and solid tumors) at the baseline. Upon therapy (e.g., TGFβ1 inhibitor therapy), fewer MDSCs may be observed, as measured by reduced intensity of the label (such as radioisotope and fluorescence), indicative of therapeutic effects.

In some embodiments, the in vivo imaging comprises tracking or localization of LRRC33-positive cells. LRRC33-positive cells include, for example, MDSCs and activated M2-like macrophages (e.g., TAMs and activated macrophages associated with fibrotic tissues). For example, LRRC33-positive cells may be enriched at a disease site (such as fibrotic tissues and solid tumors) at the baseline. Upon therapy (e.g., TGFβ1 inhibitor therapy), fewer cells expressing cell surface LRRC33 may be observed, as measured by reduced intensity of the label (such as radioisotope and fluorescence), indicative of therapeutic effects.

In some embodiments, the in vivo imaging techniques described herein may comprise the use of PET-SPECT, MRI and/or optical fluorescence/bioluminescence in order to detect cells of interest.

In some embodiments, labeling of antibodies or antibody-like molecules with a detection moiety may comprise direct labeling or indirect labeling.

In some embodiments, the detection moiety may be a tracer. In some embodiments, the tracer may be a radioisotope, wherein optionally the radioisotope may be a positron-emitting isotope. In some embodiments, the radioisotope is selected from the group consisting of: 18F, 11C, 13N, 15O, 68Ga, 177Lu, 18F and 89Zr.

Thus, such methods may be employed to carry out in vivo imaging with the use of labeled antibodies in immune-PET.

Accordingly, the invention also includes a method for treating a TGFβ1 indication in a subject, which incorporates a step of diagnosis, patient selection, and/or monitoring therapeutic effects, which employs an imaging technique. In some embodiments, a high-affinity, isoform-selective TGFβ1 inhibitor according to the present disclosure is used in the treatment of a TGFβ1 indication, wherein the treatment comprises administration of an effective amount of the TGFβ1 inhibitor to treat the indication, and further comprising a step of monitoring therapeutic effects in the subject by in vivo imaging. Optionally, the subject may be selected as a candidate for receiving the TGFβ1 inhibitor therapy, using a diagnostic or selection step that comprises in vivo imaging. The TGFβ1 indication may be a proliferative disorder (such as cancer with a solid tumor and myelofibrosis) or a fibrotic disorder (such as organ fibrosis).

In some embodiments, the subject has cancer, wherein the method comprises the following steps: i) selecting a patient diagnosed with cancer comprising a solid tumor, wherein the solid tumor is or is suspected to be an immune excluded tumor; and, ii) administering to the patient an antibody or the fragment encompassed herein in an amount effective to treat the cancer. Preferably, the patient has received, or is a candidate for receiving a cancer therapy such as immune checkpoint inhibition therapies (e.g., PD-(L)1 antibodies), chemotherapies, radiation therapies, engineered immune cell therapies, and cancer vaccine therapies. In some embodiments, the selection step (i) comprises detection of immune cells or one or more markers thereof, wherein optionally the detection comprises a tumor biopsy analysis, serum marker analysis, and/or in vivo imaging. In some embodiments, the selection step (i) comprises an in vivo imaging technique as described here. In some embodiments, the method further comprises monitoring for a therapeutic response as described herein.

Assays for Detecting Large Latent Complexes (LLCs)

In some embodiments, methods and compositions provided herein relate to a method for detecting a GARP-TGFβ1 complex, a LTBP1-TGFβ1 complex, a LTBP3-TGFβ1 complex, and/or a LRRC33-TGFβ1 complex in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, poultry, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a GARP-TGFβ1 complex, a LTBP1-TGFβ1 complex, a LTBP3-TGFβ1 complex, and/or a LRRC33-TGFβ1 complex in a sample obtained from a subject involves (a) contacting the sample with an antibody that specifically binds a GARP-TGFβ1 complex, a LTBP1-TGFβ1 complex, a LTBP3-TGFβ1 complex, and/or a LRRC33-TGFβ1 complex under conditions suitable for binding of the antibody to the antigen, if the antigen is present in the sample, thereby forming binding complexes; and (b) determining the level of the antibody bound to the antigen (e.g., determining the level of the binding complexes).

In one embodiment, a screening assay that utilizes biotinylated latent TGFβ1 complexes immobilized onto a surface, which allows for the activation of latent TGFβ by integrins by providing tether. Other, non-integrin activators could also be tested in that system. Readout can be through reporter cells or other TGFβ3-dependent cellular responses.

Cell-Based Assays for Measuring TGFβ Activation

Activation of TGFβ (and inhibition thereof by a TGFβ test inhibitor, such as an antibody) may be measured by any suitable method known in the art. For example, integrin-mediated activation of TGFβ can be utilized in a cell-based potency assay, such as the "CAGA12" reporter (e.g., luciferase) assay, described in more detail herein. As shown, such an assay system may comprise the following components: i) a source of TGFβ (recombinant, endogenous or transfected); ii) a source of activator such as integrin (recombinant, endogenous, or transfected); and iii) a reporter system that responds to TGFβ activation, such as cells expressing TGFβ receptors capable of responding to TGFβ and translating the signal into a readable output (e.g., luciferase activity in CAGA12 cells or other reporter cell lines). In some embodiments, the reporter cell line comprises a reporter gene (e.g., a luciferase gene) under the control of a TGFβ3-responsive promoter (e.g., a PAI-1 promoter). In some embodiments, certain promoter elements that confer sensitivity may be incorporated into the reporter system. In some embodiments, such promoter element is the CAGA12 element. Reporter cell lines that may be used in the assay have been described, for example, in Abe et al. (1994) Anal Biochem. 216(2):

276-84, incorporated herein by reference. In some embodiments, each of the aforementioned assay components are provided from the same source (e.g., the same cell). In some embodiments, two of the aforementioned assay components are provided from the same source, and a third assay component is provided from a different source. In some embodiments, all three assay components are provided from different sources. For example, in some embodiments, the integrin and the latent TGFβ complex (proTGFβ and a presenting molecule) are provided for the assay from the same source (e.g., the same transfected cell line). In some embodiments, the integrin and the TGF are provided for the assay from separate sources (e.g., two different cell lines, a combination of purified integrin and a transfected cell). When cells are used as the source of one or more of the assay components, such components of the assay may be endogenous to the cell, stably expressed in the cell, transiently transfected, or any combination thereof.

A skilled artisan could readily adapt such assays to various suitable configurations. For instance, a variety of sources of TGFβ may be considered. In some embodiments, the source of TGFβ is a cell that expresses and deposits TGFβ (e.g., a primary cell, a propagated cell, an immortalized cell or cell line, etc.). In some embodiments, the source of TGFβ is purified and/or recombinant TGFβ immobilized in the assay system using suitable means. In some embodiments, TGFβ immobilized in the assay system is presented within an extracellular matrix (ECM) composition on the assay plate, with or without de-cellularization, which mimics fibroblast-originated TGFβ. In some embodiments, TGFβ is presented on the cell surface of a cell used in the assay. Additionally, a presenting molecule of choice may be included in the assay system to provide suitable latent-TGFβ complex. One of ordinary skill in the art can readily determine which presenting molecule(s) may be present or expressed in certain cells or cell types. Using such assay systems, relative changes in TGFβ activation in the presence or absence of a test agent (such as an antibody) may be readily measured to evaluate the effects of the test agent on TGFβ activation in vitro. Data from exemplary cell-based assays are provided in the Example section below.

Such cell-based assays may be modified or tailored in a number of ways depending on the TGFβ isoform being studied, the type of latent complex (e.g., presenting molecule), and the like. In some embodiments, a cell known to express integrin capable of activating TGFβ may be used as the source of integrin in the assay. Such cells include SW480/36 cells (e.g., clone 1E7). In some embodiments, integrin-expressing cells may be co-transfected with a plasmid encoding a presenting molecule of interest (such as GARP, LRRC33, LTBP (e.g., LTBP1 or LTBP3), etc.) and a plasmid encoding a pro-form of the TGFβ isoform of interest (such as proTGFβ1). After transfection, the cells are incubated for sufficient time to allow for the expression of the transfected genes (e.g., about 24 hours), cells are washed, and incubated with serial dilutions of a test agent (e.g., an antibody). Then, a reporter cell line (e.g., CAGA12 cells) is added to the assay system, followed by appropriate incubation time to allow TGFβ signaling. After an incubation period (e.g., about 18-20 hours) following the addition of the test agent, signal/read-out (e.g., luciferase activity) is detected using suitable means (e.g., for luciferase-expressing reporter cell lines, the BRIGHT-GLO™ reagent (Promega) can be used). In some embodiments, Luciferase fluorescence may be detected using a BIOTEK® (SYNERGY™ H1) plate reader, with autogain settings.

Data demonstrate that exemplary antibodies of the invention which are capable of selectively inhibiting the activation of TGFβ1 in a context-independent manner.

Nucleic Acids

In some embodiments, antibodies, antigen binding portions thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure. In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

List of Certain Embodiments

Non-limiting embodiments of the present disclosure are listed below:

1. An antibody or an antigen-binding fragment thereof that binds each of the following antigen complexes with a $K_D$ of ≤10 nM, optionally ≤5 nM, as measured by a solution equilibrium titration-based assay:
   i) hLTBP1-proTGFβ1;
   ii) hLTBP3-proTGFβ1;
   iii) hGARP-proTGFβ1; and,
   iv) hLRRC33-proTGFβ1;
   wherein the antibody or the fragment thereof is a fully human or humanized antibody or fragment thereof.

2. The antibody or the antigen-binding fragment according to embodiment 1, which binds each of the i) hLTBP1-proTGFβ1 and the ii) hLTBP3-proTGFβ1 complexes with a $K_D$ of ≤5 nM as measured by a solution equilibrium titration-based assay, wherein optionally, the antibody or the fragment binds each of the complexes with a $K_D$ of ≤1 nM as measured by a solution equilibrium titration-based assay 3. An antibody or an antigen-binding fragment thereof that binds each of the following antigen complexes with a $K_D$ of ≤200 μM, optionally ≤100 μM, as measured by a solution equilibrium titration-based assay:
   i) hLTBP1-proTGFβ1;
   ii) hLTBP3-proTGFβ1;
   iii) hGARP-proTGFβ1; and,
   iv) hLRRC33-proTGFβ1;
   wherein the antibody or the fragment thereof is a fully human or humanized antibody or fragment thereof.

4. The antibody or the antigen-binding fragment according to any one of the preceding embodiments, which comprises CDR-H1, CDR-H2, CDR-H3, CDR-L1, CDR-L2, and CDR-L3, wherein:
   the CDR-H1 has an amino acid sequence represented by FTF($X_1$)($X_2$)($X_3$)($X_4$)M($X_5$), wherein optionally, $X_1$ is S, G or A; $X_2$ is S or F; $X_3$ is F or Y; $X_4$ is S or A; and/or, $X_5$ is D, N or Y (SEQ ID NO: 143);
   the CDR-H2 has an amino acid sequence represented by YI($X_1$)($X_2$)($X_3$)A($X_4$)TIYYA($X_5$)SVKG, wherein optionally, $X_1$ is S or H; $X_2$ is P or S; $X_3$ is S or D; $X_4$ is D or S; and/or, $X_5$ is D or G (SEQ ID NO: 144);
   the CDR-H3 has an amino acid sequence represented by ($X_1$)R($X_2$)($X_3$)($X_4$)D($X_5$)GDML($X_6$)P, wherein optionally, $X_1$ is A or V; $X_2$ is G or A; $X_3$ is V or T; $X_4$ is L or W; $X_5$ is Y or M; and/or, $X_6$ is M or D (SEQ ID NO: 145);

the CDR-L1 has an amino acid sequence QASQDITNYLN (SEQ ID NO: 105), with optionally 1 or 2 amino acid changes;

the CDR-L2 has an amino acid sequence DASNLET (SEQ ID NO: 106), with optionally 1 or 2 amino acid changes; and, the CDR-L3 has an amino acid sequence QQADNHPPWT (SEQ ID NO: 12), with optionally 1 or 2 amino acid changes.

5. The antibody or the antigen-binding fragment according to any one of the preceding embodiments, which comprises CDR-H1, CDR-H2, CDR-H3, CDR-L1, CDR-L2, and CDR-L3, wherein:

the CDR-H1 has an amino acid sequence FTFSSFSMD (SEQ ID NO: 107), with optionally up to 4 amino acid changes, or, up to 2 amino acid changes;

the CDR-H2 has an amino acid sequence YISPSADTIYYADSVKG (SEQ ID NO: 103), with optionally up to 4 amino acid changes;

the CDR-H3 has an amino acid sequence ARGVLDYGDMLMP (SEQ ID NO: 6), with optionally up to 3 amino acid changes;

the CDR-L1 has an amino acid sequence QASQDITNYLN (SEQ ID NO: 105), with optionally 1 or 2 amino acid changes;

the CDR-L2 has an amino acid sequence DASNLET (SEQ ID NO: 106), with optionally 1 or 2 amino acid changes; and, the CDR-L3 has an amino acid sequence QQADNHPPWT (SEQ ID NO: 12), with optionally 1 or 2 amino acid changes.

6. The antibody or the antigen-binding fragment according to any one of the preceding embodiments, wherein the CDR-H1 comprises GFTFSSFS (SEQ ID NO: 2); the CDR-H2 comprises ISPSADTI (SEQ ID NO: 4); the CDR-H3 comprises ARGVLDYGDMLMP (SEQ ID NO: 6); the CDR-L1 comprises QDITNY (SEQ ID NO: 8); the CDR-L2 comprises DAS (SEQ ID NO: 10); and, the CDR-L3 comprises QQADNHPPWT (SEQ ID NO: 12).

7. The antibody or the antigen-binding fragment according to any one of the preceding embodiments, which binds an epitope that includes one or more amino acid residues of Latent Lasso, wherein optionally the epitope is a combinatorial epitope, wherein further optionally, the combinatorial epitope comprises one or more amino acid residues of Finger-1 and/or Finger-2 of the growth factor domain.

8. The antibody or the antigen-binding fragment of embodiment 7, wherein the epitope comprises one or more amino acid residues of KLRLASPPSQGEVPPGPLPEAVL (SEQ ID NO: 169), and wherein optionally the epitope further comprises one or more amino acid residues of RKDLGWKWIHEPKGYHANF (SEQ ID NO: 165) and/or VGRKPKVEQL (SEQ ID NO: 168).

9. The antibody or the antigen-binding fragment of embodiment 8, wherein the epitope comprises one or more amino acid residues of KLRLASPPSQGEVPPGPLPEAVL (SEQ ID NO: 169), and one or more amino acid residues of RKDLGWKWIHEPKGYHANF (SEQ ID NO: 165).

10. The antibody or the antigen-binding fragment of embodiment 8, wherein the epitope comprises one or more amino acid residues of KLRLASPPSQGEVPPGPLPEAVL (SEQ ID NO: 169) and one or more amino acid residues of VGRKPKVEQL (SEQ ID NO: 168).

11. The antibody or the antigen-binding fragment of embodiment 7, wherein the epitope comprises one or more amino acid residues of KLRLASPPSQGEVPPGPLPEAVL (SEQ ID NO: 169), one or more amino acid residues of RKDLGWKWIHEPKGYHANF (SEQ ID NO: 165) and, one or more amino acid residues of VGRKPKVEQL (SEQ ID NO: 168).

12. The antibody or the antigen-binding fragment according to any one of the preceding embodiments, wherein the antibody or the antigen-binding fragment is a fully human or humanized antibody or the antigen-binding fragment.

13. The antibody or the antigen-binding fragment according to any one of the preceding embodiments, wherein the antibody or the antigen-binding fragment cross-reacts with human and mouse proTGFβ1 complexes.

14. The antibody or the antigen-binding fragment according to any one of the preceding embodiments, wherein the antibody or the antigen-binding fragment is a human IgG4 or IgG1 subtype.

15. The antibody or the antigen-binding fragment according to any one of the preceding embodiments, wherein the antibody or the antigen-binding fragment comprises a backbone substitution of Ser to Pro that produces an IgG1-like hinge.

16. The antibody or the antigen-binding fragment according to any one of the preceding embodiments, which has an IC50 of ≤2 nM towards each of the following complexes as measured by a cell-based reporter assay.
  i) hLTBP1-proTGFβ1;
  ii) hLTBP3-proTGFβ1;
  iii) hGARP-proTGFβ1; and,
  iv) hLRRC33-proTGFβ1.

17. An isolated monoclonal antibody or a fragment thereof that specifically binds each of the following antigen with an affinity of ≤1 nM as measured by Biolayer Interferometry or surface plasmon resonance:
  a) a human LTBP1-proTGFβ1 complex;
  b) a human LTBP3-proTGFβ1 complex;
  c) a human GARP-proTGFβ1 complex; and,
  d) a human LRRC33-proTGFβ1 complex;
  wherein the monoclonal antibody shows no more than a three-fold bias in affinity towards any one of the above complexes over the other complexes, and,
  wherein the monoclonal antibody inhibits release of mature TGFβ1 growth factor from each of the proTGFβ1 complexes but not from proTGFβ2 or proTGFβ3 complexes.

18. An isolated monoclonal antibody or a fragment thereof that specifically binds a proTGFβ1 complex at a binding region having an amino acid sequence PGPLPEAV (SEQ ID NO: 161) or a portion thereof, characterized in that when bound to the proTGFβ1 complex in a solution, the antibody or the fragment protects the binding region from solvent exposure as determined by hydrogen-deuterium exchange mass spectrometry (HDX-MS); and,
  wherein the antibody or the fragment specifically binds each of the following complexes: LTBP1-proTGFβ1, LTBP3-proTGFβ1, GARP-proTGFβ1, and LRRC33-proTGFβ1, with an affinity of ≤5 nM as measured by Biolayer Interferometry or surface plasmon resonance.

19. An isolated monoclonal antibody or a fragment thereof that specifically binds a proTGFβ1 complex at a binding region having an amino acid sequence LVKRKRIEA (SEQ ID NO: 159) or a portion thereof, characterized in that when bound to the proTGFβ1 complex in a solution, the antibody or the fragment protects the binding region from solvent exposure as determined by hydrogen-deuterium exchange mass spectrometry (HDX-MS); and, wherein the antibody or the fragment specifically binds each of the following complexes: LTBP1-proTGFβ1, LTBP3-proTGFβ1, GARP-proTGFβ1, and LRRC33-proTGFβ1, with an affinity of ≤5 nM as measured by Biolayer Interferometry or surface plasmon resonance.

20. An isolated monoclonal antibody or a fragment thereof that specifically binds a proTGFβ1 complex at
   i) a first binding region comprising at least a portion of Latency Lasso (SEQ ID NO: 153); and
   ii) a second binding region comprising at least a portion of Finger-1 (SEQ ID NO: 151);
   characterized in that when bound to the proTGFβ1 complex in a solution, the antibody or the fragment protects the binding regions from solvent exposure as determined by hydrogen-deuterium exchange mass spectrometry (HDX-MS).

21. The antibody or the fragment according to claim 45, wherein the first binding region comprises PGPLPEAV (SEQ ID NO: 161) or a portion thereof and the second binding region comprises RKDLGWKW (SEQ ID NO: 170) or a portion thereof.

22. The antibody or the fragment according to any one of the preceding embodiments, wherein the antibody is a context-independent antibody such that it binds matrix-associated proTGFβ1 complexes and cell-associated proTGFb1 complexes with less than five-fold bias in affinity, as measured by Biolayer Interferometry or surface plasmon resonance.

23. The antibody or the fragment according to any one of claims 43-47, which specifically binds each of the following complexes: mLTBP1-proTGFβ1, mLTBP3-proTGFβ1, mGARP-proTGFβ1, and mLRRC33-proTGFβ1, with an affinity of ≤1 nM.

24. The antibody or the fragment according to any one of the preceding embodiments that binds the proTGFβ1 complex at one or more of the following binding regions or a portion thereof:

```
                        (SEQ ID NO: 159)
LVKRKRIEA;

(SEQ ID NO: 153)
LASPPSQGEVPPGPL;

(SEQ ID NO: 161)
PGPLPEAV;

(SEQ ID NO: 162)
LALYNSTR;

(SEQ ID NO: 163)
REAVPEPVL;

(SEQ ID NO: 164)
YQKYSNNSWR;

(SEQ ID NO: 171)
RKDLGWKWIHE;

(SEQ ID NO: 172)
HEPKGYHANF;

(SEQ ID NO: 166)
LGPCPYIWS;

(SEQ ID NO: 167)
ALEPLPIV; and, (SEQ ID NO: 168)
VGRKPKVEQL.
```

25. The antibody or the fragment according to any one of the preceding embodiments, having a CDR sequence selected from the group consisting of:

```
                        (SEQ ID NO: 2)
GFTFSSFS (SEQ ID NO: 4)
ISPSADTI (SEQ ID NO: 6)
ARGVLDYGDMLMP (SEQ ID NO: 8)
QDITNY (SEQ ID NO: 10)
DAS
and (SEQ ID NO: 12)
QQADNHPPWT.
```

26. The antibody according to embodiment 25, which comprises all of the CDRs.

27. An antibody or an antigen-binding fragment thereof that binds each of the following antigen:
   hLTBP1-proTGFβ1
   hLTBP3-proTGFβ1
   hGARP-proTGFβ1; and,
   hLRRC33-proTGFβ1;
   wherein the antibody or the fragment binds each of the hLTBP1-proTGFβ1 and hLTBP3-proTGFβ1 with a $K_D$ of ≤1 nM as measured by a solution equilibrium titration-based assay;
   wherein the antibody or the fragment binds an epitope comprising one or more amino acid residues of LRLASPPSQGEVPPGPLPEAV (SEQ ID NO: 173), and optionally the epitope further comprises one or more amino acid residues of RKDLGWKWIHEPKGYHANF (SEQ ID NO: 165).

28. The antibody or the antigen-binding fragment according to any one of the preceding embodiments,
   wherein the antibody or the fragment binds each of LTBP1-proTGFβ1 and LTBP3-proTGFβ1 with an affinity of ≤1 nM; and
   wherein the antibody or the fragment binds matrix-associated proTGFβ1 complexes with at least 10-fold higher affinities than cell-associated proTGFβ1 complexes.

29. The antibody or the antigen-binding fragment according to the preceding embodiment, wherein the $IC_{50}$ is <5 nM, wherein optionally the $IC_{50}$ is <1 nM.

30. The antibody or the antigen-binding fragment according to any one of the preceding embodiments, wherein the antibody or the antigen-binding fragment is capable of inhibiting integrin-dependent activation of TGFβ1.

31. The antibody or the antigen-binding fragment according to any one of the preceding embodiments, wherein the antibody or the antigen-binding fragment is capable of inhibiting protease-dependent activation of TGFβ1.

32. The antibody or the antigen-binding fragment according to any one of the preceding embodiments, wherein the antibody or the antigen-binding fragment is capable of inhibiting integrin-dependent activation of TGFβ1 and protease-dependent activation of TGFβ1.

33. The antibody or the fragment thereof according any one of the preceding embodiments, which does not specifically bind proTGFβ2 or proTGFβ3.

34. The antibody or the fragment thereof according any one of the preceding embodiments, which does not specifically bind free TGFβ1 growth factor which is not in association with a proTGFβ1 complex.

35. An antibody or an antigen-binding fragment thereof that cross-blocks with the antibody or the fragment according any one of the preceding embodiments.

36. A kit comprising the antibody or the fragment according to any one of the preceding embodiments.

37. A composition comprising the antibody or the fragment according to any one of the preceding embodiments, and a pharmaceutically acceptable excipient.

38. The composition of embodiment 37 for use in therapy in the treatment of a TGFβ-related indication in a subject.

39. The composition for use according to embodiment 38, wherein the TGFβ-related indication is cancer, myelofibrosis, stem cell disorder, and/or fibrotic disorder.

40. The composition for use according to embodiment 38, wherein the TGFβ-related indication is selected from the following:
i) disease in which TGFβ1 is overexpressed or TGFβ1 signaling is dysregulated;
ii) disease associated with abnormal stem cell differentiation or repopulation, which is optionally:
  a) stem cell/progenitor cell differentiation/reconstitution is halted or perturbed due to a disease or induced as a side effect of a therapy/mediation;
  b) patients are on a therapy or mediation that causes healthy cells to be killed or depleted;
  c) patients may benefit from increased stem cell/progenitor cell differentiation/reconstitution;
  d) disease is associated with abnormal stem cell differentiation or reconstitution
iii) conditions involving hematopoietic dysregulation, such as treatment-induced hematopoietic dysregulation;
iv) diseases with aberrant gene expression of one or more genes selected from the group consisting of: Serpine 1 (encoding PAI-1), MCP-1 (also known as CCL2), CCL3, Col1a1, Col3a1, FN1, TGFB1, CTGF, ACTA2 (encoding α-SMA), ITGA11, SNAI1, MMP2, MMP9, TIMP1, FOXP3, CDH1 (E cadherin), and, CDH2;
v) diseases involving proteases
vi) diseases Involving mesenchymal transition, such as Epithelial-to-Mesenchymal Transition (EMT) and/or Endothelial-to-Mesenchymal Transition (EndMT);
vii) diseases Involving immunosuppression, wherein optionally the immunosuppression comprises increased immunosuppressive cells at disease site, wherein further optionally the immunosuppressive cells are M2 macrophages and/or MDSCs;
viii) diseases involving Matrix Stiffening and Remodeling; optionally comprising ECM stiffness;
ix) organ fibrosis, optionally advanced organ fibrosis
x) primary and secondary myelofibrosis
xi) Malignancies/cancer
  a) solid tumor, optionally advanced solid tumor or metastatic tumor;
  b) blood cancer.

41. The composition for use according to embodiment 40, wherein the cancer comprises a solid tumor, or, wherein the cancer is a blood cancer.

42. The composition for use according to embodiment 41, wherein the solid tumor is poorly responsive to a cancer therapy, wherein optionally the cancer therapy is a checkpoint inhibitor therapy, cancer vaccine, chemotherapy, radiation therapy, oncolytic virus therapy, IDO inhibitor therapy, and/or an engineered immune cell therapy.

43. The composition for use according to embodiment 41, wherein the solid tumor is an immune-excluded tumor.

44. The composition for use according to embodiment 41, wherein the solid tumor comprises Tregs, intratumoral M2 macrophages and/or MDSCs.

45. The composition for use according to embodiment 41, wherein the solid tumor comprises stroma enriched with CAFs and/or myofibroblasts.

46. The composition for use according to embodiment 41, wherein the subject is receiving or is a candidate for receiving a cancer therapy selected from the group consisting of: chemotherapy, radiation therapy, CAR-T, cancer vaccine, oncolytic viral therapy and checkpoint inhibitor therapy.

47. The composition for use according to embodiment 41, wherein the cancer is characterized by acquired resistance or primary resistance to the cancer therapy.

48. The composition for use according to any one of embodiment 38-47, wherein the treatment of cancer comprises administration of a therapeutically effective amount of the composition to reduce the growth of the solid tumor, wherein optionally the administration of the composition increases survival.

49. The composition for use according to any one of embodiment 38-48, wherein the treatment comprises administration of the composition at a dose ranging between 1-30 mg/kg.

50. A method for selecting a subject likely to respond to a TGFβ1 inhibition therapy, comprising the step of:
identifying a subject diagnosed with cancer, wherein, i) the cancer is a type of cancer known to be susceptible for resistance to a cancer therapy, and/or, ii) the subject is resistant to a cancer therapy, wherein optionally the subject is a primary non-responder to the cancer therapy;
wherein optionally the cancer therapy is chemotherapy, radiation therapy and/or immune checkpoint inhibition therapy; and,
selecting the subject as a candidate for a TGFβ1 inhibition therapy.

51. A method for treating cancer, the method comprising steps of:
i) selecting a patient diagnosed with cancer comprising a solid tumor, wherein the solid tumor is or is suspected to be an immune excluded tumor;
ii) administering to the patient the antibody or the fragment according to any one of claims 1-10 in an amount effective to treat the cancer,
wherein (a) the patient has received, or is a candidate for receiving a cancer therapy selected from the group consisting of: immune checkpoint inhibition therapies (CBTs), chemotherapies, radiation therapies, engineered immune cell therapies, and cancer vaccine therapies; or, (b) the patient has a cancer with statistically low primary response rates, and wherein the patient has not received a CBT.

52. The method of claim 25, wherein the immune checkpoint inhibitor is a PD-1 inhibitor or a PD-L1 inhibitor.

53. The method of claim 26, wherein the selection step (i) comprises detection of immune cells or one or more markers thereof.

54. The method of claim 27, wherein the detection comprises a tumor biopsy analysis, serum marker analysis, and/or in vivo imaging.

55. The method of claim 27 or 28, wherein the immune cells are selected from the group consisting of: cytotoxic T lymphocytes, regulatory T cells, MDSCs, tumor-associated macrophages, NK cells, dendritic cells, and neutrophils.

56. The method of any one of claims 27-29, wherein the immune cell marker is selected from the group consisting of: CD8, CD3, CD4, CD11b, CD163, CD68, CD14, CD34, CD25, CD47. 57. The method of claim 28, wherein the in vivo imaging comprises T cell tracking.

58. The method of claim 28 or 31, wherein the in vivo imaging comprises the use of PET-SPECT, MRI and/or optical fluorescence/bioluminescence.

59. The method of claim 31 or 32, wherein the in vivo imaging comprises direct or indirect labeling of immune cells or antibody that binds a cell-surface marker of immune cells.

60. The method of any one of claims 28-33, wherein the in vivo imaging comprises the use of a tracer.

61. The method of claim 34, wherein the tracer is a radioisotope.

62. The method of claim 35, wherein the radioisotope is a positron-emitting isotope.

63. The method of claim 36, wherein the radioisotope is selected from the group consisting of: $^{18}$F, $^{11}$C, $^{13}$N, $^{15}$O, $^{68}$Ga, $^{177}$Lu, $^{18}$F and $^{89}$Zr.

64. The method of any one of claims 28-37, wherein the in vivo imaging comprise the use of labeled antibodies in immuno-PET.

65. The method of any one of claims 28-38, wherein the in vivo imaging is performed for monitoring a therapeutic response to the TGFβ1 inhibition therapy in the subject.

66. The method of claim 39, wherein the therapeutic response comprises conversion of an immune excluded tumor into an inflamed tumor.

67. A method of identifying an isoform-selective inhibitor of TGFβ1 activation for therapeutic use, the method comprising the steps of:
  i) selecting a pool of antibodies or antigen-binding fragments capable of binding each of: hLTBP1-proTGFβ1; hLTBP3-proTGFβ1; hGARP-proTGFβ1; and, hLRRC33-proTGFβ1 in vitro with a $K_D$ of ≤10 nM as measured by a solution equilibrium titration-based assay;
  ii) selecting a pool of antibodies or antigen-binding fragments capable of inhibiting TGFβ activation, optionally in a cell-based assay;
  iii) testing one or more antibodies or antigen-binding fragments thereof from steps i) and ii) in an in vivo efficacy study;
  iv) testing one or more antibodies or antigen-binding fragments thereof from steps i)-iii) in an in vivo toxicology/safety study; and,
  v) identifying one or more antibodies or antigen-binding fragments from steps i)-iv), wherein the antibodies or the fragments show efficacious doses determined in the in vivo efficacy study that are below a NOAEL determined in the in vivo toxicology/safety study.

68. Use of the antibody or the fragment according to any one of embodiments 1-35 in the manufacture of a medicament for the treatment of a TGFβ1 indication.

69. The use according to embodiment 68, further comprising a step of sterile filtration of a formulation comprising the antibody or the fragment.

70. The use according to embodiment 68 or 69, further comprising a step of filling and/or packaging into a vial or a syringe.

71. A method for making a pharmaceutical composition comprising an isoform-selective TGFβ1 inhibitor, the method comprising:
  i) providing an antibody capable of binding each of hLTBP1-proTGFβ1, hLTBP3-proTGFβ1, hGARP-proTGFβ1 and hLRRC33-proTGFβ1 with a $K_D$ of 1 nM or less,
  ii) carrying out an in vivo efficacy study wherein the antibody of step (i) is administered to a preclinical model to determine effective amounts,
  iii) carrying out a toxicology study using an animal model known to be sensitive to TGFβ inhibition, to determine amounts at which undesirable toxicities are observed;
  iv) determining or confirming a sufficient therapeutic window based on steps (ii) and (iii); and, v) manufacturing a pharmaceutical composition comprising the antibody.

72. A method of manufacturing the antibody or the fragment according to any one of embodiments 1-35, the method comprising steps of:
  i) providing an antigen that comprises a proTGFβ1 complex, optionally comprising at least two of: LTBP1, LTBP3, GARP, LRRC33 or a fragment thereof,
  ii) selecting for a pool of antibodies or fragments for ability to bind the antigen of step (i); iii) optionally removing antibodies or fragments from the pool that show undesirable binding profiles; iv) selecting for a pool of antibodies or fragments selected from step(s) (ii) and/or (iii) for ability to inhibit TGFβ1;
  v) optionally generating a fully human or humanized antibody or fragment of an antibody, antibodies or fragments selected from step (iv) so as to provide a human or humanized inhibitor;
  vi) carrying out in vitro binding assay to determine affinities for LTBP1-proTGFβ1, LTBP3-proTGFβ1, GARP-proTGFβ1 and LRRC33-proTGFβ1,
  vii) carrying out functional assay to determine or confirm activity of the inhibitor towards TGFβ1 and optionally TGFβ2 and/or TGFβ3.

73. The method of embodiment 72, further comprising a step of evaluating a candidate antibody or a fragment thereof in an in vivo efficacy study and in vivo toxicology study in a preclinical animal model, thereby determining effective amounts shown to be both efficacious and safe or tolerable.

74. The method of embodiment 72 or 73, further comprising a step of formulating into a pharmaceutical composition.

75. The composition according to embodiment 74 for therapeutic use in the treatment of fibrosis in a human subject.

76. The composition according to embodiment 74 for therapeutic use in the treatment of myelofibrosis in a human subject.

77. The composition according to embodiment 74 for therapeutic use in the treatment of cancer in a human subject.

78. The composition for use according to embodiment 77, wherein the cancer comprises a solid tumor.

79. The composition for use according to embodiment 78, wherein the solid tumor is a locally advanced solid tumor.

80. The composition for use according to any one of embodiments 77-79, wherein the cancer is poorly responsive to a cancer therapy, wherein optionally the cancer therapy is a checkpoint inhibitor therapy, cancer vaccine, chemotherapy, radiation therapy, IDO inhibitor therapy, and/or an engineered immune cell therapy.

81. The composition for use according to embodiment 80, wherein the cancer is characterized by acquired resistance or primary resistance.

82. The composition for use according to embodiment 81, wherein the tumor is characterized by immune exclusion.

83. The composition for use according to any one of embodiments 78-82, wherein the tumor comprises intratumoral M2 macrophages and/or MDSCs.

84. The composition for use according to any one of embodiments 78-82, wherein the tumor comprises stroma enriched with CAFs.

85. The composition for use according to embodiment 80, wherein the subject is receiving or is a candidate for receiving a cancer therapy selected from the group consisting of: chemotherapy, radiation therapy, CAR-T, cancer vaccine, oncolytic viral therapy and checkpoint inhibitor therapy.

86. The composition for use according to any one of embodiments, wherein the subject is further treated with a TGFβ3 inhibitor.

87. The composition for use according to embodiment 70, wherein the subject has TGFβ1-positive and TGFβ3-positive cancer and wherein the subject has been, is on or is a candidate for receiving a checkpoint inhibitor therapy.

88. The composition for use according to any one of embodiments 77-84, wherein the subject is not a candidate for undergoing surgical resection of the tumor.

89. The composition according to embodiment 37 for use in the enhancement of host immunity in a human subject, wherein the subject has cancer, and wherein the immune responses comprise anti-cancer immunity.

90. The composition for use according to embodiment 89 wherein the enhancement of host immunity includes reducing immune-exclusion from a tumor or promoting immune cell infiltrates into a tumor.

91. The composition for use according to embodiment 89 wherein the enhancement of host immunity includes inhibiting plasmin-dependent activation of TGFβ1. 92. The composition for use according to embodiment 37, wherein the subject is at risk of developing a cytokine storm.

93. The composition for use according to embodiment 37, wherein the subject is receiving or a candidate for receiving an engineered immune cell therapy.

94. The composition for use according to embodiment 37, wherein the subject is receiving or is a candidate for receiving a cancer vaccine.

95. The composition for use according to any one of embodiments 76-94, wherein the subject is receiving or is a candidate for receiving an immune checkpoint inhibitor therapy, wherein optionally the subject is poorly responsive to the immune checkpoint inhibitor therapy.

96. The composition according to embodiment 37 for use in the prevention of a cytokine release syndrome, (e.g., cytokine storm or sepsis) in a human subject, wherein optionally the subject is suffering from an infection or MS.

97. The composition according to claim 37 for use in a method for inhibiting plasmin-dependent activation of TGFβ1 in a subject.

98. A method for treating a TGFβ1 indication in a subject, the method comprising a step of administering to the subject a therapeutically effective amount of an isoform-selective TGFβ1 inhibitor to treat the indication, wherein, the isoform-selective TGFβ1 inhibitor is a monoclonal antibody that specifically binds each of hLTBP1-proTGFβ1; hLTBP3-proTGFβ1; hGARP-proTGFβ1; and, hLRRC33-proTGFβ1 with a $K_D$ of ≤10 nM as measured by solution equilibrium titration.

99. The method of embodiment 98, wherein the antibody binds each of the hLTBP1-proTGFβ1 and hLTBP3-proTGFβ1 with a $K_D$ of ≤1 nM as measured by solution equilibrium titration, wherein optionally, the antibody binds each of the hLTBP1-proTGFβ1; hLTBP3-proTGFβ1; hGARP-proTGFβ1; and, hLRRC33-proTGFβ1 complexes with a $K_D$ of ≤1 nM.

100. The method of embodiment 98 or 99, wherein the antibody binds Latency Lasso or a portion thereof.

101. The method of embodiment 100, wherein the antibody further binds Finger-1, Finger-2, or a portion(s) thereof.

102. The method of any one of embodiments 98-101, wherein the TGFβ1 indication is a proliferative disorder selected from cancer and myeloproliferative disorders.

103. The method of embodiment 102, wherein the subject is a poor responder of a cancer therapy, wherein optionally the cancer therapy comprises a checkpoint inhibition therapy, chemotherapy and/or radiation therapy.

104. The method of embodiment 102, wherein the subject is further treated with a cancer therapy in conjunction with the isoform-selective TGFβ1 inhibitor.

This invention is further illustrated by the following examples which should not be construed as limiting.

EXAMPLES

Example 1: In Vitro Binding Profiles

1) BLI-Based Assay:

The affinity of Ab4, Ab5, Ab6 and Ab3 was measured by OCTET® assay on human proTGFβ1 cells, while activity was measured by CAGA12 reporter cells testing human proTGFβ1 inhibition. The protocol used to measure the affinity of the antibodies to the complexes provided herein is summarized in Table 19 below, and a summary list of in affinity profiles of exemplary antibodies of the present disclosure is provide in Table 8 herein.

TABLE 19

Exemplary protocol for performing Octet ® binding assay

Materials:
96 well black polypropylene plates
Streptavidin-coated tips for Octet ®
10× kinetics buffer (diluted 1:10 in PBS)
1. Soak required amount of streptavidin tips in 1× kinetics buffer; place in machine to equilibrate
2. Load sample plate:
200 µl of buffer or antibody dilution to each well
a) Column 1-baseline (buffer)
b) Column 2-biotinylated protein (e.g., sGARP-proTGFβ1 or LTBP1-proTGFβ1); diluted to 5 µg/mL
c) Column 3-baseline 2 (buffer)
d) Column 4-antibody association for Ab
e) Column 5-antibody association for Ab
f) Column 6-dissociation Ab (buffer)

TABLE 19-continued

Exemplary protocol for performing Octet ® binding assay g) Column 7-dissociation Ab (buffer)
3. Make dilutions in the 96 well plate:
a) Dilute both antibodies to 50 µg/mL in 300 µl of 1× buffer in row A.
b) Add 200 µl of buffer to the rest of each column
c) Transfer 100 µl down the column to make 3-fold dilutions
4. Place the sample plate in the machine next to the tips plate
5. Set up the software
a) Indicate buffer, load, sample (one assay per antibody tested)
b) Indicate steps of the protocol (baseline, load, association, dissociation) for set amounts of time:
Baseline: 60 seconds
Loading: 300 seconds
Baseline 2: 60 seconds
Association: 300 seconds
Dissociation: 600 seconds
6. Analyze data
a) Subtract baseline from reference well
b) Set normalization to last five seconds of baseline
c) Align to dissociation
d) Analyze to association and dissociation (1:1 binding model, fit curves)
e) Determine the best $R^2$ values; include concentrations with best $R^2$ values
f) Select global fit
g) Set colors of samples by sensor type
h) Analyze
Save table and export As an example, Ab6 binding to TGFβ antigens was measured by biolayer interferometry on a FortéBio OCTET® Red384 using polystyrene 96-well black half area plates (Greiner Bio-One). Binding of Ab6 to human mature TGFβ1, TGFβ2, and TGFβ3 growth factors as well as human latent TGFβ1 was done after coupling the antigens to amine reactive second-generation (AR2G) biosensors (Fort6Bio) using the amine-reactive second-generation (AR2G) reagent kit (Fort6Bio) according to the manufacturer's specifications. AR2G biosensors were first allowed to hydrate in water offline for at least 10 minutes before initiation of the experiment. Upon initiation of the experiment, AR2G tips were equilibrated in water for 1 minute. Then, the tips were moved into a freshly prepared activation solution (18 parts water, 1 part 400 mM EDC (1-Ethyl-3-[3-dimethylaminopropyl] carbodiimide hydrochloride), and 1 part 200 mM sulfo-NHS (N-hydroxysulfosuccinimide)) for 5 minutes. Recombinant TGFβ protein (10 ug/mL in 10 mM sodium acetate buffer pH 5) was coupled to the activated tips for 3 minutes before quenching with ethanolamine pH 8.5 for 15 minutes. The baseline was determined with a 20 min incubation of the coupled tips in EKB buffer (Kinetics buffer (Fort6Bio) supplemented with 2% BSA (Sigma), 0.5 M NaCl, and 0.09% Tween-20 (Sigma). Tips were then allowed to associate in a 15 µg/mL solution of Ab6 in EKB for 10 minutes before 10 minutes of dissociation in EKB. Binding of Ab6 to human large latent complexes was measured after immobilizing Ab6 to the surface of anti-human Fc capture biosensors (FortéBio) (1 ug/mL in EKB) for 5 minutes. An additional 1 minute baseline was then performed before the association of LTBP1-proTGFβ1, LTBP1-proTGFβ2, or LTBP1-proTGFβ3 (100 nM in EKB) for ten minutes. Finally, a ten minute dissociation was performed.

2) Solution Equilibrium Titration-Based Assay:

MSD-SET is a well-characterized technique which can be used for the determination of solution-phase equilibrium $K_D$. Solution-based equilibrium assays such as MSD-SET are based on the principle of kinetic exclusion, in which free ligand binding at equilibrium rather than real-time association and dissociation rates is measured to determine affinity.

MSD-SET assays were performed to measure affinities of the antibodies at equilibrium. Briefly, each test antibody was diluted 3-5 fold and samples were mixed with biotinylated antigen in a 48-well dish. The SET samples were equilibrated for 20-24 hours at room temperature. Meanwhile, a capture plate was coated with IgG (20 nM) and incubated overnight at 4° C. or 30 minutes at room temperature, followed by a blocking step with 5% BSA. After the capture plate was washed three times, SET samples were added and incubated for 150 seconds. The plate was washed once to remove unbound complexes. 250 ng/ml SA-Sulfotag was added then washed 3 times. 2× Read Buffer was added, and signals from the labeled bound complexes were read with the use of QUICKPLEX™ SQ 120 instrument.

Summary lists of affinity profiles of exemplary antibodies of the present disclosure as measured by MSD-SET are provide in Tables 9 and 10 herein.

As an example, MSD standard plates (MSD) were coated with a 20 nM solution of monoclonal antibody in PBS for 30 min at room temperature or overnight at 4° C. Increasing concentrations of the same monoclonal antibody used for coating were then mixed with biotinylated antigen (between 50 and 400 µM for binding to Ab6; between 0.8 and 1.6 nM for binding to Ab4) overnight at room temperature without shaking. After 20-24 hours of equilibration, the antibody-coated plate was blocked with Blocking Buffer A (MSD) for 30 minutes at room temperature and washed with wash buffer (PBS, 0.1% BSA, 0.05% Tween-20) before adding the equilibrated antibody-antigen complexes to the plate for exactly 2.5 minutes. The plate was washed again with wash buffer before adding 250 ng/ml SULFO-TAG-labeled streptavidin secondary reagent (MSD) in PBS with 0.1% BSA. After washing with wash buffer, plates were read in MSD read buffer (MSD) using the MESO QuickPlex SQ 120 (MSD). The binding data were processed by nonlinear curve fitting in Prism 7 software (Graphpad) to calculate equilibrium binding $K_D$ values.

Example 2: Functional Assays to Measure Inhibition of Latent TGFβ1 Activation

The development of novel context-dependent cell-based potency assays of TGFβ1 activation is described in WO 2019/023661, incorporated by reference in its entirety herein. Previous assay formats could not differentiate between the activation of proTGFβ1 presented by endogenous presenting molecules and the activation of proTGFβ1 presented by exogenous LTBPs. By directly transfecting integrin-expressing cells, the novel assays disclosed in WO 2019/023661, and used herein, establish a window between endogenous presenter-proTGFβ1 activity and exogenous LTBP-proTGFβ1 activity. As LTBP-proTGFβ1 complexes are embedded in the extracellular matrix, the assay plate coating is also an important component of the assay. The use of high binding plates, coated with the ECM protein Fibronectin, made the LTBP assays more robust.

To determine if the Ab4, Ab5, Ab6 and Ab3 antibodies were functional (e.g., having inhibitory potency), cell-based assays were developed, in which αV3 integrin-dependent release of TGFβ1 growth factor from large latent complexes (LLCs) were measured. Each assay is specific for each of the LLCs comprising LTBP1, LTBP3, GARP or LRRC33. Through the process of assay development and optimization, it was determined that fibronectin is a critical ECM protein for the integrin-dependent in vitro activation of LTBP-presented proTGFβ1.

Assay I. Activation of Latent TGFβ1 Deposited in the ECM

Figure 2:
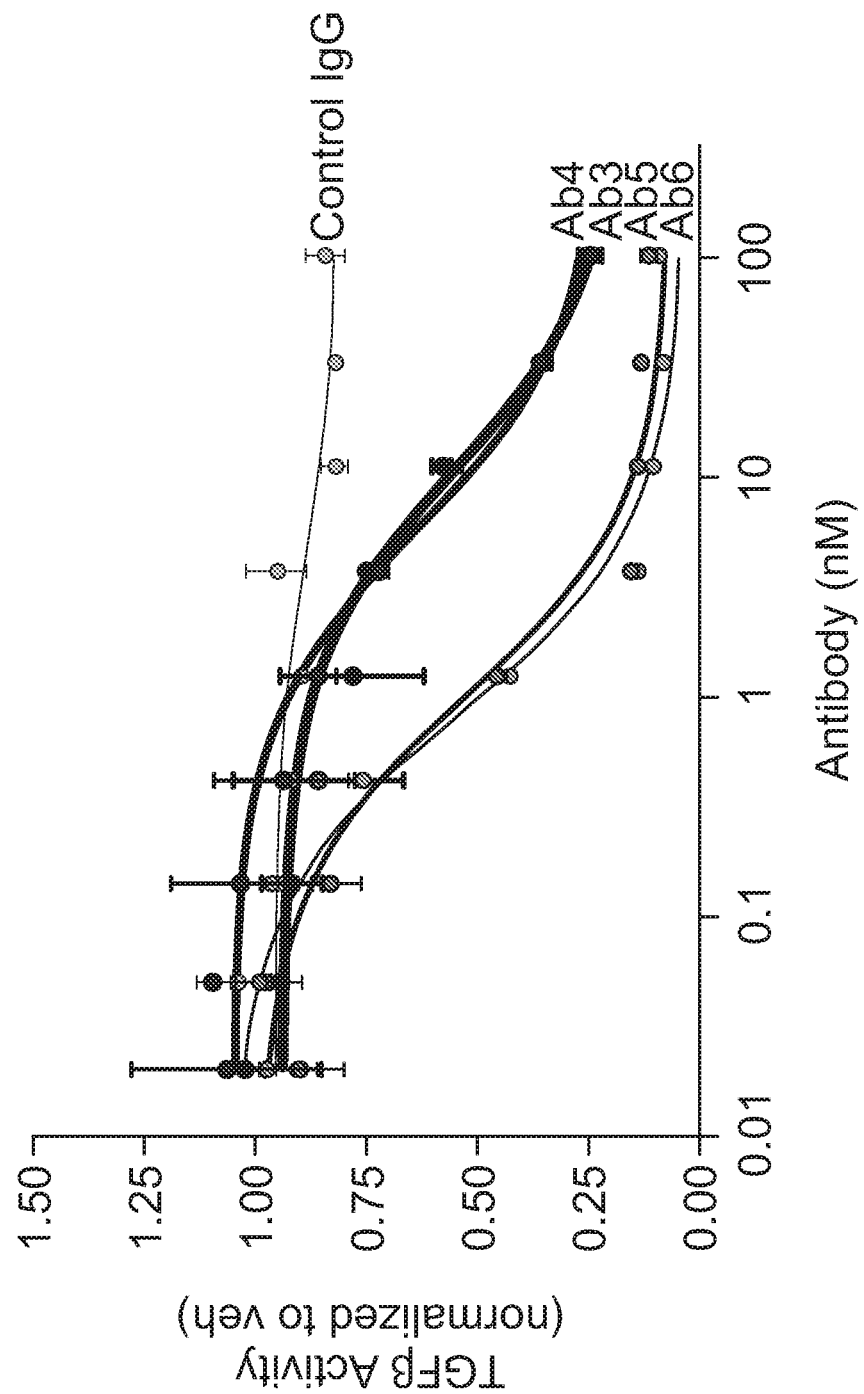
FIG. 2 is a graph that shows inhibition of proTGFβ1 complex activation in an LN229 assay.

For the assays depicted in FIG. 1 and FIG. 2, the following protocol was developed. This assay is optimal for measuring integrin-dependent release of TGFβ1 from ECM-associated latent proTGFβ1 complexes (LTBP1-proTGFβ1 or LTBP3-proTGFβ1).

Materials

MvLu1-CAGA12 cells (Clone 4A4)
SW480/p6 cells (Clone 1E7) (αV subunit is endogenously expressed at high levels; (36 subunit is stably overexpressed)
LN229 cell line (high levels of endogenous αVβ8 integrin)
Costar white walled TC treated 96 well assay plate #3903
Greiner Bio-One High Binding white uclear 96 well assay plate #655094
Human Fibronectin (Corning #354008)
P200 multichannel pipet
P20, P200, and P1000 pipets with sterile filter tips for each
Sterile microfuge tubes and rack
Sterile reagent reservoirs
0.4% trypan blue
2 mL, 5 mL, 10 mL, and 25 mL sterile pipets
Tissue culture treated 100 mm or 150 mm plates
70% Ethanol
Opti-MEM reduced serum media (Life Tech #31985-070)
LIPOFECTAMINE® 3000 (Life Tech #L3000015)
BRIGHT-GLO™ luciferase assay reagent (Promega #E2620)
0.25% Tryspin+0.53 mM EDTA
proTGFβ1 expression plasmid, human
LTBP1S expression plasmid, human
LTBP3 expression plasmid, human
LRRC32 (GARP) expression plasmid, human
LRRC33 expression plasmid, human Equipment BIOTEK® SYNERGY™ H1 plate reader
TC hood
Bench top centrifuge
CO2 incubator 37C 5% CO2
37 C water/bead bath
Platform shaker
Microscope
Hemocytometer/countess Definitions CAGA12 4A4 cells: Derivative of MvLu1 cells (Mink Lung Epithelial Cells), stably transfected with CAGA12 synthetic promoter, driving luciferase gene expression
DMEM-0.1% BSA: Assay media; base media is DMEM (Gibco Cat #11995-065), media also contains BSA diluted to 0.1% w/v, penicillin/streptinomycin, and 4 mM glutamine
D10: DMEM 10% FBS, P/S, 4 mM glutamine, 1% NEAA, 1× GlutaMAX (Gibco Cat #35050061)
SW480/p6 Media: D10+1000ug/mL G-418
CAGA12 (4A4) media: D10+0.75ug/mL puromycin Procedure:

On Day 0, cells were seeded for transfection. SW480/36 (clone 1E7) cells were detached with trypsin and pellet (spin 5 min @ 200×g). Cell pellet was resuspended in D10 media and viable cells per ml were counted. Cells were seeded at $5.0 \times 10^6$ cells/12 ml/100 mm tissue culture dish. For CAGA12 cells, cells were passaged at a density of 1.0 million per T75 flask, to be used for the assay on Day 3. Cultures were incubated at 37° C. and 5% $CO_2$.

On Day 1, integrin-expressing cells were transfected. Manufacturer's protocol for transfection with LIPOFECTAMINE® 3000 reagent was followed. Briefly, the following were diluted into OPTIMEM™ I, for 125 μl per well: 7.5 μg DNA (presenting molecule)+7.5 μg DNA (proTGFβ1), 30 μl P3000, and Up to 125 μl with OPTIMEM™ I.

The well was mixed by pipetting DNA together, then OPTIMEM™ was added. P3000 was added, and everything was mixed well by pipetting. A master mix of LIPOFECTAMINE®3000 was made, to be added to DNA mixes: for the LTBP1 assay: 15 μl LIPOFECTAMINE®3000, up to 125 μl in OPTIMEM™ I, per well; for the LTBP3 assay: 45 μl LIPOFECTAMINE®3000, up to 125 μl in OPTIMEM™ I, per well. Diluted LIPOFECTAMINE®3000 was added to DNA, mixed well by pipetting, and incubated at room temp for 15 min. After the incubation, the solution was mixed a few times by pipetting, and then 250 μl of DNA: LIPOFECTAMINE®3000 (2×125 μl) per dish was added dropwise. Each dish was gently swirled to mix and the dish was returned to the tissue culture incubator for ~ 24 hours.

On Days 1-2, the assay plates were coated with human fibronectin. Specifically, lyophilized fibronectin was diluted to 1 mg/ml in ultra-pure distilled water (sterile). 1 mg/ml stock solution was diluted to 19.2 μg/ml in PBS (sterile). Added 50 μl/well to assay plate (high binding) and incubated overnight in tissue culture incubator (37° C. and 5% $CO_2$). Final concentration was 3.0 μg/cm².

On Day 2, transfected cells were plated for assay and inhibitor addition. First, the fibronectin coating was washed by adding 200 μl/well PBS to the fibronectin solution already in the assay plate. Removed wash manually with multichannel pipette. Wash was repeated for two washes total. The plate was allowed to dry at room temperature with lid off prior to cell addition. The cells were then plated by detaching with trypsin and pellet (spin 5 min @ 200×g.). The pellet was resuspended in assay media and viable cells were counted per ml. For the LTBP1 assay cells were diluted to 0.10×10⁶ cells/ml and seed 50 µl per well (5,000 cells per well). For the LTBP3 assay, cells were diluted to 0.05×10⁶ cells/ml and seed 50 µl per well (2,500 cells per well). To prepare functional antibody dilutions, antibodies were pre-diluted to a consistent working concentration in vehicle. Stock antibodies were serially diluted in vehicle (PBS is optimal, avoid sodium citrate buffer). Each point of serial dilution was diluted into assay media for a 4× final concentration of antibody. Added 25 µl per well of 4× antibody and incubated cultures at 37° C. and 5% $CO_2$ for ~ 24 hours.

On Day 3, the TGFβ reporter cells were added. CAGA12 (clone 4A4) cells for the assay were detached with trypsin and pellet (spin 5 min @ 200×g.). The pellet was resuspended in assay media and count viable cells per ml. Cells were diluted to 0.4×10⁶ cells/ml and seed 50 µl per well (20,000 cells per well). Cells were returned to incubator.

On Day 4, the assay was read (16-20 hours after antibody and/or reporter cell addition). BRIGHT-GLO™ reagent and test plate were allowed to come to room temperature before reading. Read settings on BIOTEK® SYNERGY™ H1 were set using TMLC_std protocol—this method has an auto-gain setting. Selected positive control wells for autoscale (high). 100 µl of BRIGHT-GLO™ reagent was added per well. Incubated for 2 minutes with shaking, at room temperature, protected plate from light. The plate was read on BIOTEK® SYNERGY™ H1.

Inhibition of LTBP1-proTGBβ1 activation by Ab3, Ab4, Ab5, Ab6 or control IgG was measured in an LN229 reporter assay (FIG. 1).

Inhibition of LTBP3-proTGBβ1 activation by Ab3, Ab4, Ab5, Ab6 or control IgG was measured in an LN229 reporter assay (FIG. 2).

Assay II. Activation of Latent TGFβ1 Presented on the Cell Surface

Figure 3:
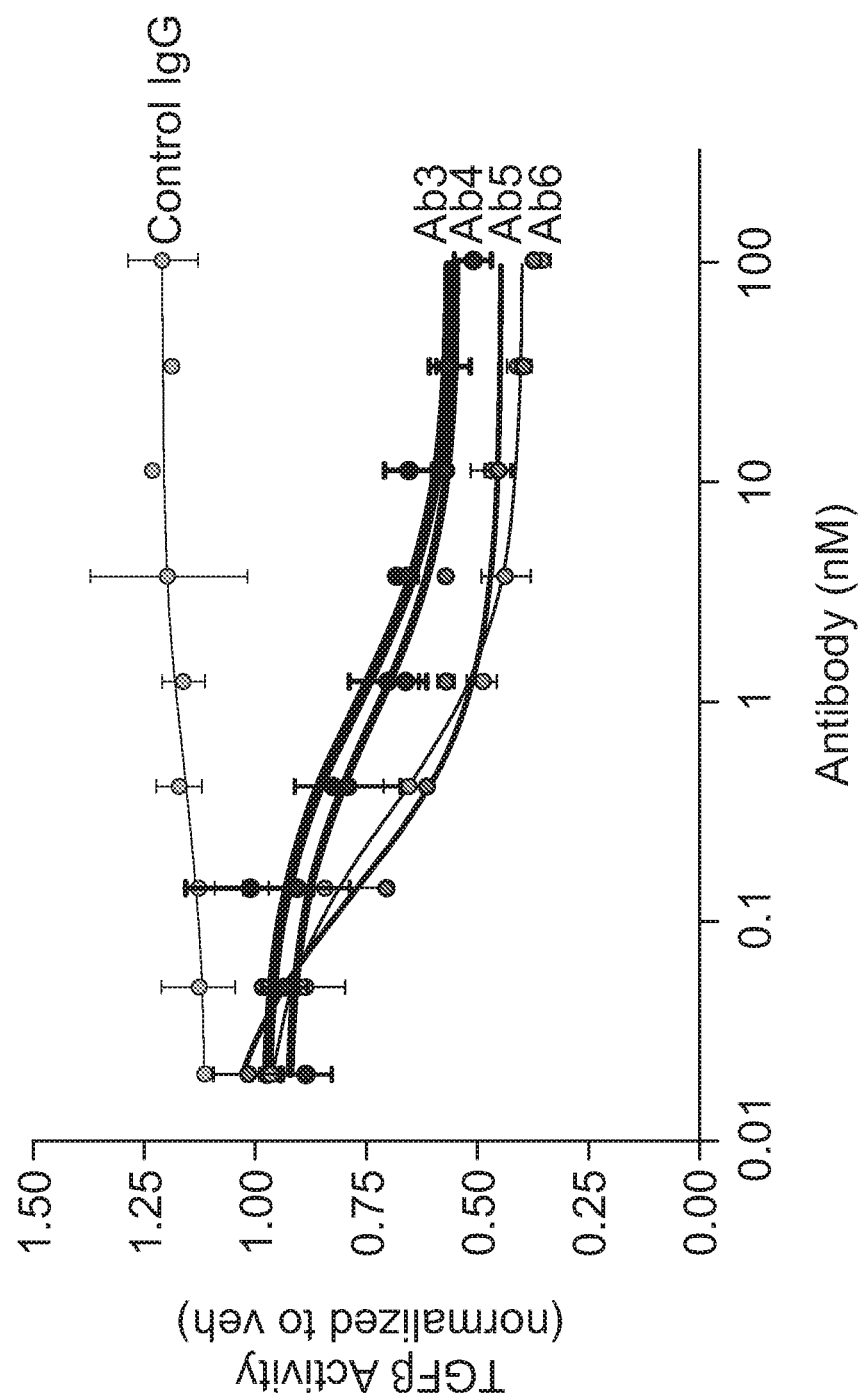
FIG. 3 is a graph that shows inhibition of GARP-proTGFβ1 activation in an SW48036 assay.
Figure 4:
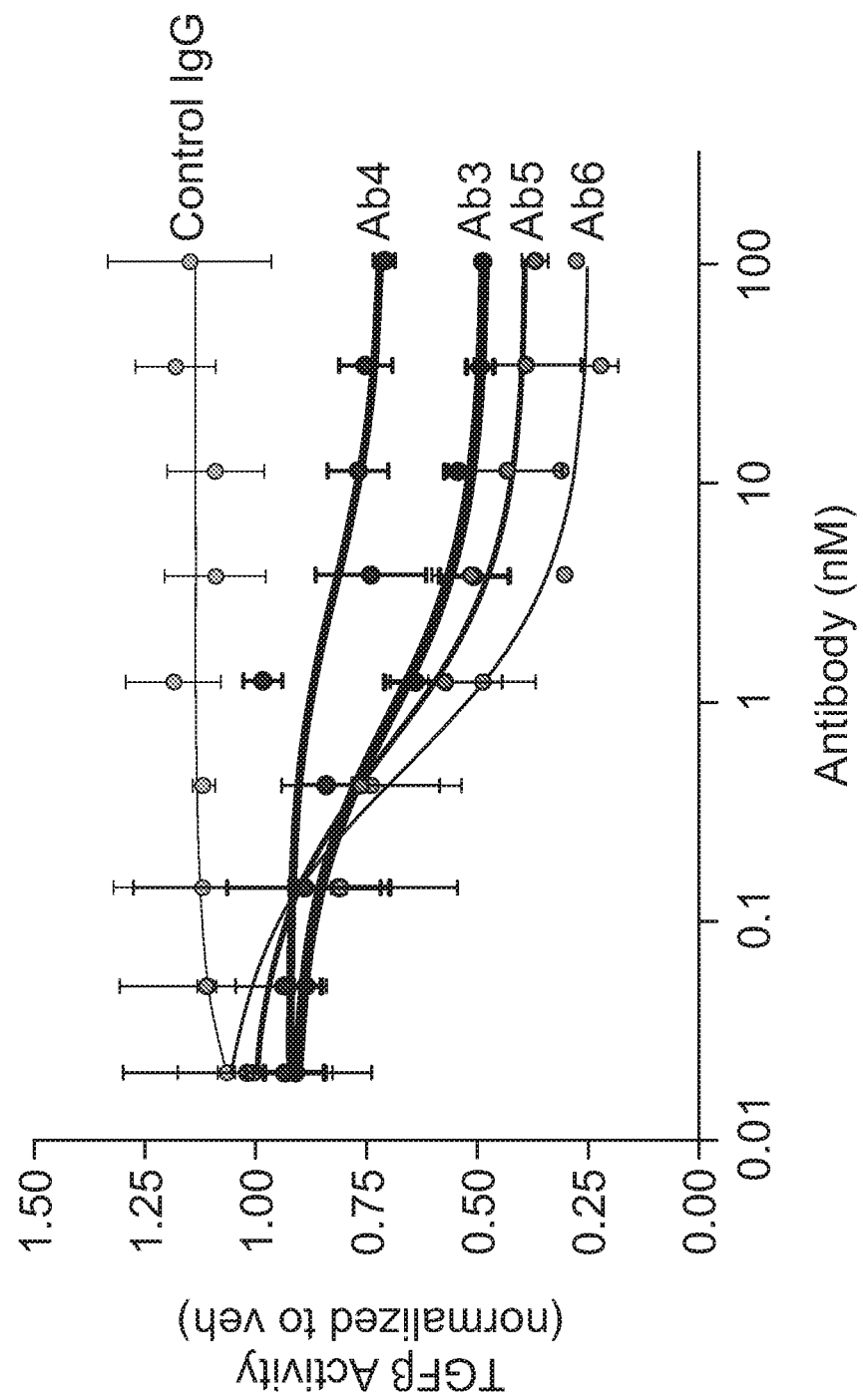
FIG. 4 is a graph that shows inhibition of LRRC33-proTGFβ1 activation in an SW48036 assay.

For the assay depicted in FIG. 3 and FIG. 4, the following protocol was developed. This assay, or "direct-transfection" protocol, is optimal for measuring integrin-dependent release (activation) of TGFβ1 from cell-associated latent proTGBβ1 complexes (GARP-proTGBβ1 or LRRC33-proTGBβ1).

Materials

MvLu1-CAGA12 cells (Clone 4A4)
SW480/p6 cells (Clone 1E7) (αV subunit is endogenously expressed at high levels; β6 subunit is stably overexpressed)
LN229 cell line (high levels of endogenous αVβ8 integrin)
Costar white walled TC treated 96 well assay plate #3903
Greiner Bio-One High Binding white uclear 96 well assay plate #655094
Human Fibronectin (Corning #354008)
P200 multichannel pipet
P20, P200, and P1000 pipets with sterile filter tips for each
Sterile microfuge tubes and rack
Sterile reagent reservoirs
0.4% trypan blue
2 mL, 5 mL, 10 mL, and 25 mL sterile pipets
Tissue culture treated 100 mm or 150 mm plates
70% Ethanol
Opti-MEM reduced serum media (Life Tech #31985-070)
LIPOFECTAMINE® 3000 (Life Tech #L3000015)
BRIGHT-GLO™ luciferase assay reagent (Promega #E2620)
0.25% Tryspin+0.53 mM EDTA
proTGFβ1 expression plasmid, human
LTBP1S expression plasmid, human
LTBP3 expression plasmid, human
LRRC32 (GARP) expression plasmid, human
LRRC33 expression plasmid, human Equipment BIOTEK® SYNERGY™ H1 plate reader
Tissue culture hood
Bench top centrifuge
$CO_2$ incubator, 37° C., 5% $CO_2$
37° C. water/bead bath
Platform shaker
Microscope
Hemocytometer/countess Definitions CAGA12 4A4 cells: Derivative of MvLu1 cells (Mink Lung Epithelial Cells), stably transfected with CAGA12 synthetic promoter, driving luciferase gene expression
DMEM-0.1% BSA: Assay media; base media is DMEM (Gibco Cat #11995-065), media also contains BSA diluted to 0.1% w/v, penicillin/streptinomycin, and 4 mM glutamine
D10: DMEM 10% FBS, P/S, 4 mM glutamine, 1% NEAA, 1× GlutaMAX (Gibco Cat #35050061)
SW480/p6 Media: D10+1000ug/mL G-418
CAGA12 (4A4) media: D10+0.75ug/mL puromycin Methods On Day 0, integrin expressing cells were seeded for transfection. Cells were detached with trypsin and pelleted (spin 5 min @ 200×g). Cell pellet was resuspended in D10 media and count viable cells per ml. Cells were diluted to 0.1e⁶ cells/ml and seeded 100 µl per well (10,000 cells per well) in an assay plate. For CAGA12 cells, passaged at a density of 1.5 million per T75 flask, to be used for the assay on Day 2. Cultures were incubated at 37° C. and 5% $CO_2$.

On Day 1, cells were transfected. The manufacturer's protocol was followed for transfection with LIPOFECTAMINE® 3000 reagent. Briefly, the following was diluted into OPTIMEM™ I, for 5 µl per well: 0.1 ug DNA (presenting molecule)+0.1ug DNA (proTGFβ1), 0.4 µl P3000, and up to 5 µl with OPTIMEM™ I. The well was mixed by pipetting DNA together, then add OPTIMEM™. Add P3000 and mix everything well by pipetting. A master mix was made with LIPOFECTAMINE®3000, to be added to DNA mixes: 0.2 µl LIPOFECTAMINE®3000, up to 5ul in OPTIMEM™ I, per well. Diluted LIPOFECTAMINE®3000 was added to DNA, mixed well by pipetting, and incubated at room temp for 15 min. After the incubation, the solution was mixed a few times by pipetting, and then 10 µl per well of DNA: LIPOFECTAMINE®3000 (2×5 µl) was added. The cell plate was returned to the tissue culture incubator for 24 hrs.

On Day 2, the antibody and TGFβ reporter cells were added. In order to prepare functional antibody dilutions, stock antibody in vehicle (PBS is optimal) was serially diluted. Then each point was diluted into assay media for 2× final concentration of antibody. After preparing antibodies, the cell plate was wished twice with assay media, by aspirating (vacuum aspirator) followed by the addition of 100 µl per well assay media. After second wash, the assay media was replaced with 50 µl per well of 2× antibody. The cell plate was returned to the incubator for ~ 15-20 min.

In order to prepare the CAGA12 (clone 4A4) cells for the assay, the cells were detached with trypsin and pelleted (spin 5 min @ 200×g.). The pellet was resuspended in assay media and viable cells per ml were counted. Cells were diluted to $0.3e^6$ cells/ml and seeded 50 µl per well (15,000 cells per well). Cells were returned to incubator.

On Day 3, the assay was read about 16-20 hours after the antibody and/or reporter cell addition. BRIGHT-GLO™ reagent and test plate were allowed to come to room temperature before reading. The read settings on BIOTEK® SYNERGY™ H1 were set to use TMLC_std protocol—this method has an auto-gain setting. Positive control wells were set for autoscale (high). 100 µL of BRIGHT-GLO™ reagent was added per well. Incubated for 2 min with shaking, at room temperature, protected plate from light. The plate was read on BIOTEK® SYNERGY™ H1.

Inhibition of GARP-proTGFβ1 activation by Ab3, Ab4, Ab5, Ab6 or IgG control was measured in in the SW48036 assay (FIG. 3).

Inhibition of LRRC33-proTGFβ1 activation by Ab3, Ab4, Ab5, Ab6 or IgG control was measured in in the SW48036 assay (FIG. 4).

The cell-based reporter assays used to obtain the in vitro potency data provided in FIG. 33B are as follows:

Two days before the assay, 12,500 LN229 cells per well were plated into white-walled 96-well tissue culture-treated assay plates. The LN229 cells were transfected the next day with plasmids encoding either proTGFβ1 (LTBP assay), proTGFβ1 plus GARP (GARP assay), or proTGFβ1 plus LRRC33 (a chimeric construct of LRRC33 ectodomain fused to GARP transmembrane and cytoplasmic domains using LIPOFECTAMINE® 3000. As control for TGFβ1 isoform specificity, LN229 cells were transfected with proTGFβ3, which is also activated by αV integrins due to the presence of an RGD sequence in its prodomain. About 24 h later, Ab6 was serially diluted and added to the transfectants together with CAGA12 reporter cells suspended in DMEM+0.1% BSA (15,000 cells per well). Around 16-20 hours after setting up the co-culture, the assay was developed for 2 min using BrightGlo reagent, and luminescence read out on a plate reader. The luciferase activity in presence of antibody vehicle determined 100% activity, and the signal in presence of 167 nM (25 µg/ml) of the high affinity panTGFβ antibody 12.7 was set as 0% activity.

Dose-response activities were nonlinearly fit to a three-parameter log inhibitor vs. response model using Prism 7 and best-fit IC50 values calculated.

To test the inhibition of proteolytic TGFβ1 activation, CAGA12 reporter cells were seeded into white-walled 96-well luminescence assay plates (12,500 cells per well). Twenty-four hours later, cells were washed with assay medium (DMEM+0.1% BSA), and Ab6 (2.5 µg/ml) and small latent complex proTGFβ1 C4S (1.5 ng/ml) were added in assay medium to the CAGA cells. This mixture was incubated at 37° C. for 4 h to allow antibody binding. Following this incubation, recombinant human plasma kallikrein protease (EMD Millipore) was added at 500 ng/ml final concentration. The assay mixture was incubated with CAGA cells for approximately 18 hours, after which TGFβ1 activation was read out by bioluminescence as described above.

Example 3: Effects of TGFβ1-Specific, Context-Independent Antibodies on Protease-Induced Activation of TGFβ1 In Vitro Previously, Applicant showed that the Ab3 (an isoform-selective, context-biased TGFβ1 inhibitor) was capable of inhibiting both integrin-dependent and Kallikrein-dependent activation of TGFβ1 in vitro and in cell-based/CAGA assays.

To test the ability of Ab6 (an isoform-selective, high-affinity, context-independent TGFβ1 inhibitor) to inhibit protease-dependent activation of TGFβ1, and to further compare the effects of Ab3 and Ab6, two cell-based/CAGA assays were established: i) Kallikrein-dependent TGFβ1 activation and effects of Ab3 and Ab6; and ii) Plasmin-dependent TGFβ1 activation and effects of Ab3 and Ab6.

Briefly, CAGA reporter cells were seeded 24 hours prior to the start of the assay. ProTGFβ1-C4S was titered onto CAGA cells. Protease (Plasma-KLK or Plasmin) was added at a fixed concentration as indicated. The assay mixture was incubated for approximately 18 hours. TGFβ activation was measured by Luciferase assay.

In the first study, in the presence of KLK, proTGFβ1 was activated (positive control). This TGFβ activation was effectively inhibited by the addition of Ab3, confirming the previous results. Similarly, Ab6 also inhibited Kallikrein-induced activation of TGFβ1. These results indicate that, in addition to integrin-dependent activation of TGFβ1, the isoform-specific, context-independent inhibitory antibody (both biased and unbiased) can block KLK-dependent activation of TGFβ1 in vitro (FIG. 5A).

In the second study, in the presence of recombinant human Plasmin, proTGFβ1 was activated (positive control). Surprisingly, this TGFβ activation was effectively inhibited only by AB6, but not by Ab3. These results reveal unexpected functional differences between the context-biased inhibitor (Ab3) and the context-unbiased inhibitor (Ab6) (FIG. 5B).

Example 4: Inhibition of Acute Fibrosis by Anti-TGFβ1 Antibodies Ab3 and Ab6 in the Unilateral Ureteral Obstruction (UUO) Model of Acute Kidney Fibrosis Inhibition of acute fibrosis by anti-TGFβ1 antibodies was tested in the unilateral ureteral obstruction (UUO) model of acute kidney fibrosis. In this model, fibrosis is induced in male mice by permanent surgical ligation of the left ureter on study day 0. Sham-treated mice, which underwent surgery but did not have their ureters obstructed, were included as a healthy control in these experiments.

Control (IgG) or test antibodies (Ab3, Ab6) were administered to mice by intraperitoneal (i.p.) injection on study days 1 and 4. Kidneys were collected at the end of study, on day 5 after surgery, and RNA was harvested from these tissues. The degree of fibrosis induction was subsequently assessed by quantitative polymerase chain reaction (qPCR) for a panel of fibrosis-associated genes, including Collagen I (Col1a1), Collagen III (Co/3a1), Fibronectin 1 (Fn1), Lysyl Oxidase (Lox), Lysyl Oxidase-like 2 (Lox/2), Smooth muscle actin (Acta2), Matrix metalloprotease (Mmp2), and Integrin alpha 11 (Itga11) (Rolfe, Irvine, Grobbelaar, & Linge, 2007)(Tamaki et al., 1994)(Bansal et al., 2017)(Leaf & Duffield, 2016).

Effect of Ab3 or Ab6 Treatment on Collagen Gene Expression

Figure 7:
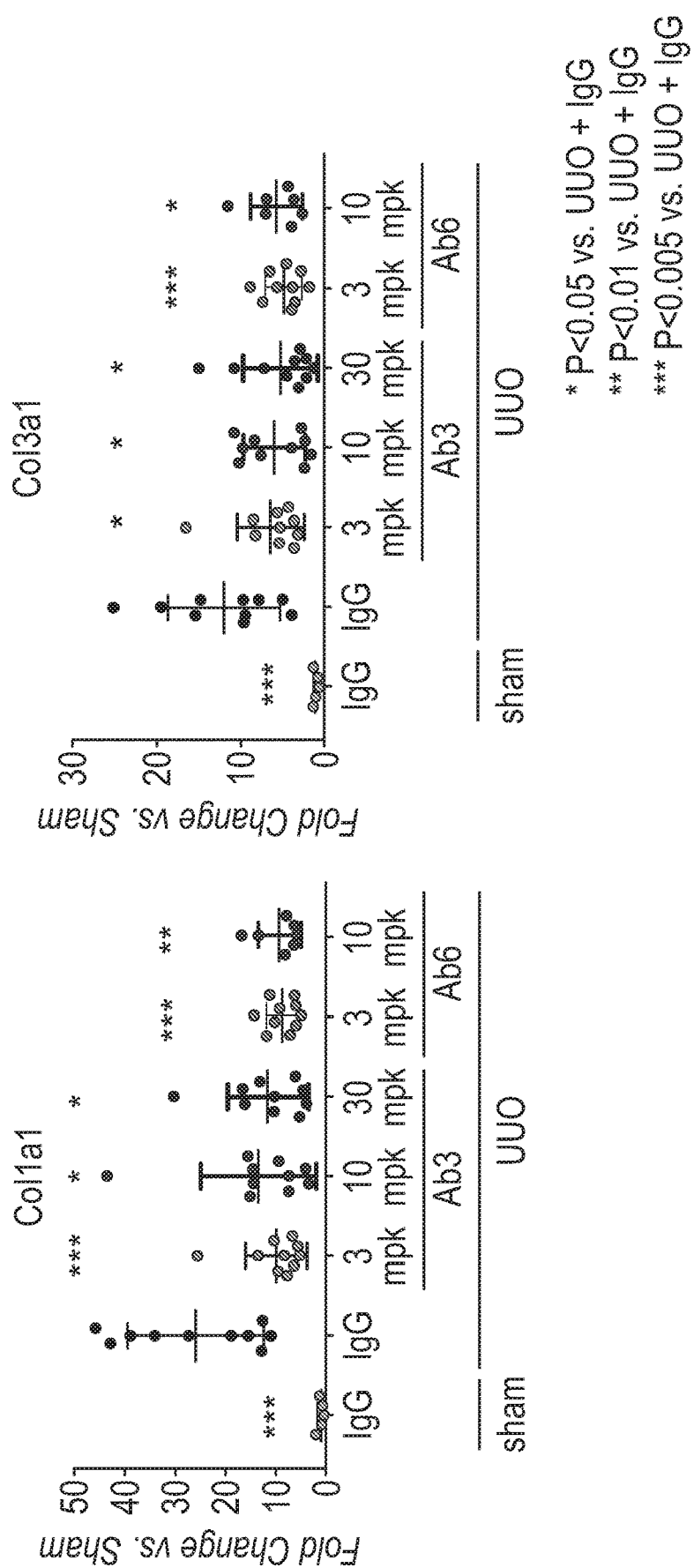
FIG. 7 provides two graphs showing effect of Ab6 or Ab3 on expression of collagen genes (Col1a1 and Col3a1) in UUO mice. Mice were treated with 3, 10, or 30 mg/kg/wk of Ab3 or 3 or 10 mg/kg/week of Ab6. IgG alone was used as control.

Col1a1 and Co/3a1 are key drivers of fibrosis. Col1a1 is induced 10- to 40-fold in obstructed kidneys and Co/3a1 is upregulated 5- to 25-fold (P<0.005, compare sham+IgG treated mice to UUO+IgG group). As shown in FIG. 7, UUO mice treated with 3, 10, or 30 mg/kg/wk of Ab3 show reduced expression of both collagen genes compared to the UUO+IgG (P<0.05). Treatment with 3 or 10 mg/kg/wk of Ab6 also suppressed fibrotic gene induction by UUO (P<0.05 compared to UUO+IgG). Taken together, these data suggest that TGFβ1 inhibition with either Ab3 or Ab6 potently ameliorates the collagen induction associated with UUO.

Figure 8:
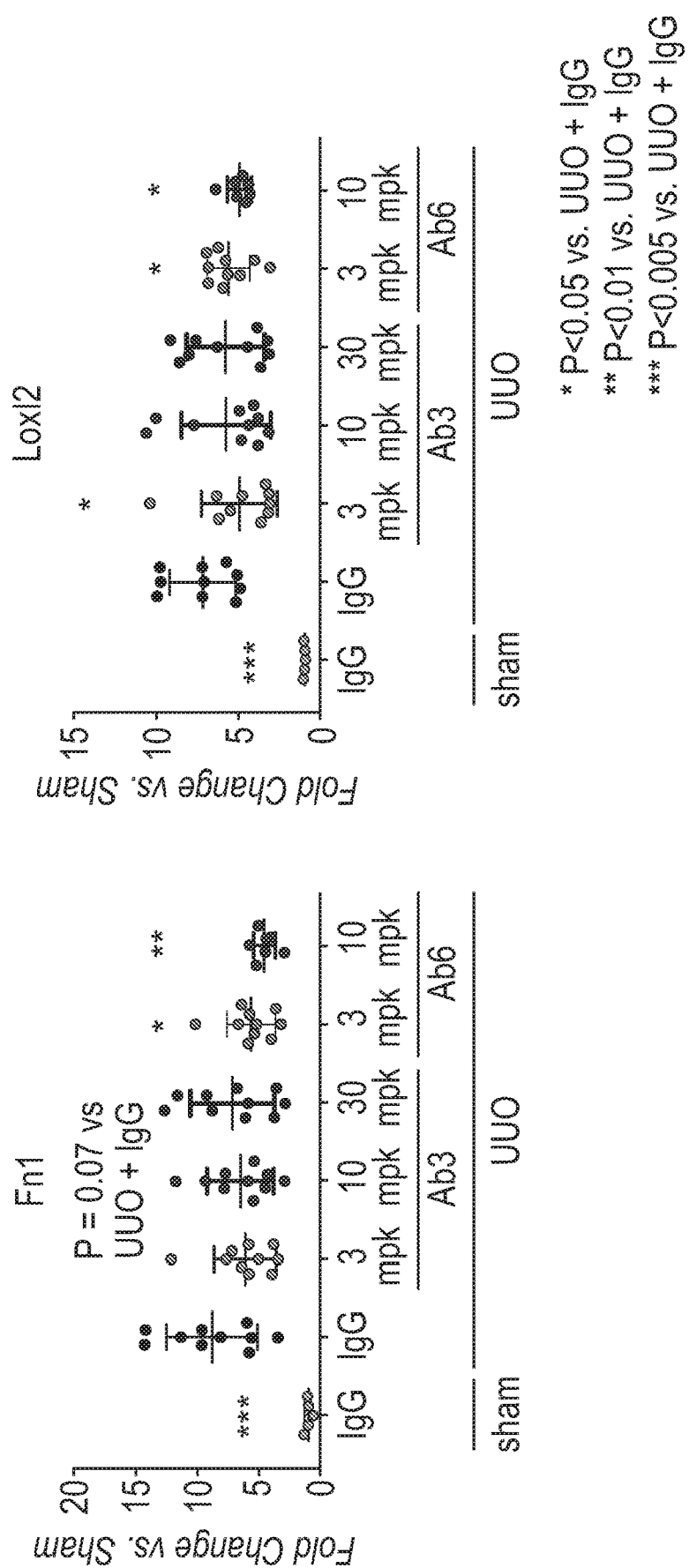
FIG. 8 provides two graphs showing effect of Ab3 or Ab6 on expression of Fn1 and Lox12 genes in UUO mice. Mice were treated with 3, 10, or 30 mg/kg/wk of Ab3 or 3 or 10 mg/kg/week of Ab6. IgG alone was used as control.

Effect of Ab3 or Ab6 Treatment on Fibronectin and Lysyl Oxidase-Like 2 Gene Expression Fn1 and Lox/2 encode proteins that play roles in deposition and stiffness of extracellular matrix in fibrosis. As shown in FIG. 8, both genes are upregulated in samples from the UUO+IgG group (P<0.005 vs. Sham+IgG), though the fold increase in gene expression for both genes, but particularly for Lox/2, is smaller than for the Collagen genes. In samples treated with 3, 10, or 30 mg/kg/wk of Ab3, we note a trend towards reduced Fn1 and Lox/2 (vs. UUO+IgG), but this treatment effect is only statistically significant for Lox/2 expression, and only at the 3 mg/kg/wk dose (Fn1 at the 10 mg/kg/wk dose is approaching statistical significance, with P=0.07). Treatment with either 3 or 10 mg/kg/wk Ab6, however, leads to inhibition of both Fn1 and Lox/2 (P<0.05 vs. UUO+IgG).

Figure 9:
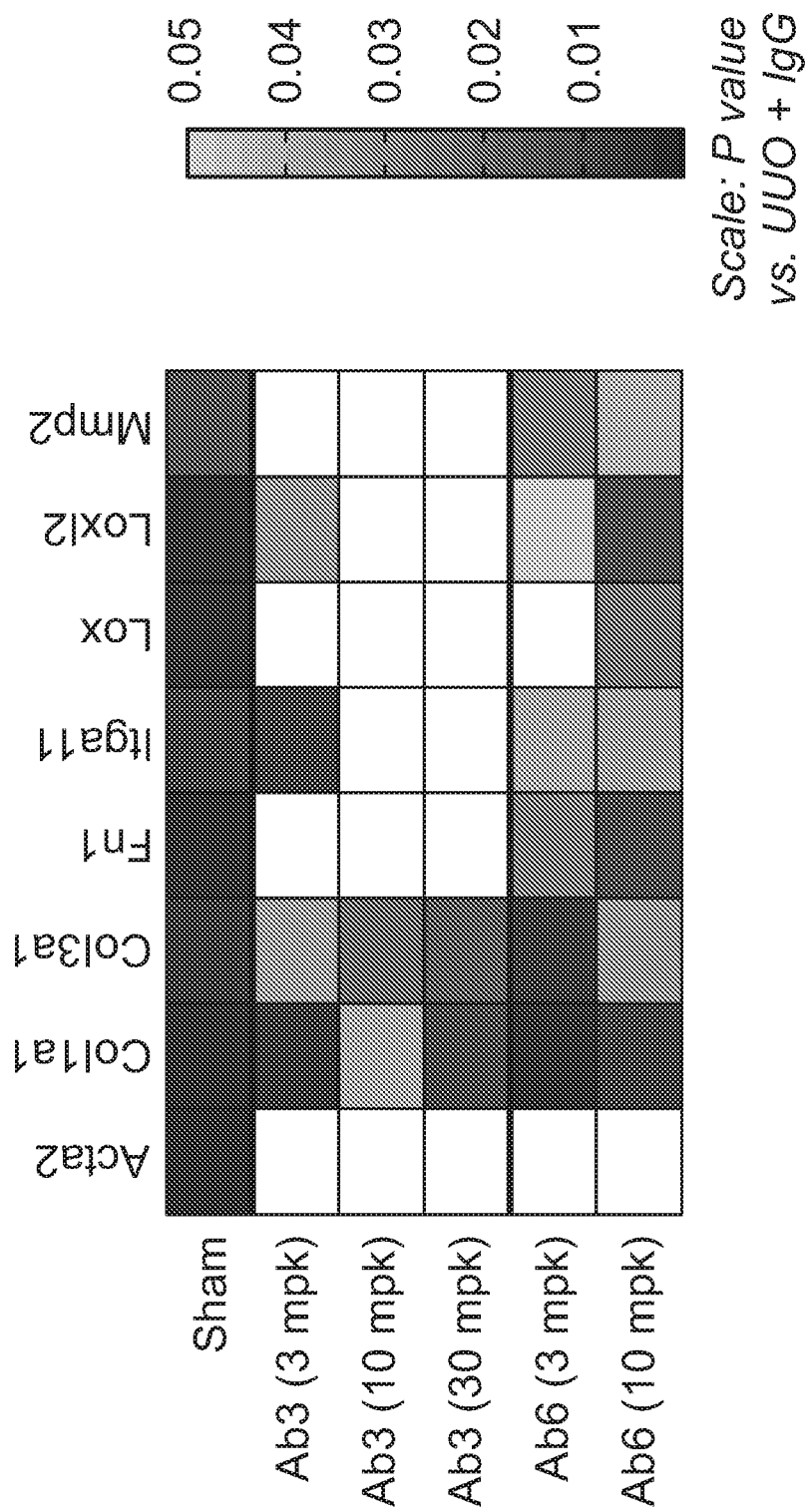
FIG. 9 summarizes the statistical significance of the changes in gene expression (vs. UUO+IgG) after treatment in the UUO model.

FIG. 9 summarizes the statistical significance of the changes in gene expression (vs. UUO+IgG) after treatment in the UUO model. Ab3 showed reduction in Col1a1 and Co/3a1 at all doses tested. Statistically significant changes were also observed in Itga11 and Lox/2 (both levels were reduced relative to UUO+IgG), but only in the 3 mg/kg/wk dose. In contrast, all genes examined except Acta2 showed a statistically significant change in expression (all levels reduced relative to UUO+IgG) after treatment with 10 mg/kg/wk Ab6. Furthermore, all genes examined except Acta2 and Lox also showed a statistically significant reduction in mice treated with 3 mg/kg/wk Ab6.

Example 5: Effects of Ab3 and Ab6 in Combination with Anti-PD-1 Antibody on Tumor Progression in the Cloudman S91 Melanoma Model Based on the recognition that many human tumors are characterized by the phenotype: i) a subset is responsive to PD-(L)1 axis blockade; ii) evidence of immune exclusion; and, iii) evidence of TGFB1 expression and TGFβ signaling, and further based on the observation that commonly used syngeneic immune-oncology mouse models do not recapitulate TGFβ1 bias or anti-PD-(L)1 resistance, the inventors sought to specifically select in vivo preclinical models that exhibit similar profiles as human tumors for improved translatability (see Example 11). Taking these factors into consideration, suitable in vivo models were selected for conducting efficacy studies, including the Cloudman S91 melanoma model described in these studies.

To evaluate the effects of Ab3 and Ab6 in combination with an anti-PD-1 antibody to decrease melanoma tumor progression, the Cloudman S91 mouse melanoma model was used.

Tumor Cell Culture

Clone M3 [Cloudman S91 melanoma] (ATCC® CCL-53.1™) cells were obtained from the American Type Culture Collection (ATCC), and were maintained at CR Discovery Services as exponentially growing suspension cultures in Kaighn's modified Ham's F12 Medium supplemented with 2.5% fetal bovine serum, 15% horse serum, 2 mM glutamine, 100 units/mL penicillin G sodium, 100 μg/mL streptomycin sulfate and 25 μg/mL gentamicin. The tumor cells were grown in tissue culture flasks in a humidified incubator at 37° C., in an atmosphere of 5% $CO_2$ and 95% air.

In Vivo Implantation and Tumor Growth

On the day of tumor implant, each female DBA/2 test mouse was injected subcutaneously in the flank with $5\times10^6$ Cloudman S91 cells in 50% matrigel, and tumor growth was monitored. When tumors reached a volume of 125-175 mm³ mice were randomized into groups of 12 with identical mean tumor volumes and dosing began. Tumors were measured in two dimensions using calipers, and volume was calculated using the formula:

$$\text{Tumor Volume (mm}^3) = w^2 \times l/2$$

where w=width and l=length, in mm, of the tumor. Tumor weight may be estimated with the assumption that 1 mg is equivalent to 1 mm³ of tumor volume.

Treatment

Briefly, mice (n=12) bearing subcutaneous C91 tumors (125-175 mm³) on Day 1 were administered intraperitoneally (i.p.) once a week for 60 days Ab3 at 10 mg/kg in a dosing volume of 10 mL/kg; Ab3 at 30 mg/kg in a dosing volume of 10 mL/kg; Ab6 at 3 mg/kg in a dosing volume of 10 mL/kg; or Ab6 at 10 mg/kg in a dosing volume of 10 mL/kg. Rat anti mouse PD-1 antibody (RMP1-14-rIgG2a, BioXCel) was administered i.p. twice a week at 10 mg/kg in a dosing volume of 10 mL/kg for 60 days.

Group 1 received anti-PD-1 antibody only. Group 2 received Ab3 (10 mg/kg) in combination with anti-PD-1 antibody. Group 3 received Ab3 (30 mg/kg) in combination with anti-PD-1 antibody. Group 4 received Ab6 (10 mg/kg) in combination with anti-PD-1 antibody. Group 5 received Ab6 (30 mg/kg) in combination with anti-PD-1 antibody. An untreated control was used, data not shown.

Endpoint and Tumor Growth Delay (TGD) Analysis

Tumors were measured using calipers twice per week, and each animal was euthanized when its tumor reached the endpoint volume of 2,000 mm³ or at the end of the study (Day 60), whichever happened earlier. Mice that exited the study for tumor volume endpoint were documented as euthanized for tumor progression (TP), with the date of euthanasia. The time to endpoint (TTE) for analysis was calculated for each mouse according to the methods described in WO 2018/129329.

Percent tumor growth delay (% TGD) is defined as the increase in the median time to endpoint in a treatment group compared to the untreated control, expressed as a percentage of the median time to endpoint (TTE) of the control:

T=median TTE for treatment
C=median TTE for control $$\% \text{ TGD} = ((T-C)/C)*100$$

Anti-PD1 treatment resulted in 25% TGD compared to isotype control treatment. Anti-PD1/Ab3 at 10 mg/kg had 14% TGD while Anti-PD1/Ab3 at 30 mg/kg had 92% TGD. Median time to endpoint for Anti-PD1/Ab3 at 30 mg/kg as 45.8 days compared to 29.8 days in Anti-PD1 treatment alone.

In a second Cloudman S91 study, anti-PD-1 treatment resulted in 48% TGD compared to isotype control treatment. Anti-PD-1/Ab3 at 10 mg/kg had 122% TGD while Anti-PD-1/Ab3 at 30 mg/kg had 217% TGD. Anti-PD-1/Ab6 at both 10 mg/kg and 30 mg/kg had 217% TGD. Median time to endpoint for Anti-PD-1 was 34.6 days, Anti-PD-1/Ab3 at 10 mg/kg was 51.7 days and 30 mg/kg was until the end of study at 74 days. Anti-PD-1/Ab6 at 10 mg/kg and 30 mg/kg both did not reach median survival at the end of study at 74 days.

Figure 10:
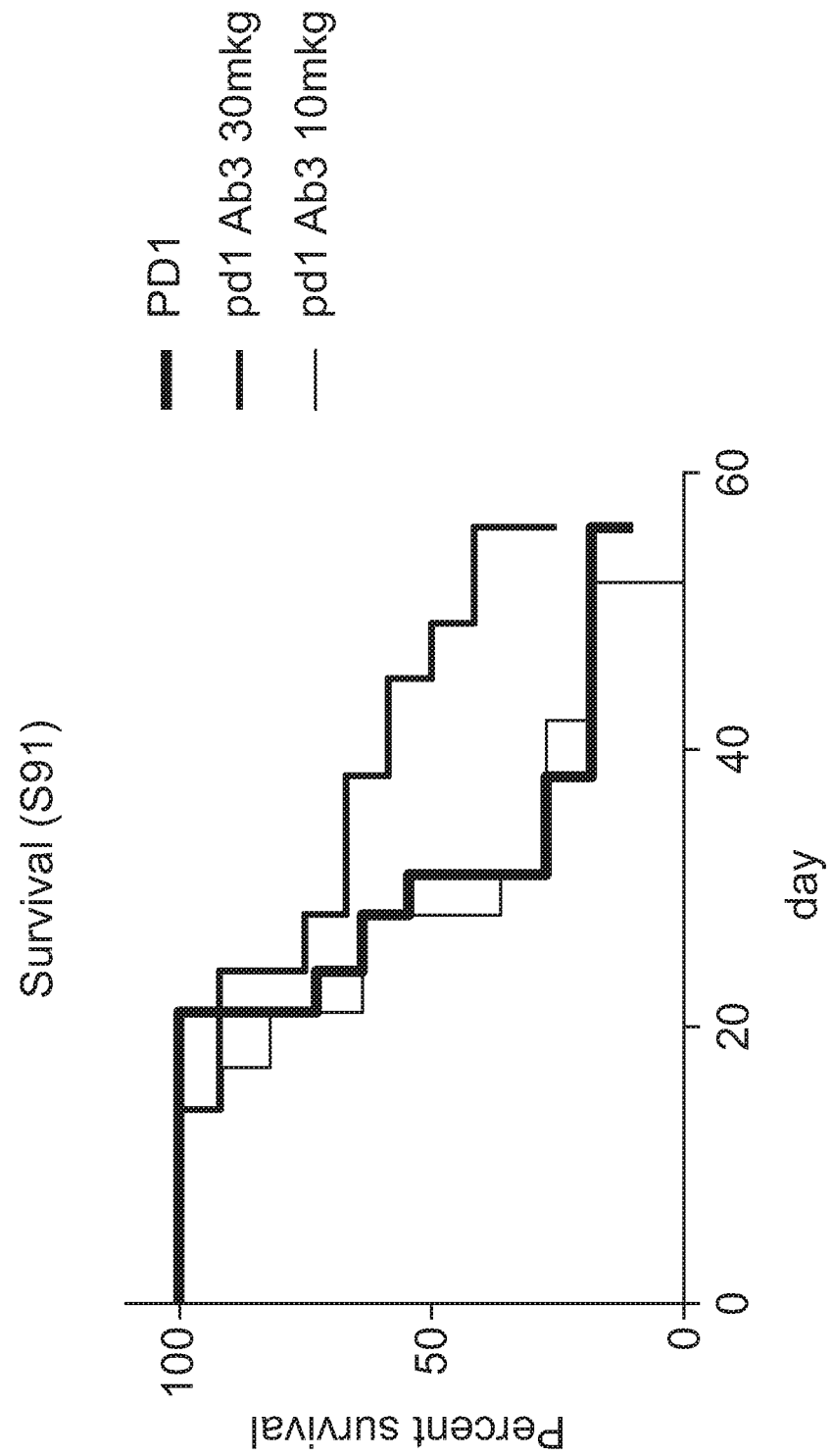
FIG. 10 is a graph that shows percent survival over time (days) in Cloudman S91 melanoma model, after administration of Ab3 at 30 mg/kg or 10 mg/kg, in combination with anti-PD-1. Anti-PD-1 alone, anti-SR-AB3, and was used as a control.

Results from the study show that administration of Ab3 at 30 mg/kg, in combination with anti-PD-1, prolonged survival in treated mice. As shown in FIG. 10, to reach 50% survival, mice treated with anti-PD-1/Ab3 at 30 mg/kg took about 45 days, while mice treated with Ab3 at 10 mg/kg and PD-1 alone reached 50% survival in less than about 30 days, indicating that concurrent inhibition of PD-1 and TGFβ1 resulted in survival benefit.

As shown in FIG. 11A, administration of Ab3 or Ab6 at 10 mg/kg and 30 mg/kg, in combination with anti-PD1, delayed tumor growth. 8 mice treated with PD-1 alone reached a tumor volume of 2000 mm$^3$ (as indicated by the dotted line), whereas only 6 mice treated with anti-PD-1 and Ab3 at 10 mg/kg and 4 mice treated with anti-PD-1 and Ab3 at 30 mg/kg reached a tumor volume of 2000 mm$^3$. Only 3 mice treated with anti-PD-1 and Ab6 at 10 mg/kg and 5 mice treated with anti-PD-1 and Ab6 at 30 mg/kg reached a tumor volume of 2000 mm$^3$. FIG. 11B shows the median tumor progression after treatment with Ab3 or Ab6 in combination with anti-PD-1 antibody.

A separate S91 study was performed to evaluate effective tumor control achieved by a combination of anti-PD-1 antibody and Ab6 (at 3, 10 and 30 mg/kg). To quantify the anti-tumor response, "effective tumor control" in response to treatment was defined as percentage of animals within each test group that achieved a tumor volume at study end of less than 25% of the 2,000 mm$^3$ survival threshold (e.g., endpoint tumor volume). Results are summarized below (see FIGS. 11C, 11E & 11F).

TABLE 20

Cloudman S91 efficacy summary

| Treatment Group | Cloudman S91 tumor model (effective tumor control: %, N) |
|---|---|
| Control | 0% (0/11) |
| Anti-PD1 monotherapy | 17% (2/12) |
| Ab6 monotherapy | 0% (0/12) |
| Anti-PD1/Ab6, 3 mg/kg | 83% (10/12) |
| Anti-PD1/Ab6, 10 mg/kg | 78% (7/9) |
| Anti-PD1/Ab6, 30 mg/kg | 73% (8/11) |

Figure 11C:
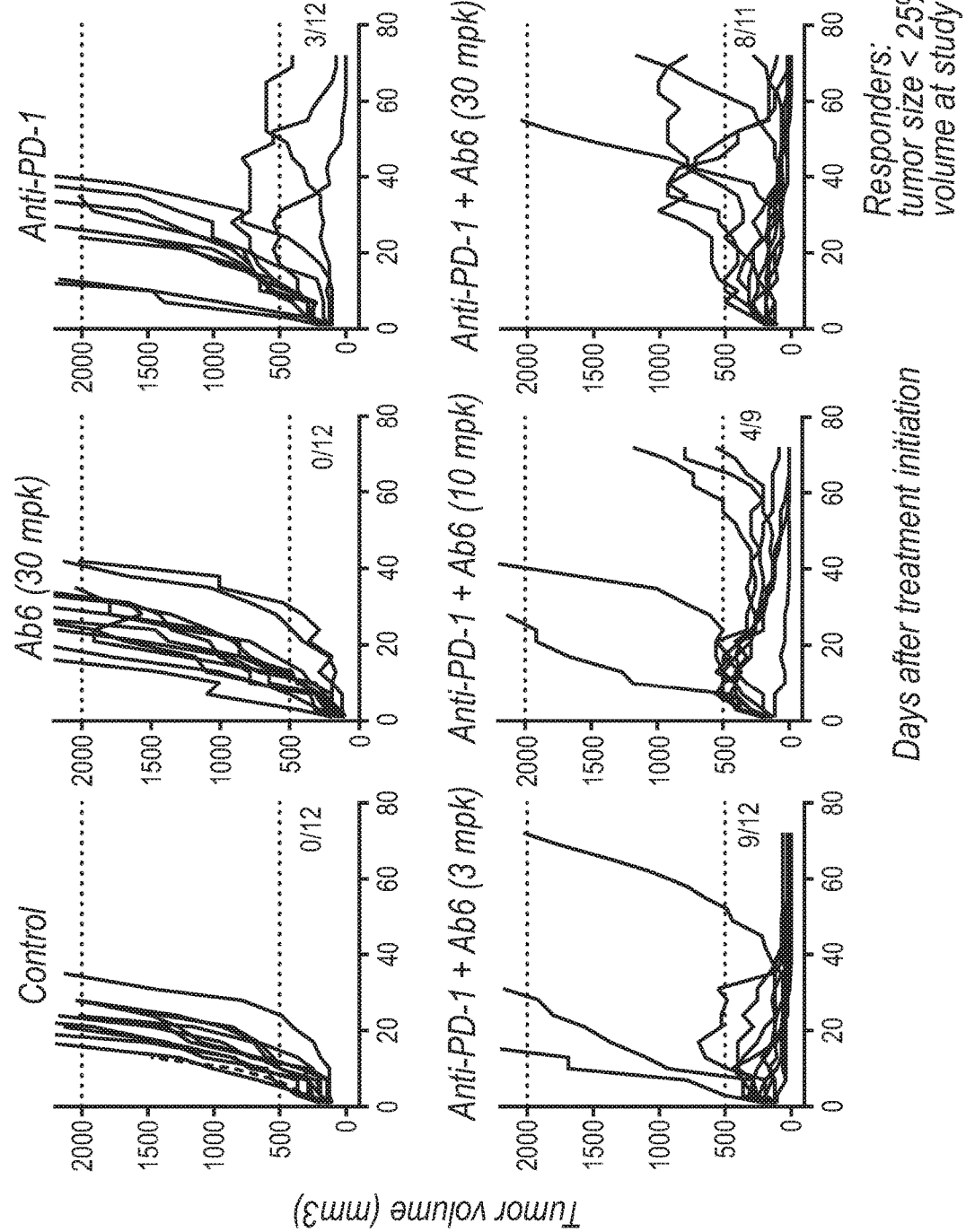
FIG. 11C provides six graphs showing changes in S91 tumor volume as a function of time in mice treated with (1) control IgG; (2) Ab6 only; (3) anti-PD1 only; (4) anti-PD1/Ab6 (3 mg/kg); (5) anti-PD1/Ab6 (10 mg/kg); and (6) anti-PD1/Ab6 (30 mg/kg). Endpoint tumor volume of 2,000 mm$^3$ is indicated in the upper dotted line; and the 25% threshold volume of 500 mm$^3$ is shown in the lower dotted line. Responders were defined as those that achieved tumor size of less than 25% of the endpoint volume.

As shown in FIG. 11C, most animals that received the combination treatment at all three doses (83%, 78% and 73%, respectively) achieved effective tumor control (e.g., tumor volume is reduced to 500 mm$^3$ or less), even though Cloudman S91 model is recognized as poorly responsive to PD-1 blockade as a monotherapy, demonstrating robust synergistic effects of Ab6. Thus, in syngeneic mouse tumor model that reflects human primary resistance to checkpoint blockade therapy (such as anti-PD-(L)1), treatment with Ab6 rendered the Cloudman S91 (melanoma) tumors vulnerable to anti-PD1 therapy. Combination treatment with Ab6 (as low as 3 mg/kg per week) and an anti-PD1 antibody resulted in significant tumor regression or effective tumor control. The synergistic tumor growth delay achieved here indicate that isoform-selective TGFβ1 inhibitors can be used in conjunction with checkpoint blockade therapy for the treatment of subjects with TGFβ1-positive tumor that is resistance to checkpoint inhibition. In the combination treatment groups, all doses of Ab6 tested (3 mg/kg in light blue;

10 mg/kg in dark blue, and 30 mg/kg in purple), in conjunction with anti-PD-1, achieved significant tumor control (9 out of 12, 4 out of 9, and 8 out of 11, respectively). Collectively, over 65% of these animals achieved tumor volume reduction that is less than 25% of the endpoint tumor volume. The results were also shown as median tumor volume (FIG. 11E). All combination treatment groups (Ab6 at 3, 10 or 30 mg/kg) showed similar anti-tumor effects at the doses tested, suggesting that in this model Ab6 is efficacious at as low as 3 mg/kg. This is also reflected in the survival benefit (see FIG. 11F).

Figure 11D:
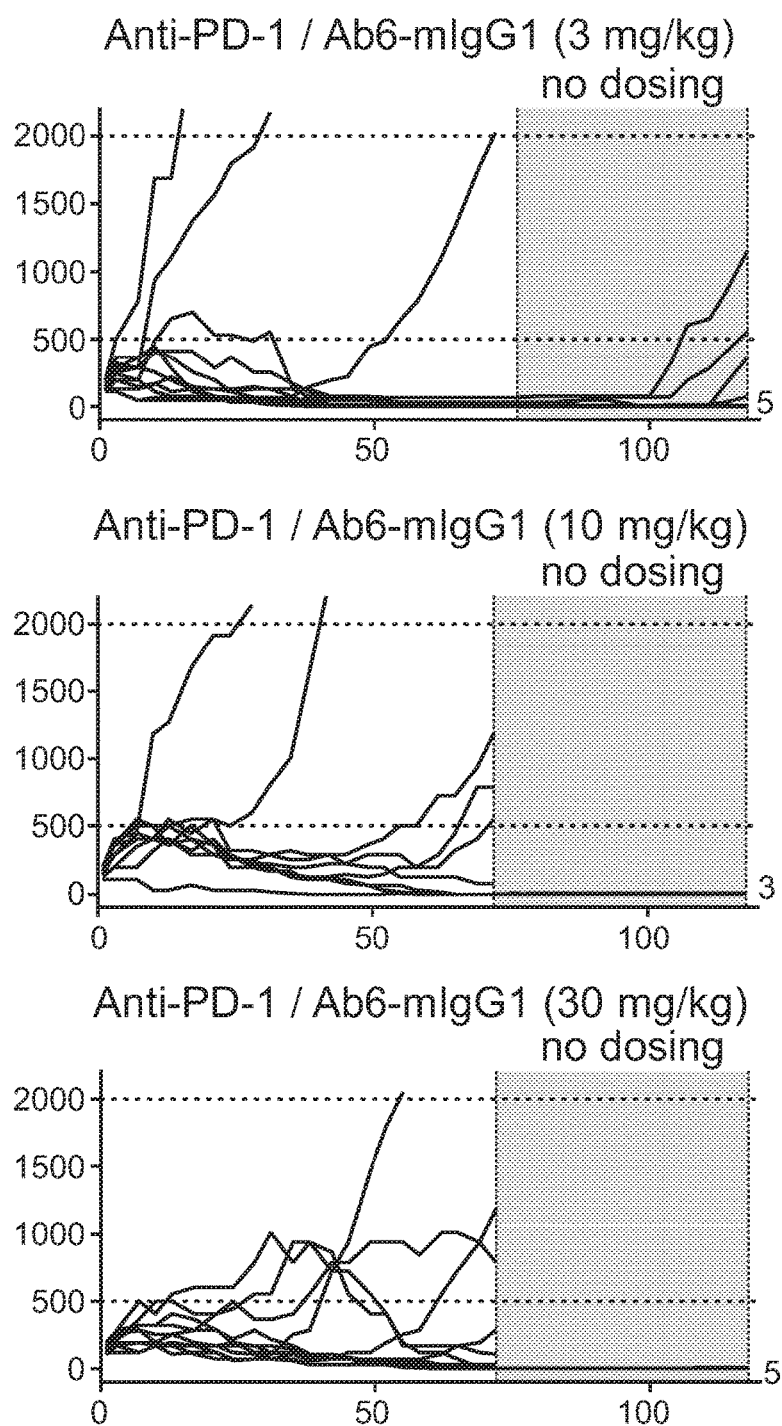
FIG. 11D provides three graphs showing changes in S91 tumor volume as a function of time in mice treated with combination of anti-PD-1 and Ab6 at 3 dosage levels (3, 10 and 30 mg/kg). Durable anti-tumor effects are shown post-treatment.

Durable anti-tumor effects of combined inhibition of TGFβ1 and PD-1 were examined by ceasing the treatment at the end of the efficacy study described above and extending to monitor changes in tumor volume in those animals that achieved significant tumor control. CloudmanS91 tumor-experienced responders from FIG. 11C were followed for six weeks without dosing (gray box). As shown in FIG. 11D, prolonged tumor control with Ab6/anti-PD-1 combination was achieved. Number reported is the number of animals with controlled tumors at study end.

Furthermore, in an ongoing study of S91 tumor model in which Ab6 (at 3 mgk, 10 mgk or 30 mgk per dose) is being evaluated in animals that are treated with anti-PD1, combination treatment leads to significant survival benefit, as shown in FIG. 11F. At day 38, all of the animals that received the anti-PD1/Ab6 (30 mgk) combination have survived (e.g., 100% survival at day 38 in 30 mgk dose group), and none of the animals in the combination groups (3, 10 and 30 mgk) has reached median survival (study ongoing). At the end of the study, 90% of the animals in the combination treatment group survived. These data indicate that isoform-selective inhibitors TGFβ1 such as Ab6 can be used to treat checkpoint inhibition-resistant tumors in subjects receiving a checkpoint blockade therapy to achieve survival benefits. For FIGS. 11C-11F: green=IgG control (30 mg/kg weekly); orange=Ab6 (30 mg/kg weekly); red=anti-PD1 (5 mg/kg twice weekly); light blue=anti-PD1+Ab6 (3 mg/kg); dark blue=anti-PD1+Ab6 (10 mg/kg); purple=anti-PD1+Ab6 (30 mg/kg).

Example 6: Inhibition of TGFβ Phospho-SMAD2/3 Pathway by Ab3 and Ab5 in Combination with Anti-PD-1 in MBT2 Syngeneic Bladder Cancer Model The MBT-2 urothelial cancer model was selected as a TGFβ1-predominated tumor to test TGFβ1-specific inhibition in combination with a checkpoint inhibitor. In a pharmacodynamics study, effects of Ab3 or Ab5 in combination with anti-PD1 on downstream TGFβ signaling were evaluated in MBT-2 model. Phospho-SMAD2/3 assays were performed by ELISA (Cell Signaling Technologies) according to the manufacturer's instructions.

In Vivo Implantation and Tumor Growth

On the day of tumor implant, each female C3H/HeN test mouse was injected subcutaneously in the flank with $5 \times 10^5$ MBT2 tumor cells, and tumor growth was monitored. When tumors reached a volume of 40-80 mm$^3$ mice were randomized into groups of 10 with identical mean tumor volumes and dosing began. Tumors were measured in two dimensions using calipers, and volume was calculated using the formula:

$$\text{Tumor Volume (mm}^3\text{)} = w^2 \times l/2$$

where w=width and l=length, in mm, of the tumor. Tumor weight may be estimated with the assumption that 1 mg is equivalent to 1 mm³ of tumor volume.

Treatment

Briefly, mice (n=10) bearing subcutaneous MBT2 tumors (40 to 80 mm³) on Day 1 were administered intraperitoneally (i.p.) on days 1 and 8 Ab5 at 3 mg/kg in a dosing volume of 10 mL/kg, Ab5 at 10 mg/kg in a dosing volume of 10 mL/kg, Ab3 at 10 mg/kg in a dosing volume of 10 mL/kg or Ab3 at 30 mg/kg in a dosing volume of 10 mL/kg. Rat anti mouse PD-1 antibody (RMP1-14-rIgG2a, BioXCel) was administered i.p. on days 1, 4 and 8 at 10 mg/kg in a dosing volume of 10 mL/kg.

Group 1 received anti-PD-1 antibody only. Group 2 received Ab5 (3 mg/kg) in combination with anti-PD-1 antibody. Group 3 received Ab5 (10 mg/kg) in combination with anti-PD-1 antibody. Group 4 received Ab3 (10 mg/kg) in combination with anti-PD-1 antibody. Group 5 received Ab3 (30 mg/kg) in combination with anti-PD-1 antibody. An untreated control was used, not shown.

Suppression of SMAD 2/3 Signaling

Animals were sacrificed and tumors removed 8 hours post last dose on day 8 and flash frozen. Tumors were pulverized on dry ice and protein lysates generated with spiked phosphatase inhibitors added.

Results were assessed by phosphorylated-to-total SMAD2/3 ratios. As shown in FIG. 12, tonic SMAD2/3 signaling was significantly suppressed in animals treated with both Ab3 or Ab5, in combination with anti-PD-1, with Ab5 (10 mg/kg) showing the most significant suppression. These data demonstrate effective target engagement of the TGFβ1 activation inhibitors, resulting in the suppression of the downstream signaling.

Example 7: Effects of Ab3 and Ab6 in Combination with Anti-PD-1 Antibody on Tumor Progression in the MBT2 Syngeneic Bladder Cancer Mouse Model To evaluate the ability of Ab3 and Ab6 in combination with an anti-PD-1 antibody to decrease bladder carcinoma tumor progression, the MBT2 syngeneic bladder cancer mouse model was used. This is a very aggressive and fast-growing tumor model, and is very difficult to overcome tumor progression with drug treatment.

Tumor Cell Culture

MBT2 is a poorly differentiated murine bladder cancer cell line derived from a transplantable N-[4-(5-nitro-2-furyl)-2-thiazolyl] formamide-induced bladder cancer in a female C3H/He mouse. The cells were cultured in Roswell Park Memorial Institute (RPMI)-1600 medium with 10% fetal bovine serum and 100 µg/ml streptomycin in a 5% CO₂ atmosphere at 37° C. The culture medium was replaced every other day, and subculture was performed when the cellular confluence reached 90%. Cells were harvested from sub-confluent cultures by trypsinization and were washed in serum-free medium. Single cell suspensions with >90% cell viability were determined by Trypan blue exclusion. The cells were resuspended in phosphate-buffered saline (PBS) before injection.

In Vivo Implantation and Tumor Growth

The MBT2 cells used for implantation were harvested during log phase growth and resuspended in phosphate buffered saline (PBS). On the day of tumor implant, each test mouse was injected subcutaneously in the flank with $5\times10^5$ cells (0.1 mL cell suspension), and tumor growth was monitored. When tumors reached an average between 40-80 mm³ mice were randomized into groups of 15.

Tumors were measured in two dimensions using calipers, and volume was calculated using the formula:

$$\text{Tumor Volume (mm}^3) = w^2 \times l/2$$

where w=width and l=length, in mm, of the tumor. Tumor weight may be estimated with the assumption that 1 mg is equivalent to 1 mm³ of tumor volume.

Treatment

Briefly, mice (n=15) bearing subcutaneous MBT2 tumors (40 to 80 mm³) on Day 1 were administered intraperitoneally (i.p.) once a week for 29 days Ab3 at 10 mg/kg in a dosing volume of 10 mL/kg, Ab3 at 30 mg/kg in a dosing volume of 10 mL/kg, Ab6 at 3 mg/kg in a dosing volume of 10 mL/kg or Ab6 at 10 mg/kg in a dosing volume of 10 mL/kg. Rat anti mouse PD-1 antibody (RMP1-14-rIgG2a, BioXCel) was administered i.p. twice a week at 10 mg/kg in a dosing volume of 10 mL/kg for 29 days.

Group 1 received anti-PD-1 antibody only. Group 2 received Ab3 (10 mg/kg) in combination with anti-PD-1 antibody. Group 3 received Ab3 (30 mg/kg) in combination with anti-PD-1 antibody. Group 4 received Ab6 (3 mg/kg) in combination with anti-PD-1 antibody. Group 5 received Ab6 (10 mg/kg) in combination with anti-PD-1 antibody.

An untreated control was used, not shown.

Endpoint and Tumor Growth Delay (TGD) Analysis

Tumors were measured using calipers twice per week, and each animal was euthanized when its tumor reached the endpoint volume of 1,200 mm³ or at the end of the study. Mice that exited the study for tumor volume endpoint were documented as euthanized for tumor progression (TP), with the date of euthanasia. The time to endpoint (TTE) for analysis was calculated for each mouse according to the methods described in WO 2018/129329.

Anti-PD1/Ab3 at 10 mg/kg had 191% TGD and at 30 mg/kg was 196% TGD. Anti-PD1/Ab6 at 3 mg/kg was 68% TGD and at 10 mg/mk was 196% TGD. Partial response (PR) due to treatment is defined as the tumor volume was 50% or less of its Day 1 volume for three consecutive measurements during the course of the study and equal to or greater than 13.5 mm³ for one or more of these three measurements. In a complete response (CR) the tumor volume was less than 13.5 mm³ for three consecutive measurements during the course of the study. Anti-PD-1/Ab3 at 10 mg/kg had 0 PR and 4 CR at end of study. Anti-PD-1/Ab3 at 30 mg/kg had 1 PR and 1 CR at end of study. Anti-PD-1/Ab6 at 3 mg/kg had 0 PR and 3 CR. Anti-PD-1/Ab6 at 10 mg/kg had 0 PR and 5 CR.

Figure 13A:
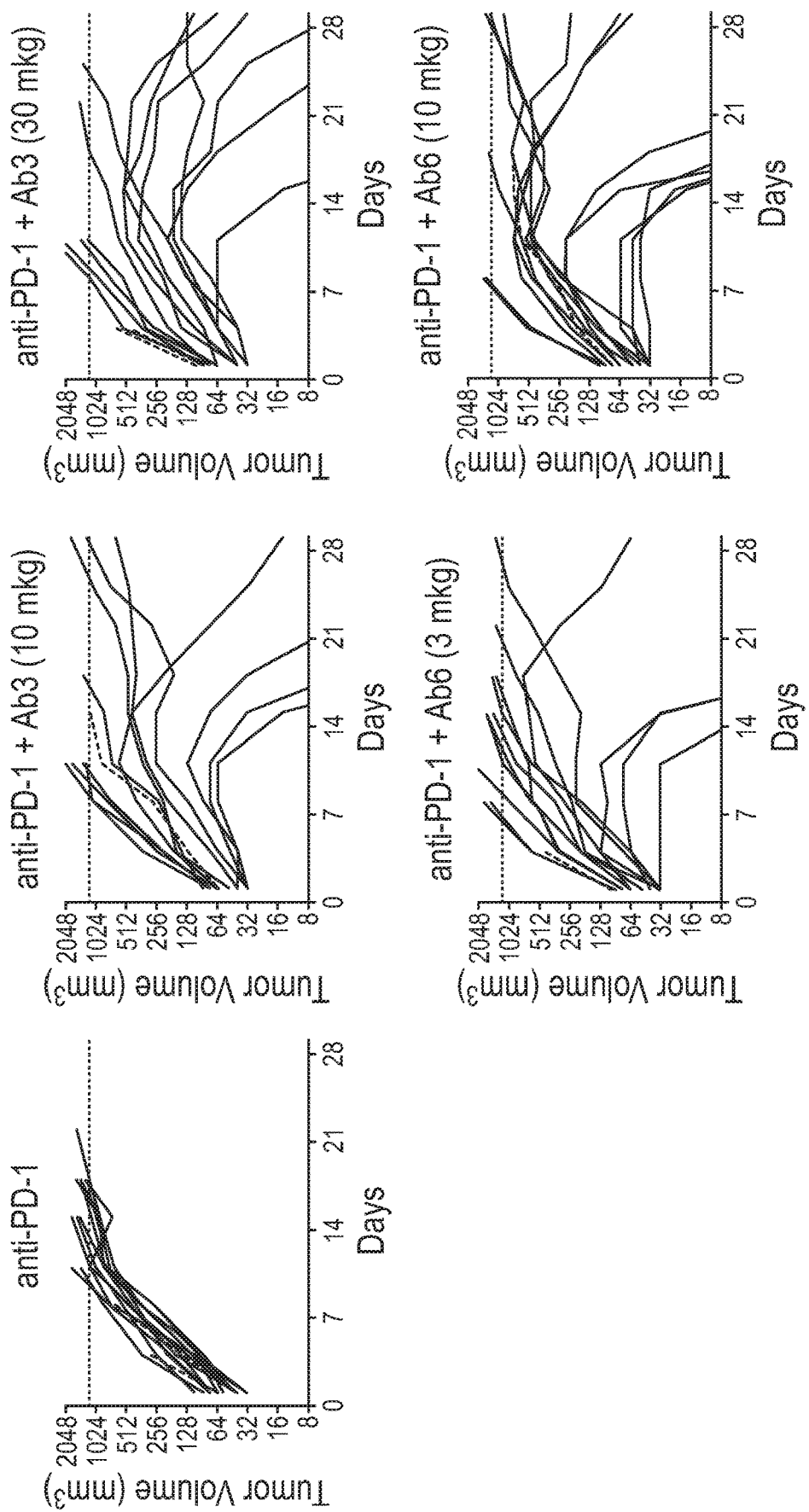
Figure 13C:
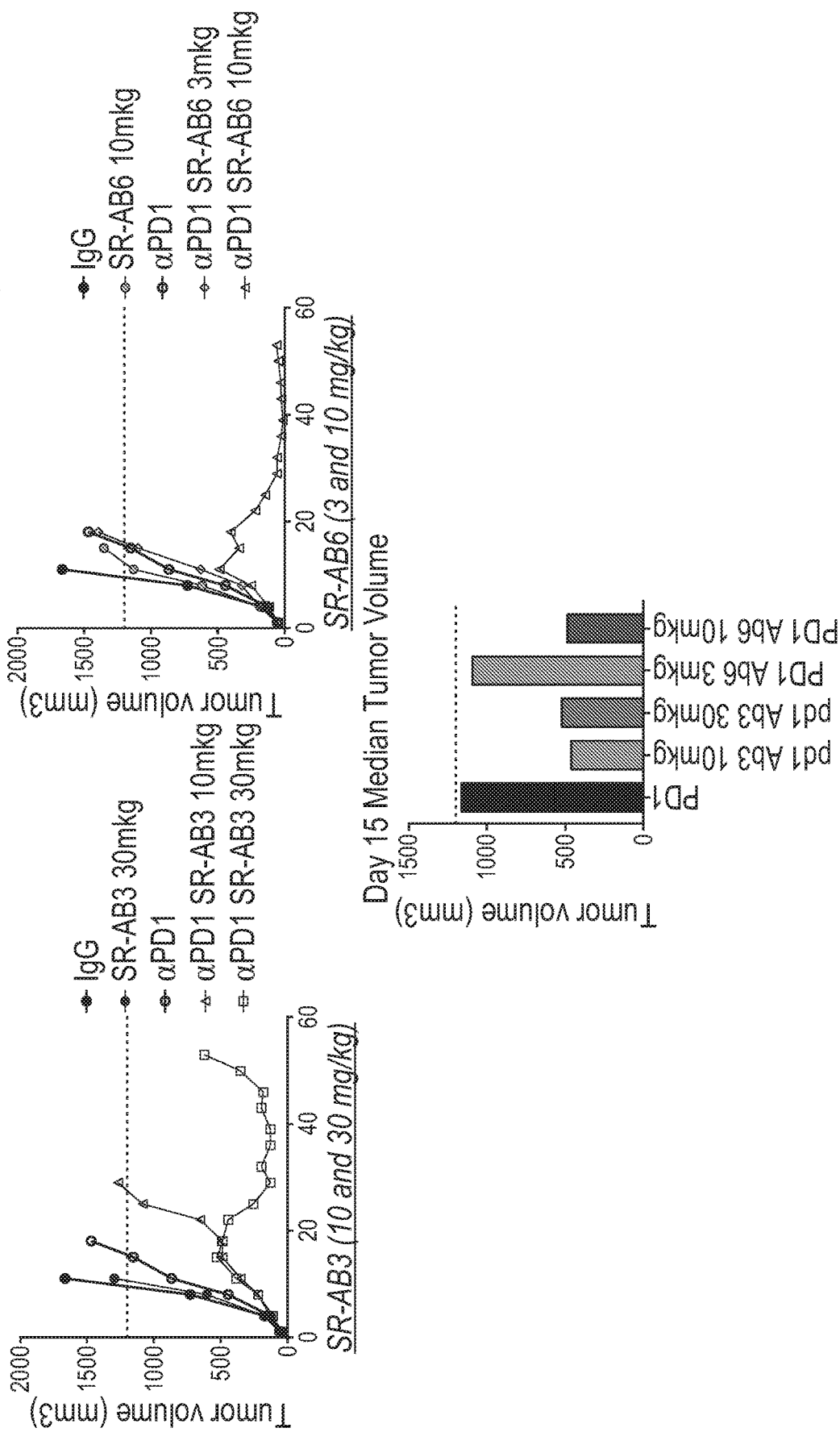
FIG. 13C provides graphs showing the median tumor volumes as a function of time after administration of Ab3 (upper left) at 30 mg/kg or 10 mg/kg or Ab6 (upper right) at 10 mg/kg or 3 mg/kg, in combination with anti-PD-1 in an MBT2 syngeneic bladder cancer model. Anti-PD-1 alone, Ab3 alone, Ab6 alone, and IgG alone were used as controls. Median tumor volume at day 15 is summarized in the lower graph.

As shown in FIGS. 13A and 13B, administration of Ab3, at both the 10 mg/kg and 30 mg/kg doses, in combination with anti-PD-1, delayed tumor growth. Some animals showed complete regression of the tumor. Also, administration of Ab6, at both the 3 mg/kg and 10 mg/kg doses, in combination with anti-PD-1, delayed tumor growth. Some animals showed complete regression of the tumor. Most of the mice treated with PD-1 alone reached a tumor volume of 1024 mm³ (as indicated by the dotted line) between about day 8 and day 14, whereas mice treated with Ab3 at 10 mg/kg, Ab3 at 30 mg/kg, Ab6 at 3 mg/kg, or Ab6 at 10 mg/kg took up to as many as 28 days to reach a tumor volume of 1024 mm³. FIG. 13C shows the median tumor progression after treatment with Ab3 (upper left) or Ab6 (upper right) in combination with anti-PD-1 antibody. The lower graph summarizes the median tumor volume (mm³) at day 15 in mice administered Ab3 or Ab6, in combination with anti-PD-1. The median tumor volume at day 15 in mice treated with Ab3 (10 mg/kg), Ab3 (30 mg/kg), or Ab6 (10 mg/kg), in combination with anti-PD-1, was about 500 mm³ or less, while the median tumor volume at day 15 in mice treated with anti-PD-1 alone was 1000 mm³ or more (lower graph).

FIG. 13D highlights the efficacy of Ab6 in MBT2. Tumor progression in mice from five treatment groups are shown. None of the animals that received control IgG, Ab6 alone or anti-PD-1 alone achieved effective tumor control, defined as tumor volume reduced to 25% or less of the end point volume (shown with lower and upper dotted lines, respectively). By contrast, a combined 12 out of 28 animals (~43%) that received Ab6/anti-PD-1 combination treatment achieved effective tumor control, indicating that concurrent inhibition of PD-1 and TGFβ1 pathways can significantly reduce (e.g., delay or regress) tumor growth.

Moreover, the combination treatment was effective to prolong survival in all three treated groups, as compared to anti-PD-1 alone. As shown in FIG. 14, to reach 50% survival, mice treated with Ab3 at 10 mg/kg or Ab6 at 10 mg/kg took over 28 days, while mice treated with PD-1 alone reached 50% survival in about 16 days. Collectively, these results demonstrate survival benefit of the combination therapy.

Summary of Results and Discussion

Synergistic effects of Ab6-anti-PD-1 on tumor growth: The discovery of Ab6 enables direct evaluation of the hypothesis that selective inhibition of TGFβ1 activation will be sufficient to overcome tumor primary resistance to CBT. For preclinical testing, we sought to identify murine syngeneic tumor models that recapitulate some of the key features of human tumors that exhibit primary resistance to CBT. Criteria for model selection included 1) little to no response to anti-PD-(L)1 single-agent treatment at doses shown to be efficacious in other syngeneic tumor models, 2) evidence for immune exclusion with a dearth of infiltrating CD3+ T cells, 3) evidence of active TGFβ signaling, and 4) evidence of TGFβ1 isoform expression.

Exploration of tumor response and tumor profiling data, including publicly available RNAseq datasets of whole tumor-derived RNA, resulted in the selection of 3 tumor models that met these criteria: the MBT-2 bladder cancer model (MBT-2), the CloudmanS91 (S91) melanoma model, and the EMT-6 breast cancer model (EMT-6). Analysis of whole tumor RNAseq data demonstrated upregulation of TGFβ response genes indicative of TGFβ pathway activation, and low expression of effector T cell genes, consistent with an immune excluded phenotype (FIG. 20F). Analysis of whole tumor lysates by ELISA to probe for total TGFβ isoform protein expression found TGFβ1 growth factor to be prevalent in all three models.

In order to evaluate Ab6 in mouse syngeneic models, we expressed Ab6 as a chimeric antibody with the human V domains of Ab6 fused to mouse IgG1/kappa constant domains to minimize immunogenicity. Ab6-mIgG1 has similar inhibitory activity as the fully human Ab6. We confirmed that MBT-2 tumor-bearing animals are resistant to anti-PD-1 (RMP1-14) when dosed at therapeutic levels, as well as to Ab6-mIgG1 alone. However, in combination, anti-PD-1 and Ab6-mIgG1 dosed at either 3 mg/kg per week or 10 mg/kg per week resulted in significant reductions in tumor burden, including 21% and 36% tumor-free survivors respectively, as well as significant survival benefit over the duration of each study (FIGS. 13D and 14). In total, 4/14 animals responded to anti-PD-1/Ab6-mIgG1 (3 mg/kg per week) and 8/14 responded to anti-PD-1/Ab6-mIgG (10 mg/kg per week) compared to 0/13 on anti-PD-1 alone. We observed similar responses in the mildly anti-PD-1-responsive CloudmanS91 melanoma model. Again, anti-PD-1/Ab6-mIgG1 combination treatment resulted in profound tumor suppression with up to 75% response rate and a significant survival advantage at all dose levels (see Example 5).

We next assessed the durability of the anti-tumor response in MBT-2 tumor-free survivors. Treatment was discontinued and animals were followed for 7 weeks. We observed no detectable tumor recurrence in any animals (see Example 8).

The clinically-derived hypothesis that TGFβ signaling drives immune exclusion to the detriment of CBT efficacy, as well as the previously reported preclinical demonstration that pan-TGFβ inhibition can enable the immune system to overcome this resistance mechanism and promote CBT efficacy, in part prompted us to examine whether the significant tumor responses and survival benefit seen with the antibodies of the invention might correspond to relevant changes in tumor immune contexture.

To study the immune effects of anti-PD-1 or AB6-mIgG1 treatment as single agents or in combination, MBT-2 tumors were harvested from mice 10 days after treatment initiation and then subjected to immunohistochemical and flow cytometry analyses of select immune cell markers. While flow cytometry analysis revealed that the overall percentage of CD45+ immune compartment did not change with treatment, the combination of anti-PD-1 and Ab6-mIgG1 caused a ten-fold increase in the CD8+ T cell representation within this compartment, relative to isotype control antibody treatment (average of 34% versus 3.5%, respectively (FIG. 27B). Of note, single-agent treatment with anti-PD-1 appears to effect modest increases in CD8+ cell representation, but the observed increases did not reach significance in this study. Additionally, analysis of RNA derived from these tumors showed increases in markers of cytotoxic T cell activation that are consistent with the increase in CD8+ cell number and indicative of active effector function of these cells (FIG. 32D). It is notable that a significant increase in the representation of CD4+FoxP3+ Treg cells was also observed with combination treatment. The relevance of this increase in Treg cells is unclear given the significant anti-tumor effects observed with combination treatment. However, the ratio of Treg:CD8 was not altered in response to combination treatment. Interestingly, anti-PD-1/Ab6-mIgG1 combination treatment also induced a significant reduction in overall CD11b+ cell representation within MBT-2 tumors. This appears to be due to selective reduction in CD11b+CD206+ and CD11b+Gr1+ subpopulations, which correspond to immunosuppressive M2-like macrophages and myeloid-derived suppressor cells (MDSC), respectively. Collectively, the representation of these two populations of cells is reduced from an average of 47% of the CD45+ cell population to 14% after combination treatment (FIG. 28B). The M1-like macrophage subpopulation (CD11b+CD206−) did not appear to change with treatment, indicating that PD-1/TGFβ1 blockade has a selective but broad impact on the immunosuppressive milieu within tumors, beneficially affecting both lymphoid and myeloid compartments.

Figures 30A, 30B:
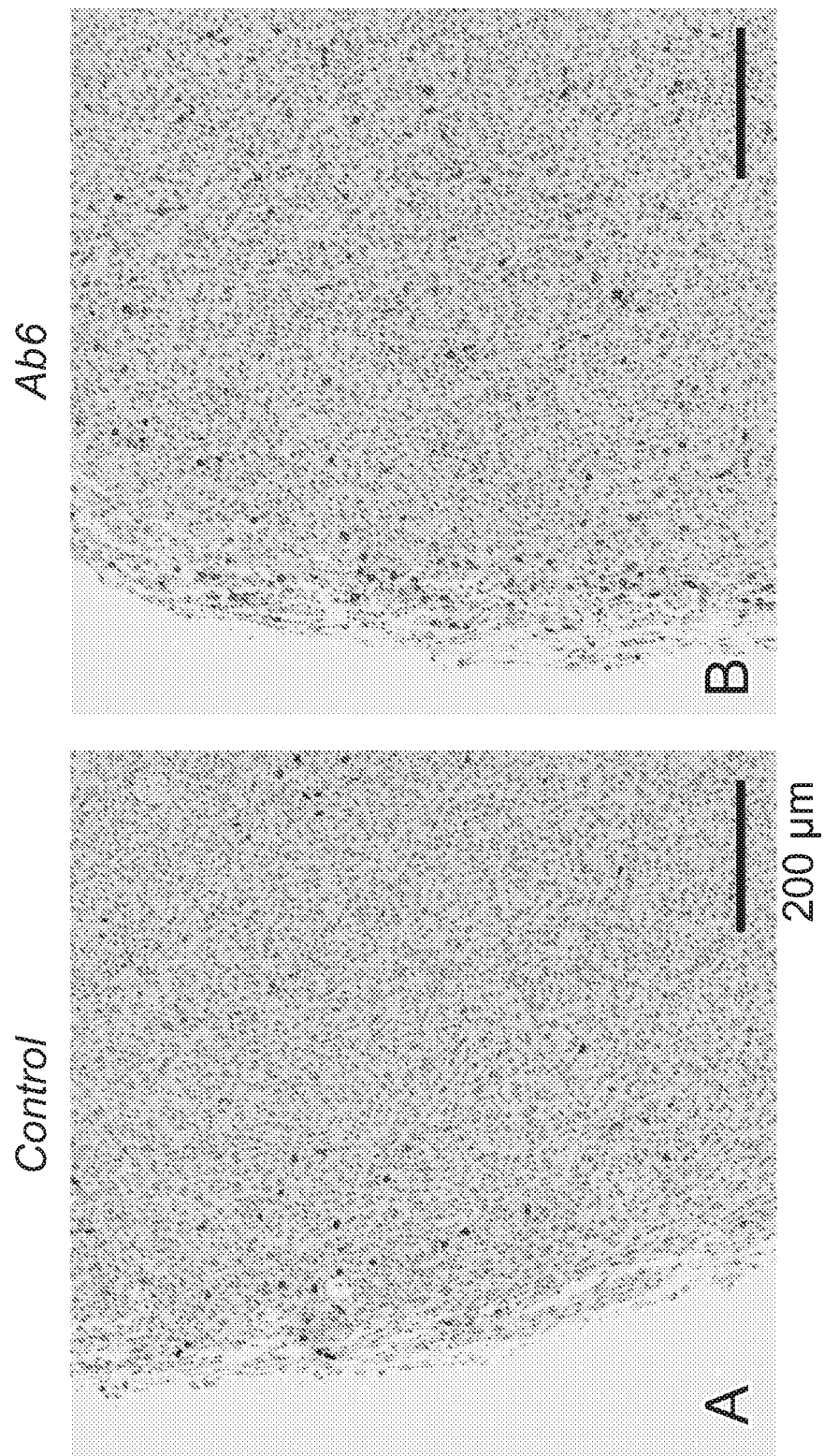
FIGS. 30A-30D provide IHC images of representative MBT2 tumor sections showing intratumoral CD8-positive T cells.

The specific mechanism by which combined PD-1 and TGFβ1 inhibition results in significant CD8+ T cell entry and/or expansion into the tumor microenvironment is not clear. As such, we undertook a more detailed histological analysis in order to glean additional insights into the relationship between TGFβ pathway activity and immune exclusion. First, we confirmed by immunohistochemical analysis a significant increase in CD8+ staining throughout control group MBT-2 tumors, in agreement with the flow cytometry data (FIG. 30). Next, we performed immunohistochemical analysis of phospho-Smad3 (pSmad3), a transcription factor that mediates activation of TGFβ-responsive genes, in an attempt to determine which cells in the tumor microenvironment may be responding to activated TGFβ1.

Figures 30C, 30D:
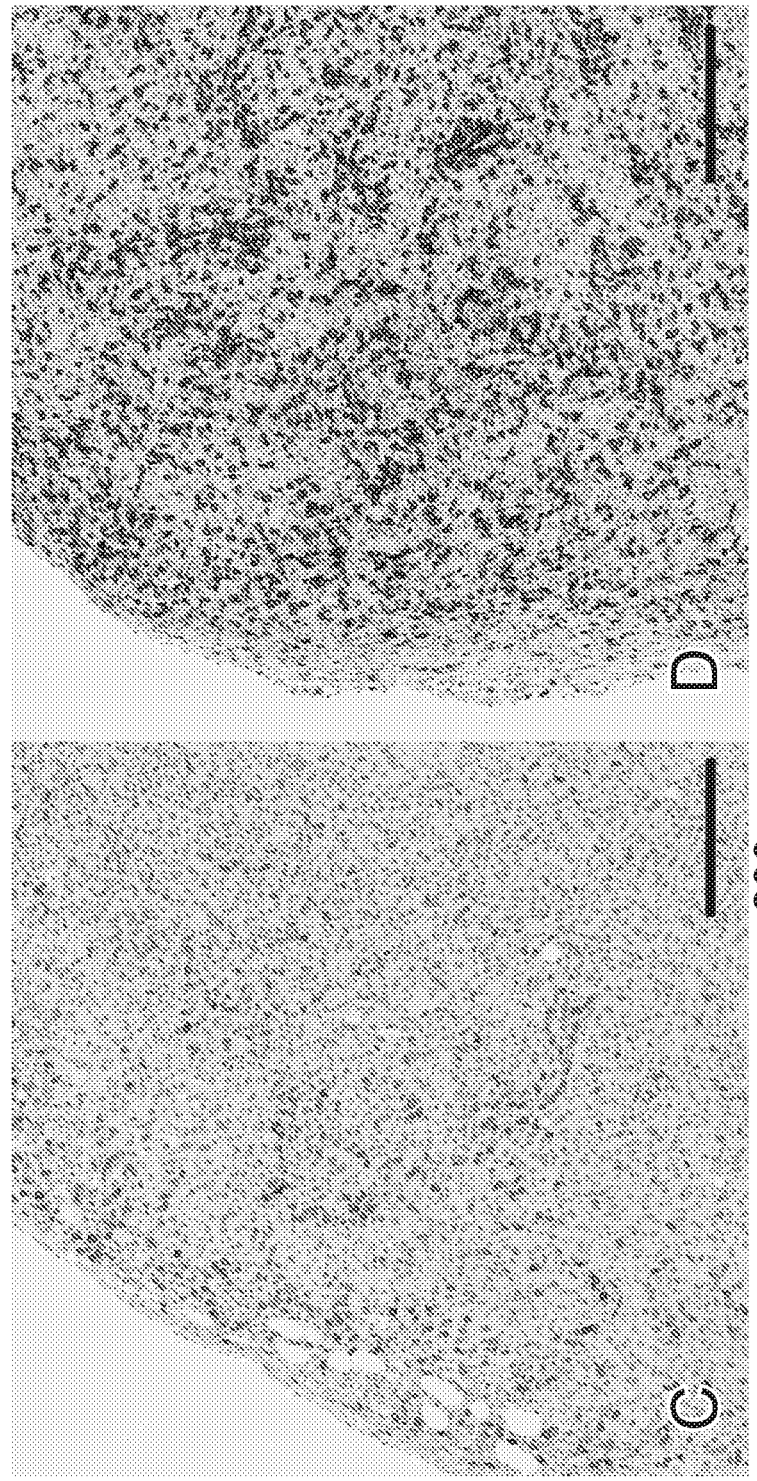
Figure 30F:
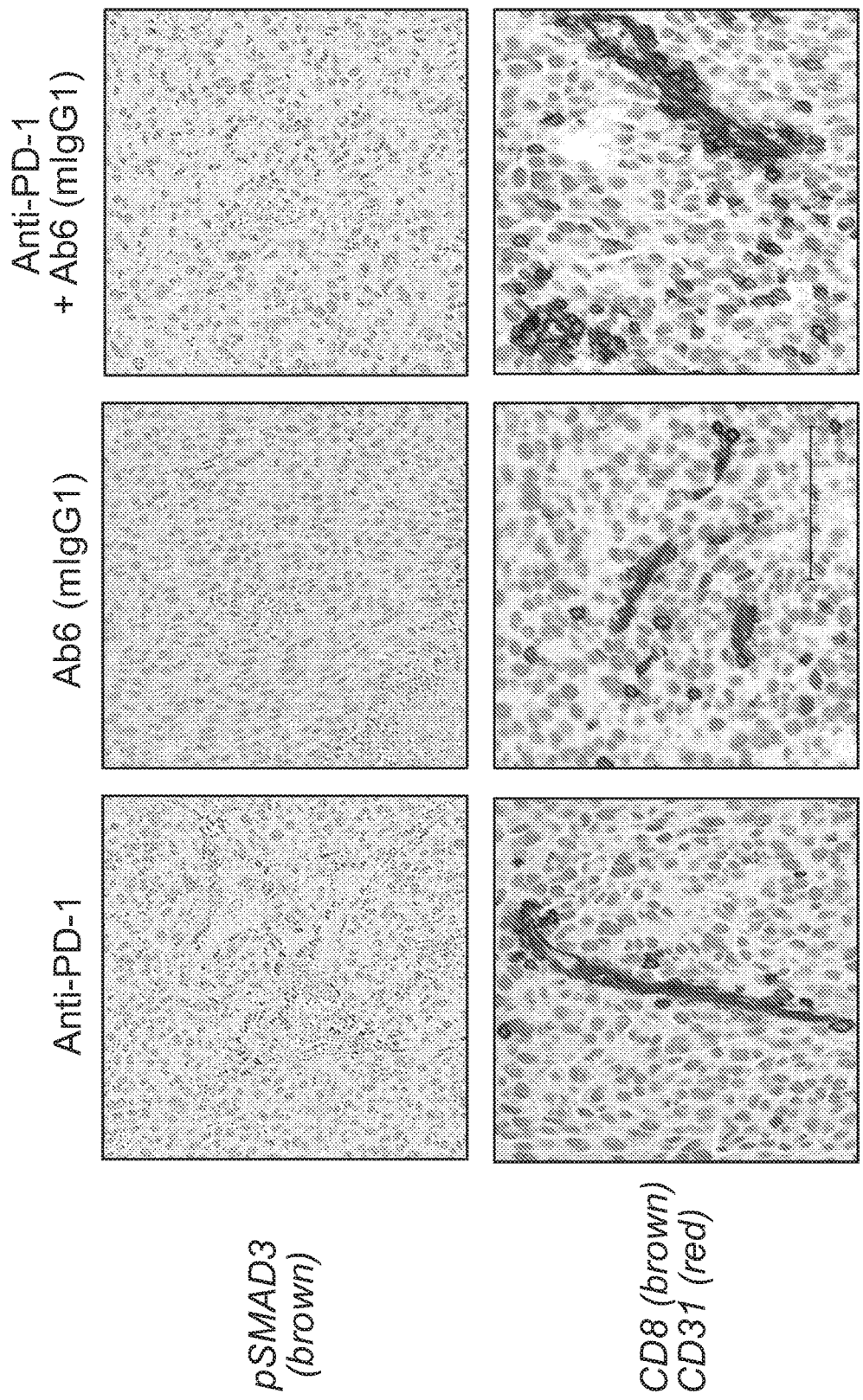
FIG. 30F provides immunohistochiemical analyses of the effect of Ab6 and anti-PD-1 treatment in MBT2 tumors. Tumor sections were visualized for phospho-SMAD3 (top panels) or CD8 and CD31 (lower panels) in animals from three treatment groups as shown.

Surprisingly, in tumors from anti-PD-1 treated and control mice pSmad3 staining appears largely confined to nuclei of the tumor vascular endothelium, and this signal was much diminished upon treatment with Ab6-mIgG (FIG. 30F).

To further explore the relevance of peri-vascular TGFβ signaling, we co-stained CD8+ T cells and CD31+ vascular endothelia. CD8+ T cells appear to be enriched in areas adjacent to CD31+ tumor blood vessels (FIGS. 30F & 30G). This observation raises the possibility that tumor vasculature may serve as a route of T cell entry. While others have reported that TGFβ signaling is associated with the presence of fibroblast-rich peri-tumoral stroma that forms a barrier for T cell entry into the tumor, our preliminary observations suggest that an additional, TGFβ1-dependent vascular barrier may also play a prominent role in prevention of CD8+ T cell entry into the tumor Example 8: Development of Durable, Anti-Tumor Adaptive Immune Memory Response in Anti-PD1/Ab3 and Anti-PD1/Ab6 Complete Responders in MBT-2, Cloudman S91 and EMT-6 Tumors 1. Anti-Tumor Memory in MBT-2 Tumor To ascertain if potent and durable adaptive immune response was generated in complete responders that had previously cleared MBT2 tumors, a tumor re-challenge experiment was conducted.

Methods 8-12 week old female C3H/HeN mice were implanted subcutaneously in the flank with $5 \times 10^5$ MBT2 tumor cells. Animals were randomized to treatment groups when tumors reached an average size of 40-80 mm$^3$ to begin treatment. Starting mean tumor volume was equal across groups. Anti-PD1 (RMP1-14) was dosed twice a week, i.p. at 10 mg/kg; Ab3 was dosed once a week at 10 mg/kg or 30 mg/kg and Ab6 was dosed 3 mg/kg or 10 mg/kg for 5 weeks. After 5 weeks, animals in all anti-PD1/Ab3 and anti-PD1/Ab6 with tumor volumes less than 13.5 mm$^3$ for at least 3 consecutive measurements were deemed "complete responders (CR)". Measurements were taken twice per week. There were no such complete responders in mice that received anti-PD1 alone. For the re-challenge experiment, complete responder animals did not have any measurable tumors (e.g., 0 mm$^3$). These complete responders were followed (e.g., "rested") for 7 weeks without dosing ("washout" period) so as to allow for washout of previously dosed compounds. At the end of 7 weeks, complete responders and age-matched naïve controls animals were injected with $5 \times 10^5$ MBT2 tumor cells subcutaneously in the contralateral flank. Animals were followed for 25 days or until tumor volume exceeded 1200 mm$^3$, whichever came first. Endpoint was defined as tumor volume of 1200 mm$^3$. Upon reaching endpoint, animals were sacrificed.

Results

Figure 15:
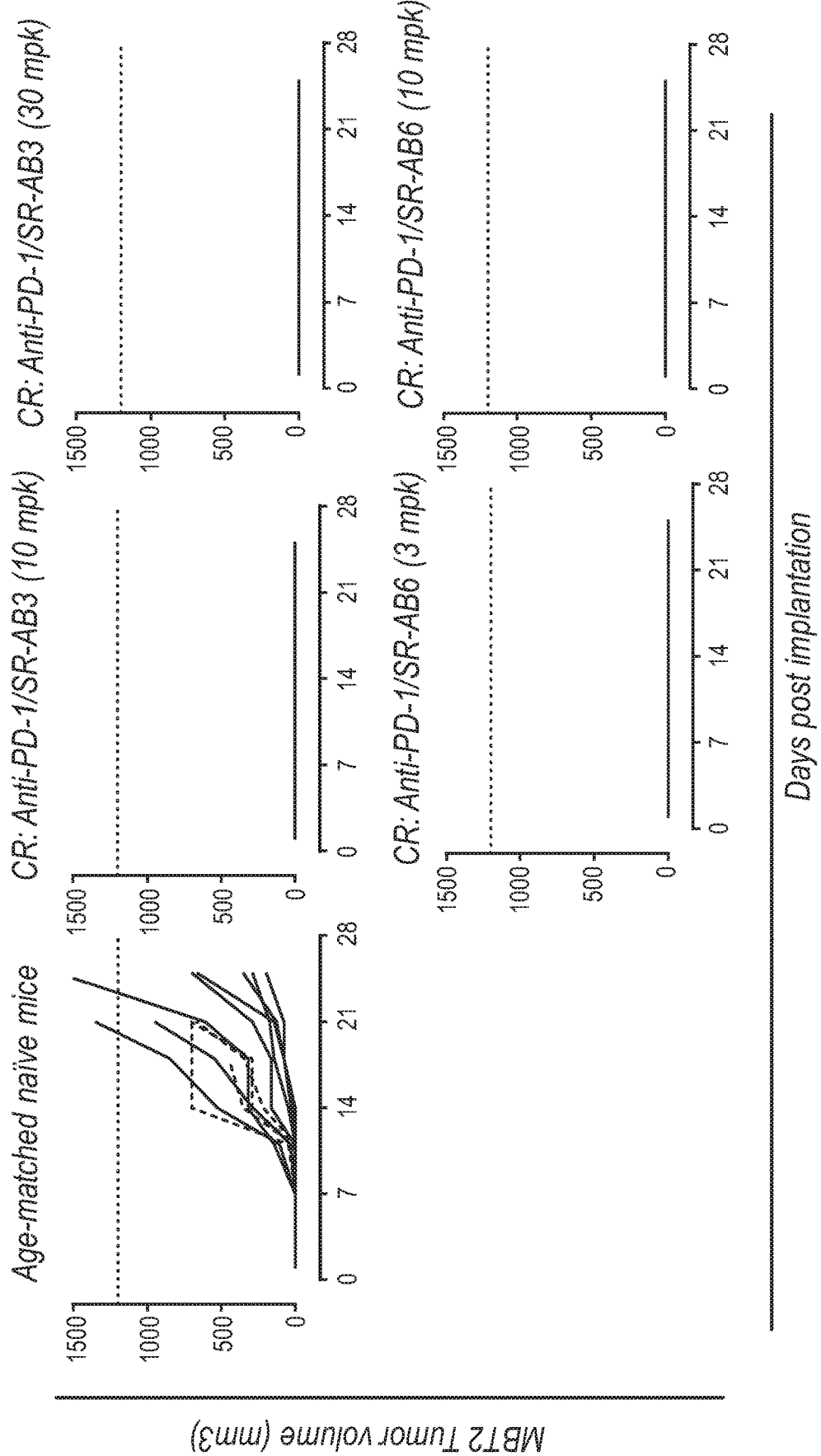
FIG. 15 provides a set of graphs that shows the change in tumor growth (tumor volume $mm^3$) measured over time (days) in a tumor re-challenge study. Animals previously treated with anti-PD-1/Ab3 or anti-PD-1/Ab6 that had cleared tumors (complete responders that achieved complete regression) were re-challenged with MBT2 tumor cells. Naïve, untreated, animals were used as a control. Dashed lines represent animals that had to be sacrificed prior to reaching the 1200 $mm^3$ endpoint criteria due to tumor ulceration.

When complete responders from the efficacy study were subcutaneously re-implanted with MBT-2 cells in the flank contralateral to the original implantation, without further treatment, there was no detectable tumor growth observed in any of the complete responder mice, whereas all mice in a control, age-matched, tumor-naïve group of mice developed measurable tumors within three weeks of implantation (FIG. 15).

More specifically, tumor re-challenge models are a means of demonstrating immunological memory and surveillance against metastases or tumor recurrence. In these instances, complete responders (animals that achieved complete tumor regression in response to treatment) were re-implanted with tumor cells and growth was compared to age-matched naïve mice. Appearance of tumor in naïve animals was 100% (12/12) by day 25 (FIG. 15), with a number of animals reaching endpoint criteria. Complete responders from the study in FIGS. 13A and 13B, which were re-challenged with MBT2 cells as described above, had no detectable tumors by end of study (0/9 complete responders combined), showing that 100% of complete responders retain robust immune memory to MBT2 tumor rechallenge. These results indicate that a durable and potent memory response to tumor antigens was generated in tumor-experienced animals and suggests that tumor-clearance in the initial exposure was related to an adaptive immune response. This adaptive immune response is sufficient to destroy tumor cells, prevent tumor establishment and would suggest continued suppression of metastases or tumor recurrence in these animals.

Furthermore, it demonstrates that TGFβ1 inhibition during the primary immune response does not interfere with the development of memory lymphocyte populations.

These re-challenge results from MBT-2 tumor model indicate that the combined inhibition of TGFβ1 and PD-1 is sufficient to establish durable and potent anti-tumor immunological memory in these animals.

2. Durable Anti-Tumor Effects in CloudmanS91

Notably, while several CloudmanS91 tumor-bearing mice in the anti-PD-1/Ab6 combination groups experienced complete responses, some animals supported a small yet stable, residual tumor mass over the remaining treatment period. We sought to recapitulate tumor rechallenge data in this model as we had in MBT-2. However, tumor take rate is variable in this model, rendering this analysis more challenging. Instead, we chose to stop treatment and follow animals for several weeks.

Six weeks after treatment cessation, mice with no measurable tumor at treatment cessation remained tumor-free. Measurable tumors at dosing cessation had mixed responses where many cleared but few remained stable or outgrew (FIG. 11D). These data underscore the importance of maintaining treatment until full tumor clearance is achieved (also see Example 5).

3. Durable Anti-Tumor Effects in EMT-6

Figure 34B:
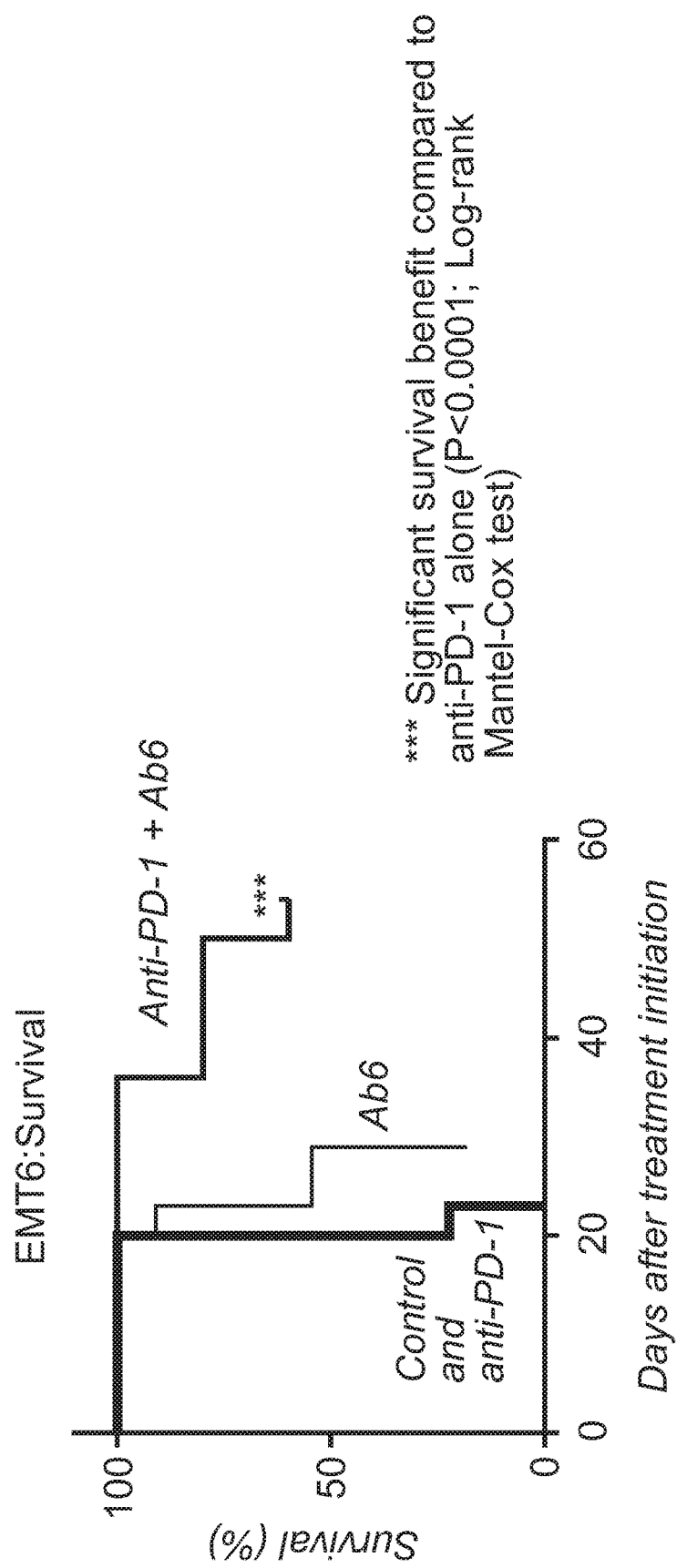
FIG. 34B provides a graph showing percent survival over time (days after treatment initiation) in EMT6 (Study 1). Treatment groups that included both anti-PD-1 and Ab6 showed significant survival benefit as compared to anti-PD-1 alone.
Figure 34C:
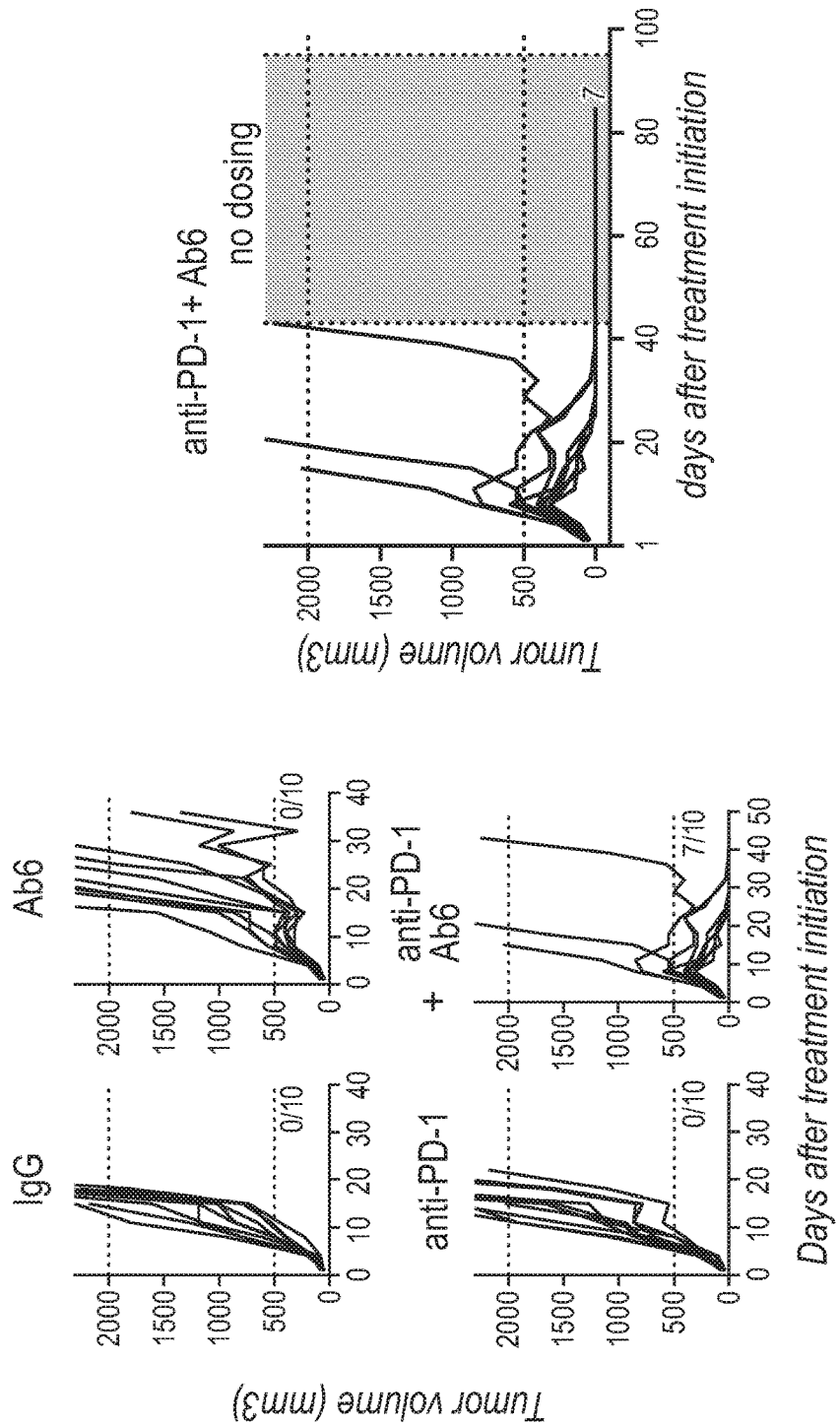
FIG. 34C provides data showing percent survival over time (days after treatment initiation) in EMT6 (Study 2). Treatment groups that include both anti-PD-1 and Ab6 have shown significant survival benefit as compared to anti-PD-1 alone, and the anti-tumor effects are durable after treatment ended.

Strikingly, we observed similar responses to the anti-PD-1/Ab6-mIgG1 combination in the EMT-6 breast carcinoma model, with a 50% complete response rate following combination treatment and a significant survival advantage over anti-PD-1 (FIGS. 34A & 34C). In contrast to MBT-2 and CloudmanS91, in which TGFβ1 is the predominantly expressed isoform, EMT6 expresses similar levels of TGFβ1 and TGFβ3 at both the RNA and protein level. This treatment combination was more efficacious than anti-PD-1/pan-TGFβ inhibition, suggesting that even in the presence of multiple TGFβ isoforms, TGFβ1 is the main driver of immune exclusion and thus primary resistance. In this model, we halted treatment and again saw that six weeks post dosing cessation complete responders remained tumor free, again demonstrating the durability of response (FIG. 34C, right).

Example 9: Antibody Screening, Selection Methodology and Characterization

Given the high sequence and structural similarity between mature TGFβ1 growth factor and its closely related family members, TGFβ2 and TGFβ3, we reasoned that the generation of selective and sufficiently high affinity antibody-based inhibitors targeting this active form of TGFβ1 growth factor would prove to be challenging. The recently reported insights into the latent TGFβ1 structure and mechanical aspects of its activation via interaction with certain integrins have pointed to the possibility of targeting the prodomain in latent TGFβ1 complexes aimed to prevent latent complex activation as the mechanism of action.

Achievement of isoform selectivity in both binding and activation inhibition would take advantage of the lower sequence similarity between the family member prodomains that confine and render inactive the respective growth factor homodimers. An additional key consideration for the identification of a selective inhibitor of TGFβ1 activation is the fact that latent TGFβ1 is assembled into disulfide-linked large Latent Complexes (LLCs) that allow for deposition of the inactive growth factor complexes onto either the extracellular matrix or their elaboration on the cell surface. Given the plausibility that multiple TGFβ1 LLCs may be expressed in the tumor microenvironment, RNAseq data from TCGA were analyzed. Essentially all tumor types show evidence of expression of the four proTGFβ1l-presenting molecules LTBP1, LTBP3, GARP, and LRRC33 (FIG. 20E). We therefore sought to identify specific antibodies that would bind and inhibit latent TGFβ1 activation in all of these local contexts.

Soluble murine and human forms of each TGFβ1 LLC were designed, expressed, purified, characterized, and used for the positive selection steps in a carefully designed screen of a yeast-based naïve human antibody display library. To ensure the identification of selective latent TGFβ1 binders, non-complexed LLC-presenting molecules were also used in negative selection steps.

The parental antibody was identified via selection of a yeast-based, naïve, fully human IgG antibody library using human and murine forms of TGFβ1 LLCs (LTBP1-proTGFβ1, LTBP3-proTGFβ1 and GARP-proTGFβ1) as positive selection antigens and counter-selecting on the human and murine LLC-presenting molecules (LTBP1, LTBP3 and GARP). The selection was a multi-round process including two rounds of Magnetic Bead Assisted Cell Sorting (MACS) and several subsequent rounds of Fluorescence Activated Cell Sorting (FACS). The MACS rounds included pre-clearing (to remove non-specific binders), incubation with biotinylated antigen, washing, elution and yeast amplification. The FACS selection rounds included incubation with the biotinylated antigen, washing and selection of binding (for positive selection) or non-binding (for negative or de-selection) population by flow cytometry followed by amplification of the selected yeast by growth in appropriate yeast growth media. All selections were performed in solution phase.

Several hundred unique antibodies were expressed as full-length human IgG1agly (aglycosylated Fc) monoclonal antibodies. These antibodies were then characterized by biolayer interferometry to determine their ability to bind human and murine LTBP1-proTGFβ1, LTBP3-proTGFβ1 and GARP-proTGFβ1. Antibodies that bound to these TGFβ1 LLCs were tested and rank-ordered in cell-based potency screening assays (LTBP-proTGFβ1, GARP-proTGFβ1, and LRRC33-proTGFβ1 assays). Inhibitory antibodies were expressed recombinantly with a human IgG4sdk Fc (hinge stabilized by S228P mutation; Angal, 1993) and their inhibitory activity tested in integrin-mediated TGFβ1 activation assays (LTBP-proTGFβ1, GARP-proTGFβ1, and LRRC33-proTGFβ1 assays; see Example 2). Several antibodies were able to significantly inhibit proTGFβ1 in the reporter cell assay. Antibody Ab4 was chosen as a lead antibody for affinity maturation based on its ability to bind human and mouse proTGFβ1 complexes and inhibit integrin-mediated activation of all human and mouse proTGFβ1 LLCs.

Affinity maturation of Ab4 was done in two stages using two different antibody engineering strategies. In the first phase, a library of antibody molecules was generated wherein the parental CDRH3 was combined with a premade antibody library with CDRH1 and CDRH2 variants (H1/H2 shuffle). This library was selected for binding to the human and mouse proTGFβ1 complexes. The strongest binders from this phase of the affinity maturation campaign were then moved forward to the second phase of affinity maturation wherein the heavy chain CDR3 of the parent molecule was subjected to mutagenesis using a primer dimer walking approach (H3 oligo mutation), and the library of variants generated was selected for binding to the human and mouse proTGFβ1 complexes.

A total of 14 antibodies representing affinity-optimized progenies of lead antibody Ab4 from both affinity maturation stages were tested again for antigen binding and inhibition of latent TGFβ1 LLCs. Ab6 was selected due to its high affinity for all four latent TGFβ1 LLCs, crossreactivity to mouse, rat, and cynomolgus monkey proteins, and increased potency in cell-based assays.

To further characterize binding properties of Ab6, in vitro binding activities were measured in an MSD-SET assay. Ab6 was confirmed to be selective for latent TGFβ1 complexes (see FIG. 33A); no meaningful binding was detected to latent TGFβ2 or latent TGFβ3 complexes. Similarly, no binding was detected to active (mature) TGFβ1 growth factor itself that is not in association with a prodomain. As shown below, Ab6 binds with high affinity to all large latent TGFβ1 complexes (i.e., presenting molecule+proTGFβ1). Furthermore, Ab6 was shown to have desirable species cross-reactivity; it recognize and bind with high affinity to rat and cynomolgus counterparts.

TABLE 21

Ab6 cross-species specificity

| Large Latent Complex | Human $K_D$ (pM) | Mouse $K_D$ (pM) | Rat $K_D$ (pM) | Cyno $K_D$ (pM) |
|---|---|---|---|---|
| LTBP1-proTGFβ1 | 18 ± 0 | 24 ± 0 | 35 ± 2 | 39 ± 2 |
| LTBP3-proTGFβ1 | 29 ± 3 | 22 ± 0 | n.d. | n.d. |
| GARP-proTGFβ1 | 27 ± 2 | 21 ± 3 | n.d. | n.d. |
| LRRC33-proTGFβ1 | 63 ± 0 | 48 ± 0 | 86 ± 8 | 93 ± 10 |

To test the ability of Ab6 to inhibit latent TGFβ1 activation by integrins, a series of cell-based activation assays was developed, which corresponds to each of the LLC contexts that enable TGFβ1 presentation and activation. Human LN229 glioblastoma cells express αVβ8 integrins, which can activate latent TGFβ1 complexes. These cells also endogenously express LTBP1 and LTBP3 (as measured by qPCR) which, when transfected with a TGFβ1-encoding plasmid, enable production and deposition of these TGFβ1 LLCs (LTBP1-proTGFβ1 and LTBP3-proTGFβ1) into extracellular matrix. In order to produce cell-associated GARP- or LRRC33-containing TGFβ1 LLCs (GARP-proTGFβ1 and LRRC33-proTGFβ1), LN229 cells (which do not express these genes, by qPCR) were co-transfected with expression constructs encoding one of these presentation molecules along with a TGFβ1 expression construct. Once deposited into extracellular matrix or elaborated on the cell surface of LN229 cells, TGFβ1 LLCs can then become activated by αVβ8 integrin expressed by the same cells. Mature (active) TGFβ1 growth factor that is released from the latent complex by integrin activation is then free to engage its cognate receptor on co-cultured cells engineered with a CAGA12-luciferase promoter-reporter that enables measurement of growth factor activity.

All TGFβ1 LLCs were readily activated under the above-mentioned assay conditions. Co-transfection of GARP or LRRC33 into LN229 cells expressing latent TGFβ1 resulted in a significantly higher TGFβ signal, consistent with formation and activation of TGFβ1 LLCs on the cell surface and outcompeting endogenous LTBPs. Ab6 inhibited the activation of all complexes in a concentration-dependent fashion with IC50 values between 1.15 and 1.42 nM. The inhibitory potency for mouse TGFβ1 complexes was similar, in line with the species crossreactivity of Ab6. Consistent with the lack of significant binding of Ab6 to the LTBP1-TGFβ3 complex, little to no inhibition of integrin-mediated LTBP-TGFβ3 LLC activation complex was observed in an identically designed assay, thus demonstrating selectivity for inhibition of TGFβ1 activation (FIG. 33B).

Notably, Ab6 also inhibited the activation of latent TGFβ1 by human plasma kallikrein and Plasmin (See FIGS. 5A & 5B), indicating that multiple putative mechanisms of activation may be inhibited by this antibody.

To further assess the ability of Ab6 to inhibit a biologically relevant consequence of TGFβ1 activation, we assessed the ability of this antibody to inhibit a key suppressive activity of primary human Treg cells. Sorted CD4+ CD25$^{hi}$CD127$^{lo}$ Treg cells upregulate surface expression of TGFβ1-GARP LLC upon T cell receptor stimulation (FIG. 26A). These activated Treg cells suppressed proliferation of autologous effector CD4 T cells, and Ab6 blocked this suppressive Treg activity at concentrations as low as 1 µg/ml (FIG. 26B). These results are consistent with previous observations that Treg cells harness TGFβ signaling to suppress T cells.

Example 10. Epitope Mapping to Determine where in the proTGFβ Complex Ab5, Ab6, and Ab3 are Binding To gain initial insights into the inhibitory mechanism of action for the isoform-selective inhibitors of TGFβ1 activation, we performed Hydrogen-Deuterium Exchange Mass Spectrometry (H/DX-MS) analysis to identify possible sites of latent TGFβ1 interaction with the antibody. Hydrogen/Deuterium exchange mass spectrometry (HDX-MS) is a widely used technique for exploring protein conformation in solution. HDX-MS methodology is described in Wei et al., Drug Discov Today. 2014 January; 19(1): 95-102, incorporated by reference in its entirety herein. Briefly, HDX-MS relies on the exchange of the protein backbone amide hydrogens with deuterium in solution. The backbone amide hydrogens involved in weak hydrogen bonds or located at the surface of the protein may exchange rapidly while those buried in the interior or those involved in stabilizing hydrogen bonds exchange more slowly. By measuring HDX rates of backbone amide hydrogens, one can obtain information on protein dynamics and conformation.

Latent TGFβ1 (15 µM) and proTGFβ1/Ab Fab (1:3 molar ratio) were prepared in sample buffer (20 mM HEPES, 150 mM NaCl, pH 7.5). In the non-deuterated experiments, each sample was mixed with sample buffer (1:15, v/v) at room temperature, then mixed with 1:1 (v/v) quenching buffer (100 mM sodium phosphate, 4 M guanidine HCl, 0.5 M TCEP) at 0° C. Quenched samples were immediately injected into a NANOACQUITY UPLC™ system with HDX technology (WATERS™ Corp., Milford, MA, USA) for on-column pepsin digestion. The eluent was directed into a SYNAPT® G2 HDMS mass spectrometer (WATERS™ Corp., Milford, MA, USA) for analysis in MSE mode. For H/D exchange experiments, each sample was mixed with labeling buffer (20 mM HEPES, 150 mM NaCl in deuterium oxide, pD 7.5) (1:15, v/v) to start the labeling reactions at 25° C. Five aliquots of each sample were labeled at various time intervals: 10 s, 1 min, 10 min, 1 h, and 2 h. At the end of each labeling time point, the reaction was quenched by adding 1:1 (v/v) quenching buffer, and the quenched samples were injected into the WATERS™ H/DX-MS system for analysis. Between each sample run, a clean blank was run by injecting pepsin wash buffer (1.5 M guanidine HCl, 4% acetonitrile, 0.8% formic acid) into the H/DX-MS system.

Accurate mass and collision-induced dissociation in data-independent acquisition mode (MSE) and ProteinLynx Global Server (PLGS) 3.0 software (WATERS™ Corp., Milford, MA) were used to determine the peptic peptides in the undeuterated protein samples analyzed on the same UPLC-ESI-QToF system used for H/DX-MS experiments. Peptic peptides generated from PLGS were imported into DynamX 3.0 (WATERS™ Corp., Milford, MA) with peptide quality thresholds of MS1 signal intensity ≥1000, and maximum mass error of 1 ppm. Automated results were manually inspected to ensure the corresponding m/z and isotopic distributions at various charge states were properly assigned to the appropriate peptic peptide. DynamX 3.0 was used to generate the relative deuterium incorporation plot and H/DX heat map for each peptic peptide. The relative deuterium incorporation of each peptide was determined by subtracting the weight-averaged centroid mass of the isotopic distribution of undeuterated control sample from that of the weight-averaged centroid mass of the isotopic distribution of deuterium-labeled samples at each labeling time point. All comparisons were performed under identical experimental conditions, thus negating the need for back exchange correction in the determination of the deuterium incorporation. Thus, H/D exchange levels are reported as relative. The fractional relative deuterium uptake was calculated by dividing the relative deuterium uptake of each peptic peptide by its theoretical maximum uptake. All H/DX-MS experiments were performed in duplicate and a 98% confidence limit for the uncertainty of the mean relative deuterium uptake was calculated as described. Differences in deuterium uptake between the unbound and Fab-bound latent TGFβ1 that exceed 0.5 Da were considered significant.

HDX-MS was carried out to determine where in the proTGFβ complex Ab5 and Ab6 were binding. In HDX-MS, the regions of an antigen that are tightly bound by an antibody are protected from proton exchange, due to protein-protein interaction, while regions that are exposed to solvent can readily undergo proton exchange. Based on this, binding regions of the antigen were identified.

Figure 16:
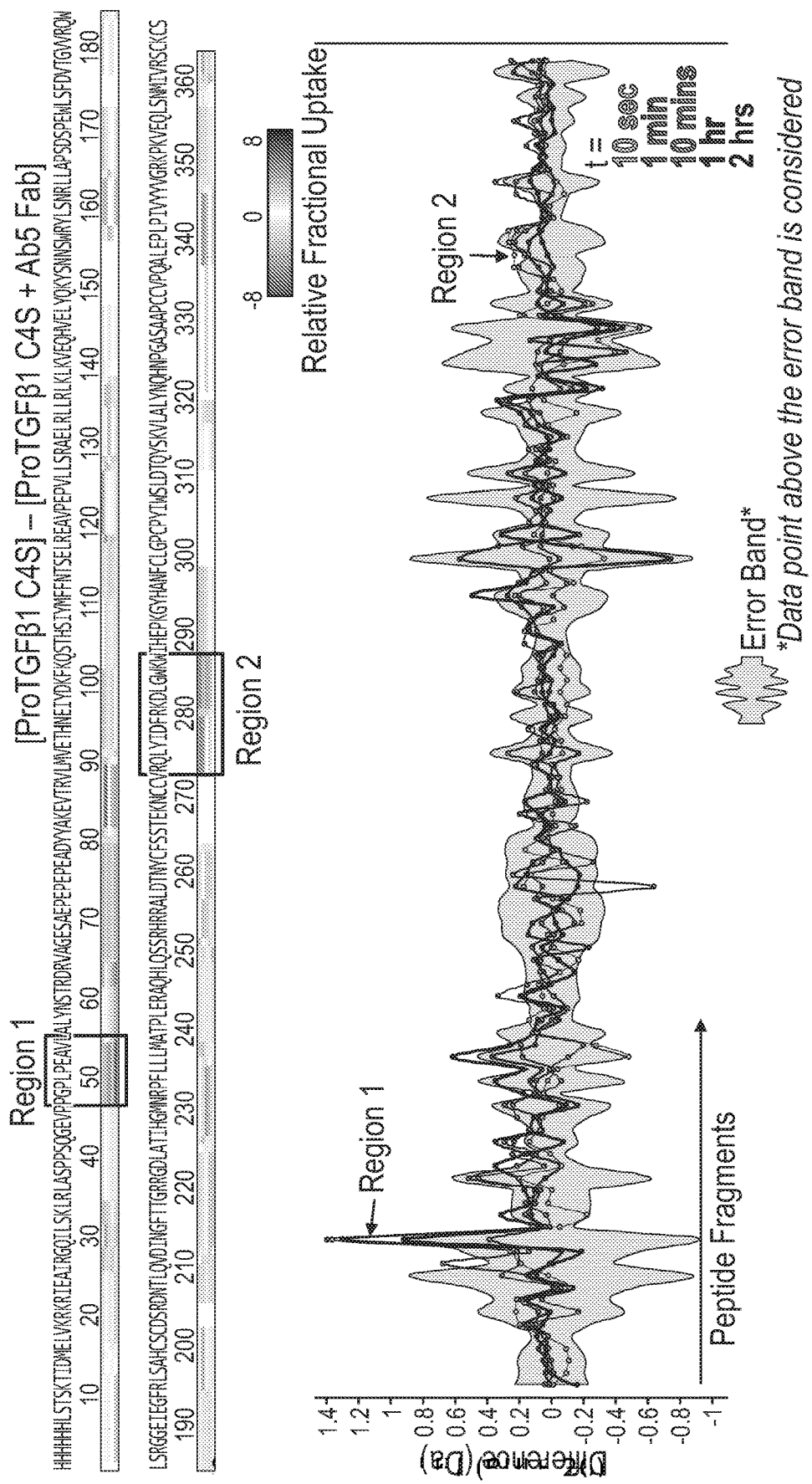
FIG. 16 is a heat map that shows Ab5 Fab binding results in HDX protection in regions (Region 1 and Region 2) of proTGFβ1 (SEQ ID NO: 183).
Figure 17:
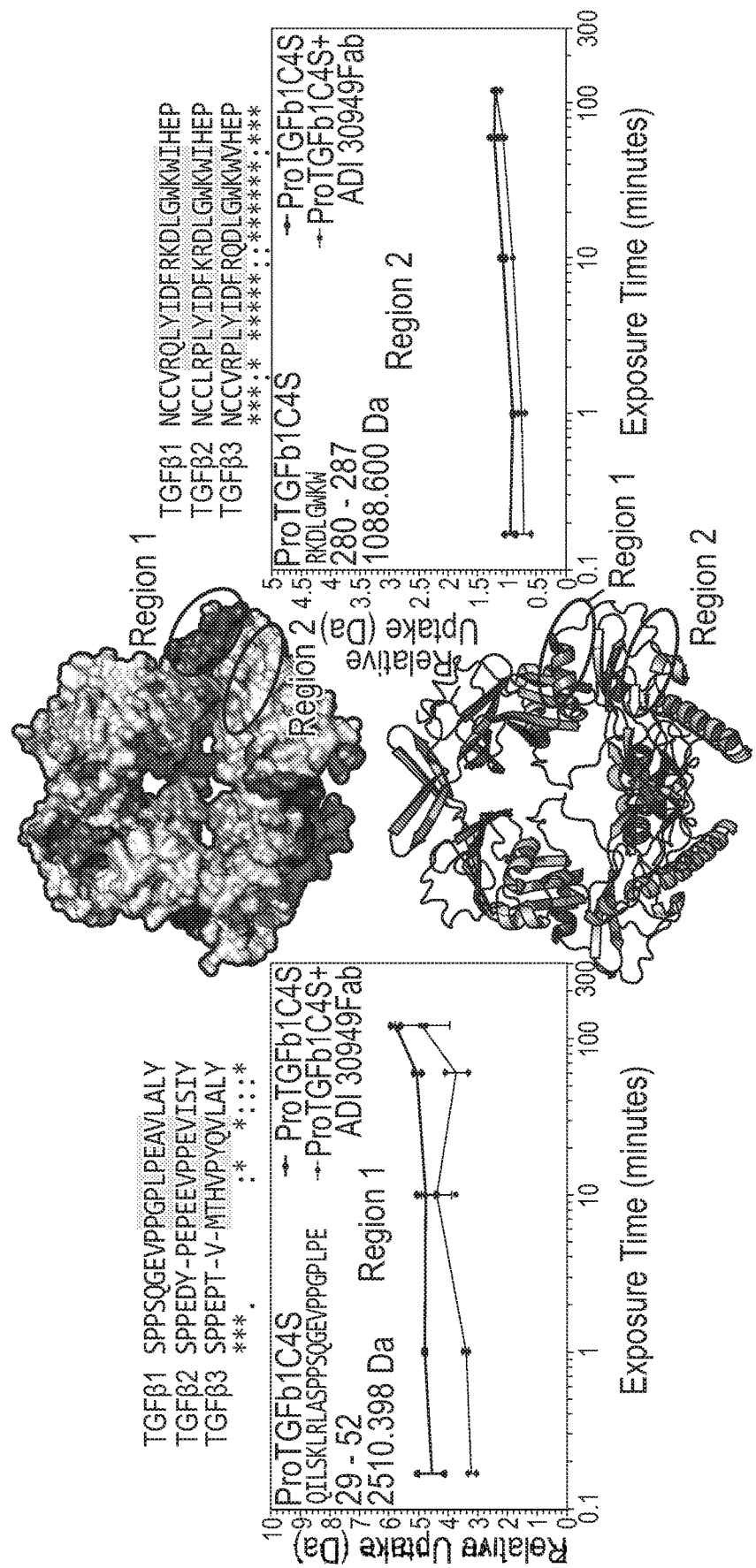
FIG. 17 illustrates the regions of the proTGFβ1 complex that are protected from solvent exchange as measured by HDX (see FIG. 16) upon Ab5 binding. SEQ ID NOS: 184-187 are listed from top to bottom on the left side, and SEQ ID NOS: 188-191 are listed from top to bottom on the right side of the figure

Heat map shows Ab5 Fab binding results in HDX protection in regions (Region 1 and Region 2) of ProTGFβ1 (FIG. 16). FIG. 17 depicts the structure of the proTGFβ1 complex, overlaid with the HDX-protected regions bound by Ab5. Notably, HDX-MS showed that Ab5 potentially binds to a unique epitope in the LAP/Growth Factor Region of ProTGFβ1.

Similar HDX studies were carried out to identify the binding regions involved in Ab6 binding to proTGFβ1. An excellent peptide coverage of ~90% was achieved. The analysis revealed three regions on latent TGFβ1 that were protected from deuterium exchange by Ab6 Fab binding. The heat map provided in FIG. 18A shows certain regions of ProTGFβ1 affected by the interaction of Ab6 with the antigen. These areas of the antigen were noted by red boxes shown in the figure. FIG. 18B shows the structure of the proTGFβ1 complex, and the regions identified in FIG. 18A were marked accordingly to show the spatial relationship of these areas within the proTGFβ1 complex.

As shown in FIG. 18A, the protected region marked with an asterisk (*) was found to be the same as Region 1 identified for Ab5. The protected region marked with a double asterisk (**) was found to be a subset of Region 2 identified for Ab5. These data suggest that preferred antibodies that show advantageous inhibitory activities may bind an epitope that includes a portion of Latency Lasso (Latency Loop) of the latent complex. The data also suggest that such epitope may be a combinatorial epitope that is formed by a portion of Latency Lasso and a portion of the growth factor domain, which may effectively "clamp" the growth factor in the locked-in state, thereby preventing its release.

Figure 19A:
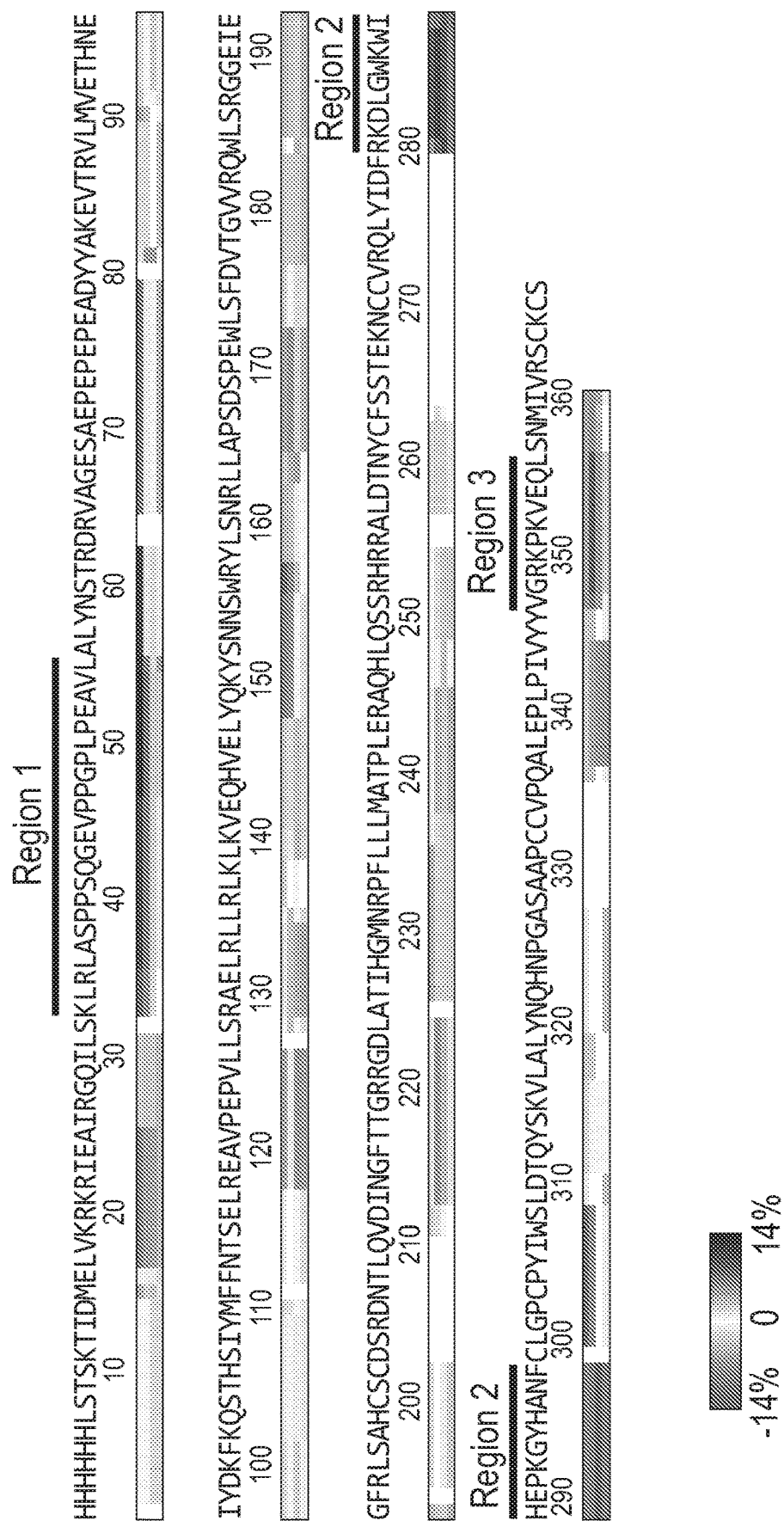
FIG. 19A illustrates identification of three binding regions (Region 1, Region 2 & Region 3) following statistical analyses. Region 1 overlaps with so-called "Latency Lasso" within the prodomain of proTGFβ1 (SEQ ID NO: 183), while Regions 2 and 3 are within the growth factor domain.
Figure 19B:
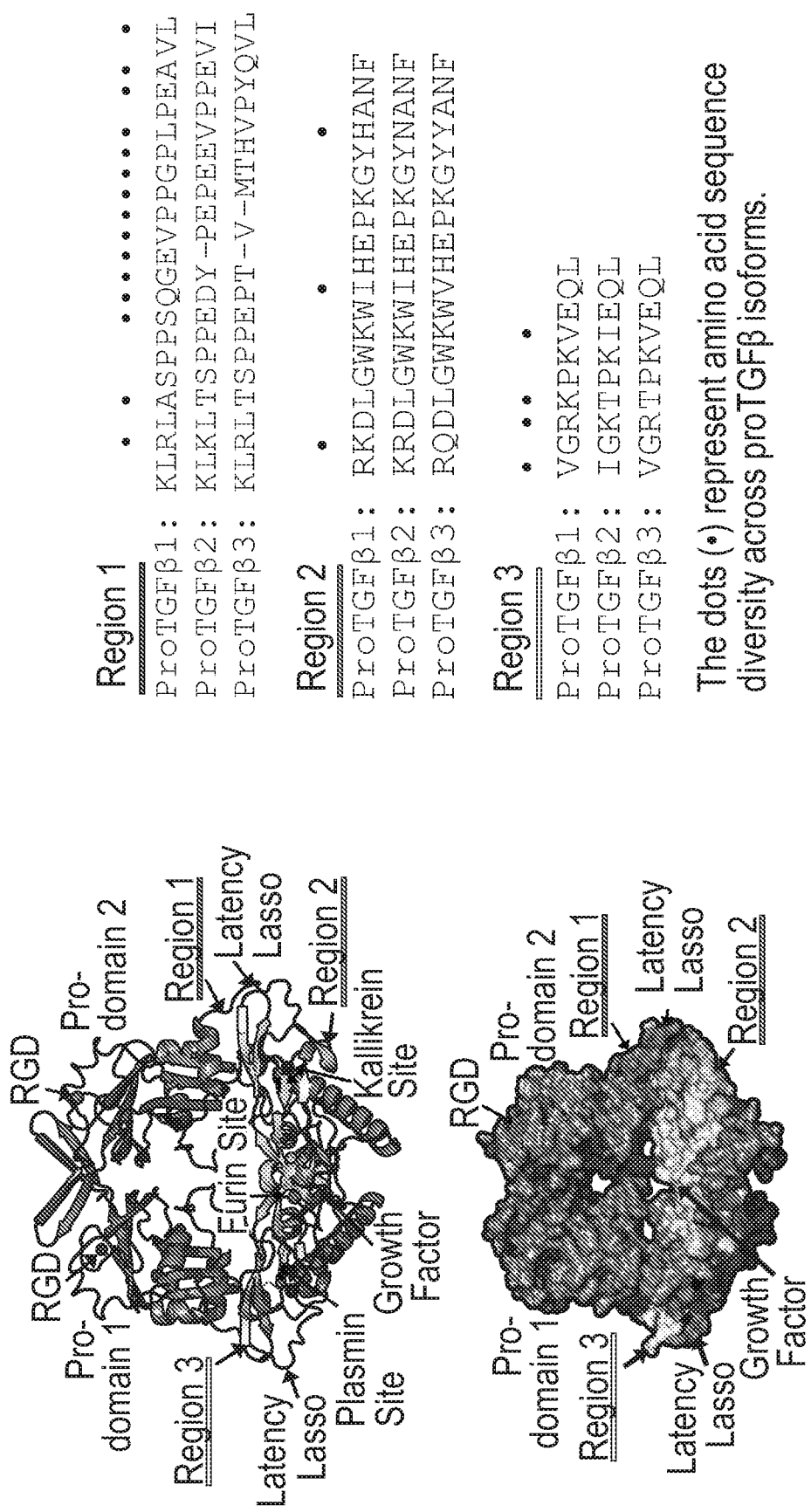
FIG. 19B depicts various domains and motifs of proTGFβ1, relative to the three binding regions involved in Ab6 binding. Sequence alignment among the three isoforms is also provided. SEQ ID NOS: 192-200 are listed from top to bottom on the right side of the figure.

Statistical analyses revealed three binding regions on proTGFβ1 that were strongly protected from deuterium exchange by Ab6 Fab binding (FIG. 19A). Region 1 is within the latent TGFβ1 prodomain, whereas regions 2 and 3 map to the TGFβ1 growth factor. Interestingly, region 1 largely spans the latency lasso and contains the proteolytic cleavage sites for both plasmin and kallikrein proteases; protection of this region is consistent with our observation that Ab6 inhibits kallikrein- and Palsmin-mediated activation of latent TGFβ1 (FIGS. 5A & 5B). It is also important to reiterate that Ab6 does not bind to any of the three TGFβ growth factor dimers in free form (e.g., not in association with the prodomain), which implies that any potential interactions with sites on the growth factor domain are dependent on prodomain interactions. Moreover, Ab6 and integrin αVβ6 can bind to latent TGFβ1 simultaneously. This observation suggests an allosteric inhibition mechanism of integrin-dependent TGFβ1 activation, as the antibody binding regions are distal to the trigger loop in the TGFβ1 prodomain that carries the integrin recognition site (RGD; FIG. 19B). In addition, sequence alignment of putative epitope regions 1-3 (particularly Regions 1 & 2) revealed significant sequence divergence across the three TGFβ isoforms, which likely explains the observed selectivity of Ab6 for proTGFβ1 versus proTGFβ2 and proTGFβ3 complexes (FIG. 19B).

Example 11: Bioinformatic Analysis of Relative Expressions of TGFB1, TGFB2 and TGFB3

Previous analyses of human tumor samples implicated TGFβ signaling as an important contributor to primary resistance to CBT (Hugo et al. 2016). One of these studies revealed that TGFB1 gene expression in urothelial cancers was one of the top-scoring TGFβ pathway genes associated with anti-PD-L1 treatment non-responders suggesting that activity of this isoform may be driving TGFβ signaling.

To evaluate the expression of TGFβ isoforms in cancerous tumors, gene expression (RNAseq) data from publically available datasets was examined. Using a publically available online interface tool (Firebrowse) to examine expression of TGFβ isoforms (TGFB1, TGFB2 and TGFB3) in The Cancer Genome Atlas (TCGA), the differential expression of RNA encoding TGFβ isoforms in both normal and cancerous tissue were first examined. TGFB1, TGFB2, and TGFB3 mRNA expression was evaluated across populations of human cancer types as well as within individual tumors. All tumor RNAseq datasets in the TCGA database for which there were normal tissue comparators were selected, and expression of the TGFB1, TGFB2, and TGFB3 genes was examined (FIG. 20A). Data from the Firebrowse interface are represented as log 2 of reads per kilobase million (RPKM).

These data suggest that in most tumor types (gray), TGFB1 is the most abundantly expressed transcript of the TGFβ isoforms, with log 2(RPKM) values generally in the range of 4-6, vs. 0-2 for TGFB2 and 2-4 for TGFB3. We also note that in several tumor types, the average level of both TGFB1 and TGFB3 expression are elevated relative to normal comparator samples (black), suggesting that increased expression of these TGFβ isoforms may be associated with cancerous cells. Because of the potential role of TGFβ signaling in suppressing the host immune system in the cancer microenvironment, we were interested to note that TGFB1 transcripts were elevated in cancer types for which anti-PD-1 or anti-PDL1 therapies are approved—these indications are labeled in gray on FIG. 20A.

Note that while RPKM >1 is generally considered to be the minimum value associated with biologically relevant gene expression (Hebenstreit et al., 2011; Wagner et al., 2013), however for subsequent analyses, more stringent cutoffs of RPKM (or of the related measure FPKM (see Conesa et al, 2016)) >10 or >30 to avoid false positives were used. For comparison, all three of those thresholds are indicated on FIG. 20A.

The large interquartile ranges in FIG. 20A indicate significant variability in TGFβ isoform expression among individual patients. To identify cancers where at least a subset of the patient population have tumors that differentially express the TGFβ1 isoform, RNAseq data from individual tumor samples in the TCGA dataset was analyzed, calculating the number of fragments per kilobase million (FPKM). RPKM and FPKM are roughly equivalent, though FPKM corrects for double-counting reads at opposite ends of the same transcript (Conesa et al., 2016). Tumor samples were scored as positive for TGFβ1, TGFβ2, or TGFβ3 expression if the FPKM value the transcript was >30 and the fraction of patients (expressed as %) of each cancer type that expressed each TGFβ isoform were calculated (FIG. 20B).

Comparative analysis of RNAseq data from The Cancer Genome Atlas (TCGA) revealed that, amongst the three family members, TGFB1 expression appeared to be the most prevalent across the majority of tumor types. Notable exceptions are breast cancer, mesothelioma, and prostate cancer, where expression of other family members, particularly TGFB3, is at least equally prevalent in comparison to TGFB1. As shown in FIG. 20B, a majority of tumor types show a significant percentage of individual samples that are TGFβ1 positive, with some cancer types, including acute myeloid leukemia, diffuse large B-cell lymphoma, and head and neck squamous cell carcinoma, expressing TGFβ1 in more than 80% of all tumor samples. Consistent with the data in FIG. 20A, fewer cancer types are positive for TGFβ2 or TGFβ3, though several cancers show an equal or greater percentage of tumor samples that are TGFβ3 positive, including breast invasive carcinoma, mesothelioma, and sarcoma. These data suggest that cancer types may be stratified for TGFβ isoform expression, and that such stratification may be useful in identifying patients who are candidates for treatment with TGFβ isoform-specific inhibitors.

To further investigate this hypothesis, the log 2(FPKM) RNAseq data from a subset of individual tumor samples was analyzed and plotted in a heat map (FIG. 20C), setting the color threshold to reflect FPKM >30 as a minimum transcript level to be scored TGFβ isoform-positive. Rank-ordering TGFB1 mRNA expression in individual tumor samples among seven CBT-approved tumor types confirmed higher and more frequent expression of TGFB1 mRNA in comparison to TGFB2 and TGFB3, again with the notable exception of breast carcinoma. These and the previously published observations in urothelial cancer suggest that TGFβ pathway activity is likely driven by TGFβ1 activation in most human tumors.

Each sample is represented as a single row in the heat map, and samples are arranged by level of TGFβ1 expression (highest expression levels at top). Consistent with the analysis in FIG. 20B, a significant number of samples in each cancer type are positive for TGFB1 expression. However, this representation also highlights the fact that many tumors express solely TGFB1 transcripts, particularly in the esophageal carcinoma, bladder urothelial, lung adenocarcinoma, and cutaneous melanoma cancer types. Interestingly, such TGFB1 skewing is not a feature of all cancers, as samples from breast invasive carcinoma show a much larger number of samples that are TGFB3-positive than are TGFB1 positive. Nonetheless, this analysis indicates that the β1 isoform is the predominant, and in most cases, the only, TGFβ family member present in tumors from a large number of cancer patients. Taken together with data suggesting that TGFβ signaling plays a significant role in immunosuppression in the cancer microenvironment, these findings also point to the utility of TGFβ1-specific inhibition in treatment of these tumors.

To identify mouse models in which to test the efficacy of TGFβ1-specific inhibition as a cancer therapeutic, TGFβ isoform expression in RNAseq data from a variety of cell lines used in mouse syngeneic tumor models was analyzed. For this analysis, two representations of the data were generated. First, we generated a heat map of the log 2(FPKM) values for tumors derived from each cell line (FIG. 20D, left). Because this analysis was carried out to identify syngeneic models that would recapitulate human tumors (predominantly TGFB1), we were primarily concerned with avoiding false negatives, and we set our "positive" threshold at FPKM>1, well below that in the representations in FIGS. 20B and 20C.

As the data representation in FIG. 20D (left) makes clear, a number of syngeneic tumors, including MC-38, 4T-1, and EMT6, commonly express significant levels of both TGFβ1 and TGFβ3. In contrast, the A20 and EL4 models express TGFβ1 almost exclusively, and the S91 and P815 tumors show a strong bias for TGFB1 expression.

To further evaluate the differential expression of TGFB1 vs TGFB2 and/or TGFB3, the minΔTGFB1 was calculated, defined as the smaller value of log 2($FPKM_{TGFB1}$) –log 2($FPKM_{TGFB2}$) or log 2($FPKM_{TGFB1}$) –log 2($FPKM_{TGFB3}$). The minΔTGFB1 for each model is shown as a heat map in FIG. 20D (right), and underscores the conclusion from FIG. 20D (left) that syngeneic tumors from the A20, EL4, S91, and/or P815 cell lines may represent excellent models in which to test the efficacy of TGFβ1-specific inhibitors.

To further confirm the association of TGFβ1 expression with primary resistance to CBT over TGFβ2 or TGFβ3, we correlated isoform expression with the Innate anti-PD-1 Resistance Signature ("IPRES") (Hugo et al., Cell. 2016 Mar. 24; 165(1):35-44). In brief, IPRES is a collection of 26 transcriptomic signatures, which collectively indicate tumor resistance to anti-PD-1 therapy. The IPRES signature indicates up-expression of genes involved in the regulation of mesenchymal transition, cell adhesion, ECM remodeling, angiogenesis, and wound healing. Across seven CBT-approved tumor types we found more consistently a positive and significant correlation between TGFB1 mRNA levels and IPRES score than mRNA expression of the other two TGFβ isoforms (FIG. 37A). Taken together, these data suggest that that selective inhibition of TGFβ1 activity may overcome primary resistance to CBT.

Geneset variation analysis (GSVA) of the IPRES (Innate anti-PD-1 resistance) transcriptional signature across TCGA-defined tumor types with CBT-approved therapies correlates (Pearson coefficient) most strongly and significantly with TGFβ1 RNA abundance, with cut-off of FPKM ≥30 for presence of expression. Taken together, these data suggest that that selective inhibition of TGFβ1 activity may overcome primary resistance to CBT.

Geneset variation analysis (GSVA) of the IPRES (Innate anti-PD-1 resistance) transcriptional signature across TCGA-defined tumor types with CBT-approved therapies correlates (Pearson coefficient) most strongly and significantly with TGFβ1 RNA abundance, with cut-off of FPKM ≥30 for presence of expression.

Figure 37B:
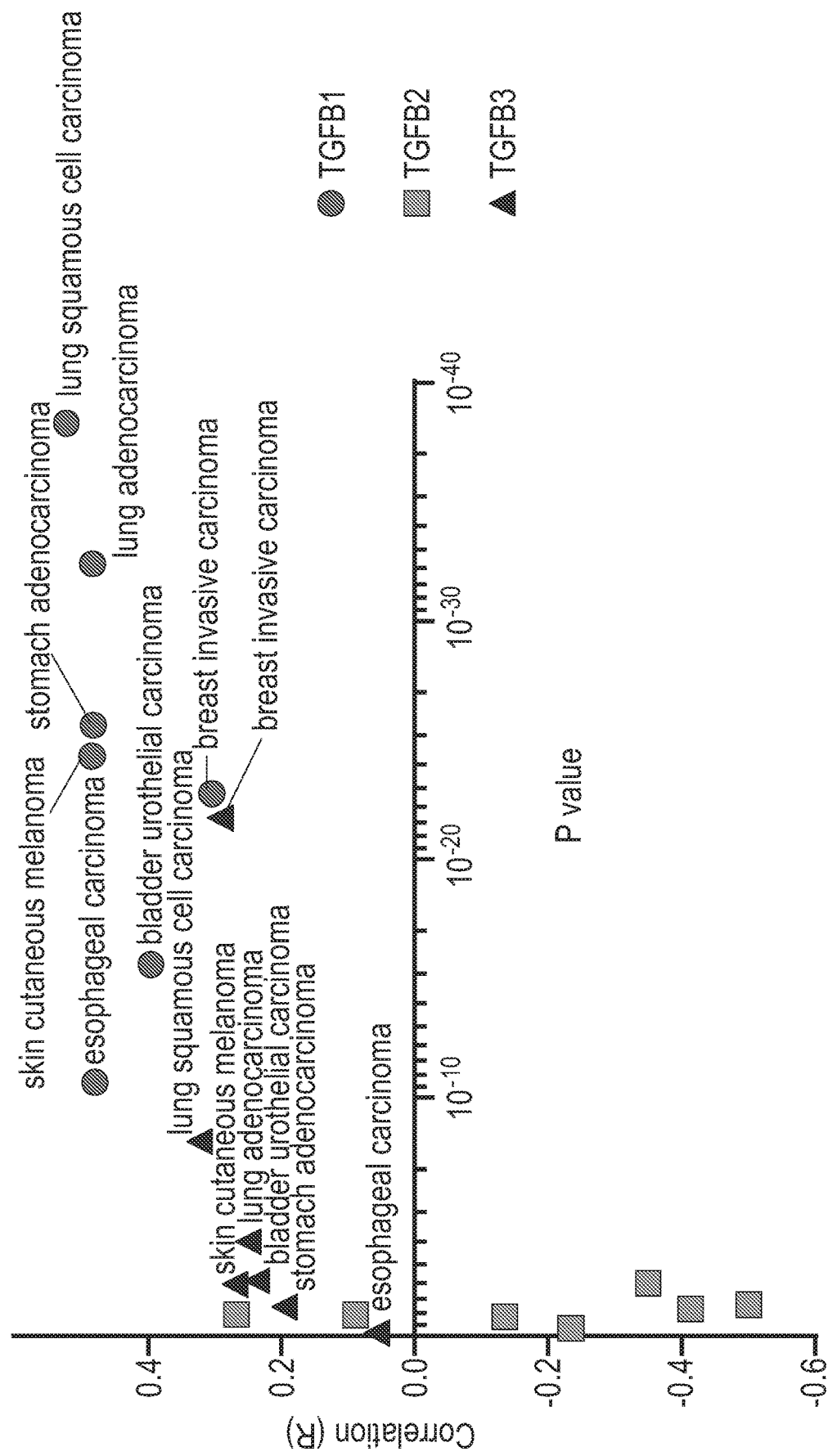
FIG. 37B provides a gene set variation analysis (GSVA) showing correlation between TGFβ isoform expression and Plasari geneset. TGFb1 isoform expression correlates with TGFβ pathway activation. The Plasari geneset of TGFβ3-responsive genes significantly and strongly correlates with TGFb1 RNA isoform expression across many TCGA annotated tumor types. Correlation of TGFB1 mRNA and TGFβ signaling signature

To assess further the correlate TGFβ1 expression with resistance to CBT, TGFβ1 RNA abundance was compared to a geneset variation analysis (GSVA) of the Plasari TGFβ pathway (Innate anti-PD-1 resistance) transcriptional signature across TCGA-defined tumor types with CDT-approved therapies. The plasari geneset was obtained from the mSigDB web portal (software.broadinstitute.org/gsea/msigdb/index.jsp) and Gene Set Score calculation was determined using the GSVA package in R (Hanzelmann et al., BMC Bioinformatics 201314:7, 2013; and Liberzon et al., Bioinformatics. 2011 Jun. 15; 27(12): 1739-1740). As shown in FIG. 37B, the GSVA correlated (Pearson coefficient) most strongly and significantly with TGFβ1 RNA abundance, with cut-off of FPKM ≥30 for presence of expression.

These data suggest that TGFβ pathway activity is likely driven by TGFβ1 activation in most human tumors.

Following resources were used for the bioinformatics analyses described above: TGFBeta Isoform TCGA expression data were downloaded from the UCSC Xena Browser datasets resource (xenabrowser.net/datapages/). Expression cutoff to determine high expression was ascertained by examining the distribution of FPKM values of TGFBeta Isoform data. Heatmaps and scatter plots were generated using GraphPad Prism. Plasari geneset was obtained from the mSigDB web portal (software.broadinstitute.org/gsea/msigdb/index.jsp) and Gene Set Score calculation was determined using the GSVA package in R.

Example 12: TGFβ1-Selective Inhibitors Exhibit Reduced Toxicity as Compared to the ALK5 Kinase Inhibitor LY2109761 and a Pan-TGFβ Antibody in Safety/Toxicology Studies To evaluate the potential in vivo toxicity of Ab3 and Ab6, as compared to the small molecule TGF-β type I receptor (ALK5) kinase inhibitor LY2109761 and to a pan-TGFβ antibody (hIgG4; neutralizing), safety/toxicology studies were performed in rats. The rat was selected as selection of the species for this safety study was based on the previous reports that rats are more sensitive to TGFβ inhibition as compared to mice. Similar toxicities observed in rats have been also observed in other mammalian species, such as dogs, non-human primates, as well as humans.

Briefly, female Fisher344 rats (FIGS. 21A and 21B) or Sprague Dawly rats (FIG. 21C) were administered with either Ab3 at 3 mg/kg (1 group, n=5), at 30 mg/kg (1 group, n=5), or at 100 mg/kg (1 group, n=5); Ab6 at 10 mg/kg (1 group, n=5), at 30 mg/kg (1 group, n=5), or at 100 mg/kg (1 group, n=5); pan-TGFβ antibody at 3 mg/kg (1 group, n=5), at 30 mg/kg (1 group, n=5), or at 100 mg/kg (1 group, n=5); LY2109761 at 200 mg/kg (1 group, n=5) or 300 mg/kg (1 group, n=5); or PBS (pH 7.4) vehicle control (1 group, n=5).

Animals receiving pan-TGFβ antibody were dosed once intravenously (at day 1) at a volume of 10 mL/kg and sacrificed at day 8 and necropsies performed. Animals receiving either Ab3 or Ab6 were dosed i.v. once weekly for 4 weeks (on Day 1, 8, 15 and 22) at a volume of 10 mL/kg. Animals receiving LY2109761 were dosed by oral gavage once daily for five or seven days. Animals were sacrificed on Day 29 and necropsies performed.

General clinical observations of animals were performed twice daily and cageside observations were conducted post-dose to assess acute toxicity. Other observations performed included an assessment of food consumption and measurement of body weight once weekly. These also included clinical pathology (hematology, serum chemistry and coagulation) and anatomic pathology (gross and microscopic) evaluations. A comprehensive set of tissues were collected at necropsy for microscopic evaluation. Tissues were preserved in 10% neutral buffered formalin, trimmed, processed routinely, and embedded in paraffin. Paraffin blocks were microtomed and sections stained with hematoxylin and eosin (H&E). In particular, the heart was trimmed by longitudinally bisecting along a plane perpendicular to the plane of the pulmonary artery to expose the right atrioventricular, left atrioventricular, and aortic valves. Both halves were submitted for embedding. Each heart hemisection was embedded in paraffin with the cut surface down. Blocks were sectioned to obtain at least three heart valves. The tissue sections were examined by light microscopy by a board-certified member of the American College of Veterinary Pathologists (ACVP).

As shown in Table 20 and FIG. 21, animals administered 3 mg/kg of the pan-TGFβ antibody exhibited heart valve findings (i.e., valvulopathy) similar to those described in animals administered LY2109761. Animals administered ≥30 mg/kg of the pan-TGFβ antibody exhibited atrium findings similar to those animals administered LY2109761. Animals administered 100 mg/kg of the pan-TGFβ antibody exhibited myocardium findings similar to those described in animals administered LY2109761, and animals administered 30 mg/kg of pan-TGFβ antibody had hemorrhage in the myocardium. One animal administered 100 mg/kg of the pan-TGFβ antibody had moderate intramural necrosis with hemorrhage in a coronary artery, which was associated with slight perivascular mixed inflammatory cell infiltrates. Bone findings in animals administered the pan-TGFβ antibody and LY2109761 consisted of macroscopic abnormally shaped sternum and microscopic increased thickness of the hypertrophic zone in the endplate of the sternum and physis of the femur and tibia; these findings were of higher incidence and/or severity in animals administered LY2109761 compared with pan-TGFβ antibody.

TABLE 22

Microscopic Heart Findings in Animals Receiving the Pan-TGFβ Antibody

| | | Pan-TGFβ Antibody | | | |
|---|---|---|---|---|---|
| Dose Level (mg/kg/day) | | 0 | 3 | 30 | 100 |
| Heart | | | | | |
| Heart valves | | | | | |
| Valvulopathy | Minimal | 0 | 2 | 0 | 0 |
| | Slight | 0 | 2 | 4 | 5 |
| | Moderate | 0 | 0 | 1 | 0 |
| Atrium | | | | | |
| Infiltrate, mixed cell | Minimal | 0 | 0 | 1 | 2 |
| | Slight | 0 | 0 | 1 | 1 |
| Hyperplasia, endothelium | Minimal | 0 | 0 | 3 | 1 |
| Hemorrhage | Minimal | 0 | 0 | 1 | 0 |
| Myocardium | | | | | |
| Degeneration/necrosis | Slight | 0 | 0 | 0 | 2 |
| Hemorrhage | Minimal | 0 | 0 | 2 | 1 |
| | Slight | 0 | 0 | 1 | 1 |
| Infiltrate, mixed cell, base Coronary artery | Slight | 0 | 0 | 0 | 1 |
| Necrosis with hemorrhage | Moderate | 0 | 0 | 0 | 1 |
| Infiltrate, mixed cell, perivascular | Slight | 0 | 0 | 0 | 1 |

Figure 21B:
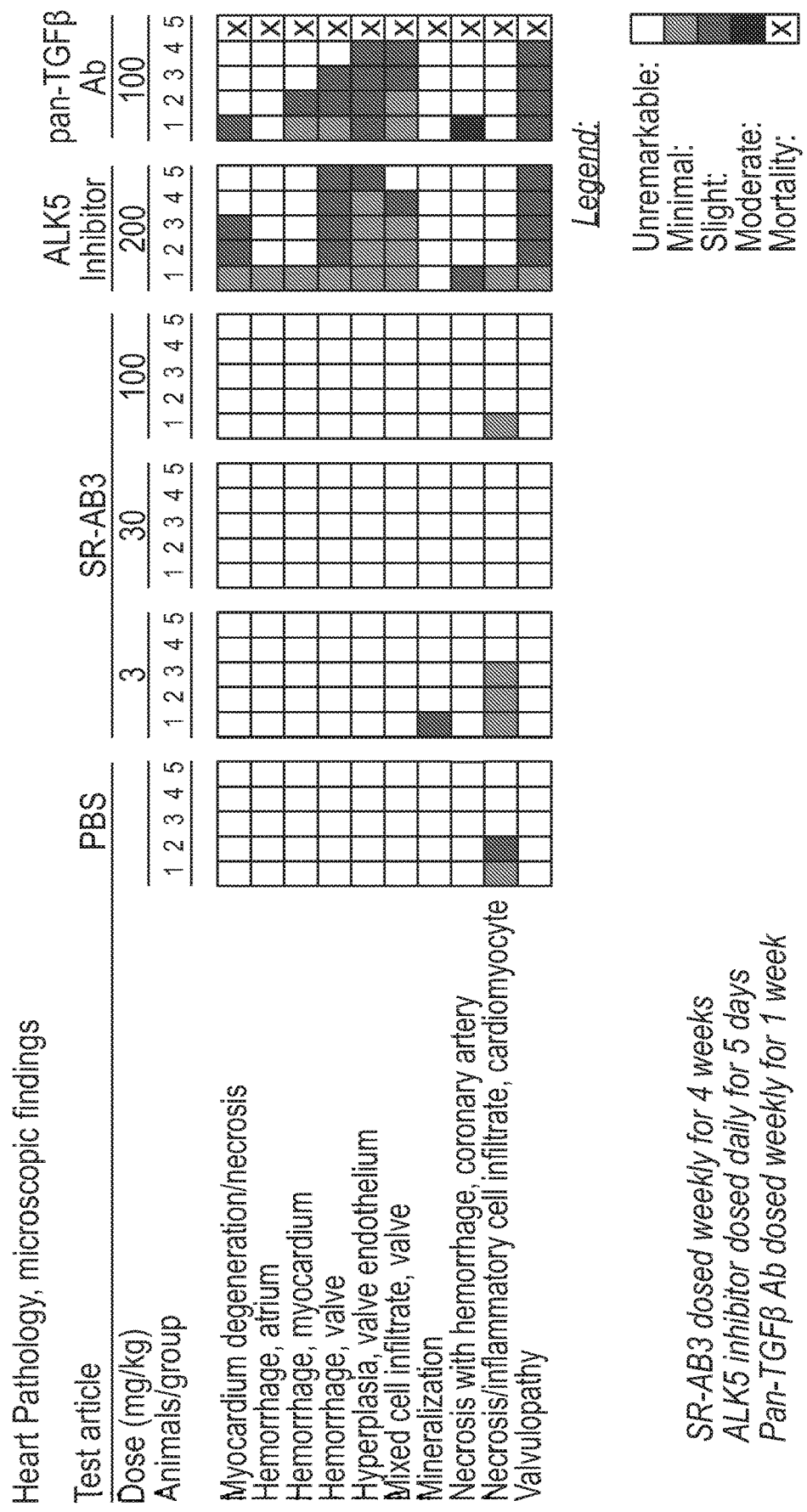
FIG. 21B depicts microscopic heart findings from Ab3 as compared to an ALK5 inhibitor or pan-TGFβ antibody from a 4-week rat toxicology study.

As shown in FIG. 21A, animals administered pan-TGFβ antibody exhibited similar toxicities to those described in animals administered LY2109761 as described in PCT/US2018/012601, which is incorporated herein by reference in its entirety. Specifically, animals administered 3 mg/kg of the pan-TGFβ antibody exhibited heart valve findings (e.g., valvulopathy) similar to those described in the animals administered LY2109761. Animals administered 30 mg/kg of the pan-TGFβ antibody exhibited atrium findings similar to those described in animals administered LY2109761. Animals administered 100 mg/kg of the pan-TGFβ antibody exhibited myocardium findings similar to those described in animals administered LY2109761, and animals administered 30 mg/kg of pan-TGFβ antibody had hemorrhage in the myocardium. One animal administered 100 mg/kg of the pan-TGFβ antibody had moderate intramural necrosis with hemorrhage in a coronary artery, which was associated with slight perivascular mixed inflammatory cell infiltrates. Bone findings in animals administered the pan-TGFβ antibody and LY2109761 consisted of macroscopic abnormally shaped sternum and microscopic increased thickness of the hypertrophic zone in the endplate of the sternum and physis of the femur and tibia. Subsequent studies with LY2109761 and pan-TGFβ as shown in FIGS. 21B and 21C also demonstrated similar toxicities. The observed heart valvulopathies in animals treated with pan-inhibitors of TGFβ characterized by heart valve thickening due to hemorrhage, endothelial hyperplasia, mixed inflammatory cell infiltrate, and/or stromal hyperplasia are consistent with previously reported findings.

By contrast, unlike pan-TGFβ antibody or LY2109761-treated animals, rats administered with TGFβ1-selective inhibitors, namely, Ab3 or Ab6, the no-observed-adverse-effect-level (NOAEL) of both Ab6 and Ab3 in these studies was the 100 mg/kg weekly dose, the highest dose tested. As shown in FIG. 21B, only minimal or slight heart valve findings occurred in a small number of animals treated with Ab3, and these finding were considered unlikely test article-related due to the low incidence (animal and number of heart valves within an animal), lack of a dose response or correlation thereto, and/or lack of concurrent bone findings. Additionally, no findings occurred in animals treated with Ab6 (FIG. 21C).

Pharmacokenetics analysis showed that serum concentrations of Ab6 reached 2,300 µg/ml in animals dosed at 100 mg/kg for 4 weeks. Mean Ab6 serum concentrations at study termination (on Day 29) reached 2.3 mg/ml for the highest evaluated dose of 100 mg/kg. These results suggest that selective inhibition of TGFβ1 activation appears to avoid the key dose-limiting toxicity at doses well above those required for therapeutic effect observed in multiple in vivo models.

In summary, animals treated with Ab3 or Ab6 at all doses tested (3 mg/kg, 30 mg/kg or 100 mg/kg) over a period of 4 weeks in rats (a species known to be sensitive to TGFβ inhibition) exhibited no toxic effects over background in any of the following parameters: myocardium degeneration or necrosis, atrium hemorrhage, myocardium hemorrhage, valve hemorrhage, valve endothelium hyperplasia, valve stroma hyperplasia, mixed inflammatory cell infiltrates in heart valves, mineralization, necrosis with hemorrhage in coronary artery, necrosis with inflammation in aortic root, necrosis or inflammatory cell infiltrate in cardiomyocyte, and valvulopathy. Thus, treatment with isoform-specific inhibitors of TGFβ1 activation surprisingly resulted in significantly improved safety profiles, e.g., reduced mortality, reduced cardiotoxicity, and reduced bone findings as compared to pan-TGFβ inhibitor treatment (e.g., the ALK5 kinase inhibitor LY2109761 or the pan-TGFβ antibody).

GLP Toxicology study was also carried out in non-human primates (cynomolgus monkeys) to evaluate safety profiles of the high-affinity, TGFβ1-selective inhibitor, Ab6. The protocol involved 4-week repeat-dose at 30, 100 and 300 mg/kg per week, followed by 4 week recovery.

Ab6 was well-tolerated at 30, 100 and 300 mg/kg/week. No adverse Ab6-related findings were noted in both main and recovery cohorts. No Ab6-related findings were noted in target organs that are sites of toxicities observed with pan-TGFβ inhibitors (for example: no cardiotoxicities, hyperplasia and inflammation, dental and gingival findings).

Ab6 serum concentrations reached 15,600 µg/mL following 5 weekly doses of 300 mg/kg. At the end of recovery time, Ab6 serum concentration levels remained high at about ~2,000-3,000 µg/mL.

Based on these data, the NOAEL for Ab6 in cynomolgus monkey is 300 mg/kg/week, which is the highest doses tested.

Example 13: Effects of Anti-PD-1/Ab3 Combination on Intratumoral Immune Cells

Previous reports examined exclusion of effector T cells from immunosuppressed tumors in preclinical animal models.

However, these reports did not provide insights on macrophages. To evaluate the relationship of macrophage infiltration in immunosuppressed syngeneic tumor model and effects of TGFβ1 inhibition in the context, immunohistochemistry was performed on CloudmanS91 tumor samples treated with anti-PD1 and Ab3 at 30 mg/kg from Example 7 above (see FIGS. 24A-24D).

Figure 24B:
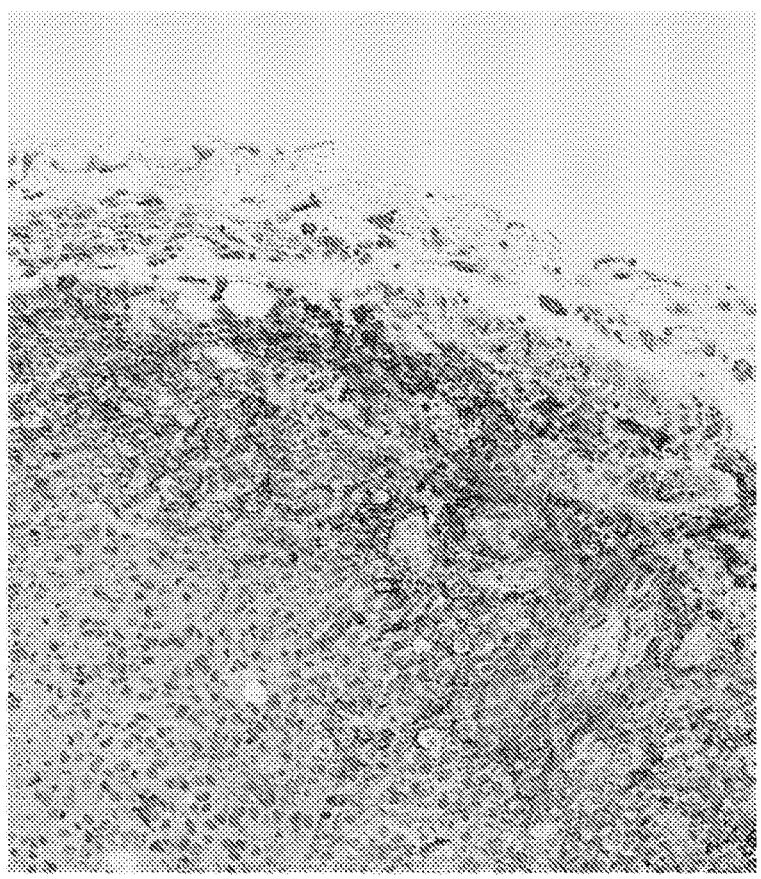
FIGS. 24A-24D provide representative immunohistochemistry sections of S91 tumors, stained with macrophage markers.
Figure 24A:
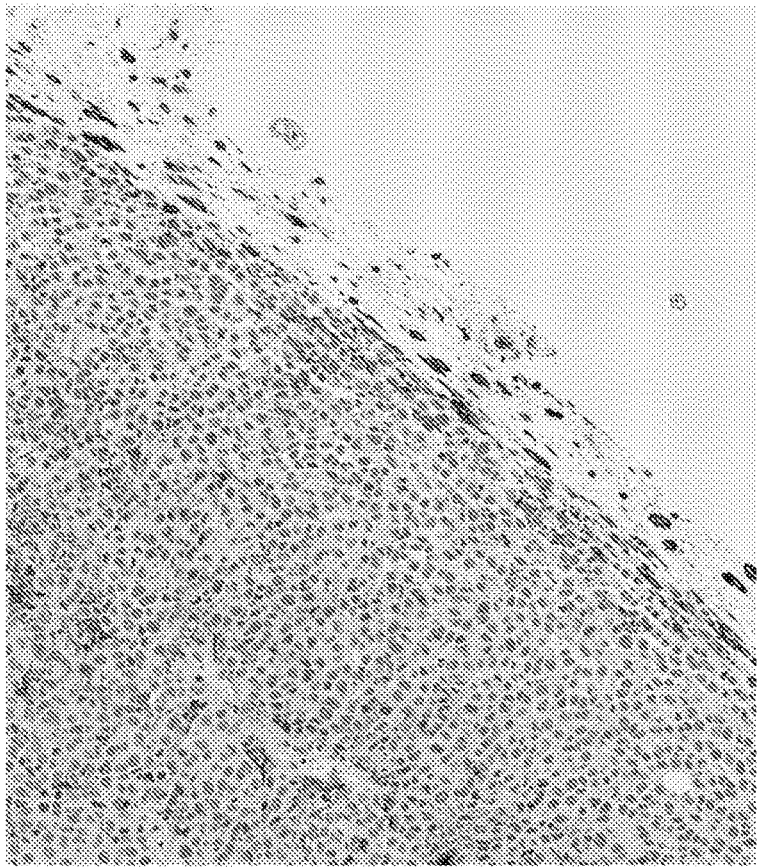
Figure 24D:
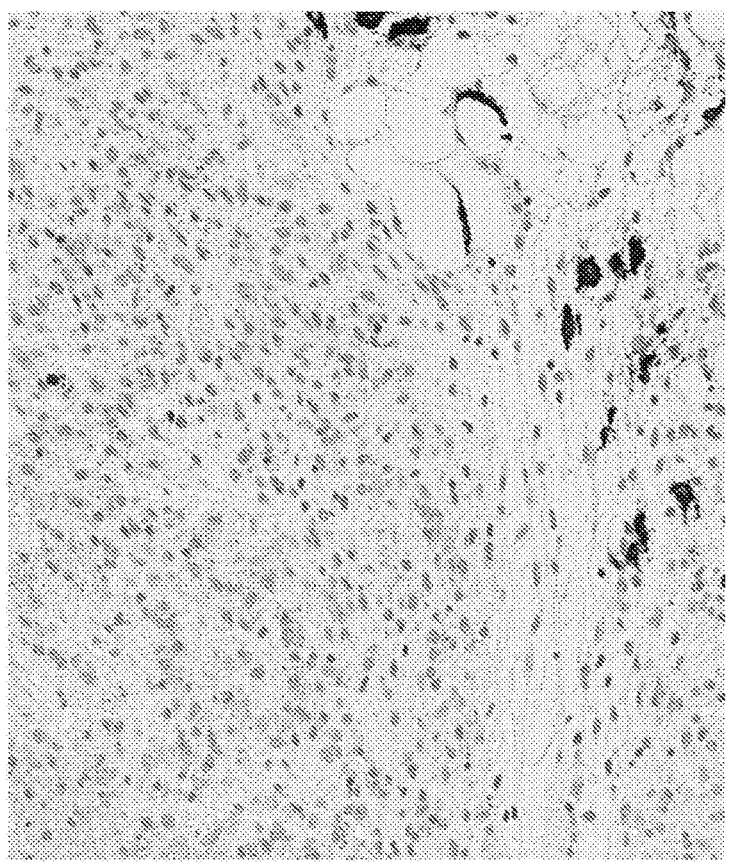
Figure 24C:
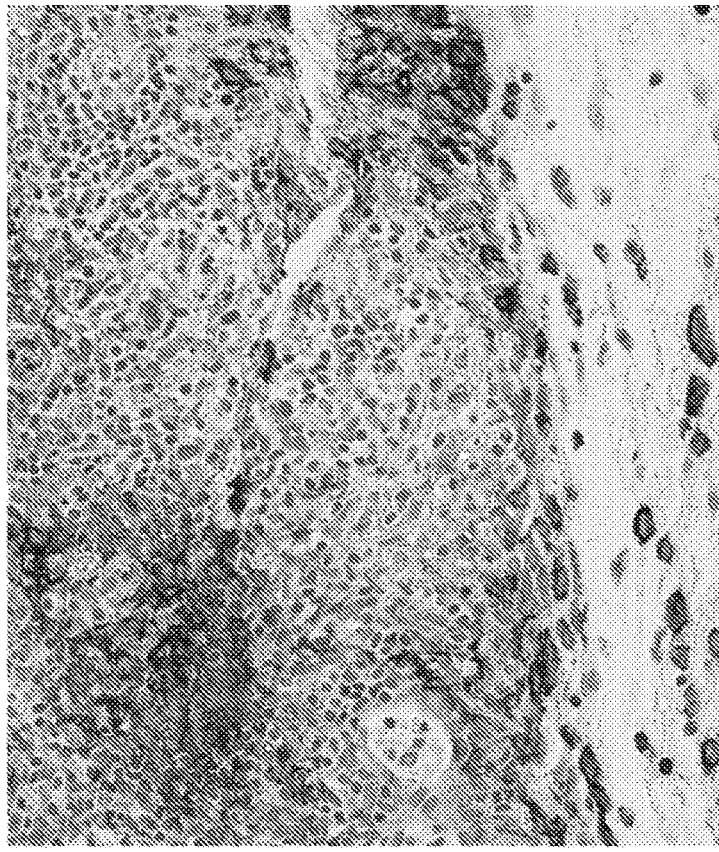

In control tumor sections from animals that did not receive anti-PD1/Ab3 combination, some F4/80-positive cells were detected, indicating that the tumor contains some macrophages, which are likely M2-type, so-called tumor-associated macrophages, or TAMs. In comparison, in sections prepared from animals that were treated with the anti-PD1/Ab3 combination, a marked increase in the number of F4/80-positive cells was observed within the tumor (see FIGS. 24A-24C). This extensive infiltration of the tumor by F4/80-positive macrophages in anti-PD-1/Ab3-treated animal, as compared to anti-PD1 alone, suggests that the combination treatment, but not anti-PD1 alone, induced a large influx of cells, presumably due to recruitment of circulating monocytes which infiltrated the tumor. To identify the phenotype of these macrophages, anti-CD163 was used as an M2 macrophage marker. As shown in FIG. 24D, most of these cells were shown to be CD163-negative, suggesting that the macrophages that were recruited into the tumor in response to the anti-PD1/Ab3 combination treatment are likely M1-type, thus anti-tumor subtype. This may be indicative of macrophages clearing cancer cell debris generated by cytotoxic cells and is presumably a direct consequence of TGFβ1 inhibition.

Example 14. Effect of TGFβ1 Inhibitors on Cytotoxic Cells in MBT2 Tumors

Granual exocytosis is one mechanism by which cytotoxic T cells engage and kill resident tumor cells. Upon activation, the granuals fuse with the plasma membrane and release their contents, including cytotoxins, such as perforin and granzym B, which results in tumor cell elimination. Additionally, CD8 antigen (CD8α) is a cell surface glycoprotein found on most cytotoxic T cells that acts as a coreceptor with the T-cell receptor. Accordingly, CD8α, Perforin, and Granzyme B levels were measured in tumors treated with Ab3 or Ab6, each in combination with anti-PD-1, to assess effector T cell activity.

Methods 8-12 week old C3H/HeN female mice were implanted with $5 \times 10^5$ MBT2 tumor cells in the flank. Animals were randomized to dosing groups with an average tumor size of 40-80 mm³ prior to treatment initiation. Anti-PD1 (RMP1-14) was dosed twice a week at 10 mg/kg. Ab3 was dosed once a week at 30 mg/kg. After 8 days of dosing, 8 hours post final dose (three total doses of anti-PD1, two total doses of Ab3) animals were sacrificed and tumors excised.

For Ab6, immune contexture analyzed at day 10 or day 13 post-treatment. Anti-PD-1 was dosed at 10 mkg twice weekly. Ab6 was dosed weekly at 10 mkg. Tumors were flash frozen in liquid nitrogen, pulverized in Covaris bags using a cryoPREP impactor and RNA was extracted using Trizol/Chloroform. cDNA was generated using Taqman Fast Advanced Master Mix and CDNA was loaded into a custom Taqman Array Card with primers and probes directed against genes of interest. qPCR was run on a Viia7 thermocycler. Expression for CTL genes were normalized to HPRT per each sample and fold change was expressed in anti-PD1/Ab3 or anti-PD1/Ab6 vs anti-PD1 alone.

Results

Combination of anti-PD1/Ab3 induced potent upregulation of CTL genes associated with anti-tumor response over anti-PD1 alone within the tumor (see FIG. 25). In the MBT2 tumor model, anti-PD1 alone afforded very little suppression of tumor growth and anti-tumor immunity. Thus, these results indicate that the addition of anti-TGFβ antibodies allows complete activation and infiltration of effector CD8 T cells.

Example 15: Effect of Ab3 and Ab6 on Treg Activity In Vitro

Methods

Human PBMC were isolated from healthy donor buffy-coat with Ficoll. CD4 cells were selected via magnetic selection and then $CD25^+CD127^{lo}$ Tregs were sorted Clone BC96 (ThermoFisher) was used for CD25hi and clone HIL 7Rm21 (BD Bioscience) was used for CD127lo, using a Biorad S3E. Sorted Tregs were stimulated 1 week with plate-bound anti-CD3 (clone OKT3, Biolegend) and soluble anti-CD28 (clone 28.2, Biolegend) in TexMacs media (Miltenyi). In some studies, IL2 was additionally added to upregulate GARP and pro-TGFβ expression. Tregs were co-cultured 1:1 with autologous CD4 T cells dyed with Cell Trace Violet 9invitrogen) and again stimulated with anti-CD3/anti-CD28 for five days. After 5 days, cell division was measured by flow cytometry (Attune flow cytometer, ThermoFisher Scientific), gating on dilution of the Cell Trace Violet dye, and analyzed with FlowJo (BD Bioscience).

Results

Over 5 days in culture, 80% of effector CD4 T cells (Teffs) had divided. Addition of Tregs 1:1 suppressed Teff division to nearly 15% and further addition of Ab3 at 10 μg/ml completely suppressed Treg-mediated inhibition of T-effector division (see FIG. 26A). 1 μg/ml Ab3 less potently inhibited Tregsuppression. Both 1 μg/ml and 10 μg/ml Ab6 equally inhibited Treg-derived TGFβ. Thus, Ab6 appears to be a more potent inhibitor of TGFβ1 activation of the GARP-proTGFβ1 complex on Tregs.

Example 16: Effects of Ab6/Anti-PD-1 Combination Treatment on Intratumoral Immune Cell Populations/Contexture in MBT2 Tumors To begin to elucidate various immune cell populations that may mediate the observed tumor regression effects in mice treated with a combination of anti-PD-1 and Ab6, MBT2 tumor model was used for FACS studies. Study design is summarized below.

TABLE 23

MBT2 tumor immune contexture study design

Figures 31A, 31B:
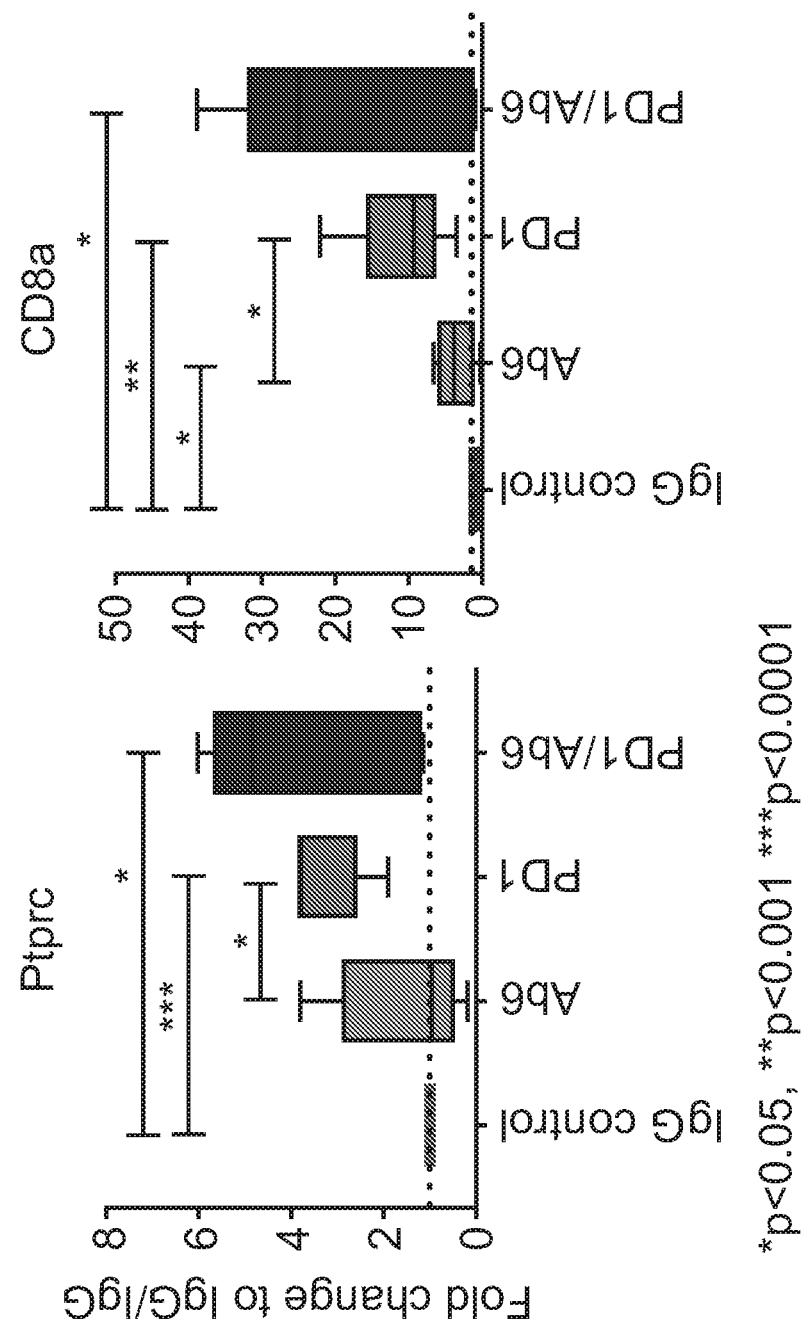
FIGS. 31A-31D provide gene expression of immune response markers, Ptprc (FIG. 31A); CD8a (FIG. 31B); CD4 (FIG. 31C) and Foxp3 (FIG. 31D) collected from MBT2 tumors from the 4 treatment groups as shown.
Figures 31C, 31D:
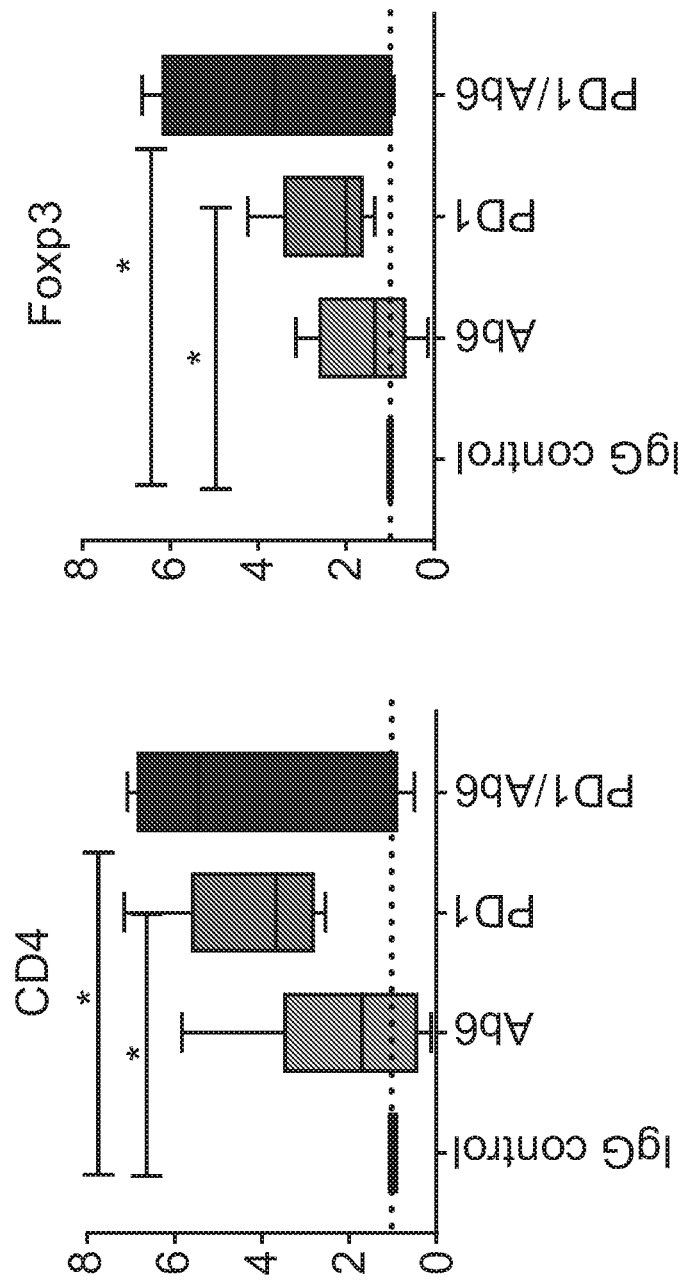

| Group | Group description | Dosing schedule | Sample collections & analyses |
|---|---|---|---|
| 1 | Anti-PD1 Control IgG + Ab6 Control IgG (n = 12) | Same as Groups 2 & 3 (see below) | For each Group: i) Whole tumors from 6 animals for flow cytometry (FIGS. 27-29) |
| 2 | Ab6 (n = 12) | 10 mgk on days 1 and 8 (10 mg/kg/wk) | For the remaining 6 animals: ii) ½ tumor each for RNA analysis (FIGS. 31 & 32) |
| 3 | Anti-PD1 (n = 12) | 10 mgk on days 1, 4, 8 and 11 (20 mg/kg/wk) | iii) ½ tumor each for IHC (FIGS. 30A-D & F) |
| 4 | Ab6 + anti-PD1 (n = 12) | Same as Groups 2 & 3 (see above) | |

Each study group contained 12 mice with MBT2 tumors as described herein. Ab6-treatment group received the antibody weekly, on day 1 and day 8, at 10 mg/kg. Anti-PD1 treatment group was treated biweekly at 10 mg/kg per injection, on days 1, 4, 8 and 11, total of 20 mg/kg per week. Each control IgG group was treated accordingly to match the IgG subtype of anti-PD1 and Ab6. On day 13, tumors were collected from the mice as shown above.

Flow cytometric analysis: Tumor-associated immune cell subsets were also analyzed by tumor flow cytometry in MBT-2 tumors. Briefly, tumors were excised and weighed prior to dissociation using the Tumor Dissociation Kit for gentleMACS (Miltenyi). Samples were filtered through a 70 μm cell strainer to remove any aggregates. Lve, singlet cells were washed with FACs buffer prior to applying staining cocktail containing: MuTruStain FCX (Biolegend), Anti-FcγRIV (Biolegend), Live/Dead (Thermofisher), CD45-AF700 clone 30-F11 (Biolegend), CD3-PE clone 17A2 (Biolegend), CD4-BUV395 clone GK1.5 (BD Biosciences), CD8-APC-H7 clone 53-6.7 (BD Biosciences), CD11b-PerCP-Cy5.5 clone M1/70 (Biolegend), GR-1-FITC clone RB6-8C5 (Biolegend), FoxP3-APC clone FJK-16s (ThermoFisher), F4/80-PE-Dazzle clone BM8 (Biolegend), CD206-BV421 clone C068C2 (Biolegend). Flow cytometry was performed on a Attune NxT (ThermoFisher) and analyzed with FlowJo (BD Bioscience).

Figure 27A:
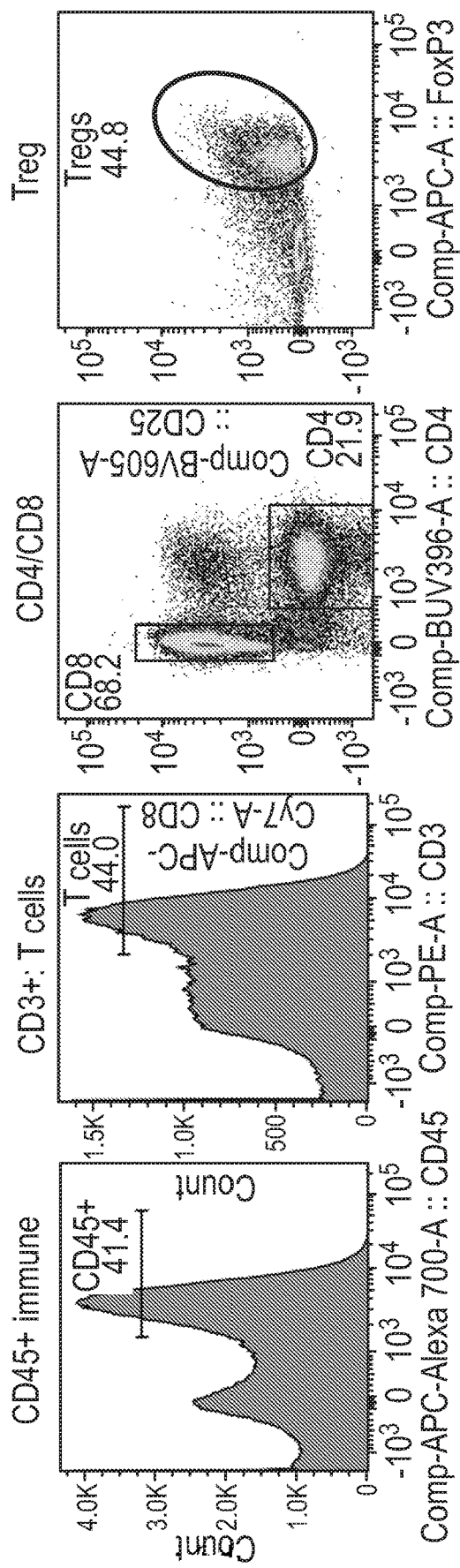
FIG. 27A shows gating strategy for sorting T cell sub-populations in MBT2 tumors.
Figure 27B:
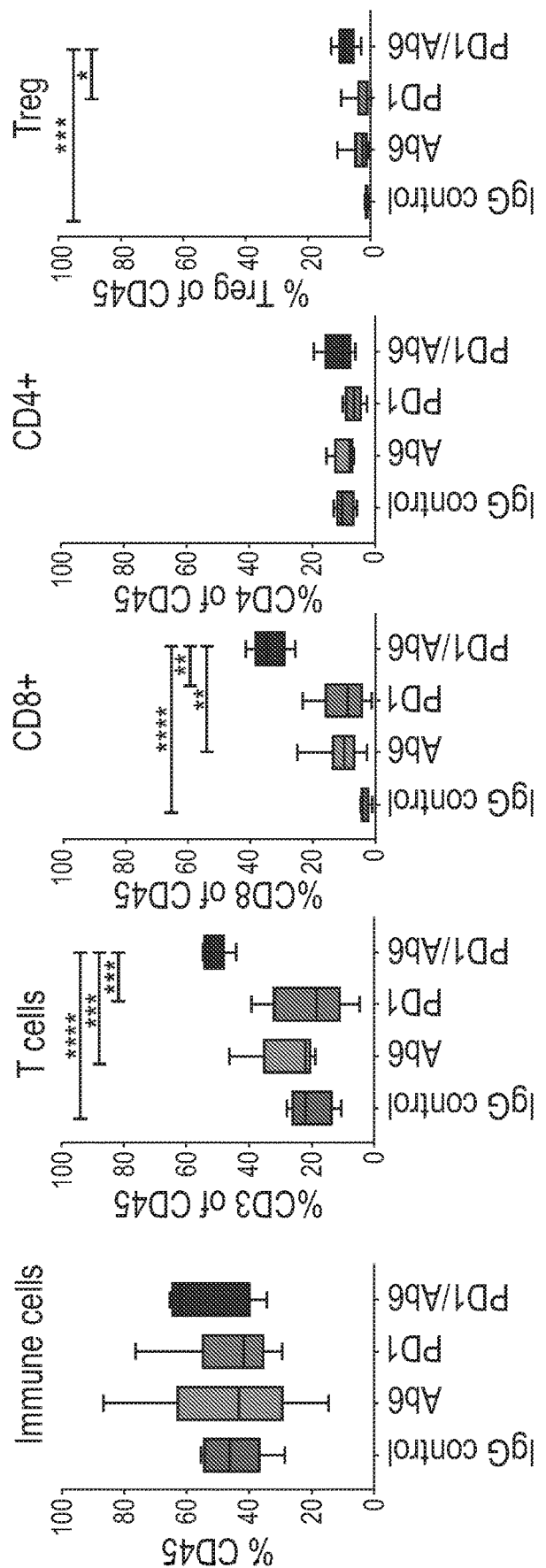
FIG. 27B provides a set of graphs showing T cell sub-populations at day 13, expressed as percent of CD45+ cells.

Gating strategy to elucidate T cell subpopulations in MBT2 tumors is provided in FIG. 27A. Results are summarized in FIG. 27B, measured in tumors collected on day 13 post-treatment start. As demonstrated, Ab6 used in conjunction with anti-PD1 was able to overcome immune exclusion by enabling infiltration and expansion of CD8+ T cells in tumors. Specifically, anti-PD1/Ab6 combination induced significant increase in the number (frequencies) of intratumoral CD8+ T cells, while no changes in % CD45+ cells of total live cells were observed across treatment groups. Anti-PD1/Ab6 combination caused significant increase in Tregs; however, the CD8+:Treg ratio is not significantly changed, relative to anti-PD1 treatment.

Figure 28A:
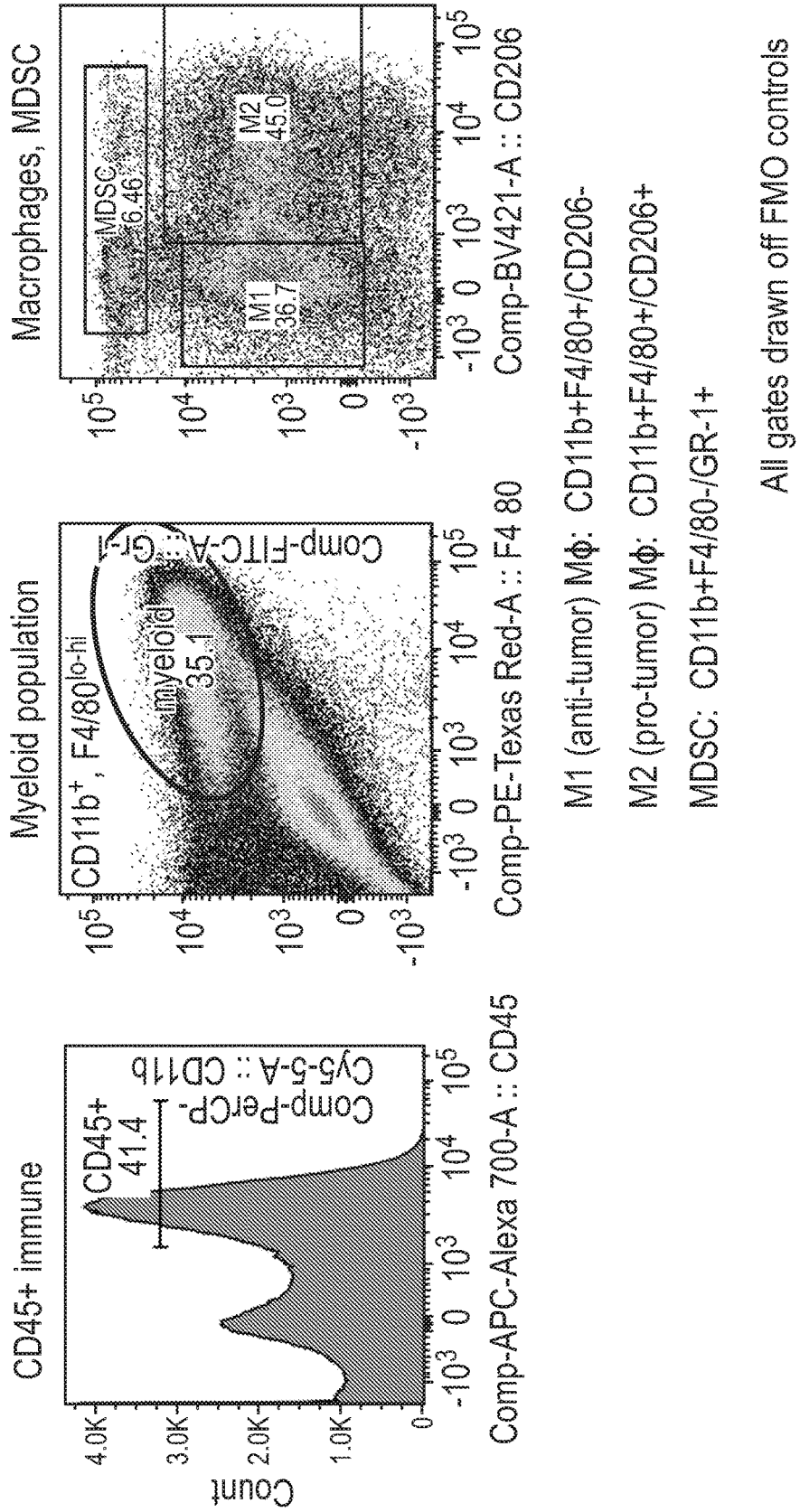
FIG. 28A provides gating strategy for sorting myeloid sub-populations in MBT2 tumors.
Figure 28B:
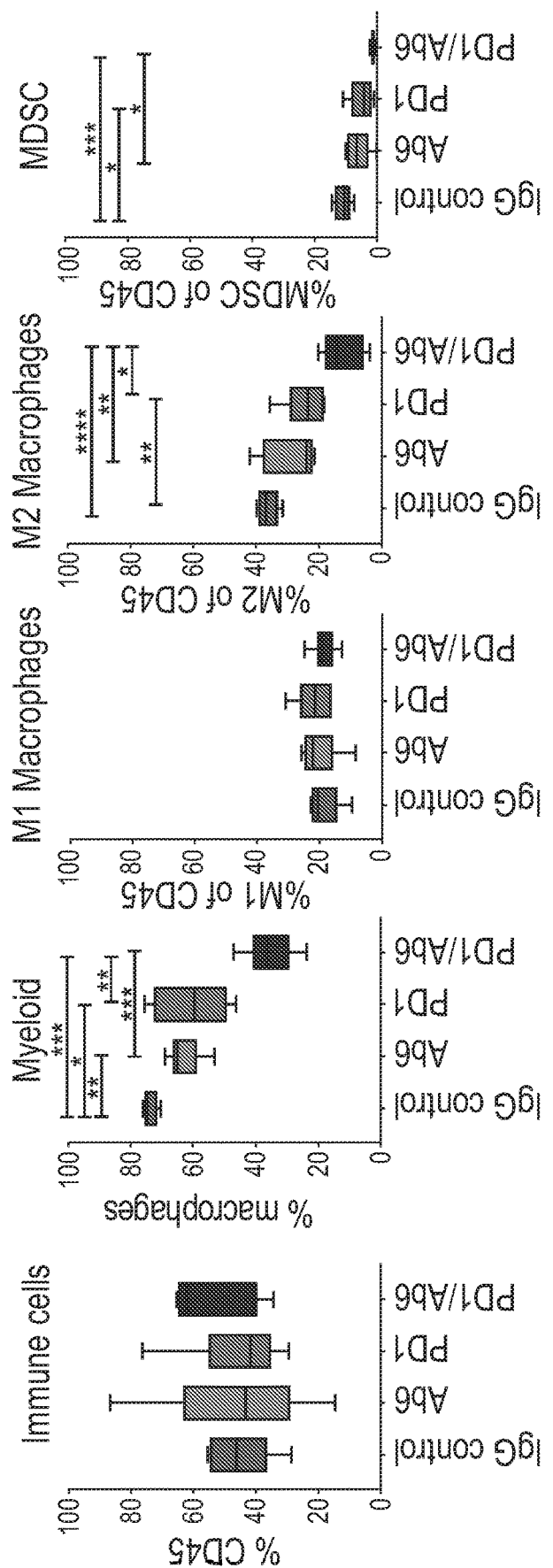
FIG. 28B provides a set of graphs showing myeloid cell sub-populations at day 13.
Figure 28C:
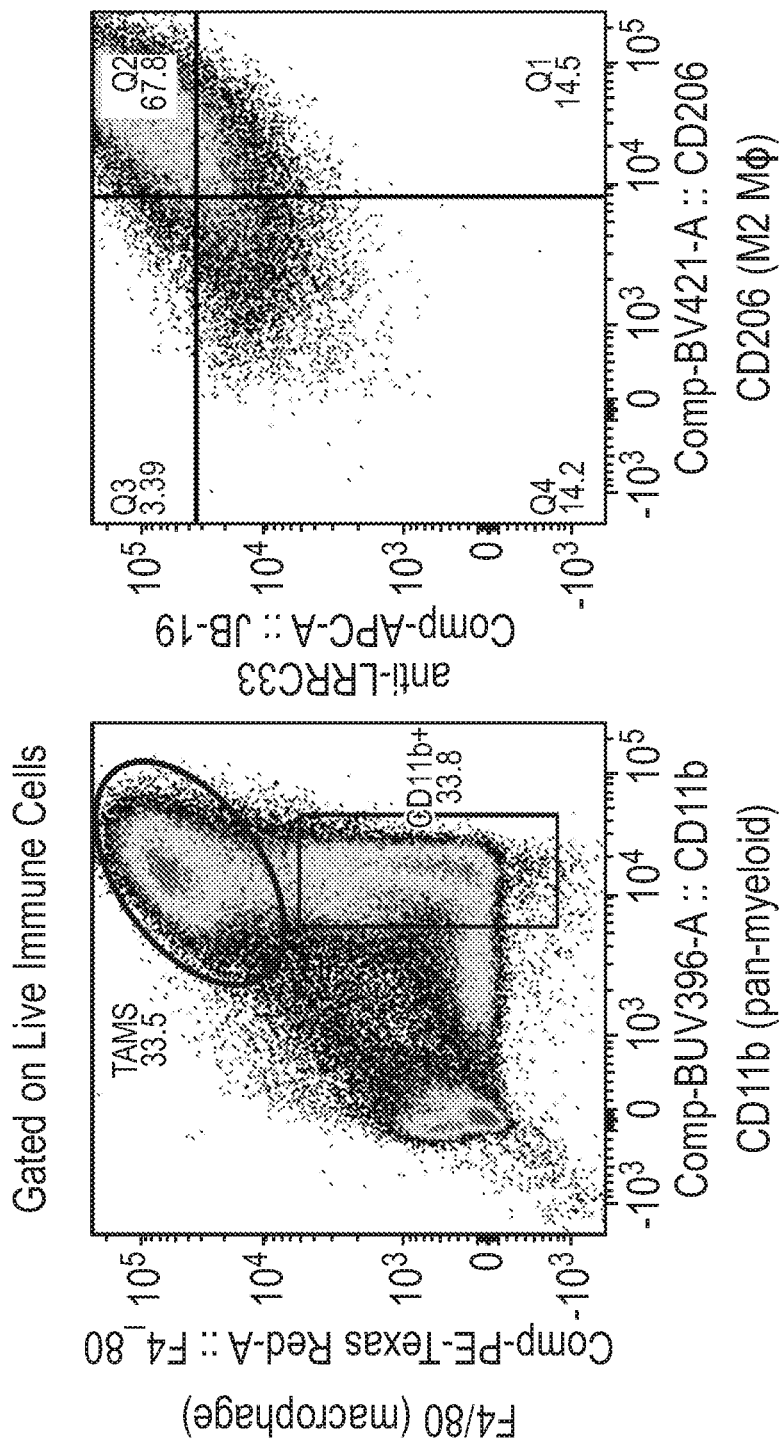
FIG. 28C provides FACS data showing that tumor-associated macrophages in MBT-2 express cell surface LRRC33.
Figure 28D:
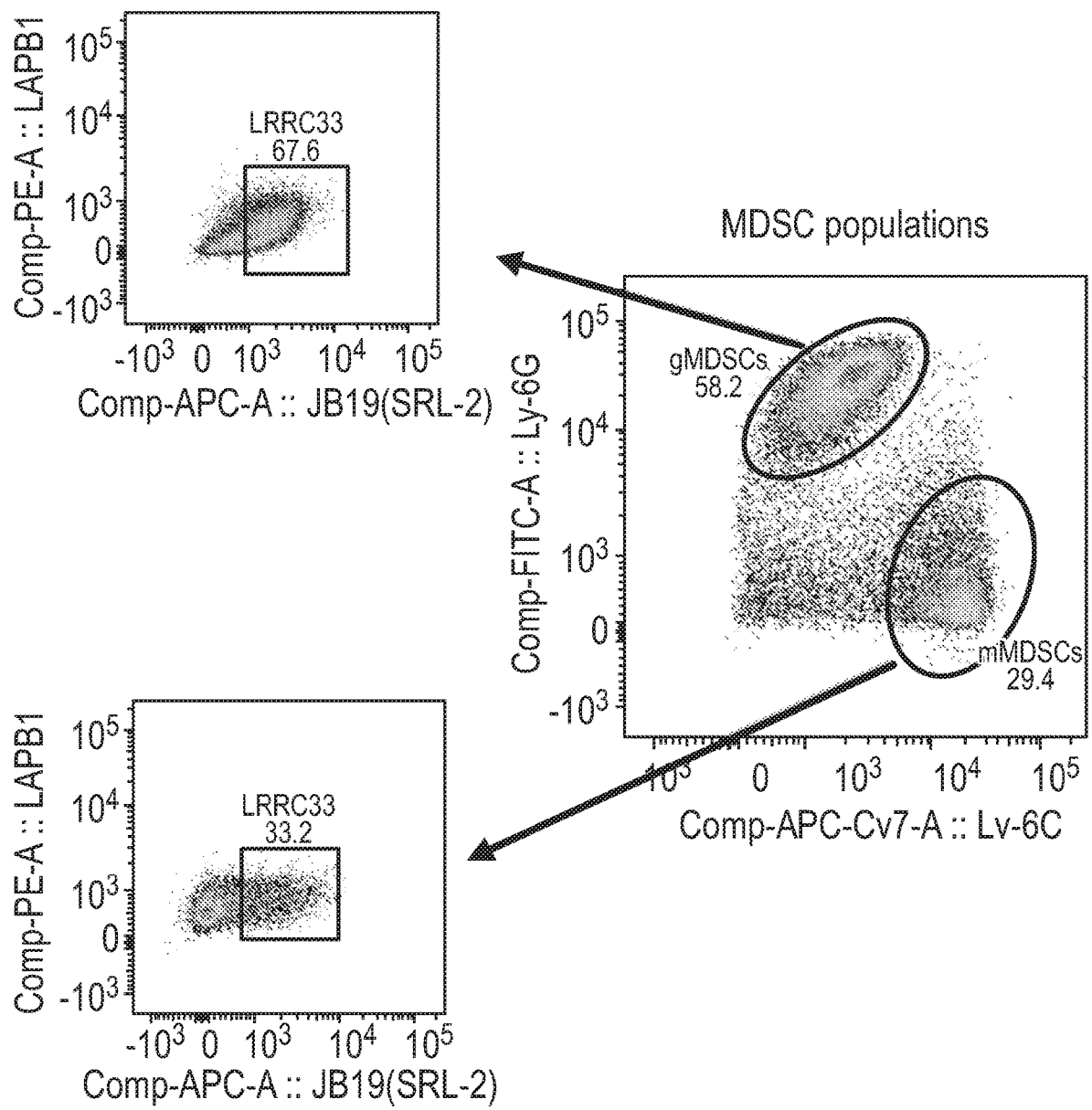
FIG. 28D shows that MBT-2 tumor-infiltrating MDSCs express cell surface LRRC33.

Gating strategy to elucidate myeloid cell subpopulations is provided in FIG. 28A. Results are summarized in FIG. 28B, measured in tumors collected on day 13 post-treatment start. Day 13 myeloid infiltrate shows that the number of total immune cells (e.g., CD45+) remains stable across treatment groups. The number of total myeloid cells (e.g., CD11b+, $F4/80^{lo-hi}$) was significantly altered by anti-PD1/Ab6 treatment. Specifically, in control group, the myeloid fraction constituted almost 75% of macrophage populations in the tumor. This fraction was reduced to less than half in the combination-treatment group, which coincided with a marked reduction in the number (frequencies) of M2-type pro-tumor macrophages, as well as almost complete elimination of the MDSC fraction in this group, while M1-type macrophages remained relatively unchanged.

Among the myeloid subpopulations of cells, MBT-2 tumor-associated M2 macrophages showed high cell surface expression of LRRC33 (FIG. 28C). MDSC subpopulations also showed strong LRRC33 expression. Most (67.8%) of the G-MDSC subtype isolated from MBT-2 tumor expressed cell surface LRRC, while about one third of the M-MDSC subtype isolated from MBT-2 tumor expressed cell surface LRRC33 (FIG. 28D).

Figures 29A, 29B:
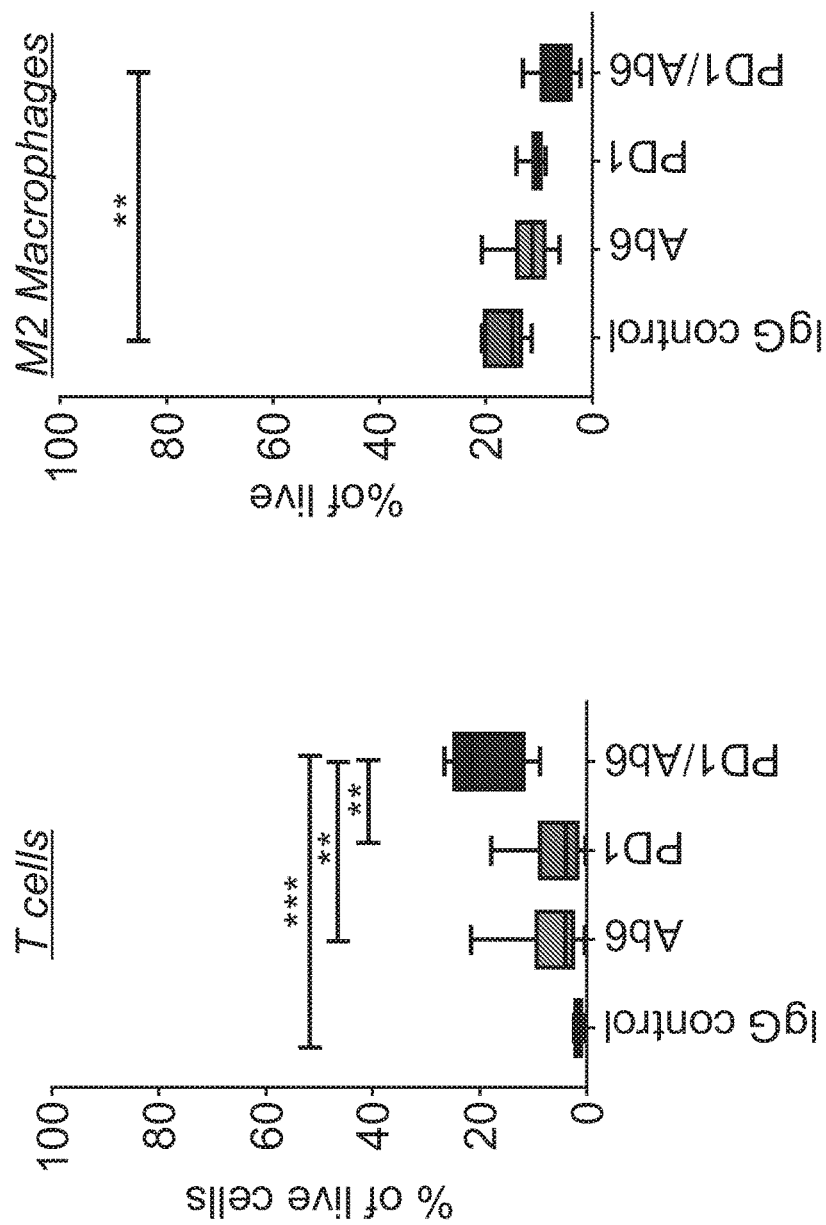

Furthermore, there was a dramatic increase in the ratio of CD8+ T cells:M2 macrophages observed in the anti-PD1/Ab6 treatment group (see FIG. 29C). Taken together, the data demonstrate that isoform-selective inhibitors of TGFβ1 can be used to overcome tumor immune exclusion when used in conjunction with a checkpoint blockade therapy. This may be at least in part mediated by promoting CD8+ T cell infiltration and expansion, while reducing pro-tumor macrophages (M2) and immunosuppressive MDSCs in the tumor environment. It is possible that these effects may be mediated by the GARP arm and the LRRC33 arm of TGFβ1, respectively.

For immunohistochemical analysis, tumors from six animals were cut in halves and fixed. Sections were prepared for IHC and were stained with various immune cell markers. FIG. 30 provides representative images at day 10 or day 13. As shown, marked increase in the frequency of CD8+ T cells within the tumor was observed in the anti-PD1/Ab6 combination-treated group (FIG. 30D). The data indicate that Ab6 can be used in conjunction with a checkpoint blockade therapy to overcome immune exclusion by inducing infiltration and expansion of cytotoxic T cells. FIG. 30E provides the quantitation of the IHC data, shown as % of CD8-positive cells of total nuclei. In this tumor model, few baseline CD8+ cells were present (e.g., "cold" tumor). In the groups treated with either Ab6 alone or anti-PD-1 alone, a slight increase in the percentage of CD8+ was observed (each ~10%). By contrast, in the combination-treated group, a market increase in the frequency of CD8+ cells within the tumor was achieved, indicating that TGFβ1 inhibition in combination with checkpoint inhibition can synergistically elicit anti-tumor effects by overcoming immune exclusion. The data suggest that the combination can effectively convert an "immune excluded" tumor into an "inflamed/hot" tumor.

To confirm gene expression changes that correlate the observed immune response in MBT2 tumors, RNA expression analysis was performed. RNA preparations from day 13 MBT2 tumors were subjected to qPCR-based gene expression analysis. RNA prepared from 5-6 animals per group was used for the study. Analyses included expression levels of the following genes, used as the indicated marker: Ptprc (CD45); Cd8a (CD8 T cell); Cd8b1 (CD8 T cell); Cd4 (CD4 T cell); Cd3e (T cell); Foxp3 (Treg); Ifng (Th1 immunity); Prf1 (CTL protein); Gzmb (CTL protein); Gzma (CTL protein); Klrk1 (NK/CTL); Adgre1 (F4/80 macrophage); Mrc1 (M2 macrophage); Cd163 (M2 macrophage); Cd80 (APC co-stim/M1 macrophage); Ptger2 (tumor angiogenesis); Nrros (LRRC33); Tgfb1 (immune tolerance); 18S (housekeeper); and, Ppib (housekeeper).

FIGS. 31A-31D provide changes in immune response gene expression of Ptprc, CD8α, CD4 and Foxp3, respectively. Anti-PD1/Ab6 combination treatment induced significant increases in the level of these transcripts in MBT2 tumors. These observations confirm that anti-PD1/Ab6 treatment elicits massive influx of CD8+ T cells, armed with cytotoxic effector proteins such as perforin and granzyme.

Figures 32A, 32B, 32C:
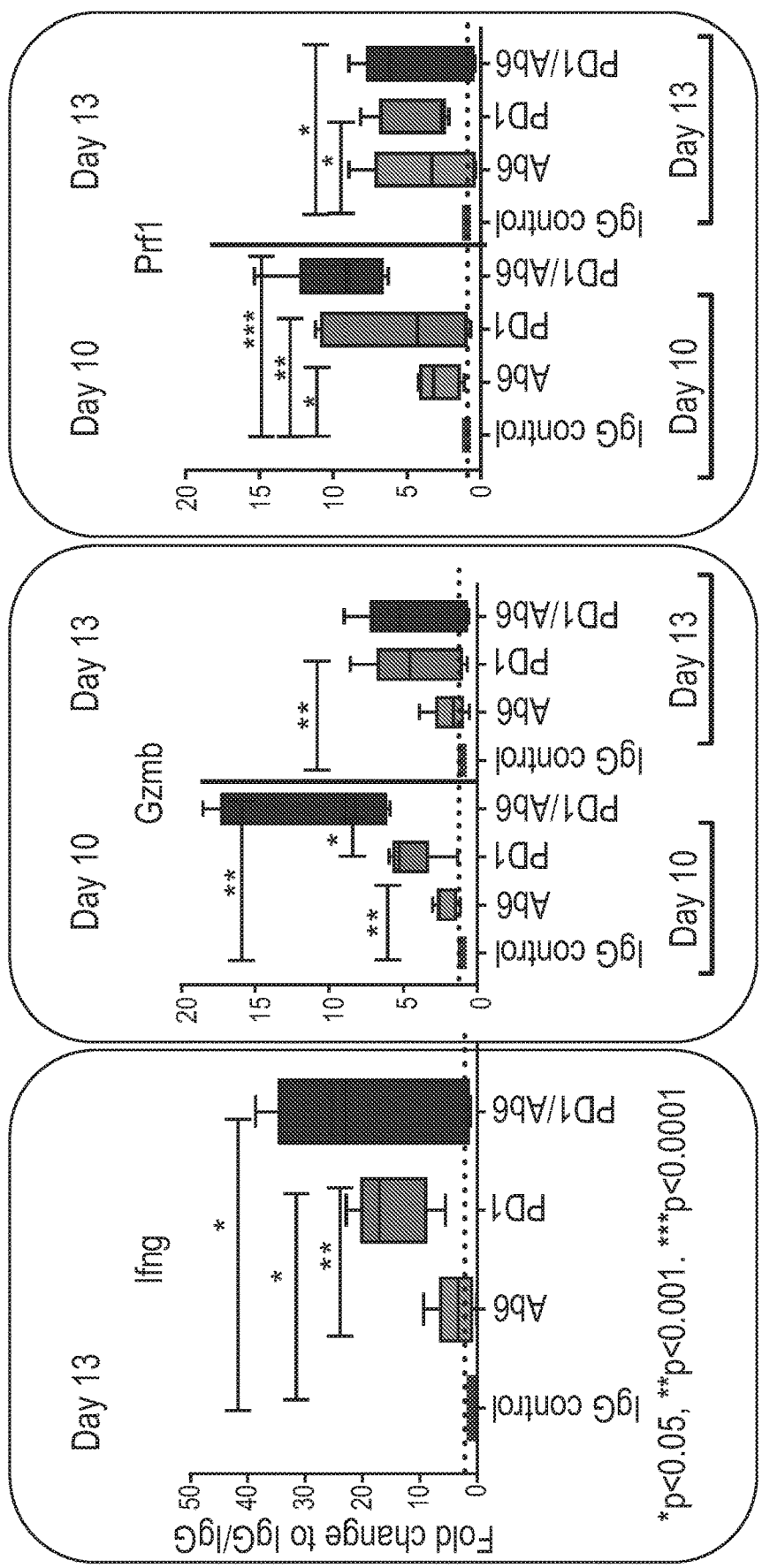
FIGS. 32A-32C provide gene expression of effector function markers, Ifng (FIG. 32A); Gzmb (FIG. 32B); and Prf1 (FIG. 32C) at day 10 and/or day 13, as indicated.
Figure 32D:
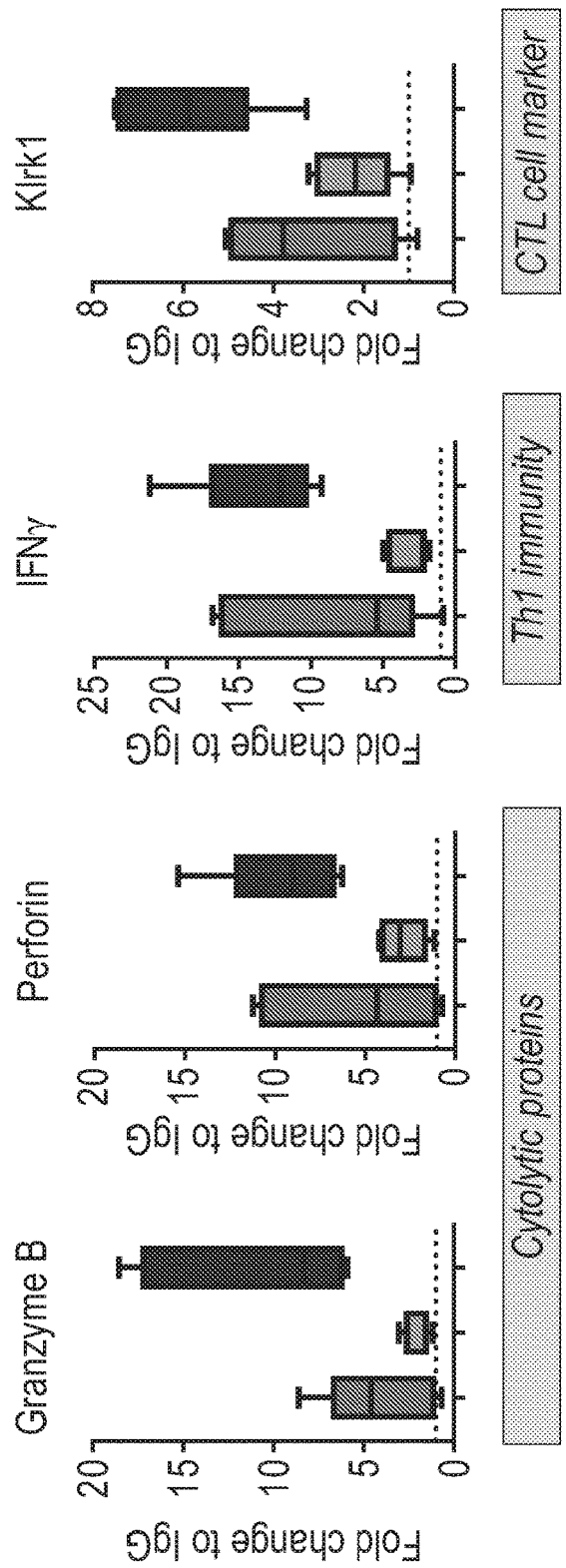
FIG. 32D provides a set of graphs showing expression of four gene markers (Granzyme B, Perforin, IFNγ and Klrk1) as measured by qPCR in MBT2 tumor samples at day 10. Each graph provides fold change of expression in the three treatment groups: anti-PD-1 alone (left); Ab6 alone (center); and combination of anti-PD-1 and Ab6 (right).
Figure 33A:
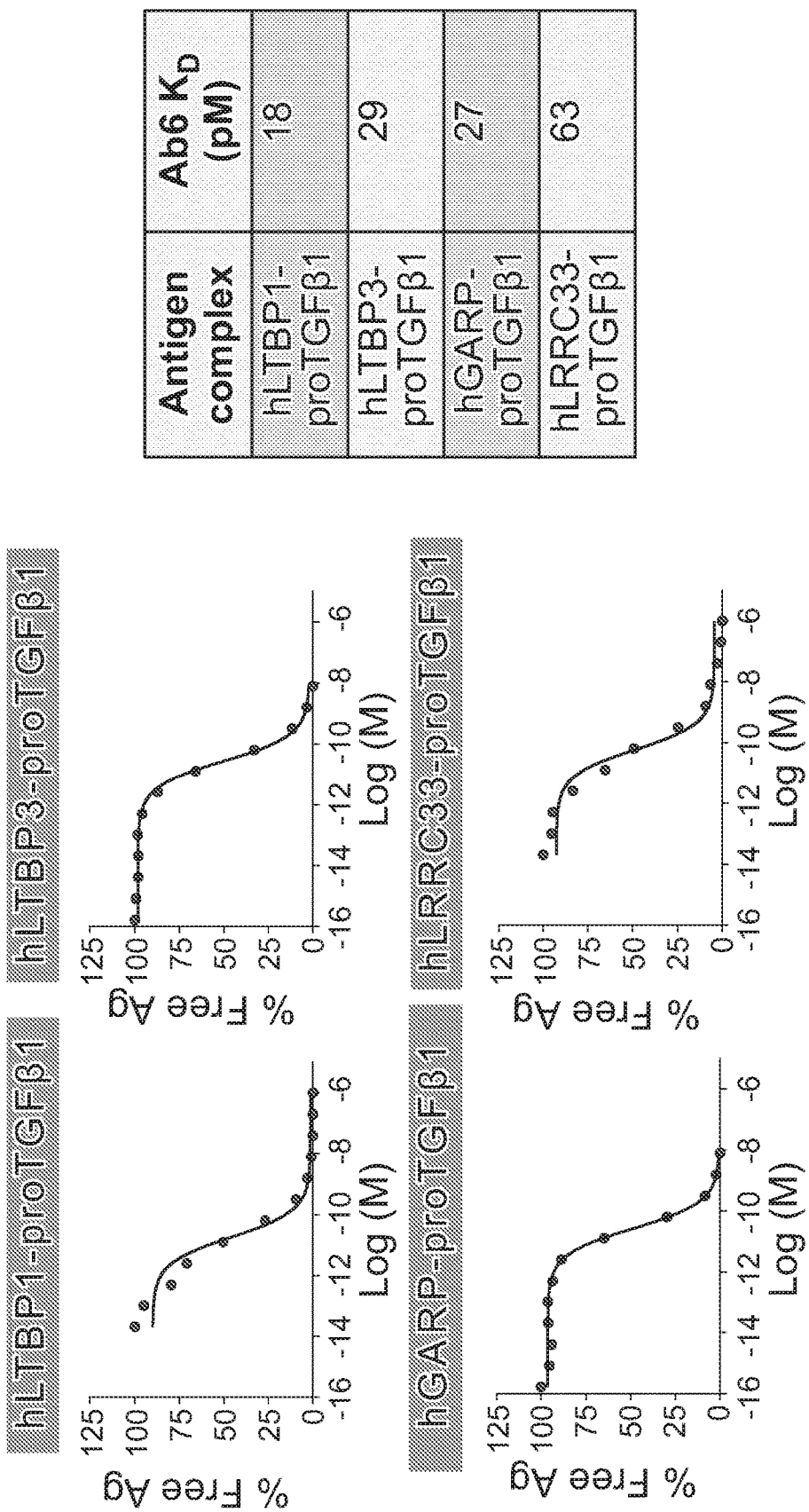
FIG. 33A shows in vitro binding of Ab6 towards four large latent complexes as shown, as measured by a solution equilibrium titration-based assay (MSD-SET). Measured KD values (in picomolar) are shown on right.

FIG. 32 provides gene expression changes in immune markers, Ifng, Gzmb, Prf1 and Klrk1 at day 10 or day 13. As shown, pPCR analyses of these marker genes demonstrate that combination treatment of anti-PD-1 and TGFβ1 inhibitor induces gene expression of markers of cytolytic proteins (Granzyme B and Perforin), Th1 immunity (IFNγ), and CTL/NK cell marker (Klrk1) in the tumor. These data provide further evidence supporting synergistic effects of checkpoint inhibition and TGFβ1 inhibition that mediate anti-tumor effects.

In sum, these results collectively show robust mobilization of anti-tumor immunity elicited by checkpoint blockade and TGFβ1 inhibition. Specifically, while the overall tumor-infiltrating immune cell fraction remains constant across treatment groups, anti-PD-1/Ab6 combination causes a) significant increase in intratumoral CD8+ T cells (* P<0.05, two-sided T test vs. anti-PD-1 group); b) significant increase in Tregs (* P<0.05), however, the CD8+:Treg ratio is unchanged (n.s., not significant vs anti-PD-1); and, c) significant reduction of myeloid cells compared to any other group, driven by a reduction of immunosuppressive M2 macrophage and myeloid-derived suppressor cell (MDSC) populations (* P<0.05, two-sided T test vs. anti-PD-1 group). Quantitative PCR analysis of whole tumor lysates confirms robust increase in CD8 effector genes. Similarly, combination of anti-PD-1 and Ab6 induces a marked increase in frequency of CD8+ T cells within the tumor mass, overcoming immune exclusion.

To confirm effects on TGFβ1 downstream signaling, additional immunohistochemical analyses were carried out to detect and localize phosphorylated SMAD3 in MBT2 tumors. As shown in FIG. 30F, PhosphoSMAD3 was found to be enriched near vascular endothelium within anti-PD-1-treated tumors. Treatment with Ab6 abrogates this signal, supporting the notion that TGFβ1 inhibition can promote intratumoral immune cell infiltration, thereby converting an immune excluded tumor into an inflamed tumor that is responsive to checkpoint blockade.

Anti-PD-1-treated animals show some infiltrating CD8+ T cells closely associated with tumor vasculature (CD31 staining; endothelial marker). Combination treatment supports further T cell infiltration. Proximity of CD8+ T cells to vascular endothelium suggests that T cells may infiltrate the tumor from the intratumoral vasculature. The relationship between CD8-positive areas of the tumor and the distance from CD31-positive vasculature is shown in FIG. 30G. The histogram demonstrates that the combination treatment (TGFβ1 inhibition and checkpoint blockade) increases the fraction of CD8+ area especially in areas that are distant from blood vessels, suggesting that TGFβ1 inhibition promotes CD8+ cell infiltration into the tumor via the vasculature, effectively overcoming or reversing immunosuppression.

Example 17: Effects of Isoform-Selective Context Independent TGFβ1 Inhibitors on MPL Model of Myeloproliferative Disorder The preclinical MPLW515L model of myelofibrosis has been previously described (see, e.g., Wen et al., Nature Medicine volume 21, pages 1473-1480 (2015)). In brief, recipient mice are lethally irradiated and subsequently transplanted with donor bone marrow cells transduced with human thrombopoietin receptor MPL having a constitutive activating mutation at W515L (MPLW515L). Recipient mice in this model will developed leukocytosis, polycythemia, and thrombocytosis in 2-3 weeks.

To evaluate effects of TGFβ1-selective inhibition in the murine model of myelofibrosis, a high affinity, isoform-specific, context-independent inhibitor of TGFβ1 (Ab6) was tested in the MPL$^{W515L}$ model. Briefly, half a million MPL+ ckit+ cells were transplanted into 8-10 week old female BALB/c mice. After 3 weeks, recipient mice received weekly i.p. injections of Ab6 at 10 or 30 mg/kg/week, or negative control IgG (30 mg/kg/week) for 4 weeks (total of 5 doses). Mice were scarified 24h after last dose.

Figure 36A:
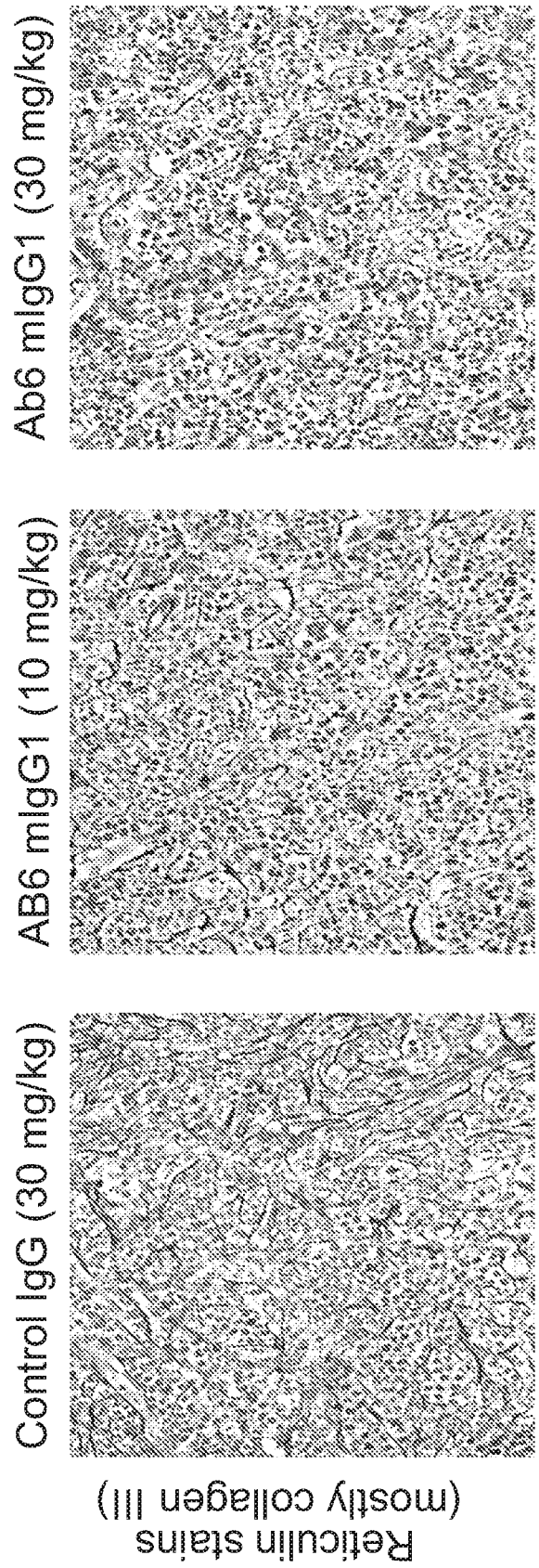
FIG. 36A provides a set of histology images showing silver staining of reticulin as a marker of a fibrotic phenotype of the bone marrow in a murine myeloproliferative disorder model.

Histopathology of the bone marrow was performed to evaluate antifibrotic effect of Ab6, as assessed by reticulin staining. Preliminary data indicate that bone marrow sections taken from the animals treated with Ab6 showed an antifibrotic effect. Images collected from reticulin staining of representative bone marrow sections are provided in FIG. 36A. Apparent reduction of reticulin fibers (mostly collagen III) was observed in mice that received Ab6 at 10 and 30 mg/kg weekly. Similar but lesser degree of anti-fibrotic effects were also observed with a second TGFβ1-selective inhibitor antibody tested (data not shown).

For quantitative analysis based on pathologist-performed fibrosis scoring of bone marrow sections, reticulin staining was scored using a classification system published by the WHO (Thiele J, Kvasnicka H M, Tefferi A et al. Primary myelofibrosis In: Swerdlow S H, Campo E, Harris N L, et al (eds). WHO Classifications of Tumours of Haematopoietic and Lymphoid Tissues 4th edn. IARC Press: Lyon, France, 2008, pp 44-47). Briefly, histological sections are scored using a four-tier system (MF-0, MF-1, MF-2, and MF-3). A score of MF-0 indicates scattered linear reticulin with no intersections (crossovers), corresponding to normal bone marrow. A score of MF-1 indicates a loose network of reticulin with many intersections, especially in perivascular areas. A score of MF-2 indicates a diffuse and dense increase in reticulin with extensive intersections, occasionally with focal bundles of collagen and/or focal osteosclerosis. A score of MF-3 indicates diffuse and dense reticulin with extensive intersections and coarse bindles of collagen, often associated with osteosclerosis.

Figure 36B:
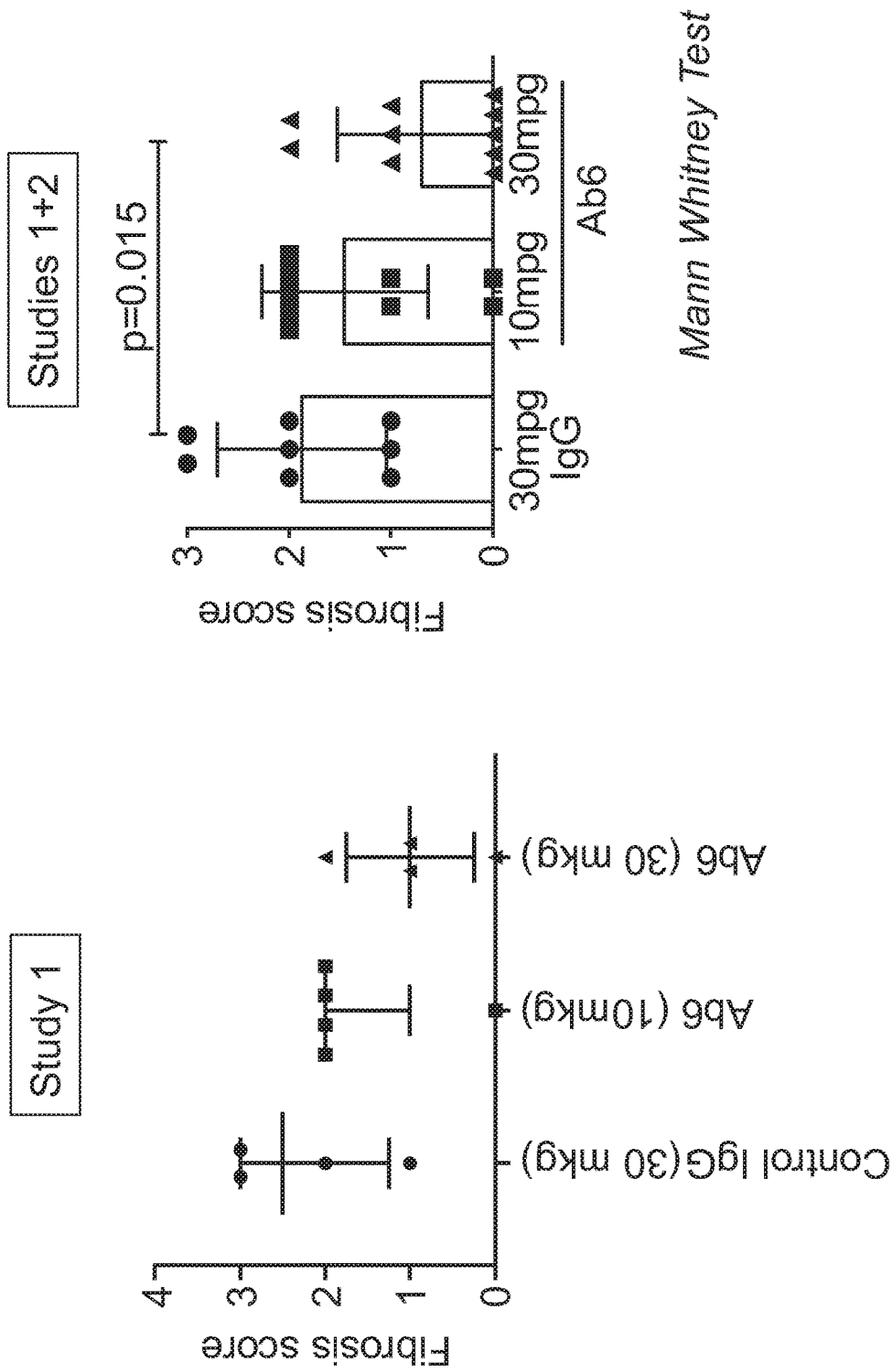
FIG. 36B provides two graphs showing histopathological analysis of bone marrow fibrosis and effect of TGFβ1 inhibition in MPL$^{W515L}$ mice with high disease burden from two separate repeat studies.

Fibrosis scores are provided in FIG. 36B, indicating a dose-dependent antifibrotic effect of Ab6, as compared to animals that received control IgG. The left graph shows the fibrosis scores from the first study (Study 1) in which the animals with high disease burden (>50%) at the start of treatment were treated with Ab6 or control IgG as shown. The study was repeated (Study 2). Data from corresponding cohorts were combined and are presented in the right graph (Studies 1+2). Weekly dosing of 30 mg/kg Ab6 significantly reduced fibrosis.

The animals were also evaluated for various hematological parameters, e.g., complete blood count (CBC) after bone marrow transplantation (including white blood cells (WBC), platelets (Plt), hemoglobin (HB) and hematocrit (HCT)) using standard techniques (FIGS. 36C & 36D). Not surprisingly, after 4 weeks of treatment initiation, MPL mice treated with IgG control appear to manifest hematological abnormalities characteristic of myelofibrosis, including increased levels of WBC and Plt. Animals treated with Ab6 showed dose-dependent trend toward normalization of WBC, Plt and HB concentrations, as well as change over baseline, as compared to control IgG animals. In addition, Ab6-treated animals showed statistically significant normalization of HCT concentrations, as well as change over baseline, as compared to control IgG animals, where Hct levels appeared to be restored to the baseline by 4 weeks.

Example 18: Effects of High-Affinity TGFβ1 Inhibitor on EMT-6 Syngeneic Breast Carcinoma Model Breast cancer is the most common cancer among women in the United States and is the fourth leading cause of cancer death. As shown in FIG. 20D (left) and FIG. 35, EMT6 tumors express significant levels of both TGFβ1 and TGFβ3 (e.g., TGFβ1 and TGFβ3 co-dominant), unlike many tumors that predominantly express TGFβ1. The contribution of TGFβ3 in these tumors to immune exclusion and CBT resistance has been unclear.

Previously, it was shown that Ab3 (an isoform-selective, context-biased inhibitor of TGFβ1) showed partial effects on tumor growth and survival in this model, as described in WO 2018/129329.

In these studies, effects of a combination of an isoform-selective TGFβ1 inhibitor and an isoform-selective TGFβ3 inhibitor was evaluated in the EMT6 model, in conjunction with an immune checkpoint inhibitor. It was reasoned that because this tumor is co-dominant with both the TGFβ1 and TGFβ3 isoforms, such combination therapy might show efficacy in tumor regression, while it was hypothesized that either of the isoform-selective inhibitors alone (TGFβ1 or TGFβ3) in conjunction with a checkpoint inhibitor, should produce a partial effect in inhibiting tumor growth.

EMT6 tumors were implanted subcutaneously. Treatment began when EMT6 tumors reached 30-80 mm$^3$. Anti-PD-1 was dosed at 10 mkg twice weekly. Ab6 was dosed once weekly at 10 mkg. Anti-TGFβ3 neutralizing antibody was dosed at 30 mkg once weekly.

Responders are defined as those achieving tumor size of ≤25% of the endpoint volume at study end.

Surprisingly, Ab6, a high affinity, isoform-selective inhibitor of TGFβ1, used in combination with an anti-PD-1 antibody, was sufficient to overcome checkpoint inhibition resistance in EMT6. FIG. 34A shows effects of Ab6 and/or anti-PD-1 on tumor growth. Neither antibody achieved significant tumor regression when used alone. In combination, however, 50% of the treated animals (5 out of 10) achieved significant tumor regression (reduction to 25% or less of the endpoint tumor volume). These data show synergistic antitumor efficacy, as evidenced by either complete responders or tumor growth delay, in combination therapy groups. Unexpectedly, addition of an isoform-selective inhibitor of TGFβ3 did not produce added effects. The observation that inhibition of TGFβ1 isoform with Ab6 was sufficient to sensitize tumors to anti-PD-1, even in the presence of intratumoral TGFβ3, supports the hypothesis that TGFβ1 is the isoform that drives disease-associated TGFβ signaling, immune exclusion, and primary resistance to CBT.

Correspondingly, the combination therapy (TGFβ1+anti-PD-1) achieved significant survival benefit in the treated animals, as compared to anti-PD-1 alone (***, P<0.001 Log Rank test) (see FIG. 34B). 56 days after treatment initiation, 60% of the animals were alive in the combination group, while in the other treatment groups, all animals had died or needed to be euthanized by day 28.

A separate study (Study 2), also showed significant improvement in survival in animas with TGFβ1/3-positive EMT6 tumors treated with combination of Ab6 and anti-PD-1, but not in animals with either antibody alone (FIG. 34C). In this model, we halted treatment and the EMT-6 tumor-free survivors were followed for 6 weeks without dosing (gray box). Six weeks post dosing cessation, complete responders remained tumor free, again demonstrating the durability of response (FIG. 34C, right). Number reported is the number of animals with no measurable tumor at study end. Significant survival benefits of the combination treatment (Ab6+anti-PD-1) were observed, as compared to animals treated with anti-PD-1 alone (FIG. 34D).

Example 19: Recombinant Protein Expression

Recombinant proteins were expressed in EXPI293F™ cells (Thermo Fisher) transiently transfected with pTT5 plasmids (NRC Canada) containing the cDNA of interest. Large latent TGFβ complexes were generated by co-transfecting EXPI 293F™ cells with a plasmid encoding proTGFβ1, proTGFβ2 or proTGFβ3, and a plasmid encoding an LLC-presenting protein. LTBP fragments that contain the TGFβ-binding TB3 domain and flanking EGF-like domains were used to improve yields and protein quality over full-length LTBPs (E873 to 11507 for human LTBP1; D866 to E1039 for human LTBP3). The LTBP fragments had a C-terminal His-tag to facilitate purification. Stable Expi293 cell lines were made that expressed C-terminally His-tagged GARP or LRRC33 ectodomains. These stable cells were transiently transfected with a plasmid encoding proTGFβ1 to generate GARP or LRRC33 complexes with latent TGFβ1. The small latent TGFβ complexes were expressed with an N-terminal His-tag and the large latent complex-forming cysteine mutated to serine (C4S in TGFβ1, C5S in TGFβ2, and C7S in TGFβ3 prodomains). The active TGFβ growth factors were purchased from R&D Systems. Transfectants were cultured in EXPI293™ Expression medium (Thermo Fisher) for 5 days before the conditioned supernatant was collected. Recombinant proteins were purified by Ni2+ affinity chromatography followed by size-exclusion chromatography (SEC). Protein quality and formation of disulfide-linked complexes was confirmed by SDS PAGE and analytical SEC. Antibodies were expressed by co-transfection of EXPI293F™ cells with pTT5 plasmids encoding heavy and light chains of interest. Human IgG4 and mouse IgG1 antibodies were purified by Protein A capture followed by SEC. The identity of antibodies that were used in animal models was confirmed by mass spectrometry.

Example 20: Syngeneic Mouse Models

Murine models were performed at Charles River Discovery Labs in Morrisville, NC according to IACUC. For the MBT-2 model, 8-12 week old C3H/HeN (Charles River) female mice were anesthetized with isoflurane to implant $5\times10^5$ MBT-2 tumors cells subcutaneously in the flank. Animals were distributed into groups of average tumor volumes of 40-80 mm$^3$ such that all groups had equal starting volume means and ranges. For CloudmanS91, 8-12 week old DBA/2 (Charles River) female mice were anesthetized with isoflurane to implant $5\times10^5$ CloudmanS91 tumor cells in 50% matrigel subcutaneously in the flank. Animals were distributed into groups when average tumor volume reached 125-175 mm$^3$ such that all groups had equal starting volume mean and range. For the EMT-6 model, 8-12 week old female BALB/c mice (Charles River) were implanted with $5\times10^6$ EMT-6 tumor cells subcutaneously in the flank. Animals were distributed into groups of average starting volume between 30-60 mm$^3$ such that all groups had equal starting volume mean and range. Control HuNeg-rIgG1 or anti-PD-1 (RMP1-14; BioXCell) were dosed at 10 mg/kg twice a week. Ab6-mIgG1 or the control antibody HuNeg-mIgG1 were dosed at the indicated dose level once a week. All antibodies were dosed intraperitoneally. Tumor volume was measured twice a week and animals were sacrificed by $CO_2$ asphyxiation when tumors reached 1,200 mm$^3$ (MBT-2, EMT6) or 2,000 mm$^3$ (CloudmanS91) or upon ulceration. Tumor volume was calculated as mm$^3$= (w$^2$×l)/2. Responders or response rate was defined as a tumor volume at or below 25% of the endpoint volume for that model. Complete response was classified as a tumor less than 13.5 mm$^3$ for three or more consecutive measurements. Tumor-free survivors had no palpable tumor at study end. Animals sacrificed due to necrosis as per IACUC were removed entirely from analysis.

Figure 20G:
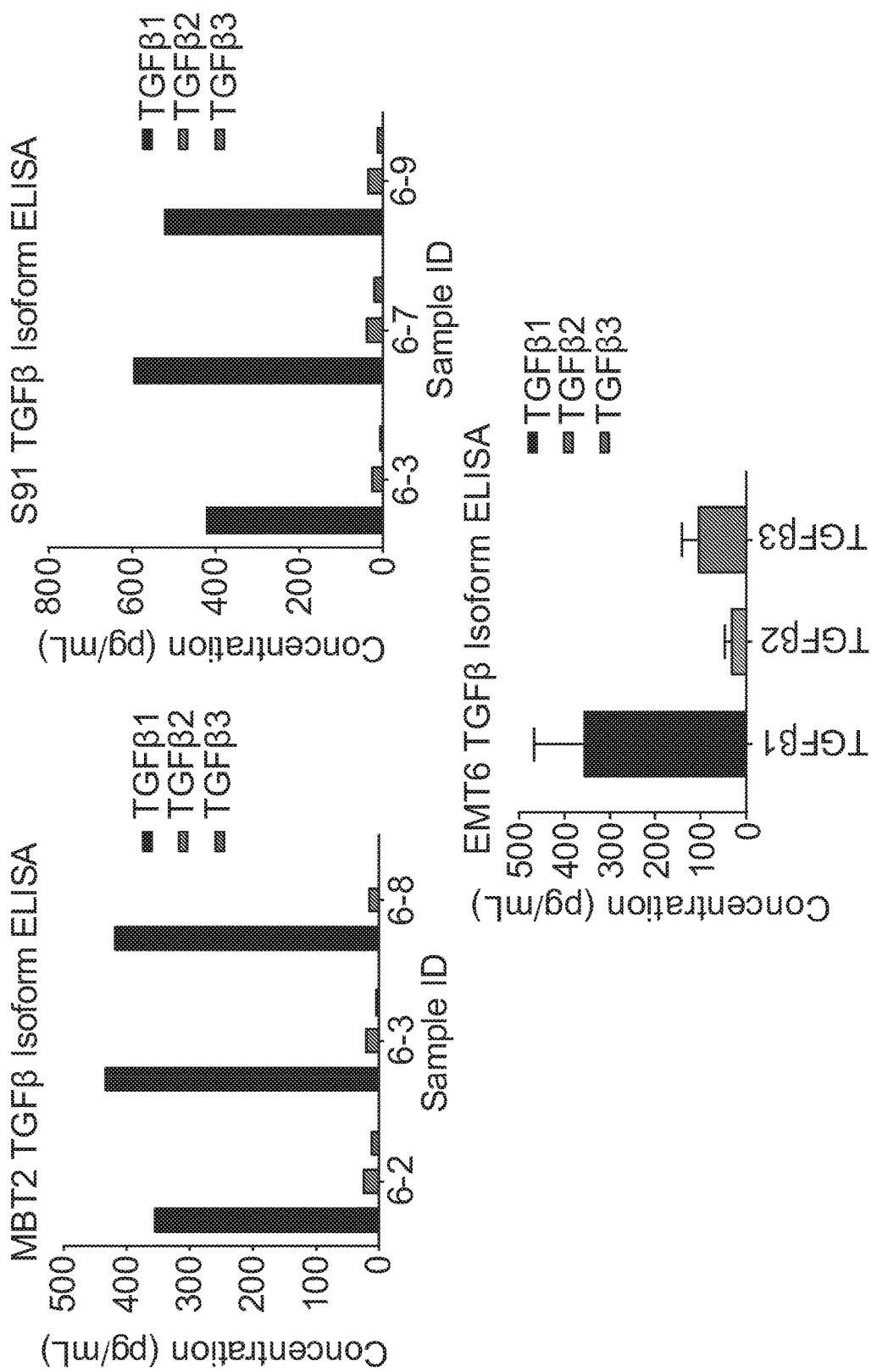
FIG. 20G provides three graphs comparing protein expressions by ELISA of 3 TGFβ isoforms in the Cloudman S91, MBT-2 and EMT-6 tumor models.

Relative expressions of three TGFβ isoforms and presenting molecules were taken into consideration for the selection of preclinical pharmacology models that recapitulate human clinical data. ELISA analyses of relative protein expressions of the three isoforms in the MBT-2, S91 and EMT6 are provided in FIG. 20G. In both MBT-2 and S91 tumors, TGFβ1 the dominant isoform, mirroring most human cancers. EMT-6 still showed predominant TGFβ1 expression, but also co-expressed, albeit lesser degree, TGFβ3, which is more similar to what is observed in certain human carcinomas.

All four presenting molecules (LTBP1, LTBP3, GARP and LRRC33) are expressed by RNA in the MBT-2, S91 and EMT-6 tumors (FIG. 20H).

Example 21: Antibody-Induced Internalization of LRRC33-proTGFβ1

We observed that among cell types that express LRRC33 RNA, only a subset appears to express the LRRC33 protein on cell surface. We hypothesized that LRRC33 may be regulated by protein trafficking at the plasma membrane. To asses this possibility, we designed internalization assays.

An Expi293 cell line was generated, which express cell-surface LRRC33-proTGFβ1. Using the Incucyte system, internalization of LRRC33 upon Ab6 binding to cell-surface LRRC33-proTGFβ1 was measured. Briefly, the Incycyte system employs a pH-sensitive detection label that can be detected when the target is internalized into the intracellular compartment with an acidic pH (e.g., lysosome). Rapid internalization of LRRC33-proTGFβ1 upon Ab6-binding in cells expressing LRRC33 and proTGFβ1 was observed (FIG. 6) but not the Expi293 parental line (data not shown). Internalization observed here was similar to internalization on primary human macrophages.

LRRC33-proTGFβ1 internalization is not FcR-mediated because Expi293 cells do not have Fc receptors (data not shown). These results indicate that Ab6 engagement can facilitate target downregulation. This may provide an additional or alternative mechanism of TGFβ1 inhibition in vivo, by reducing available proTGFβ1 levels at the disease site, such as TME and FME.

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for screening an isoform-selective TGFβ1 inhibitor suitable for therapeutic use, the method comprising:
  i) providing an antibody that specifically binds each of: human LTBP1-proTGFβ1, human LTBP3-proTGFβ1, human GARP-proTGFβ1 and human LRRC33-proTGFβ1 complexes with a $K_D \leq 1$ nM,
  ii) carrying out an in vivo efficacy study in a preclinical animal model, wherein the preclinical animal model is a syngeneic tumor model that recapitulates a human condition, wherein the antibody is administered to the preclinical animal model at a dosage of about 10 mg/kg/week or less in combination with an immune checkpoint inhibitor, wherein the in vivo efficacy study comprises measurement of tumor volume in the animal model, and selecting the antibody as achieving efficacy when the tumor volume is less than 25% of endpoint tumor volume in the preclinical animal model;
  iii) carrying out a cardiovascular toxicology study in a preclinical model that is sensitive to pharmacological inhibition of TGFβ, to determine a maximally tolerated and/or minimum toxic amount of the antibody, wherein the cardiovascular toxicity comprises a cardiac lesion, a valvulopathy, hyperplasia in aortic valve, right AV valve or left AV valve, inflammation in aortic valve, left AV valve or ascending aorta, hemorrhage in ascending aorta, aortic valve or left AV valve, and/or connective tissue degeneration in ascending aorta; wherein the antibody is administered to the animal model at a dosage of about 10 mg/kg/week or less; and selecting the antibody as lacking cardiovascular toxicity when the maximally tolerated amount or minimum toxic amount is achieved with administration of the antibody at a dosage of greater than 10 mg/kg/week;
  (iv) selecting the antibody as a therapeutic candidate if the antibody is selected as achieving efficacy in step (ii), and if the antibody is selected as lacking cardiovascular toxicity in step (iii).

2. The method according to claim 1, wherein the antibody is selected as lacking cardiovascular toxicity when the maximally tolerated amount or minimum toxic amount is achieved with administration of the antibody at a dosage of at least 100 mg/kg/week.

3. The method of claim 1, wherein the syngeneic tumor model that recapitulates a human condition comprises a Cloudman S91 model or an MBT-2 tumor model.

4. The method of claim 1, wherein endpoint tumor volume is 2,000 mm$^3$.

5. The method of claim 1, wherein the in vivo efficacy study performed in the preclinical model further comprises immunohistochemical analyses, measurement of tumor growth, regression of tumor volume, regression of tumor growth, incidence of regression responses, or magnitude of regression responses.

* * * * *

UNITED STATES PATENT AND TRADEMARK OFFICE
CERTIFICATE OF CORRECTION

| | | |
|---|---|---|
| PATENT NO. | : 12,252,531 B2 | |
| APPLICATION NO. | : 17/258771 | |
| DATED | : March 18, 2025 | |
| INVENTOR(S) | : Datta et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 798 days.

Signed and Sealed this
Sixth Day of January, 2026

John A. Squires
*Director of the United States Patent and Trademark Office*

SEQUENCE LISTING

<160> NUMBER OF SEQ ID NOS: 266

<210> SEQ ID NO 1

```
<400> SEQUENCE: 1

000

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Phe Thr Phe Ser Ser Phe Ser
1               5

<210> SEQ ID NO 3

<400> SEQUENCE: 3

000

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ile Ser Pro Ser Ala Asp Thr Ile
1               5

<210> SEQ ID NO 5

<400> SEQUENCE: 5

000

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Arg Gly Val Leu Asp Tyr Gly Asp Met Leu Met Pro
1               5                   10

<210> SEQ ID NO 7

<400> SEQUENCE: 7

000

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 8

Gln Asp Ile Thr Asn Tyr
1               5

<210> SEQ ID NO 9

<400> SEQUENCE: 9

000

<210> SEQ ID NO 10
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asp Ala Ser
1

<210> SEQ ID NO 11

<400> SEQUENCE: 11

000

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 12

Gln Gln Ala Asp Asn His Pro Pro Trp Thr
1               5                   10

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Ser Ala Asp Thr Ile Tyr Tyr Ala Asp Ser Val
    50                  55                  60

Lys Gly Arg Phe Thr Ile Ser Arg Asp Asn Ala Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Arg Gly Val Leu Asp Tyr Gly Asp Met Leu Met Pro Trp Gly Gln
                100                 105                 110

Gly Thr Leu Val Thr Val Ser Ser
            115                 120
```

<210> SEQ ID NO 14

<400> SEQUENCE: 14

000

<210> SEQ ID NO 15
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Asn His Pro Pro
                85                  90                  95

Trp Thr Phe Gly Gly Gly Thr Lys Val Glu Ile Lys
                100                 105
```

<210> SEQ ID NO 16

<400> SEQUENCE: 16

000

<210> SEQ ID NO 17
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Phe
                20                  25                  30

Ser Met Asp Trp Val Arg Gln Ala Pro Gly Lys Gly Leu Glu Trp Val
            35                  40                  45
```

```
Ser Tyr Ile Ser Pro Ser Ala Asp Thr Ile Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Leu Asp Tyr Gly Asp Met Leu Met Pro Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
            435                 440                 445

<210> SEQ ID NO 18
<211> LENGTH: 1338
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic nucleic acid"

<400> SEQUENCE: 18

```
gaggtgcagc tggtggagtc tgggggaggc ttggtacagc ctggggggtc cctgagactc    60
tcctgtacag cctctggatt caccttcagt agcttcagca tggactgggt ccgccaggct   120
ccagggaagg ggctggagtg ggtttcatac attagtccca gtgcagacac catatactac   180
gcagactctg tgaagggccg attcaccatc tccagagaca tgccaagaa cacgctgtat    240
ctgcaaatga acagcctgag agccgaggac acggcggtgt actactgcgc cagaggggtg   300
ctcgactacg agacatgtt aatgccatgg ggccagggaa ccctggtcac cgtctcctca    360
gcgtcgacca agggcccttc cgtgttccct ctggcccctt gctcccggtc cacctccgag   420
tccaccgccg ctctgggctg tctggtgaag gactacttcc ctgagcctgt gaccgtgagc   480
tggaactctg gcgccctgac ctccggcgtg cacaccttcc ctgccgtgct gcagtcctcc   540
ggcctgtact ccctgtcctc cgtggtgacc gtgccttcct cctccctggg caccaagacc   600
tacacctgca acgtggacca caagccttcc aacaccaagg tggacaagcg ggtggagtcc   660
aagtacggcc ctccttgccc tccctgccct gcccctgagt tcctgggcgg accctccgtg   720
ttcctgttcc ctcctaagcc taaggacacc ctgatgatct cccggacccc tgaggtgacc   780
tgcgtggtgg tggacgtgtc ccaggaagat cctgaggtcc agttcaattg gtacgtggat   840
ggcgtggagg tgcacaacgc caagaccaag cctcgggagg aacagttcaa ctccacctac   900
cgggtggtgt ctgtgctgac cgtgctgcac caggactggc tgaacggcaa ggaatacaag   960
tgcaaggtca gcaacaaggg cctgccctcc tccatcgaga aaaccatctc caaggccaag  1020
ggccagcctc gcgagcctca ggtgtacacc ctgcctccta gccaggaaga tgaccaag    1080
aatcaggtgt ccctgacatg cctggtgaag ggcttctacc cttccgatat cgccgtggag  1140
tgggagagca cggccagcc agagaacaac tacaagacca cccctcctgt gctggactcc  1200
gacggctcct tcttcctgta ctccaggctg accgtggaca gtccggtg caggaaggc    1260
aacgtctttt cctgctccgt gatgcacgag gccctgcaca accactacac ccagaagtcc  1320
ctgtccctgt ctctgggc                                                1338
```

<210> SEQ ID NO 19
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
```

```
                65                  70                  75                  80
        Glu Asp Ile Ala Thr Tyr Tyr Cys Gln Gln Ala Asp Asn His Pro Pro
                        85                  90                  95

Trp Thr Phe Gly Gly Gly Thr Lys Val Glu Ile Lys Arg Thr Val Ala
                        100                 105                 110

Ala Pro Ser Val Phe Ile Phe Pro Pro Ser Asp Glu Gln Leu Lys Ser
                        115                 120                 125

Gly Thr Ala Ser Val Val Cys Leu Leu Asn Asn Phe Tyr Pro Arg Glu
                        130                 135                 140

Ala Lys Val Gln Trp Lys Val Asp Asn Ala Leu Gln Ser Gly Asn Ser
        145                 150                 155                 160

Gln Glu Ser Val Thr Glu Gln Asp Ser Lys Asp Ser Thr Tyr Ser Leu
                        165                 170                 175

Ser Ser Thr Leu Thr Leu Ser Lys Ala Asp Tyr Glu Lys His Lys Val
                        180                 185                 190

Tyr Ala Cys Glu Val Thr His Gln Gly Leu Ser Ser Pro Val Thr Lys
                        195                 200                 205

Ser Phe Asn Arg Gly Glu Cys
                        210                 215

<210> SEQ ID NO 20
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic nucleic acid"

<400> SEQUENCE: 20
gacatccaga tgacccagtc tccatcctcc ctgtctgcat ctgtaggaga cagagtcacc        60
atcacttgcc aggcgagtca ggacattacc aactatttaa attggtatca gcagaaacca      120
gggaaagccc ctaagctcct gatctacgat gcatccaatt tggaaacagg ggtcccatca      180
aggttcagtg aagtggatc tgggacagat tttactttca ccatcagcag cctgcagcct      240
gaagatattg caacatatta ctgtcagcag gccgacaatc accctccttg acttttggc      300 ggagggacca aggttgagat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgt                       645

<210> SEQ ID NO 21

<400> SEQUENCE: 21

000

<210> SEQ ID NO 22

<400> SEQUENCE: 22

000

<210> SEQ ID NO 23
```

<400> SEQUENCE: 23

000

<210> SEQ ID NO 24
<211> LENGTH: 361
<212> TYPE: PRT
<213> ORGANISM: Homo sapiens

<400> SEQUENCE: 24

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350
```

```
Met Ile Val Arg Ser Cys Lys Cys Ser
         355                 360
```

<210> SEQ ID NO 25
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
```

```
            340                 345                 350
Met Ile Val Arg Ser Cys Lys Cys Ser
            355                 360

<210> SEQ ID NO 26
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335
```

```
Val Tyr Tyr Val Gly Arg Lys Pro Lys Val Glu Gln Leu Ser Asn Met
                340                 345                 350
Ile Val Arg Ser Cys Lys Cys Ser
            355                 360
```

<210> SEQ ID NO 27
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Leu Ser Thr Ser Lys Thr Ile Asp Met Glu Leu Val Lys Arg Lys Arg
1               5                   10                  15
Ile Glu Ala Ile Arg Gly Gln Ile Leu Ser Lys Leu Arg Leu Ala Ser
                20                  25                  30
Pro Pro Ser Gln Gly Glu Val Pro Pro Gly Pro Leu Pro Glu Ala Val
            35                  40                  45
Leu Ala Leu Tyr Asn Ser Thr Arg Asp Arg Val Ala Gly Glu Ser Ala
50                  55                  60
Glu Pro Glu Pro Glu Pro Glu Ala Asp Tyr Tyr Ala Lys Glu Val Thr
65                  70                  75                  80
Arg Val Leu Met Val Glu Thr His Asn Glu Ile Tyr Asp Lys Phe Lys
                85                  90                  95
Gln Ser Thr His Ser Ile Tyr Met Phe Phe Asn Thr Ser Glu Leu Arg
            100                 105                 110
Glu Ala Val Pro Glu Pro Val Leu Leu Ser Arg Ala Glu Leu Arg Leu
        115                 120                 125
Leu Arg Leu Lys Leu Lys Val Glu Gln His Val Glu Leu Tyr Gln Lys
130                 135                 140
Tyr Ser Asn Asn Ser Trp Arg Tyr Leu Ser Asn Arg Leu Leu Ala Pro
145                 150                 155                 160
Ser Asp Ser Pro Glu Trp Leu Ser Phe Asp Val Thr Gly Val Val Arg
                165                 170                 175
Gln Trp Leu Ser Arg Gly Gly Glu Ile Glu Gly Phe Arg Leu Ser Ala
            180                 185                 190
His Cys Ser Cys Asp Ser Arg Asp Asn Thr Leu Gln Val Asp Ile Asn
        195                 200                 205
Gly Phe Thr Thr Gly Arg Arg Gly Asp Leu Ala Thr Ile His Gly Met
210                 215                 220
Asn Arg Pro Phe Leu Leu Leu Met Ala Thr Pro Leu Glu Arg Ala Gln
225                 230                 235                 240
His Leu Gln Ser Ser Arg His Gly Ala Leu Asp Thr Asn Tyr Cys Phe
                245                 250                 255
Ser Ser Thr Glu Lys Asn Cys Cys Val Arg Gln Leu Tyr Ile Asp Phe
            260                 265                 270
Arg Lys Asp Leu Gly Trp Lys Trp Ile His Glu Pro Lys Gly Tyr His
        275                 280                 285
Ala Asn Phe Cys Leu Gly Pro Cys Pro Tyr Ile Trp Ser Leu Asp Thr
        290                 295                 300
Gln Tyr Ser Lys Val Leu Ala Leu Tyr Asn Gln His Asn Pro Gly Ala
305                 310                 315                 320
```

```
Ser Ala Ala Pro Cys Cys Val Pro Gln Ala Leu Glu Pro Leu Pro Ile
            325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 28
<211> LENGTH: 395
<212> TYPE: PRT
<213> ORGANISM: Homo sapiens

<400> SEQUENCE: 28

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285

Tyr Cys Phe Arg Asn Val Gln Asp Asn Cys Cys Leu Arg Pro Leu Tyr
    290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335
```

```
Ser Asp Thr Gln His Ser Arg Val Leu Ser Leu Tyr Asn Thr Ile Asn
            340                 345                 350

Pro Glu Ala Ser Ala Ser Pro Cys Val Ser Gln Asp Leu Glu Pro
            355                 360                 365

Leu Thr Ile Leu Tyr Tyr Ile Gly Lys Thr Pro Lys Ile Glu Gln Leu
            370                 375                 380

Ser Asn Met Ile Val Lys Ser Cys Lys Cys Ser
385                 390                 395

<210> SEQ ID NO 29
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285
```

```
Tyr Cys Phe Arg Asn Val Gln Asp Asn Cys Cys Leu Arg Pro Leu Tyr
        290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
                355                 360                 365

Leu Thr Ile Leu Tyr Tyr Ile Gly Lys Thr Pro Lys Ile Glu Gln Leu
        370                 375                 380

Ser Asn Met Ile Val Lys Ser Cys Lys Cys Ser
385                 390                 395

<210> SEQ ID NO 30
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Val Pro Pro Glu Val
        35                  40                  45

Ile Ser Ile Tyr Asn Ser Thr Arg Asp Leu Leu Gln Glu Lys Ala Ser
50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
```

```
                      245                 250                 255
Gly Lys Thr Pro His Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
            275                 280                 285

Cys Phe Arg Asn Val Gln Asp Asn Cys Cys Leu Arg Pro Leu Tyr Ile
            290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
                340                 345                 350

Glu Ala Ser Ala Ser Pro Cys Cys Val Ser Gln Asp Leu Glu Pro Leu
                355                 360                 365

Thr Ile Leu Tyr Tyr Ile Gly Lys Thr Pro Lys Ile Glu Gln Leu Ser
            370                 375                 380

Asn Met Ile Val Lys Ser Cys Lys Cys Ser
385                 390

<210> SEQ ID NO 31
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
        130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205
```

-continued

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
        245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
370                 375                 380

Asn Met Ile Val Lys Ser Cys Lys Cys Ser
385                 390

<210> SEQ ID NO 32
<211> LENGTH: 392
<212> TYPE: PRT
<213> ORGANISM: Homo sapiens

<400> SEQUENCE: 32

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu

```
                180                 185                 190
Leu Arg Arg Glu Ser Asn Leu Gly Leu Glu Ile Ser Ile His Cys Pro
            195                 200                 205
Cys His Thr Phe Gln Pro Asn Gly Asp Ile Leu Glu Asn Ile His Glu
        210                 215                 220
Val Met Glu Ile Lys Phe Lys Gly Val Asp Asn Glu Asp His Gly
225                 230                 235                 240
Arg Gly Asp Leu Gly Arg Leu Lys Lys Gln Lys Asp His His Asn Pro
                245                 250                 255
His Leu Ile Leu Met Met Ile Pro Pro His Arg Leu Asp Asn Pro Gly
            260                 265                 270
Gln Gly Gly Gln Arg Lys Lys Arg Ala Leu Asp Thr Asn Tyr Cys Phe
        275                 280                 285
Arg Asn Leu Glu Glu Asn Cys Cys Val Arg Pro Leu Tyr Ile Asp Phe
    290                 295                 300
Arg Gln Asp Leu Gly Trp Lys Trp Val His Glu Pro Lys Gly Tyr Tyr
305                 310                 315                 320
Ala Asn Phe Cys Ser Gly Pro Cys Pro Tyr Leu Arg Ser Ala Asp Thr
                325                 330                 335
Thr His Ser Thr Val Leu Gly Leu Tyr Asn Thr Leu Asn Pro Glu Ala
            340                 345                 350
Ser Ala Ser Pro Cys Cys Val Pro Gln Asp Leu Glu Pro Leu Thr Ile
        355                 360                 365
Leu Tyr Tyr Val Gly Arg Thr Pro Lys Val Glu Gln Leu Ser Asn Met
370                 375                 380
Val Val Lys Ser Cys Lys Cys Ser
385                 390

<210> SEQ ID NO 33
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ser Leu Ser Leu Ser Thr Ser Thr Thr Leu Asp Phe Gly His Ile Lys
1               5                   10                  15
Lys Lys Arg Val Glu Ala Ile Arg Gly Gln Ile Leu Ser Lys Leu Arg
            20                  25                  30
Leu Thr Ser Pro Pro Glu Pro Thr Val Met Thr His Val Pro Tyr Gln
        35                  40                  45
Val Leu Ala Leu Tyr Asn Ser Thr Arg Glu Leu Leu Glu Glu Met His
    50                  55                  60
Gly Glu Arg Glu Glu Gly Cys Thr Gln Glu Asn Thr Glu Ser Glu Tyr
65                  70                  75                  80
Tyr Ala Lys Glu Ile His Lys Phe Asp Met Ile Gln Gly Leu Ala Glu
                85                  90                  95
His Asn Glu Leu Ala Val Cys Pro Lys Gly Ile Thr Ser Lys Val Phe
            100                 105                 110
Arg Phe Asn Val Ser Ser Val Glu Lys Asn Arg Thr Asn Leu Phe Arg
        115                 120                 125
Ala Glu Phe Arg Val Leu Arg Val Pro Asn Pro Ser Ser Lys Arg Asn
    130                 135                 140
```

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
        355                 360                 365

Leu Tyr Tyr Val Gly Arg Thr Pro Lys Val Glu Gln Leu Ser Asn Met
    370                 375                 380

Val Val Lys Ser Cys Lys Cys Ser
385                 390

<210> SEQ ID NO 34
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
                100                 105                 110

Arg Phe Asn Val Ser Ser Val Glu Lys Asn Arg Thr Asn Leu Phe Arg
            115                 120                 125

Ala Glu Phe Arg Val Leu Arg Val Pro Asn Pro Ser Ser Lys Arg Asn
        130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
        210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
        290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
        370                 375                 380

Val Lys Ser Cys Lys Cys Ser
385                 390

<210> SEQ ID NO 35
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His

```
            50                  55                  60
Gly Glu Arg Glu Glu Gly Cys Thr Gln Glu Asn Thr Glu Ser Glu Tyr
 65                  70                  75                  80

Tyr Ala Lys Glu Ile His Lys Phe Asp Met Ile Gln Gly Leu Ala Glu
                 85                  90                  95

His Asn Glu Leu Ala Val Cys Pro Lys Gly Ile Thr Ser Lys Val Phe
                100                 105                 110

Arg Phe Asn Val Ser Ser Val Glu Lys Asn Arg Thr Asn Leu Phe Arg
            115                 120                 125

Ala Glu Phe Arg Val Leu Arg Val Pro Asn Pro Ser Ser Lys Arg Asn
        130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
    370                 375                 380

Val Lys Ser Cys Lys Cys Ser
385                 390

<210> SEQ ID NO 36
<211> LENGTH: 361
<212> TYPE: PRT
<213> ORGANISM: Mus sp.

<400> SEQUENCE: 36

Leu Ser Thr Cys Lys Thr Ile Asp Met Glu Leu Val Lys Arg Lys Arg
  1               5                  10                  15

Ile Glu Ala Ile Arg Gly Gln Ile Leu Ser Lys Leu Arg Leu Ala Ser
             20                  25                  30
```

Pro Pro Ser Gln Gly Glu Val Pro Gly Pro Leu Pro Glu Ala Val
            35                  40                  45

Leu Ala Leu Tyr Asn Ser Thr Arg Asp Arg Val Ala Gly Glu Ser Ala
 50                  55                  60

Asp Pro Glu Pro Glu Pro Glu Ala Asp Tyr Tyr Ala Lys Glu Val Thr
 65                  70                  75                  80

Arg Val Leu Met Val Asp Arg Asn Asn Ala Ile Tyr Glu Lys Thr Lys
                 85                  90                  95

Asp Ile Ser His Ser Ile Tyr Met Phe Phe Asn Thr Ser Asp Ile Arg
                100                 105                 110

Glu Ala Val Pro Glu Pro Pro Leu Leu Ser Arg Ala Glu Leu Arg Leu
            115                 120                 125

Gln Arg Leu Lys Ser Ser Val Glu Gln His Val Glu Leu Tyr Gln Lys
        130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 37
<211> LENGTH: 361
<212> TYPE: PRT
<213> ORGANISM: Macaca sp.

<400> SEQUENCE: 37

Leu Ser Thr Cys Lys Thr Ile Asp Met Glu Leu Val Lys Arg Lys Arg
1               5                  10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
            35                  40                  45

```
Leu Ala Leu Tyr Asn Ser Thr Arg Asp Arg Val Ala Gly Glu Ser Ala
 50                  55                  60

Glu Pro Glu Pro Glu Pro Ala Asp Tyr Tyr Ala Lys Glu Val Thr
 65                  70                  75                  80

Arg Val Leu Met Val Glu Thr His Asn Glu Ile Tyr Asp Lys Phe Lys
                 85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
                115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Lys Asp Asn Thr Leu Gln Val Asp Ile Asn
                195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
                275                 280                 285

His Ala Asn Phe Cys Leu Gly Pro Cys Pro Tyr Ile Trp Ser Leu Asp
290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
                355                 360

<210> SEQ ID NO 38
<211> LENGTH: 249
<212> TYPE: PRT
<213> ORGANISM: Mus sp.

<400> SEQUENCE: 38

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
                35                  40                  45

Leu Ala Leu Tyr Asn Ser Thr Arg Asp Arg Val Ala Gly Glu Ser Ala
```

```
            50                  55                  60
Asp Pro Glu Pro Glu Pro Ala Asp Tyr Tyr Ala Lys Glu Val Thr
 65                  70                  75                  80

Arg Val Leu Met Val Asp Arg Asn Asn Ala Ile Tyr Glu Lys Thr Lys
                 85                  90                  95

Asp Ile Ser His Ser Ile Tyr Met Phe Phe Asn Thr Ser Asp Ile Arg
                100                 105                 110

Glu Ala Val Pro Glu Pro Pro Leu Leu Ser Arg Ala Glu Leu Arg Leu
                115                 120                 125

Gln Arg Leu Lys Ser Ser Val Glu Gln His Val Glu Leu Tyr Gln Lys
130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
                180                 185                 190

His Cys Ser Cys Asp Ser Lys Asp Asn Lys Leu His Val Glu Ile Asn
                195                 200                 205

Gly Ile Ser Pro Lys Arg Arg Gly Asp Leu Gly Thr Ile His Asp Met
210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245

<210> SEQ ID NO 39
<211> LENGTH: 249
<212> TYPE: PRT
<213> ORGANISM: Macaca sp.

<400> SEQUENCE: 39

Leu Ser Thr Ser Lys Thr Ile Asp Met Glu Leu Val Lys Arg Lys Arg
  1               5                  10                  15

Ile Glu Ala Ile Arg Gly Gln Ile Leu Ser Lys Leu Arg Leu Ala Ser
                 20                  25                  30

Pro Pro Ser Gln Gly Glu Val Pro Pro Gly Pro Leu Pro Glu Ala Val
                 35                  40                  45

Leu Ala Leu Tyr Asn Ser Thr Arg Asp Arg Val Ala Gly Glu Ser Ala
 50                  55                  60

Glu Pro Glu Pro Glu Pro Ala Asp Tyr Tyr Ala Lys Glu Val Thr
 65                  70                  75                  80

Arg Val Leu Met Val Glu Thr His Asn Glu Ile Tyr Asp Lys Phe Lys
                 85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
                115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175
```

```
Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
            195                 200                 205

Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 40
<211> LENGTH: 360
<212> TYPE: PRT
<213> ORGANISM: Mus sp.

<400> SEQUENCE: 40

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
            195                 200                 205

Gly Ile Ser Pro Lys Arg Arg Gly Asp Leu Gly Thr Ile His Asp Met
        210                 215                 220

Asn Arg Pro Phe Leu Leu Leu Met Ala Thr Pro Leu Glu Arg Ala Gln
225                 230                 235                 240

His Leu His Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
290                 295                 300
```

-continued

```
Gln Tyr Ser Lys Val Leu Ala Leu Tyr Asn Gln His Asn Pro Gly Ala
305                 310                 315                 320

Ser Ala Ser Pro Cys Cys Val Pro Gln Ala Leu Glu Pro Leu Pro Ile
            325                 330                 335

Val Tyr Tyr Val Gly Arg Lys Pro Lys Val Glu Gln Leu Ser Asn Met
        340                 345                 350

Ile Val Arg Ser Cys Lys Cys Ser
            355                 360

<210> SEQ ID NO 41
<211> LENGTH: 361
<212> TYPE: PRT
<213> ORGANISM: Mus sp.

<400> SEQUENCE: 41

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
```

```
                    305                 310                 315                 320

Ala Ser Ala Ser Pro Cys Cys Val Pro Gln Ala Leu Glu Pro Leu Pro
                    325                 330                 335

Ile Val Tyr Tyr Val Gly Arg Lys Pro Lys Val Glu Gln Leu Ser Asn
                    340                 345                 350

Met Ile Val Arg Ser Cys Lys Cys Ser
                    355                 360

<210> SEQ ID NO 42
<211> LENGTH: 361
<212> TYPE: PRT
<213> ORGANISM: Macaca sp.

<400> SEQUENCE: 42

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                    20                  25                  30

Pro Pro Ser Gln Gly Glu Val Pro Pro Gly Pro Leu Pro Glu Ala Val
                    35                  40                  45

Leu Ala Leu Tyr Asn Ser Thr Arg Asp Arg Val Ala Gly Glu Ser Ala
                    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                    85                  90                  95

Gln Ser Thr His Ser Ile Tyr Met Phe Phe Asn Thr Ser Glu Leu Arg
                    100                 105                 110

Glu Ala Val Pro Glu Pro Val Leu Leu Ser Arg Ala Glu Leu Arg Leu
                    115                 120                 125

Leu Arg Leu Lys Leu Lys Val Glu Gln His Val Glu Leu Tyr Gln Lys
                    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                    165                 170                 175

Gln Trp Leu Ser Arg Gly Gly Glu Ile Glu Gly Phe Arg Leu Ser Ala
                    180                 185                 190

His Cys Ser Cys Asp Ser Lys Asp Asn Thr Leu Gln Val Asp Ile Asn
                    195                 200                 205

Gly Phe Thr Thr Gly Arg Arg Gly Asp Leu Ala Thr Ile His Gly Met
                    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                    245                 250                 255

Phe Ser Ser Thr Glu Lys Asn Cys Cys Val Arg Gln Leu Tyr Ile Asp
                    260                 265                 270

Phe Arg Lys Asp Leu Gly Trp Lys Trp Ile His Glu Pro Lys Gly Tyr
                    275                 280                 285

His Ala Asn Phe Cys Leu Gly Pro Cys Pro Tyr Ile Trp Ser Leu Asp
                    290                 295                 300

Thr Gln Tyr Ser Lys Val Leu Ala Leu Tyr Asn Gln His Asn Pro Gly
305                 310                 315                 320
```

Ala Ser Ala Ala Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 43
<211> LENGTH: 360
<212> TYPE: PRT
<213> ORGANISM: Macaca sp.

<400> SEQUENCE: 43

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
            195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
            325                 330                 335

Val Tyr Tyr Val Gly Arg Lys Pro Lys Val Glu Gln Leu Ser Asn Met
                340                 345                 350

Ile Val Arg Ser Cys Lys Cys Ser
            355                 360

<210> SEQ ID NO 44
<211> LENGTH: 1260
<212> TYPE: PRT
<213> ORGANISM: Macaca sp.

<400> SEQUENCE: 44

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
            35                  40                  45

Leu Ile Gly Glu Asn Gly His Ser Thr Asp Thr Leu Thr Gly Ser Gly
        50                  55                  60

Phe Arg Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Ala Gly Gly Thr Gly Ser Gly
            100                 105                 110

Pro Gly Leu Ser Arg Ala Gly Ala Leu Ser Thr Gly Ala Leu Pro Pro
        115                 120                 125

Leu Ala Pro Glu Gly Asp Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
            180                 185                 190

Pro Glu Ala Ser Val Gln Val His Arg Ile Glu Ser Ser Asn Ala Glu
        195                 200                 205

Gly Ala Ala Pro Ser Gln His Leu Leu Pro His Pro Lys Pro Ser His
    210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Gly
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile

```
                340             345             350
Ala Asp Lys Pro Glu Lys Ser Leu Cys Phe Arg Leu Val Ser Pro
                355             360             365
Glu His Gln Cys Gln His Pro Leu Thr Thr Arg Leu Thr Arg Gln Leu
        370             375             380
Cys Cys Cys Ser Val Gly Lys Ala Trp Gly Ala Arg Cys Gln Arg Cys
385             390             395             400
Pro Ala Asp Gly Thr Ala Ala Phe Lys Glu Ile Cys Pro Ala Gly Lys
                405             410             415
Gly Tyr His Ile Leu Thr Ser His Gln Thr Leu Thr Ile Gln Gly Glu
            420             425             430
Ser Asp Phe Ser Leu Phe Leu His Pro Asp Gly Pro Pro Lys Pro Gln
        435             440             445
Gln Leu Pro Glu Ser Pro Ser Gln Ala Pro Pro Glu Asp Thr Glu
        450             455             460
Glu Arg Gly Val Thr Thr Asp Ser Pro Val Ser Glu Glu Arg Ser
465             470             475             480
Val Gln Gln Ser His Pro Thr Ala Thr Thr Ser Pro Ala Arg Pro Tyr
            485             490             495
Pro Glu Leu Ile Ser Arg Pro Ser Pro Pro Thr Met Arg Trp Phe Leu
            500             505             510
Pro Asp Leu Pro Pro Ser Arg Ser Ala Val Glu Ile Ala Pro Thr Gln
            515             520             525
Val Thr Glu Thr Asp Glu Cys Arg Leu Asn Gln Asn Ile Cys Gly His
            530             535             540
Gly Glu Cys Val Pro Gly Pro Pro Asp Tyr Ser Cys His Cys Asn Pro
545             550             555             560
Gly Tyr Arg Ser His Pro Gln His Arg Tyr Cys Val Asp Val Asn Glu
                565             570             575
Cys Glu Ala Glu Pro Cys Gly Pro Gly Arg Gly Ile Cys Met Asn Thr
            580             585             590
Gly Gly Ser Tyr Asn Cys His Cys Asn Arg Gly Tyr Arg Leu His Val
        595             600             605
Gly Ala Gly Gly Arg Ser Cys Val Asp Leu Asn Glu Cys Ala Lys Pro
        610             615             620
His Leu Cys Gly Asp Gly Gly Phe Cys Ile Asn Phe Pro Gly His Tyr
625             630             635             640
Lys Cys Asn Cys Tyr Pro Gly Tyr Arg Leu Lys Ala Ser Arg Pro Pro
            645             650             655
Val Cys Glu Asp Ile Asp Glu Cys Arg Asp Pro Ser Ser Cys Pro Asp
            660             665             670
Gly Lys Cys Glu Asn Lys Pro Gly Ser Phe Lys Cys Ile Ala Cys Gln
            675             680             685
Pro Gly Tyr Arg Ser Gln Gly Gly Gly Ala Cys Arg Asp Val Asn Glu
        690             695             700
Cys Ala Glu Gly Ser Pro Cys Ser Pro Gly Trp Cys Glu Asn Leu Pro
705             710             715             720
Gly Ser Phe Arg Cys Thr Cys Ala Gln Gly Tyr Ala Pro Ala Pro Asp
            725             730             735
Gly Arg Ser Cys Val Asp Val Asp Glu Cys Glu Ala Gly Asp Val Cys
            740             745             750
Asp Asn Gly Ile Cys Thr Asn Thr Pro Gly Ser Phe Gln Cys Gln Cys
        755             760             765
```

-continued

```
Leu Ser Gly Tyr His Leu Ser Arg Asp Arg Ser His Cys Glu Asp Ile
            770                 775                 780
Asp Glu Cys Asp Phe Pro Ala Ala Cys Ile Gly Asp Cys Ile Asn
785                 790                 795                 800
Thr Asn Gly Ser Tyr Arg Cys Leu Cys Pro Gln Gly His Arg Leu Val
                805                 810                 815
Gly Gly Arg Lys Cys Gln Asp Ile Asp Glu Cys Thr Gln Asp Pro Gly
                820                 825                 830
Leu Cys Leu Pro His Gly Ala Cys Lys Asn Leu Gln Gly Ser Tyr Val
                835                 840                 845
Cys Val Cys Asp Glu Gly Phe Thr Pro Thr Gln Asp Gln His Gly Cys
850                 855                 860
Glu Glu Val Glu Gln Pro His His Lys Lys Glu Cys Tyr Leu Asn Phe
865                 870                 875                 880
Asp Asp Thr Val Phe Cys Asp Ser Val Leu Ala Thr Asn Val Thr Gln
                885                 890                 895
Gln Glu Cys Cys Cys Ser Leu Gly Ala Gly Trp Gly Asp His Cys Glu
                900                 905                 910
Ile Tyr Pro Cys Pro Val Tyr Ser Ser Ala Glu Phe His Ser Leu Cys
                915                 920                 925
Pro Asp Gly Lys Gly Tyr Thr Gln Asp Asn Asn Ile Val Asn Tyr Gly
930                 935                 940
Ile Pro Ala His Arg Asp Ile Asp Glu Cys Met Leu Phe Gly Ala Glu
945                 950                 955                 960
Ile Cys Lys Glu Gly Lys Cys Val Asn Thr Gln Pro Gly Tyr Glu Cys
                965                 970                 975
Tyr Cys Lys Gln Gly Phe Tyr Tyr Asp Gly Asn Leu Leu Glu Cys Val
                980                 985                 990
Asp Val Asp Glu Cys Leu Asp Glu Ser Asn Cys Arg Asn Gly Val Cys
                995                 1000                1005
Glu Asn Thr Arg Gly Gly Tyr Arg Cys Ala Cys Thr Pro Pro Ala
      1010                1015                1020
Glu Tyr Ser Pro Ala Gln Arg Gln Cys Leu Ser Pro Glu Glu Met
      1025                1030                1035
Asp Val Asp Glu Cys Gln Asp Pro Ala Ala Cys Arg Pro Gly Arg
      1040                1045                1050
Cys Val Asn Leu Pro Gly Ser Tyr Arg Cys Glu Cys Arg Pro Pro
      1055                1060                1065
Trp Val Pro Gly Pro Ser Gly Arg Asp Cys Gln Leu Pro Glu Ser
      1070                1075                1080
Pro Ala Glu Arg Ala Pro Glu Arg Arg Asp Val Cys Trp Ser Gln
      1085                1090                1095
Arg Gly Glu Asp Gly Met Cys Ala Gly Pro Gln Ala Gly Pro Ala
      1100                1105                1110
Leu Thr Phe Asp Asp Cys Cys Cys Arg Gln Gly Arg Gly Trp Gly
      1115                1120                1125
Ala Gln Cys Arg Pro Cys Pro Pro Arg Gly Ala Gly Ser Gln Cys
      1130                1135                1140
Pro Thr Ser Gln Ser Glu Ser Asn Ser Phe Trp Asp Thr Ser Pro
      1145                1150                1155
Leu Leu Leu Gly Lys Pro Arg Arg Asp Glu Asp Ser Ser Glu Glu
      1160                1165                1170
```

```
Asp Ser Asp Glu Cys Arg Cys Val Ser Gly Arg Cys Val Pro Arg
    1175                1180                1185

Pro Gly Gly Ala Val Cys Glu Cys Pro Gly Gly Phe Gln Leu Asp
    1190                1195                1200

Ala Ser Arg Ala Arg Cys Val Asp Ile Asp Glu Cys Arg Glu Leu
    1205                1210                1215

Asn Gln Arg Gly Leu Leu Cys Lys Ser Glu Arg Cys Val Asn Thr
    1220                1225                1230

Ser Gly Ser Phe Arg Cys Val Cys Lys Ala Gly Phe Ala Arg Ser
    1235                1240                1245

Arg Pro His Gly Ala Cys Val Pro Gln Arg Arg Arg
    1250                1255                1260

<210> SEQ ID NO 45
<211> LENGTH: 1228
<212> TYPE: PRT
<213> ORGANISM: Mus sp.

<400> SEQUENCE: 45

Gly Pro Ala Gly Glu Arg Gly Thr Gly Gly Gly Ala Leu Ala Arg
1               5                   10                  15

Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
                35                  40                  45

Leu Ile Gly Glu Asn Gly His Ser Thr Asp Thr Leu Thr Gly Ser Ala
        50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Ala Gly Thr Gly Ala Gly Thr Gly Ser Ser Gly
                100                 105                 110

Pro Gly Leu Ala Arg Thr Gly Ala Met Ser Thr Gly Pro Leu Pro Pro
        115                 120                 125

Leu Ala Pro Glu Gly Glu Ser Val Ala Ser Lys His Ala Ile Tyr Ala
        130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Pro Val Val Asn Val Arg Val His His Pro
                180                 185                 190

Pro Glu Ala Ser Val Gln Val His Arg Ile Glu Gly Pro Asn Ala Glu
        195                 200                 205

Gly Pro Ala Ser Ser Gln His Leu Leu Pro His Pro Lys Pro Pro His
        210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
                260                 265                 270

Cys His Lys Cys Pro Gln Leu Gln Tyr Thr Gly Val Gln Lys Pro Val
                275                 280                 285
```

```
Pro Val Arg Gly Glu Val Gly Ala Asp Cys Pro Gln Gly Tyr Lys Arg
    290                 295                 300
Leu Asn Ser Thr His Cys Gln Asp Ile Asn Glu Cys Ala Met Pro Gly
305                 310                 315                 320
Asn Val Cys His Gly Asp Cys Leu Asn Asn Pro Gly Ser Tyr Arg Cys
                325                 330                 335
Val Cys Pro Pro Gly His Ser Leu Gly Pro Leu Ala Ala Gln Cys Ile
            340                 345                 350
Ala Asp Lys Pro Glu Glu Lys Ser Leu Cys Phe Arg Leu Val Ser Thr
        355                 360                 365
Glu His Gln Cys Gln His Pro Leu Thr Thr Arg Leu Thr Arg Gln Leu
    370                 375                 380
Cys Cys Cys Ser Val Gly Lys Ala Trp Gly Ala Arg Cys Gln Arg Cys
385                 390                 395                 400
Pro Ala Asp Gly Thr Ala Ala Phe Lys Glu Ile Cys Pro Gly Lys Gly
                405                 410                 415
Tyr His Ile Leu Thr Ser His Gln Thr Leu Thr Ile Gln Gly Glu Ser
            420                 425                 430
Asp Phe Ser Leu Phe Leu His Pro Asp Gly Pro Pro Lys Pro Gln Gln
        435                 440                 445
Leu Pro Glu Ser Pro Ser Arg Ala Pro Pro Leu Glu Asp Thr Glu Glu
    450                 455                 460
Glu Arg Gly Val Thr Met Asp Pro Pro Val Ser Glu Glu Arg Ser Val
465                 470                 475                 480
Gln Gln Ser His Pro Thr Thr Thr Thr Ser Pro Pro Arg Pro Tyr Pro
                485                 490                 495
Glu Leu Ile Ser Arg Pro Ser Pro Pro Thr Phe His Arg Phe Leu Pro
            500                 505                 510
Asp Leu Pro Pro Ser Arg Ser Ala Val Glu Ile Ala Pro Thr Gln Val
        515                 520                 525
Thr Glu Thr Asp Glu Cys Arg Leu Asn Gln Asn Ile Cys Gly His Gly
    530                 535                 540
Gln Cys Val Pro Gly Pro Ser Asp Tyr Ser Cys His Cys Asn Ala Gly
545                 550                 555                 560
Tyr Arg Ser His Pro Gln His Arg Tyr Cys Val Asp Val Asn Glu Cys
                565                 570                 575
Glu Ala Glu Pro Cys Gly Pro Gly Lys Gly Ile Cys Met Asn Thr Gly
            580                 585                 590
Gly Ser Tyr Asn Cys His Cys Asn Arg Gly Tyr Arg Leu His Val Gly
        595                 600                 605
Ala Gly Gly Arg Ser Cys Val Asp Leu Asn Glu Cys Ala Lys Pro His
    610                 615                 620
Leu Cys Gly Asp Gly Gly Phe Cys Ile Asn Phe Pro Gly His Tyr Lys
625                 630                 635                 640
Cys Asn Cys Tyr Pro Gly Tyr Arg Leu Lys Ala Ser Arg Pro Pro Ile
                645                 650                 655
Cys Glu Asp Ile Asp Glu Cys Arg Asp Pro Ser Thr Cys Pro Asp Gly
            660                 665                 670
Lys Cys Glu Asn Lys Pro Gly Ser Phe Lys Cys Ile Ala Cys Gln Pro
        675                 680                 685
Gly Tyr Arg Ser Gln Gly Gly Gly Ala Cys Arg Asp Val Asn Glu Cys
    690                 695                 700
```

-continued

Ser Glu Gly Thr Pro Cys Ser Pro Gly Trp Cys Glu Asn Leu Pro Gly
705                 710                 715                 720

Ser Tyr Arg Cys Thr Cys Ala Gln Tyr Glu Pro Ala Gln Asp Gly Leu
            725                 730                 735

Ser Cys Ile Asp Val Asp Glu Cys Ala Gly Lys Val Cys Gln Asp
        740                 745                 750

Gly Ile Cys Thr Asn Thr Pro Gly Ser Phe Gln Cys Gln Cys Leu Ser
            755                 760                 765

Gly Tyr His Leu Ser Arg Asp Arg Ser Arg Cys Glu Asp Ile Asp Glu
        770                 775                 780

Cys Asp Phe Pro Ala Ala Cys Ile Gly Gly Asp Cys Ile Asn Thr Asn
785                 790                 795                 800

Gly Ser Tyr Arg Cys Leu Cys Pro Leu Gly His Arg Leu Val Gly Gly
            805                 810                 815

Arg Lys Cys Lys Lys Asp Ile Asp Glu Cys Ser Gln Asp Pro Gly Leu
        820                 825                 830

Cys Leu Pro His Ala Cys Glu Asn Leu Gln Gly Ser Tyr Val Cys Val
            835                 840                 845

Cys Asp Glu Gly Phe Thr Leu Thr Gln Asp Gln His Gly Cys Glu Glu
850                 855                 860

Val Glu Gln Pro His His Lys Lys Glu Cys Tyr Leu Asn Phe Asp Asp
865                 870                 875                 880

Thr Val Phe Cys Asp Ser Val Leu Ala Thr Asn Val Thr Gln Gln Glu
            885                 890                 895

Cys Cys Cys Ser Leu Gly Ala Gly Trp Gly Asp His Cys Glu Ile Tyr
        900                 905                 910

Pro Cys Pro Val Tyr Ser Ser Ala Glu Phe His Ser Leu Val Pro Asp
        915                 920                 925

Gly Lys Arg Leu His Ser Gly Gln Gln His Cys Glu Leu Cys Ile Pro
        930                 935                 940

Ala His Arg Asp Ile Asp Glu Cys Ile Leu Phe Gly Ala Glu Ile Cys
945                 950                 955                 960

Lys Glu Gly Lys Cys Val Asn Thr Gln Pro Gly Tyr Glu Cys Tyr Cys
            965                 970                 975

Lys Gln Gly Phe Tyr Tyr Asp Gly Asn Leu Leu Glu Cys Val Asp Val
        980                 985                 990

Asp Glu Cys Leu Asp Glu Ser Asn Cys Arg Asn Gly Val Cys Glu Asn
            995                 1000                1005

Thr Arg Gly Gly Tyr Arg Cys Ala Cys Thr Pro Ala Glu Tyr
    1010                1015                1020

Ser Pro Ala Gln Ala Gln Cys Leu Ile Pro Glu Arg Trp Ser Thr
    1025                1030                1035

Pro Gln Arg Asp Val Lys Cys Ala Gly Ala Ser Glu Glu Arg Thr
    1040                1045                1050

Ala Cys Val Trp Gly Pro Trp Ala Gly Pro Ala Leu Thr Phe Asp
    1055                1060                1065

Asp Cys Cys Cys Arg Gln Pro Arg Leu Gly Thr Gln Cys Arg Pro
    1070                1075                1080

Cys Pro Pro Arg Gly Thr Gly Ser Gln Cys Pro Thr Ser Gln Ser
    1085                1090                1095

Glu Ser Asn Ser Phe Trp Asp Thr Ser Pro Leu Leu Leu Gly Lys
    1100                1105                1110

Ser Pro Arg Asp Glu Asp Ser Ser Glu Glu Asp Ser Asp Glu Cys

```
                    1115               1120                1125
Arg Cys Val Ser Gly Arg Cys Val Pro Arg Pro Gly Gly Ala Val
        1130               1135                1140

Cys Glu Cys Pro Gly Gly Phe Gln Leu Asp Ala Ser Arg Ala Arg
        1145               1150                1155

Cys Val Asp Ile Asp Glu Cys Arg Glu Leu Asn Gln Arg Gly Leu
        1160               1165                1170

Leu Cys Lys Ser Glu Arg Cys Val Asn Thr Ser Gly Ser Phe Arg
        1175               1180                1185

Cys Val Cys Lys Ala Gly Phe Thr Arg Ser Arg Pro His Gly Pro
        1190               1195                1200

Ala Cys Leu Ser Ala Ala Ala Asp Asp Ala Ala Ile Ala His Thr
        1205               1210                1215

Ser Val Ile Asp His Arg Gly Tyr Phe His
        1220               1225

<210> SEQ ID NO 46
<211> LENGTH: 1373
<212> TYPE: PRT
<213> ORGANISM: Macaca sp.

<400> SEQUENCE: 46

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Leu Cys His Leu Pro Cys Met Asn Gly
    50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
            100                 105                 110

His Ser Thr His Thr Leu Pro Leu Thr Val Thr Ser Gln Gln Gly Val
        115                 120                 125

Lys Val Lys Phe Pro Pro Asn Ile Val Asn Ile His Val Lys His Pro
    130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
            180                 185                 190

Ser His Gln Gln Val Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255
```

```
Tyr His Gly Tyr Asn Gln Met Met Glu Cys Leu Pro Gly Tyr Lys Arg
            260                 265                 270

Val Asn Asn Thr Phe Cys Gln Asp Ile Asn Glu Cys Gln Leu Gln Gly
            275                 280                 285

Val Cys Pro Asn Gly Glu Cys Leu Asn Thr Met Gly Ser Tyr Arg Cys
            290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
            340                 345                 350

Lys Gln Leu Cys Cys Cys Ser Val Gly Lys Ala Trp Gly Pro His Cys
            355                 360                 365

Glu Lys Cys Pro Leu Pro Gly Thr Ala Ala Phe Lys Glu Ile Cys Pro
            370                 375                 380

Gly Gly Met Gly Tyr Thr Val Ser Gly Val His Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Leu Pro Ala Lys Glu
            420                 425                 430

Glu Pro Val Glu Ala Leu Thr Phe Ser Arg Glu His Gly Pro Gly Val
            435                 440                 445

Ala Glu Pro Glu Val Ala Thr Ala Pro Pro Glu Lys Glu Ile Pro Ser
450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
                485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
            515                 520                 525

Asn Glu Cys Thr Val Asn Pro Asp Ile Cys Gly Ala Gly His Cys Ile
530                 535                 540

Asn Leu Pro Val Arg Tyr Thr Cys Ile Cys Tyr Glu Gly Tyr Lys Phe
545                 550                 555                 560

Ser Glu Gln Gln Arg Lys Cys Val Asp Ile Asp Glu Cys Thr Gln Val
                565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
            595                 600                 605

Cys Ile Asp Val Asp Glu Cys Leu Arg Pro Asp Val Cys Gly Glu Gly
610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
```

```
                    675                 680                 685
Gln Cys Leu Asp Val Asp Glu Cys Leu Glu Pro Asn Val Cys Thr Asn
    690                 695                 700
Gly Asp Cys Ser Asn Leu Glu Gly Ser Tyr Met Cys Ser Cys His Lys
705                 710                 715                 720
Gly Tyr Thr Arg Thr Pro Asp His Lys His Cys Lys Asp Ile Asp Glu
            725                 730                 735
Cys Gln Gln Gly Asn Leu Cys Val Asn Gly Gln Cys Lys Asn Thr Glu
            740                 745                 750
Gly Ser Phe Arg Cys Thr Cys Gly Gln Gly Tyr Gln Leu Ser Ala Ala
            755                 760                 765
Lys Asp Gln Cys Glu Asp Ile Asp Glu Cys Gln His His Leu Cys
770                 775                 780
Ala His Gly Gln Cys Arg Asn Thr Glu Gly Ser Phe Gln Cys Val Cys
785                 790                 795                 800
Asp Gln Gly Tyr Arg Ala Ser Gly Leu Gly Asp His Cys Glu Asp Ile
            805                 810                 815
Asn Glu Cys Leu Glu Asp Lys Ser Val Cys Gln Arg Gly Asp Cys Ile
            820                 825                 830
Asn Thr Ala Gly Ser Tyr Asp Cys Thr Cys Pro Asp Gly Phe Gln Leu
            835                 840                 845
Asp Asp Asn Lys Thr Cys Gln Asp Ile Asn Glu Cys Glu His Pro Gly
850                 855                 860
Leu Cys Gly Pro Gln Gly Glu Cys Leu Asn Thr Glu Gly Ser Phe His
865                 870                 875                 880
Cys Val Cys Gln Gln Gly Phe Ser Ile Ser Ala Asp Gly Arg Thr Cys
                885                 890                 895
Glu Asp Ile Asp Glu Cys Val Asn Asn Thr Val Cys Asp Ser His Gly
            900                 905                 910
Phe Cys Asp Asn Thr Ala Gly Ser Phe Arg Cys Leu Cys Tyr Gln Gly
            915                 920                 925
Phe Gln Ala Pro Gln Asp Gly Gln Gly Cys Val Asp Val Asn Glu Cys
    930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Thr Ser Thr Asp Leu Asp Val Glu
            980                 985                 990
Gln Pro Lys Glu Glu Lys Lys Glu Cys Tyr Tyr Asn Leu Asn Asp Ala
        995                 1000                1005
Ser Leu Cys Asp Asn Val Leu Ala Pro Asn Val Thr Lys Gln Glu
    1010                1015                1020
Cys Cys Cys Thr Ser Gly Ala Gly Trp Gly Asp Asn Cys Glu Ile
    1025                1030                1035
Phe Pro Cys Pro Val Leu Gly Thr Ala Glu Phe Thr Glu Met Cys
    1040                1045                1050
Pro Lys Gly Lys Gly Phe Val Pro Ala Gly Glu Ser Ser Ser Glu
    1055                1060                1065
Ala Gly Gly Glu Asn Tyr Lys Asp Ala Asp Glu Cys Leu Leu Phe
    1070                1075                1080
Gly Gln Glu Ile Cys Lys Asn Gly Phe Cys Leu Asn Thr Arg Pro
    1085                1090                1095
```

Gly Tyr Glu Cys Tyr Cys Lys Gln Gly Thr Tyr Tyr Asp Pro Val
    1100                1105                1110

Lys Leu Gln Cys Phe Asp Met Asp Glu Cys Gln Asp Pro Ser Ser
    1115                1120                1125

Cys Ile Asp Gly Gln Cys Val Asn Thr Glu Gly Ser Tyr Asn Cys
    1130                1135                1140

Phe Cys Thr His Pro Met Val Leu Asp Ala Ser Glu Lys Arg Cys
    1145                1150                1155

Ile Arg Pro Ala Glu Ser Asn Glu Gln Ile Glu Glu Thr Asp Val
    1160                1165                1170

Tyr Gln Asp Leu Cys Trp Glu His Leu Ser Asp Glu Tyr Val Cys
    1175                1180                1185

Ser Arg Pro Leu Val Gly Lys Gln Thr Thr Tyr Thr Glu Cys Cys
    1190                1195                1200

Cys Leu Tyr Gly Glu Ala Trp Gly Met Gln Cys Ala Leu Cys Pro
    1205                1210                1215

Met Lys Asp Ser Asp Asp Tyr Ala Gln Leu Cys Asn Ile Pro Val
    1220                1225                1230

Thr Gly Arg Arg Gln Pro Tyr Gly Arg Asp Ala Leu Val Asp Phe
    1235                1240                1245

Ser Glu Gln Tyr Ala Pro Glu Ala Asp Pro Tyr Phe Ile Gln Asp
    1250                1255                1260

Arg Phe Leu Asn Ser Phe Glu Glu Leu Gln Ala Glu Glu Cys Gly
    1265                1270                1275

Ile Leu Asn Gly Cys Glu Asn Gly Arg Cys Val Arg Val Gln Glu
    1280                1285                1290

Gly Tyr Thr Cys Asp Cys Phe Asp Gly Tyr His Leu Asp Thr Ala
    1295                1300                1305

Lys Met Thr Cys Val Asp Val Asn Glu Cys Asp Glu Leu Asn Asn
    1310                1315                1320

Arg Met Ser Leu Cys Lys Asn Ala Lys Cys Ile Asn Thr Glu Gly
    1325                1330                1335

Ser Tyr Lys Cys Leu Cys Leu Pro Gly Tyr Val Pro Ser Asp Lys
    1340                1345                1350

Pro Asn Tyr Cys Thr Pro Leu Asn Thr Ala Leu Asn Leu Glu Lys
    1355                1360                1365

Asp Ser Asp Leu Glu
    1370

<210> SEQ ID NO 47
<211> LENGTH: 1374
<212> TYPE: PRT
<213> ORGANISM: Mus sp.

<400> SEQUENCE: 47

Asn His Thr Gly Arg Ile Lys Val Val Phe Thr Pro Ser Ile Cys Lys
1               5                   10                  15

Val Thr Cys Thr Lys Gly Asn Cys Gln Asn Ser Cys Gln Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Ile Cys His Leu Pro Cys Met Asn Gly
        50                  55                  60

Gly Gln Cys Ser Ser Arg Asp Lys Cys Gln Cys Pro Pro Asn Phe Thr

```
                65                  70                  75                  80

Gly Lys Leu Cys Gln Ile Pro Val Leu Gly Ala Ser Met Pro Lys Leu
                            85                  90                  95

Tyr Gln His Ala Gln Gln Gly Lys Ala Leu Gly Ser His Val Ile
                        100                 105                 110

His Ser Thr His Thr Leu Pro Leu Thr Met Thr Ser Gln Gln Gly Val
                    115                 120                 125

Lys Val Lys Phe Pro Pro Asn Ile Val Asn Ile His Val Lys His Pro
                130                 135                 140

Pro Glu Ala Ser Val Gln Ile His Gln Val Ser Arg Ile Asp Ser Pro
        145                 150                 155                 160

Gly Gly Gln Lys Val Lys Glu Ala Gln Pro Gly Gln Ser Gln Val Ser
                        165                 170                 175

Tyr Gln Gly Leu Pro Val Gln Lys Thr Gln Thr Val His Ser Thr Tyr
                    180                 185                 190

Ser His Gln Gln Leu Ile Pro His Val Tyr Pro Val Ala Ala Lys Thr
                195                 200                 205

Gln Leu Gly Arg Cys Phe Gln Glu Thr Ile Gly Ser Gln Cys Gly Lys
            210                 215                 220

Ala Leu Pro Gly Leu Ser Lys Gln Glu Asp Cys Cys Gly Thr Val Gly
        225                 230                 235                 240

Thr Ser Trp Gly Phe Asn Lys Cys Gln Lys Cys Pro Lys Lys Gln Ser
                        245                 250                 255

Tyr His Gly Tyr Thr Gln Met Met Glu Cys Leu Gln Gly Tyr Lys Arg
                    260                 265                 270

Val Asn Asn Thr Phe Cys Gln Asp Ile Asn Glu Cys Gln Leu Gln Gly
                275                 280                 285

Val Cys Pro Asn Gly Glu Cys Leu Asn Thr Met Gly Ser Tyr Arg Cys
            290                 295                 300

Ser Cys Lys Met Gly Phe Gly Pro Asp Pro Thr Phe Ser Ser Cys Val
        305                 310                 315                 320

Pro Asp Pro Pro Val Ile Ser Glu Glu Lys Gly Pro Cys Tyr Arg Leu
                        325                 330                 335

Val Ser Pro Gly Arg His Cys Met His Pro Leu Ser Val His Leu Thr
                    340                 345                 350

Lys Gln Ile Cys Cys Cys Ser Val Gly Lys Ala Trp Gly Pro His Cys
                355                 360                 365

Glu Lys Cys Pro Leu Pro Gly Thr Ala Ala Phe Lys Glu Ile Cys Pro
            370                 375                 380

Gly Gly Met Gly Tyr Thr Val Ser Gly Val His Arg Arg Arg Pro Ile
        385                 390                 395                 400

His Gln His Ile Gly Lys Glu Ala Val Tyr Val Lys Pro Lys Asn Thr
                        405                 410                 415

Gln Pro Val Ala Lys Ser Thr His Pro Pro Leu Pro Ala Lys Glu
                    420                 425                 430

Glu Pro Val Glu Ala Leu Thr Ser Ser Trp Glu His Gly Pro Arg Gly
                435                 440                 445

Ala Glu Pro Glu Val Val Thr Ala Pro Glu Lys Glu Ile Pro Ser
            450                 455                 460

Leu Asp Gln Glu Lys Thr Arg Leu Glu Pro Gly Gln Pro Gln Leu Ser
        465                 470                 475                 480

Pro Gly Val Ser Thr Ile His Leu His Pro Gln Phe Pro Val Val Val
                        485                 490                 495
```

```
Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
            515                 520                 525

Asn Glu Cys Thr Val Asn Pro Asp Ile Cys Gly Ala Gly His Cys Ile
            530                 535                 540

Asn Leu Pro Val Arg Tyr Thr Cys Ile Cys Tyr Glu Gly Tyr Lys Phe
545                 550                 555                 560

Ser Glu Gln Leu Arg Lys Cys Val Asp Ile Asp Glu Cys Ala Gln Val
            565                 570                 575

Arg His Leu Cys Ser Gln Gly Arg Cys Glu Asn Thr Glu Gly Ser Phe
            580                 585                 590

Leu Cys Val Cys Pro Ala Gly Phe Met Ala Ser Glu Glu Gly Thr Asn
            595                 600                 605

Cys Ile Asp Val Asp Glu Cys Leu Arg Pro Asp Met Cys Arg Asp Gly
            610                 615                 620

Arg Cys Ile Asn Thr Ala Gly Ala Phe Arg Cys Glu Tyr Cys Asp Ser
625                 630                 635                 640

Gly Tyr Arg Met Ser Arg Arg Gly Tyr Cys Glu Asp Ile Asp Glu Cys
            645                 650                 655

Leu Lys Pro Ser Thr Cys Pro Glu Glu Gln Cys Val Asn Thr Pro Gly
            660                 665                 670

Ser Tyr Gln Cys Val Pro Cys Thr Glu Gly Phe Arg Gly Trp Asn Gly
            675                 680                 685

Gln Cys Leu Asp Val Asp Glu Cys Leu Gln Pro Lys Val Cys Thr Asn
            690                 695                 700

Gly Ser Cys Thr Asn Leu Glu Gly Ser Tyr Met Cys Ser Cys His Arg
705                 710                 715                 720

Gly Tyr Ser Pro Thr Pro Asp His Arg His Cys Gln Asp Ile Asp Glu
            725                 730                 735

Cys Gln Gln Gly Asn Leu Cys Met Asn Gly Gln Cys Arg Asn Thr Asp
            740                 745                 750

Gly Ser Phe Arg Cys Thr Cys Gly Gln Gly Tyr Gln Leu Ser Ala Ala
            755                 760                 765

Lys Asp Gln Cys Glu Asp Ile Asp Glu Cys Glu His His Leu Cys
770                 775                 780

Ser His Gly Gln Cys Arg Asn Thr Glu Gly Ser Phe Gln Cys Val Cys
785                 790                 795                 800

Asn Gln Gly Tyr Arg Ala Ser Val Leu Gly Asp His Cys Glu Asp Ile
            805                 810                 815

Asn Glu Cys Leu Glu Asp Ser Ser Val Cys Gln Gly Gly Asp Cys Ile
            820                 825                 830

Asn Thr Ala Gly Ser Tyr Asp Cys Thr Cys Pro Asp Gly Phe Gln Leu
            835                 840                 845

Asn Asp Asn Lys Gly Cys Gln Asp Ile Asn Glu Cys Ala Gln Pro Gly
            850                 855                 860

Leu Cys Gly Ser His Gly Glu Cys Leu Asn Thr Gln Gly Ser Phe His
865                 870                 875                 880

Cys Val Cys Glu Gln Gly Phe Ser Ile Ser Ala Asp Gly Arg Thr Cys
            885                 890                 895

Glu Asp Ile Asp Glu Cys Val Asn Asn Thr Val Cys Asp Ser His Gly
            900                 905                 910
```

```
                -continued

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
945                 950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Val Thr Glu Asp Ser Gly Val Asp
            980                 985                 990

Arg Gln Pro Arg Glu Glu Lys Lys Glu Cys Tyr Tyr Asn Leu Asn Asp
        995                 1000                1005

Ala Ser Leu Cys Asp Asn Val Leu Ala Pro Asn Val Thr Lys Gln
    1010                1015                1020

Glu Cys Cys Cys Thr Ser Gly Ala Gly Trp Gly Asp Asn Cys Glu
    1025                1030                1035

Ile Phe Pro Cys Pro Val Gln Gly Thr Ala Glu Phe Thr Glu Met
    1040                1045                1050

Cys Pro Arg Gly Lys Gly Leu Val Pro Ala Gly Glu Ser Ser Tyr
    1055                1060                1065

Asp Thr Gly Gly Glu Asn Tyr Lys Asp Ala Asp Glu Cys Leu Leu
    1070                1075                1080

Phe Gly Glu Glu Ile Cys Lys Asn Gly Tyr Cys Leu Asn Thr Gln
    1085                1090                1095

Pro Gly Tyr Glu Cys Tyr Cys Lys Gln Gly Thr Tyr Tyr Asp Pro
    1100                1105                1110

Val Lys Leu Gln Cys Phe Asp Met Asp Glu Cys Gln Asp Pro Asn
    1115                1120                1125

Ser Cys Ile Asp Gly Gln Cys Val Asn Thr Glu Gly Ser Tyr Asn
    1130                1135                1140

Cys Phe Cys Thr His Pro Met Val Leu Asp Ala Ser Glu Lys Arg
    1145                1150                1155

Cys Val Gln Pro Thr Glu Ser Asn Glu Gln Ile Glu Glu Thr Asp
    1160                1165                1170

Val Tyr Gln Asp Leu Cys Trp Glu His Leu Ser Glu Glu Tyr Val
    1175                1180                1185

Cys Ser Arg Pro Leu Val Gly Lys Gln Thr Thr Tyr Thr Glu Cys
    1190                1195                1200

Cys Cys Leu Tyr Gly Glu Ala Trp Gly Met Gln Cys Ala Leu Cys
    1205                1210                1215

Pro Met Lys Asp Ser Asp Tyr Ala Gln Leu Cys Asn Ile Pro
    1220                1225                1230

Val Thr Gly Arg Arg Arg Pro Tyr Gly Arg Asp Ala Leu Val Asp
    1235                1240                1245

Phe Ser Glu Gln Tyr Gly Pro Glu Thr Asp Pro Tyr Phe Ile Gln
    1250                1255                1260

Asp Arg Phe Leu Asn Ser Phe Glu Glu Leu Gln Ala Glu Glu Cys
    1265                1270                1275

Gly Ile Leu Asn Gly Cys Glu Asn Gly Arg Cys Val Arg Val Gln
    1280                1285                1290

Glu Gly Tyr Thr Cys Asp Cys Phe Asp Gly Tyr His Leu Asp Met
    1295                1300                1305

Ala Lys Met Thr Cys Val Asp Val Asn Glu Cys Ser Glu Leu Asn
```

```
                1310                1315                1320
Asn Arg Met Ser Leu Cys Lys Asn Ala Lys Cys Ile Asn Thr Glu
    1325                1330                1335

Gly Ser Tyr Lys Cys Leu Cys Leu Pro Gly Tyr Ile Pro Ser Asp
    1340                1345                1350

Lys Pro Asn Tyr Cys Thr Pro Leu Asn Ser Ala Leu Asn Leu Asp
    1355                1360                1365

Lys Glu Ser Asp Leu Glu
    1370

<210> SEQ ID NO 48
<211> LENGTH: 646
<212> TYPE: PRT
<213> ORGANISM: Mus sp.

<400> SEQUENCE: 48

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
                20                  25                  30

Leu Asp Ile Gln Ala Leu Tyr Leu Ser Gly Asn Gln Leu Gln Ser Ile
            35                  40                  45

Leu Val Ser Pro Leu Gly Phe Tyr Thr Ala Leu Arg His Leu Asp Leu
        50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
                100                 105                 110

Leu Asp Leu Ser Gly Asn Ser Leu His Gly Asn Leu Val Glu Arg Leu
            115                 120                 125

Leu Gly Glu Thr Pro Arg Leu Arg Thr Leu Ser Leu Ala Glu Asn Ser
        130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
                180                 185                 190

Leu Thr Cys Ile Ser Asp Phe Ser Leu Gln Gln Leu Gln Val Leu Asp
            195                 200                 205

Leu Ser Cys Asn Ser Ile Glu Ala Phe Gln Thr Ala Pro Glu Pro Gln
        210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
                260                 265                 270

Asp Leu His Ala Pro Ser Glu Gly Trp Ser Ala Ser Pro Leu Ser Asn
            275                 280                 285

Pro Ser Arg Asn Ala Ser Thr His Pro Leu Ser Gln Leu Leu Asn Leu
        290                 295                 300
```

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
            325                 330                 335

Ser Phe Glu Ala Arg Gln Val Asp Ser Leu Pro Cys Leu Val Leu Leu
        340                 345                 350

Asp Leu Ser His Asn Val Leu Glu Ala Leu Glu Leu Gly Thr Lys Val
    355                 360                 365

Leu Gly Ser Leu Gln Thr Leu Leu Gln Asp Asn Ala Leu Gln Glu
370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
            405                 410                 415

Pro Pro Gly Cys Val Asp Phe Ser Gly Ile Pro Thr Leu His Val Leu
            420                 425                 430

Asn Met Ala Gly Asn Ser Met Gly Met Leu Arg Ala Gly Ser Phe Leu
        435                 440                 445

His Thr Pro Leu Thr Glu Leu Asp Leu Ser Thr Asn Pro Gly Leu Asp
450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
            485                 490                 495

Phe Leu Arg Leu Lys Arg Leu Asn Leu Ala Glu Asn Gln Leu Ser His
        500                 505                 510

Leu Pro Ala Trp Thr Arg Ala Val Ser Leu Glu Val Leu Asp Leu Arg
        515                 520                 525

Asn Asn Ser Phe Ser Leu Leu Pro Gly Asn Ala Met Gly Gly Leu Glu
530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
            565                 570                 575

Asp Ala Thr Gln Asp Leu Ile Cys Arg Phe Gly Ser Gln Glu Glu Leu
        580                 585                 590

Ser Leu Ser Leu Val Arg Pro Glu Asp Cys Glu Lys Gly Gly Leu Lys
        595                 600                 605

Asn Val Asn Leu Ile Leu Leu Ser Phe Thr Leu Val Ser Ala Ile
    610                 615                 620

Val Leu Thr Thr Leu Ala Thr Ile Cys Phe Leu Arg Arg Gln Lys Leu
625                 630                 635                 640

Ser Gln Gln Tyr Lys Ala
            645

<210> SEQ ID NO 49
<211> LENGTH: 611
<212> TYPE: PRT
<213> ORGANISM: Mus sp.

<400> SEQUENCE: 49

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
            20                  25                  30

```
Leu Asp Ile Gln Ala Leu Tyr Leu Ser Gly Asn Gln Leu Gln Ser Ile
         35                  40                  45

Leu Val Ser Pro Leu Gly Phe Tyr Thr Ala Leu Arg His Leu Asp Leu
 50                  55                  60

Ser Asp Asn Gln Ile Ser Phe Leu Gln Ala Gly Val Phe Gln Ala Leu
 65                  70                  75                  80

Pro Tyr Leu Glu His Leu Asn Leu Ala His Asn Arg Leu Ala Thr Gly
                 85                  90                  95

Met Ala Leu Asn Ser Gly Leu Gly Arg Leu Pro Leu Leu Val Ser
                100                 105                 110

Leu Asp Leu Ser Gly Asn Ser Leu His Gly Asn Leu Val Glu Arg Leu
                115                 120                 125

Leu Gly Glu Thr Pro Arg Leu Arg Thr Leu Ser Leu Ala Glu Asn Ser
    130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
                180                 185                 190

Leu Thr Cys Ile Ser Asp Phe Ser Leu Gln Gln Leu Gln Val Leu Asp
                195                 200                 205

Leu Ser Cys Asn Ser Ile Glu Ala Phe Gln Thr Ala Pro Glu Pro Gln
    210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
                260                 265                 270

Asp Leu His Ala Pro Ser Glu Gly Trp Ser Ala Ser Pro Leu Ser Asn
    275                 280                 285

Pro Ser Arg Asn Ala Ser Thr His Pro Leu Ser Gln Leu Leu Asn Leu
    290                 295                 300

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
                325                 330                 335

Ser Phe Glu Ala Arg Gln Val Asp Ser Leu Pro Cys Leu Val Leu Leu
                340                 345                 350

Asp Leu Ser His Asn Val Leu Glu Ala Leu Glu Leu Gly Thr Lys Val
    355                 360                 365

Leu Gly Ser Leu Gln Thr Leu Leu Leu Gln Asp Asn Ala Leu Gln Glu
    370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
                405                 410                 415

Pro Pro Gly Cys Val Asp Phe Ser Gly Ile Pro Thr Leu His Val Leu
                420                 425                 430

Asn Met Ala Gly Asn Ser Met Gly Met Leu Arg Ala Gly Ser Phe Leu
                435                 440                 445
```

-continued

```
His Thr Pro Leu Thr Glu Leu Asp Leu Ser Thr Asn Pro Gly Leu Asp
    450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
                500                 505                 510

Leu Pro Ala Trp Thr Arg Ala Val Ser Leu Glu Val Leu Asp Leu Arg
                515                 520                 525

Asn Asn Ser Phe Ser Leu Leu Pro Gly Asn Ala Met Gly Gly Leu Glu
530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Leu
                580                 585                 590

Ser Leu Ser Leu Val Arg Pro Glu Asp Cys Glu Lys Gly Gly Leu Lys
                595                 600                 605

Asn Val Asn
    610

<210> SEQ ID NO 50
<211> LENGTH: 1375
<212> TYPE: PRT
<213> ORGANISM: Unknown
<220> FEATURE:
<221> NAME/KEY: source
<223> OTHER INFORMATION: /note="Description of Unknown:
      LTBP1S sequence"

<400> SEQUENCE: 50

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Ile Cys His Leu Pro Cys Met Asn Gly
    50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
                100                 105                 110

His Ser Thr His Thr Leu Pro Leu Thr Val Thr Ser Gln Gln Gly Val
            115                 120                 125

Lys Val Lys Phe Pro Pro Asn Ile Val Asn Ile His Val Lys His Pro
        130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
```

```
                180             185             190
Ser His Gln Gln Val Ile Pro His Val Tyr Pro Val Ala Ala Lys Thr
                195                 200                 205
Gln Leu Gly Arg Cys Phe Gln Glu Thr Ile Gly Ser Gln Cys Gly Lys
                210                 215                 220
Ala Leu Pro Gly Leu Ser Lys Gln Glu Asp Cys Cys Gly Thr Val Gly
225                 230                 235                 240
Thr Ser Trp Gly Phe Asn Lys Cys Gln Lys Cys Pro Lys Lys Pro Ser
                245                 250                 255
Tyr His Gly Tyr Asn Gln Met Met Glu Cys Leu Pro Gly Tyr Lys Arg
                260                 265                 270
Val Asn Asn Thr Phe Cys Gln Asp Ile Asn Glu Cys Gln Leu Gln Gly
                275                 280                 285
Val Cys Pro Asn Gly Glu Cys Leu Asn Thr Met Gly Ser Tyr Arg Cys
                290                 295                 300
Thr Cys Lys Ile Gly Phe Gly Pro Asp Pro Thr Phe Ser Ser Cys Val
305                 310                 315                 320
Pro Asp Pro Pro Val Ile Ser Glu Glu Lys Gly Pro Cys Tyr Arg Leu
                325                 330                 335
Val Ser Ser Gly Arg Gln Cys Met His Pro Leu Ser Val His Leu Thr
                340                 345                 350
Lys Gln Leu Cys Cys Cys Ser Val Gly Lys Ala Trp Gly Pro His Cys
                355                 360                 365
Glu Lys Cys Pro Leu Pro Gly Thr Ala Ala Phe Lys Glu Ile Cys Pro
                370                 375                 380
Gly Gly Met Gly Tyr Thr Val Ser Gly Val His Arg Arg Arg Pro Ile
385                 390                 395                 400
His His His Val Gly Lys Gly Pro Val Phe Val Lys Pro Lys Asn Thr
                405                 410                 415
Gln Pro Val Ala Lys Ser Thr His Pro Pro Leu Pro Ala Lys Glu
                420                 425                 430
Glu Pro Val Glu Ala Leu Thr Phe Ser Arg Glu His Gly Pro Gly Val
                435                 440                 445
Ala Glu Pro Glu Val Ala Thr Ala Pro Pro Glu Lys Glu Ile Pro Ser
                450                 455                 460
Leu Asp Gln Glu Lys Thr Lys Leu Glu Pro Gly Gln Pro Gln Leu Ser
465                 470                 475                 480
Pro Gly Ile Ser Thr Ile His Leu His Pro Gln Phe Pro Val Val Ile
                485                 490                 495
Glu Lys Thr Ser Pro Pro Val Pro Val Glu Val Ala Pro Glu Ala Ser
                500                 505                 510
Thr Ser Ser Ala Ser Gln Val Ile Ala Pro Thr Gln Val Thr Glu Ile
                515                 520                 525
Asn Glu Cys Thr Val Asn Pro Asp Ile Cys Gly Ala Gly His Cys Ile
                530                 535                 540
Asn Leu Pro Val Arg Tyr Thr Cys Ile Cys Tyr Glu Gly Tyr Arg Phe
545                 550                 555                 560
Ser Glu Gln Gln Arg Lys Cys Val Asp Ile Asp Glu Cys Thr Gln Val
                565                 570                 575
Gln His Leu Cys Ser Gln Gly Arg Cys Glu Asn Thr Glu Gly Ser Phe
                580                 585                 590
Leu Cys Ile Cys Pro Ala Gly Phe Met Ala Ser Glu Glu Gly Thr Asn
                595                 600                 605
```

```
Cys Ile Asp Val Asp Glu Cys Leu Arg Pro Asp Val Cys Gly Glu Gly
        610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
                660                 665                 670

Ser Tyr Gln Cys Val Pro Cys Thr Glu Gly Phe Arg Gly Trp Asn Gly
            675                 680                 685

Gln Cys Leu Asp Val Asp Glu Cys Leu Glu Pro Asn Val Cys Ala Asn
        690                 695                 700

Gly Asp Cys Ser Asn Leu Glu Gly Ser Tyr Met Cys Ser Cys His Lys
705                 710                 715                 720

Gly Tyr Thr Arg Thr Pro Asp His Lys His Cys Arg Asp Ile Asp Glu
                725                 730                 735

Cys Gln Gln Gly Asn Leu Cys Val Asn Gly Gln Cys Lys Asn Thr Glu
                740                 745                 750

Gly Ser Phe Arg Cys Thr Cys Gly Gln Gly Tyr Gln Leu Ser Ala Ala
            755                 760                 765

Lys Asp Gln Cys Glu Asp Ile Asp Glu Cys Gln His Arg His Leu Cys
770                 775                 780

Ala His Gly Gln Cys Arg Asn Thr Glu Gly Ser Phe Gln Cys Val Cys
785                 790                 795                 800

Asp Gln Gly Tyr Arg Ala Ser Gly Leu Gly Asp His Cys Glu Asp Ile
                805                 810                 815

Asn Glu Cys Leu Glu Asp Lys Ser Val Cys Gln Arg Gly Asp Cys Ile
                820                 825                 830

Asn Thr Ala Gly Ser Tyr Asp Cys Thr Cys Pro Asp Gly Phe Gln Leu
            835                 840                 845

Asp Asp Asn Lys Thr Cys Gln Asp Ile Asn Glu Cys Glu His Pro Gly
        850                 855                 860

Leu Cys Gly Pro Gln Gly Glu Cys Leu Asn Thr Glu Gly Ser Phe His
865                 870                 875                 880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
        930                 935                 940

Glu Leu Leu Ser Gly Val Cys Gly Glu Ala Phe Cys Glu Asn Val Glu
945                 950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Thr Ser Thr Asp Leu Asp Val Asp
                980                 985                 990

Val Asp Gln Pro Lys Glu Glu Lys  Lys Glu Cys Tyr Tyr  Asn Leu Asn
            995                 1000                1005

Asp Ala  Ser Leu Cys Asp Asn  Val Leu Ala Pro Asn  Val Thr Lys
        1010                1015                1020
```

-continued

Gln Glu Cys Cys Cys Thr Ser Gly Val Gly Trp Gly Asp Asn Cys
1025                1030                1035

Glu Ile Phe Pro Cys Pro Val Leu Gly Thr Ala Glu Phe Thr Glu
1040                1045                1050

Met Cys Pro Lys Gly Lys Gly Phe Val Pro Ala Gly Glu Ser Ser
1055                1060                1065

Ser Glu Ala Gly Gly Glu Asn Tyr Lys Asp Ala Asp Glu Cys Leu
1070                1075                1080

Leu Phe Gly Gln Glu Ile Cys Lys Asn Gly Phe Cys Leu Asn Thr
1085                1090                1095

Arg Pro Gly Tyr Glu Cys Tyr Cys Lys Gln Gly Thr Tyr Tyr Asp
1100                1105                1110

Pro Val Lys Leu Gln Cys Phe Asp Met Asp Glu Cys Gln Asp Pro
1115                1120                1125

Ser Ser Cys Ile Asp Gly Gln Cys Val Asn Thr Glu Gly Ser Tyr
1130                1135                1140

Asn Cys Phe Cys Thr His Pro Met Val Leu Asp Ala Ser Glu Lys
1145                1150                1155

Arg Cys Ile Arg Pro Ala Glu Ser Asn Glu Gln Ile Glu Glu Thr
1160                1165                1170

Asp Val Tyr Gln Asp Leu Cys Trp Glu His Leu Ser Asp Glu Tyr
1175                1180                1185

Val Cys Ser Arg Pro Leu Val Gly Lys Gln Thr Thr Tyr Thr Glu
1190                1195                1200

Cys Cys Cys Leu Tyr Gly Glu Ala Trp Gly Met Gln Cys Ala Leu
1205                1210                1215

Cys Pro Leu Lys Asp Ser Asp Asp Tyr Ala Gln Leu Cys Asn Ile
1220                1225                1230

Pro Val Thr Gly Arg Arg Gln Pro Tyr Gly Arg Asp Ala Leu Val
1235                1240                1245

Asp Phe Ser Glu Gln Tyr Thr Pro Glu Ala Asp Pro Tyr Phe Ile
1250                1255                1260

Gln Asp Arg Phe Leu Asn Ser Phe Glu Glu Leu Gln Ala Glu Glu
1265                1270                1275

Cys Gly Ile Leu Asn Gly Cys Glu Asn Gly Arg Cys Val Arg Val
1280                1285                1290

Gln Glu Gly Tyr Thr Cys Asp Cys Phe Asp Gly Tyr His Leu Asp
1295                1300                1305

Thr Ala Lys Met Thr Cys Val Asp Val Asn Glu Cys Asp Glu Leu
1310                1315                1320

Asn Asn Arg Met Ser Leu Cys Lys Asn Ala Lys Cys Ile Asn Thr
1325                1330                1335

Asp Gly Ser Tyr Lys Cys Leu Cys Leu Pro Gly Tyr Val Pro Ser
1340                1345                1350

Asp Lys Pro Asn Tyr Cys Thr Pro Leu Asn Thr Ala Leu Asn Leu
1355                1360                1365

Glu Lys Asp Ser Asp Leu Glu
1370                1375

<210> SEQ ID NO 51
<211> LENGTH: 1260
<212> TYPE: PRT
<213> ORGANISM: Unknown
<220> FEATURE:
<221> NAME/KEY: source
<223> OTHER INFORMATION: /note="Description of Unknown: LTBP3 sequence"

<400> SEQUENCE: 51

```
Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
            35                  40                  45

Leu Ile Gly Glu Asn Gly His Ser Thr Asp Thr Leu Thr Gly Ser Gly
        50                  55                  60

Phe Arg Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Thr Gly Gly Ser Gly
                100                 105                 110

Pro Gly Leu Ser Arg Thr Gly Ala Leu Ser Thr Gly Ala Leu Pro Pro
            115                 120                 125

Leu Ala Pro Glu Gly Asp Ser Val Ala Ser Lys His Ala Ile Tyr Ala
        130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
                180                 185                 190

Pro Glu Ala Ser Val Gln Val His Arg Ile Glu Ser Ser Asn Ala Glu
            195                 200                 205

Ser Ala Ala Pro Ser Gln His Leu Leu Pro His Pro Lys Pro Ser His
210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
                260                 265                 270

Cys His Lys Cys Pro Gln Leu Gln Tyr Thr Gly Val Gln Lys Pro Gly
            275                 280                 285

Pro Val Arg Gly Glu Val Gly Ala Asp Cys Pro Gln Gly Tyr Lys Arg
        290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile
                340                 345                 350

Ala Asp Lys Pro Glu Glu Lys Ser Leu Cys Phe Arg Leu Val Ser Pro
            355                 360                 365

Glu His Gln Cys Gln His Pro Leu Thr Thr Arg Leu Thr Arg Gln Leu
        370                 375                 380

Cys Cys Cys Ser Val Gly Lys Ala Trp Gly Ala Arg Cys Gln Arg Cys
385                 390                 395                 400
```

```
Pro Thr Asp Gly Thr Ala Ala Phe Lys Glu Ile Cys Pro Ala Gly Lys
            405                 410                 415

Gly Tyr His Ile Leu Thr Ser His Gln Thr Leu Thr Ile Gln Gly Glu
            420                 425                 430

Ser Asp Phe Ser Leu Phe Leu His Pro Asp Gly Pro Pro Lys Pro Gln
            435                 440                 445

Gln Leu Pro Glu Ser Pro Ser Gln Ala Pro Pro Glu Asp Thr Glu
450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Pro Ala Arg Pro Tyr
            485                 490                 495

Pro Glu Leu Ile Ser Arg Pro Ser Pro Pro Thr Met Arg Trp Phe Leu
            500                 505                 510

Pro Asp Leu Pro Pro Ser Arg Ser Ala Val Glu Ile Ala Pro Thr Gln
            515                 520                 525

Val Thr Glu Thr Asp Glu Cys Arg Leu Asn Gln Asn Ile Cys Gly His
            530                 535                 540

Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
            565                 570                 575

Cys Glu Ala Glu Pro Cys Gly Pro Gly Arg Gly Ile Cys Met Asn Thr
            580                 585                 590

Gly Gly Ser Tyr Asn Cys His Cys Asn Arg Gly Tyr Arg Leu His Val
            595                 600                 605

Gly Ala Gly Gly Arg Ser Cys Val Asp Leu Asn Glu Cys Ala Lys Pro
610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
            645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
            675                 680                 685

Pro Gly Tyr Arg Ser Gln Gly Gly Ala Cys Arg Asp Val Asn Glu
            690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
            725                 730                 735

Gly Arg Ser Cys Leu Asp Val Asp Glu Cys Glu Ala Gly Asp Val Cys
            740                 745                 750

Asp Asn Gly Ile Cys Ser Asn Thr Pro Gly Ser Phe Gln Cys Gln Cys
            755                 760                 765

Leu Ser Gly Tyr His Leu Ser Arg Asp Arg Ser His Cys Glu Asp Ile
            770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
            805                 810                 815
```

```
Gly Gly Arg Lys Cys Gln Asp Ile Asp Glu Cys Ser Gln Asp Pro Ser
            820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
    850                 855                 860

Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
            915                 920                 925

Pro Asp Gly Lys Gly Tyr Thr Gln Asp Asn Asn Ile Val Asn Tyr Gly
        930                 935                 940

Ile Pro Ala His Arg Asp Ile Asp Glu Cys Met Leu Phe Gly Ser Glu
945                 950                 955                 960

Ile Cys Lys Glu Gly Lys Cys Val Asn Thr Gln Pro Gly Tyr Glu Cys
                965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu  Ser Asn Cys Arg Asn  Gly Val Cys
            995                 1000                1005

Glu Asn  Thr Arg Gly Gly Tyr  Arg Cys Ala Cys Thr  Pro Pro Ala
1010                1015                1020

Glu Tyr  Ser Pro Ala Gln Arg  Gln Cys Leu Ser Pro  Glu Glu Met
        1025                1030                1035

Asp Val  Asp Glu Cys Gln Asp  Pro Ala Ala Cys Arg  Pro Gly Arg
1040                1045                1050

Cys Val  Asn Leu Pro Gly Ser  Tyr Arg Cys Glu Cys  Arg Pro Pro
    1055                1060                1065

Trp Val  Pro Gly Pro Ser Gly  Arg Asp Cys Gln Leu  Pro Glu Ser
        1070                1075                1080

Pro Ala  Glu Arg Ala Pro Glu  Arg Arg Asp Val Cys  Trp Ser Gln
        1085                1090                1095

Arg Gly  Glu Asp Gly Met Cys  Ala Gly Pro Leu Ala  Gly Pro Ala
        1100                1105                1110

Leu Thr  Phe Asp Asp Cys Cys  Cys Arg Gln Gly Arg  Gly Trp Gly
        1115                1120                1125

Ala Gln  Cys Arg Pro Cys Pro  Pro Arg Gly Ala Gly  Ser His Cys
        1130                1135                1140

Pro Thr  Ser Gln Ser Glu Ser  Asn Ser Phe Trp Asp  Thr Ser Pro
        1145                1150                1155

Leu Leu  Leu Gly Lys Pro Pro  Arg Asp Glu Asp Ser  Ser Glu Glu
        1160                1165                1170

Asp Ser  Asp Glu Cys Arg Cys  Val Ser Gly Arg Cys  Val Pro Arg
        1175                1180                1185

Pro Gly  Gly Ala Val Cys Glu  Cys Pro Gly Gly Phe  Gln Leu Asp
        1190                1195                1200

Ala Ser  Arg Ala Arg Cys Val  Asp Ile Asp Glu Cys  Arg Glu Leu
        1205                1210                1215

Asn Gln  Arg Gly Leu Leu Cys  Lys Ser Glu Arg Cys  Val Asn Thr
```

```
                    1220                1225                 1230
Ser Gly Ser Phe Arg Cys Val Cys Lys Ala Gly Phe Ala Arg Ser
            1235                1240                1245

Arg Pro His Gly Ala Cys Val Pro Gln Arg Arg
    1250                1255                1260

<210> SEQ ID NO 52
<211> LENGTH: 645
<212> TYPE: PRT
<213> ORGANISM: Unknown
<220> FEATURE:
<221> NAME/KEY: source
<223> OTHER INFORMATION: /note="Description of Unknown:
      GARP sequence"

<400> SEQUENCE: 52

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
            20                  25                  30

Asp Thr Glu Thr Leu Asp Leu Ser Gly Asn Gln Leu Arg Ser Ile Leu
        35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125

Gly Glu Ala Pro Ser Leu His Thr Leu Ser Leu Ala Glu Asn Ser Leu
130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
            260                 265                 270

Ile His Ala Pro Ser Glu Gly Trp Ser Ala Leu Pro Leu Ser Ala Pro
        275                 280                 285

Ser Gly Asn Ala Ser Gly Arg Pro Leu Ser Gln Leu Leu Asn Leu Asp
290                 295                 300

Leu Ser Tyr Asn Glu Ile Glu Leu Ile Pro Asp Ser Phe Leu Glu His
305                 310                 315                 320
```

```
Leu Thr Ser Leu Cys Phe Leu Asn Leu Ser Arg Asn Cys Leu Arg Thr
            325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
            355                 360                 365

Gly Ser Leu Arg Thr Leu Leu Leu Gln Gly Asn Ala Leu Arg Asp Leu
            370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
            405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
            435                 440                 445

Thr Pro Leu Thr Glu Leu Asp Leu Ser Ser Asn Pro Gly Leu Glu Val
            450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
            485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
            515                 520                 525

Asn Ser Phe Ser Leu Leu Pro Gly Ser Ala Met Gly Gly Leu Glu Thr
            530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
            565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
            595                 600                 605

Ile Asn Leu Ile Ile Ile Leu Thr Phe Ile Leu Val Ser Ala Ile Leu
            610                 615                 620

Leu Thr Thr Leu Ala Ala Cys Cys Cys Val Arg Arg Gln Lys Phe Asn
625                 630                 635                 640

Gln Gln Tyr Lys Ala
            645

<210> SEQ ID NO 53
<211> LENGTH: 610
<212> TYPE: PRT
<213> ORGANISM: Unknown
<220> FEATURE:
<221> NAME/KEY: source
<223> OTHER INFORMATION: /note="Description of Unknown:
      sGARP sequence"

<400> SEQUENCE: 53

Ala Gln His Gln Asp Lys Val Pro Cys Lys Met Val Asp Lys Lys Val
1               5                   10                  15
```

-continued

```
Ser Cys Gln Val Leu Gly Leu Leu Gln Val Pro Ser Val Pro Pro
             20                  25                  30

Asp Thr Glu Thr Leu Asp Leu Ser Gly Asn Gln Leu Arg Ser Ile Leu
         35                  40                  45

Ala Ser Pro Leu Gly Phe Tyr Thr Ala Leu Arg His Leu Asp Leu Ser
     50                  55                  60

Thr Asn Glu Ile Ser Phe Leu Gln Pro Gly Ala Phe Gln Ala Leu Thr
 65                  70                  75                  80

His Leu Glu His Leu Ser Leu Ala His Asn Arg Leu Ala Met Ala Thr
                 85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125

Gly Glu Ala Pro Ser Leu His Thr Leu Ser Leu Ala Glu Asn Ser Leu
    130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
    210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
            260                 265                 270

Ile His Ala Pro Ser Glu Gly Trp Ser Ala Leu Pro Leu Ser Ala Pro
        275                 280                 285

Ser Gly Asn Ala Ser Gly Arg Pro Leu Ser Gln Leu Leu Asn Leu Asp
    290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
        355                 360                 365

Gly Ser Leu Arg Thr Leu Leu Leu Gln Gly Asn Ala Leu Arg Asp Leu
    370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
```

```
                435                 440                 445
Thr Pro Leu Thr Glu Leu Asp Leu Ser Ser Asn Pro Gly Leu Glu Val
    450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
        515                 520                 525

Asn Ser Phe Ser Leu Leu Pro Gly Ser Ala Met Gly Gly Leu Glu Thr
    530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
        595                 600                 605

Ile Asn
    610

<210> SEQ ID NO 54
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Cys Pro Pro Cys Pro
1               5

<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ala Ser Thr Lys Gly Pro Ser Val Phe Pro Leu Ala Pro
1               5                   10

<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ala Ser Thr Lys Gly Pro
1               5
```

```
<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Thr Val Ala Ala Pro Ser Val Phe Ile Phe Pro Pro
1               5                   10

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Thr Val Ala Ala Pro
1               5

<210> SEQ ID NO 59
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ala Lys Thr Thr Pro Lys Leu Glu Glu Gly Glu Phe Ser Glu Ala Arg
1               5                   10                  15

<210> SEQ ID NO 60
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Lys Thr Thr Pro Lys Leu Glu Glu Gly Glu Phe Ser Glu Ala Arg
1               5                   10                  15

Val

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ala Lys Thr Thr Pro Lys Leu Gly Gly
1               5
```

```
<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ser Ala Lys Thr Thr Pro Lys Leu Gly Gly
1               5                   10

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Ala Lys Thr Thr Pro
1               5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Arg Ala Asp Ala Ala Pro
1               5

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Arg Ala Asp Ala Ala Pro Thr Val Ser
1               5

<210> SEQ ID NO 66
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Arg Ala Asp Ala Ala Ala Ala Gly Gly Pro Gly Ser
1               5                   10

<210> SEQ ID NO 67
<211> LENGTH: 27
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 67

Arg Ala Asp Ala Ala Ala Ala Gly Gly Gly Ser Gly Gly Gly Gly
1               5                   10                  15
Ser Gly Gly Gly Gly Ser Gly Gly Gly Ser
            20                  25

<210> SEQ ID NO 68
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ser Ala Lys Thr Thr Pro Lys Leu Glu Glu Gly Glu Phe Ser Glu Ala
1               5                   10                  15
Arg Val

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ala Asp Ala Ala Pro
1               5

<210> SEQ ID NO 70
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ala Asp Ala Ala Pro Thr Val Ser Ile Phe Pro Pro
1               5                   10

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gln Pro Lys Ala Ala Pro
1               5

<210> SEQ ID NO 72
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gln Pro Lys Ala Ala Pro Ser Val Thr Leu Phe Pro Pro
1               5                   10

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ala Lys Thr Thr Pro Pro
1               5

<210> SEQ ID NO 74
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ala Lys Thr Thr Pro Pro Ser Val Thr Pro Leu Ala Pro
1               5                   10

<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ala Lys Thr Thr Ala Pro
1               5

<210> SEQ ID NO 76
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ala Lys Thr Thr Ala Pro Ser Val Tyr Pro Leu Ala Pro
1               5                   10

<210> SEQ ID NO 77
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Glu Asn Lys Val Glu Tyr Ala Pro Ala Leu Met Ala Leu Ser
1               5                   10                  15

<210> SEQ ID NO 79
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Pro Ala Lys Glu Leu Thr Pro Leu Lys Glu Ala Lys Val Ser
1               5                   10                  15

<210> SEQ ID NO 80
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly His Glu Ala Ala Ala Val Met Gln Val Gln Tyr Pro Ala Ser
1               5                   10                  15

<210> SEQ ID NO 81
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 82
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 82

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25

<210> SEQ ID NO 83
<211> LENGTH: 692
<212> TYPE: PRT
<213> ORGANISM: Homo sapiens

<400> SEQUENCE: 83

Met Glu Leu Leu Pro Leu Trp Leu Cys Leu Gly Phe His Phe Leu Thr
1               5                   10                  15

Val Gly Trp Arg Asn Arg Ser Gly Thr Ala Thr Ala Ala Ser Gln Gly
            20                  25                  30

Val Cys Lys Leu Val Gly Gly Ala Ala Asp Cys Arg Gly Gln Ser Leu
        35                  40                  45

Ala Ser Val Pro Ser Ser Leu Pro Pro His Ala Arg Met Leu Thr Leu
    50                  55                  60

Asp Ala Asn Pro Leu Lys Thr Leu Trp Asn His Ser Leu Gln Pro Tyr
65                  70                  75                  80

Pro Leu Leu Glu Ser Leu Ser Leu His Ser Cys His Leu Glu Arg Ile
                85                  90                  95

Ser Arg Gly Ala Phe Gln Glu Gln Gly His Leu Arg Ser Leu Val Leu
            100                 105                 110

Gly Asp Asn Cys Leu Ser Glu Asn Tyr Glu Glu Thr Ala Ala Ala Leu
        115                 120                 125

His Ala Leu Pro Gly Leu Arg Arg Leu Asp Leu Ser Gly Asn Ala Leu
    130                 135                 140

Thr Glu Asp Met Ala Ala Leu Met Leu Gln Asn Leu Ser Ser Leu Arg
145                 150                 155                 160

Ser Val Ser Leu Ala Gly Asn Thr Ile Met Arg Leu Asp Asp Ser Val
                165                 170                 175

Phe Glu Gly Leu Glu Arg Leu Arg Glu Leu Asp Leu Gln Arg Asn Tyr
            180                 185                 190

Ile Phe Glu Ile Glu Gly Gly Ala Phe Asp Gly Leu Ala Glu Leu Arg
        195                 200                 205

His Leu Asn Leu Ala Phe Asn Asn Leu Pro Cys Ile Val Asp Phe Gly
    210                 215                 220

Leu Thr Arg Leu Arg Val Leu Asn Val Ser Tyr Asn Val Leu Glu Trp
225                 230                 235                 240

Phe Leu Ala Thr Gly Gly Glu Ala Ala Phe Glu Leu Glu Thr Leu Asp
                245                 250                 255

Leu Ser His Asn Gln Leu Leu Phe Phe Pro Leu Leu Pro Gln Tyr Ser
            260                 265                 270

Lys Leu Arg Thr Leu Leu Leu Arg Asp Asn Asn Met Gly Phe Tyr Arg
        275                 280                 285

Asp Leu Tyr Asn Thr Ser Ser Pro Arg Glu Met Val Ala Gln Phe Leu
    290                 295                 300

Leu Val Asp Gly Asn Val Thr Asn Ile Thr Thr Val Ser Leu Trp Glu
305                 310                 315                 320

Glu Phe Ser Ser Ser Asp Leu Ala Asp Leu Arg Phe Leu Asp Met Ser
                325                 330                 335
```

Gln Asn Gln Phe Gln Tyr Leu Pro Asp Gly Phe Leu Arg Lys Met Pro
                340                 345                 350

Ser Leu Ser His Leu Asn Leu His Gln Asn Cys Leu Met Thr Leu His
        355                 360                 365

Ile Arg Glu His Glu Pro Pro Gly Ala Leu Thr Glu Leu Asp Leu Ser
    370                 375                 380

His Asn Gln Leu Ser Glu Leu His Leu Ala Pro Gly Leu Ala Ser Cys
385                 390                 395                 400

Leu Gly Ser Leu Arg Leu Phe Asn Leu Ser Ser Asn Gln Leu Leu Gly
                405                 410                 415

Val Pro Pro Gly Leu Phe Ala Asn Ala Arg Asn Ile Thr Thr Leu Asp
                420                 425                 430

Met Ser His Asn Gln Ile Ser Leu Cys Pro Leu Pro Ala Ala Ser Asp
        435                 440                 445

Arg Val Gly Pro Pro Ser Cys Val Asp Phe Arg Asn Met Ala Ser Leu
    450                 455                 460

Arg Ser Leu Ser Leu Glu Gly Cys Gly Leu Gly Ala Leu Pro Asp Cys
465                 470                 475                 480

Pro Phe Gln Gly Thr Ser Leu Thr Tyr Leu Asp Leu Ser Ser Asn Trp
                485                 490                 495

Gly Val Leu Asn Gly Ser Leu Ala Pro Leu Gln Asp Val Ala Pro Met
                500                 505                 510

Leu Gln Val Leu Ser Leu Arg Asn Met Gly Leu His Ser Ser Phe Met
                515                 520                 525

Ala Leu Asp Phe Ser Gly Phe Gly Asn Leu Arg Asp Leu Asp Leu Ser
        530                 535                 540

Gly Asn Cys Leu Thr Thr Phe Pro Arg Phe Gly Gly Ser Leu Ala Leu
545                 550                 555                 560

Glu Thr Leu Asp Leu Arg Arg Asn Ser Leu Thr Ala Leu Pro Gln Lys
                565                 570                 575

Ala Val Ser Glu Gln Leu Ser Arg Gly Leu Arg Thr Ile Tyr Leu Ser
                580                 585                 590

Gln Asn Pro Tyr Asp Cys Cys Gly Val Asp Gly Trp Gly Ala Leu Gln
        595                 600                 605

His Gly Gln Thr Val Ala Asp Trp Ala Met Val Thr Cys Asn Leu Ser
    610                 615                 620

Ser Lys Ile Ile Arg Val Thr Glu Leu Pro Gly Gly Val Pro Arg Asp
625                 630                 635                 640

Cys Lys Trp Glu Arg Leu Asp Leu Gly Leu Leu Tyr Leu Val Leu Ile
                645                 650                 655

Leu Pro Ser Cys Leu Thr Leu Leu Val Ala Cys Thr Val Ile Val Leu
                660                 665                 670

Thr Phe Lys Lys Pro Leu Leu Gln Val Ile Lys Ser Arg Cys His Trp
                675                 680                 685

Ser Ser Val Tyr
        690

<210> SEQ ID NO 84
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
            20                  25                  30

Ala Ser Gln Gly Val Cys Lys Leu Val Gly Gly Ala Ala Asp Cys Arg
        35                  40                  45

Gly Gln Ser Leu Ala Ser Val Pro Ser Ser Leu Pro Pro His Ala Arg
    50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
    210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
            260                 265                 270

Pro Gln Tyr Ser Lys Leu Arg Thr Leu Leu Leu Arg Asp Asn Asn Met
        275                 280                 285

Gly Phe Tyr Arg Asp Leu Tyr Asn Thr Ser Ser Pro Arg Glu Met Val
    290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Asp Leu Ala Asp Leu Arg Phe
                325                 330                 335

Leu Asp Met Ser Gln Asn Gln Phe Gln Tyr Leu Pro Asp Gly Phe Leu
        340                 345                 350

Arg Lys Met Pro Ser Leu Ser His Leu Asn Leu His Gln Asn Cys Leu
    355                 360                 365

Met Thr Leu His Ile Arg Glu His Glu Pro Pro Gly Ala Leu Thr Glu
370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn

```
                    405                 410                 415
Gln Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
            435                 440                 445

Ala Ala Ser Asp Arg Val Gly Pro Pro Ser Cys Val Asp Phe Arg Asn
    450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
            515                 520                 525

Ser Ser Phe Met Ala Leu Asp Phe Ser Gly Phe Gly Asn Leu Arg Asp
530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
            595                 600                 605

Gly Ala Leu Gln His Gly Gln Thr Val Ala Asp Trp Ala Met Val Thr
            610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu His His
                645                 650                 655

His His His His
        660

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000
```

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Ser Gly His Trp Asp Phe Asp Tyr Trp Gly Gln Gly
            100                 105                 110

Thr Leu Val Thr Val Ser Ser
        115

<210> SEQ ID NO 96

-continued

```
<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
                20                  25                  30

Ala Ser Gln Gly Val Cys Lys Leu Val Gly Gly Ala Ala Asp Cys Arg
            35                  40                  45

Gly Gln Ser Leu Ala Ser Val Pro Ser Ser Leu Pro Pro His Ala Arg
        50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
                100                 105                 110

Ser Leu Val Leu Gly Asp Asn Cys Leu Ser Glu Asn Tyr Glu Glu Thr
            115                 120                 125

Ala Ala Ala Leu His Ala Leu Pro Gly Leu Arg Arg Leu Asp Leu Ser
        130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
```

```
            180                 185                 190
Gln Arg Asn Tyr Ile Phe Glu Ile Glu Gly Gly Ala Phe Asp Gly Leu
            195                 200                 205

Ala Glu Leu Arg His Leu Asn Leu Ala Phe Asn Asn Leu Pro Cys Ile
            210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Pro Leu Leu
            260                 265                 270

Pro Gln Tyr Ser Lys Leu Arg Thr Leu Leu Leu Arg Asp Asn Asn Met
            275                 280                 285

Gly Phe Tyr Arg Asp Leu Tyr Asn Thr Ser Ser Pro Arg Glu Met Val
            290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Ser Asp Leu Ala Asp Leu Arg Phe
                325                 330                 335

Leu Asp Met Ser Gln Asn Gln Phe Gln Tyr Leu Pro Asp Gly Phe Leu
            340                 345                 350

Arg Lys Met Pro Ser Leu Ser His Leu Asn Leu His Gln Asn Cys Leu
            355                 360                 365

Met Thr Leu His Ile Arg Glu His Glu Pro Pro Gly Ala Leu Thr Glu
            370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
            435                 440                 445

Ala Ala Ser Asp Arg Val Gly Pro Pro Ser Cys Val Asp Phe Arg Asn
            450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
            515                 520                 525

Ser Ser Phe Met Ala Leu Asp Phe Ser Gly Phe Gly Asn Leu Arg Asp
            530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
            595                 600                 605
```

```
Gly Ala Leu Gln His Gly Gln Thr Val Ala Asp Trp Ala Met Val Thr
    610             615                 620
Cys Asn Leu Ser Ser Lys Ile Ile Arg Val Thr Glu Leu Pro Gly Gly
625             630                 635                 640
Val Pro Arg Asp Cys Lys Trp Glu Arg Leu Asp Leu Gly Leu Leu Ile
                645                 650                 655
Ile Ile Leu Thr Phe Ile Leu Val Ser Ala Ile Leu Leu Thr Thr Leu
            660                 665                 670
Ala Ala Cys Cys Cys Val Arg Arg Gln Lys Phe Asn Gln Gln Tyr Lys
        675                 680                 685
Ala

<210> SEQ ID NO 102
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ser Phe Ser Met Asp
1               5

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Tyr Ile Ser Pro Ser Ala Asp Thr Ile Tyr Tyr Ala Asp Ser Val Lys
1               5                   10                  15
Gly

<210> SEQ ID NO 104
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Val Leu Asp Tyr Gly Asp Met Leu Met Pro
1               5                   10

<210> SEQ ID NO 105
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"
```

```
<400> SEQUENCE: 105

Gln Ala Ser Gln Asp Ile Thr Asn Tyr Leu Asn
1               5                   10

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 106

Asp Ala Ser Asn Leu Glu Thr
1               5

<210> SEQ ID NO 107
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 107

Phe Thr Phe Ser Ser Phe Ser Met Asp
1               5

<210> SEQ ID NO 108
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Phe Thr Phe Ser Ser Tyr Ser Met Asn
1               5

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Tyr Ile Ser Ser Ser Ser Ser Thr Ile Tyr Tyr Ala Asp Ser Val Lys
1               5                   10                  15

Gly

<210> SEQ ID NO 110
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 110

Ala Arg Gly Val Leu Asp Tyr Gly Asp Met Leu Asp Pro
1               5                   10

<210> SEQ ID NO 111
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 111

Tyr Ile Ser Pro Asp Ala Ser Thr Ile Tyr Tyr Ala Asp Ser Val Lys
1               5                   10                  15

Gly

<210> SEQ ID NO 112
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Phe Thr Phe Gly Ser Phe Ser Met Asn
1               5

<210> SEQ ID NO 113
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Tyr Ile His Ser Asp Ala Ser Thr Ile Tyr Tyr Ala Asp Ser Val Lys
1               5                   10                  15

Gly

<210> SEQ ID NO 114
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
```

<223> OTHER INFORMATION: /note="See specification as filed for detailed
      description of substitutions and preferred embodiments"

<400> SEQUENCE: 114

Phe Thr Phe Ser Ser Phe Ser Met Asn
1               5

<210> SEQ ID NO 115
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Phe Thr Phe Ser Ser Phe Ala Met Tyr
1               5

<210> SEQ ID NO 116
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Phe Thr Phe Gly Ser Phe Ser Met Asp
1               5

<210> SEQ ID NO 117
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Phe Thr Phe Ser Phe Tyr Ala Met Asn
1               5

<210> SEQ ID NO 118
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Val Arg Gly Val Leu Asp Tyr Gly Asp Met Leu Asp Pro
1               5                   10

<210> SEQ ID NO 119
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

```
Phe Thr Phe Ser Ser Phe Ala Met Asn
1               5
```

<210> SEQ ID NO 120
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

```
Tyr Ile Ser Pro Asp Ala Ser Thr Ile Tyr Tyr Ala Gly Ser Val Lys
1               5                   10                  15
Gly
```

<210> SEQ ID NO 121
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

```
Val Arg Ala Val Leu Asp Tyr Gly Asp Met Leu Asp Pro
1               5                   10
```

<210> SEQ ID NO 122
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

```
Ala Arg Gly Thr Leu Asp Tyr Gly Asp Met Leu Asp Pro
1               5                   10
```

<210> SEQ ID NO 123
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

```
Ala Arg Ala Val Leu Asp Tyr Gly Asp Met Leu Asp Pro
1               5                   10
```

<210> SEQ ID NO 124
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

```
Ala Arg Gly Val Trp Asp Met Gly Asp Met Leu Asp Pro
```

```
<210> SEQ ID NO 125
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ala His Gly Val Leu Asp Tyr Gly Asp Met Leu Asp Pro
1               5                   10

<210> SEQ ID NO 126
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Phe Thr Phe Ala Phe Tyr Ser Met Asn
1               5

<210> SEQ ID NO 127
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 128
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 129
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 130
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Phe
            20                  25                  30
```

```
Ser Met Asn Trp Val Arg Gln Ala Pro Gly Lys Gly Leu Glu Trp Val
        35                  40                  45

Ser Tyr Ile His Ser Asp Ala Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 131
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                20                  25                  30

Ser Met Asn Trp Val Arg Gln Ala Pro Gly Lys Gly Leu Glu Trp Val
        35                  40                  45

Ser Tyr Ile Ser Pro Ser Ala Asp Thr Ile Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 132
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Ser Ser Phe
                20                  25                  30

Ala Met Tyr Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
 50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                        85                  90                  95

Ala Arg Gly Val Leu Asp Tyr Gly Asp Met Leu Asp Pro Trp Gly Gln
                100                 105                 110

Gly Thr Leu Val Thr Val Ser Ser
            115                 120

<210> SEQ ID NO 133
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                        85                  90                  95

Ala Arg Gly Val Leu Asp Tyr Gly Asp Met Leu Asp Pro Trp Gly Gln
                100                 105                 110

Gly Thr Leu Val Thr Val Ser Ser
            115                 120

<210> SEQ ID NO 134
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                        85                  90                  95

Ala Arg Gly Val Leu Asp Tyr Gly Asp Met Leu Asp Pro Trp Gly Gln
                100                 105                 110
```

```
Gly Thr Leu Val Thr Val Ser Ser
        115                 120

<210> SEQ ID NO 135
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Ala Met Asn Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 136
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 137
<211> LENGTH: 120
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137
```

| Glu | Val | Gln | Leu | Val | Glu | Ser | Gly | Gly | Gly | Leu | Val | Gln | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Arg | Leu | Ser | Cys | Ala | Ala | Ser | Gly | Phe | Thr | Phe | Ser | Ser | Phe |
|     |     |     | 20  |     |     |     |     | 25  |     |     |     |     | 30  |     |     |
| Ala | Met | Asn | Trp | Val | Arg | Gln | Ala | Pro | Gly | Lys | Gly | Leu | Glu | Trp | Val |
|     |     |     | 35  |     |     |     |     | 40  |     |     |     |     | 45  |     |     |
| Ser | Tyr | Ile | Ser | Pro | Asp | Ala | Ser | Thr | Ile | Tyr | Tyr | Ala | Gly | Ser | Val |
|     |     | 50  |     |     |     |     | 55  |     |     |     |     | 60  |     |     |     |
| Lys | Gly | Arg | Phe | Thr | Ile | Ser | Arg | Asp | Asn | Ala | Lys | Asn | Ser | Leu | Tyr |
| 65  |     |     |     |     | 70  |     |     |     |     | 75  |     |     |     |     | 80  |
| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |
| Val | Arg | Ala | Val | Leu | Asp | Tyr | Gly | Asp | Met | Leu | Asp | Pro | Trp | Gly | Gln |
|     |     |     | 100 |     |     |     |     | 105 |     |     |     |     | 110 |     |     |
| Gly | Thr | Leu | Val | Thr | Val | Ser | Ser |
|     |     |     | 115 |     |     |     | 120 |

```
<210> SEQ ID NO 138
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138
```

| Glu | Val | Gln | Leu | Val | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Arg | Leu | Ser | Cys | Ala | Ala | Ser | Gly | Phe | Thr | Phe | Ser | Ser | Phe |
|     |     |     | 20  |     |     |     |     | 25  |     |     |     |     | 30  |     |     |
| Ser | Met | Asp | Trp | Val | Arg | Gln | Ala | Pro | Gly | Lys | Gly | Leu | Glu | Trp | Val |
|     |     |     | 35  |     |     |     |     | 40  |     |     |     |     | 45  |     |     |
| Ser | Tyr | Ile | Ser | Pro | Asp | Ala | Ser | Thr | Ile | Tyr | Tyr | Ala | Asp | Ser | Val |
|     |     | 50  |     |     |     |     | 55  |     |     |     |     | 60  |     |     |     |
| Lys | Gly | Arg | Phe | Thr | Ile | Ser | Arg | Asp | Asn | Ala | Lys | Asn | Ser | Leu | Tyr |
| 65  |     |     |     |     | 70  |     |     |     |     | 75  |     |     |     |     | 80  |
| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |
| Ala | Arg | Gly | Thr | Leu | Asp | Tyr | Gly | Asp | Met | Leu | Asp | Pro | Trp | Gly | Gln |
|     |     |     | 100 |     |     |     |     | 105 |     |     |     |     | 110 |     |     |
| Gly | Thr | Leu | Val | Thr | Val | Ser | Ser |
|     |     |     | 115 |     |     |     | 120 |

```
<210> SEQ ID NO 139
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asp Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Val Leu Asp Tyr Gly Asp Met Leu Asp Pro Trp Gly Gln
            100                 105                 110

Gly Thr Leu Val Thr Val Ser Ser
        115                 120

<210> SEQ ID NO 140
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Asn Trp Val Arg Gln Ala Pro Gly Lys Gly Leu Glu Trp Val
        35                  40                  45

Ser Tyr Ile Ser Pro Ser Ala Asp Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Trp Asp Met Gly Asp Met Leu Asp Pro Trp Gly Gln
            100                 105                 110

Gly Thr Leu Val Thr Val Ser Ser
        115                 120

<210> SEQ ID NO 141
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

```
Ser Met Asn Trp Val Arg Gln Ala Pro Gly Lys Gly Leu Glu Trp Val
        35                  40                  45

Ser Tyr Ile Ser Pro Ser Ala Asp Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 142
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Phe Tyr
            20                  25                  30

Ser Met Asn Trp Val Arg Gln Ala Pro Gly Lys Gly Leu Glu Trp Val
        35                  40                  45

Ser Tyr Ile Ser Pro Asp Ala Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Asp Tyr Gly Asp Met Leu Asp Pro Trp Gly Gln
            100                 105                 110

Gly Thr Leu Val Thr Val Ser Ser
        115                 120

<210> SEQ ID NO 143
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Gly" or "Ala"
<220> FEATURE:
<221> NAME/KEY: VARIANT
<222> LOCATION: (5)..(5)
<223> OTHER INFORMATION: /replace="Phe"
<220> FEATURE:
<221> NAME/KEY: VARIANT
<222> LOCATION: (6)..(6)
<223> OTHER INFORMATION: /replace="Tyr"
<220> FEATURE:
<221> NAME/KEY: VARIANT
<222> LOCATION: (7)..(7)
```

```
<223> OTHER INFORMATION: /replace="Ala"
<220> FEATURE:
<221> NAME/KEY: VARIANT
<222> LOCATION: (9)..(9)
<223> OTHER INFORMATION: /replace="Asn" or "Tyr"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 143

Phe Thr Phe Ser Ser Phe Ser Met Asp
1               5

<210> SEQ ID NO 144
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="His"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Asp"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (13)..(13)
<223> OTHER INFORMATION: /replace="Gly"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 144

Tyr Ile Ser Pro Ser Ala Asp Thr Ile Tyr Tyr Ala Asp Ser Val Lys
1               5                   10                  15

Gly

<210> SEQ ID NO 145
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

```
<222> LOCATION: (1)..(1)
<223> OTHER INFORMATION: /replace="Val"
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (5)..(5)
<223> OTHER INFORMATION: /replace="Trp"
<220> FEATURE:
<221> NAME/KEY: VARIANT
<222> LOCATION: (7)..(7)
<223> OTHER INFORMATION: /replace="Met"
<220> FEATURE:
<221> NAME/KEY: VARIANT
<222> LOCATION: (12)..(12)
<223> OTHER INFORMATION: /replace="Asp"
<220> FEATURE:
<221> NAME/KEY: SITE
<222> LOCATION: (1)..(13)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 145

Ala Arg Gly Val Leu Asp Tyr Gly Asp Met Leu Met Pro
1               5                   10

<210> SEQ ID NO 146
<211> LENGTH: 249
<212> TYPE: PRT
<213> ORGANISM: Homo sapiens

<400> SEQUENCE: 146

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175
```

-continued

Gln Trp Leu Ser Arg Gly Gly Glu Ile Glu Gly Phe Arg Leu Ser Ala
                    180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 147
<211> LENGTH: 45
<212> TYPE: PRT
<213> ORGANISM: Homo sapiens

<400> SEQUENCE: 147

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro
            35                  40                  45

<210> SEQ ID NO 148
<211> LENGTH: 112
<212> TYPE: PRT
<213> ORGANISM: Homo sapiens

<400> SEQUENCE: 148

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 149
<211> LENGTH: 4
<212> TYPE: PRT
<213> ORGANISM: Homo sapiens

<400> SEQUENCE: 149

Arg His Arg Arg
1

<210> SEQ ID NO 150
<211> LENGTH: 204
<212> TYPE: PRT
<213> ORGANISM: Homo sapiens

<400> SEQUENCE: 150

Glu Ala Val Leu Ala Leu Tyr Asn Ser Thr Arg Asp Arg Val Ala Gly
1               5                   10                  15

Glu Ser Ala Glu Pro Glu Pro Glu Ala Asp Tyr Tyr Ala Lys
            20              25                  30

Glu Val Thr Arg Val Leu Met Val Glu Thr His Asn Glu Ile Tyr Asp
            35              40                  45

Lys Phe Lys Gln Ser Thr His Ser Ile Tyr Met Phe Phe Asn Thr Ser
50                  55                  60

Glu Leu Arg Glu Ala Val Pro Glu Pro Val Leu Leu Ser Arg Ala Glu
65                  70              75                  80

Leu Arg Leu Leu Arg Leu Lys Leu Lys Val Glu Gln His Val Glu Leu
                85                  90                  95

Tyr Gln Lys Tyr Ser Asn Asn Ser Trp Arg Tyr Leu Ser Asn Arg Leu
            100                 105                 110

Leu Ala Pro Ser Asp Ser Pro Glu Trp Leu Ser Phe Asp Val Thr Gly
            115                 120                 125

Val Val Arg Gln Trp Leu Ser Arg Gly Gly Glu Ile Glu Gly Phe Arg
130                 135                 140

Leu Ser Ala His Cys Ser Cys Asp Ser Arg Asp Asn Thr Leu Gln Val
145                 150                 155                 160

Asp Ile Asn Gly Phe Thr Thr Gly Arg Arg Gly Asp Leu Ala Thr Ile
            165                 170                 175

His Gly Met Asn Arg Pro Phe Leu Leu Leu Met Ala Thr Pro Leu Glu
            180                 185                 190

Arg Ala Gln His Leu Gln Ser Ser Arg His Arg Arg
            195                 200

<210> SEQ ID NO 151
<211> LENGTH: 29
<212> TYPE: PRT
<213> ORGANISM: Homo sapiens

<400> SEQUENCE: 151

Cys Val Arg Gln Leu Tyr Ile Asp Phe Arg Lys Asp Leu Gly Trp Lys
1               5                   10                  15

Trp Ile His Glu Pro Lys Gly Tyr His Ala Asn Phe Cys
            20                  25

<210> SEQ ID NO 152
<211> LENGTH: 35
<212> TYPE: PRT
<213> ORGANISM: Homo sapiens

<400> SEQUENCE: 152

Cys Val Pro Gln Ala Leu Glu Pro Leu Pro Ile Val Tyr Tyr Val Gly
1               5                   10                  15

Arg Lys Pro Lys Val Glu Gln Leu Ser Asn Met Ile Val Arg Ser Cys
            20                  25                  30

Lys Cys Ser
        35

<210> SEQ ID NO 153
<211> LENGTH: 15
<212> TYPE: PRT
<213> ORGANISM: Homo sapiens

<400> SEQUENCE: 153

```
Leu Ala Ser Pro Pro Ser Gln Gly Glu Val Pro Pro Gly Pro Leu
1               5                   10                  15
```

<210> SEQ ID NO 154
<211> LENGTH: 27
<212> TYPE: PRT
<213> ORGANISM: Homo sapiens

<400> SEQUENCE: 154

```
Leu Ala Ser Pro Pro Ser Gln Gly Glu Val Pro Pro Gly Pro Leu Pro
1               5                   10                  15

Glu Ala Val Leu Ala Leu Tyr Asn Ser Thr Arg
            20                  25
```

<210> SEQ ID NO 155
<211> LENGTH: 29
<212> TYPE: PRT
<213> ORGANISM: Homo sapiens

<400> SEQUENCE: 155

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg
            20                  25
```

<210> SEQ ID NO 156
<211> LENGTH: 10
<212> TYPE: PRT
<213> ORGANISM: Homo sapiens

<400> SEQUENCE: 156

```
Ala Val Leu Ala Leu Tyr Asn Ser Thr Arg
1               5                   10
```

<210> SEQ ID NO 157
<211> LENGTH: 20
<212> TYPE: PRT
<213> ORGANISM: Homo sapiens

<400> SEQUENCE: 157

```
Asn Gly Phe Thr Thr Gly Arg Arg Gly Asp Leu Ala Thr Ile His Gly
1               5                   10                  15

Met Asn Arg Pro
            20
```

<210> SEQ ID NO 158
<211> LENGTH: 13
<212> TYPE: PRT
<213> ORGANISM: Homo sapiens

<400> SEQUENCE: 158

```
Cys Ser Cys Asp Ser Arg Asp Asn Thr Leu Gln Val Asp
1               5                   10
```

<210> SEQ ID NO 159
<211> LENGTH: 9
<212> TYPE: PRT
<213> ORGANISM: Homo sapiens

<400> SEQUENCE: 159

```
Leu Val Lys Arg Lys Arg Ile Glu Ala
1               5
```

```
<210> SEQ ID NO 160
<211> LENGTH: 11
<212> TYPE: PRT
<213> ORGANISM: Homo sapiens

<400> SEQUENCE: 160

Leu Ala Ser Pro Pro Ser Gln Gly Glu Val Pro
1               5                   10

<210> SEQ ID NO 161
<211> LENGTH: 8
<212> TYPE: PRT
<213> ORGANISM: Homo sapiens

<400> SEQUENCE: 161

Pro Gly Pro Leu Pro Glu Ala Val
1               5

<210> SEQ ID NO 162
<211> LENGTH: 8
<212> TYPE: PRT
<213> ORGANISM: Homo sapiens

<400> SEQUENCE: 162

Leu Ala Leu Tyr Asn Ser Thr Arg
1               5

<210> SEQ ID NO 163
<211> LENGTH: 9
<212> TYPE: PRT
<213> ORGANISM: Homo sapiens

<400> SEQUENCE: 163

Arg Glu Ala Val Pro Glu Pro Val Leu
1               5

<210> SEQ ID NO 164
<211> LENGTH: 10
<212> TYPE: PRT
<213> ORGANISM: Homo sapiens

<400> SEQUENCE: 164

Tyr Gln Lys Tyr Ser Asn Asn Ser Trp Arg
1               5                   10

<210> SEQ ID NO 165
<211> LENGTH: 19
<212> TYPE: PRT
<213> ORGANISM: Homo sapiens

<400> SEQUENCE: 165

Arg Lys Asp Leu Gly Trp Lys Trp Ile His Glu Pro Lys Gly Tyr His
1               5                   10                  15

Ala Asn Phe

<210> SEQ ID NO 166
<211> LENGTH: 9
<212> TYPE: PRT
<213> ORGANISM: Homo sapiens

<400> SEQUENCE: 166

Leu Gly Pro Cys Pro Tyr Ile Trp Ser
1               5
```

-continued

```
<210> SEQ ID NO 167
<211> LENGTH: 8
<212> TYPE: PRT
<213> ORGANISM: Homo sapiens

<400> SEQUENCE: 167

Ala Leu Glu Pro Leu Pro Ile Val
1               5

<210> SEQ ID NO 168
<211> LENGTH: 10
<212> TYPE: PRT
<213> ORGANISM: Homo sapiens

<400> SEQUENCE: 168

Val Gly Arg Lys Pro Lys Val Glu Gln Leu
1               5                   10

<210> SEQ ID NO 169
<211> LENGTH: 23
<212> TYPE: PRT
<213> ORGANISM: Homo sapiens

<400> SEQUENCE: 169

Lys Leu Arg Leu Ala Ser Pro Pro Ser Gln Gly Glu Val Pro Pro Gly
1               5                   10                  15

Pro Leu Pro Glu Ala Val Leu
            20

<210> SEQ ID NO 170
<211> LENGTH: 8
<212> TYPE: PRT
<213> ORGANISM: Homo sapiens

<400> SEQUENCE: 170

Arg Lys Asp Leu Gly Trp Lys Trp
1               5

<210> SEQ ID NO 171
<211> LENGTH: 11
<212> TYPE: PRT
<213> ORGANISM: Homo sapiens

<400> SEQUENCE: 171

Arg Lys Asp Leu Gly Trp Lys Trp Ile His Glu
1               5                   10

<210> SEQ ID NO 172
<211> LENGTH: 10
<212> TYPE: PRT
<213> ORGANISM: Homo sapiens

<400> SEQUENCE: 172

His Glu Pro Lys Gly Tyr His Ala Asn Phe
1               5                   10

<210> SEQ ID NO 173
<211> LENGTH: 21
<212> TYPE: PRT
<213> ORGANISM: Homo sapiens

<400> SEQUENCE: 173

Leu Arg Leu Ala Ser Pro Pro Ser Gln Gly Glu Val Pro Pro Gly Pro
1               5                   10                  15
```

```
Leu Pro Glu Ala Val
            20

<210> SEQ ID NO 174
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 175
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 175

Trp Val Arg Gln Ala Pro Gly Lys Gly Leu Glu Trp Val Ser
1               5                   10

<210> SEQ ID NO 176
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="See specification as filed for detailed
      description of substitutions and preferred embodiments"

<400> SEQUENCE: 176

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 177
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"
```

```
-continued

<400> SEQUENCE: 177

Trp Gly Gln Gly Thr Leu Val Thr Val Ser Ser
1               5                   10

<210> SEQ ID NO 178
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 179
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 179

Trp Tyr Gln Gln Lys Pro Gly Lys Ala Pro Lys Leu Leu Ile Tyr
1               5                   10                  15

<210> SEQ ID NO 180
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="See specification as filed for detailed
      description of substitutions and preferred embodiments"

<400> SEQUENCE: 180

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 181
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="See specification as filed for detailed
      description of substitutions and preferred embodiments"

<400> SEQUENCE: 181

Phe Gly Gly Gly Thr Lys Val Glu Ile Lys
1               5                   10

<210> SEQ ID NO 182
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      TGFbeta sequence"

<400> SEQUENCE: 182

Leu Ser Lys Leu Arg Leu
1               5

<210> SEQ ID NO 183
<211> LENGTH: 367
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

His His His His His His Leu Ser Thr Ser Lys Thr Ile Asp Met Glu
1               5                   10                  15

Leu Val Lys Arg Lys Arg Ile Glu Ala Ile Arg Gly Gln Ile Leu Ser
                20                  25                  30

Lys Leu Arg Leu Ala Ser Pro Pro Ser Gln Gly Glu Val Pro Pro Gly
            35                  40                  45

Pro Leu Pro Glu Ala Val Leu Ala Leu Tyr Asn Ser Thr Arg Asp Arg
        50                  55                  60

Val Ala Gly Glu Ser Ala Glu Pro Glu Pro Glu Pro Glu Ala Asp Tyr
65                  70                  75                  80

Tyr Ala Lys Glu Val Thr Arg Val Leu Met Val Glu Thr His Asn Glu
                85                  90                  95

Ile Tyr Asp Lys Phe Lys Gln Ser Thr His Ser Ile Tyr Met Phe Phe
            100                 105                 110

Asn Thr Ser Glu Leu Arg Glu Ala Val Pro Glu Pro Val Leu Leu Ser
        115                 120                 125

Arg Ala Glu Leu Arg Leu Leu Arg Leu Lys Leu Lys Val Glu Gln His
    130                 135                 140

Val Glu Leu Tyr Gln Lys Tyr Ser Asn Asn Ser Trp Arg Tyr Leu Ser
145                 150                 155                 160

Asn Arg Leu Leu Ala Pro Ser Asp Ser Pro Glu Trp Leu Ser Phe Asp
                165                 170                 175

Val Thr Gly Val Val Arg Gln Trp Leu Ser Arg Gly Gly Glu Ile Glu
            180                 185                 190

Gly Phe Arg Leu Ser Ala His Cys Ser Cys Asp Ser Arg Asp Asn Thr
        195                 200                 205

Leu Gln Val Asp Ile Asn Gly Phe Thr Thr Gly Arg Arg Gly Asp Leu
    210                 215                 220

Ala Thr Ile His Gly Met Asn Arg Pro Phe Leu Leu Leu Met Ala Thr
```

```
            225                 230                 235                 240

Pro Leu Glu Arg Ala Gln His Leu Gln Ser Ser Arg His Arg Arg Ala
                245                 250                 255

Leu Asp Thr Asn Tyr Cys Phe Ser Ser Thr Glu Lys Asn Cys Cys Val
            260                 265                 270

Arg Gln Leu Tyr Ile Asp Phe Arg Lys Asp Leu Gly Trp Lys Trp Ile
        275                 280                 285

His Glu Pro Lys Gly Tyr His Ala Asn Phe Cys Leu Gly Pro Cys Pro
    290                 295                 300

Tyr Ile Trp Ser Leu Asp Thr Gln Tyr Ser Lys Val Leu Ala Leu Tyr
305                 310                 315                 320

Asn Gln His Asn Pro Gly Ala Ser Ala Ala Pro Cys Cys Val Pro Gln
                325                 330                 335

Ala Leu Glu Pro Leu Pro Ile Val Tyr Tyr Val Gly Arg Lys Pro Lys
            340                 345                 350

Val Glu Gln Leu Ser Asn Met Ile Val Arg Ser Cys Lys Cys Ser
        355                 360                 365
```

<210> SEQ ID NO 184
<211> LENGTH: 21
<212> TYPE: PRT
<213> ORGANISM: Homo sapiens

<400> SEQUENCE: 184

```
Ser Pro Pro Ser Gln Gly Glu Val Pro Gly Pro Leu Pro Glu Ala
1               5                   10                  15

Val Leu Ala Leu Tyr
            20
```

<210> SEQ ID NO 185
<211> LENGTH: 20
<212> TYPE: PRT
<213> ORGANISM: Homo sapiens

<400> SEQUENCE: 185

```
Ser Pro Pro Glu Asp Tyr Pro Glu Pro Glu Glu Val Pro Pro Glu Val
1               5                   10                  15

Ile Ser Ile Tyr
            20
```

<210> SEQ ID NO 186
<211> LENGTH: 19
<212> TYPE: PRT
<213> ORGANISM: Homo sapiens

<400> SEQUENCE: 186

```
Ser Pro Pro Glu Pro Thr Val Met Thr His Val Pro Tyr Gln Val Leu
1               5                   10                  15

Ala Leu Tyr
```

<210> SEQ ID NO 187
<211> LENGTH: 24
<212> TYPE: PRT
<213> ORGANISM: Homo sapiens

<400> SEQUENCE: 187

```
Gln Ile Leu Ser Lys Leu Arg Leu Ala Ser Pro Pro Ser Gln Gly Glu
1               5                   10                  15

Val Pro Pro Gly Pro Leu Pro Glu
```

```
<210> SEQ ID NO 188
<211> LENGTH: 23
<212> TYPE: PRT
<213> ORGANISM: Homo sapiens

<400> SEQUENCE: 188

Asn Cys Cys Val Arg Gln Leu Tyr Ile Asp Phe Arg Lys Asp Leu Gly
1               5                   10                  15

Trp Lys Trp Ile His Glu Pro
            20

<210> SEQ ID NO 189
<211> LENGTH: 23
<212> TYPE: PRT
<213> ORGANISM: Homo sapiens

<400> SEQUENCE: 189

Asn Cys Cys Leu Arg Pro Leu Tyr Ile Asp Phe Lys Arg Asp Leu Gly
1               5                   10                  15

Trp Lys Trp Ile His Glu Pro
            20

<210> SEQ ID NO 190
<211> LENGTH: 23
<212> TYPE: PRT
<213> ORGANISM: Homo sapiens

<400> SEQUENCE: 190

Asn Cys Cys Val Arg Pro Leu Tyr Ile Asp Phe Arg Gln Asp Leu Gly
1               5                   10                  15

Trp Lys Trp Val His Glu Pro
            20

<210> SEQ ID NO 191
<211> LENGTH: 8
<212> TYPE: PRT
<213> ORGANISM: Homo sapiens

<400> SEQUENCE: 191

Arg Lys Asp Leu Gly Trp Lys Trp
1               5

<210> SEQ ID NO 192
<211> LENGTH: 23
<212> TYPE: PRT
<213> ORGANISM: Homo sapiens

<400> SEQUENCE: 192

Lys Leu Arg Leu Ala Ser Pro Pro Ser Gln Gly Glu Val Pro Pro Gly
1               5                   10                  15

Pro Leu Pro Glu Ala Val Leu
            20

<210> SEQ ID NO 193
<211> LENGTH: 22
<212> TYPE: PRT
<213> ORGANISM: Homo sapiens

<400> SEQUENCE: 193

Lys Leu Lys Leu Thr Ser Pro Pro Glu Asp Tyr Pro Glu Pro Glu Glu
1               5                   10                  15
```

Val Pro Pro Glu Val Ile
            20

<210> SEQ ID NO 194
<211> LENGTH: 21
<212> TYPE: PRT
<213> ORGANISM: Homo sapiens

<400> SEQUENCE: 194

Lys Leu Arg Leu Thr Ser Pro Pro Glu Pro Thr Val Met Thr His Val
1               5                   10                  15

Pro Tyr Gln Val Leu
            20

<210> SEQ ID NO 195
<211> LENGTH: 19
<212> TYPE: PRT
<213> ORGANISM: Homo sapiens

<400> SEQUENCE: 195

Arg Lys Asp Leu Gly Trp Lys Trp Ile His Glu Pro Lys Gly Tyr His
1               5                   10                  15

Ala Asn Phe

<210> SEQ ID NO 196
<211> LENGTH: 19
<212> TYPE: PRT
<213> ORGANISM: Homo sapiens

<400> SEQUENCE: 196

Lys Arg Asp Leu Gly Trp Lys Trp Ile His Glu Pro Lys Gly Tyr Asn
1               5                   10                  15

Ala Asn Phe

<210> SEQ ID NO 197
<211> LENGTH: 19
<212> TYPE: PRT
<213> ORGANISM: Homo sapiens

<400> SEQUENCE: 197

Arg Gln Asp Leu Gly Trp Lys Trp Val His Glu Pro Lys Gly Tyr Tyr
1               5                   10                  15

Ala Asn Phe

<210> SEQ ID NO 198
<211> LENGTH: 10
<212> TYPE: PRT
<213> ORGANISM: Homo sapiens

<400> SEQUENCE: 198

Val Gly Arg Lys Pro Lys Val Glu Gln Leu
1               5                   10

<210> SEQ ID NO 199
<211> LENGTH: 10
<212> TYPE: PRT
<213> ORGANISM: Homo sapiens

<400> SEQUENCE: 199

Ile Gly Lys Thr Pro Lys Ile Glu Gln Leu
1               5                   10

<210> SEQ ID NO 200
<211> LENGTH: 10
<212> TYPE: PRT
<213> ORGANISM: Homo sapiens

<400> SEQUENCE: 200

Val Gly Arg Thr Pro Lys Val Glu Gln Leu
1               5                   10

<210> SEQ ID NO 201
<211> LENGTH: 18
<212> TYPE: PRT
<213> ORGANISM: Homo sapiens

<400> SEQUENCE: 201

Ser Pro Pro Ser Gln Gly Glu Val Pro Pro Gly Pro Leu Pro Glu Ala
1               5                   10                  15

Val Leu

<210> SEQ ID NO 202
<211> LENGTH: 14
<212> TYPE: PRT
<213> ORGANISM: Homo sapiens

<400> SEQUENCE: 202

Trp Lys Trp Ile His Glu Pro Lys Gly Tyr His Ala Asn Phe
1               5                   10

<210> SEQ ID NO 203
<211> LENGTH: 9
<212> TYPE: PRT
<213> ORGANISM: Homo sapiens

<400> SEQUENCE: 203

Pro Gly Pro Leu Pro Glu Ala Val Leu
1               5

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

```
<210> SEQ ID NO 220
<400> SEQUENCE: 220
000

<210> SEQ ID NO 221
<400> SEQUENCE: 221
000

<210> SEQ ID NO 222
<400> SEQUENCE: 222
000

<210> SEQ ID NO 223
<400> SEQUENCE: 223
000

<210> SEQ ID NO 224
<400> SEQUENCE: 224
000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
```

<400> SEQUENCE: 231

000

<210> SEQ ID NO 232

<400> SEQUENCE: 232

000

<210> SEQ ID NO 233
<211> LENGTH: 7
<212> TYPE: PRT
<213> ORGANISM: Homo sapiens

<400> SEQUENCE: 233

Gly Phe Thr Phe Ser Ser Phe
1               5

<210> SEQ ID NO 234
<211> LENGTH: 6
<212> TYPE: PRT
<213> ORGANISM: Homo sapiens

<400> SEQUENCE: 234

Ser Pro Ser Ala Asp Thr
1               5

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266
<211> LENGTH: 14
<212> TYPE: PRT
<213> ORGANISM: Homo sapiens

<400> SEQUENCE: 266

Ala Ser Pro Pro Ser Gln Gly Glu Val Pro Pro Gly Pro Leu
1               5                   10